US008367706B2

(12) United States Patent
Altman et al.

(10) Patent No.: US 8,367,706 B2
(45) Date of Patent: Feb. 5, 2013

(54) INHIBITORS OF JANUS KINASES

(75) Inventors: Michael Altman, Cambridge, MA (US); Matthew Christopher, Wallingford, CT (US); Jonathan B. Grimm, Newton, MA (US); Andrew Haidle, Cambridge, MA (US); Kaleen Konrad, Newton, MA (US); Jongwon Lim, Lexington, MA (US); Rachel N. MacCoss, Brookline, MA (US); Michelle Machacek, Brookline, MA (US); Ekundayo Osimboni, Ashland, MA (US); Ryan D. Otte, Natick, MA (US); Tony Siu, Brookline, MA (US); Kerrie Spencer, Woonsocket, RI (US); Brandon Taoka, Allston, MA (US); Paul Tempest, Brookline, MA (US); Kevin Wilson, West Newton, MA (US); Hyun Chong Woo, Brookline, MA (US); Jonathan Young, Southborough, MA (US); Anna Zabierek, Salem, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 385 days.

(21) Appl. No.: 12/665,045

(22) PCT Filed: Jun. 16, 2008

(86) PCT No.: PCT/US2008/007486
§ 371 (c)(1),
(2), (4) Date: Dec. 17, 2009

(87) PCT Pub. No.: WO2008/156726
PCT Pub. Date: Dec. 24, 2008

(65) Prior Publication Data

US 2010/0256097 A1    Oct. 7, 2010

Related U.S. Application Data

(60) Provisional application No. 60/936,572, filed on Jun. 20, 2007.

(51) Int. Cl.
*A61K 31/4436* (2006.01)
*C07D 409/12* (2006.01)
(52) U.S. Cl. .................................. 514/336; 546/281.4
(58) Field of Classification Search ............... 546/281.4; 514/336
See application file for complete search history.

(56) References Cited

U.S. PATENT DOCUMENTS

| | | |
|---|---|---|
| 7,112,594 B2 | 9/2006 | Ushio et al. |
| 7,179,836 B2 | 2/2007 | Adams et al. |
| 2005/0154014 A1 | 7/2005 | Bloxham et al. |

FOREIGN PATENT DOCUMENTS

| | | |
|---|---|---|
| WO | 0198290 A2 | 12/2001 |
| WO | WO02/30353 | 4/2002 |
| WO | WO2005/033102 | 4/2005 |
| WO | 2007115999 A1 | 10/2007 |

*Primary Examiner* — Patricia Morris
(74) *Attorney, Agent, or Firm* — Laura M. Ginkel; David A. Muthard

(57) ABSTRACT

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer.

8 Claims, No Drawings

INHIBITORS OF JANUS KINASES

PRIORITY CLAIM

This application is a §371 National Stage Application of PCT/US2008/007486 filed on Jun. 16, 2008, which claims priority from U.S. Provisional Application Ser. No. 60/936,572, filed on Jun. 20, 2007.

BACKGROUND OF THE INVENTION

Janus kinase (JAK) is a family of intracellular non-receptor tyrosine kinases, ranging from 120-140 kDa, that transduce cytokine-mediated signals via the JAK-STAT pathway. The JAK family plays a role in the cytokine-dependent regulation of proliferation and function of cells involved in immune response. Currently, there are four known mammalian JAK family members: JAK1, JAK2, JAK3 and TYK2.

JAK1, JAK2 and TYK2 are ubiquitously expressed whereas JAK3 is expressed in the myeloid and lymphoid lineages. The JAK family members are non-receptor tyrosine kinases that associate with many hematopoietin cytokines, receptor tyrosine kinases and GPCR's. JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2(−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human prostate cancer cell line Du-145 (Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of prostate cancer.

Campbell et al (Journal of Biological Chemistry 1997, 272, 2591-2594) as reported that STAT3 is constitutively activated v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

JAK2 is a cytoplasmic protein-tyrosine kinase that catalyzes the transfer of the gamma-phosphate group of adenosine triphosphate to the hydroxyl groups of specific tyrosine residues in signal transduction molecules. JAK2 mediates signaling downstream of cytokine receptors after ligand-induced autophosphorylation of both receptor and enzyme. The main downstream effectors of JAK2 are a family of transcription factors known as signal transducers and activators of transcription (STAT) proteins. Studies have disclosed an association between an activating JAK2 mutation (JAK2V617F) and myeloproliferative disorders. The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalities in signal transduction mechanisms, including constitutive activation of protein tyrosine kinases, initiate MPD.

JAK3 associates with the common gamma chain of the extracellular receptors for the following interleukins: IL-2, IL-4, IL-7, IL-9 and IL-15. A JAK3 deficiency is associated with an immune compromised (SCID) phenotype in both rodents and humans. The SCID phenotype of JAK3 −/− mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders.

PDK1 signalling regulates multiple critical steps in angiogenesis. Inhibitors of the activity of PDK1 are thus useful in the treatment of cancer, in particular cancers associated with deregulated activity of the PTEN/PI3K pathway including, but not limited to PTEN loss of function mutations and receptor tyrosine kinase gain of function mutations.

SUMMARY OF THE INVENTION

The instant invention provides for compounds that inhibit mammalian JAK kinases (such as JAK1, JAK2, JAK3 and TYK2) and PDK1. The invention also provides for compositions comprising such inhibitory compounds and methods of inhibiting the activity of JAK1, JAK2, JAK3 TYK2 and PDK1 by administering the compound to a patient in need of treatment for myeloproliferative disorders or cancer. One embodiment of the invention is illustrated by a compound of formula I, and the pharmaceutically acceptable salts and stereoisomers thereof:

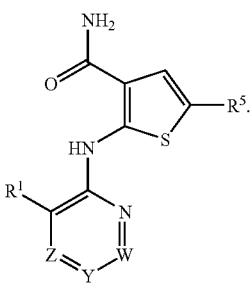

DETAILED DESCRIPTION OF THE INVENTION

The instant invention provides for compounds that inhibit the four known mammalian JAK kinases (JAK1, JAK2, JAK3 and TYK2) and PDK1. The invention also provides for compositions comprising such inhibitory compounds and methods of inhibiting the activity of JAK1, JAK2, JAK3, TYK2 and PDK1 by administering the compound to a patient in need of treatment for myeloproliferative disorders or cancer. One embodiment of the invention is illustrated by a compound of formula I:

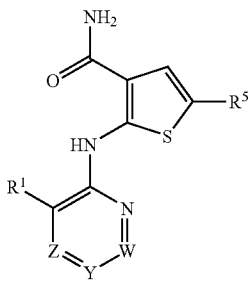

wherein W is N or $CR^4$;
Y is N or $CR^3$;
Z is N or $CR^2$;
$R^1$ is hydrogen, halo, cyano or $C_{1-3}$ alkyl, wherein said alkyl group is optionally substituted with one to three halo;
$R^2$ is hydrogen, halo, cyano or $C_{1-3}$ alkyl, wherein said alkyl group is optionally substituted with one to three halo;
$R^3$ is hydrogen, halo, cyano, oxo, $SO_mR^8$, $C_{1-6}$ alkyl, $C_{2-6}$ alkenyl, $C_{2-6}$ alkynyl, $R^{11}$, $(C_{1-6}$ alkyl)$NR^7R^8$, $(C_{1-6}$ alkyl)$OR^{12}$, $(C=O)NH_2$, $NH(C=O)R^{12}$, $NH(SO_mR^8)$, $N(SO_mR^8)_2$, $NHCH_2(C_{3-6}$ cycloalkyl), $(C_{1-6}$alkyl)$R^{11}$, $O(C_{1-6}$ alkyl)$R^{11}$, $CH_2OR^{11}$, $CH_2NH(C=O)OR^{12}$, wherein said alkyl, alkenyl and alkynyl groups are optionally substituted with one to four substituents independently selected from the group consisting of halo and hydroxyl;
$R^4$ is hydrogen, halo, cyano, oxo, $NR^6R^7$, $C_{1-6}$ alkyl, $(C_{1-6}$ alkyl)$OR^{12}$, $OR^{12}$, $(C=O)OR^{12}$, $(C_{1-6}$ alkyl)$O(C_{1-6}$ alkyl)$OR^{12}$, $(C_{1-6}$ alkyl)$O(C_{1-6}$ alkyl)$R^{11}$, $CH_2NR^{10}CH_2(C=O)NHR^{11}$, $CH_2NR^{10}CH_2(C=O)NHOR^{12}$, $CH_2NR^{10}CH_2CH_2NH(C=O)OR^{12}$, $CH_2NR^{10}(C=O)R^{12}$, $CH_2NR^{10}CH_2(C=O)R^{11}$, $CH_2NR^{10}CH_2(C=O)OR^{12}$, $CH_2NR^{10}CH_2(C=O)NHR^{12}$, $CH_2NR^{10}CH_2(C=O)NHR^{11}$, $CH_2NR^{10}CH_2(C=O)NHR^{11}$, $CH_2NR^{10}CH_2(C=O)NR^6R^7$, $CH_2NR^{10}CH_2R^{11}$, $CH_2NR^{10}R^{11}$, $CH_2NR^{10}R^{12}$, $CH=NOR^{12}$, $CH_2OCH_2(C=O)NHCH_2R^{11}$, $CH_2OCH_2(C=O)R^{11}$, $CH_2OCH_2(C=O)NHR^{12}$, $CH_2OCH_2(C=O)NR^{10}R^{12}$, $CH_2OR^{11}$, $CH_2O(C_{2-7}$ alkynyl), $CH_2OR^{12}$, $CH_2O$ $(C=O)NHR^{12}$, $(C=O)NR^{10}R^{11}$, $(C=O)NR^{10}CH_2R^{11}$, $(C=O)R^{11}$, $(C=O)NR^{10}CH_2CH_2R^{11}$, $(C=O)NR^{10}R^{12}$, $(C=O)NH(C_{1-6}$ alkenyl), $CH(NH_2)(C=O)NH_2$, $CH(NH(C=O)CH_3)((C=O)NH_2$, $CH(NH(C=O)OCH_3)((C=O)NH_2)$, $CH_2NH(C=O)OCH_3$, $CH_2NH(C=O)SO_2CH_3$, $CH_2NH(C=O)R^{10}$, $CH_2NH(C=O)R^{12}$, $CH_2(C=O)NR^{10}R^{12}$, $CH_2(C=O)N(R^{10})(C_{2-6}$ alkynyl), $C_{1-6}$ alkyl$(C=O)NR^{10}R^{11}$, $CHR^{11}(C=O)NR^{10}R^{12}$, $(C=O)NR^{10}R^{12}$, $CHR^{11}(C=O)OR^{12}$, $CH_2SO_2R^{12}$, $CH_2SO_2-(C_{1-6}$ alkyl)-$(C=O)NR^{10}R^{12}$, $CH_2SO_2R^{11}$, $NHSO_2NR^{10}R^{12}$, $SO_2R^{12}$ or $R^{11}$, wherein said alkyl groups are optionally substituted with one to four substituents independently selected from the group consisting of halo, hydroxyl, cyano, $NR^6R^7$, $CH_2OR^{12}$, $OP=O(CH_3)_2$, $P=O(CH_3)(OCH_3)$ and $R^{11}$, and said alkenyl group is optionally substituted with one to three halo;
$R^5$ is aryl or heteroaryl, wherein said aryl and heteroaryl groups are optionally substituted on either the carbon or the heteroatom with one to three substituents independently selected from the group consisting of halo, hydroxyl, cyano, $R^{12}$, $OR^{12}$, $R^{11}$, $NH_2$, $(C_{1-6}$ alkyl)$R^{11}$, $(C=O)R^{11}$, $CH_2NH$ $(C=O)R^{12}$, $CH_2O(C=O)R^{12}$, $SO_mR^8$, $CH_2$(trimethylsilyl), trimethylsilylethoxy and $NH(C=O)OR^{12}$;
$R^6$ is hydrogen or $C_{1-6}$ alkyl, wherein said alkyl group is optionally substituted with $SO_m$, —$NR^8R^9$, hydroxyl or —$OR^8$;
$R^7$ is hydrogen or $C_{1-6}$ alkyl, wherein said alkyl group is optionally substituted with $SO_m$, —$NR^8R^9$ or —$OR^8$;
or $R^6$ and $R^7$ can be taken together with the nitrogen atom to which they are attached to form a 4 to 8 membered heterocyclic or heteroaryl ring (wherein the heterocyclic or heteroaryl ring may further incorporate another heteroatom selected from the group consisting of O, $SO_m$ and $NR^8$), wherein said heterocyclic or heteroaryl ring is optionally substituted on either the carbon or heteroatom with one to three substituents independently selected from the group consisting of $C_{1-6}$ alkyl, —$C(O)C_{1-6}$ alkyl, hydroxyl and halo;
$R^8$ is hydrogen or $C_{1-6}$ alkyl;
$R^9$ is hydrogen or $C_{1-6}$ alkyl;
$R^{10}$ is hydrogen, carbobenzoxy, $SO_mR^8$, $C_{1-6}$ alkyl, $(C_{1-6}$ alkyl)OH or (C=O)H;
$R^{11}$ is hydrogen, $C_{3-6}$ cycloalkyl (which is optionally substituted with one to three substituents independently selected from the group consisting of fluoro, hydroxyl and $(C_{1-6}$ alkyl) $OR^{12}$), heterocyclyl (which is optionally substituted on either the carbon or heteroatom with one to three substituents independently selected from the group consisting of halo, oxo, $C_{1-6}$ alkyl, $OR^{12}$, $(C_{1-6}$ alkyl)OH, $C(O)R^8$, $C(O)OR^8$, (C=O) $NH_2$, $P=O(OCH_2CH_3)_2$, $NR^6R^7$, $C_{1-6}$ haloalkyl and $SO_mR^8$), heteroaryl (which is optionally substituted on either the carbon or heteroatom with one to three substituents independently selected from the group consisting of $C_{3-6}$ cycloalkyl, $(C=O)N(R^{12})_2$, $(C=O)R^{12}$, $(C=O)OR^{12}$, $CH_2$ $(C=O)OR^{12}$, $(C=O)N(R^{12})_2$, $CH_2(C=O)N(R^{12})_2$, $CH_2N$ $(R^{12})_2$, $R^{12}$, $Si(CH_3)_3$, oxo, $SO_mR^8$ and $(C_{1-6}$ alkyl)$OR^{12}$) or aryl (which is optionally substituted with one to three substituents independently selected from the group consisting of halo and $SO_mR^8$);
$R^{12}$ is hydrogen or $C_{1-6}$ alkyl, wherein said alkyl group is optionally substituted with one to four substituents independently selected from the group consisting of halo, hydroxyl, cyano, $SO_mR^8$, $P=O(CH_3)_2$, $NR^8R^9$ and $OR^8$;
m is an integer from zero to two;
or a pharmaceutically acceptable salt or stereoisomer thereof.

In an embodiment of the invention, $R^1$ is hydrogen or $C_{1-3}$ alkyl. In a class of the invention, $R^1$ is hydrogen.

In an embodiment of the invention, $R^2$ is hydrogen or $C_{1-3}$ alkyl. In a class of the invention, $R^2$ is hydrogen.

In an embodiment of the invention, $R^3$ is $SO_m(C_{1-3}$ alkyl).

In an embodiment of the invention, $R^4$ is $C_{1-6}$ alkyl, $CH_2OR^{12}$, $CH_2O(C=O)NHR^{12}$ or $CH_2SO_2R^{12}$, wherein said alkyl group is optionally substituted with one to four substituents independently selected from the group consisting of hydroxyl and $R^{11}$; and $R^{12}$ is $C_{1-6}$ alkyl, wherein said alkyl group is optionally substituted with one to two hydroxyl. In a class of the invention, $R^4$ is $CH_2OR^{12}$, and $R^{12}$ is $C_{1-6}$ alkyl, wherein said alkyl group is optionally substituted with hydroxyl.

In an embodiment of the invention, $R^5$ is aryl, wherein said aryl group is substituted with one to three substituents independently selected from the group consisting of halo, $R^{12}$, $R^{11}$ and $SO_mR^8$. In a class of the invention, $R^5$ is aryl, wherein said aryl group is substituted with one to three substituents independently selected from the group consisting of halo and $R^{12}$. In a class of the invention, $R^5$ is phenyl, wherein said phenyl group is substituted with one to three substituents independently selected from the group consisting of halo and $R^{12}$, and $R^{12}$ is hydrogen or $C_{1-6}$ alkyl, wherein said alkyl group is optionally substituted with one to two hydroxyl.

In an embodiment of the invention, $R^{11}$ is heterocyclyl (which is optionally substituted on either the carbon or heteroatom with one to three substituents independently selected from the group consisting of oxo and $OR^{12}$). In a class of the invention, $R^{11}$ is heterocyclyl (which is optionally substituted with one to two oxo or $OR^{12}$), and $R^{12}$ is hydrogen.

Reference to the preferred embodiments set forth above is meant to include all combinations of particular and preferred groups unless stated otherwise.

Specific embodiments of the present invention include, but are not limited to:

5-(2,4-Difluorophenyl)-2-{[6-(hydroxymethyl)pyridin-2-yl]amino}thiophene-3-carboxamide;
5-(2-Fluorophenyl)-2-{[6-(1-hydroxy-1-methylethyl)pyridin-2-yl]amino}thiophene-3-carboxamide;
5-(2-Fluorophenyl)-2-{[6-(1-hydroxyethyl)pyridin-2-yl]amino}thiophene-3-carboxamide;
2-{[5-(1-Hydroxy-1-methylethyl)pyridin-2-yl]amino}-5-phenylthiophene-3-carboxamide;
5-phenyl-2-(pyridin-2-ylamino)thiophene-3-carboxamide;
2-[(6-methylpyridin-2-yl)amino]-5-phenylthiophene-3-carboxamide;
2-[(4-methylpyridin-2-yl)amino]-5-phenylthiophene-3-carboxamide;
2-[(5-methylpyridin-2-yl)amino]-5-phenylthiophene-3-carboxamide;
2-[(3-methylpyridin-2-yl)amino]-5-phenylthiophene-3-carboxamide;
2-[(5-fluoropyridin-2-yl)amino]-5-phenylthiophene-3-carboxamide;
2-[(3-fluoropyridin-2-yl)amino]-5-phenylthiophene-3-carboxamide;
2-[(4-fluoropyridin-2-yl)amino]-5-phenylthiophene-3-carboxamide;
2-[(4-cyanopyridin-2-yl)amino]-5-phenylthiophene-3-carboxamide;
2-[(3-cyanopyridin-2-yl)amino]-5-phenylthiophene-3-carboxamide;
2-[(5-cyanopyridin-2-yl)amino]-5-phenylthiophene-3-carboxamide;
5-phenyl-2-{[5-(trifluoromethyl)pyridin-2-yl]amino}thiophene-3-carboxamide;
5-phenyl-2-{[4-(trifluoromethyl)pyridin-2-yl]amino}thiophene-3-carboxamide;
2-[(5-chloropyridin-2-yl)amino]-5-phenylthiophene-3-carboxamide;
2-{[6-(hydroxymethyl)pyridin-2-yl]amino}-5-phenylthiophene-3-carboxamide;
5-phenyl-2-{[3-(trifluoromethyl)pyridin-2-yl]amino}thiophene-3-carboxamide;
5-phenyl-2-{[6-(trifluoromethyl)pyridin-2-yl]amino}thiophene-3-carboxamide;
2-{[5-(methylsulfonyl)pyridin-2-yl]amino}-5-phenylthiophene-3-carboxamide;
5-(2,5-dichlorophenyl)-2-{[6-(1-hydroxy-1-methylethyl)pyridin-2-yl]amino}thiophene-3-carboxamide;
5-[4-(1-cyano-1-methylethyl)phenyl]-2-[(2-methylpyrimidin-4-yl)amino]thiophene-3-carboxamide;
5-[2,6-difluoro-4-(1-hydroxy-1-methylethyl)phenyl]-2-[(6-methoxypyridin-2-yl)amino]thiophene-3-carboxamide;
5-[2,6-difluoro-4-(1-hydroxy-1-methylethyl)phenyl]-2-(pyridin-2-ylamino)thiophene-3-carboxamide;
5-[2,6-difluoro-4-(1-hydroxy-1-methylethyl)phenyl]-2-[(6-fluoropyridin-2-yl)amino]thiophene-3-carboxamide;
5-[2,6-difluoro-4-(1-hydroxy-1-methylethyl)phenyl]-2-[(4-fluoropyridin-2-yl)amino]thiophene-3-carboxamide;
2-[(6-cyanopyridin-2-yl)amino]-5-[2,6-difluoro-4-(1-hydroxy-1-methylethyl)phenyl]thiophene-3-carboxamide;
5-[2-fluoro-4-(1-hydroxy-1-methylethyl)phenyl]-2-[(5-fluoropyridin-2-yl)amino]thiophene-3-carboxamide;
2-[(5-cyanopyridin-2-yl)amino]-5-[2-fluoro-4-(1-hydroxy-1-methylethyl)phenyl]thiophene-3-carboxamide;
methyl 5-({3-(aminocarbonyl)-5-[2-fluoro-4-(1-hydroxy-1-methylethyl)phenyl]-2-thienyl}amino)pyrazine-2-carboxylate;
5-[2,6-Difluoro-4-(1-hydroxy-1-methylethyl)phenyl]-2-{[5-(methylsulfonyl)pyridin-2-yl]amino}thiophene-3-carboxamide;
5-[2-Fluoro-4-(1-hydroxy-1-methylethyl)phenyl]-2-{[5-(methylsulfonyl)pyridin-2-yl]amino}thiophene-3-carboxamide;
5-[2,6-Difluoro-4-(1-hydroxy-1-methylethyl)phenyl]-2-[(6-methylpyridin-2-yl)amino]thiophene-3-carboxamide;
5-[2,6-Difluoro-4-(1-hydroxy-1-methylethyl)phenyl]-2-[(2-methylpyrimidin-4-yl)amino]thiophene-3-carboxamide;
5-[2-Fluoro-4-(1-hydroxy-1-methylethyl)phenyl]-2-[(2-methylpyrimidin-4-yl)amino]thiophene-3-carboxamide;
5-[2,6-Difluoro-4-(1-hydroxy-1-methylethyl)phenyl]-2-[(6-phenylpyridin-2-yl)amino]thiophene-3-carboxamide;
methyl6-({3-(aminocarbonyl)-5-[2-fluoro-4-(1-hydroxy-1-methylethyl)phenyl]-2-thienyl}amino)pyridine-2-carboxylate;
6-({3-(aminocarbonyl)-5-[2-fluoro-4-(1-hydroxy-1-methylethyl)phenyl]-2-thienyl}amino)pyridine-2-carboxylic acid;
5-[2-fluoro-4-(1-hydroxy-1-methylethyl)phenyl]-2-{[5-(1-hydroxy-1-methylethyl)pyridin-2-yl]amino}thiophene-3-carboxamide;
5-[2,6-difluoro-4-(1-hydroxy-1-methylethyl)phenyl]-2-{[5-(1-hydroxy-1-methylethyl)pyridin-2-yl]amino}thiophene-3-carboxamide;
5-[2-fluoro-4-(1-hydroxy-1-methylethyl)phenyl]-2-{[6-(hydroxymethyl)pyridin-2-yl]amino}thiophene-3-carboxamide;
5-(4-(1-hydroxy-1-methylethyl)phenyl)-2-(3-pyridinylamino)-3-thiophenecarboxamide;
5-(2-Fluorophenyl)-2-{[6-(morpholin-4-ylmethyl)pyridin-2-yl]amino}thiophene-3-carboxamide;
5-[2,6-Difluoro-4-(1-hydroxy-1-methylethyl)phenyl]-2-[(6-{[(2-hydroxy-1,2-dimethylpropyl)amino]methyl}pyridin-2-yl)amino]thiophene-3-carboxamide;

5-[2,6-Difluoro-4-(1-hydroxy-1-methylethyl)phenyl]2-[(6-{[(3S)-3-methylmorpholin-4-yl]methyl}pyridin-2-yl)amino]thiophene-3-carboxamide;

2-({6-[(dimethylamino)methyl]pyridin-2-yl}amino)-5-(2-fluorophenyl)thiophene-3-carboxamide;

5-(2,5-dichlorophenyl)-2-({6-[(dimethylamino)methyl]pyridin-2-yl}amino)thiophene-3-carboxamide;

5-(2,5-dichlorophenyl)-2-{[6-(pyrrolidin-1-ylmethyl)pyridin-2-yl]amino}thiophene-3-carboxamide;

5-(2,5-dichlorophenyl)-2-{[6-(piperidin-1-ylmethyl)pyridin-2-yl]amino}thiophene-3-carboxamide;

2-{[6-(azetidin-1-ylmethyl)pyridin-2-yl]amino}-5-(2,5-dichlorophenyl)thiophene-3-carboxamide;

2-{[6-(pyrrolidin-1-ylmethyl)pyridin-2-yl]amino}-5-(2,4,6-trifluorophenyl)thiophene-3-carboxamide;

2-{[6-(morpholin-4-ylmethyl)pyridin-2-yl]amino}-5-(2,4,6-trifluorophenyl)thiophene-3-carboxamide;

5-[4-(1-hydroxy-1-methylethyl)phenyl]-2-{[6-(morpholin-4-ylmethyl)pyridin-2-yl]amino}thiophene-3-carboxamide;

5-[4-(1-hydroxy-1-methylethyl)phenyl]-2-{[6-(pyrrolidin-1-ylmethyl)pyridin-2-yl]amino}thiophene-3-carboxamide;

2-({6-[(4-acetylpiperazin-1-yl)methyl]pyridin-2-yl}amino)-5-[4-(1-hydroxy-1-methylethyl)phenyl]thiophene-3-carboxamide;

methyl 4-{[6-({3-(aminocarbonyl)-5-[4-(1-hydroxy-1-methylethyl)phenyl]-2-thienyl}amino)pyridin-2-yl]methyl}piperazine-1-carboxylate;

5-[4-(1-hydroxy-1-methylethyl)phenyl]-2-[(6-{[4-(methylsulfonyl)piperazin-1-yl]methyl}pyridin-2-yl)amino]thiophene-3-carboxamide;

2-({6-[(1,1-dioxidothiomorpholin-4-yl)methyl]pyridin-2-yl}amino)-5-[4-(1-hydroxy-1-methylethyl)phenyl]thiophene-3-carboxamide;

5-[4-(1,1-dioxidothiomorpholin-4-yl)phenyl]-2-{[6-(morpholine-4-ylmethyl)pyridine-2-yl]amino}thiophene-3-carboxamide;

2-{[6-(morpholin-4-ylmethyl)pyridin-2-yl]amino}-5-(4-pyridin-4-ylphenyl)thiophene-3-carboxamide;

2-{[6-(morpholin-4-ylmethyl)pyridin-2-yl]amino}-5-[4-(1H-pyrazol-1-yl)phenyl]thiophene-3-carboxamide;

5-(4-tert-butylphenyl)-2-{[6-(morpholin-4-ylmethyl)pyridin-2-yl]amino}thiophene-3-carboxamide;

5-[4-(1-cyano-1-methylethyl)phenyl]-2-{[6-(morpholin-4-ylmethyl)pyridin-2-yl]amino}thiophene-3-carboxamide;

2-{[6-(morpholin-4-ylmethyl)pyridin-2-yl]amino}-5-(1H-1,2,4-triazol-3-yl)thiophene-3-carboxamide;

5-[4-(2-methyl-1,3-thiazol-4-yl)phenyl]-2-{[6-(morpholin-4-ylmethyl)pyridin-2-yl]amino}thiophene-3-carboxamide;

methyl[4-(4-(aminocarbonyl)-5-{[6-(morpholin-4-ylmethyl)pyridin-2-yl]amino}-2-thienyl)phenyl]carbamate;

5-(4-cyanophenyl)-2-{[6-(morpholin-4-ylmethyl)pyridin-2-yl]amino}thiophene-3-carboxamide;

2-{[6-(morpholin-4-ylmethyl)pyridin-2-yl]amino}-5-[4-(1H-1,2,3-triazol-4-yl)phenyl]thiophene-3-carboxamide;

2-{[6-(morpholin-4-ylmethyl)pyridin-2-yl]amino}-5-[4-(1H-1,2,4-triazol-3-yl)phenyl]thiophene-3-carboxamide;

5-[6-(1-hydroxy-1-methylethyl)pyridin-3-yl]-2-{[6-(morpholin-4-ylmethyl)pyridin-2-yl]amino}thiophene-3-carboxamide;

5-[2,6-difluoro-4-(1-hydroxy-1-methylethyl)phenyl]-2-({6-[(3,3-difluoropiperidin-1-yl)methyl]pyridin-2-yl}amino)thiophene-3-carboxamide;

5-[2,6-difluoro-4-(1-hydroxy-1-methylethyl)phenyl]-2-[(6-{[(3R)-3-methylmorpholin-4-yl]methyl}pyridin-2-yl)amino]thiophene-3-carboxamide;

5-(2,6-difluoro-4-morpholin-4-ylphenyl)-2-{[6-(morpholin-4-ylmethyl)pyridin-2-yl]amino}thiophene-3-carboxamide;

5-(4-cyclopropylphenyl)-2-{[6-(morpholin-4-ylmethyl)pyridin-2-yl]amino}thiophene-3-carboxamide;

5-(4-Fluorophenyl)-2-({6-[(4-hydroxypiperidin-1-yl)methyl]pyridin-2-yl}amino)thiophene-3-carboxamide;

5-[2-fluoro-4-(1-hydroxy-1-methylethyl)phenyl]-2-({6-[(4-methyl-3-oxopiperazin-1-yl)methyl]pyridin-2-yl}amino)thiophene-3-carboxamide;

5-[2,6-difluoro-4-(1-hydroxy-1-methylethyl)phenyl]-2-({6-[(4-methyl-3-oxopiperazin-1-yl)methyl]pyridin-2-yl}amino)thiophene-3-carboxamide;

2-({6-[(1,1-dioxidothiomorpholin-4-yl)methyl]pyridin-2-yl}amino)-5-[2-fluoro-4-(1-hydroxy-1-methylethyl)phenyl]thiophene-3-carboxamide;

5-[2,6-difluoro-4-(1-hydroxy-1-methylethyl)phenyl]-2-({6-[(1,1-dioxidothiomorpholin-4-yl)methyl]pyridin-2-yl}amino)thiophene-3-carboxamide;

5-(4-fluorophenyl)-2-({6-[(3-hydroxypyrrolidin-1-yl)methyl]pyridin-2-yl}amino)thiophene-3-carboxamide;

5-(4-fluorophenyl)-2-({6-[(3-hydroxyazetidin-1-yl)methyl]pyridin-2-yl}amino)thiophene-3-carboxamide;

5-(4-fluorophenyl)-2-{[6-(pyrrolidin-1-ylmethyl)pyridin-2-yl]amino}thiophene-3-carboxamide;

5-(4-chlorophenyl)-2-{[6-(morpholin-4-ylmethyl)pyridin-2-yl]amino}thiophene-3-carboxamide;

5-(4-chlorophenyl)-2-{[6-(pyrrolidin-1-ylmethyl)pyridin-2-yl]amino}thiophene-3-carboxamide;

2-{[6-({[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide;

5-[2-fluoro-4-(1-hydroxy-1-methylethyl)phenyl]-2-[(6-{[(2-morpholin-4-yl-2-oxoethyl)amino]methyl}pyridin-2-yl)amino]thiophene-3-carboxamide;

ethyl N-{[6-({3-(aminocarbonyl)-5-[2,6-difluoro-4-(1-hydroxy-1-methylethyl)phenyl]-2-thienyl}amino)pyridin-2-yl]methyl}glycinate;

5-[2-fluoro-4-(1-hydroxy-1-methylethyl)phenyl]-2-{[6-({[(5-methyl-1,3,4-oxadiazol-2-yl)methyl]amino}methyl)pyridin-2-yl]amino}thiophene-3-carboxamide;

5-[2-fluoro-4-(1-hydroxy-1-methylethyl)phenyl]-2-{[6-({[(1-methyl-1H-pyrazol-4-yl)methyl]amino}methyl)pyridin-2-yl]amino}thiophene-3-carboxamide;

5-[2-fluoro-4-(1-hydroxy-1-methylethyl)phenyl]-2-{[6-({[(1-methyl-1H-pyrazol-5-yl)methyl]amino}methyl)pyridin-2-yl]amino}thiophene-3-carboxamide;

5-[2-fluoro-4-(1-hydroxy-1-methylethyl)phenyl]-2-{[6-({[(1-methyl-1H-pyrazol-3-yl)methyl]amino}methyl)pyridin-2-yl]amino}thiophene-3-carboxamide;

5-[2,6-difluoro-4-(1-hydroxy-1-methylethyl)phenyl]-2-{[6-({[2-(dimethylamino)-2-oxoethyl]amino}methyl)pyridin-2-yl]amino}thiophene-3-carboxamide;

5-[2,6-difluoro-4-(1-hydroxy-1-methylethyl)phenyl]-2-({6-[({3-(methoxymethyl)-1,2,4-oxadiazol-5-yl]methyl}amino)methyl]pyridin-2-yl}amino)thiophene-3-carboxamide;

5-[2,6-difluoro-4-(1-hydroxy-1-methylethyl)phenyl]-2-[(6-{[(1-methyl-1H-pyrazol-3-yl)amino]methyl}pyridin-2-yl)amino]thiophene-3-carboxamide;

5-[2,6-difluoro-4-(1-hydroxy-1-methylethyl)phenyl]-2-[(6-{[(3,5-dimethylisoxazol-4-yl)amino]methyl}pyridin-2-yl)amino]thiophene-3-carboxamide;

5-[2-fluoro-4-(1-hydroxy-1-methylethyl)phenyl]-2-[(6-{[(2-oxopyrrolidin-3-yl)amino]methyl}pyridin-2-yl)amino]thiophene-3-carboxamide;

5-[2-fluoro-4-(1-hydroxy-1-methylethyl)phenyl]-2-[(6-{[(1-methyl-2-oxopyrrolidin-3-yl)amino]methyl}pyridin-2-yl)amino]thiophene-3-carboxamide;

2-[(6-{[[2-(dimethylamino)-2-oxoethyl](methyl)amino]methyl}pyridin-2-yl)amino]-5-[2-fluoro-4-(1-hydroxy-1-methylethyl)phenyl]thiophene-3-carboxamide;

5-[2-fluoro-4-(1-hydroxy-1-methylethyl)phenyl]-2-{[6-(morpholin-4-ylmethyl)pyridin-2-yl]amino}thiophene-3-carboxamide;

5-[2,6-difluoro-4-(1-hydroxy-1-methylethyl)phenyl]-2-{[6-(morpholin-4-ylmethyl)pyridin-2-yl]amino}thiophene-3-carboxamide;

5-[2,6-difluoro-4-(1-hydroxy-1-methylethyl)phenyl]-2-({6-[(1,3-thiazol-2-ylamino)methyl]pyridin-2-yl}amino)thiophene-3-carboxamide;

5-[2-Fluoro-4-(1-hydroxy-1-methylethyl)phenyl]-2-{[6-({[(3-isopropyl-1,2,4-oxadiazol-5-yl)methyl]amino}methyl)pyridin-2-yl]amino}thiophene-3-carboxamide;

5-(4-Fluorophenyl)-2-({6-[(methylamino)methyl]pyridin-2-yl}amino)thiophene-3-carboxamide;

5-(2-Fluoro-4-(1-hydroxy-1-methylethyl)phenyl)-2-((6-((2-hydroxyethyl)amino)methyl)-2-pyridinyl)amino)-3-thiophenecarboxamide;

5-(2-Fluoro-4-(1-hydroxy-1-methylethyl)phenyl)-2-((6-((3-pyrrolidinylamino)methyl)-2-pyridinyl)amino)-3-thiophenecarboxamide;

5-(2-Fluoro-4-(1-hydroxy-1-methylethyl)phenyl)-2-((6-(((4-hydroxy-1,1-dioxidotetrahydro-3-thienyl)amino)methyl)-2-pyridinyl)amino)-3-thiophenecarboxamide;

2-((6-((3-azetidinylamino)-2-pyridinyl)amino)-5-(2-fluoro-4-(1-hydroxy-1-methylethyl)phenyl)-3-thiophenecarboxamide;

5-(2-fluoro-4-(1-hydroxy-1-methylethyl)phenyl)-2-((6-((2-hydroxymethyl)-1-piperidinyl)methyl)-2-pyridinyl)amino)-3-thiophenecarboxamide;

5-[2-fluoro-4-(1-hydroxy-1-methylethyl)phenyl]-2-({6-[(4-methylpiperazin-1-yl)methyl]pyridin-2-yl}amino)thiophene-3-carboxamide;

5-[2-fluoro-4-(1-hydroxy-1-methylethyl)phenyl]-2-[(6-{[(2-hydroxyethyl)(methyl)amino]methyl}pyridin-2-yl)amino]thiophene-3-carboxamide;

5-[2-fluoro-4-(1-hydroxy-1-methylethyl)phenyl]-2-{[6-({[2-(methylsulfonyl)ethyl]amino}methyl)pyridin-2-yl]amino}thiophene-3-carboxamide;

5-[2-fluoro-4-(1-hydroxy-1-methylethyl)phenyl]-2-{[6-({[(2S)-2-hydroxypropyl]amino}methyl)pyridin-2-yl]amino}thiophene-3-carboxamide;

5-[2-fluoro-4-(1-hydroxy-1-methylethyl)phenyl]-2-{[6-({[(1R)-2-hydroxy-1-methylethyl]amino}methyl)pyridin-2-yl]amino}thiophene-3-carboxamide;

5-[2-fluoro-4-(1-hydroxy-1-methylethyl)phenyl]-2-[(6-{[(2-hydroxy-2-methylpropyl)amino]methyl}pyridin-2-yl)amino]thiophene-3-carboxamide;

2-({6-[(2,6-dimethylmorpholin-4-yl)methyl]pyridin-2-yl}amino)-5-[2-fluoro-4-(1-hydroxy-1-methylethyl)phenyl]thiophene-3-carboxamide;

5-[2-fluoro-4-(1-hydroxy-1-methylethyl)phenyl]-2-[(6-{[2-(2-hydroxyethyl)morpholin-4-yl]methyl}pyridin-2-yl)amino]thiophene-3-carboxamide;

1-{[6-({3-(aminocarbonyl)-5-[2-fluoro-4-(1-hydroxy-1-methylethyl)phenyl]-2-thienyl}amino)pyridine-2-yl]methyl}praline;

5-[2-fluoro-4-(1-hydroxy-1-methylethyl)phenyl]-2-[(6-{[(2-hydroxyethyl)amino]methyl}pyridin-2-yl)amino]thiophene-3-carboxamide;

5-[2-fluoro-4-(1-hydroxy-1-methylethyl)phenyl]-2-{[6-({[1-(hydroxymethyl)cyclopropyl]amino}methyl)pyridin-2-yl]amino}thiophene-3-carboxamide;

diethyl(1-{[6-({3-(aminocarbonyl)-5-[2-fluoro-4-(1-hydroxy-1-methylethyl)phenyl]-2-thienyl}amino)pyridin-2-yl]methyl}piperidin-4-yl)phosphonate;

2-[(6-{[3-(dimethylamino)piperidin-1-yl]methyl}pyridin-2-yl)amino]-5-[2-fluoro-4-(1-hydroxy-1-methylethyl)phenyl]thiophene-3-carboxamide;

2-[(6-{[(1,1-dioxidotetrahydro-3-thienyl)amino]methyl}pyridin-2-yl)amino]-5-[2-fluoro-4-(1-hydroxy-1-methylethyl)phenyl]thiophene-3-carboxamide;

5-[2-fluoro-4-(1-hydroxy-1-methylethyl)phenyl]-2-[(6-{[3-(methylsulfonyl)pyrrolidin-1-yl]methyl}pyridin-2-yl)amino]thiophene-3-carboxamide;

5-[2-fluoro-4-(1-hydroxy-1-methylethyl)phenyl]-2-[(6-{[(2,2,2-trifluoroethyl)amino]methyl}pyridin-2-yl)amino]thiophene-3-carboxamide;

5-[2-fluoro-4-(1-hydroxy-1-methylethyl)phenyl]-2-[(6-{[3-(hydroxymethyl)morpholin-4-yl]methyl}pyridin-2-yl)amino]thiophene-3-carboxamide;

5-[2-fluoro-4-(1-hydroxy-1-methylethyl)phenyl]-2-[(6-{[2-(hydroxymethyl)morpholin-4-yl]methyl}pyridin-2-yl)amino]thiophene-3-carboxamide;

5-[2-fluoro-4-(1-hydroxy-1-methylethyl)phenyl]-2-[(6-{[(3,3,3-trifluoro-2-hydroxypropyl)amino]methyl}pyridin-2-yl)amino]thiophene-3-carboxamide;

2-({6-[(3,3-difluoroazetidin-1-yl)methyl]pyridin-2-yl}amino)-5-[2-fluoro-4-(1-hydroxy-1-methylethyl)phenyl]thiophene-3-carboxamide;

5-[2-fluoro-4-(1-hydroxy-1-methylethyl)phenyl]-2-[(6-{[2-(trifluoromethyl)pyrrolidin-1-yl]methyl}pyridin-2-yl)amino]thiophene-3-carboxamide;

5-[2-fluoro-4-(1-hydroxy-1-methylethyl)phenyl]-2-[(6-{[(3S)-3-fluoropyrrolidin-1-yl]methyl}pyridin-2-yl)amino]thiophene-3-carboxamide;

Tert-butyl[2-({[6-({3-(aminocarbonyl)-5-[2-fluoro-4-(1-hydroxy-1-methylethyl)phenyl]-2-thienyl}amino)pyridin-2-yl]methyl}amino)ethyl]carbamate;

5-[2-Fluoro-4-(1-hydroxy-1-methylethyl)phenyl]-2-({6-[(2-oxo-3-oxa-1,8-diazaspiro[4.5]dec-8-yl)methyl]pyridin-2-yl}amino)thiophene-3-carboxamide;

5-[2-Fluoro-4-(1-hydroxy-1-methylethyl)phenyl]-2-({6-[(2-oxo-1-oxa-3,8-diazaspiro[4.5]dec-8-yl)methyl]pyridin-2-yl}amino)thiophene-3-carboxamide;

5-[2-Fluoro-4-(1-hydroxy-1-methylethyl)phenyl]-2-{[6-({[(1-methyl-5-oxopyrrolidin-2-yl)methyl]amino}methyl)pyridin-2-yl]amino}thiophene-3-carboxamide;

5-[2,6-Difluoro-4-(1-hydroxy-1-methylethyl)phenyl]-2-[(6-{[(3-oxocyclopent-1-en-1-yl)amino]methyl}yridine-2-yl)amino]thiophene-3-carboxamide;

5-[2,6-difluoro-4-(1-hydroxy-1-methylethyl)phenyl]-2-[(6-{[(3-oxocyclohex-1-en-1-yl)amino]methyl}pyridin-2-yl)amino]thiophene-3-carboxamide;

5-(4-Fluorophenyl)-2-{[6-(1-pyrrolidin-1-ylethyl)pyridin-2-yl]amino}thiophene-3-carboxamide;

5-(4-Fluorophenyl)-2-{[6-(1-pyrrolidin-1-ylethyl)pyridin-2-yl]amino}thiophene-3-carboxamide;

5-[4-(1-Hydroxy-1-methylethyl)phenyl]-2-{[6-(2-hydroxy-1-morpholin-4-ylethyl)pyridin-2-yl]amino}thiophene-3-carboxamide;

2-({6-[1-(1,1-dioxidothiomorpholin-4-yl)-2-hydroxyethyl]pyridine-2-yl}amino)-5-[4-(1-hydroxy-1-methylethyl)phenyl]thiophene-3-carboxamide;

2-({6-[1-(1,1-dioxidothiomorpholin-4-yl)-2-hydroxyethyl]
pyridin-2-yl}amino)-5-[2-fluoro-4-(1-hydroxy-1-methyl-
ethyl)phenyl]thiophene-3-carboxamide;
5-[2,6-difluoro-4-(1-hydroxy-1-methylethyl)phenyl]-2-({6-
[1-(1,1-dioxidothiomorpholin-4-yl)-2-hydroxyethyl]pyri-
din-2-yl}amino)thiophene-3-carboxamide;
Methyl-4-{1-[6-({3-aminocarbonyl)-5-[2-fluoro-4-(1-hy-
droxy-1-methylethyl)phenyl]-2-thienyl}amino)pyridine-
2-yl]-2-hydroxyethyl}piperazine-1-carboxylate;
Methyl-4-{1-[6-({3-aminocarbonyl)-5-[2,6-difluoro-4-(1-
hydroxy-1-methylethyl)phenyl]-2-thienyl}amino)pyri-
dine-2-yl]-2-hydroxyethyl}piperazine-1-carboxylate;
5-[2-fluoro-4-(1-hydroxy-1-methylethyl)phenyl]-2-({6-[2-
hydroxy-1-(2-oxo-1,3-oxazolidin-3-yl)ethyl]pyridin-2-
yl}amino)thiophene-3-carboxamide;
5-[2,6-difluoro-4-(1-hydroxy-1-methylethyl)phenyl]-2-({6-
[1-(3,3-difluoropiperidin-1-yl)-2-hydroxyethyl]pyridin-
2-yl}amino)thiophene-3-carboxamide;
5-[2-fluoro-4-(1-hydroxy-1-methylethyl)phenyl]-2-{[6-(2-
hydroxy-1-morpholin-4-ylethyl)pyridin-2-yl]
amino}thiophene-3-carboxamide;
5-[2-fluoro-4-(1-hydroxy-1-methylethyl)phenyl]-2-({6-
[(1S)-2-hydroxy-1-morpholin-4-ylethyl]pyridin-2-
yl}amino)thiophene-3-carboxamide;
5-[2-fluoro-4-(1-hydroxy-1-methylethyl)phenyl]-2-({6-
[(1R)-2-hydroxy-1-morpholin-4-ylethyl]pyridin-2-
yl}amino)thiophene-3-carboxamide;
5-[2,6-difluoro-4-(1-hydroxy-1-methylethyl)phenyl]-2-{[6-
(2-hydroxy-1-morpholin-4-ylethyl)pyridin-2-yl]
amino}thiophene-3-carboxamide;
5-[2,6-difluoro-4-(1-hydroxy-1-methylethyl)phenyl]-2-({6-
[(1S)-2-hydroxy-1-morpholin-4-ylethyl]pyridin-2-
yl}amino)thiophene-3-carboxamide;
5-[2,6-difluoro-4-(1-hydroxy-1-methylethyl)phenyl]-2-({6-
[(1R)-2-hydroxy-1-morpholin-4-ylethyl]pyridin-2-
yl}amino)thiophene-3-carboxamide;
5-[2-Fluoro-4-(1-hydroxy-1-methylethyl)phenyl]-2-{[6-(2-
hydroxy-1-morpholin-4-ylpropyl)pyridin-2-yl]
amino}thiophene-3-carboxamide;
5-[2-Fluoro-4-(1-hydroxy-1-methylethyl)phenyl]-2-{[6-(2-
hydroxy-3-methyl-1-morpholin-4-ylbutyl)pyridin-2-yl]
amino}thiophene-3-carboxamide
5-(2-Fluorophenyl)-2-{[6-(1-hydroxy-2-morpholin-4-yl-
ethyl)pyridin-2-yl]amino}thiophene-3-carboxamide;
5-[2,6-Difluoro-4-(1-hydroxy-1-methylethyl)phenyl]-2-({6-
[2-hydroxy-2-(1-methyl-1H-pyrazol-4-yl)ethyl]pyridin-
2-yl}amino)thiophene-3-carboxamide;
5-[2,6-difluoro-4-(1-hydroxy-1-methylethyl)phenyl]-2-{[6-
(2-hydroxypropyl)pyridin-2-yl]amino}thiophene-3-car-
boxamide;
5-[2,6-difluoro-4-(1-hydroxy-1-methylethyl)phenyl]-2-{[6-
(2-hydroxy-2-methylpropyl)pyridin-2-yl]
amino}thiophene-3-carboxamide;
5-[2,6-Difluoro-4-(1-hydroxy-1-methylethyl)phenyl]-2-({6-
[2-(1,1-dioxidotetrahydro-2H-thiopyran-4-yl)-2-hy-
droxyethyl]pyridin-2-yl}amino)thiophene-3-carboxam-
ide;
tert-Butyl 4-[[6-({3-(aminocarbonyl)-5-[2,6-difluoro-4-(1-
hydroxy-1-methylethyl)phenyl]-2-thienyl}amino)pyri-
din-2-yl](hydroxy)methyl]piperazine-1-carboxylate;
2-({6-[(1,1-Dioxidotetrahydro-2H-thiopyran-4-yl)(hy-
droxy)methyl]pyridin-2-yl}amino)-5-[2-fluoro-4-(1-hy-
droxy-1-methylethyl)phenyl]thiophene-3-carboxamide;
2-({6-[(1,1-dioxidotetrahydro-2H-thiopyran-4-yl)(hydroxy)
methyl]pyridin-2-yl}amino)-5-[2,6-difluoro-4-(1-hy-
droxy-1-methylethyl)phenyl]thiophene-3-carboxamide;
5-[2-fluoro-4-(1-hydroxy-1-methylethyl)phenyl]-2-({6-[hy-
droxy(tetrahydro-2H-pyran-4-yl)methyl]pyridin-2-
yl}amino)thiophene-3-carboxamide;
5-[2,6-difluoro-4-(1-hydroxy-1-methylethyl)phenyl]-2-({6-
[hydroxy(tetrahydro-2H-pyran-4-yl)methyl]pyridin-2-
yl}amino)thiophene-3-carboxamide;
5-[2,6-difluoro-4-(1-hydroxy-1-methylethyl)phenyl]-2-{[6-
(4-hydroxytetrahydro-2H-pyran-4-yl)pyridin-2-yl]
amino}thiophene-3-carboxamide;
tert-butyl 4-[[6-({3-(aminocarbonyl)-5-[4-(1-hydroxy-1-
methylethyl)phenyl]-2-thienyl}amino)pyridin-2-yl](hy-
droxy)methyl]piperidine-1-carboxylate;
2-{[6-(1,2-Dihydroxyethyl)pyridin-2-yl]amino}-5-(2-fluo-
rophenyl)thiophene-3-carboxamide;
5-(4-Chlorophenyl)-2-{[6-(1,2-dihydroxy-1-methylethyl)
pyridin-2-yl]amino}thiophene-3-carboxamide;
5-(4-Chlorophenyl)-2-({6-[(cis)-1,2-dihydroxy-1-methyl-
propyl]pyridin-2-yl}amino)thiophene-3-carboxamide;
5-(2,5-dichlorophenyl)-2-{[6-(1,2-dihydroxyethyl)pyridin-
2-yl]amino}thiophene-3-carboxamide;
2-{[6-(1,2-dihydroxyethyl)pyridin-2-yl]amino}-5-(4-fluo-
rophenyl)thiophene-3-carboxamide;
2-({6-[(1S)-1,2-dihydroxy-1-methylethyl]pyridin-2-
yl}amino)-5-[4-(1-hydroxy-1-methylethyl)phenyl]
thiophene-3-carboxamide;
2-({6-[(1R)-1,2-dihydroxy-1-methylethyl]pyridin-2-
yl}amino)-5-[4-(1-hydroxy-1-methylethyl)phenyl]
thiophene-3-carboxamide;
5-(4-chlorophenyl)-2-({6-[(trans)-1,2-dihydroxy-1-methyl-
propyl]pyridin-2-yl}amino)thiophene-3-carboxamide;
3-C-[6-({3-(Aminocarbonyl)-5-[2,6-difluoro-4-(1-hydroxy-
1-methylethyl)phenyl]-2-thienyl}amino)pyridin-2-yl]-1,
5-anhydro-2-deoxypentitol;
5-[2,6-Difluoro-4-(1-hydroxy-1-methylethyl)phenyl]-2-({6-
[(3S,4S)-3,4-dihydroxypiperidin-4-yl]pyridin-2-
yl}amino)thiophene-3-carboxamide;
5-[2,6-Difluoro-4-(1-hydroxy-1-methylethyl)phenyl]-2-{[6-
({[2-(isopropylamino)-2-oxoethyl]amino}methyl)pyri-
din-2-yl]amino}thiophene-3-carboxamide;
5-[2-Fluoro-4-(1-hydroxy-1-methylethyl)phenyl]-2-({6-
[({2-[(2-hydroxyethyl)amino]-2-oxoethyl}amino)me-
thyl]pyridin-2-yl}amino)thiophene-3-carboxamide;
Benzyl{[6-({3-(aminocarbonyl)-5-[2-fluoro-4-(1-hydroxy-
1-methylethyl)phenyl]-2-thienyl}amino)pyridin-2-yl]me-
thyl}{2-[(2-hydroxyethyl)(methyl)amino]-2-
oxoethyl}carbamate;
benzyl{[6-({3-(aminocarbonyl)-5-[2-fluoro-4-(1-hydroxy-
1-methylethyl)phenyl]-2-thienyl}amino)pyridin-2-yl]me-
thyl}(2-{[2-(methylsulfonyl)ethyl]amino}-2-oxoethyl)
carbamate;
benzyl{[6-({3-(aminocarbonyl)-5-[2-fluoro-4-(1-hydroxy-
1-methylethyl)phenyl]-2-thienyl}amino)pyridin-2-yl]me-
thyl}{2-[(2-hydroxy-2-methylpropyl)amino]-2-
oxoethyl}carbamate;
benzyl{[6-({3-(aminocarbonyl)-5-[2-fluoro-4-(1-hydroxy-
1-methylethyl)phenyl]-2-thienyl}amino)pyridin-2-yl]me-
thyl}{2-[(1,1-dioxidotetrahydro-3-thienyl)amino]-2-
oxoethyl}carbamate;
2-({6-[({2-[(1,1-dioxidotetrahydro-3-thienyl)amino]-2-
oxoethyl}amino)methyl]pyridin-2-yl}amino)-5-[2-
fluoro-4-(1-hydroxy-1-methylethyl)phenyl]thiophene-3-
carboxamide;
2-[(6-{[(2-{[2-(dimethylphosphoryl)ethyl]amino}-2-oxoet-
hyl)amino]methyl}pyridin-2-yl)amino]-5-[2-fluoro-4-(1-
hydroxy-1-methylethyl)phenyl]thiophene-3-carboxam-
ide;

2-[(6-{[[2-(Cyclopentylamino)-2-oxoethyl](methylsulfonyl)amino]methyl}pyridin-2-yl)amino]-5-[2,6-difluoro-4-(1-hydroxy-1-methylethyl)phenyl]thiophene-3-carboxamide;

2-[(6-{[[2-(Cyclopentylamino)-2-oxoethyl](methyl)amino]methyl}pyridin-2-yl)amino]-5-[2,6-difluoro-4-(1-hydroxy-1-methylethyl)phenyl]thiophene-3-carboxamide;

2-{[6-({Acetyl[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide;

5-[2-Fluoro-4-(1-hydroxy-1-methylethyl)phenyl]-2-({6-[(2-oxopyrrolidin-1-yl)methyl]pyridine-2-yl}amino)thiophene-3-carboxamide;

5-[2-Fluoro-4-(1-hydroxy-1-methylethyl)phenyl]-2-[(6-{[(4R)-4-hydroxy-2-oxopyrrolidin-1-yl]methyl}pyridin-2-yl)amino]thiophene-3-carboxamide;

5-[2,6-Difluoro-4-(1-hydroxy-1-methylethyl)phenyl]-2-({6-[(2-oxopyrrolidin-1-yl)methyl]pyridine-2-yl}amino)thiophene-3-carboxamide;

5-[2,6-difluoro-4-(1-hydroxy-1-methylethyl)phenyl]-2-[(6-{[(4R)-4-hydroxy-2-oxopyrrolidin-1-yl]methyl}pyridin-2-yl)amino]thiophene-3-carboxamide;

5-[2-fluoro-4-(1-hydroxy-1-methylethyl)phenyl]-2-[(6-{[(4S)-4-hydroxy-2-oxopyrrolidin-1-yl]methyl}pyridin-2-yl)amino]thiophene-3-carboxamide;

5-[2,6-difluoro-4-(1-hydroxy-1-methylethyl)phenyl]-2-[(6-{[(4S)-4-hydroxy-2-oxopyrrolidin-1-yl]methyl}pyridin-2-yl)amino]thiophene-3-carboxamide;

5-[2,6-difluoro-4-(1-hydroxy-1-methylethyl)phenyl]-2-[(6-{[(3S)-3-hydroxy-2-oxopyrrolidin-1-yl]methyl}pyridin-2-yl)amino]thiophene-3-carboxamide;

5-[2,6-difluoro-4-(1-hydroxy-1-methylethyl)phenyl]-2-[(6-{[3-(2-hydroxyethyl)-2-oxoimidazolidin-1-yl]methyl}pyridin-2-yl)amino]thiophene-3-carboxamide;

5-[2,6-difluoro-4-(1-hydroxy-1-methylethyl)phenyl]-2-({6-[(3-methyl-2-oxoimidazolidin-1-yl)methyl]pyridin-2-yl}amino)thiophene-3-carboxamide;

5-[2,6-difluoro-4-(1-hydroxy-1-methylethyl)phenyl]-2-({6-[(2-oxo-1,3-oxazolidin-3-yl)methyl]pyridin-2-yl}amino)thiophene-3-carboxamide;

5-[2,6-difluoro-4-(1-hydroxy-1-methylethyl)phenyl]-2-({6-[(2-oxoimidazolidin-1-yl)methyl]pyridin-2-yl}amino)thiophene-3-carboxamide;

5-[2,6-difluoro-4-(1-hydroxy-1-methylethyl)phenyl]-2-({6-[(3-oxomorpholin-4-yl)methyl]pyridin-2-yl}amino)thiophene-3-carboxamide;

5-[2-fluoro-4-(1-hydroxy-1-methylethyl)phenyl]-2-({6-[(3-oxomorpholin-4-yl)methyl]pyridin-2-yl}amino)thiophene-3-carboxamide;

5-(2,5-Dichlorophenyl)-2-{[6-(methoxymethyl)pyridin-2-yl]amino}thiophene-3-carboxamide;

5-[2-Fluoro-4-(1-hydroxy-1-methylethyl)phenyl]-2-({6-[(2-morpholin-4-yl-2-oxoethoxy)methyl]pyridin-2-yl}amino)thiophene-3-carboxamide;

5-(2-Fluoro-4-(1-hydroxy-1-methylethyl)phenyl]-2-((6-((2-oxo-2-((tetrahydro-3-furanylmethyl)amino)ethoxy)methyl)-2-pyridinyl)amino)-3-thiophenecarboxamide;

5-[2,6-Difluoro-4-(1-hydroxy-1-methylethyl)phenyl]-2-({6-[(2-morpholin-4-yl-2-oxoethoxy)methyl]pyridin-2-yl}amino)thiophene-3-carboxamide;

5-[2,6-difluoro-4-(1-hydroxy-1-methylethyl)phenyl]-2-[(6-{[2-(3-hydroxypyrrolidin-1-yl)-2-oxoethoxy]methyl}pyridin-2-yl)amino]thiophene-3-carboxamide;

5-[2,6-difluoro-4-(1-hydroxy-1-methylethyl)phenyl]-2-{6-({2-[(2-hydroxyethyl)(methyl)amino]-2-oxoethoxy}methyl)pyridin-2-yl]amino}thiophene-3-carboxamide;

5-[2,6-difluoro-4-(1-hydroxy-1-methylethyl)phenyl]-2-{[6-({2-[(2-hydroxyethyl)amino]-2-oxoethoxy}methyl)pyridin-2-yl]amino}thiophene-3-carboxamide;

5-(2-fluoro-4-(1-hydroxy-1-methylethyl)phenyl)-2-((6-((2-((2-methoxyethyl)amino)-2-oxoethoxy)methyl)-2-pyridinyl)amino)-3-thiophenecarboxamide;

5-(2-fluoro-4-(1-hydroxy-1-methylethyl)phenyl)-2-((6-((2-oxo-2-(tetrahydro-2-furanylmethyl)amino)ethoxy)methyl)-2-pyridinyl)amino)-3-thiophenecarboxamide;

2-((6-((2-cyclohexylmethyl)amino)-2-oxoethoxy)methyl)-2-pyridinyl)amino)-5-(2-fluoro-4-(1-hydroxy-1-methylethyl)phenyl)-3-thiophenecarboxamide;

5-(2-fluoro-4-(1-hydroxy-1-methylethyl)phenyl)-2-((6-((2-oxo-2-(tetrahydro-2H-pyran-4-ylmethyl)amino)ethoxy)methyl)-2-pyridinyl)amino)-3-thiophenecarboxamide;

2-((6-((2-((2-dimethylamino)ethyl)amino)-2-oxoethoxy)methyl)-2-pyridinyl)amino)-5-(2-fluoro-4-(1-hydroxy-1-methylethyl)phenyl)-3-thiophenecarboxamide;

2-((6-((2-((2-dimethylamino)ethyl)amino)-2-oxoethoxy)methyl)-2-pyridinyl)amino)-5-(2-fluoro-4-(1-hydroxy-1-methylethyl)phenyl)-3-thiophenecarboxamide;

[6-({3-(Aminocarbonyl)-5-[2,6-difluoro-4-(1-hydroxy-1-methylethyl)phenyl]-2-thienyl}amino)pyridin-2-yl]methyl methylcarbamate;

5-[2,6-Difluoro-4-(1-hydroxy-1-methylethyl)phenyl]-2-({6-[(2-hydroxy-2-methylpropoxy)methyl]pyridin-2-yl}amino)thiophene-3-carboxamide;

2-({6-[(2-Hydroxy-2-methylpropoxy)methyl]pyridin-2-yl}amino)-5-[4-(methylsulfonyl)phenyl]thiophene-3-carboxamide;

5-[4-(1-Hydroxy-1-methylethyl)phenyl]-2-({6-[(2-hydroxy-2-methylpropoxy)methyl]pyridin-2-yl}amino)thiophene-3-carboxamide;

2-({6-[(2-Hydroxy-2-methylpropoxy)methyl]pyridin-2-yl}amino)-5-[4-(methylsulfonyl)phenyl]thiophene-3-carboxamide;

5-[4-(3-Fluorooxetan-3-yl)phenyl]-2-({6-[(2-hydroxy-2-methylpropoxy)methyl]pyridin-2-yl}amino)thiophene-3-carboxamide;

2-({6-[(2-hydroxy-2-methylpropoxy)methyl]pyridin-2-yl}amino)-5-(6-morpholin-4-ylpyridin-3-yl)thiophene-3-carboxamide;

5-[4-(1-cyano-1-methylethyl)phenyl]-2-({6-[(2-hydroxy-2-methylpropoxy)methyl]pyridin-2-yl}amino)thiophene-3-carboxamide;

5-[6-(1-cyano-1-methylethyl)pyridin-3-yl]-2-({6-[(2-hydroxy-2-methylpropoxy)methyl]pyridin-2-yl}amino)thiophene-3-carboxamide;

2-({6-[(2-hydroxy-2-methylpropoxy)methyl]pyridin-2-yl}amino)-5-(1-{[2-(trimethylsilyl)ethoxy]methyl}-1H-1,2,4-triazol-3-yl)thiophene-3-carboxamide;

2-({6-[(2-hydroxy-2-methylpropoxy)methyl]pyridin-2-yl}amino)-5-(1H-1,2,4-triazol-3-yl)thiophene-3-carboxamide;

2-({6-[(2-hydroxy-2-methylpropoxy)methyl]pyridin-2-yl}amino)-5-[4-(1H-1,2,3-triazol-4-yl)phenyl]thiophene-3-carboxamide;

2-({6-[(2-hydroxy-2-methylpropoxy)methyl]pyridin-2-yl}amino)-5-[4-(1H-1,2,4-triazol-3-yl)phenyl]thiophene-3-carboxamide;

2-({6-[(2-hydroxy-2-methylpropoxy)methyl]pyridin-2-yl}amino)-5-[4-(morpholin-4-ylmethyl)phenyl]thiophene-3-carboxamide;

2-({6-[(2-hydroxy-2-methylpropoxy)methyl]pyridin-2-yl}amino)-5-[4-(morpholin-4-ylcarbonyl)phenyl]thiophene-3-carboxamide;

5-{4-[(acetylamino)methyl]phenyl}-2-({6-[(2-hydroxy-2-methylpropoxy)methyl]pyridin-2-yl}amino)thiophene-3-carboxamide;

5-[6-(1-hydroxy-1-methylethyl)pyridin-3-yl]-2-({6-[(2-hydroxy-2-methylpropoxy)methyl]pyridin-2-yl}amino)thiophene-3-carboxamide;

5-[2-fluoro-4-(1-hydroxy-1-methylethyl)phenyl]-2-({6-[(2-hydroxy-2-methylpropoxy)methyl]pyridin-2-yl}amino)thiophene-3-carboxamide;

5-[4-(1,1-Dioxidothiomorpholin-4-yl)phenyl]-2-({6-[(2-hydroxy-2-methylpropoxy)methyl]pyridin-2-yl}amino)thiophene-3-carboxamide;

5-[2,6-Difluoro-4-(1-hydroxy-1-methylethyl)phenyl]-2-{[6-(2-hydroxyethyl)pyridin-2-yl]amino}thiophene-3-carboxamide;

5-[2,6-Difluoro-4-(1-hydroxy-1-methylethyl)phenyl]-2-{[6-(2-methoxyethyl)pyridin-2-yl]amino}thiophene-3-carboxamide;

5-[2,6-difluoro-4-(1-hydroxy-1-methylethyl)phenyl]-2-{[6-(2-ethoxyethyl)pyridin-2-yl]amino}thiophene-3-carboxamide;

5-[2,6-difluoro-4-(1-hydroxy-1-methylethyl)phenyl]-2-[(6-{2-[(5-methylisoxazol-3-yl)methoxy]ethyl}pyridin-2-yl)amino]thiophene-3-carboxamide;

5-[2,6-difluoro-4-(1-hydroxy-1-methylethyl)phenyl]-2-[(6-{2-[(5-methyl-1,2,4-oxadiazol-3-yl)methoxy]ethyl}pyridin-2-yl)amino]thiophene-3-carboxamide;

5-[2,6-difluoro-4-(1-hydroxy-1-methylethyl)phenyl]-2-[(6-{2-[(3,5-dimethylisoxazol-4-yl)methoxy]ethyl}pyridin-2-yl)amino]thiophene-3-carboxamide;

5-[2,6-Difluoro-4-(1-hydroxy-1-methylethyl)phenyl]-2-[(6-{2-[(3-methyl-1,2,4-oxadiazol-5-yl)methoxy]ethyl}pyridin-2-yl)amino]thiophene-3-carboxamide;

5-[2,6-Difluoro-4-(1-hydroxy-1-methylethyl)phenyl]-2-({6-[2-(2-hydroxy-2-methylpropoxy)ethyl]pyridin-2-yl}amino)thiophene-3-carboxamide;

5-[2,6-Difluoro-4-(1-hydroxy-1-methylethyl)phenyl]-2-{[6-({[(1R,2R)-2-hydroxycyclopentyl]oxy}methyl)pyridin-2-yl]amino}thiophene-3-carboxamide;

5-[2,6-difluoro-4-(1-hydroxy-1-methylethyl)phenyl]-2-{[6-({[(1R,2S)-2-hydroxycyclopentyl]oxy}methyl)pyridin-2-yl]amino}thiophene-3-carboxamide;

5-[2,6-difluoro-4-(1-hydroxy-1-methylethyl)phenyl]-2-{[6-({[(3R,4S)-4-hydroxytetrahydrofuran-3-yl]oxy}methyl)pyridin-2-yl]amino}thiophene-3-carboxamide;

5-[2-fluoro-4-(1-hydroxy-1-methylethyl)phenyl]-2-{[6-({[(3R,4S)-4-hydroxytetrahydrofuran-3-yl]oxy}methyl)pyridin-2-yl]amino}thiophene-3-carboxamide;

5-[2,6-difluoro-4-(1-hydroxy-1-methylethyl)phenyl]-2-{[6-({[(1R,2R)-2-hydroxycyclohexyl]oxy}methyl)pyridin-2-yl]amino}thiophene-3-carboxamide;

5-[2,6-difluoro-4-(1-hydroxy-1-methylethyl)phenyl]-2-{[6-({[(1R,2S)-2-hydroxycyclohexyl]oxy}methyl)pyridin-2-yl]amino}thiophene-3-carboxamide;

5-[2,6-difluoro-4-(1-hydroxy-1-methylethyl)phenyl]-2-{[6-({[(2S)-2-hydroxypropyl]oxy}methyl)pyridin-2-yl]amino}thiophene-3-carboxamide;

2-[(6-{[(1,3-Dimethyl-1H-pyrazol-5-yl)methoxy]methyl}pyridin-2-yl)amino]-5-[2-fluoro-4-(1-hydroxy-1-methylethyl)phenyl]thiophene-3-carboxamide;

5-[2-Fluoro-4-(1-hydroxy-1-methylethyl)phenyl]-2-({6-[(tetrahydro-2H-pyran-3-ylmethoxy)methyl]pyridin-2-yl}amino)thiophene-3-carboxamide;

5-[2-fluoro-4-(1-hydroxy-1-methylethyl)phenyl]-2-({6-[(pyridin-4-ylmethoxy)methyl]pyridin-2-yl}amino)thiophene-3-carboxamide;

5-[2-fluoro-4-(1-hydroxy-1-methylethyl)phenyl]-2-({6-[(pyrazin-2-ylmethoxy)methyl]pyridin-2-yl}amino)thiophene-3-carboxamide;

5-[2-fluoro-4-(1-hydroxy-1-methylethyl)phenyl]-2-({6-[(2-isopropoxyethoxy)methyl]pyridin-2-yl}amino)thiophene-3-carboxamide;

5-[2-fluoro-4-(1-hydroxy-1-methylethyl)phenyl]-2-({6-[(tetrahydrofuran-3-ylmethoxy)methyl]pyridin-2-yl}amino)thiophene-3-carboxamide;

2-({6-[(2,2-difluoroethoxy)methyl]pyridin-2-yl}amino)-5-[2-fluoro-4-(1-hydroxy-1-methylethyl)phenyl]thiophene-3-carboxamide;

5-[2-fluoro-4-(1-hydroxy-1-methylethyl)phenyl]-2-[(6-{[(3-fluoropyridin-2-yl)methoxy]methyl}pyridin-2-yl)amino]thiophene-3-carboxamide;

5-[2-fluoro-4-(1-hydroxy-1-methylethyl)phenyl]-2-[(6-{[(3-methylisoxazol-5-yl)methoxy]methyl}pyridin-2-yl)amino]thiophene-3-carboxamide;

5-[2-fluoro-4-(1-hydroxy-1-methylethyl)phenyl]-2-[(6-{[(3-methyl-1,2,4-oxadiazol-5-yl)methoxy]methyl}pyridin-2-yl)amino]thiophene-3-carboxamide;

2-[(6-{[(1,3-dimethyl-1H-pyrazol-5-yl)methoxy]methyl}pyridin-2-yl)amino]-5-[2-fluoro-4-(1-hydroxy-1-methylethyl)phenyl]thiophene-3-carboxamide;

2-({6-[(cyclobutylmethoxy)methyl]pyridin-2-yl}amino)-5-[2-fluoro-4-(1-hydroxy-1-methylethyl)phenyl]thiophene-3-carboxamide;

5-[2-fluoro-4-(1-hydroxy-1-methylethyl)phenyl]-2-({6-[(3,3,3-trifluoropropoxy)methyl]pyridin-2-yl}amino)thiophene-3-carboxamide;

5-[2-fluoro-4-(1-hydroxy-1-methylethyl)phenyl]-2-({6-[(3-methoxy-3-methylbutoxy)methyl]pyridin-2-yl}amino)thiophene-3-carboxamide;

2-[(6-{[(2,4-dimethyl-1,3-thiazol-5-yl)methoxy]methyl}pyridin-2-yl)amino]-5-[2-fluoro-4-(1-hydroxy-1-methylethyl)phenyl]thiophene-3-carboxamide;

5-[2-fluoro-4-(1-hydroxy-1-methylethyl)phenyl]-2-[(6-{[2-(4-methylpiperazin-1-yl)ethoxy]methyl}pyridin-2-yl)amino]thiophene-3-carboxamide;

2-[(6-{[2-(dimethylamino)ethoxy]methyl}pyridin-2-yl)amino]-5-[2-fluoro-4-(1-hydroxy-1-methylethyl)phenyl]thiophene-3-carboxamide;

2-({6-[(cyclopropylmethoxy)methyl]pyridin-2-yl}amino)-5-[2-fluoro-4-(1-hydroxy-1-methylethyl)phenyl]thiophene-3-carboxamide;

2-[(6-{[(4-fluorobenzyl)oxy]methyl}pyridin-2-yl)amino]-5-[2-fluoro-4-(1-hydroxy-1-methylethyl)phenyl]thiophene-3-carboxamide;

5-[2-fluoro-4-(1-hydroxy-1-methylethyl)phenyl]-2-({6-[(hept-3-yn-1-yloxy)methyl]pyridin-2-yl}amino)thiophene-3-carboxamide;

5-[2-fluoro-4-(1-hydroxy-1-methylethyl)phenyl]-2-({6-[(1,3-oxazol-2-ylmethoxy)methyl]pyridin-2-yl}amino)thiophene-3-carboxamide;

5-[2-fluoro-4-(1-hydroxy-1-methylethyl)phenyl]-2-({6-[(pyrimidin-2-ylmethoxy)methyl]pyridin-2-yl}amino)thiophene-3-carboxamide;

2-[(6-{[2-(2-Azaspiro[3.3]hept-2-yl)ethoxy]methyl}pyridin-2-yl)amino]-5-[2-fluoro-4-(1-hydroxy-1-methylethyl)phenyl]thiophene-3-carboxamide;

5-[2-Fluoro-4-(1-hydroxy-1-methylethyl)phenyl]-2-{[6-(methoxymethyl)pyridin-2-yl]amino}thiophene-3-carboxamide;

2-{[6-(Ethoxymethyl)pyridin-2-yl]amino}-5-[2-fluoro-4-(1-hydroxy-1-methylethyl)phenyl]thiophene-3-carboxamide;

5-[2-Fluoro-4-(1-hydroxy-1-methylethyl)phenyl]-2-({6-[(2-methoxyethoxy)methyl]pyridin-2-yl}amino)thiophene-3-carboxamide;

5-[2-Fluoro-4-(1-hydroxy-1-methylethyl)phenyl]-2-[(6-{[(5-methyl-1,3,4-oxadiazol-2-yl)methoxy]methyl}pyridin-2-yl)amino]thiophene-3-carboxamide;

5-[2,6-Difluoro-4-(1-hydroxy-1-methylethyl)phenyl]-2-[(6-{[(1,1-dioxidotetrahydro-2H-thiopyran-4-yl)oxy]methyl}pyridin-2-yl)amino]thiophene-3-carboxamide;

5-[2,6-difluoro-4-(1-hydroxy-1-methylethyl)phenyl]-2-[(6-{[2-(methylsulfonyl)ethoxy]methyl}pyridin-2-yl)amino]thiophene-3-carboxamide;

5-[2-Fluoro-4-(1-hydroxy-1-methylethyl)phenyl]-2-{[6-(2-hydroxyethoxy)pyridin-2-yl]amino}thiophene-3-carboxamide;

2-{[6-(2-hydroxyethoxy)pyridin-2-yl]amino}-5-[4-(1-hydroxy-1-methylethyl)phenyl]thiophene-3-carboxamide;

5-[2,6-difluoro-4-(1-hydroxy-1-methylethyl)phenyl]-2-{[6-(2-hydroxyethoxy)pyridin-2-yl]amino}thiophene-3-carboxamide;

6-({3-(Aminocarbonyl)-5-[2-fluoro-4-(1-hydroxy-1-methylethyl)phenyl]-2-thienyl}amino)-N-(trans-4-hydroxycyclohexyl)pyridine-2-carboxamide;

6-({3-(Aminocarbonyl)-5-[2-fluoro-4-(1-hydroxy-1-methylethyl)phenyl]-2-thienyl}amino)-N-(cyclopropylmethyl)pyridine-2-carboxamide;

5-[2-Fluoro-4-(1-hydroxy-1-methylethyl)phenyl]-2-[(6-{[(3R)-3-methoxypyrrolidin-1-yl]carbonyl}pyridin-2-yl)amino]thiophene-3-carboxamide;

6-({3-(aminocarbonyl)-5-[2,6-difluoro-4-(1-hydroxy-1-methylethyl)phenyl]-2-thienyl}amino)-N-(trans-4-hydroxycyclohexyl)pyridine-2-carboxamide;

6-({3-(aminocarbonyl)-5-[2-fluoro-4-(1-hydroxy-1-methylethyl)phenyl]-2-thienyl}amino)-N-[2-(tetrahydro-2H-pyran-4-yl)ethyl]pyridine-2-carboxamide;

6-({3-(aminocarbonyl)-5-[2,6-difluoro-4-(1-hydroxy-1-methylethyl)phenyl]-2-thienyl}amino)-N-[2-(tetrahydro-2H-pyran-4-yl)ethyl]pyridine-2-carboxamide;

6-({3-(aminocarbonyl)-5-[2-fluoro-4-(1-hydroxy-1-methylethyl)phenyl]-2-thienyl}amino)-N-(tetrahydro-2H-pyran-4-ylmethyl)pyridine-2-carboxamide;

6-({3-(aminocarbonyl)-5-[2,6-difluoro-4-(1-hydroxy-1-methylethyl)phenyl]-2-thienyl}amino)-N-(tetrahydro-2H-pyran-4-ylmethyl)pyridine-2-carboxamide;

6-({3-(aminocarbonyl)-5-[2-fluoro-4-(1-hydroxy-1-methylethyl)phenyl]-2-thienyl}amino)-N-(tetrahydrofuran-2-ylmethyl)pyridine-2-carboxamide;

6-({3-(aminocarbonyl)-5-[2,6-difluoro-4-(1-hydroxy-1-methylethyl)phenyl]-2-thienyl}amino)-N-(tetrahydrofuran-2-ylmethyl)pyridine-2-carboxamide;

5-[2,6-difluoro-4-(1-hydroxy-1-methylethyl)phenyl]-2-{[6-(morpholin-4-ylcarbonyl)pyridin-2-yl]amino}thiophene-3-carboxamide;

5-[2,6-difluoro-4-(1-hydroxy-1-methylethyl)phenyl]-2-({6-[(4-methylpiperazin-1-yl)carbonyl]pyridin-2-yl}amino)thiophene-3-carboxamide;

5-[2,6-difluoro-4-(1-hydroxy-1-methylethyl)phenyl]-2-({6-[(3-hydroxypyrrolidin-1-yl)carbonyl]pyridin-2-yl}amino)thiophene-3-carboxamide;

6-({3-(aminocarbonyl)-5-[2,6-difluoro-4-(1-hydroxy-1-methylethyl)phenyl]-2-thienyl}amino)-N-(2-hydroxyethyl)-N-methylpyridine-2-carboxamide;

6-({3-(aminocarbonyl)-5-[2,6-difluoro-4-(1-hydroxy-1-methylethyl)phenyl]-2-thienyl}amino)-N-(2-hydroxyethyl)pyridine-2-carboxamide;

6-({3-(aminocarbonyl)-5-[2-fluoro-4-(1-hydroxy-1-methylethyl)phenyl]-2-thienyl}amino)-N-(2-hydroxyethyl)pyridine-2-carboxamide;

6-({3-(aminocarbonyl)-5-[2-fluoro-4-(1-hydroxy-1-methyleth)phenyl]-2-thienyl}amino)-N-(2-fluoroprop-2-en-1-yl)pyridine-2-carboxamide;

5-[2-fluoro-4-(1-hydroxy-1-methylethyl)phenyl]-2-[(6-{[4-(hydroxymethyl)piperidin-1-yl]carbonyl}pyridin-2-yl)amino]thiophene-3-carboxamide;

6-({3-(aminocarbonyl)-5-[2-fluoro-4-(1-hydroxy-1-methylethyl)phenyl]-2-thienyl}amino)-N-methylpyridine-2-carboxamide;

6-({3-(aminocarbonyl)-5-[2-fluoro-4-(1-hydroxy-1-methylethyl)phenyl]-2-thienyl}amino)-N-ethyl-N-methylpyridine-2-carboxamide;

6-({3-(aminocarbonyl)-5-[2-fluoro-4-(1-hydroxy-1-methylethyl)phenyl]-2-thienyl}amino)-N-(2-methoxyethyl)pyridine-2-carboxamide;

5-[2-fluoro-4-(1-hydroxy-1-methylethyl)phenyl]-2-({6-[(3-methoxyazetidin-1-yl)carbonyl]pyridin-2-yl}amino)thiophene-3-carboxamide;

6-({3-(aminocarbonyl)-5-[2-fluoro-4-(1-hydroxy-1-methylethyl)phenyl]-2-thienyl}amino)-N-(1,1-dioxidotetrahydro-3-thienyl)pyridine-2-carboxamide;

6-({3-(aminocarbonyl)-5-[2-fluoro-4-(1-hydroxy-1-methylethyl)phenyl]-2-thienyl}amino)-N-[(2,5-dimethyl-1,3-oxazol-4-yl)methyl]-N-methylpyridine-2-carboxamide;

6-({3-(aminocarbonyl)-5-[2-fluoro-4-(1-hydroxy-1-methylethyl)phenyl]-2-thienyl}amino)-N-{3-(hydroxymethyl)oxetan-3-yl]methyl}pyridine-2-carboxamide;

5-[2-fluoro-4-(1-hydroxy-1-methylethyl)phenyl]-2-[(6-{[6-(hydroxymethyl)-3-azabicyclo[3.1.0]hex-3-yl]carbonyl}pyridin-2-yl)amino]thiophene-3-carboxamide;

5-[2-fluoro-4-(1-hydroxy-1-methylethyl)phenyl]-2-({6-[(3-hydroxyazetidin-1-yl)carbonyl]pyridin-2-yl}amino)thiophene-3-carboxamide;

6-({3-(aminocarbonyl)-5-[2-fluoro-4-(1-hydroxy-1-methylethyl)phenyl]-2-thienyl}amino)-N-(2-hydroxypropyl)pyridine-2-carboxamide;

5-[2-fluoro-4-(1-hydroxy-1-methylethyl)phenyl]-2-({6-[(3-hydroxypyrrolidin-1-yl)carbonyl]pyridin-2-yl}amino)thiophene-3-carboxamide;

6-({3-(aminocarbonyl)-5-[2-fluoro-4-(1-hydroxy-1-methylethyl)phenyl]-2-thienyl}amino)-N-(2-hydroxy-2-methylpropyl)pyridine-2-carboxamide;

6-({3-(aminocarbonyl)-5-[2-fluoro-4-(1-hydroxy-1-methylethyl)phenyl]-2-thienyl}amino)-N,N-bis(2-hydroxyethyl)pyridine-2-carboxamide;

6-({3-(aminocarbonyl)-5-[2-fluoro-4-(1-hydroxy-1-methylethyl)phenyl]-2-thienyl}amino)-N-[(1R)-2-hydroxy-1-methylethyl]pyridine-2-carboxamide;

6-({3-(aminocarbonyl)-5-[2-fluoro-4-(1-hydroxy-1-methylethyl)phenyl]-2-thienyl}amino)-N-[(2S)-2-hydroxypropyl]pyridine-2-carboxamide;

5-[2-fluoro-4-(1-hydroxy-1-methylethyl)phenyl]-2-[(6-{[2-(hydroxymethyl)morpholin-4-yl]carbonyl}pyridin-2-yl)amino]thiophene-3-carboxamide;

5-[2-fluoro-4-(1-hydroxy-1-methylethyl)phenyl]-2-[(6-{[3-(hydroxymethyl)morpholin-4-yl]carbonyl}pyridin-2-yl)amino]thiophene-3-carboxamide;

5-[2-fluoro-4-(1-hydroxy-1-methylethyl)phenyl]-2-[(6-{[(3R)-3-methylmorpholin-4-yl]carbonyl}pyridin-2-yl)amino]thiophene-3-carboxamide;

5-[2-fluoro-4-(1-hydroxy-1-methylethyl)phenyl]-2-[(6-{[(3S)-3-methoxypyrrolidin-1-yl]carbonyl}pyridin-2-yl)amino]thiophene-3-carboxamide;

6-({3-(aminocarbonyl)-5-[2-fluoro-4-(1-hydroxy-1-methylethyl)phenyl]-2-thienyl}amino)-N-[(3-methyloxetan-3-yl)methyl]pyridine-2-carboxamide;

6-({3-(aminocarbonyl)-5-[2-fluoro-4-(1-hydroxy-1-methylethyl)phenyl]-2-thienyl}amino)-N-(1,3-oxazol-2-ylmethyl)pyridine-2-carboxamide;

5-[2-fluoro-4-(1-hydroxy-1-methylethyl)phenyl]-2-({6-[(2-methyl-6,7-dihydro[1,3]oxazolo[4,5-c]pyridin-5(4H)-yl)carbonyl]pyridin-2-yl}amino)thiophene-3-carboxamide;

6-({3-(aminocarbonyl)-5-[2-fluoro-4-(1-hydroxy-1-methylethyl)phenyl]-2-thienyl}amino)-N-methyl-N-(pyrazin-2-ylmethyl)pyridine-2-carboxamide;

6-({3-(aminocarbonyl)-5-[2-fluoro-4-(1-hydroxy-1-methylethyl)phenyl]-2-thienyl}amino)-N-[(2,4-dimethyl-1,3-thiazol-5-yl)methyl]pyridine-2-carboxamide;

2-{[6-(5,6-Dihydroimidazo[1,2-a]pyrazin-7(8H)-ylcarbonyl)pyridin-2-yl]amino}-5-[2-fluoro-4-(1-hydroxy-1-methylethyl)phenyl]thiophene-3-carboxamide;

5-[2-Fluoro-4-(1-hydroxy-1-methylethyl)phenyl]-2-[(6-{[(2R)-2-methylmorpholin-4-yl]carbonyl}pyridin-2-yl)amino]thiophene-3-carboxamide;

5-[2-Fluoro-4-(1-hydroxy-1-methylethyl)phenyl]-2-[(6-{[(2S)-2-methylmorpholin-4-yl]carbonyl}pyridin-2-yl)amino]thiophene-3-carboxamide;

6-({3-(Aminocarbonyl)-5-[2-fluoro-4-(1-hydroxy-1-methylethyl)phenyl]-2-thienyl}amino)-N-methyl-N-[2-(1-methyl-1H-pyrazol-4-yl)ethyl]pyridine-2-carboxamide;

6-({3-(Aminocarbonyl)-5-[2-fluoro-4-(1-hydroxy-1-methylethyl)phenyl]-2-thienyl}amino)-N-(oxetan-2-ylmethyl)pyridine-2-carboxamide;

2-[(6-{[(Cyanoacetyl)amino]methyl}pyridin-2-yl)amino]-5-[2,6-difluoro-4-(1-hydroxy-1-methylethyl)phenyl]thiophene-3-carboxamide;

2-{[6-(1-Cyano-3-hydroxypropyl)pyridin-2-yl]amino}-5-[2-fluoro-4-(1-hydroxy-1-methylethyl)phenyl]thiophene-3-carboxamide;

2-{[6-(cyanomethyl)pyridin-2-yl]amino}-5-[2-fluoro-4-(1-hydroxy-1-methylethyl)phenyl]thiophene-3-carboxamide;

2-{[6-(cyanomethyl)pyridin-2-yl]amino}-5-[2,6-difluoro-4-(1-hydroxy-1-methylethyl)phenyl]thiophene-3-carboxamide;

2-{[6-(1,2-Diamino-2-oxoethyl)pyridin-2-yl]amino}-5-[2,6-difluoro-4-(1-hydroxy-1-methylethyl)phenyl]thiophene-3-carboxamide;

methyl{2-amino-1-[6-({3-(aminocarbonyl)-5-[2,6-difluoro-4-(1-hydroxy-1-methylethyl)phenyl]-2-thienyl}amino)pyridin-2-yl]-2-oxoethyl}carbamate;

2-({6-[1-(acetylamino)-2-amino-2-oxoethyl]pyridin-2-yl}amino)-5-[2,6-difluoro-4-(1-hydroxy-1-methylethyl)phenyl]thiophene-3-carboxamide;

Methyl{[6-({3-(aminocarbonyl)-5-[2,6-difluoro-4-(1-hydroxy-1-methylethyl)phenyl]-2-thienyl}amino)pyridin-2-yl]methyl}carbamate;

5-[2,6-difluoro-4-(1-hydroxy-1-methylethyl)phenyl]-2-[(6-{[(methylsulfonyl)amino]methyl}pyridin-2-yl)amino]thiophene-3-carboxamide;

N-{[6-({3-(Aminocarbonyl)-5-[2,6-difluoro-4-(1-hydroxy-1-methylethyl)phenyl]-2-thienyl}amino)pyridin-2-yl]methyl}pyrimidine-2-carboxamide;

N-{[6-({3-(aminocarbonyl)-5-[2,6-difluoro-4-(1-hydroxy-methylethyl)phenyl]-2-thienyl}amino)pyridin-2-yl]methyl}-2-(hydroxymethyl)isonicotinamide;

N-{[6-({3-(aminocarbonyl)-5-[2,6-difluoro-4-(1-hydroxy-methylethyl)phenyl]-2-thienyl}amino)pyridin-2-yl]methyl}-1,3-oxazole-5-carboxamide;

N-{[6-({3-(aminocarbonyl)-5-[2,6-difluoro-4-(1-hydroxy-methylethyl)phenyl]-2-thienyl}amino)pyridin-2-yl]methyl}-1H-pyrazole-5-carboxamide;

N-{[6-({3-(aminocarbonyl)-5-[2,6-difluoro-4-(1-hydroxy-1-methylethyl)phenyl]-2-thienyl}amino)pyridin-2-yl]methyl}pyrimidine-5-carboxamide;

N-{[6-({3-(aminocarbonyl)-5-[2,6-difluoro-4-(1-hydroxy-1-methylethyl)phenyl]-2-thienyl}amino)pyridin-2-yl]methyl}-1-methyl-1H-pyrazole-5-carboxamide;

N-{[6-({3-(aminocarbonyl)-5-[2,6-difluoro-4-(1-hydroxy-1-methylethyl)phenyl]-2-thienyl}amino)pyridin-2-yl]methyl}-1-methyl-1H-pyrazole-4-carboxamide;

N-{[6-({3-(aminocarbonyl)-5-[2,6-difluoro-4-(1-hydroxy-1-methylethyl)phenyl]-2-thienyl}amino)pyridin-2-yl]methyl}-1-methyl-1H-pyrazole-3-carboxamide;

5-[2,6-difluoro-4-(1-hydroxy-1-methylethyl)phenyl]-2-[(6-{[(2-hydroxy-2methylpropanoyl)amino]methyl}pyridin-2-yl)amino]thiophene-3-carboxamide;

5-[2,6-difluoro-4-(1-hydroxy-1-methylethyl)phenyl]-2-{[6-({[(1-hydroxycyclopropyl)carbonyl]amino}methyl)pyridin-2-yl]amino}thiophene-3-carboxamide;

N-{[6-({3-(Aminocarbonyl)-5-[2,6-difluoro-4-(1-hydroxy-1-methylethyl)phenyl]-2-thienyl}amino)pyridin-2-yl]methyl}-3-methyl-1,2,4-oxadiazole-5-carboxamide;

N-{[6-({3-(aminocarbonyl)-5-[2,6-difluoro-4-(1-hydroxy-1-methylethyl)phenyl]-2-thienyl}amino)pyridin-2-yl]methyl}-5-methyl-1,3,4-oxadiazole-2-carboxamide;

2-({6-[2-(Dimethylamino)-2-oxoethyl]pyridin-2-yl}amino)-5-[2-fluoro-4-(1-hydroxy-1-methylethyl)phenyl]thiophene-3-carboxamide;

2-{[6-(2-amino-2-oxoethyl)pyridin-2-yl]amino}-5-[2-fluoro-4-(1-hydroxy-1-methylethyl)phenyl]thiophene-3-carboxamide;

5-(4-chlorophenyl)-2-({6-[2-(methylamino)-2-oxoethyl]pyridin-2-yl}amino)thiophene-3-carboxamide;

5-(4-chlorophenyl)-2-({6-[2-oxo-2-(prop-2-yn-1-ylamino)ethyl]pyridin-2-yl}amino)thiophene-3-carboxamide;

5-(4-chlorophenyl)-2-[(6-{2-[(cyanomethyl)amino]-2-oxoethyl}pyridin-2-yl)amino]thiophene-3-carboxamide;

5-[2,6-Difluoro-4-(1-hydroxy-1-methylethyl)phenyl]-2-[(6-{2-[(1-methyl-1H-pyrazol-4-yl)amino]-2-oxoethyl}pyridin-2-yl)amino]thiophene-3-carboxamide;

5-[2,6-difluoro-4-(1-hydroxy-1-methylethyl)phenyl]-2-[(6-{2-[(1-methyl-1H-pyrazol-3-yl)amino]-2-oxoethyl}pyridin-2-yl)amino]thiophene-3-carboxamide;

5-[2,6-difluoro-4-(1-hydroxy-1-methylethyl)phenyl]-2-[(6-{2-[(1-methyl-1H-pyrazol-5-yl)amino]-2-oxoethyl}pyridin-2-yl)amino]thiophene-3-carboxamide;

5-[2,6-difluoro-4-(1-hydroxy-1-methylethyl)phenyl]-2-{[6-(2-{[3-(hydroxymethyl)isothiazol-5-yl]amino}-2-oxoethyl)pyridin-2-yl]amino}thiophene-3-carboxamide;

5-[2,6-difluoro-4-(1-hydroxy-1-methylethyl)phenyl]-2-[(6-{2-[(2-methyl-2H-1,2,3-triazol-4-yl)amino]-2-oxoethyl}pyridin-2-yl)amino]thiophene-3-carboxamide;

5-[2,6-Difluoro-4-(1-hydroxy-1-methylethyl)phenyl]-2-({6-[2-(methylamino)-1-morpholin-4-yl-2-oxoethyl]pyridin-2-yl}amino)thiophene-3-carboxamide;

methyl[6-({3-(aminocarbonyl)-5-[2,6-difluoro-4-(1-hydroxy-1-methylethyl)phenyl]-2-thienyl}amino)pyridin-2-yl](morpholin-4-yl)acetate;

2-{[6-(2-amino-1-morpholin-4-yl-2-oxoethyl)pyridin-2-yl]amino}-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-({6-[2-(dimethylamino)-1-morpholin-4-yl-2-oxoethyl]pyridin-2-yl}amino)thiophene-3-carboxamide;

5-[2,6-Difluoro-4-(1-hydroxy-1-methylethyl)phenyl]-2-({6-[1-hydroxy-2-(methylamino)-2-oxoethyl]pyridin-2-yl}amino)thiophene-3-carboxamide;

2-{[6-(2-amino-1-hydroxy-2-oxoethyl)pyridin-2-yl]amino}-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-({6-[2-(dimethylamino)-1-hydroxy-2-oxoethyl]pyridin-2-yl}amino)thiophene-3-carboxamide;

2-{[6-(1-Cyano-1-methylethyl)pyridin-2-yl]amino}-5-[2,6-difluoro-4-(1-hydroxy-1-methylethyl)phenyl]thiophene-3-carboxamide;

2-{[6-(1-cyanoethyl)pyridin-2-yl]amino}-5-[2,6-difluoro-4-(1-hydroxy-1-methylethyl)phenyl]thiophene-3-carboxamide;

2-{[6-(1-Cyanocyclopropyl)pyridin-2-yl]amino}-5-[2,6-difluoro-4-(1-hydroxy-1-methylethyl)phenyl]thiophene-3-carboxamide;

2-{[6-(2-Amino-1,1-dimethyl-2-oxoethyl)pyridin-2-yl]amino}-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-[(6-{1,1-dimethyl-2-[(1-methyl-1H-pyrazol-4-yl)amino]-2-oxoethyl}pyridin-2-yl)amino]thiophene-3-carboxamide;

5-[2-Fluoro-4-(1-hydroxy-1-methylethyl)phenyl]-2-[(6-{[(2-hydroxy-2-methylpropyl)sulfonyl]methyl}pyridin-2-yl)amino]thiophene-3-carboxamide;

5-[2,6-difluoro-4-(1-hydroxy-1-methylethyl)phenyl]-2-[(6-{[(2-hydroxy-2-methylpropyl)sulfonyl]methyl}pyridin-2-yl)amino]thiophene-3-carboxamide;

5-[2,6-difluoro-4-(1-hydroxy-1-methylethyl)phenyl]-2-({6-[(ethylsulfonyl)methyl]pyridin-2-yl}amino)thiophene-3-carboxamide;

2-({6-[(tert-butylsulfonyl)methyl]pyridin-2-yl}amino)-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-({6-[(propylsulfonyl)methyl]pyridin-2-yl}amino)thiophene-3-carboxamide;

5-[2,6-difluoro-4-(1-hydroxy-1-methylethyl)phenyl]-2-({6-[(isobutylsulfonyl)methyl]pyridin-2-yl}amino)thiophene-3-carboxamide;

5-[2,6-difluoro-4-(1-hydroxy-1-methylethyl)phenyl]-2-[(6-{[(2-hydroxypropyl)sulfonyl]methyl}pyridin-2-yl)amino]thiophene-3-carboxamide;

5-[2,6-difluoro-4-(1-hydroxy-1-methylethyl)phenyl]-2-[(6-{[(4-hydroxybutyl)sulfonyl]methyl}pyridin-2-yl)amino]thiophene-3-carboxamide;

5-[2,6-difluoro-4-(1-hydroxy-1-methylethyl)phenyl]-2-{[6-({[2-(methylamino)-2-oxoethyl]sulfonyl}methyl)pyridin-2-yl]amino}thiophene-3-carboxamide;

5-[2,6-difluoro-4-(1-hydroxy-1-methylethyl)phenyl]-2-[(6-{[(4-methyl-4H-1,2,4-triazol-3-yl)sulfonyl]methyl}pyridin-2-yl)amino]thiophene-3-carboxamide;

5-[2,6-difluoro-4-(1-hydroxy-1-methylethyl)phenyl]-2-{[6-({[(2R,3S)-2-methyltetrahydrofuran-3-yl]sulfonyl}methyl)pyridin-2-yl]amino}thiophene-3-carboxamide;

5-[2,6-difluoro-4-(1-hydroxy-1-methylethyl)phenyl]-2-{[6-({[(2S,3S)-2-methyltetrahydrofuran-3-yl]sulfonyl}methyl)pyridin-2-yl]amino}thiophene-3-carboxamide;

5-[2,6-difluoro-4-(1-hydroxy-1-methylethyl)phenyl]-2-({6-[(isopropylsulfonyl)methyl]pyridin-2-yl}amino)thiophene-3-carboxamide;

5-[2,6-difluoro-4-(1-hydroxy-1-methylethyl)phenyl]-2-({2-[(ethylsulfonyl)methyl]pyrimidin-4-yl}amino)thiophene-3-carboxamide;

5-[2,6-difluoro-4-(3-hydroxyoxetan-3-yl)phenyl]-2-({6-[(ethylsulfonyl)methyl]pyridin-2-yl}amino)thiophene-3-carboxamide;

5-[2,6-difluoro-4-(3-hydroxyoxetan-3-yl)phenyl]-2-({6-[(isopropylsulfonyl)methyl]pyridin-2-yl}amino)thiophene-3-carboxamide;

5-[2,6-Difluoro-4-(1-hydroxy-1-methylethyl)phenyl]-2-({6-[(methylsulfonyl)methyl]pyridin-2-yl}amino)thiophene-3-carboxamide;

5-[2-fluoro-4-(1-hydroxy-1-methylethyl)phenyl]-2-({6-[(methylsulfonyl)methyl]pyridin-2-yl}amino)thiophene-3-carboxamide;

5-[2-Fluoro-4-(1-hydroxy-1-methylethyl)phenyl]-2-{[6-(methylsulfonyl)pyridin-2-yl]amino}thiophene-3-carboxamide;

5-[2,6-difluoro-4-(1-hydroxy-1-methylethyl)phenyl]-2-{[6-(methylsulfonyl)pyridin-2-yl]amino}thiophene-3-carboxamide;

5-[2,6-Difluoro-4-(1-hydroxy-1-methylethyl)phenyl]-2-{[6-(3-hydroxypyrrolidin-1-yl)pyridin-2-yl]amino}thiophene-3-carboxamide;

5-[2,6-difluoro-4-(1-hydroxy-1-methylethyl)phenyl]-2-({6-[(2-hydroxyethyl)(methyl)amino]pyridin-2-yl}amino)thiophene-3-carboxamide;

5-[2,6-Difluoro-4-(1-hydroxy-1-methylethyl)phenyl]-2-[(6-pyrrolidin-1-ylpyridin-2-yl)amino]thiophene-3-carboxamide;

5-[2,6-Difluoro-4-(1-hydroxy-1-methylethyl)phenyl]-2-{[6-(4-methylpiperazin-1-yl)pyridin-2-yl]amino}thiophene-3-carboxamide;

5-(4-(1-hydroxy-1-methylethyl)phenyl-2-((6-(4-morpholinyl)-2-pyridinyl)amino)-3-thiophenecarboxamide;

5-(2,6-difluoro-4-(1-hydroxy-1-methylethyl)phenyl)-2-((6-(4-morpholinyl)-2-pyridinyl)amino)-3-thiophenecarboxamide;

5-[2-Fluoro-4-(1-hydroxy-1-methylethyl)phenyl]-2-{[6-(1H-pyrazol-4-yl)pyridin-2-yl]amino}thiophene-3-carboxamide;

5-[2,6-Difluoro-4-(1-hydroxy-1-methylethyl)phenyl]-2-{[6-(1-methyl-1H-pyrazol-4-yl)pyridin-2-yl]amino}thiophene-3-carboxamide;

5-[2-fluoro-4-(1-hydroxy-1-methylethyl)phenyl]-2-({6-[3-(methylsulfonyl)phenyl]pyridin-2-yl}amino)thiophene-3-carboxamide;

5-[2-fluoro-4-(1-hydroxy-1-methylethyl)phenyl]-2-{[6'-(hydroxymethyl)-2,3'-bipyridin-6-yl]amino}thiophene-3-carboxamide;

2-(2,3'-bipyridin-6-ylamino)-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-({6-[1-(2-hydroxyethyl)-1H-pyrazol-4-yl]pyridin-2-yl}amino)thiophene-3-carboxamide;

5-[2,6-Difluoro-4-(1-hydroxy-1-methylethyl)phenyl]-2-[(1'-methyl-6'-oxo-1',6'-dihydro-2,3'-bipyridin-6-yl)amino]thiophene-3-carboxamide;

6-({3-(Aminocarbonyl)-5-[2-fluoro-4-(1-hydroxy-1-methylethyl)phenyl]-2-thienyl}amino)-N,N-dimethylnicotinamide;

6-({3-(aminocarbonyl)-5-[2-fluoro-4-(1-hydroxy-1-methylethyl)phenyl]-2-thienyl}amino)-N-methylnicotinamide;

6-({3-(aminocarbonyl)-5-[2-fluoro-4-(1-hydroxy-1-methylethyl)phenyl]-2-thienyl}amino)-N-oxetan-3-ylnicotinamide;

5-[2,6-Difluoro-4-(1-hydroxy-1-methylethyl)phenyl]-2-({5-[(1,1-dioxidothiomorpholin-4-yl)methyl]pyridin-2-yl}amino)thiophene-3-carboxamide;

5-[2,6-Difluoro-4-(1-hydroxy-1-methylethyl)phenyl]-2-({5-[(4,4-difluoro piperidin-1-yl)methyl]pyridin-2-yl}amino)thiophene-3-carboxamide;

5-[2,6-difluoro-4-(1-hydroxy-1-methylethyl)phenyl]-2-({5-[(dimethylamino)methyl]pyridin-2-yl}amino)thiophene-3-carboxamide;

5-[2,6-Difluoro-4-(1-hydroxy-1-methylethyl)phenyl]-2-{[5-(pyrrolidin-1-ylmethyl)pyridin-2-yl]amino}thiophene-3-carboxamide;

5-[2-Fluoro-4-(1-hydroxy-1-methylethyl)phenyl]-2-{[5-(5-methyl-1,3,4-oxadiazol-2-yl)pyridin-2-yl]amino}thiophene-3-carboxamide;

Ethyl{4-[6-({3-(aminocarbonyl)-5-[2,6-difluoro-4-(1-hydroxy-1-methylethyl)phenyl]-2-thienyl}amino)pyridin-3-yl]-1H-1,2,3-triazol-1-yl}acetate;

5-[2,6-Difluoro-4-(1-hydroxy-1-methylethyl)phenyl]-2-({5-[1-(2-hydroxyethyl)-1H-1,2,3-triazol-4-yl]pyridin-2-yl}amino)thiophene-3-carboxamide;

5-[2,6-Difluoro-4-(1-hydroxy-1-methylethyl)phenyl]-2-({5-[(1,1-dioxidothiomorpholin-4-yl)methyl]-6-methylpyridin-2-yl}amino)thiophene-3-carboxamide;

5-[2,6-Difluoro-4-(1-hydroxy-1-methylethyl)phenyl]-2-[(5-{[(2-hydroxy-1,2-dimethylpropyl)amino]methyl}-6-methylpyridin-2-yl)amino]thiophene-3-carboxamide;

5-[2,6-difluoro-4-(1-hydroxy-1-methylethyl)phenyl]-2-[(5-{[(2-hydroxy-1,2-dimethylpropyl)amino]methyl}-6-methylpyridin-2-yl)amino]thiophene-3-carboxamide;

5-[2,6-difluoro-4-(1-hydroxy-1-methylethyl)phenyl]-2-({5-[(3-hydroxyazetidin-1-yl)methyl]-6-methylpyridin-2-yl}amino)thiophene-3-carboxamide;

2-({5-[(3,3-difluoroazetidin-1-yl)methyl]-6-methylpyridin-2-yl}amino)-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-({5-[(3,3-difluoropyrrolidin-1-yl)methyl]-6-methylpyridin-2-yl}amino)thiophene-3-carboxamide;

5-[2,6-Difluoro-4-(1-hydroxy-1-methylethyl)phenyl]-2-{[6-methyl-5-(morpholin-4-ylmethyl)pyridin-2-yl]amino}thiophene-3-carboxamide;

5-[2,6-difluoro-4-(1-hydroxy-1-methylethyl)phenyl]-2-{[5-(morpholin-4-ylmethyl)pyridin-2-yl]amino}thiophene-3-carboxamide;

5-[2-Fluoro-4-(1-hydroxy-1-methylethyl)phenyl]-2-{[5-(hydroxymethyl)-6-(morpholin-4-ylmethyl)pyridin-2-yl]amino}thiophene-3-carboxamide;

6-({3-(Aminocarbonyl)-5-[2-fluoro-4-(1-hydroxy-1-methylethyl)phenyl]-2-thienyl}amino)-2-(morpholin-4-ylmethyl)nicotinamide;

5-[2,6-Difluoro-4-(1-hydroxy-1-methylethyl)phenyl]-2-{[6-methyl-5-(5-methyl-1,3,4-oxadiazol-2-yl)pyridin-2-yl]amino}thiophene-3-carboxamide;

5-[2,6-difluoro-4-(1-hydroxy-1-methylethyl)phenyl]-2-({5-[5-(1-hydroxy-1-methylethyl)-1,3,4-oxadiazol-2-yl]-6-methylpyridin-2-yl}amino)thiophene-3-carboxamide;

2-{[5-(5-cyclopropyl-1,3,4-oxadiazol-2-yl)-6-methylpyridin-2-yl]amino}-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-({5-[5-(2-methoxyethyl)-1,3,4-oxadiazol-2-yl]-6-methylpyridin-2-yl}amino)thiophene-3-carboxamide;

5-[2,6-difluoro-4-(1-hydroxy-1-methylethyl)phenyl]-2-({6-methyl-5-[5-(trifluoromethyl)-1,3,4-oxadiazol-2-yl]pyridin-2-yl}amino)thiophene-3-carboxamide;

5-[2,6-Difluoro-4-(1-hydroxy-1-methylethyl)phenyl]-2-({5-[3-(2-hydroxyethyl)-1,2,4-oxadiazol-5-yl]-6-methylpyridin-2-yl}amino)thiophene-3-carboxamide;

5-[2,6-Difluoro-4-(1-hydroxy-1-methylethyl)phenyl]-2-{[6-methyl-5-(5-oxo-4,5-dihydro-1,3,4-oxadiazol-2-yl)pyridin-2-yl]amino}thiophene-3-carboxamide;

5-[2,6-Difluoro-4-(1-hydroxy-1-methylethyl)phenyl]-2-({5-[1-(2-hydroxyethyl)-1H-1,2,3-triazol-4-yl]-6-methylpyridin-2-yl}amino)thiophene-3-carboxamide;

5-[2,6-Difluoro-4-(1-hydroxy-1-methylethyl)phenyl]-2-({5-[1-(2-hydroxy-2-methylpropyl)-1H-1,2,3-triazol-5-yl]-6-methylpyridin-2-yl}amino)thiophene-3-carboxamide;

5-[2,6-Difluoro-4-(1-hydroxy-1-methylethyl)phenyl]-2-{[6-methyl-5-(1H-1,2,3-triazol-4-yl)pyridin-2-yl]amino}thiophene-3-carboxamide;

5-[2,6-Difluoro-4-(1-hydroxy-1-methylethyl)phenyl]-2-({5-[(2-hydroxy-2-methylpropoxy)methyl]-6-methylpyridin-2-yl}amino)thiophene-3-carboxamide;

5-[2,6-Difluoro-4-(1-hydroxy-1-methylethyl)phenyl]-2-[(6-methyl-5-{[2-(3-oxomorpholin-4-yl)ethoxy]methyl}pyridin-2-yl)amino]thiophene-3-carboxamide;

2-({5-[(Azetidin-3-yloxy)methyl]-6-methylpyridin-2-yl}amino)-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-{[6-(2,2,2-trifluoro-1-hydroxyethyl)pyridin-2-yl]amino}thiophene-3-carboxamide;

5-[2-fluoro-4-(1-hydroxy-1-methylethyl)phenyl]-2-{[6-(2,2,2-trifluoro-1-hydroxyethyl)pyridin-2-yl]amino}thiophene-3-carboxamide;

4-{[6-({3-(Aminocarbonyl)-5-[2-fluoro-4-(1-hydroxy-1-methylethyl)phenyl]-2-thienyl}amino)pyridin-2-yl]methyl}morpholine-3-carboxamide;

5-[2-Fluoro-4-(1-hydroxy-1-methylethyl)phenyl]-2-{[6-(1-fluoro-2-morpholin-4-ylethyl)pyridin-2-yl]amino}thiophene-3-carboxamide;

5-[2-Fluoro-4-(1-hydroxy-1-methylethyl)phenyl]-2-{[6-(2-methoxy-1-morpholin-4-ylethyl)pyridin-2-yl]amino}thiophene-3-carboxamide;

5-[2-Fluoro-4-(1-hydroxy-1-methylethyl)phenyl]-2-{[6-(2-fluoro-1-morpholin-4-ylethyl)pyridin-2-yl]amino}thiophene-3-carboxamide;

5-[2,6-Difluoro-4-(1-hydroxy-1-methylethyl)phenyl]-2-{[6-(2-fluoro-1-hydroxyethyl)pyridin-2-yl]amino}thiophene-3-carboxamide;

5-[2-Fluoro-4-(1-hydroxy-1-methylethyl)phenyl]-2-{[5-(2,2,2-trifluoro-1-hydroxyethyl)pyridin-2-yl]amino}thiophene-3-carboxamide;

2-{[6-Methyl-5-(2,2,2-trifluoro-1-hydroxyethyl)pyridin-2-yl]amino}-5-(6-morpholin-4-ylpyridin-3-yl)thiophene-3-carboxamide;

5-[2,6-Difluoro-4-(1-hydroxy-1-methylethyl)phenyl]-2-{[5-(1-hydroxy-1-methylethyl)-6-methylpyridin-2-yl]amino}thiophene-3-carboxamide;

2-{[5-(1-Hydroxy-1-methylethyl)-6-methylpyridin-2-yl]amino}-5-(6-morpholin-4-ylpyridin-3-yl)thiophene-3-carboxamide;

5-[2,6-Difluoro-4-(1-hydroxy-1-methylethyl)phenyl]-2-{[5-(1-hydroxyethyl)-6-methylpyridin-2-yl]amino}thiophene-3-carboxamide;

5-[2-fluoro-4-(1-hydroxy-1-methylethyl)phenyl]-2-{[5-(1-hydroxyethyl)-6-methylpyridin-2-yl]amino}thiophene-3-carboxamide;

2-{[5-(1-hydroxyethyl)-6-methylpyridin-2-yl]amino}-5-(6-morpholin-4-ylpyridin-3-yl)thiophene-3-carboxamide;

5-[2-Fluoro-4-(1-methoxy-1-methylethyl)phenyl]-2-{[5-(1-methoxyethyl)-6-methylpyridin-2-yl]amino}thiophene-3-carboxamide;

2-{[6-Chloro-5-(1-hydroxy-1-methylethyl)pyridin-2-yl]amino}-5-[2-fluoro-4-(1-hydroxy-1-methylethyl)phenyl]thiophene-3-carboxamide;

5-[2,6-Difluoro-4-(1-hydroxy-1-methylethyl)phenyl]-2-{[6-fluoro-5-(1-hydroxy-1-methylethyl)pyridin-2-yl]amino}thiophene-3-carboxamide;

5-[2,6-Difluoro-4-(1-hydroxy-1-methylethyl)phenyl]-2-{[6-fluoro-5-(methylsulfonyl)pyridin-2-yl]amino}thiophene-3-carboxamide;

5-[2,6-Difluoro-4-(1-hydroxy-1-methylethyl)phenyl]-2-({5-[(1,1-dioxidothiomorpholin-4-yl)methyl]-6-fluoropyridin-2-yl}amino)thiophene-3-carboxamide;

Methyl{[6-({3-(aminocarbonyl)-5-[2,6-difluoro-4-(1-hydroxy-1-methylethyl)phenyl]-2-thienyl}amino)-2-methylpyridin-3-yl]methyl}carbamate;

5-[2,6-Difluoro-4-(1-hydroxy-1-methylethyl)phenyl]-2-{[5-(1-hydroxy-1-methylethyl)-6-methoxypyridin-2-yl]amino}thiophene-3-carboxamide;

5-[2,6-Difluoro-4-(1-hydroxy-1-methylethyl)phenyl]-2-{[6-(hydroxymethyl)-5-(1-hydroxy-1-methylethyl)pyridin-2-yl]amino}thiophene-3-carboxamide;

2-[(5-Cyano-6-methylpyridin-2-yl)amino]-5-[2,6-difluoro-4-(1-hydroxy-1-methylethyl)phenyl]thiophene-3-carboxamide;

2-{[5-(Acetylamino)-6-methylpyridin-2-yl]amino}-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-({6-methyl-5-[(methylsulfonyl)amino]pyridin-2-yl}amino)thiophene-3-carboxamide;

2-({5-[bis(Methylsulfonyl)amino]-6-methylpyridin-2-yl}amino)-5-[2,6-difluoro-4-(1-hydroxy-1-methylethyl)phenyl]thiophene-3-carboxamide;

2-({5-[(Cyclopropylmethyl)amino]-6-methylpyridin-2-yl}amino)-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-{[5-(3-hydroxy-3-methylbut-1-yn-1-yl)-6-methylpyridin-2-yl]amino}thiophene-3-carboxamide;

5-[2,6-Difluoro-4-(1-hydroxy-1-methylethyl)phenyl]-2-{[6-(3-hydroxy-3-methylbut-1-yn-1-yl)pyridin-2-yl]amino}thiophene-3-carboxamide;

[6-({3-(Aminocarbonyl)-5-[2-fluoro-4-(1-hydroxy-1-methylethyl)phenyl]-2-thienyl}amino)pyridin-2-yl]methyl dimethylphosphinate;

5-[2,6-Difluoro-4-(1-hydroxy-1-methylethyl)phenyl]-2-({6-[(4-methyl-4-oxido-1,4-azaphosphinan-1-yl)methyl]pyridin-2-yl}amino)thiophene-3-carboxamide;

5-[2-fluoro-4-(1-hydroxy-1-methylethyl)phenyl]-2-({6-[(4-methyl-4-oxido-1,4-azaphosphinan-1-yl)methyl]pyridin-2-yl}amino)thiophene-3-carboxamide;

Methyl{[6-({3-(aminocarbonyl)-5-[2-fluoro-4-(1-hydroxy-1-methylethyl)phenyl]-2-thienyl}amino)pyridin-2-yl]methyl}methylphosphinate;

1-{[6-({3-(Aminocarbonyl)-5-[2,6-difluoro-4-(1-hydroxy-1-methylethyl)phenyl]-2-thienyl}amino)pyridin-2-yl]methyl}-N-methyl-1H-1,2,3-triazole-4-carboxamide;

5-[2-fluoro-4-(1-hydroxy-1-methylethyl)phenyl]-2-[(6-{[4-(hydroxymethyl)-1H-1,2,3-triazol-1-yl]methyl}pyridin-2-yl)amino]thiophene-3-carboxamide;

5-[2-fluoro-4-(1-hydroxy-1-methylethyl)phenyl]-2-[(6-{[4-(2-hydroxyethyl)-1H-1,2,3-triazol-1-yl]methyl}pyridin-2-yl)amino]thiophene-3-carboxamide;

5-[2-fluoro-4-(1-hydroxy-1-methylethyl)phenyl]-2-[(6-{[4-(1-hydroxy-1-methylethyl)-1H-1,2,3-triazol-1-yl]methyl}pyridin-2-yl)amino]thiophene-3-carboxamide;

5-[4-(1,1-dioxidothiomorpholin-4-yl)phenyl]-2-[(6-{[4-(1-hydroxy-1-methylethyl)-1H-1,2,3-triazol-1-yl]methyl}pyridine-2-yl)amino]thiophene-3-carboxamide;

2-[(6-{[4-(1-hydroxy-1-methylethyl)-1H-1,2,3-triazol-1-yl]methyl}pyridin-2-yl)amino]-5-(4-morpholin-4-ylphenyl)thiophene-3-carboxamide;

2-[(6-{[4-(1-hydroxy-1-methylethyl)-1H-1,2,3-triazol-1-yl]methyl}pyridin-2-yl)amino]-5-(4-pyridin-4-ylphenyl)thiophene-3-carboxamide;

2-[(6-{[4-(1-hydroxy-1-methylethyl)-1H-1,2,3-triazol-1-yl]methyl}pyridin-2-yl)amino]-5-[4-(1H-pyrazol-1-yl)phenyl]thiophene-3-carboxamide;

2-[(6-{[4-(1-hydroxy-1-methylethyl)-1H-1,2,3-triazol-1-yl]methyl}pyridin-2-yl)amino]-5-(4-hydroxyphenyl)thiophene-3-carboxamide;

2-[(6-{[4-(1-hydroxy-1-methylethyl)-1H-1,2,3-triazol-1-yl]methyl}pyridin-2-yl)amino]-5-(2-hydroxyphenyl)thiophene-3-carboxamide;

5-(2-aminophenyl)-2-[(6-{[4-(1-hydroxy-1-methylethyl)-1H-1,2,3-triazol-1-yl]methyl}pyridin-2-yl)amino]thiophene-3-carboxamide;

2-[(6-{[4-(1-hydroxy-1-methylethyl)-1H-1,2,3-triazol-1-yl]methyl}pyridin-2-yl)amino]-5-[6-(1-methyl-1H-pyrazol-5-yl)pyridin-3-yl]thiophene-3-carboxamide;

2-[(6-{[4-(1-hydroxy-1-methylethyl)-1H-1,2,3-triazol-1-yl]methyl}pyridin-2-yl)amino]-5-[6-(1-methyl-1H-pyrazol-4-yl)pyridin-3-yl]thiophene-3-carboxamide;

5-(2,4'-bipyridin-5-yl)-2-[(6-{[4-(1-hydroxy-1-methylethyl)-1H-1,2,3-triazol-1-yl]methyl}pyridin-2-yl)amino]thiophene-3-carboxamide;

methyl 1-{[6-({3-(aminocarbonyl)-5-[2-fluoro-4-(1-hydroxy-1-methylethyl)phenyl]-2-thienyl}amino)pyridin-2-yl]methyl}-1H-1,2,3-triazole-4-carboxylate;

1-{[6-({3-(aminocarbonyl)-5-[2-fluoro-4-(1-hydroxy-1-methylethyl)phenyl]-2-thienyl}amino)pyridin-2-yl]methyl}-1H-1,2,3-triazole-4-carboxamide;

1-{[6-({3-(aminocarbonyl)-5-[2-fluoro-4-(1-hydroxy-1-methylethyl)phenyl]-2-thienyl}amino)pyridin-2-yl]methyl}-N-methyl-1H-1,2,3-triazole-4-carboxamide;

5-[2,6-difluoro-4-(1-hydroxy-1-methylethyl)phenyl]-2-[(6-{[4-(hydroxymethyl)-1H-1,2,3-triazol-1-yl]methyl}pyridin-2-yl)amino]thiophene-3-carboxamide;

5-[2,6-difluoro-4-(1-hydroxy-1-methylethyl)phenyl]-2-{[6-({4-[(dimethylamino)methyl]-1H-1,2,3-triazol-1-yl}methyl)pyridin-2-yl]amino}thiophene-3-carboxamide;

5-[2,6-difluoro-4-(1-hydroxy-1-methylethyl)phenyl]-2-[(6-{[4-(2-hydroxyethyl)-1H-1,2,3-triazol-1-yl]methyl}pyridin-2-yl)amino]thiophene-3-carboxamide;

5-[2,6-difluoro-4-(1-hydroxy-1-methylethyl)phenyl]-2-[(6-{[4-(1-hydroxy-1-methylethyl)-1H-1,2,3-triazol-1-yl]methyl}pyridin-2-yl)amino]thiophene-3-carboxamide;

1-{[6-({3-(aminocarbonyl)-5-[2,6-difluoro-4-(1-hydroxy-1-methylethyl)phenyl]-2-thienyl}amino)pyridin-2-yl]methyl}-N,N-dimethyl-1H-1,2,3-triazole-4-carboxamide;

1-{[6-({3-(aminocarbonyl)-5-[2,6-difluoro-4-(1-hydroxy-1-methylethyl)phenyl]-2-thienyl}amino)pyridin-2-yl]methyl}-N-(2-hydroxyethyl)-1H-1,2,3-triazole-4-carboxamide;

5-[2,6-difluoro-4-(1-hydroxy-1-methylethyl)phenyl]-2-[(6-{[4-(pyrrolidin-1-ylcarbonyl)-1H-1,2,3-triazol-1-yl]methyl}pyridin-2-yl)amino]thiophene-3-carboxamide;

2-[(6-{[4-(Aminomethyl)-1H-1,2,3-triazol-1-yl]methyl}pyridin-2-yl)amino]-5-[2,6-difluoro-4-(1-hydroxy-1-methylethyl)phenyl]thiophene-3-carboxamide;

1-{[6-({3-(Aminocarbonyl)-5-[2,6-difluoro-4-(1-hydroxy-1-methylethyl)phenyl]-2-thienyl}amino)pyridin-2-yl]methyl}-N-methyl-1H-1,2,3-triazole-5-carboxamide;

5-[2,6-difluoro-4-(1-hydroxy-1-methylethyl)phenyl]-2-[(6-{[5-(2-hydroxyethyl)-1H-1,2,3-triazol-1-yl]methyl}pyridin-2-yl)amino]thiophene-3-carboxamide;

5-[2-Fluoro-4-(1-hydroxy-1-methylethyl)phenyl]-2-({6-[2-hydroxy-1-(1H-1,2,3-triazol-1-yl)ethyl]pyridin-2-yl}amino)thiophene-3-carboxamide;

5-[2-fluoro-4-(1-hydroxy-1-methylethyl)phenyl]-2-{[6-(1H-1,2,3-triazol-1-ylmethyl)pyridin-2-yl]amino}thiophene-3-carboxamide;

5-[2,6-difluoro-4-(1-hydroxy-1-methylethyl)phenyl]-2-{[6-(1H-1,2,3-triazol-1-ylmethyl)pyridin-2-yl]amino}thiophene-3-carboxamide;

5-[2,6-difluoro-4-(1-hydroxy-1-methylethyl)phenyl]-2-{[6-(2H-1,2,3-triazol-2-ylmethyl)pyridin-2-yl]amino}thiophene-3-carboxamide;

5-(4-chlorophenyl)-2-{[6-(1H-1,2,3-triazol-1-ylmethyl)pyridin-2-yl]amino}thiophene-3-carboxamide;

5-[2,6-difluoro-4-(1-hydroxy-1-methylethyl)phenyl]-2-{[6-(1H-pyrazol-1-ylmethyl)pyridin-2-yl]amino}thiophene-3-carboxamide;

5-[2,6-difluoro-4-(1-hydroxy-1-methylethyl)phenyl]-2-{[6-(1H-imidazol-1-ylmethyl)pyridin-2-yl]amino}thiophene-3-carboxamide;

5-[2,6-difluoro-4-(1-hydroxy-1-methylethyl)phenyl]-2-{[5-(1H-1,2,3-triazol-1-ylmethyl)pyridin-2-yl]amino}thiophene-3-carboxamide;

5-[2,6-difluoro-4-(1-hydroxy-1-methylethyl)phenyl]-2-{[5-(2H-1,2,3-triazol-2-ylmethyl)pyridin-2-yl]amino}thiophene-3-carboxamide;

5-[2,6-Difluoro-4-(1-hydroxy-1-methylethyl)phenyl]-2-{[6-methyl-5-(1H-1,2,3-triazol-1-ylmethyl)pyridin-2-yl]amino}thiophene-3-carboxamide;

5-[2,6-difluoro-4-(1-hydroxy-1-methylethyl)phenyl]-2-{[6-methyl-5-(2H-1,2,3-triazol-2-ylmethyl)pyridin-2-yl]amino}thiophene-3-carboxamide;

5-[2,6-Difluoro-4-(1-hydroxy-1-methylethyl)phenyl]-2-{[6-(1H-1,2,3-triazol-1-yl)pyridin-2-yl]amino}thiophene-3-carboxamide;

5-[2,6-Difluoro-4-(1-hydroxy-1-methylethyl)phenyl]-2-({6-[4-(2-hydroxyethyl)-1H-1,2,3-triazol-1-yl]pyridin-2-yl}amino)thiophene-3-carboxamide;

5-[2,6-Difluoro-4-(1-hydroxy-1-methylethyl)phenyl]-2-{[6-(1-methyl-1H-1,2,3-triazol-4-yl)pyridin-2-yl]amino}thiophene-3-carboxamide;

5-[2,6-Difluoro-4-(1-hydroxy-1-methylethyl)phenyl]-2-({6-[1-(2-hydroxyethyl)-1H-1,2,3-triazol-4-yl]pyridin-2-yl}amino)thiophene-3-carboxamide;

5-[2-Fluoro-4-(1-hydroxy-1-methylethyl)phenyl]-2-({6-[fluoro(1-methyl-1H-1,2,3-triazol-4-yl)methyl]pyridin-2-yl}amino)thiophene-3-carboxamide;

5-[2-Fluoro-4-(1-hydroxy-1-methylethyl)phenyl]-2-[(6-{1-hydroxy-1-[1-(2-hydroxyethyl)-1H-1,2,3-triazol-4-yl]ethyl}pyridin-2-yl)amino]thiophene-3-carboxamide;

5-[2-fluoro-4-(1-hydroxy-1-methylethyl)phenyl]-2-({6-[hydroxy(1-methyl-1H-1,2,3-triazol-4-yl)methyl]pyridin-2-yl}amino)thiophene-3-carboxamide;

5-[2-fluoro-4-(1-hydroxy-1-methylethyl)phenyl]-2-[(6-{hydroxy[1-(2-hydroxyethyl)-1H-1,2,3-triazol-4-yl]methyl}pyridin-2-yl)amino]thiophene-3-carboxamide;

5-[2-fluoro-4-(1-hydroxy-1-methylethyl)phenyl]-2-({6-[1-hydroxy-1-(1-methyl-1H-1,2,3-triazol-4-yl)ethyl]pyridin-2-yl}amino)thiophene-3-carboxamide;

2-({6-[[1-(2-Amino-2-oxoethyl)-1H-1,2,3-triazol-4-yl](hydroxy)methyl]pyridin-2-yl}amino)-5-[2-fluoro-4-(1-hydroxy-1-methylethyl)phenyl]thiophene-3-carboxamide;

2-({6-[{1-[2-(dimethylamino)-2-oxoethyl]-1H-1,2,3-triazol-4-yl}(hydroxy)methyl]pyridin-2-yl}amino)-5-[2-fluoro-4-(1-hydroxy-1-methylethyl)phenyl]thiophene-3-carboxamide;

5-[2,6-Difluoro-4-(1-hydroxy-1-methylethyl)phenyl]-2-[(6-{[2-(2-hydroxyethyl)-2H-tetrazol-5-yl]methyl}pyridin-2-yl)amino]thiophene-3-carboxamide;

5-[2,6-difluoro-4-(1-hydroxy-1-methylethyl)phenyl]-2-[(6-{[1-(2-hydroxyethyl)-1H-tetrazol-5-yl]methyl}pyridin-2-yl)amino]thiophene-3-carboxamide;

5-[2-fluoro-4-(1-hydroxy-1-methylethyl)phenyl]-2-[(6-{[2-(2-hydroxyethyl)-2H-tetrazol-5-yl]methyl}pyridin-2-yl)amino]thiophene-3-carboxamide;

5-[2-fluoro-4-(1-hydroxy-1-methylethyl)phenyl]-2-[(6-{[1-(2-hydroxyethyl)-1H-tetrazol-5-yl]methyl}pyridin-2-yl)amino]thiophene-3-carboxamide;

5-[2,6-difluoro-4-(1-hydroxy-1-methylethyl)phenyl]-2-({6-[(2-methyl-2H-tetrazol-5-yl)methyl]pyridin-2-yl}amino)thiophene-3-carboxamide;

5-[2,6-difluoro-4-(1-hydroxy-1-methylethyl)phenyl]-2-({6-[(1-methyl-1H-tetrazol-5-yl)methyl]pyridin-2-yl}amino)thiophene-3-carboxamide;

5-[2-fluoro-4-(1-hydroxy-1-methylethyl)phenyl]-2-({6-[(2-methyl-2H-tetrazol-5-yl)methyl]pyridin-2-yl}amino)thiophene-3-carboxamide;

5-[2-fluoro-4-(1-hydroxy-1-methylethyl)phenyl]-2-({6-[(1-methyl-1H-tetrazol-5-yl)methyl]pyridin-2-yl}amino)thiophene-3-carboxamide;

2-({6-[(5-Cyclopropyl-1,3,4-oxadiazol-2-yl)methyl]pyridin-2-yl}amino)-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-({6-[(5-methyl-1,3,4-oxadiazol-2-yl)methyl]pyridin-2-yl}amino)thiophene-3-carboxamide;

5-[2-Fluoro-4-(1-hydroxy-1-methylethyl)phenyl]-2-{[2-(morpholin-4-ylmethyl)pyrimidin-4-yl]amino}thiophene-3-carboxamide;

5-(4-tert-butylphenyl)-2-{[2-(morpholin-4-ylmethyl)pyrimidin-4-yl]amino}thiophene-3-carboxamide;

5-[4-(1-cyano-1-methylethyl)phenyl]-2-{[2-(morpholin-4-ylmethyl)pyrimidin-4-yl]amino}thiophene-3-carboxamide;

5-[2,6-difluoro-4-(1-hydroxy-1-methylethyl)phenyl]-2-{[2-(morpholin-4-ylmethyl)pyrimidin-4-yl]amino}thiophene-3-carboxamide;

5-[4-(1-hydroxyethyl)phenyl]-2-{[2-(morpholin-4-ylmethyl)pyrimidin-4-yl]amino}thiophene-3-carboxamide;

5-[4-(1,1-dioxidothiomorpholin-4-yl)phenyl]-2-{[2-(morpholin-4-ylmethyl)pyrimidin-4-yl]amino}thiophene-3-carboxamide;

5-[4-(hydroxymethyl)phenyl]-2-{[2-(morpholin-4-ylmethyl)pyrimidin-4-yl]amino}thiophene-3-carboxamide;

2-{[2-(morpholin-4-ylmethyl)pyrimidin-4-yl]amino}-5-(6-morpholin-4-ylpyridin-3-yl)thiophene-3-carboxamide;

5-[4-(3-hydroxyoxetan-3-yl)phenyl]-2-{[2-(morpholin-4-ylmethyl)pyrimidin-4-yl]amino}thiophene-3-carboxamide;

5-[4-(3-fluorooxetan-3-yl)phenyl]-2-{[2-(morpholin-4-ylmethyl)pyrimidin-4-yl]amino}thiophene-3-carboxamide;

5-(4-cyanophenyl)-2-{[2-(morpholin-4-ylmethyl)pyrimidin-4-yl]amino}thiophene-3-carboxamide;

2-{[2-(morpholin-4-ylmethyl)pyrimidin-4-yl]amino}-5-[4-(1H-1,2,3-triazol-4-yl)phenyl]thiophene-3-carboxamide;

5-[4-(morpholin-4-ylmethyl)phenyl]-2-{[2-(morpholin-4-ylmethyl)pyrimidin-4-yl]amino}thiophene-3-carboxamide;

5-[4-(morpholin-4-ylcarbonyl)phenyl]-2-{[2-(morpholin-4-ylmethyl)pyrimidin-4-yl]amino}thiophene-3-carboxamide;

5-{4-[(acetylamino)methyl]phenyl}-2-{[2-(morpholin-4-ylmethyl)pyrimidin-4-yl]amino}thiophene-3-carboxamide;

5-[6-(1-hydroxy-1-methylethyl)pyridin-3-yl]-2-{[2-(morpholin-4-ylmethyl)pyrimidin-4-yl]amino}thiophene-3-carboxamide;

2-({2-[(1,1-dioxidothiomorpholin-4-yl)methyl]pyrimidin-4-yl}amino)-5-[2-fluoro-4-(1-hydroxy-1-methylethyl)phenyl]thiophene-3-carboxamide;

5-{4-[(1S)-1-Hydroxyethyl]phenyl}-2-{[2-(morpholin-4-ylmethyl)pyrimidin-4-yl]amino}thiophene-3-carboxamide;

5-{4-[(1R)-1-hydroxyethyl]phenyl}-2-{[2-(morpholin-4-ylmethyl)pyrimidin-4-yl]amino}thiophene-3-carboxamide;

5-[2-Fluoro-4-(1-hydroxy-1-methylethyl)phenyl]-2-[(2-{[3-(fluoromethyl)morpholin-4-yl]methyl}pyrimidin-4-yl)amino]thiophene-3-carboxamide;

5-[2-Fluoro-4-(1-hydroxy-1-methylethyl)phenyl]-2-{[2-(hydroxymethyl)pyrimidin-4-yl]amino}thiophene-3-carboxamide;

5-[2,6-Difluoro-4-(1-hydroxy-1-methylethyl)phenyl]-2-{[2-(fluoromethyl)pyrimidin-4-yl]amino}thiophene-3-carboxamide;

[4-({3-(Aminocarbonyl)-5-[2,6-difluoro-4-(1-hydroxy-1-methylethyl)phenyl]-2-thienyl}amino)pyrimidin-2-yl]methyl methylcarbamate;

5-[2,6-Difluoro-4-(1-hydroxy-1-methylethyl)phenyl]-2-({2-[(2-oxo-1,3-oxazolidin-3-yl)methyl]pyrimidin-4-yl}amino)thiophene-3-carboxamide;

5-[2,6-difluoro-4-(1-hydroxy-1-methylethyl)phenyl]-2-{[2-({[(1-methyl-1H-pyrazol-4-yl)methyl]amino}methyl)pyrimidin-4-yl]amino}thiophene-3-carboxamide;

5-[2,6-difluoro-4-(1-hydroxy-1-methylethyl)phenyl]-2-{[2-({[(1-methyl-1H-pyrazol-4-yl)methyl]amino}methyl)pyrimidin-3-yl]amino}thiophene-3-carboxamide;

5-[2,6-difluoro-4-(1-hydroxy-1-methylethyl)phenyl]-2-[(2-{[(2-hydroxy-1,2dimethylpropyl)amino]methyl}pyrimidin-4-yl)amino]thiophene-3-carboxamide;

5-[2,6-Difluoro-4-(1-hydroxy-1-methylethyl)phenyl]-2-[(2-pyrrolidin-1-ylpyrimidin-4-yl)amino]thiophene-3-carboxamide;

5-[2,6-Difluoro-4-(1-hydroxy-1-methylethyl)phenyl]-2-{[2-(3-hydroxypyrrolidin-1-yl)pyrimidin-4-yl]amino}thiophene-3-carboxamide;

5-[2,6-difluoro-4-(1-hydroxy-1-methylethyl)phenyl]-2-{[2-(4-methylpiperazin-1-yl)pyrimidin-4-yl]amino}thiophene-3-carboxamide;

5-[2,6-Difluoro-4-(1-hydroxy-1-methylethyl)phenyl]-2-[(2-{[4-(trimethylsilyl)-1H-1,2,3-triazol-1-yl]methyl}pyrimidin-4-yl)amino]thiophene-3-carboxamide;

2-[(2-Cyanopyrimidin-4-yl)amino]-5-[2,6-difluoro-4-(1-hydroxy-1-methylethyl)phenyl]thiophene-3-carboxamide;

5-[2-Fluoro-4-(1-hydroxy-1-methylethyl)phenyl]-2-{[2-(2,2,2-trifluoro-1-hydroxyethyl)pyrimidin-4-yl]amino}thiophene-3-carboxamide;

2-[(2-Cyclopropylpyrimidin-4-yl)amino]-5-[2,6-difluoro-4-(1-hydroxy-1-methylethyl)phenyl]thiophene-3-carboxamide;

2-[(2-cyclopropylpyrimidin-4-yl)amino]-5-[2-fluoro-4-(1-hydroxy-1-methylethyl)phenyl]thiophene-3-carboxamide;

5-[2,6-Difluoro-4-(1-hydroxy-1-methylethyl)phenyl]-2-[(2-{[(dimethylamino)sulfonyl]amino}pyrimidin-4-yl)amino]thiophene-3-carboxamide;

5-[2-Fluoro-4-(1-hydroxy-1-methylethyl)phenyl]-2-[(2-{[2-(2-hydroxyethyl)morpholin-4-yl]methyl}pyrimidin-4-yl)amino]thiophene-3-carboxamide;

5-[2-Fluoro-4-(1-hydroxy-1-methylethyl)phenyl]-2-{[6-(1-hydroxy-1-methylethyl)pyridazin-3-yl]amino}thiophene-3-carboxamide;

5-[2,6-difluoro-4-(1-hydroxy-1-methylethyl)phenyl]-2-{[6-(1-hydroxy-1-methylethyl)pyridazin-3-yl]amino}thiophene-3-carboxamide;

2-{[6-(1-hydroxy-1-methylethyl)pyridazin-3-yl]amino}-5-(6-morpholin-4-ylpyridin-3-yl)thiophene-3-carboxamide;

2-[(6-cyanopyridazin-3-yl)amino]-5-[2,6-difluoro-4-(1-hydroxy-1-methylethyl)phenyl]thiophene-3-carboxamide;

2-[(6-aminopyridazin-3-yl)amino]-5-[2-fluoro-4-(1-hydroxy-1-methylethyl)phenyl]thiophene-3-carboxamide;

5-[2,6-difluoro-4-(1-hydroxy-1-methylethyl)phenyl]-2-{[6-(1H-imidazol-1-yl)pyridazin-3-yl]amino}thiophene-3-carboxamide;

5-[2,6-difluoro-4-(1-hydroxy-1-methylethyl)phenyl]-2-({6-[(1E)-3-hydroxy-3-methylbut-1-en-1-yl]pyridazin-3-yl}amino)thiophene-3-carboxamide;

2-{[6-(3,3-difluoroazetidin-1-yl)pyridazin-3-yl]amino}-5-[2,6-difluoro-4-(1-hydroxy-1-methylethyl)phenyl]thiophene-3-carboxamide;

5-[2,6-difluoro-4-(1-hydroxy-1-methylethyl)phenyl]-2-{[6-(3-hydroxy-3-methylbut-1-yn-1-yl)pyridazin-3-yl]amino}thiophene-3-carboxamide;

5-[2,6-difluoro-4-(1-hydroxy-1-methylethyl)phenyl]-2-{[6-(1H-pyrazol-5-yl)pyridazin-3-yl]amino}thiophene-3-carboxamide;

5-[2,6-Difluoro-4-(1-hydroxy-1-methylethyl)phenyl]-2-{[6-(1H-pyrazol-5-yl)pyridazin-3-yl]amino}thiophene-3-carboxamide;

5-[2,6-Difluoro-4-(1-hydroxy-1-methylethyl)phenyl]-2-[(2-oxo-1,2-dihydropyrimidin-4-yl)amino]thiophene-3-carboxamide;

5-[4-(1-Cyano-1-methylethyl)phenyl]-2-[(2-oxo-1,2-dihydropyrimidin-4-yl)amino]thiophene-3-carboxamide;

5-[2,6-Difluoro-4-(1-hydroxy-1-methylethyl)phenyl]-2-[(6-oxo-1,6-dihydropyridazin-3-yl)amino]thiophene-3-carboxamide;

Methyl[3-({3-(aminocarbonyl)-5-[2,6-difluoro-4-(1-hydroxy-1-methylethyl)phenyl]-2-thienyl}amino)-6-oxopyridazin-1(6H)-yl]acetate;

5-[2,6-Difluoro-4-(1-hydroxy-1-methylethyl)phenyl]-2-[(1-methyl-6-oxo-1,6-dihydropyridazin-3-yl)amino]thiophene-3-carboxamide;

2-{[6-Morpholin-4-ylmethyl)pyridine-2-yl]amino}-5-pyridin-3-ylthiophene-3-carboxamide;

5-[6-(hydroxymethyl)pyridin-3-yl]-2-{[6-(morpholin-4-ylmethyl)pyridin-2-yl]amino}thiophene-3-carboxamide;

2-{[6-(morpholin-4-ylmethyl)pyridin-2-yl]amino}-5-(6-morpholin-4-ylpyridin-3-yl)thiophene-3-carboxamide;

5-(6-aminopyridin-3-yl)-2-{[6-(morpholin-4-ylmethyl)pyridin-2-yl]amino}thiophene-3-carboxamide;

2-{[6-(morpholin-4-ylmethyl)pyridin-2-yl]amino}-5-pyridin-4-ylthiophene-3-carboxamide;

5-(2-aminopyrimidin-5-yl)-2-{[6-(morpholin-4-ylmethyl) pyridin-2-yl]amino}thiophene-3-carboxamide;

2-{[6-(morpholin-4-ylmethyl)pyridin-2-yl]amino}-5-pyrimidin-5-ylthiophene-3-carboxamide;

2-{[6-(morpholin-4-ylmethyl)pyridin-2-yl]amino}-5-(2-piperazin-1-ylpyridin-4-yl)thiophene-3-carboxamide;

2-{[6-(2-Hydroxy-1-morpholin-4-ylethyl)pyridine-2-yl] amino}-5-(6-piperidin-1-ylpyridin-3-yl)thiophene-3-carboxamide;

2-{[6-(2-hydroxy-1-morpholin-4-ylethyl)pyridin-2-yl] amino}-5-[6-(4-methylpiperazin-1-yl)pyridin-3-yl] thiophene-3-carboxamide;

2-{[6-(2-Hydroxy-1-morpholin-4-ylethyl)pyridine-2-yl] amino}-5-(6-morpholin-4-ylpyridin-3-yl)thiophene-3-carboxamide;

2-[(6-{{4-(1-Hydroxy-1-methylethyl)-1H-1,2,3-triazol-1-yl]methyl}pyridine-2-yl}amino)-5-(6-morpholin-4-ylpyridin-3-yl)thiophene-3-carboxamide;

2-{[6-(2-hydroxy-1-morpholin-4-ylethyl)pyridin-2-yl] amino}-5-(4-morpholin-4-ylphenyl)thiophene-3-carboxamide;

2-{[6-(2-hydroxy-1-morpholin-4-ylethyl)pyridin-2-yl] amino}-5-(6-piperidin-1-ylpyridin-3-yl)thiophene-3-carboxamide;

2-({6-[(1R or S)-2-hydroxy-1-morpholin-4-ylethyl]pyridin-2-yl}amino)-5-(6-morpholin-4-ylpyridin-3-yl)thiophene-3-carboxamide;

2-({6-[(1R or S)-2-hydroxy-1-morpholin-4-ylethyl]pyridin-2-yl}amino)-5-(6-morpholin-4-ylpyridin-3-yl)thiophene-3-carboxamide;

2-({6-[(1R or S)-2-hydroxy-1-morpholin-4-ylethyl]pyridin-2-yl}amino)-5-(4-morpholin-4-ylphenyl)thiophene-3-carboxamide;

2-({6-[(1R or S)-2-hydroxy-1-morpholin-4-ylethyl]pyridin-2-yl}amino)-5-(4-morpholin-4-ylphenyl)thiophene-3-carboxamide;

2-{[6-(Morpholin-4-ylmethyl)pyridin-2-yl]amino}-5-(1H-1,2,3-triazol-4-yl)thiophene-3-carboxamide;

5-(1-Methyl-1H-1,2,3-triazol-4-yl)-2-{[6-(morpholin-4-ylmethyl)pyridin-2-yl]amino}thiophene-3-carboxamide;

5-ethynyl-2-{[2-(morpholin-4-ylmethyl)pyrimidin-4-yl] amino}thiophene-3-carboxamide;

[4-(4-(aminocarbonyl)-5-{[2-(morpholin-4-ylmethyl)pyrimidin-4-yl]amino}-2-thienyl)-1H-1,2,3-triazol-1-yl]methyl pivalate;

2-{[2-(morpholin-4-ylmethyl)pyrimidin-4-yl]amino}-5-(1H-1,2,3-triazol-4-yl)thiophene-3-carboxamide;

2-{[2-(morpholin-4-ylmethyl)pyrimidin-4-yl]amino}-5-{1-[(trimethylsilyl)methyl]-1H-1,2,3-triazol-4-yl}thiophene-3-carboxamide;

5-(1-methyl-1H-1,2,3-triazol-4-yl)-2-{[2-(morpholin-4-ylmethyl)pyrimidin-4-yl]amino}thiophene-3-carboxamide;

2-{[2-(Morpholin-4-ylmethyl)pyrimidin-4-yl]amino}-5-(1H-1,2,4-triazol-3-yl)thiophene-3-carboxamide;

5-(1-Methyl-1H-pyrazol-4-yl)-2-[(6-methylpyridin-2-yl) amino]thiophene-3-carboxamide;

5-(2,4-difluorophenyl)-2-[(6-methylpyridin-2-yl)amino] thiophene-3-carboxamide;

5-(4-fluorophenyl)-2-[(6-methylpyridin-2-yl)amino] thiophene-3-carboxamide;

5-(3-fluorophenyl)-2-[(6-methylpyridin-2-yl)amino] thiophene-3-carboxamide;

5-(2-fluorophenyl)-2-[(6-methylpyridin-2-yl)amino] thiophene-3-carboxamide;

5-(2,3-difluorophenyl)-2-[(6-methylpyridin-2-yl)amino] thiophene-3-carboxamide;

5-(2-chlorophenyl)-2-[(6-methylpyridin-2-yl)amino] thiophene-3-carboxamide;

5-(2,5-dichlorophenyl)-2-[(6-methylpyridin-2-yl)amino] thiophene-3-carboxamide;

5-[2-chloro-5-(trifluoromethyl)phenyl]-2-[(6-methylpyridin-2-yl)amino]thiophene-3-carboxamide;

5-(3-chlorophenyl)-2-[(6-methylpyridin-2-yl)amino] thiophene-3-carboxamide;

2-[(6-methylpyridin-2-yl)amino]-5-[3-(trifluoromethyl)phenyl]thiophene-3-carboxamide;

2-[(6-methylpyridin-2-yl)amino]-5-[4-(trifluoromethyl)phenyl]thiophene-3-carboxamide;

5-(5-chloro-2-fluorophenyl)-2-[(6-methylpyridin-2-yl) amino]thiophene-3-carboxamide;

5-(2-fluoro-5-methoxyphenyl)-2-[(6-methylpyridin-2-yl) amino]thiophene-3-carboxamide;

5-(3,4-dichlorophenyl)-2-[(6-methylpyridin-2-yl)amino] thiophene-3-carboxamide;

5-(2,5-difluorophenyl)-2-[(6-methylpyridin-2-yl)amino] thiophene-3-carboxamide;

2-[(6-methylpyridin-2-yl)amino]-5-(1,3,5-trimethyl-1H-pyrazol-4-yl)thiophene-3-carboxamide;

5-(1-isobutyl-1H-pyrazol-4-yl)-2-[(6-methylpyridin-2-yl) amino]thiophene-3-carboxamide;

or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. For example the following is within the scope of the instant invention:

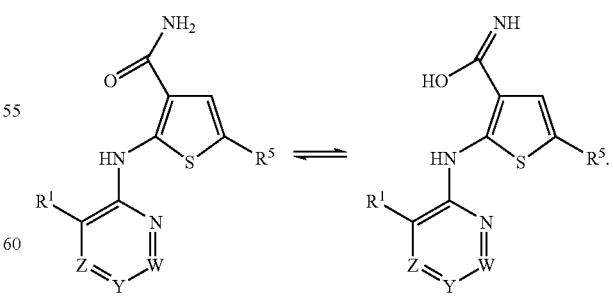

Many heteroaryl groups, such as imidazoles, exist as a mixture of 1H/2H tautomers. The tautomeric forms of these heteroaryl moieties are also within the scope of the instant invention.

When any variable (e.g. $R^{11}$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrange-ment. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

As used herein, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

As used herein, the term "alkynyl" refers to a non-aromatic hydrocarbon radical, straight or branched, containing from 2 to 10 carbon atoms and at least 1 carbon to carbon triple bond. Preferably 1 carbon to carbon triple bond is present. Thus, "$C_2$-$C_6$ alkynyl" means an alkynyl radical having from 2 to 6 carbon atoms. Alkynyl groups include ethynyl, propynyl, butynyl, and the like. As described above with respect to alkyl, the straight or branched portion of the alkynyl group may be substituted if a substituted alkynyl group is indicated.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

"Alkoxy" represents either a cyclic or non-cyclic alkyl group of indicated number of carbon atoms attached through an oxygen bridge. "Alkoxy" therefore encompasses the definitions of alkyl and cycloalkyl above.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties include but are not limited to: 2-benzimidazolyl, 2-quinolinyl, 3-quinolinyl, 4-quinolinyl, 1-isoquinolinyl, 3-isoquinolinyl, 4-isoquinolinyl, dihydroimidazopyrazinyl and dihydrooxozolopyridinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: azabicyclohexyl, azaphosphinyl, azaspiroheptyl, benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, dioxidothiomorpholinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, oxadiazaspirodecyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

The compounds of the present invention are inhibitors of JAK 1, JAK2, JAK 3, TYK2 and PDK1, and are therefore useful to treat or prevent myeloproliferative disorders or cancer in mammals, preferably humans.

An embodiment of the invention provides a method for inhibiting JAK1 tyrosine kinase, comprising administering to the mammal a therapeutically effective amount of any of the compounds or any of the pharmaceutical compositions described above.

An embodiment of the invention provides a method for inhibiting JAK2 tyrosine kinase, comprising administering to the mammal a therapeutically effective amount of any of the compounds or any of the pharmaceutical compositions described above.

An embodiment of the invention provides a method for inhibiting wild type or mutant JAK2 tyrosine kinase, comprising administering to the mammal a therapeutically effective amount of any of the compounds or any of the pharmaceutical compositions described above.

An embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JAK2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison, C. N. *Br. J. Haematol.* 130(2): 153-165 (2005); *Leukemia* (2005) 19, 1843-1844; and Tefferi, A. and Barbui, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma; and Adrenal glands: neuroblastoma. Thus, the term "cancerous cell" as provided herein, includes a cell afflicted by any one of the above-identified conditions.

The compounds, compositions and methods of the invention may also be useful in treating the following disease states: keloids and psoriasis.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung (non-small cell lung).

Cancers that may be treated by the compounds, compositions and methods of the invention include: breast, colon, colorectal and lung.

Cancers that may be treated by the compounds, compositions and methods of the invention include: lymphoma and leukemia.

The compounds of the instant invention are also inhibitors of the activity of PDK1 and are thus useful in the treatment of cancer, in particular cancers associated with deregulated activity of the PTEN/PI3K pathway including, but not limited to PTEN loss of function mutations and receptor tyrosine kinase gain of function mutations. Such cancers include, but are not limited to, ovarian, pancreatic, breast and prostate cancer, as well as cancers (including glioblastoma) where the tumor suppressor PTEN is mutated. See, Feldman, Richard I., et al., "Novel Small Molecule Inhibitors of 3-Phosphoinositide-dependent Kinase-1," *The Journal of Biological Chemistry*, Vol. 280, No. 20, Issue of May 20, pp. 19867-19874, 2005.

PDK1 signaling regulates multiple critical steps in angiogenesis. See, Mora, Alfonso et al., "PDK1, the master regulator of AGC kinase signal transduction," *Seminars in Cell & Developmental Biology* 15 (2004) 161-170. The utility of angiogenesis inhibitors in the treatment of cancer is known in the literature, see J. Rak et al. *Cancer Research*, 55:4575-4580, 1995 and Dredge et al., *Expert Opin. Biol. Ther.* (2002) 2(8):953-966, for example. The role of angiogenesis in cancer has been shown in numerous types of cancer and tissues: breast carcinoma (G. Gasparini and A. L. Harris, *J. Clin. Oncol.*, 1995, 13:765-782; M. Toi et al., *Japan. J. Cancer Res.*, 1994, 85:1045-1049); bladder carcinomas (A. J. Dickinson et al., *Br. J. Urol.*, 1994, 74:762-766); colon carcinomas (L. M. Ellis et al., *Surgery*, 1996, 120(5):871-878); and oral cavity tumors (J. K. Williams et al., *Am. J. Surg.*, 1994, 168:373-380). Other cancers include, advanced tumors, hairy cell leukemia, melanoma, advanced head and neck, metastatic renal cell, non-Hodgkin's lymphoma, metastatic breast, breast adenocarcinoma, advanced melanoma, pancreatic, gastric, glioblastoma, lung, ovarian, non-small cell lung, prostate, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer (Dredge et al., *Expert Opin. Biol. Ther.* (2002) 2(8): 953-966). Thus, the PDK1 inhibitors disclosed in the instant application are also useful in the treatment of these angiogenesis related cancers.

Tumors which have undergone neovascularization show an increased potential for metastasis. In fact, angiogenesis is essential for tumor growth and metastasis. (S. P. Cunningham, et al., *Can. Research*, 61:3206-3211 (2001)). The PDK1 inhibitors disclosed in the present application are therefore also useful to prevent or decrease tumor cell metastasis.

Further included within the scope of the invention is a method of treating or preventing a disease in which angiogenesis is implicated, which is comprised of administering to a mammal in need of such treatment a therapeutically effective amount of a compound of the present invention. Ocular neovascular diseases are an example of conditions where much of the resulting tissue damage can be attributed to aberrant infiltration of blood vessels in the eye (see WO 00/30651, published 2 Jun. 2000). The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Further included within the scope of the invention is a method of treating or preventing a non-malignant disease in which angiogenesis is implicated, including but not limited to: ocular diseases (such as, retinal vascularization, diabetic retinopathy and age-related macular degeneration), atherosclerosis, arthritis, psoriasis, obesity and Alzheimer's disease (Dredge et al., *Expert Opin. Biol. Ther.* (2002) 2(8):953-966). In another embodiment, a method of treating or preventing a disease in which angiogenesis is implicated includes: ocular diseases (such as, retinal vascularization, diabetic retinopathy and age-related macular degeneration), atherosclerosis, arthritis and psoriasis.

Further included within the scope of the invention is a method of treating hyperproliferative disorders such as restenosis, inflammation, autoimmune diseases and allergy/asthma.

Further included within the scope of the instant invention is the use of the instant compounds to coat stents and therefore the use of the instant compounds on coated stents for the treatment and/or prevention of restenosis (WO03/032809).

Further included within the scope of the instant invention is the use of the instant compounds for the treatment and/or prevention of osteoarthritis (WO03/035048).

Further included within the scope of the invention is a method of treating hypoinsulinism.

An embodiment of the invention provides a method for inhibiting JAK3 tyrosine kinase, comprising administering to the mammal a therapeutically effective amount of any of the compounds or any of the pharmaceutical compositions described above.

An embodiment of the invention provides a method for inhibiting TYK2 tyrosine kinase, comprising administering to the mammal a therapeutically effective amount of any of the compounds or any of the pharmaceutical compositions described above.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000 mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature*, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Opthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α, agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG- CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

The abbreviations used herein have the following tabulated meanings. Abbreviations not tabulated below have their meanings as commonly used unless specifically stated otherwise.

| | |
|---|---|
| Ac = | Acetyl |
| Bn = | Benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| Et₃N = | Triethylamine |
| GST | glutathione transferase |
| HMDS | Hexamethyldisilazide |
| LDA = | lithium diisopropylamide |
| mCPBA = | metachloroperbenzoic acid |
| MMPP = | monoperoxyphthalic acid |
| MPPM = | monoperoxyphthalic acid, magnesium salt 6H₂O |
| Ms = | methanesulfonyl = mesyl = SO₂Me |
| MsO = | methanesulfonate = mesylate |
| NSAID = | non-steroidal anti-inflammatory drug |
| o-Tol = | ortho-tolyl |
| OXONE ® = | 2KHSO₅•KHSO₄•K₂SO₄ |
| PCC = | pyridinium chlorochromate |
| PDC = | pyridinium dichromate |
| PDE | Phosphodiesterase |
| Ph = | Phenyl |
| Phe = | Benzenediyl |
| PMB = | para-methoxybenzyl |
| Pye = | Pyridinediyl |
| r.t. = | room temperature |
| Rac. = | Racemic |
| SAM = | aminosulfonyl or sulfonamide or SO₂NH₂ |
| SEM = | 2-(trimethylsilyl)ethoxymethoxy |
| SPA = | scintillation proximity assay |
| TBAF = | tetra-n-butylammonium fluoride |
| TEA = | triethylamine |
| Th = | 2- or 3-thienyl |
| TFA = | trifluoroacetic acid |
| TFAA = | trifluoroacetic acid anhydride |
| THF = | Tetrahydrofuran |
| Thi = | Thiophenediyl |
| TLC = | thin layer chromatography |

-continued

| | |
|---|---|
| TMS-CN = | trimethylsilyl cyanide |
| TMSI | trimethylsilyl iodide |
| Tz = | 1H (or 2H)-tetrazol-5-yl |
| CAN | ceric ammonium nitrate |
| C₃H₅ = | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

The compounds of the present invention can be prepared according to the following general schemes, using appropriate materials, and are further exemplified by the subsequent specific examples. The compounds illustrated in the examples are not, however, to be construed as forming the only genus that is considered as the invention. The illustrative Examples below, therefore, are not limited by the compounds listed or by any particular substituents employed for illustrative purposes. Those skilled in the art will readily understand that known variations of the conditions and processes of the following preparative procedures can be used to prepare these compounds. All temperatures are degrees Celsius unless otherwise noted.

Methods of Synthesis

Method 1

General procedures to prepare compounds of the instant invention are described in Scheme 1. Treatment of 2-aminothiophene-3-carboxamide (I) with benzyloxychloroformate in the presence of a tertiary amine base followed by exposure to N-iodosuccinimide leads to protected 5-iodothiophene III. 5-Iodothiophene III can be coupled to various aryl and heteroaryl boron species in the presence of a palladium catalyst to afford the 5-aryl thiophene IV, which can be deprotected by hydrogenolysis to give 2-amino thiophene V. The 2-amino thiophene V is then elaborated to the final product 2-amino thiophene VI through palladium catalyzed coupling with an appropriate six-membered halogenated heterocycle optionally substituted (R₂).

SCHEME 1

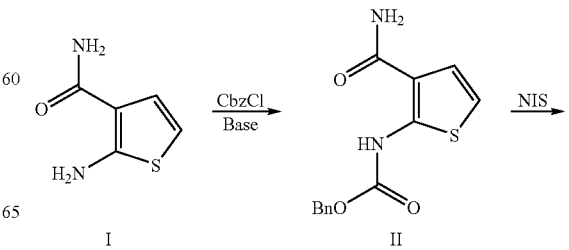

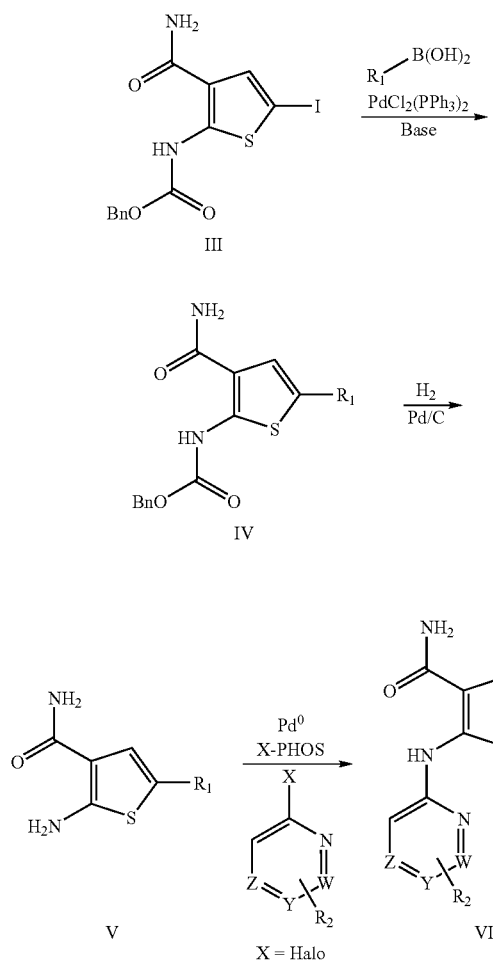

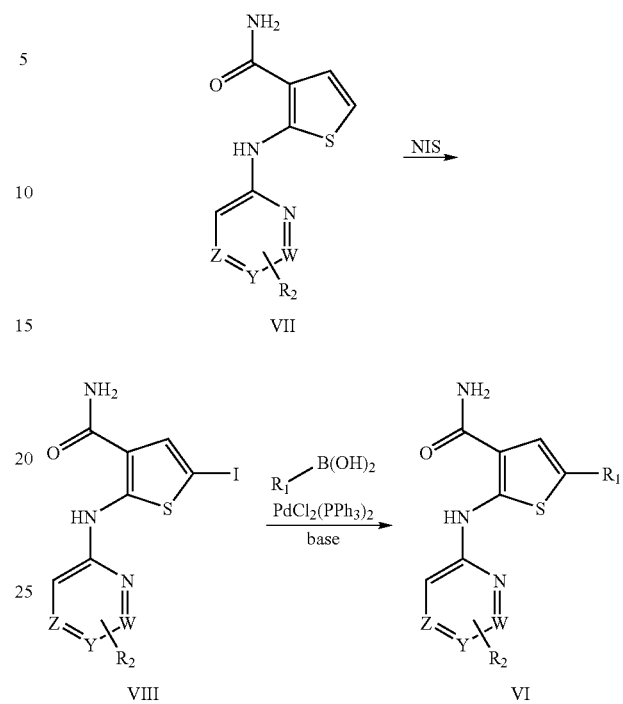

Method 3

General procedures to prepare compounds of the instant invention are also described in Scheme 3. Aryl or heteroaryl aldehyde IX can be homologated by one carbon using the appropriate Wittig agent and base, and the corresponding methyl enol ether X can be hydrolyzed under acidic conditions to give the aryl or heteroaryl acetaldehyde XI. The aldehyde can be condensed with 2-cyanoacetamide and sulfur in the presence of a tertiary amine base to afford thiophene XII, which can be coupled with an appropriate six-membered halogenated heterocycle optionally substituted ($R_2$) using palladium catalysis to give the 2-aminopyridyl thiophene VI.

Method 2

General procedures to prepare compounds of the instant invention are also described in Scheme 2. Coupling of 2-aminothiophene-3-carboxamide (I) with an appropriate six-membered halogenated heterocycle optionally substituted ($R_2$) using palladium catalysis affords 2-aminothiophene VII, which can be further elaborated by treatment with N-iodosuccinimide to give iodothiophene VIII. The iodothiophene can be coupled to various aryl and heteroaryl boron species in the presence of a palladium catalyst to afford the final product thiophene VI with an aryl or heteroaryl ring in the 5-position.

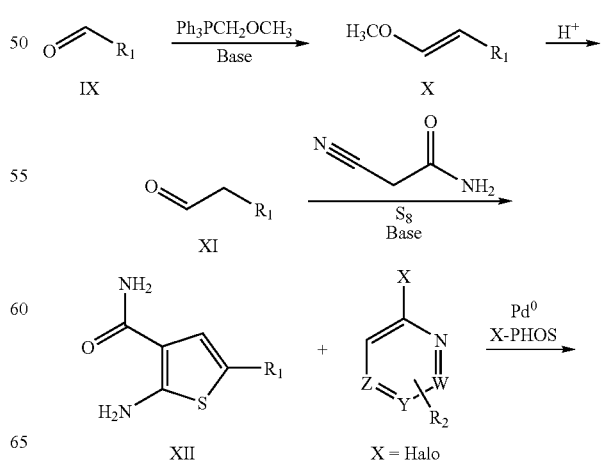

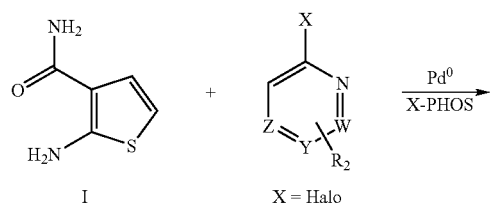

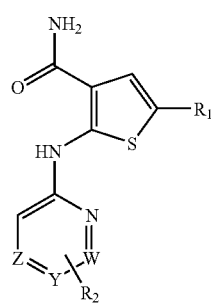

VI

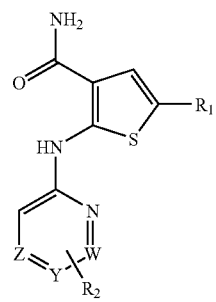

VI

Method 5

General procedures to prepare compounds of the instant invention are described in Scheme 5. Nitrothiophene XVI can be alkylated with chloroform using a variety of strongly basic conditions to afford the dichloromethyl adduct XVII. Hydrolysis to the aldehyde XVIII under acidic or basic conditions followed by condensation with hydroxylamine affords oxime XIV. Transition metal-catalyzed rearrangement to the amide XV followed by palladium catalyzed cross coupling with a variety of aryl and heteroaryl boronates affords the functionalized nitro thiophene intermediate XVI. Reduction of the nitro group and coupling with an appropriate six-membered halogenated heterocycle optionally substituted ($R_2$) using palladium catalysis gives the 2-aminopyridyl thiophene VI.

Method 4

General procedures to prepare compounds of the instant invention are also described in Scheme 4. An appropriate aryl or heteroaryl iodide XV can be coupled to allyl bromide by first performing an iodo-magnesium exchange and then introducing allyl bromide in the presence of a copper cyanide-lithium chloride complex. The resulting allylated aromatic XVI can be dihydroxylated using a catalytic amount of osmium tetroxide in the presence of a stoichiometric reoxidant, giving the diol XV that can be cleaved to give the aryl or heteroaryl acetylaldehyde XI. The aldehyde can be condensed with 2-cyanoacetamide and sulfur to afford thiophene XII, which can be coupled with an appropriate six-membered halogenated heterocycle optionally substituted ($R_2$) using palladium catalysis to give the 2-aminopyridyl thiophene VI.

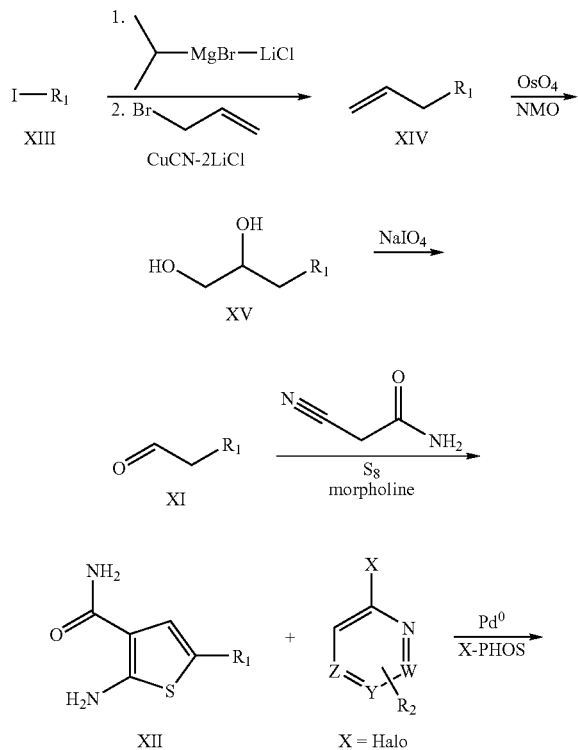

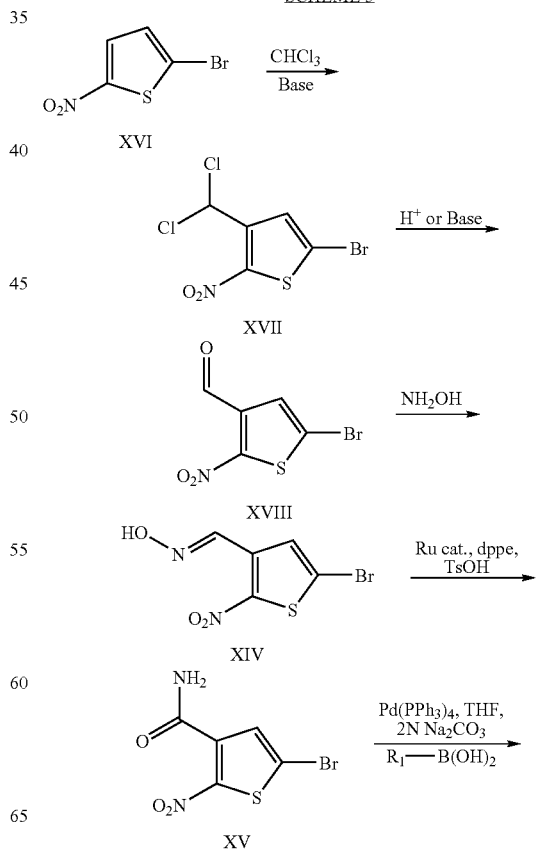

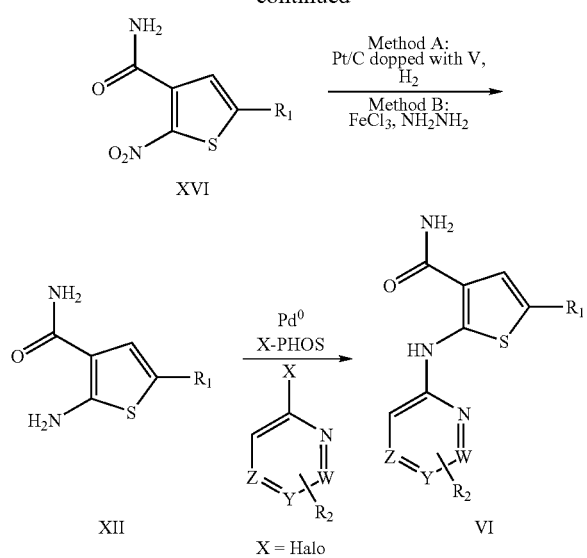

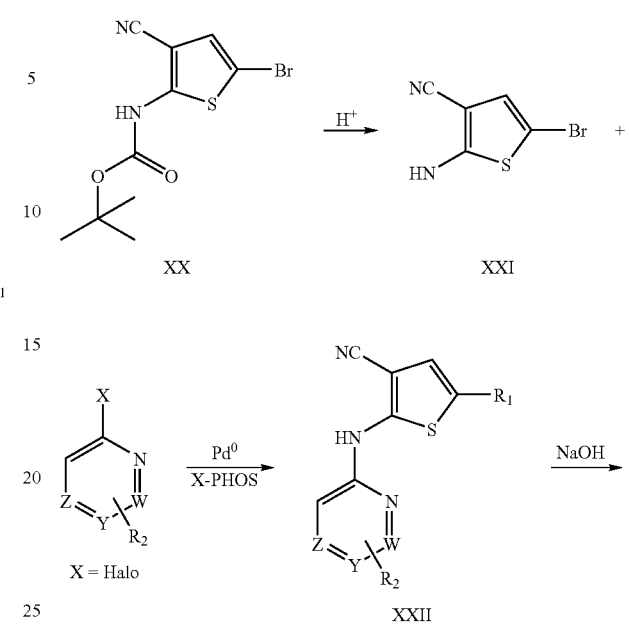

Method 6

General procedures to prepare compounds of the instant invention are described in Scheme 6. Treatment of 2-aminothiophene-3-nitrile (XVII) with di-tert-butyl dicarbonate in the presence of a tertiary amine base followed by exposure to N-iodosuccinimide leads to protected 5-iodothiophene XIX. 5-Iodothiophene XIX can be coupled to various aryl and heteroaryl boron species in the presence of a palladium catalyst to afford the 5-aryl or heteroaryl thiophene XX, which can be deprotected by treatment with acid to give 2-amino thiophene XXI. The 2-amino thiophene XXI is then elaborated to the 2-aminopyridyl thiophene VII through palladium catalyzed coupling with an appropriate six-membered halogenated heterocycle optionally substituted ($R_2$) using palladium catalysis. Finally, the 2-aminopyridyl thiophene XXII is hydrolyzed with base to give the final 3-amide thiophene product VI.

The invention will now be illustrated in the following non-limiting Examples in which, unless otherwise stated:

1. All the end products of the formula I were analyzed by NMR, LCMS.
2. Intermediates were analyzed by NMR and/or TLC and/or LCMS.
3. Most compounds were purified by flash chromatography on silica gel, recrystallization and/or swish (suspension in a solvent followed by filtration of the solid).
4. The course of the reactions were followed by thin layer chromatography (TLC) and/or LCMS and reaction times are given for illustration only.

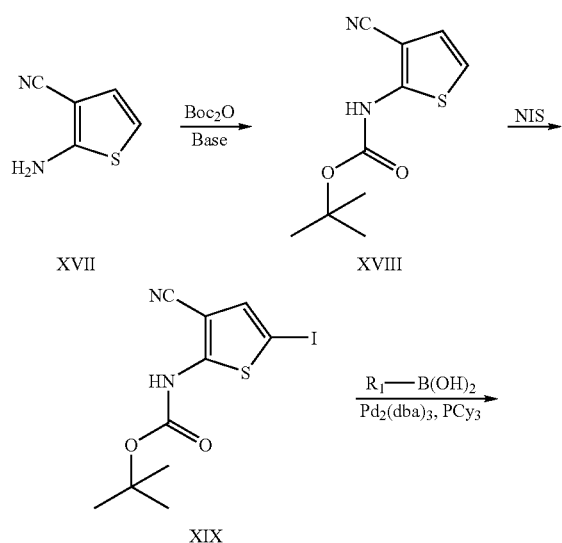

2-Amino-5-(2,4-difluorophenyl)thiophene-3-carboxamide

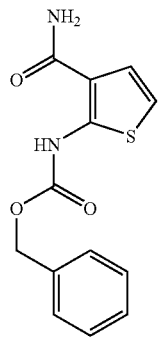 [SMILES: NC(=O)c1ccsc1NC(=O)OCc1ccccc1]

Step 1.
Benzyl[3-(aminocarbonyl)-2-thienyl]carbamate

To a stirred solution of 2-aminothiophene-3-carboxamide (5 g, 35.2 mmol) in tetrahydrofuran (200 mL) under argon was added diisopropylethylamine (9.52 ml, 54.5 mmol) and benzyloxycarbonyl chloride (7.53 mL, 52.8 mmol). After stirring for 60 hours, more diisopropylethylamine (9.52 mL, 54.5 mmol) and benzyloxycarbonyl chloride (7.53 mL, 52.8 mmol) were added. After an additional 24 hours, the suspension was filtered and the resulting solution was concentrated to ~30 mL and diluted with ethyl acetate (100 mL) The organic layer was washed sequentially with saturated aqueous sodium bicarbonate (3×40 mL), a 3:1 mixture of saturated aqueous sodium bicarbonate and water (40 mL), and brine (40 mL), dried with sodium sulfate, filtered, and concentrated. The resulting mixture of white solid and brown oil was triturated with a mixture of ethyl acetate (10 mL) and hexanes (10 mL), and then the solid was collected by filtration. Drying under vacuum afforded the title compound as a solid.

Calc'd for $C_{13}H_{13}N_2O_3S$ [M+H]$^+$: 277. Found: 277.

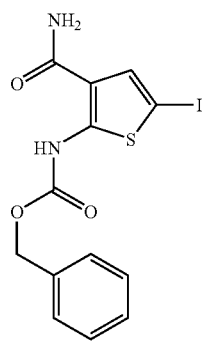 [SMILES: NC(=O)c1cc(I)sc1NC(=O)OCc1ccccc1]

Step 2. Benzyl[3-(aminocarbonyl)-5-iodo-2-thienyl]carbamate

To a solution of benzyl[3-(aminocarbonyl)-2-thienyl]carbamate (4.39 g, 15.88 mmol) in dichloromethane (440 mL) was added N-iodosuccinimide (3.57 g, 15.88 mmol). An additional amount of N-iodosuccinimide (1.07 g) was added in 3 portions over the next 60 min to drive the reaction to completion. The dark reaction mixture was diluted with ethyl acetate (700 mL), hexanes (100 mL), aqueous sodium thiosulfate (1 M, 150 mL), and aqueous sodium hydroxide (1 M, 300 mL). The layers were separated, and the organic layer was washed with saturated aqueous sodium bicarbonate (100 mL) and brine (150 mL), dried over sodium sulfate, filtered, and concentrated to afford the title compound as a solid.

Calc'd for $C_{13}H_{12}IN_2O_3S$ [M+H]$^+$: 403. Found: 403.

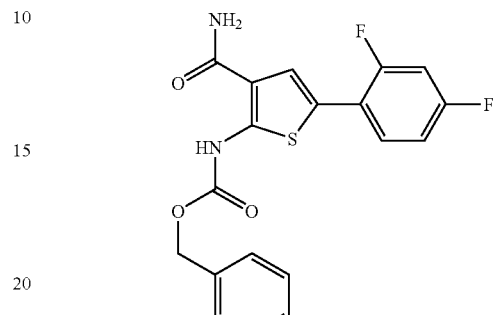

Step 3: Benzyl[3-(aminocarbonyl)-5-(2,4-difluorophenyl)-2-thienyl]carbamate

A suspension of benzyl[3-(aminocarbonyl)-5-iodo-2-thienyl]carbamate (250 mg, 0.622 mmol), 2,4-difluorophenylboronic acid (349 mg, 2.21 mmol), dichlorobis(triphenylphosphine)palladium (21.8 mg, 0.031 mmol), and sodium carbonate (6.22 mL, 12.43 mmol) in 1,2-dimethoxyethane (10 mL) sealed in a 5 mL microwave reaction vessel was purged of oxygen by doing 5 vacuum/argon flush cycles. The reaction solution was heated in a Biotage microwave for five minutes at 100° C. The resulting mixture was partitioned between ethyl acetate (30 mL) and saturated aqueous sodium bicarbonate (20 mL). The layers were separated and the organic layer was washed with saturated sodium bicarbonate (20 mL) and brine (2×20 mL), dried over sodium sulfate, filtered, and concentrated. The crude material was purified by silica gel chromatography using a 0-4% methanol/dichloromethane elution to afford the title compound.

Calc'd for $C_{19}H_{15}F_2N_2O_3S$ [M+H]$^+$: 389. Found: 389.

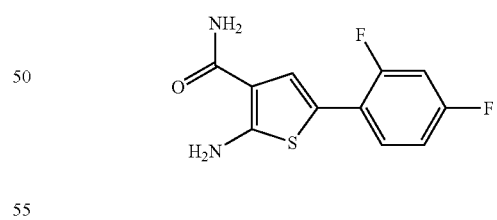

Step 4: 2-Amino-5-(2,4-difluorophenyl)thiophene-3-carboxamide

A suspension of benzyl[3-(aminocarbonyl)-5-(2,4-difluorophenyl)-2-thienyl]carbamate (240 mg, 0.618 mmol) and 10% palladium on carbon (326 mg, 0.306 mmol) in ethanol (130 mL) was placed under a hydrogen atmosphere by performing 5×15 second vacuum/hydrogen purge (supplied by balloon) fill cycles while vigorously stirring the mixture. The reaction was heated to reflux for 18 hours and then allowed to cool to ambient temperature. The suspension was filtered; the filtrate was collected and concentrated to yield the title compound as a light yellow solid.

Calc'd for $C_{11}H_9F_2N_2OS$ [M+H]⁺: 255. Found: 255.

INTERMEDIATE 2

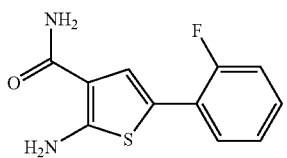

2-Amino-5-(2-fluorophenyl)thiophene-3-carboxamide

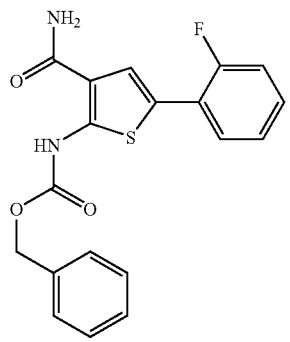 [SMILES: NC(=O)c1cc(-c2ccccc2F)sc1NC(=O)OCc1ccccc1]

Step 1: Benzyl[3-(aminocarbonyl)-5-(2-fluorophenyl)-2-thienyl]carbamate

The title compound was synthesized from benzyl[3-(aminocarbonyl)-5-iodo-2-thienyl]carbamate (Intermediate 1, Step 2) (300 mg, 0.746 mmol) and 2-fluorophenyl boronic acid (157 mg, 1.12 mmol) as the starting materials as described in Intermediate 1 Step 3.

Calc'd for $C_{19}H_{16}FN_2O_3S$ [M+H]⁺: 371. Found: 371.

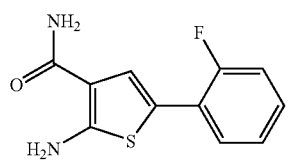

Step 2:
2-Amino-5-(2-fluorophenyl)thiophene-3-carboxamide

The title compound was prepared as described in Intermediate 1 Step 4 using benzyl[3-(aminocarbonyl)-5-(2-fluorophenyl)-2-thienyl]carbamate (1.39 g, 3.74 mmol) as the starting material.

Calc'd for $C_{11}H_{10}FN_2OS$ [M+H]⁺: 237. Found: 237.

INTERMEDIATE 3

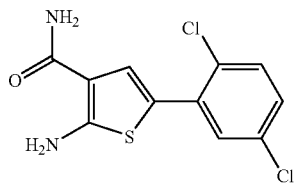

2-Amino-5-(2,5-dichlorophenyl)thiophene-3-carboxamide

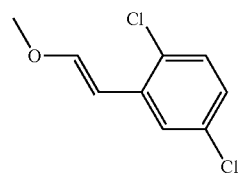

Step 1: General Procedure for the Preparation of Phenylvinyl Ethers Via Wittig Homologation of Benzaldehydes(E,Z)-2-(2,5-Dichlorophenyl)Vinyl Methyl Ether A suspension of (methoxymethyl)triphenylphosphonium chloride (9.79 g, 28.6 mmol) in tetrahydrofuran (60 mL) under argon was charged with potassium tert-butoxide (3.21 g, 28.6 mmol) to give a red suspension. After 45 minutes a solution of 2,5-dichlorobenzaldehyde (5 g, 28.6 mmol) in tetrahydrofuran (10 mL) was added via cannula, and the transfer was quantitated with additional (2×2.5 mL) tetrahydrofuran. After stirring for two hours, the suspension was filtered and the filtrate was concentrated. Addition of hexanes (50 mL) gave a precipitate that was removed by filtration, which afforded a mixture of 2,5-dichlorobenzaldehyde and 2-(2,5-dichlorophenyl)vinyl methyl ether. This crude product mixture was added into another mixture of (methoxymethyl)triphenylphosphonium chloride (9.79 g, 28.6 mmol) and potassium tert-butoxide (3.21 g, 28.6 mmol) in tetrahydrofuran (60 mL) and allowed to react for another two hours. The suspension was filtered and the filtrate was concentrated. Addition of hexanes (50 mL) gave a precipitate that was removed by filtration. Concentration of the filtrated afforded a crude product that was purified by silica gel chromatography (10% ethyl acetate/hexanes) to afford 2-(2,5-dichlorophenyl)vinyl methyl ether.

¹H NMR (600 MHz, DMSO) (*denotes minor isomer): 7.96 (d, J=2.6 Hz, 1H)*, 7.64 (d, J=2.6 Hz, 1H), 7.42 (d, J=12.9 Hz, 1H), 7.40 (d, J=8.5 Hz, 1H)*, 7.38 (d, J=8.5 Hz, 1H), 7.18 (dd, J=8.5, 2.6 Hz, 1H)*, 7.16 (dd, J=8.5, 2.6 Hz, 1H), 6.56 (d, J=7.3 Hz, 1H)*, 5.90 (d, J=12.9 Hz, 1H), 5.44 (d, J=7.3 Hz, 1H)*, 3.82 (s, 3H)*, 3.63 (s, 3H).

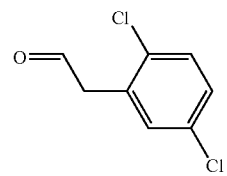 [SMILES: O=CCc1cc(Cl)ccc1Cl]

Step 2: General Procedure for the Hydrolysis of Phenylvinylethers to Phenylacetaldehydes (2,5-Dichlorophenyl)acetaldehyde A solution of 2-(2,5-dichlorophenyl)vinyl methyl ether (3.78 g, 18.61 mmol) and hydrogen chloride in dioxane (4 M, 34.9 mL, 140 mmol) was stirred for 30 minutes, and then diluted with diethyl ether (50 mL). After placing the reaction mixture in a water bath, saturated aqueous sodium bicarbonate (75 mL) was added (CAUTION: gas evolution). The two layers were separated, and the organic layer was washed with aqueous phosphate buffer (1 M, pH=8, 20 mL) and brine (20 mL), dried over sodium sulfate, filtered, and concentrated to give the title compound.

$^1$H NMR (600 MHz, DMSO): 9.65 (t, J=0.9 Hz, 1H), 7.47 (m, 2H), 7.37 (dd, J=8.6, 2.5 Hz, 1H), 3.93 (s, 2H).

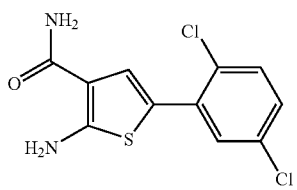 [SMILES: NC(=O)c1cc(-c2cc(Cl)ccc2Cl)sc1N]

Step 3: General Procedure for Thiophene Synthesis from Phenylacetaldehydes 2-Amino-5-(2,5-dichlorophenyl)thiophene-3-carboxamide A suspension of (2,5-dichlorophenyl)acetaldehyde (3.34 g, 17.67 mmol), 2-cyanoacetamide (1.485 g, 17.67 mmol), sulfur (0.567 g, 17.67 mmol), and morpholine (1.539 mL, 17.67 mmol) in ethanol (35 mL) in a 100 mL flask with an attached condenser was placed under an argon atmosphere with 3 vacuum/argon flush cycles and then heated to 70° C. After 14 hours, the reaction mixture was cooled to room temperature, filtered, and concentrated. The crude oil was diluted with ethyl acetate (140 mL), isopropyl alcohol (10 mL), and aqueous citric acid (1 M, 25 mL). The layers were separated and the organic layer was washed with water (25 mL), 5:1 saturated aqueous sodium bicarbonate brine (30 mL), and brine (25 mL), dried over sodium sulfate, filtered, and concentrated. The crude yellow solid was triturated with dichloromethane to give the title compound.

$^1$H NMR (600 MHz, DMSO): 7.63 (s, 1H), 7.59 (d, J=2.6 Hz, 1H), 7.53 (s, 2H), 7.46 (d, J=8.5 Hz, 1H), 7.32 (bs, 1H), 7.25 (dd, J=8.5, 2.6 Hz, 1H), 6.84 (bs, 1H).

INTERMEDIATE 4

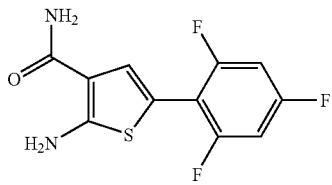

2-Amino-5-(2,4,6-trifluorophenyl)thiophene-3-carboxamide

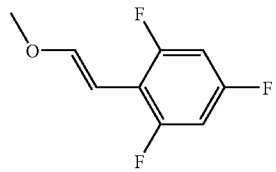

Step 1: 1,3,5-Trifluoro-2-[(E,Z)-2-methoxyvinyl]benzene

The title compound was prepared from 2,4,6-trifluorobenzaldehyde (5 g, 31.2 mmol) as the starting material according to the general procedure described in Intermediate 3 Step 1

$^1$H NMR (600 MHz, DMSO) (*denotes minor isomer): 7.22 (d, J=13.2 Hz, 1H), 7.14 (m, 2H), 7.08 (m, 2H)*, 6.44 (d, J=6.8 Hz, 1H)*, 5.57 (d, J=13.2 Hz, 1H), 5.02 (d, J=6.2 Hz, 1H)*, 3.64 (s, 3H), 3.62 (s, 3H)*.

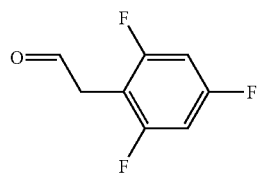 [SMILES: O=CCc1c(F)cc(F)cc1F]

Step 2: (2,4,6-Trifluorophenyl)acetaldehyde

The title compound was prepared from 1,3,5-trifluoro-2-[(E,Z)-2-methoxyvinyl]benzene (5.87 g, 31.2 mmol) as the starting material according to the general procedure described in Intermediate 3 Step 2.

$^1$H NMR (600 MHz, DMSO): 9.63 (s, 1H), 7.18 (m, 2H), 3.84 (s, 2H).

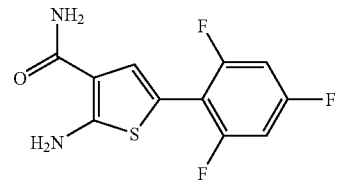 [SMILES: NC(=O)c1cc(-c2c(F)cc(F)cc2F)sc1N]

Step 3: 2-Amino-5-(2,4,6-trifluorophenyl)thiophene-3-carboxamide

The title compound was prepared from (2,4,6-trifluorophenyl)acetaldehyde (3.64 g, 20.9 mmol) as the starting material according to the general procedure described in Intermediate 3 Step 3.

Calc'd for $C_{11}H_8F_3N_2OS$ [M+H]: 273. Found: 273.

INTERMEDIATE 5

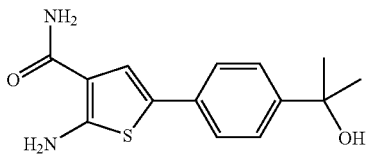

2-Amino-5-[4-(1-hydroxy-1-methylethyl)phenyl]thiophene-3-carboxamide

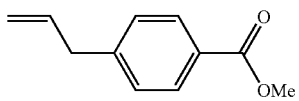

Step 1: General Procedure for the Preparation of Allylbenzenes from Iodobenzenes Methyl 4-allylbenzoate A 100 mL flask containing copper(I) cyanide (0.854 g, 9.54 mmol) and lithium chloride (0.809 g, 19.08 mmol) was placed under vacuum and heated to 150° C. for 90 minutes, and then cooled to room temperature. A 500 mL flask containing a solution of methyl 4-iodobenzoate (12.5 g, 47.7 mmol) in tetrahydrofuran (75 mL) under argon was cooled to −25° C. and isopropylmagnesium chloride-lithium chloride complex (49.1 mL, 1 M, 49.1 mmol) was added over 16 minutes while the internal temperature was maintained at or below −20° C. After 45 minutes, the copper(I) cyanide and lithium chloride were dissolved in tetrahydrofuran (20 mL) with sonication, and the resulting solution was transferred to the clear, orange reaction mixture via cannula. After an additional 25 minutes, allyl bromide (4.13 mL, 47.7 mmol) was added over 10 min while the reaction temperature was kept below −15° C., and then the reaction was kept at −5° C. for 24 hours. 60 mL of 9:1 NH$_4$Cl(sat):NH$_3$(sat) was then added, followed by 50 mL of water and 200 mL dichloromethane. The layers were separated, and the aqueous layer was extracted with dichloromethane (2×100 mL). The combined organic layers were washed with 100 mL water and then diluted with 100 mL dichloromethane and 100 mL chloroform. The organic layer was washed with 150 mL brine, dried over MgSO$_4$ and Na$_2$SO$_4$, filtered, and concentrated to yield an oil and a solid. The oil was filtered through a cotton plug and the entire flask was then rinsed with hexanes (4×2 mL); these rinses were combined with the oil after filtering through cotton. Concentration of this solution yielded the title compound.

$^1$H NMR (600 MHz, DMSO): 7.86 (d, J=8.2 Hz, 2H), 7.31 (d, J=8.5 Hz, 2H), 5.93 (m, 1H), 5.07 (m, 1H), 5.05 (m, 1H), 3.79 (s, 3H), 3.41 (d, J=6.7 Hz, 1H).

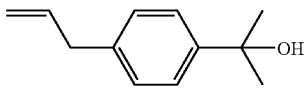

Step 2: 2-(4-Allylphenyl)propan-2-ol

A solution of methyl 4-allylbenzoate (5.66 g, 32.1 mmol) in tetrahydrofuran (37 mL) at 0° C. under an argon atmosphere was charged with a solution of methyl magnesium bromide in diethyl ether (3 M, 26.8 mL, 80 mmol). The reaction mixture was allowed to warm to room temperature and then it was cooled to 0° C. after an additional four hours, at which time a saturated aqueous ammonium chloride solution (50 mL) was added slowly followed by diethyl ether (100 mL). The layers were separated, and the aqueous layer was extracted with diethyl ether (2×50 mL) The combined organic layers were dried over magnesium sulfate, filtered, and concentrated to afford the title compound.

$^1$H NMR (600 MHz, DMSO): 7.34 (d, J=8.5 Hz, 2H), 7.06 (d, J=8.5 Hz, 2H), 5.90 (m, 1H), 5.02 (m, 1H), 4.99 (m, 1H), 4.88 (s, 1H), 3.27 (m, 2H), 1.35 (s, 6H).

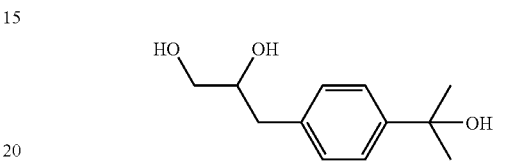

Step 3: 3-[4-(1-Hydroxy-1-methylethyl)phenyl]propane-1,2-diol

To a biphasic mixture of 2-(4-allylphenyl)propan-2-ol (5.53 g, 31.4 mmol) and N-Methyl morpholine N-oxide (3.86 g, 32.9 mmol) in acetone (11 mL) and water (22 mL) was added osmium tetroxide (3.14 mL, 0.157 mmol) with vigorous stirring. After 24 hours, dithionite (0.15 g), Florisil (1.5 g), and water (8 mL) were added and allowed to stir for an additional 15 minutes before filtering through a pad of Celite. The filter was rinsed with acetone (2×5 mL, then 2×10 mL), and filtrate was concentrated by rotary evaporation to remove the acetone. The remaining liquid was diluted with 9:1 chloroform:isopropanol (20 mL) and aqueous hydrogen chloride (1 M, 20 mL), the layers were separated, and the acidic (pH=1) aqueous layer was extracted with 9:1 chloroform:isopropanol (2×20 mL). The combined organic layers were washed with 3:1 water:brine (12 mL), saturated sodium bicarbonate (10 mL), and brine (10 mL). The aqueous layers were combined and saturated with solid sodium chloride by stirring for 90 minutes, and then extracted with 9:1 chloroform:isopropanol (3×50 mL). The combined organic extracts were dried over sodium sulfate, filtered, and concentrated, and the crude material was purified by silica gel chromatography (5-20% methanol/dichloromethane) to afford the title compound as an oil.

$^1$H NMR (600 MHz, DMSO): 7.29 (d, J=8.5 Hz, 2H), 7.08 (d, J=8.5 Hz, 2H), 4.86 (s, 1H), 4.50 (t, J=5.7 Hz, 1H), 4.47 (d, J=5.3 Hz, 1H), 3.55 (m, 1H), 3.23 (m, 2H), 2.67 (dd, J=13.8, 8.8 Hz, 1H), 2.43 (dd, J=13.6, 7.6 Hz, 1H), 1.35 (s, 6H).

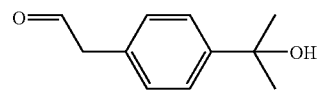

Step 4: [4-(1-Hydroxy-1-methylethyl)phenyl]acetaldehyde

A biphasic mixture of 3-[4-(1-hydroxy-1-methylethyl)phenyl]propane-1,2-diol (5.44 g, 25.9 mmol) in water (85 mL) and diethyl ether (170 mL) was charged with sodium periodate (11.07 g, 51.7 mmol) and stirred vigorously for two hours. The reaction mixture was then partitioned between diethyl ether (50 mL) and saturated aqueous sodium thiosulfate (50 mL), and the layers were separated. The aqueous layer was extracted with diethyl ether (2×100 mL), and the combined organic layers were washed with brine (25 mL), dried over sodium sulfate, filtered, and concentrated. To remove water left over, the concentrated material was dissolved in dichloromethane (70 mL), washed with brine (20 mL), dried over sodium sulfate, filtered, and concentrated to yield the title compound.

$^1$H NMR (600 MHz, DMSO): 9.63 (t, J=2.0 Hz, 1H), 7.40 (d, J=8.5 Hz, 2H), 7.12 (d, J=8.5 Hz, 2H), 4.95 (s, 1H), 3.68 (d, J=2.0 Hz, 2H), 1.35 (s, 6H).

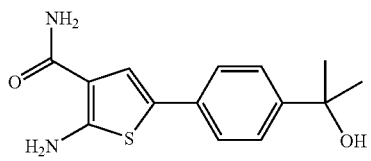 [SMILES: CC(C)(O)c1ccc(-c2cc(C(N)=O)c(N)s2)cc1]

Step 5: 2-Amino-5-[4-(1-hydroxy-1-methylethyl) phenyl]thiophene-3-carboxamide

The title compound was prepared using [4-(1-hydroxy-1-methylethyl)phenyl]acetaldehyde (3.65 g, 20.5 mmol) as the starting material according to the general thiophene synthesis procedure in Intermediate 3 Step 3.

Calc'd for $C_{14}H_{17}N_2O_2S$ [M+H]$^+$: 277. Found: 277.

INTERMEDIATE 6

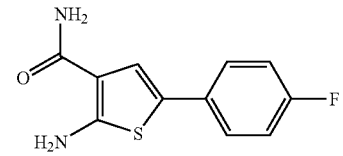

2-Amino-5-(4-fluorophenyl)thiophene-3-carboxamide

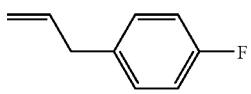

Step 1: 1-Allyl-4-fluorobenzene

Allyl bromide (4.33 mL, 50 mmol) was added dropwise to a solution of 4-fluorophenyl magnesium bromide (50 mmol) in tetrahydrofuran (25 mL) and diethyl ether (25 mL). After 16 hours, the reaction suspension was diluted with diethyl ether (100 mL) and saturated aqueous ammonium chloride (50 mL). The layers were separated, and the organic layer was washed with water (25 mL) and brine (25 mL), dried over magnesium sulfate, filtered, and concentrated to afford the title compound.

$^1$H NMR (600 MHz, DMSO): 7.18 (m, 2H), 7.08 (d, 2H), 5.90 (m, 1H), 5.03 (m, 1H), 5.00 (m, 1H), 3.32 (d, J=6.7 Hz, 2H).

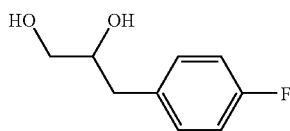 [SMILES: OCC(O)Cc1ccc(F)cc1]

Step 2: 3-(4-Fluorophenyl)propane-1,2-diol

The title compound was prepared according to the procedure in Intermediate 5 Step 3 using 1-allyl-4-fluorobenzene (3.76 g, 27.6 mmol) as the starting material.

$^1$H NMR (600 MHz, DMSO): 7.18 (m, 2H), 7.02 (m, 2H), 4.52 (m, 2H), 3.55 (m, 1H), 3.25 (m, 1H), 3.21 (m, 1H), 2.72 (dd, J=13.7, 4.6 Hz, 1H), 2.46 (m, 1H).

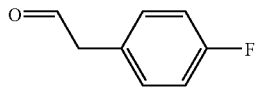

Step 3: (4-Fluorophenyl)acetaldehyde

The title compound was prepared according to the procedure in Intermediate 5 Step 4 using 3-(4-fluorophenyl)propane-1,2-diol (3.69 g, 21.7 mmol) as the starting material.

$^1$H NMR (600 MHz, DMSO): 9.63 (t, J=1.8 Hz, 1H), 7.24 (m, 2H), 7.14 (m, 2H), 3.78 (d, J=1.5 Hz, 2H).

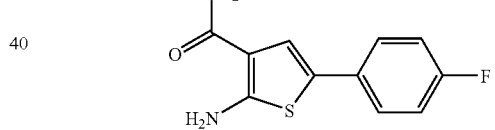

Step 4: 2-Amino-5-(4-fluorophenyl)thiophene-3-carboxamide

The title compound was prepared according to the general thiophene synthesis procedure in Intermediate 3 Step 3 using (4-fluorophenyl)acetaldehyde (2.93 g, 21.2 mmol) as the starting material.

Calc'd for $C_{11}H_{10}FN_2OS$ [M+H]$^+$: 237. Found: 237.

INTERMEDIATE 7

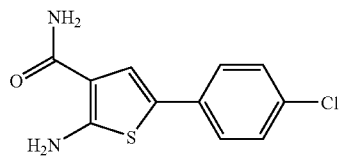

71

2-Amino-5-(4-chlorophenyl)thiophene-3-carboxamide

Step 1: 3-(4-Chlorophenyl)propane-1,2-diol

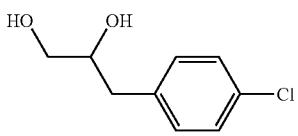 [SMILES: OCC(O)Cc1ccc(Cl)cc1]

The title compound was prepared according to the procedure in Intermediate 5 Step 3 using 1-allyl-4-chlorobenzene (6.19 g, 40.6 mmol) as the starting material.

$^1$H NMR (600 MHz, DMSO): 7.24 (d, 2H), 7.18 (d, 2H), 4.56 (m, 2H), 3.55 (m, 1H), 3.26 (m, 1H), 3.21 (m, 1H), 2.72 (dd, 1H), 2.46 (m, 1H).

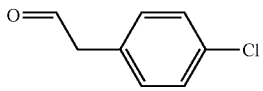

Step 2: (4-Chlorophenyl)acetaldehyde

The title compound was prepared according to the procedure in Intermediate 5 Step 4 using 3-(4-chlorophenyl)propane-1,2-diol (5.42 g, 29.0 mmol) as the starting material.

$^1$H NMR (600 MHz, DMSO): 9.63 (t, 1H), 7.36 (d, 2H), 7.22 (d, 2H), 3.77 (d, 2H).

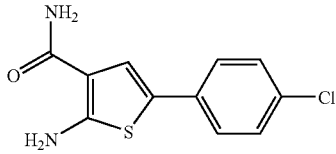

Step 3:
2-Amino-5-(4-chlorophenyl)thiophene-3-carboxamide

The title compound was prepared according to the general thiophene synthesis procedure in Intermediate 3 Step 3 using (4-chlorophenyl)acetaldehyde (4.04 g, 26.1 mmol) as the starting material.

Calc'd for $C_{11}H_{10}ClN_2OS$ [M+H]$^+$: 253. Found: 253.

INTERMEDIATE 8

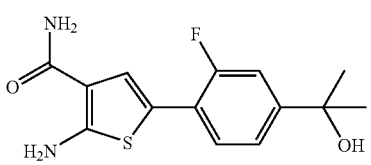

72

2-Amino-5-[2-fluoro-4-(1-hydroxy-1-methylethyl)phenyl]thiophene-3-carboxamide

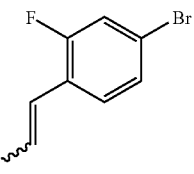

Step 1. 2-(4-Bromo-2-fluorophenyl)vinyl methyl ether

Methoxymethyl)triphenylphosphonium chloride (147 g, 0.48 mol) was suspended in tetrahydrofuran (1.5 L) under an argon atmosphere, and cooled to 0° C. t-BuOK (51.6 g, 0.46 mol) was added in portions. A solution of 4-bromo-2-fluorobenzaldehyde (40.6 g, 0.2 mol) in tetrahydrofuran (500 mL) was then added to the reaction mixture. The solution was stirred at room temperature for 1 hour. The solution was poured into ice-water and extracted with ethyl acetate (2×). The combined organic phases were dried and concentrated in vacuo. Purification via flash chromatography afforded the title compound.

$^1$H NMR (300 MHz, CDCl$_3$): δ 7.2-7.3 (m, 3H), 6.2 (d, 1H), 5.8 (d, 1H), 3.7 (s, 3H).

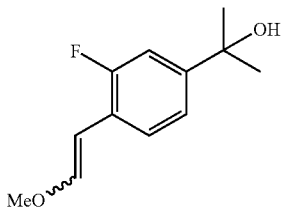

Step 2. 2-{3-Fluoro-4-[2-methoxyvinyl]phenyl}propan-2-ol

To a solution of compound 2-(4-bromo-2-fluorophenyl)vinyl methyl ether (115.5 g, 0.5 mol) in tetrahydrofuran (666 mL) at −78° C. was added n-butyllithium (240 mL of 2.5M in hexanes, 0.6 mol), and the resulting mixture was stirred at −78° C. for 1 hour. A solution of acetone (37.7 g, 0.65 mol) in tetrahydrofuran (283 mL) was added dropwise to the reaction mixture. Then the reaction solution was slowly warmed to 0° C., stirred for 30 minutes, and then at room temperature for 30 minutes. Water (300 mL) was added to quench the reaction. The biphasic mixture was extracted with ethyl acetate (2×). The combined organics were dried and concentrated in vacuo. Purification via flash chromatography afforded the title compound.

$^1$H NMR (300 MHz, CDCl$_3$): δ 6.9-7.3 (m, 3H), 6.2 (d, 1H), 5.8 (d, 1H), 3.73 (s, 3H), 1.55 (s, 6H).

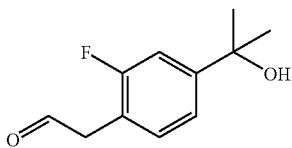

Step 3. [2-Fluoro-4-(1-hydroxy-1-methylethyl)phenyl]acetaldehyde

To a room temperature solution of 2-{3-fluoro-4-[2-methoxyvinyl]phenyl}propan-2-ol (100 mg, 0.48 mmol) in acetone (5 mL) was added dropwise 4 M aqueous hydrochloric acid (5 mL, 20 mmol). The reaction was stirred at room temperature for two hours. The mixture was then diluted with 25 mL of water and 50 mL of diethyl ether. The water phase was extracted with diethyl ether (2×) and the combined organic layers were washed with saturated aqueous sodium bicarbonate and brine, dried and concentrated in vacuo to afford the title compound.

$^1$H NMR (400 MHz, CDCl$_3$): δ 9.76 (s, 1H), 7.14-7.28 (m, 3H), 3.73 (s, 2H), 1.57 (s, 6H).

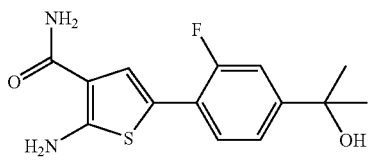

Step 4. [2-Amino-5-[2-fluoro-4-(1-hydroxy-1-methylethyl)phenyl]thiophene-3-carboxamide A solution of [2-fluoro-4-(1-hydroxy-1-methylethyl)phenyl]acetaldehyde (74.5 g, 0.38 mol) in dry dimethylformamide (240 mL) was treated with 2-cyanoacetamide (44.5 g, 0.53 mmol) and sulfur (17 g, 0.53 mmol). Triethylamine (53.6 g, 0.53 mmol) was added dropwise to the reaction mixture using an ice-bath to control the resulting exotherm. The reaction was stirred at room temperature overnight, and then poured into a mixture of ice-water (800 mL) and ethyl acetate (80 mL). An emulsion formed and the insoluble material was filtered. The filtrate was extracted with ethyl acetate (2×). The organic layers were concentrated in vacuo and the resulting residue was combined with the filter cake from the previous filtration. This combined material was washed with ethyl acetate. Purification via flash chromatography afforded the title compound.

$^1$H NMR (400 MHz, DMSO): δ 7.55 (s, 4H), 7.46 (s, 4H), 7.41 (t, 1H), 6.23-6.26 (br, 2H), 5.11 (s, 1H), 1.39 (s, 6H). Calc'd for C$_{14}$H$_{16}$FN$_2$O$_2$S [M+H]$^+$: 295. found 295.

INTERMEDIATE 9

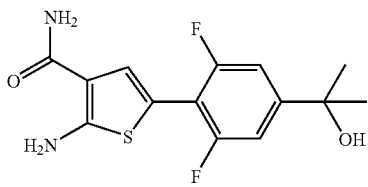

2-Amino-5-[2,6-difluoro-4-(1-hydroxy-1-methylethyl)phenyl]thiophene-3-carboxamide

Step 1. 4-Bromo-2,6-difluorobenzaldehyde

To a solution of diisopropylamine (93 mL, 0.66 mol) in dry tetrahydrofuran (300 mL) at −50° C. was added n-BuLi (212 mL of 2.M in hexanes, 0.53 moL) dropwise. The solution was stirred at room temperature for 30 mins. This solution was then added dropwise to a cooled (−75° C.) solution of 1-bromo-3,5-difluorobenzene (84 g, 0.44 mol) in dry tetrahydrofuran (900 mL). The mixture was stirred at −78° C. for one hour. Dry dimethylformamide (63.6 mL, 0.82 mol) was added and the mixture was stirred for two hours. The cooling bath was removed and the mixture was slowly warmed to room temperature. The mixture was diluted with diethyl ether and poured into cooled 1 M aqueous hydrochloric acid (1 L). The aqueous phase was extracted with diethyl ether. The combined phases were dried, filtered, and the solvent was removed in vacuo to give the crude product. The crude was re-crystallized with ethyl acetate and petroleum ether to afford the title compound.

$^1$H NMR (300 MHz, CDCl$_3$): δ 10.16 (s, 1H), 7.66 (d, 2H).

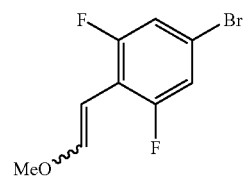 [SMILES: COC=Cc1c(F)cc(Br)cc1F]

Step 2. 2-(4-Bromo-2,6-difluorophenyl)vinyl methyl ether (Methoxymethyl)triphenylphosphonium chloride (1133 g, 3.7 mol) was suspended in tetrahydrofuran (7.0 L) under an argon atmosphere, and stirred with ice-water cooling. t-BuOK (397 g, 3.54 mol) was added in portions. Then a solution of 4-bromo-2,6-difluorobenzaldehyde (340 g, 1.54 mol) in tetrahydrofuran (2.7 L) was added and the reaction was stirred at room temperature for 6 hours. The solution was then poured into ice-water and extracted with ethyl acetate (2×). The combined organic phases were dried and concentrated in vacuo. This material was purified by flash chromatography to afford the title compound.

$^1$H NMR (400 MHz, CDCl$_3$): δ 7.02 (d, 2H), 6.30 (d, 0.3H), 5.70 (d, 0.6H), 5.10 (d, 0.3H), 3.75 (s, 3H).

75

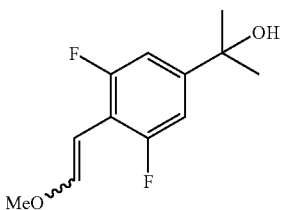 [SMILES: COC=Cc1c(F)cc(C(C)(C)O)cc1F]

Step 3. 2-{3,5-Difluoro-4-[2-methoxyvinyl]phenyl}propan-2-ol

To a cooled (−78° C.) solution of 2-(4-bromo-2,6-difluorophenyl)vinyl methyl ether (45 g, 0.18 mol) in methyl tert-butyl ether (300 mL) was added n-BuLi (75 mL of 2.5M in hexanes, 0.19 mol), and the mixture was stirred at −78° C. for one hour. A solution of acetone (13.6 g, 0.24 mol) in methyl tert-butyl ether (100 mL) was added dropwise to the reaction mixture and the resulting solution was stirred at −78° C. for two hours. Water (90 ml) was added to quench the reaction. The resulting biphasic mixture was extracted with ethyl acetate (2×). The organic layers were dried and concentrated in vacuo. Purification via flash chromatography afforded the title compound.

$^1$H NMR (400 MHz, CDCl$_3$): 7.35 (d, 1H), 6.96 (d, 2H), 5.72 (d, 1H), 3.72 (s, 3H), 1.50 (s, 6H).

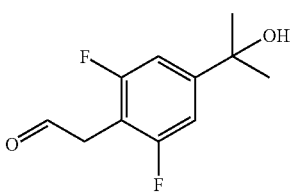

Step 4. [2,6-Difluoro-4-(1-hydroxy-1-methylethyl)phenyl]acetaldehyde

A solution of 2-{3,5-difluoro-4-[2-methoxyvinyl]phenyl}propan-2-ol (5.0 g, 22 mmol) in acetone (25 mL) was added dropwise to 4 M aqueous hydrochloric acid (25 mL, 100 mmol) with ice-water cooling, keeping the temperature below 10° C. Then the mixture was stirred at room temperature for six hours. The resulting mixture was extracted with ethyl acetate (2×) and the combined organic phases were washed with saturated aqueous sodium bicarbonate and brine. The organic layer was then dried and concentrated in vacuo to afford the title compound.

$^1$H NMR (400 MHz, CDCl$_3$): δ 9.70 (s, 1H), 7.00 (d, 21-1), 3.72 (s, 2H), 1.50 (s, 6H).

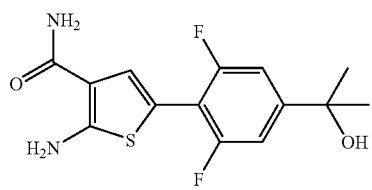

Step 5. 2-Amino-5-[2,6-difluoro-4-(1-hydroxy-1-methylethyl)phenyl]thiophene-3-carboxamide A solution of [2,6-difluoro-4-(1-hydroxy-1-methylethyl)phenyl]acetaldehyde (84.5 g, 0.395 mol) in dry dimethylformamide (250 mL) was treated with 2-cyanoacetamide (36.5 g, 0.434 mol) and sulfur (13.9 g, 0.434 mol). Triethylamine (43.8 g, 0.434 mol) was added dropwise to the reaction mixture using an ice-bath to control the heat release. The reaction was stirred at room temperature overnight, and then poured into a mixture of ice-water (2500 mL) and ethyl acetate (50 mL). An emulsion formed and the insoluble material was filtered. The filtrate was extracted with ethyl acetate (2×). The combined organic phases were dried and concentrated in vacuo. The resulting residue was combined with the filter cake from the previous filtration. This combined material was washed with ethyl acetate. Purification via flash chromatography afforded the title compound.

$^1$H NMR (400 MHz, DMSO): δ 7.50 (s, 4H), 7.18 (d, 2H), 6.70-6.90 (br, 1H), 5.25 (s, 1H), 1.40 (s, 6H). Calc'd for C$_{14}$H$_{15}$FN$_2$O$_2$S [M+H]$^+$: 313. found 313.

INTERMEDIATE 10

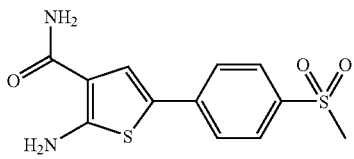

2-Amino-5-[4-(methylsulfonyl)phenyl]thiophene-3-carboxamide

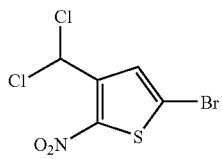 [SMILES: O=[N+]([O-])c1sc(Br)cc1C(Cl)Cl]

Step 1. 5-Bromo-3-(dichloromethyl)-2-nitrothiophene

A solution of 2-bromo-5-nitrothiophene (29 g, 139 mmol) and chloroform (12.37 mL, 153 mmol) in DMF (110 mL) was added dropwise to a solution of potassium tert-butoxide (62.6 g, 558 mmol) in THF (225 mL)/DMF (180 mL). The internal temperature was monitored and maintained at <−60° C. during the addition. Upon complete addition, the reaction was stirred at −78° C. for 30 minutes. 2 N HCl was added and the products were extracted into EtOAc (3×). The combined organic extracts were washed with brine, dried over MgSO$_4$, filtered, and concentrated in vacuo. Purification of the residue by flash silica gel column chromatography (0-10% EtOAc-hexanes) gave the title compound as a brown oil.

$^1$H NMR (600 MHz, DMSO): 7.88 (s, 1H), 7.70 (s, 1H).

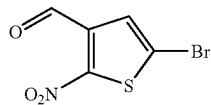

Step 2. 5-Bromo-2-nitrothiophene-3-carbaldehyde

5-Bromo-3-(dichloromethyl)-2-nitrothiophene (60.5 g, 208 mmol) and zinc chloride (113 g, 832 mmol) were stirred in refluxing formic acid (800 mL) overnight. After cooling to ambient temperature, water was added and the products extracted into EtOAc (4×). The combined organic extracts were washed with brine, dried over $MgSO_4$, filtered, and concentrated in vacuo to give the title compound as an orange solid.

$^1$H NMR (600 MHz, DMSO): 10.27 (s, 1H), 7.66 (s, 1H).

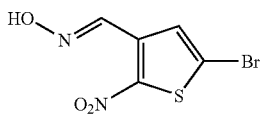

Step 3. 5-Bromo-2-nitrothiophene-3-carbaldehyde oxime

5-Bromo-2-nitrothiophene-3-carbaldehyde (22.5 g, 95 mmol), hydroxylamine hydrochloride (6.96 g, 100 mmol) and sodium acetate (8.21 g, 100 mmol) were stirred in ethanol (225 mL) at room temperature overnight. The solvent was removed in vacuo, saturated $NaHCO_3$ was added and the products extracted into EtOAc (3×). The combined organic extracts were washed with brine, dried over $MgSO_4$, filtered, and concentrated in vacuo to give the title compound as an orange solid.

Calc'd for $C_5H_4BrN_2O_3S$ [M+1]$^+$: 251, 253. Found: 251, 253.

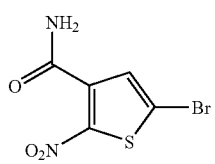 [SMILES: NC(=O)c1cc(Br)sc1[N+](=O)[O-]]

Step 4. 5-Bromo-2-nitrothiophene-3-carboxamide

5-Bromo-2-nitrothiophene-3-carbaldehyde oxime (45 g, 179 mmol), p-toluenesulfonic acid monohydrate (2.73 g, 14.34 mmol), dppe (1.428 g, 3.58 mmol) and $Ru(PPh_3)_3(CO)H_2$ (3.29 g, 3.58 mmol) were taken up in toluene (750 mL). The flask was evacuated and back-filled with $N_2$ (3×) before stirring at 111° C. under $N_2$ for 24 hours. After cooling to room temperature, the reaction mixture was purified directly by flash silica gel column chromatography (0-100% EtOAc-toluene) to give the title compound as brown needles after recrystallising from EtOH-hexanes.

$^1$H NMR (600 MHz, DMSO): 8.07 (s, 1H), 7.87 (s, 1H), 7.52 (s, 1H).

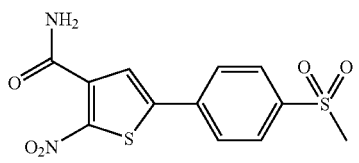 [SMILES: CS(=O)(=O)c1ccc(-c2cc(C(N)=O)c([N+](=O)[O-])s2)cc1]

Step 5. 5-[4-(Methylsulfonyl)phenyl]-2-nitrothiophene-3-carboxamide

5-Bromo-2-nitrothiophene-3-carboxamide (1 g, 3.98 mmol), 4,4,5,5-tetramethyl-2-[4-(methylsulfonyl)phenyl]-1,3,2-dioxaborolane (1.236 g, 4.38 mmol) and tetrakis(triphenylphosphine)palladium(0) (0.230 g, 0.199 mmol) were taken up in THF (14 mL)/2 N $Na_2CO_3$ (6 mL) The reaction was stirred at 80° C. overnight. Room temperature was attained and the resulting precipitate was collected by filtration, washed with water and triturated in EtOH to give the title compound as a yellow solid.

$^1$H NMR (600 MHz, DMSO): 8.13 (s, 1H), 8.10 (d, 2H), 7.99 (d, 2H), 7.92 (s, 1H), 7.90 (s, 1H), 3.25 (s, 3H).

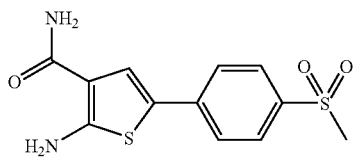

Step 6. 2-Amino-5-[4-(methylsulfonyl)phenyl]thiophene-3-carboxamide

Nitro reduction, Method A: 5-[4-(Methylsulfonyl)phenyl]-2-nitrothiophene-3-carboxamide (0.96 g, 2.94 mmol) and Pt/C, doped with V (0.191 g, 0.029 mmol) were stirred in MeOH (60 mL) at room temperature under a balloon of $H_2$ for 90 minutes. The catalyst was removed by filtering through Celite, which was subsequently washed with DMF. The solvent was removed in vacuo and the residue triturated in EtOH to give the title compound as a dark brown solid.

$^1$H NMR (600 MHz, DMSO): 7.81 (m, 3H), 7.70 (s, 2H), 7.53 (d, 2H), 7.31 (br s, 1H), 6.89 (br s, 1H), 3.15 (s, 3H).

Calc'd for $C_{12}H_{13}N_2O_3S_2$ [M+H]$^+$: 297. Found: 297.

INTERMEDIATE 11

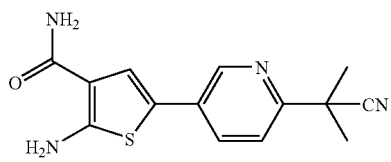

2-Amino-5-[6-(1-cyano-1-methylethyl)pyridin-3-yl]thiophene-3-carboxamide

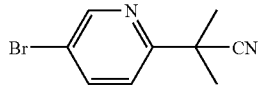

Step 1: 2-(5-Bromopyridin-2-yl)-2-methylpropanenitrile 2,5-Dibromopyridine (2 g, 8.44 mmol) was placed in a vial that was evacuated and backfilled with argon three times. Anhydrous dioxane (8.4 ml) was then added and the suspension was stirred. In a separate vial, 2-methylpropanenitrile (0.76 ml, 8.44 mmol) was added to a solution of sodium 1,1,1,3,3,3-hexamethyldisilazan-2-ide (28.1 ml of 0.6 M in toluene, 16.9 mmol). This was stirred for 10 minutes then added to the suspension. The reaction was heated to 70° C. for 1.5 hours. It was then cooled to room temperature, quenched with water, and extracted with ethyl acetate. Purification was performed via silica gel chromatography (0-75% ethyl acetate in hexane) to yield the title compound.

$^1$H NMR (600 MHz, d6-DMSO): δ 8.75 (d, 1H), 8.16 (dd, 1H), 7.60 (d, 1H), 1.70 (s, 6H).

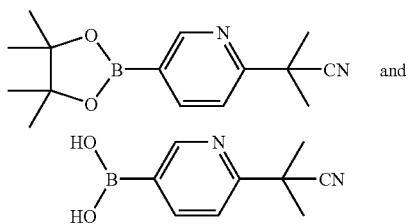

Step 2: 2-Methyl-2-[5-(4,4,5,5-tetramethyl-1,3,2-dioxaborolan-2-yl)pyridin-2-yl]propanenitrile and [6-(1-cyano-1-methylethyl)pyridin-3-yl]boronic acid 2-(5-Bromopyridin-2-yl)-2-methylpropanenitrile (300 mg, 1.33 mmol), 4,4,4',4',5,5,5',5'-octamethyl-2,2'-bi-1,3,2-dioxaborolane (355 mg, 1.40 mmol), dichlorobis-(1,1'-bis(diphenylphosphanyl)ferrocene) palladium-dichloromethane adduct (54.4 mg, 0.067 mmol), and potassium acetate (392 mg, 4.00 mmol) were taken up in degassed dioxane (9 ml). The suspension was heated to 80° C. for 4 hours. After cooling to room temperature, the reaction mixture was washed with aqueous ammonium chloride and extracted with ethyl acetate. The combined extracts were taken up in methanol and 1 N hydrochloric acid (3 mL) and the solution stirred for 1 hour. The reaction mixture was concentrated under reduced pressure, taken up in aqueous sodium bicarbonate, and extracted in ethyl acetate. The organic layers were combined and concentrated under reduced pressure, and the resulting solid was purified via reverse phase HPLC to yield a mixture of the title compounds as trifluoroacetic acid salts.

MS for the boronic acid: Calc'd for $C_9H_{12}BN_2O_2$ [M+H]$^+$: 191. Found: 191.

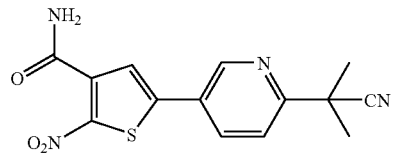

Step 3: 5-[6-(1-Cyano-1-methylethyl)pyridin-3-yl]-2-nitrothiophene-3-carboxamide A mixture of 2-methyl-2-[5-(4,4,5,5-tetramethyl-1,3,2-dioxaborolan-2-yl)pyridin-2-yl]propanenitrile and [6-(1-cyano-1-methylethyl)pyridin-3-yl]boronic acid as trifluoroacetic acid salts (260 mg, approx. 0.673 mmol combined), 5-bromo-2-nitrothiophene-3-carboxamide (169 mg, 0.673 mmol) (Intermediate 10 Step 4), and tetrakis(triphenylphosphine)palladium(0) (38.9 mg, 0.034 mmol) were dissolved in fully degassed tetrahydrofuran (2.7 ml) and fully degassed 2 M aqueous sodium carbonate (0.7 ml). The reaction was stirred at 70° C. for 4 hours. It was then allowed to cool to room temperature, taken up in ethyl acetate, and washed with water (2×) and brine (2×). The organic layer was dried over magnesium sulfate, filtered, and concentrated under reduced pressure. The resulting residue was purified via reverse phase HPLC to yield the title compound.

Calc'd for $C_{14}H_{13}N_4O_3S$ [M+H]$^+$: 317. Found: 317.

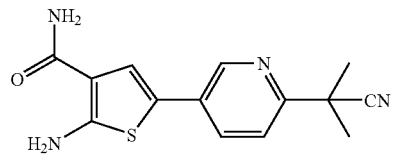

Step 4: 2-Amino-5-[6-(1-cyano-1-methylethyl)pyridin-3-yl]thiophene-3-carboxamide Nitro reduction, Method B: 5-[6-(1-Cyano-1-methylethyl)pyridin-3-yl]-2-nitrothiophene-3-carboxamide (95 mg, 0.29 mmol) and iron (III) chloride (2.33 mg, 0.014 mmol) were put in a vial. The vial was evacuated and backfilled with argon three times. Degassed methanol (4.1 mL) was added and the solution was heated to 65° C. for 10 minutes. Hydrazine hydrate (0.04 mL, 0.86 mmol) was then added and the reaction was stirred at 65° C. for 4 hours. After cooling to room temperature, the reaction mixture was filtered through Celite. The filtrate was concentrated in vacuo. The residue was taken up in water and ethyl acetate. The organic layer was separated, dried over magnesium sulfate, filtered, and concentrated under reduced pressure to afford the title compound as a solid.

$^1$H NMR (600 MHz, d6-DMSO): δ 8.82 (d, 1H), 7.80 (dd, 1H), 7.73 (s, 1H), 7.64 (s, 2H), 7.57 (d, 1H), 1.70 (s, 6H).

INTERMEDIATE 12

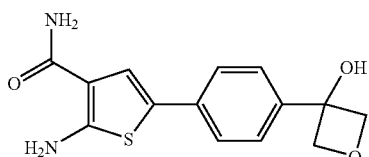

2-Amino-5-[4-(3-hydroxyoxetan-3-yl)phenyl]thiophene-3-carboxamide

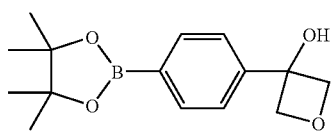 [SMILES: CC1(C)OB(c2ccc(C3(O)COC3)cc2)OC1(C)C]

Step 1. 3-[4-(4,4,5,5-Tetramethyl-1,3,2-dioxaborolan-2-yl)phenyl]oxetan-3-ol 1,4-Dibromobenzene (3.3 g, 13.99 mmol) and 2-isopropoxy-4,4,5,5-tetramethyl-1,3,2-dioxaborolane (2.91 mL, 14.27 mmol) were taken up in THF (60 mL) and cooled to −78° C. before adding t-BuLi (16.46 mL, 28.0 mmol) dropwise. After stirring at −78° C. for 40 minutes, additional t-BuLi (16.46 mL, 28.0 mmol) was added. After 30 minutes oxetan-3-one (1.01 g, 13.99 mmol) was added and the reaction mixture was allowed to room temperature over 90 minutes. Water was added followed by saturated NH$_4$Cl and the products were extracted into EtOAc (2×). The combined organic extracts were washed with brine, dried over MgSO$_4$, filtered, and concentrated in vacuo. Purification of the residue by flash silica gel column chromatography (6-50% EtOAc-hexanes) gave the title compound as a white solid.

$^1$H NMR (600 MHz, DMSO): δ 7.67 (d, 2H), 7.59 (d, 2H), 6.38 (s, 1H), 4.74 (d, 2H), 4.60 (d, 2H), 1.26 (s, 12H).

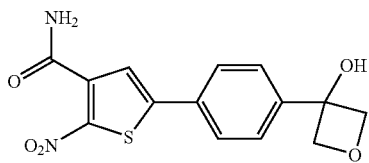 [SMILES: NC(=O)c1cc(-c2ccc(C3(O)COC3)cc2)sc1[N+](=O)[O-]]

Step 2. 5-[4-(3-Hydroxyoxetan-3-yl)phenyl]-2-nitrothiophene-3-carboxamide

5-Bromo-2-nitrothiophene-3-carboxamide (Intermediate 10, Step 4) (1.44 g, 5.74 mmol), 3-[4-(4,4,5,5-tetramethyl-1,3,2-dioxaborolan-2-yl)phenyl]oxetan-3-ol (1.821 g, 6.60 mmol) and tetrakis(triphenylphosphine)palladium(0) (0.331 g, 0.287 mmol) were taken up in THF (25 mL)/2 N Na$_2$CO$_3$ (10 mL) and the reaction mixture was stirred at 80° C. overnight. After cooling to room temperature, saturated NH$_4$Cl and EtOAc were added. The resulting precipitate was collected by filtration, washed with water and dried to give 5-[4-(3-hydroxyoxetan-3-yl)phenyl]-2-nitrothiophene-3-carboxamide as a brown solid (batch 1). The organic phase from the filtrate was separated, washed with brine, dried over MgSO$_4$, filtered, and concentrated in vacuo while loading onto silica. Purification of the residue by flash silica gel column chromatography (12-100% EtOAc-hexanes followed by 0-10% MeOH-EtOAc) gave the title compound as an orange solid after recrystallising from EtOH (batch 2).

$^1$H NMR (600 MHz, DMSO): δ 8.11 (s, 1H), 7.86 (m, 3H), 7.73 (s, 1H), 7.69 (d, 2H), 6.48 (s, 1H), 4.76 (d, 2H), 4.65 (d, 2H).

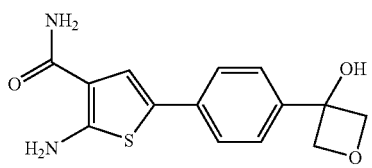

Step 3. 2-Amino-5-[4-(3-hydroxyoxetan-3-yl)phenyl]thiophene-3-carboxamide

The title compound was prepared according to the general procedure for nitro reduction, Method A in Example 10 Step 6 using 5-[4-(3-hydroxyoxetan-3-yl)phenyl]-2-nitrothiophene-3-carboxamide (1.284 g, 4.01 mmol) as the starting material.

$^1$H NMR (600 MHz, DMSO): 7.54 (s, 1H), 7.52 (d, 2H), 7.45 (s, 1H), 7.37 (d, 2H), 7.25 (br s, 1H), 6.79 (br s, 1H), 6.30 (s, 1H), 4.72 (d, 2H), 4.64 (d, 2H).

INTERMEDIATE 13

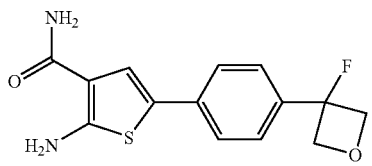

2-Amino-5-[4-(3-fluorooxetan-3-yl)phenyl]thiophene-3-carboxamide

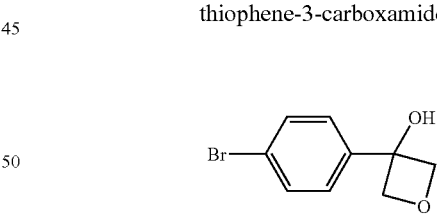

Step 1. 3-(4-Bromophenyl)oxetan-3-ol 1,4-Dibromobenzene (2 g, 8.48 mmol) was taken up in THF (35 mL) and cooled to −78° C. before adding n-BuLi (3.39 mL, 8.48 mmol) dropwise. After stirring at −78° C. for 30 minutes, oxetan-3-one (0.611 g, 8.48 mmol) was added and the reaction was warmed to room temperature for 1 hour at which time water and saturated NH$_4$Cl were added and the products were extracted into EtOAc (2×). The combined organic extracts were washed with brine, dried over MgSO$_4$, filtered, and concentrated in vacuo. Purification of the residue by flash silica gel column chromatography (6-50% EtOAc-hexanes) gave the title compound as a white solid.

¹H NMR (600 MHz, CDCl₃): δ 7.53 (d, 2H), 7.48 (d, 2H), 4.88 (d, 2H), 4.84 (d, 2H), 2.63 (s, 1H).

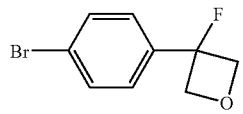

Step 2. 3-(4-Bromophenyl)-3-fluorooxetane 3-(4-Bromophenyl)oxetan-3-ol (1.55 g, 6.77 mmol) was taken up in DCM (100 mL) and cooled to −78° C. DAST (1.073 mL, 8.12 mmol) was added and the mixture was stirred at −78° C. for 90 minutes followed by 0° C. for 20 minutes. Saturated NaHCO₃ was added and the products extracted into DCM (2×). The combined organic extracts were washed with brine, dried over MgSO₄, filtered, and concentrated in vacuo. Purification of the residue by flash silica gel column chromatography (0-10% EtOAc-hexanes) gave the title compound as a yellow oil.

¹H NMR (600 MHz, CDCl₃): δ 7.55 (d, 2H), 7.42 (d, 2H), 5.08 (dd, 2H), 4.80 (dd, 2H).

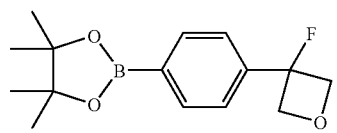 [SMILES: CC1(C)OB(c2ccc(C3(F)COC3)cc2)OC1(C)C]

Step 3. 2-[4-(3-Fluorooxetan-3-yl)phenyl]-4,4,5,5-tetramethyl-1,3,2-dioxaborolane 3-(4-Bromophenyl)-3-fluorooxetane (0.35 g, 1.515 mmol), bis(pinacolato)diboron (0.404 g, 1.590 mmol), PdCl₂(dppf)-CH₂Cl₂ adduct (0.062 g, 0.076 mmol) and potassium acetate (0.446 g, 4.54 mmol) were taken up in dioxane (10 mL) in a 20 mL microwave vial. The mixture was stirred at 80° C. for 4 hours. Saturated NH₄Cl was added and the products extracted into EtOAc (2×). The combined organic extracts were washed with brine, dried over MgSO₄, filtered, and concentrated in vacuo. Purification of the residue by flash silica gel column chromatography (2-20% EtOAc-hexanes) gave the title compound as a white solid.

¹H NMR (600 MHz, CDCl₃): δ 7.86 (d, 2H), 7.55 (d, 2H), 5.09 (dd, 2H), 4.85 (dd, 2H), 1.33 (s, 12H).

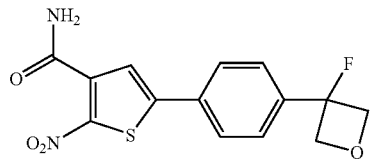

Step 4. 5-[4-(3-Fluorooxetan-3-yl)phenyl]-2-nitrothiophene-3-carboxamide

The title compound was prepared according to the general procedure in Intermediate 10 Step 5 using 5-bromo-2-nitrothiophene-3-carboxamide (Intermediate 10, Step 4) (0.31 g, 1.23 mmol) and 2-[4-(3-fluorooxetan-3-yl)phenyl]-4,4,5,5-tetramethyl-1,3,2-dioxaborolane (0.378 g, 1.36 mmol) as the starting materials.

¹H NMR (600 MHz, DMSO): δ 8.12 (s, 1H), 7.94 (d, 2H), 7.87 (s, 1H), 7.80 (s, 1H), 7.65 (d, 2H), 4.93 (m, 4H).

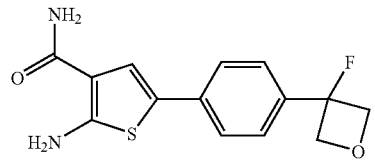 [SMILES: NC(=O)c1cc(-c2ccc(C3(F)COC3)cc2)sc1[N+](=O)[O-]]

Step 5. 2-Amino-5-[4-(3-fluorooxetan-3-yl)phenyl]thiophene-3-carboxamide

The title compound was prepared according to the general procedure in Intermediate 10 Step 6 using 5-[4-(3-fluorooxetan-3-yl)phenyl]-2-nitrothiophene-3-carboxamide (272 mg, 0.84 mmol) as the starting material.

Calc'd for C₁₄H₁₄FN₂O₂S [M+H]⁺: 293. Found: 293.

INTERMEDIATE 14

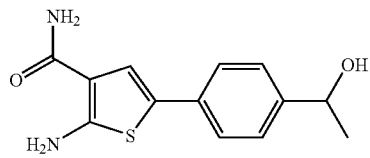

2-Amino-5-[4-(1-hydroxyethyl)phenyl]thiophene-3-carboxamide

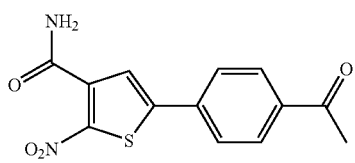 [SMILES: CC(=O)c1ccc(-c2cc(C(N)=O)c([N+](=O)[O-])s2)cc1]

Step 1. 5-(4-Acetylphenyl)-2-nitrothiophene-3-carboxamide

The title compound was prepared according to the general procedure in Intermediate 10 Step 5 using 5-bromo-2-nitrothiophene-3-carboxamide (Intermediate 10, Step 4) (0.5 g, 1.992 mmol) and (4-acetylphenyl)boronic acid (0.392 g, 2.390 mmol) as the starting materials.

¹H NMR (600 MHz, DMSO): 8.12 (s, 1H), 8.00 (m, 4H), 7.88 (s, 2H), 2.58 (s, 3H).

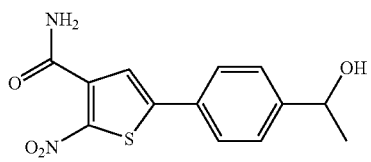

Step 2. 5-[4-(1-Hydroxyethyl)phenyl]-2-nitrothiophene-3-carboxamide 5-(4-Acetylphenyl)-2-nitrothiophene-3-carboxamide (0.21 g, 0.723 mmol) was taken up in MeOH (4 mL), followed by the addition of sodium borohydride (0.027 g, 0.723 mmol). The reaction mixture stirred at room temperature for 3 hours. Water was added and the products extracted into EtOAc (2×). The combined organic extracts were washed with brine, dried over MgSO$_4$, filtered, and concentrated in vacuo to give the title compound as a yellow solid.

$^1$H NMR (600 MHz, DMSO): δ 8.10 (s, 1H), 7.84 (s, 1H), 7.7 (d, 2H), 7.68 (s, 1H), 7.43 (d, 2H), 5.26 (d, 1H), 4.73 (m, 1H), 1.30 (t, 3H).

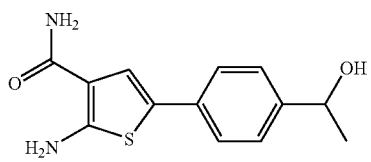 [SMILES: CC(O)c1ccc(-c2cc(C(N)=O)c(N)s2)cc1]

Step 3. 2-Amino-5-[4-(1-hydroxyethyl)phenyl]thiophene-3-carboxamide

The title compound was prepared according to the general procedure in Intermediate 10 Step 6 using 5-[4-(1-hydroxyethyl)phenyl]-2-nitrothiophene-3-carboxamide (198 mg, 0.68 mmol) as the starting material.

Calc'd for $C_{13}H_{15}N_2O_2S$ [M+H]$^+$: 263. Found: 263.

INTERMEDIATE 15

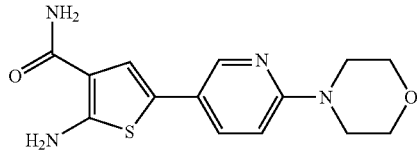

2-Amino-5-(6-morpholin-4-ylpyridin-3-yl)thiophene-3-carboxamide

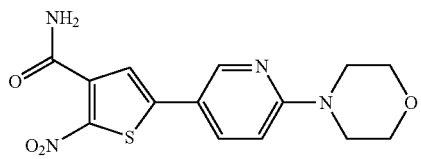

Step 1: 5-(6-Morpholin-4-ylpyridin-3-yl)-2-nitrothiophene-3-carboxamide

The title compound was prepared from 5-bromo-2-nitrothiophene-3-carboxamide (Intermediate 10, Step 4) (2.50 g, 9.96 mmol) and 4-[5-(4,4,5,5-tetramethyl-1,3,2-dioxaborolan-2-yl)pyridine-2-yl]morpholine (2.89 g, 9.96 mmol) according to the general procedure described in Intermediate 10, Step 5.

Calc'd for $C_{14}H_{15}N_4O_4S$ [M+H]$^+$: 335. Found: 335.

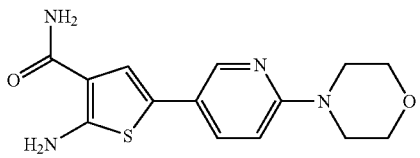

Step 2: 2-Amino-5-(6-morpholin-4-ylpyridin-3-yl)thiophene-3-carboxamide

The title compound was prepared from 5-(6-morpholin-4-ylpyridin-3-yl)-2-nitrothiophene-3-carboxamide (2.77 g, 8.28 mmol) according to the general procedure described in Intermediate 11, Step 4 (nitro reduction method B).

Calc'd for $C_{14}H_{17}N_4O_2S$ [M+H]$^+$: 305. Found: 305.

INTERMEDIATE 16

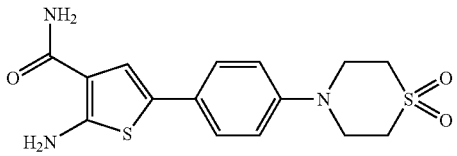

2-Amino-5-[4-(1,1-dioxidothiomorpholin-4-yl)phenyl]thiophene-3-carboxamide

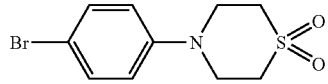 [SMILES: O=S1(=O)CCN(c2ccc(Br)cc2)CC1]

Step 1: 4-(4-Bromo-phenyl)-thiomorpholine 1,1-dioxide 1,1'-Sulfonyldiethylene divinyl sulfone (25 g, 21.18 mmol; 0.02 M in proan-2-ol) was added dropwise to a stirred refluxing solution of 4-bromoaniline (36.44 g, 21.18 mmol; 0.01 M in propan-2-ol/water, 1:1). The reaction mixture was refluxed for 48 h. The reaction mixture was cooled to room temperature and the precipitate was collected by filtration and washed with water followed by hexane/diethylether (1:1) to afford the title compound as a white solid. The mother liquor was concentrated to half volume under reduced pressure, cooled to room temperature, and the precipitate was collected and washed as above.

$^1$H NMR (400 MHz, CDCl$_3$) δ: 3.1 (t, 4H, J=5.68), 3.81 (t, 4H, J=5.24), 6.79 (d, 2H, J=9.04), 7.38 (d, 2H, J=9.0).

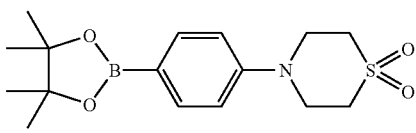 [SMILES: CC1(C)OB(c2ccc(N3CCS(=O)(=O)CC3)cc2)OC1(C)C]

Step 2: 4-[4-(4,4,5,5-Tetramethyl-{1,3,2}dioxaborolan-2-yl)-phenyl]-thiomorpholine 1,1-dioxide 4-(4-Bromo-phenyl)-thiomorpholine 1,1-dioxide (46 g, 159 mmol) was dissolved in dioxane (1 L). Subsequently bispinacolatodiborane (60.6 g, 239 mmol) and PdCl$_2$(dppf)$_2$ (5.82 g, 7.9 mmol) were added and degassed with argon while stirring. The reaction mixture was warmed up to 50° C. for 30 min and potassium acetate (46.7 g, 47 mmol) was added. The resulting reaction mixture was refluxed for 3 h. The reaction mixture was cooled to room temperature and filtered through a celite pad. The filtrate was concentrated under reduced pressure and the residue was dissolved in ethyl acetate (800 mL). The ethyl acetate layer was washed with water (2×250 mL) and the organic layer separated, dried over sodium sulfate and filtered. The solvent was removed under reduced pressure and the residue was purified on silica gel column chromatography, using 20% ethyl acetate in hexane. Removal of solvent under reduced pressure furnished the product as a yellowish white solid. The solid was washed with hexane/diethylether (1:1) to afford pure white solid of the title compound.

$^1$H NMR (400 MHz, CDCl$_3$) δ: 1.33 (s, 12H), 3.1 (t, 4H, J=5.32), 3.92 (t, 4H, J=5.12), 6.86 (d, 2H, J=8.64), 7.73 (d, 2H, J=8.6).

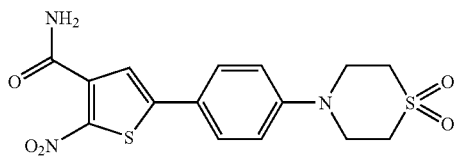

Step 3: 5-[4-(1,1-Dioxidothiomorpholin-4-yl)phenyl]-2-nitrothiophene-3-carboxamide The title compound was prepared from 5-bromo-2-nitrothiophene-3-carboxamide (Intermediate 10 Step 4) (300 mg, 1.20 mmol) and 4-[4-(4,4,5,5-tetramethyl-1,3,2-dioxaborolan-2-yl)phenyl]thiomorpholine 1,1-dioxide (403 mg, 1.20 mmol) according to the general procedure described in Intermediate 10 Step 5.

Calc'd for C$_{15}$H$_{16}$N$_3$O$_5$S$_2$ [M+H]: 382. Found: 382.

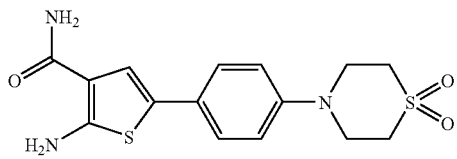

Step 4: 2-Amino-5-[4-(1,1-dioxidothiomorpholin-4-yl)phenyl]thiophene-3-carboxamide The title compound was prepared from 5-[4-(1,1-dioxidothiomorpholin-4-yl)phenyl]-2-nitrothiophene-3-carboxamide (366 mg, 0.96 mmol) according to the general procedure described in Intermediate 10 Step 6 (nitro reduction method A).

Calc'd for C$_{15}$H$_{18}$N$_3$O$_3$S$_2$ [M+H]: 352. Found: 352.

INTERMEDIATE 17

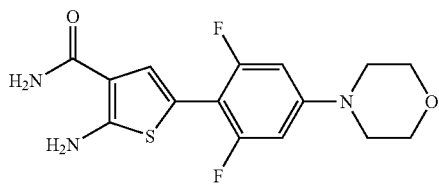

2-Amino-5-(2,6-difluoro-4-morpholin-4-ylphenyl)thiophene-3-carboxamide

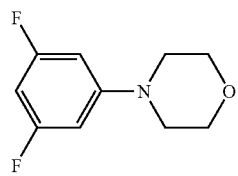 [SMILES: Fc1cc(F)cc(N2CCOCC2)c1]

Step 1: 4-(3,5-Difluorophenyl)morpholine

A sealed tube was charged with 1-bromo-3,5-difluorobenzene (1.79 ml, 15.5 mmol), Pd$_2$(dba)$_3$ (0.85 g, 0.93 mmol), X-PHOS (2.22 g, 4.66 mmol), and potassium carbonate (4.73 g, 34.2 mmol). The tube was evacuated and backfilled with argon 3×. Fully degassed tert-amyl alcohol (51 mL) was added followed immediately by the addition of morpholine (2.71 ml, 31.1 mmol). The tube was then sealed and placed in an oil bath at 100° C. and stirred overnight. The reaction mixture was taken up in diethyl ether and water. The aqueous layer was extracted twice with diethyl ether. The organics were combined, dried over anhydrous magnesium sulfate, filtered, and concentrated in vacuo. Purification via flash chromatography (silica, 0-17% diethylether/hexanes) afforded the title compound as a light yellow solid.

$^1$H NMR (500 MHz, d6-DMSO): δ 6.61 (m, 2H), 6.49 (m, 1H), 3.68 (m, 4H), 3.14 (m, 4H).

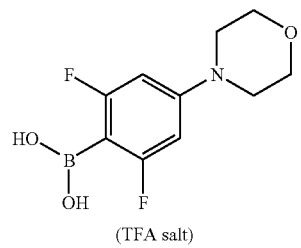

(TFA salt)

Step 2: (2,6-Difluoro-4-morpholin-4-ylphenyl)boronic acid (TFA salt)

To a solution of diisopropylamine (2.4 ml, 16.8 mmol) in tetrahydrofuran (43.5 ml) at −78° C. was added n-butyllithium (9 ml, 14.4 mmol). After addition, the mixture was stirred for 30 minutes at 0° C. and then recooled to −78° C. A solution of 4-(3,5-difluorophenyl)morpholine (2.6 g, 13.1 mmol) in tetrahydrofuran (15 ml) was added dropwise. After stirring for 30 minutes at −78° C., trimethyl borate (4.4 ml, 39.4 mmol) was added dropwise. The reaction was allowed to warm to room temperature overnight. The reaction was then quenched with 2 N aqueous hydrochloric acid and stirred for 10 minutes at room temperature. The biphasic mixture was then extracted with ethyl acetate (2×). The combined organic layers were washed with brine, dried over magnesium sulfate, and concentrated in vacuo. The crude material was purified via reverse phase HPLC (10-100% acetonitrile/water+0.05% TFA modifier) to afford title compound as the trifluoroacetic acid salt.

Calc'd for $C_{10}H_{13}BF_2NO_3$ [M+H]: 244. found 244.

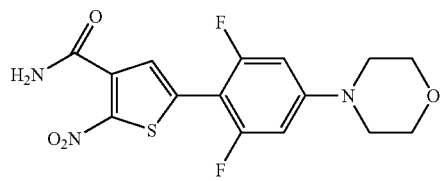 [SMILES: NC(=O)c1cc(-c2c(F)cc(N3CCOCC3)cc2F)sc1[N+](=O)[O-]]

Step 3: 5-(2,6-Difluoro-4-morpholin-4-ylphenyl)-2-nitrothiophene-3-carboxamide

The title compound was prepared as described in Intermediate 10 Step 5 using 5-bromo-2-nitrothiophene-3-carboxamide (Intermediate 10 Step 4) (582 mg, 2.32 mmol) and (2,6-difluoro-4-morpholin-4-ylphenyl)boronic acid (TFA salt) (830 mg, 2.33 mmol) as starting materials.

$^1$H NMR (500 MHz, d6-DMSO): δ 8.11 (s, 1H), 7.86 (s, 1H), 7.38 (s, 1H), 6.89 (d, 2H), 3.69 (m, 4H), 3.33 (m, 4H).

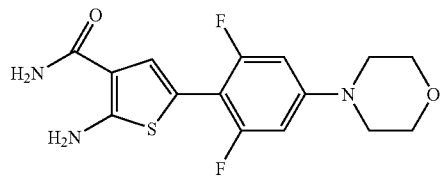

Step 4: 2-Amino-5-(2,6-difluoro-4-morpholin-4-ylphenyl)thiophene-3-carboxamide

The title compound was prepared as described in Intermediate 11 Step 4 (nitro reduction method B) using 5-(2,6-difluoro-4-morpholin-4-ylphenyl)-2-nitrothiophene-3-carboxamide (292 mg, 0.79 mmol) as starting material.

Calc'd for $C_{15}H_{16}F_2N_3O_2S$ [M+H]: 340. found 340.

INTERMEDIATE 18

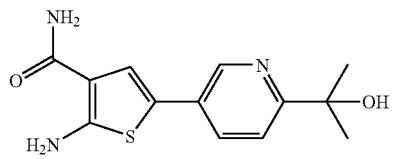

2-Amino-5-[6-(1-hydroxy-1-methylethyl)pyridin-3-yl]thiophene-3-carboxamide

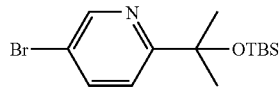

Step 1: 5-Bromo-2-(1-{[tert-butyl(dimethyl)silyl]oxy}-1-methylethyl)pyridine

To a solution of 2-(5-bromopyridin-2-yl)propan-2-ol (1.20 g, 5.55 mmol, prepared according to the method in *Tetrahedron Lett.* 2000, 41, 4335) and 2,6-lutidine (1.29 mL, 11.11 mmol) in $CH_2Cl_2$ (12 mL) was added TBSOTf (1.91 mL, 8.33 mmol). After stirring at room temperature for 2 h, the reaction was diluted with water and extracted with $CH_2Cl_2$ (2×). The combined organic layers were dried ($MgSO_4$), filtered, and evaporated. The crude residue was purified on silica gel (0-10% EtOAc/hexanes) which afforded the title compound as a colorless oil.

Calc'd for $C_{14}H_{25}BrNOSi$ [M+H]$^+$ 330. found 330.

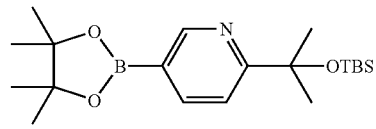

Step 2: 2-(1-{[tert-Butyl(dimethyl)silyl]oxy}-1-methylethyl)-5-(4,4,5,5-tetramethyl-1,3,2-dioxaborolan-2-yl)pyridine A solution of 5-bromo-2-(1-{[tert-butyl(dimethyl)silyl]oxy}-1-methylethyl)pyridine (1.63 g, 4.93 mmol) in THF (30 mL) was cooled to −78° C. followed by the addition of n-butyllithium (2.5 M in hexanes, 2.17 mL, 5.43 mmol). After 5 min at −78° C., 2-isopropoxy-4,4,5,5-tetramethyl-1,3,2-dioxaborolane (1.31 mL, 6.41 mmol) in THF (5.0 mL) was added dropwise, and the reaction was maintained at −78° C. for 10 min. The reaction was allowed to warm to room temperature, quenched with saturated $NH_4Cl$, and extracted with EtOAc (2×). The combined organic layers were washed with brine, dried ($MgSO_4$), filtered, and evaporated. Flash chromatography of the crude residue (0-50% EtOAc/hexanes) afforded the title compound as a colorless solid.

$^1$H NMR (600 MHz, DMSO-d$_6$) δ 8.65 (dd, 1H), 7.97 (dd, 1H), 7.61 (dd, 1H), 1.49 (s, 6H), 1.26 (s, 12H), 0.88 (s, 9H), 0.04 (s, 6H).

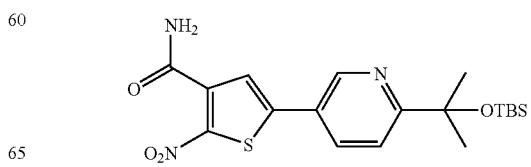

Step 3: 5-[6-(1-{[tert-Butyl(dimethyl)silyl]oxy}-1-methylethyl)pyridin-3-yl]-2-nitrothiophene-3-carboxamide 5-Bromo-2-nitrothiophene-3-carboxamide (602 mg, 2.40 mmol), 2-(1-{[tert-butyl(dimethyl)silyl]oxy}-1-methylethyl)-5-(4,4,5,5-tetramethyl-1,3,2-dioxaborolan-2-yl)pyridine (905 mg, 2.40 mmol), and Pd(PPh$_3$)$_4$ (139 mg, 0.12 mmol) were combined in a vial and evacuated/backfilled with nitrogen. THF (5.6 mL) and 2 N Na$_2$CO$_3$ (2.4 mL) were added, and the reaction was stirred at 90° C. overnight. The reaction mixture was cooled to room temperature, diluted with water, and extracted with EtOAc (2×). The combined organic layers were washed with brine, dried (MgSO$_4$), filtered, and evaporated. Flash chromatography of the crude residue (10-100% EtOAc/hexanes) afforded the title compound as a yellow solid.

Calc'd for C$_{19}$H$_{28}$N$_3$O$_4$SSi [M+H]$^+$ 422. found 422.

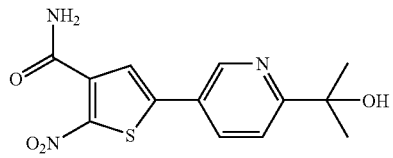 [SMILES: CC(C)(O)c1ccc(-c2cc(C(N)=O)c([N+](=O)[O-])s2)cn1]

Step 4: 5-[6-(1-Hydroxy-1-methylethyl)pyridin-3-yl]-2-nitrothiophene-3-carboxamide To a solution of 5-[6-(1-{[tert-butyl(dimethyl)silyl]oxy}-1-methylethyl)pyridin-3-yl]-2-nitrothiophene-3-carboxamide (665 mg, 1.58 mmol) in THF (10 mL) were added AcOH (0.36 ml, 6.13 mmol) and TBAF (1.0 M in THF, 6.31 mL, 6.31 mmol). The sealed reaction was stirred at 90° C. for 18 h. Additional AcOH (0.361 ml, 6.13 mmol) and TBAF (6.31 mL, 6.31 mmol) were added, and the reaction was stirred at 90° C. for another 24 h. The brown solution was cooled to room temperature, diluted with water, and extracted with EtOAc (2×). The combined organic extracts were washed with brine (2×), dried (MgSO$_4$), filtered, and evaporated. Flash chromatography of the crude residue (50-100% EtOAc/hexanes) provided a yellow residue that was triturated with Et$_2$O and filtered to isolate the title compound as a yellow solid.

Calc'd for C$_{13}$H$_{14}$N$_3$O$_4$S [M+H]$^+$ 308. found 308.

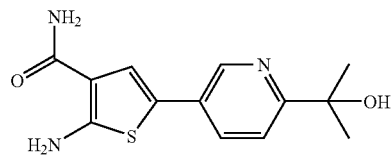

Step 5: 2-Amino-5-[6-(1-hydroxy-1-methylethyl)pyridin-3-yl]thiophene-3-carboxamide To 5-[6-(1-hydroxy-1-methylethyl)pyridin-3-yl]-2-nitrothiophene-3-carboxamide (245 mg, 0.80 mmol) in MeOH (20 mL) was added 3% Pt/C doped with 0.6% V (52 mg, 8.0 μmol). The reaction was stirred under a hydrogen balloon at room temperature for 4 h. The solution was diluted with MeOH, filtered through Celite, and evaporated to give the title compound as a gray solid.

Calc'd for C$_{13}$H$_{16}$N$_3$O$_2$S [M+H]$^+$ 278. found 278.

Additional 2-aminothiophene intermediates were prepared in accordance to the synthetic sequences described above and are illustrated in the table below.

TABLE 1

| Intermediate # | Structure | Compound Name | Characterization [M + H]$^+$ | Nitro Reduction Method |
|---|---|---|---|---|
| 19 | 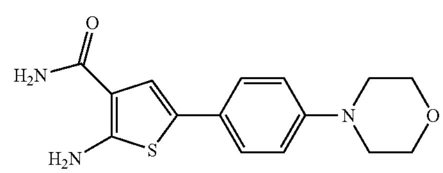 [SMILES: NC(=O)c1cc(-c2ccc(N3CCOCC3)cc2)sc1N] | 2-amino-5-(4-morpholin-4-ylphenyl)thiophene-3-carboxamide | Calc'd 304, found 304 | A |
| 20 | 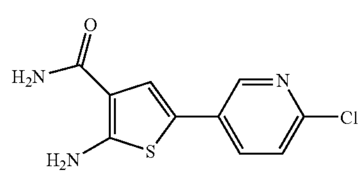 [SMILES: NC(=O)c1cc(-c2ccc(Cl)nc2)sc1N] | 2-amino-5-(6-chloropyridin-3-yl)thiophene-3-carboxamide | Calc'd 254, found 254 | B |
| 21 | 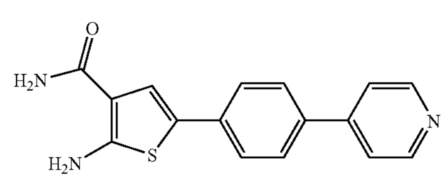 [SMILES: NC(=O)c1cc(-c2ccc(-c3ccncc3)cc2)sc1N] | 2-amino-5-(4-pyridin-4-ylphenyl)thiophene-3-carboxamide | Calc'd 296, found 296 | B |

TABLE 1-continued

| Intermediate # | Structure | Compound Name | Characterization [M + H]$^+$ | Nitro Reduction Method |
|---|---|---|---|---|
| 22 | 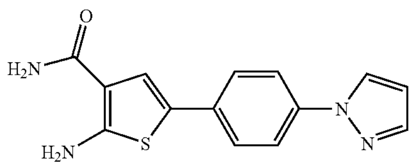 [SMILES: NC(=O)c1cc(-c2ccc(-n3cccn3)cc2)sc1N] | 2-amino-5-[4-(1H-pyrazol-1-yl)phenyl]thiophene-3-carboxamide | Calc'd 285, found 285 | B |
| 23 | 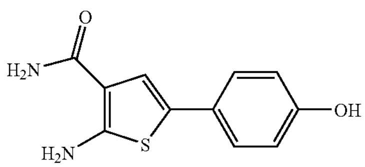 [SMILES: NC(=O)c1cc(-c2ccc(O)cc2)sc1N] | 2-amino-5-(4-hydroxyphenyl)thiophene-3-carboxamide | Calc'd 235, found 235 | B |
| 24 | 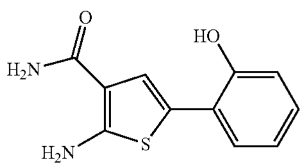 [SMILES: NC(=O)c1cc(-c2ccccc2O)sc1N] | 2-amino-5-(2-hydroxyphenyl)thiophene-3-carboxamide | Calc'd 235, found 235 | B |
| 25 | 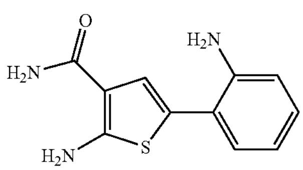 [SMILES: NC(=O)c1cc(-c2ccccc2N)sc1N] | 2-amino-5-(2-aminophenyl)thiophene-3-carboxamide | Calc'd 234, found 234 | B |
| 26 | 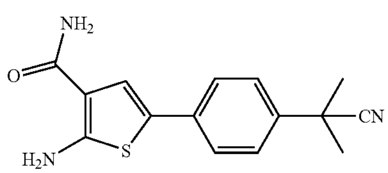 | 2-amino-5-[4-(1-cyano-1-methylethyl)phenyl]thiophene-3-carboxamide | Calc'd 286, found 286 | B |
| 27 | 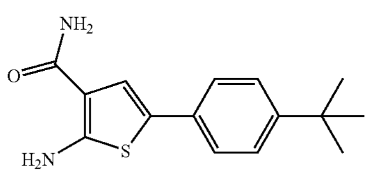 | 2-amino-5-(4-tert-butylphenyl)thiophene-3-carboxamide | Calc'd 275, found 275 | B |
| 28 | 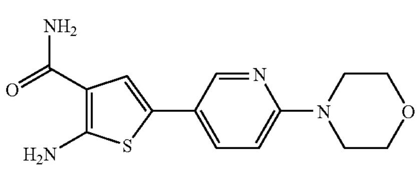 [SMILES: NC(=O)c1cc(-c2ccc(N3CCOCC3)nc2)sc1N] | 2-amino-5-(6-mopholin-4-ylpyridin-3-yl)thiophene-3-carboxamide | Calc'd 305, found 305 | A |
| 29 | 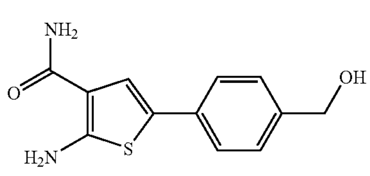 [SMILES: NC(=O)c1cc(-c2ccc(CO)cc2)sc1N] | 2-amino-5-[4-(hydroxymethyl)phenyl]thiophene-3-carboxamide | Calc'd 249, found 249 | A |

TABLE 1-continued

| Intermediate # | Structure | Compound Name | Characterization [M + H]⁺ | Nitro Reduction Method |
|---|---|---|---|---|
| 30 | 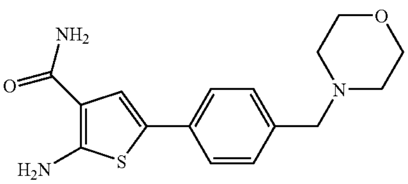 [SMILES: NC(=O)c1cc(-c2ccc(CN3CCOCC3)cc2)sc1N] | 2-amino-5-[4-(morpholin-4-ylmethyl)phenyl]thiophene-3-carboxamide | Calc'd 318, found 318 | B |
| 31 | 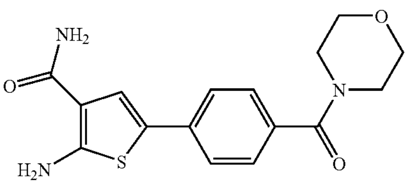 [SMILES: NC(=O)c1cc(-c2ccc(C(=O)N3CCOCC3)cc2)sc1N] | 2-amino-5-[4-(mopholin-4-ylcarbonyl)phenyl]thiophene-3-carboxamide | Calc'd 332, found 332 | B |
| 32 | 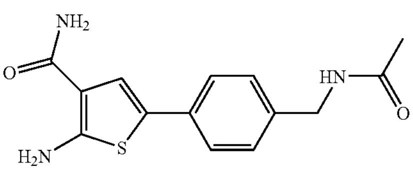 [SMILES: CC(=O)NCc1ccc(-c2cc(C(N)=O)c(N)s2)cc1] | 5-{4-[(acetylamino)methyl]phenyl}-2-aminothiophene-3-carboxamide | Calc'd 290, found 290 | B |
| 33 | 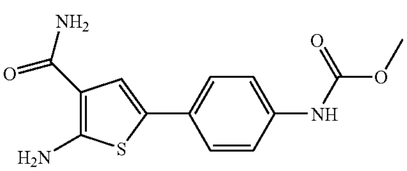 | methyl {4-[5-amino-4-(aminocarbonyl)-2-thienyl]phenyl} carbamate | Calc'd 292, found 292 | A |
| 34 | 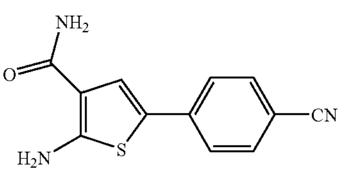 [SMILES: N#Cc1ccc(-c2cc(C(N)=O)c(N)s2)cc1] | 2-amino-5-(4-cyanophenyl)thiophene-3-carboxamide | Calc'd 244, found 244 | A |
| 35 | 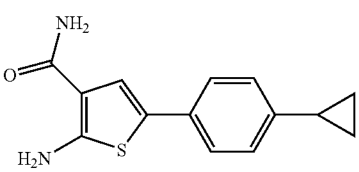 | 2-amino-5-(4-cyclopropylphenyl)thiophene-3-carboxamide | Calc'd 259, found 259 | B |
| 36 | 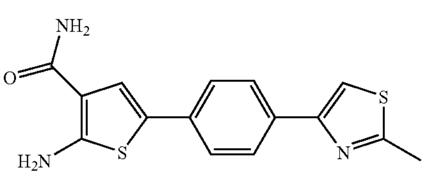 [SMILES: Cc1nc(-c2ccc(-c3cc(C(N)=O)c(N)s3)cc2)cs1] | 2-amino-5-[4-(2-methyl-1,3-thiazol-4-yl)phenyl]thiophene-3-carboxamide | Calc'd 316, found 316 | A |

Method A: Using the nitro reduction procedure described in Intermediate 10
Method B: Using the nitro reduction procedure described in Intermediate 11

INTERMEDIATE 37

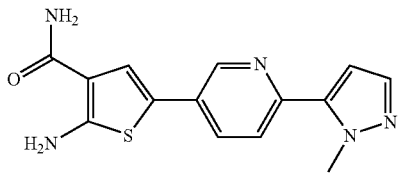

2-Amino-5-[6-(1-methyl-1H-pyrazol-5-yl)pyridin-3-yl]thiophene-3-carboxamide

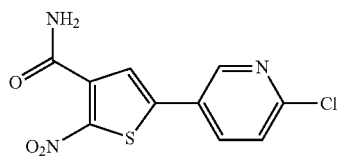 [SMILES: NC(=O)c1cc(-c2ccc(Cl)nc2)sc1[N+](=O)[O-]]

Step 1: 5-(6-Chloropyridin-3-yl)-2-nitrothiophene-3-carboxamide

The title compound was prepared from 5-bromo-2-nitrothiophene-3-carboxamide (Intermediate 10 Step 4) (2.0 g, 7.97 mmol) and 2-chloro-5-pyridine boronic acid (1.25 g, 7.97 mmol) according to the general procedure described in Intermediate 10 Step 5.

Calc'd for $C_{10}H_7ClN_3O_3S$ [M+H]: 284. Found: 284.

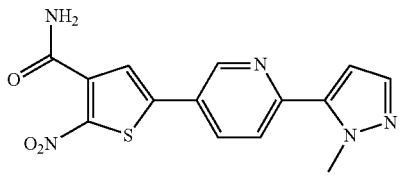 [SMILES: Cn1nccc1-c1ccc(-c2cc(C(N)=O)c([N+](=O)[O-])s2)cn1]

Step 2: 5-[6-(1-Methyl-1H-pyrazol-5-yl)pyridin-3-yl]-2-nitrothiophene-3-carboxamide 5-(6-Chloropyridin-3-yl)-2-nitrothiophene-3-carboxamide (300 mg, 1.06 mmol), 1-methyl-1H-pyrazole-5-boronic acid pinacol ester (352 mg, 1.69 mmol), and tetrakis(triphenylphosphine)palladium(0) (61.1 mg, 0.05 mmol) were dissolved in tetrahydrofuran (8.5 ml) and 2 M sodium carbonate (2.1 ml) and the mixture was bubbled with nitrogen for 5 min. The reaction was then heated in the microwave to 150° C. for 15 min. The mixture was poured into ethyl acetate and water and extracted with ethyl acetate (3×100 mL). The combined organic fractions were washed with brine, dried over magnesium sulfate, filtered and the solvent was evaporated under reduced pressure. The residue was purified by column chromatography on silica gel, eluting with ethyl acetate/hexane to yield the title compound as a yellow solid.

Calc'd for $C_{14}H_{12}N_5O_3S$ [M+H]: 330. Found: 330.

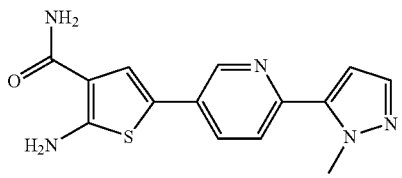

Step 3: 2-Amino-5-[6-(1-methyl-1H-pyrazol-5-yl)pyridin-3-yl]thiophene-3-carboxamide The title compound was prepared from 5-[6-(1-methyl-1H-pyrazol-5-yl)pyridin-3-yl]-2-nitrothiophene-3-carboxamide (86 mg, 0.26 mmol) according to the general procedure described in Intermediate 11 Step 4 (nitro reduction method B).

Calc'd for $C_{14}H_{14}N_5OS$ [M+1]: 300. Found: 300.

Additional 2-aminothiophene intermediates were prepared in accordance to the synthetic sequences described above and are illustrated in the table below.

TABLE 2

| Intermediate # | Structure | Compound Name | Characterization [M + H]+ | Nitro Reduction Method |
|---|---|---|---|---|
| 38 | 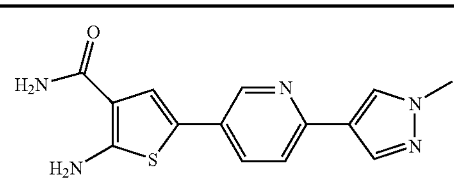 | 2-amino-5-[6-(1-methyl-1H-pyrazol-4-yl)pyridin-3-yl]thiophene-3-carboxamide | Calc'd 300, found 300 | B |
| 39 | 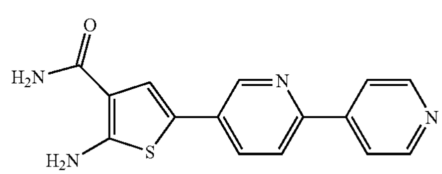 | 2-amino-5-(2,4'-bipyridin-5-yl)thiophene-3-carboxamide | Calc'd 297, found 297 | B |

Method A: Using the nitro reduction procedure described in Intermediate 10
Method B: Using the nitro reduction procedure described in Intermediate 11

INTERMEDIATE 40

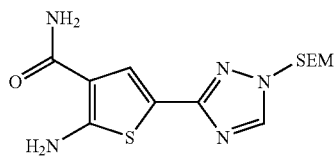

2-Amino-5-(1-{[2-(trimethylsilyl)ethoxy]methyl}-1H-1,2,4-triazol-3-yl)thiophene-3-carboxamide

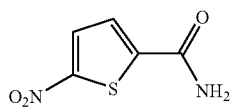 [SMILES: NC(=O)c1ccc([N+](=O)[O-])s1]

Step 1: 5-Nitrothiophene-2-carboxamide

5-Nitro-2-thiophenecarboxylic acid (7.50 g, 43.3 mmol), NH₄Cl (6.95 g, 130 mmol), HOBT (8.62 g, 56.3 mmol), and EDC (12.46 g, 65.0 mmol) were combined with DMF (100 mL) and DIEA (15.13 mL, 87.0 mmol). The reaction was stirred at room temperature overnight. The brown solution was concentrated, diluted with saturated NaHCO₃, and extracted with EtOAc (2×). The combined organic layers were washed with brine, dried (MgSO₄), filtered, and evaporated. The solid residue was triturated with CH₂Cl₂ and filtered to isolate the title compound as a colorless solid.

Calc'd for $C_5H_5N_2O_3S$ [M+H]⁺ 173. found 173.

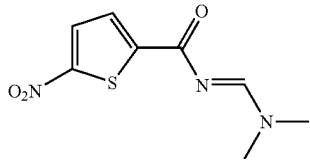

Step 2: N-[(1E)-(Dimethylamino)methylene]-5-nitrothiophene-2-carboxamide

5-Nitrothiophene-2-carboxamide (5.80 g, 33.7 mmol) was combined with N,N-dimethylformamide dimethyl acetal (75 mL, 560 mmol) and stirred at 120° C. overnight (added 10 mL DMF to help dissolve the starting material). The red-brown solution was cooled to room temperature, at which point a solid precipitated from solution. The solid was isolated by filtration, washed with Et₂O, and dried to provide the title compound as tan crystals.

Calc'd for $C_8H_{10}N_3O_3S$ [M+H]⁺ 228. found 228.

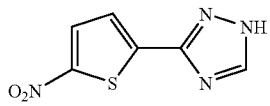

Step 3: 3-(5-Nitro-2-thienyl)-1H-1,2,4-triazole

N-[(1E)-(Dimethylamino)methylene]-5-nitrothiophene-2-carboxamide (7.00 g, 30.8 mmol) was combined with AcOH (70 mL) and hydrazine hydrate (65% wt, 2.76 mL, 37.0 mmol) and stirred at 90° C. for 1.5 h. The yellow solution was cooled to room temperature and concentrated. The resulting slurry was diluted with CH₂Cl₂ and saturated NaHCO₃ and stirred. The yellow precipitate was isolated by filtration and dried to provide the title compound as a yellow solid.

Calc'd for $C_6H_5N_4O_2S$ [M+H]⁺ 197. found 197.

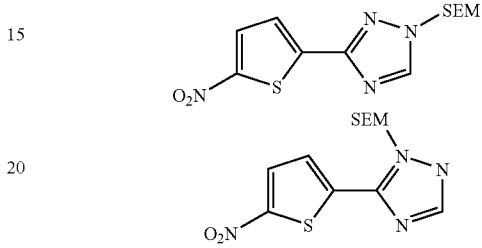

Step 4: 3-(5-Nitro-2-thienyl)-1-{[2-(trimethylsilyl)ethoxy]methyl}-1H-1,2,4-triazole and 5-(5-nitro-2-thienyl)-1-{[2-(trimethylsilyl)ethoxy]methyl}-1H-1,2,4-triazole To a solution of 3-(5-nitro-2-thienyl)-1H-1,2,4-triazole (6.00 g, 30.6 mmol), DIEA (6.94 mL, 39.8 mmol), and DMAP (374 mg, 3.06 mmol) in DMF (50 mL) was added SEM-Cl (5.97 mL, 33.6 mmol). The reaction was stirred at room temperature for 2 h. The solution was concentrated, diluted with water, and extracted with EtOAc (2×). The combined organic layers were washed with brine, dried (MgSO₄), filtered, and evaporated. Purification of the crude residue by flash chromatography (0-50% EtOAc/hexanes) separated the two regioisomeric products. The more polar (lower $R_f$) band corresponded to 3-(5-nitro-2-thienyl)-1-{[2-(trimethylsilyl)ethoxy]methyl}-1H-1,2,4-triazole, and the less polar (higher $R_f$) band corresponded to 5-(5-nitro-2-thienyl)-1-{[2-(trimethylsilyl)ethoxy]methyl}-1H-1,2,4-triazole (both were obtained as off-white solids).

Calc'd for $C_{12}H_{19}N_4O_3SSi$ [M+H]⁺ 327. found 327.

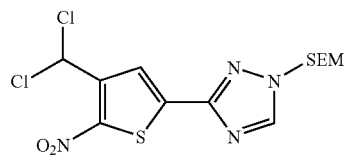 [SMILES: C[Si](C)(C)CCOCn1cnc(-c2cc(C(Cl)Cl)c([N+](=O)[O-])s2)n1]

Step 5: 3-[4-(Dichloromethyl)-5-nitro-2-thienyl]-1-{[2-(trimethylsilyl)ethoxy]methyl}-1H-1,2,4-triazole A solution of t-BuOK (9.07 g, 81 mmol) in THF (50 mL) was cooled to −78° C. before adding DMF (70 mL). A solution of 3-(5-nitro-2-thienyl)-1-{[2-(trimethylsilyl)ethoxy]methyl}-1H-1,2,4-triazole (6.60 g, 20.22 mmol) and CHCl₃ (1.79 mL, 22.24 mmol) in DMF (35 mL) was added dropwise over 1 h. After complete addition, the reaction was stirred at −78° C. for 30 min, quenched with 2 N HCl, allowed to warm to room temperature, and extracted with EtOAc (2×). The combined organic layers were washed with brine, dried (MgSO$_4$), filtered, and evaporated. Purification of the crude residue by flash chromatography (0-25% EtOAc/hexanes) afforded the title compound as a yellow solid.

Calc'd for $C_{13}H_{19}Cl_2N_4O_3SSi$ [M+H]$^+$ 409. found 409.

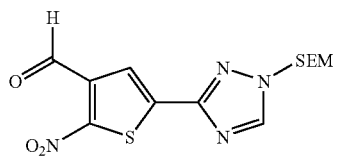 [SMILES: C[Si](C)(C)CCOCn1cnc(-c2cc(C=O)c([N+](=O)[O-])s2)n1]

Step 6: 2-Nitro-5-(1-{[2-(trimethylsilyl)ethoxy]methyl}-1H-1,2,4-triazol-3-yl)thiophene-3-carbaldehyde A mixture of 3-[4-(dichloromethyl)-5-nitro-2-thienyl]-1-{[2-(trimethylsilyl)ethoxy]methyl}-1H-1,2,4-triazole (1.00 g, 2.44 mmol) and Me$_2$NH (40% wt, 15.00 mL, 118 mmol) was stirred at 60° C. for 15 min. The reaction was cooled to room temperature, diluted with water, and extracted with CH$_2$Cl$_2$ (2×). The combined organic layers were dried (MgSO$_4$), filtered, and evaporated. Purification of the crude residue by flash chromatography (0-50% EtOAc/hexanes) provided the title compound as a yellow solid.

Calc'd for $C_{13}H_{19}N_4O_4SSi$ [M+H]$^+$ 355. found 355.

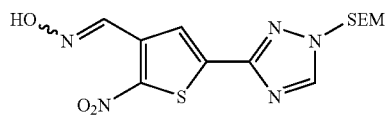 [SMILES: C[Si](C)(C)CCOCn1cnc(-c2cc(C=NO)c([N+](=O)[O-])s2)n1]

Step 7: 2-Nitro-5-(1-{[2-(trimethylsilyl)ethoxy]methyl}-1H-1,2,4-triazol-3-yl)thiophene-3-carbaldehyde oxime 2-Nitro-5-(1-{[2-(trimethylsilyl)ethoxy]methyl}-1H-1,2,4-triazol-3-yl)thiophene-3-carbaldehyde (1.85 g, 5.22 mmol), NH$_2$OH.HCl (381 mg, 5.48 mmol), and NaOAc (450 mg, 5.48 mmol) were combined in EtOH (30 mL) and stirred at room temperature for 2 h. The reaction was diluted with saturated NaHCO$_3$ and extracted with EtOAc (2×). The combined organic layers were washed with brine, dried (MgSO$_4$), filtered, and evaporated to afford the title compound as an orange solid (mixture of oxime E/Z isomers).

Calc'd for $C_{13}H_{20}N_5O_4SSi$ [M+H]$^+$ 370. found 370.

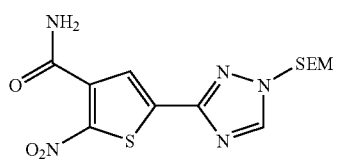 [SMILES: C[Si](C)(C)CCOCn1cnc(-c2cc(C(N)=O)c([N+](=O)[O-])s2)n1]

Step 8: 2-Nitro-5-(1-{[2-(trimethylsilyl)ethoxy]methyl}-1H-1,2,4-triazol-3-yl)thiophene-3-carboxamide 2-Nitro-5-(1-{[2-(trimethylsilyl)ethoxy]methyl}-1H-1,2,4-triazol-3-yl)thiophene-3-carbaldehyde oxime (900 mg, 2.44 mmol) and [IrCl$_2$ Cp*]$_2$ (194 mg, 0.24 mmol) were combined in a vial and purged with nitrogen. After adding degassed DMF (8.0 mL), the reaction was stirred at 110° C. overnight. The dark brown solution was evaporated to dryness, combined with MeOH and silica gel, and evaporated again. Flash chromatography (dry load, 50-100% EtOAc/hexanes) afforded a brown solid. Trituration with CH$_2$Cl$_2$ and filtration afforded the title compound as a yellow solid. The mother liquor was concentrated, triturated with CH$_2$Cl$_2$ and diethyl ether, and filtered again to provide additional quantities of the title compound.

Calc'd for $C_{13}H_{20}N_5O_4SSi$ [M+H]$^+$ 370. found 370.

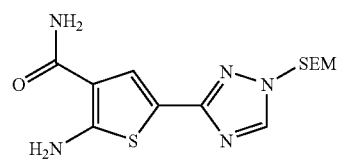 [SMILES: C[Si](C)(C)CCOCn1cnc(-c2cc(C(N)=O)c(N)s2)n1]

Step 9: 2-Amino-5-(1-{[2-(trimethylsilyl)ethoxy]methyl}-1H-1,2,4-triazol-3-yl)thiophene-3-carboxamide To 2-nitro-5-(1-{[2-(trimethylsilyl)ethoxy]methyl}-1H-1,2,4-triazol-3-yl)thiophene-3-carboxamide (600 mg, 1.62 mmol) in MeOH (25 mL) was added FeCl$_3$ (13 mg, 0.081 mmol). The solution was heated to reflux, and hydrazine hydrate (65%, 0.364 ml, 4.87 mmol) was added. After stirring for 30 minutes at reflux, the mixture was cooled to room temperature, combined with MeOH and silica gel, and evaporated to dryness. Flash chromatography (dry load, 0-10% MeOH/EtOAc) afforded the title compound as a colorless solid.

Calc'd for $C_{13}H_{22}N_5O_2SSi$ [M+H]$^+$ 340. found 340.

INTERMEDIATE 41

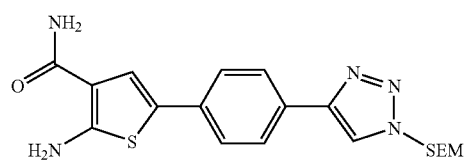

2-Amino-5-[4-(1-{[2-(trimethylsilyl)ethoxy]methyl}-1H-1,2,3-triazol-4-yl)phenyl]thiophene-3-carboxamide

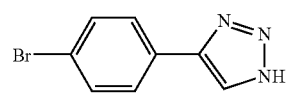

Step 1: 4-(4-Bromophenyl)-1H-1,2,3-triazole

1-Bromo-4-ethynylbenzene (650 mg, 3.59 mmol) and trimethylsilyl azide (3.57 mL, 26.9 mmol) were combined in t-BuOH (5.0 mL) and water (3.0 mL) CuSO$_4$.5H$_2$O (90 mg, 0.36 mmol) in water (1.0 mL) and sodium ascorbate (285 mg, 1.44 mmol) in water (1.0 mL) were added, and the sealed reaction mixture was stirred at 100° C. for 48 h. The mixture was diluted with water and extracted with EtOAc (3×). The combined organic layers were washed with brine, dried (MgSO$_4$), filtered, and evaporated. Flash chromatography (dry load, 0-50% EtOAc/hexanes) afforded the title compound as a colorless solid.

Calc'd for C$_8$H$_7$BrN$_3$[M+H]$^+$ 224. found 224.

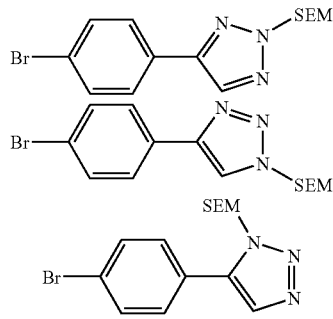

Step 2: 4-(4-Bromophenyl)-2-{[2-(trimethylsilyl) ethoxy]methyl}-2H-1,2,3-triazole, 4-(4-bromophenyl)-1-{[2-(trimethylsilyl)ethoxy]methyl}-1H-1,2,3-triazole, and 5-(4-bromophenyl)-1-{[2-(trimethylsilyl)ethoxy]methyl}-1H-1,2,3-triazole To a solution of 4-(4-bromophenyl)-1H-1,2,3-triazole (1.30 g, 5.80 mmol), DIEA (1.42 mL, 8.12 mmol), and DMAP (71 mg, 0.58 mmol) in CH$_2$Cl$_2$ (20 mL) was added SEM-Cl (1.24 mL, 6.96 mmol). The reaction was stirred at room temperature for 3 h. The solution was diluted with water and extracted with CH$_2$Cl$_2$ (2×). The combined organic layers were washed with brine, dried (MgSO$_4$), filtered, and evaporated. Flash chromatography (0-25% EtOAc/hexanes) of the crude residue allowed separation of the three regioisomeric products. The first band (least polar, highest R$_f$) corresponded to 4-(4-bromophenyl)-2-{[2-(trimethylsilyl)ethoxy]methyl}-2H-1,2,3-triazole, the second band (intermediate polarity and R$_f$) corresponded to 4-(4-bromophenyl)-1-{[2-(trimethylsilyl)ethoxy]methyl}-1H-1,2,3-triazole, and the third band (most polar, lowest R$_f$) corresponded to 5-(4-bromophenyl)-1-{[2-(trimethylsilyl)ethoxy]methyl}-1H-1,2,3-triazole; all three were isolated as colorless solids.

Calc'd for C$_{14}$H$_{21}$BrN$_3$OSi [M+H]$^+$ 354. found 354.

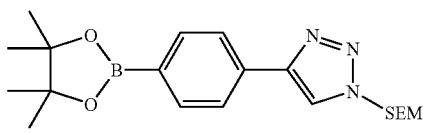

Step 3: 4-[4-(4,4,5,5-Tetramethyl-1,3,2-dioxaborolan-2-yl)phenyl]-1-{[2-(trimethylsilyl)ethoxy]methyl}-1H-1,2,3-triazole 4-(4-Bromophenyl)-1-{[2-(trimethylsilyl)ethoxy]methyl}-1H-1,2,3-triazole (870 mg, 2.46 mmol), bis(pinacolato)diboron (655 mg, 2.58 mmol), KOAc (723 mg, 7.37 mmol), and Pd(dppf)Cl$_2$CH$_2$Cl$_2$ (54 mg, 0.074 mmol) were combined in a microwave vial and evacuated/backfilled with nitrogen. Degassed DMF (7.0 mL) was added, and the reaction was stirred at 85° C. overnight. The reaction was cooled to room temperature and partitioned between water and EtOAc (2×). The combined organic layers were washed with brine, dried (MgSO$_4$), and evaporated. Flash chromatography of the crude residue (0-30% EtOAc/hexanes) afforded the title compound as a colorless solid.

Calc'd for C$_{20}$H$_{33}$BN$_3$O$_3$Si [M+H]$^+$ 402. found 402.

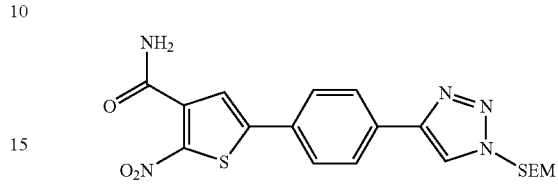

Step 4: 2-Nitro-5-[4-(1-{[2-(trimethylsilyl)ethoxy] methyl}-1H-1,2,3-triazol-4-yl)phenyl]thiophene-3-carboxamide 5-Bromo-2-nitrothiophene-3-carboxamide (Intermediate 10 Step 4) (470 mg, 1.87 mmol), 4-[4-(4,4,5,5-Tetramethyl-1,3,2-dioxaborolan-2-yl)phenyl]-1-{[2-(trimethylsilyl) ethoxy]methyl}-1H-1,2,3-triazole (751 mg, 1.87 mmol), and Pd(PPh$_3$)$_4$ (108 mg, 0.094 mmol) were combined in a vial and evacuated/backfilled with nitrogen. THF (4.4 mL) and 2 N Na$_2$CO$_3$ (1.9 mL) were added. The reaction mixture was heated to 90° C. overnight. The black reaction was diluted with water and extracted with EtOAc (2×). The combined organic layers were washed with brine, dried (MgSO$_4$), filtered, combined with silica, and evaporated. Flash chromatography (dry load, 50-100% EtOAc/hexanes) afforded a brown solid that was triturated with CH$_2$Cl$_2$ and filtered to isolate the title compound as a yellow solid. The mother liquor was concentrated, triturated again, and filtered to isolate an additional batch of the title compound.

Calc'd for C$_{19}$H$_{24}$N$_5$O$_4$SSi [M+H]$^+$ 446. found 446.

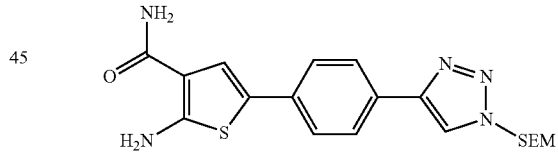

Step 5: 2-Amino-5-[4-(1-{[2-(trimethylsilyl)ethoxy] methyl}-1H-1,2,3-triazol-4-yl)phenyl]thiophene-3-carboxamide To a solution of 2-nitro-5-[4-(1-{[2-(trimethylsilyl) ethoxy]methyl}-1H-1,2,3-triazol-4-yl)phenyl]thiophene-3-carboxamide (440 mg, 0.99 mmol) in MeOH (15 mL) was added 3% Pt/C doped with 0.6% V (64 mg, 9.9 µmmol). The reaction was stirred under a hydrogen balloon at room temperature overnight. The solution was diluted with MeOH and DMF, filtered through Celite, and evaporated. The crude was triturated with MeOH and filtered to isolate the title compound as a gray solid. The mother liquor was concentrated, triturated with CH$_2$Cl$_2$, and filtered to isolate additional product.

Calc'd for C$_{19}$H$_{26}$N$_5$O$_2$SSi [M+H]$^+$ 416. found 416.

INTERMEDIATE 42

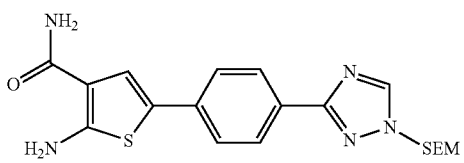

2-Amino-5-[4-(1-{[2-(trimethylsilyl)ethoxy]methyl}-1H-1,2,4-triazol-3-yl)phenyl]thiophene-3-carboxamide

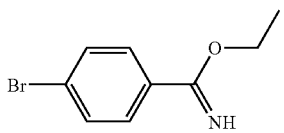

Step 1: Ethyl 4-bromobenzenecarboximidoate

Into a 3000 mL 3-necked flask purged and maintained with an atmosphere of HCl was placed a solution of 4-bromobenzonitrile (145.6 g, 800 mmol) in EtOH (2000 mL). The resulting solution was stirred overnight while the temperature was maintained at 40° C. The mixture was evaporated to provide ethyl 4-bromobenzenecarboximidoate hydrochloride as a white solid.

Into a 3000 mL 3-necked flask was placed EtOH (2000 mL). To this was added sequentially Na (7.13 g, 310 mmol) and ethyl 4-bromobenzimidate hydrochloride (82 g, 310 mmol). The resulting solution was allowed to stir for two hours at room temperature, and filtered. The filtrate was evaporated to afford ethyl 4-bromobenzenecarboximidoate as a white solid.

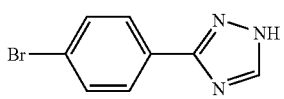

Step 2: 3-(4-Bromophenyl)-1H-1,2,4-triazole

Into a 1000 mL 3-necked flask, was placed a solution of ethyl 4-bromobenzenecarboximidoate (54.0 g, 237 mmol) in xylene (500 mL) To the mixture was added NH$_2$NHCHO (14.22 g, 237 mmol). The resulting solution was heated to reflux overnight. The reaction mixture was cooled in an ice bath and filtered. The solid was washed with 700 mL of petroleum ether and dried in an oven under reduced pressure to afford 3-(4-bromophenyl)-1H-1,2,4-triazole (crude) as a white solid.

Into a 500 mL 3-necked flask was placed a solution of 3-(4-bromophenyl)-1H-1,2,4-triazole (2.24 g, 10.0 mmol) in THF (200 mL). To this was added TEA (1.10 g, 10.9 mmol). To the mixture was added Boc$_2$O (2.39 g, 11.0 mmol). The resulting solution was stirred overnight at room temperature. The mixture was evaporated, and the residue was purified by chromatography (1:20 EtOAc/PE) to provide tert-butyl 3-(4-bromophenyl)-4H-1,2,4-triazole-4-carboxylate as a white solid.

Into a 2000 mL 3-necked flask was placed a solution of tert-butyl 3-(4-bromophenyl)-4H-1,2,4-triazole-4-carboxylate (80.0 g, 247 mmol) in CH$_2$Cl$_2$ (800 mL). To the mixture was added TFA (400 mL). The resulting solution was stirred at room temperature for 1 h. The reaction was evaporated to provide 3-(4-bromophenyl)-1H-1,2,4-triazole as a white solid.

$^1$H NMR (300 MHz, DMSO-d$_6$) 8.52 (s, 1H), 7.97 (d, 2H), 7.69 (d, 2H).

Calc'd for C$_8$H$_7$BrN$_3$[M+H]$^+$ 224. found 224.

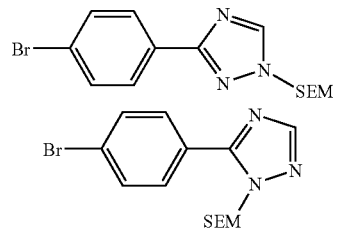

Step 3: 3-(4-Bromophenyl)-1-{[2-(trimethylsilyl)ethoxy]methyl}-1H-1,2,4-triazole and 5-(4-bromophenyl)-1-{[2-(trimethylsilyl)ethoxy]methyl}-1H-1,2,4-triazole 3-(4-Bromophenyl)-1-{[2-(trimethylsilyl)ethoxy]methyl}-1H-1,2,4-triazole and 5-(4-bromophenyl)-1-{[2-(trimethylsilyl)ethoxy]methyl}-1H-1,2,4-triazole were synthesized from 3-(4-bromophenyl)-1H-1,2,4-triazole (1.00 g, 4.46 mmol) according to the general procedure in Intermediate 41 Step 2.

Calc'd for C$_{14}$H$_{20}$BrN$_3$OSi [M+H]$^+$ 354. found 354.

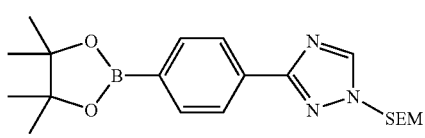 [SMILES: CC1(C)OB(c2ccc(-c3ncn(COCC[Si](C)(C)C)n3)cc2)OC1(C)C]

Step 4: 3-[4-(4,4,5,5-Tetramethyl-1,3,2-dioxaborolan-2-yl)phenyl]-1-{[2-trimethylsilyl)ethoxy]methyl}-1H-1,2,4-triazole The title compound was synthesized from 3-(4-bromophenyl)-1-{[2-(trimethylsilyl)ethoxy]methyl}-1H-1,2,4-triazole (450 mg, 1.27 mmol) according to the general procedure in Intermediate 41 Step 3.

Calc'd for C$_{20}$H$_{33}$BN$_3$O$_3$Si [M+H]$^+$ 402. found 402.

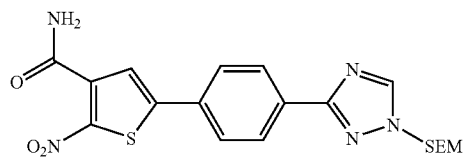 [SMILES: C[Si](C)(C)CCOCn1cnc(-c2ccc(-c3cc(C(N)=O)c([N+](=O)[O-])s3)cc2)n1]

Step 5: 2-Nitro-5-[4-(1-{[2-(trimethylsilyl)ethoxy]methyl}-1H-1,2,4-triazol-3-yl)phenyl]thiophene-3-carboxamide The title compound was synthesized from 5-bromo-2-nitrothiophene-3-carboxamide (Intermediate 10 Step 4) (240 mg, 0.96 mmol), and 3-[4-(4,4,5,5-tetramethyl-1,3,2-dioxaborolan-2-yl)phenyl]-1-{[2-(trimethylsilyl)ethoxy]methyl}-1H-1,2,4-triazole (384 mg, 0.96 mmol) according to the general procedure in Intermediate 41 Step 4.

Calc'd for $C_{19}H_{24}N_5O_4SSi$ [M+H]$^+$ 446. found 446.

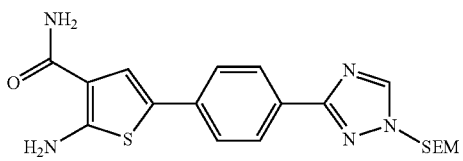

Step 6: 2-Amino-5-[4-(1-{[2-(trimethylsilyl)ethoxy]methyl}-1H-1,2,4-triazol-3-yl)phenyl]thiophene-3-carboxamide The title compound was synthesized from 2-nitro-5-[4-(1-{[2-(trimethylsilyl)ethoxy]methyl}-1H-1,2,4-triazol-3-yl)phenyl]thiophene-3-carboxamide (300 mg, 0.67 mmol) according to the general procedure in Intermediate 41 Step 5.

Calc'd for $C_{19}H_{26}N_5O_2SSi$ [M+H]$^+$ 416. found 416.

Example 1

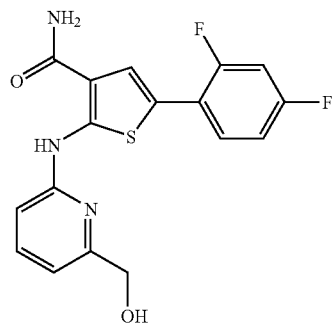 [SMILES: NC(=O)c1cc(-c2ccc(F)cc2F)sc1Nc1cccc(CO)n1]

5-(2,4-Difluorophenyl)-2-{[6-(hydroxymethyl)pyridin-2-yl]amino}thiophene-3-carboxamide General Procedure for the Coupling of 2-Aminothiophenes with 2-Halopyridines, 4-Halopyrimidines or 3-Halopyridazines A suspension containing 2-amino-5-(2,4-difluorophenyl)thiophene-3-carboxamide (60 mg, 0.24 mmol), (6-bromopyridin-2-yl)methanol (44.4 mg, 0.24 mmol), 2-dicylohexylphosphino-2',4',6'-triisopropyl-1,1-biphenyl (5.62 mg, 0.012 mmol), dibenyzlideneacetone bis(triphenylphosphine) (2.161 mg, 2.36 µmol) and potassium carbonate (35.9 mg, 0.26 mmol) in tert-butanol or tert-amyl alcohol (0.5 mL) was sealed in 5 mL microwave reaction vessel and was purged of oxygen by doing 5 vacuum/argon flush cycles. After heating the reaction at 100° C. for 2 hours, the mixture was cooled, diluted with ethyl acetate (10 mL), washed with saturated aqueous sodium bicarbonate (2×5 mL) and brine (2×5 mL), dried over sodium sulfate, filtered, and concentrated. The crude product was purified by reverse phase HPLC (35-95% acetonitrile/water with 0.05% trifluoroacetic acid), and then the appropriate fractions were diluted with ethyl acetate (20 mL) and saturated aqueous sodium bicarbonate (15 mL). The layers were separated, and the organic layer was washed with saturated aqueous sodium bicarbonate (15 mL) and water (2×15 mL), dried over sodium sulfate, filtered and concentrated to yield the title compound as a light yellow solid.

Calc'd for $C_{17}H_{14}F_2N_3O_2S$ [M+H]$^+$: 362. Found: 362.

Example 2

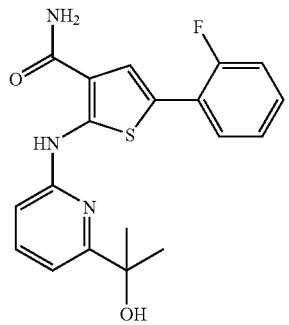 [SMILES: CC(C)(O)c1cccc(Nc2sc(-c3ccccc3F)cc2C(N)=O)n1]

5-(2-Fluorophenyl)-2-{[6-(1-hydroxy-1-methylethyl)pyridin-2-yl]amino}thiophene-3-carboxamide

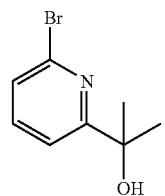

Step 1: 2-(6-Bromopyridin-2-yl)propan-2-ol

A solution of 1-(6-bromopyridin-2-yl)ethanone (5 g, 25.0 mmol) in diethyl ether (77 mL) at 0° C. was treated with methyl magnesium bromide (8.33 mL, 25.0 mmol). After 3 hours, water was added to quench the excess methyl magnesium bromide, and then concentrated aqueous hydrogen chloride solution was added until two layers were obtained. The layers were separated and the aqueous layer was extracted with diethyl ether (3×50 mL) The combined organic layers were dried over sodium sulfate, filtered, and concentrated to yield the title compound.

Calc'd for $C_8H_{11}BrNO$ [M+H]$^+$: 216. Found: 216.

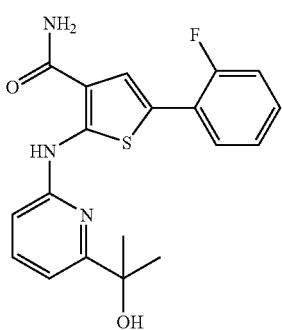 [SMILES: CC(C)(O)c1cccc(Nc2sc(-c3ccccc3F)cc2C(N)=O)n1]

Step 2: 5-(2-Fluorophenyl)-2-{[6-(1-hydroxy-1-methylethyl)pyridin-2-yl]amino}thiophene-3-carboxamide The title compound was prepared according to the general procedure in Example 1 using 2-(6-bromopyridin-2-yl)propan-2-ol (65 mg, 0.301 mmol) and 2-amino-5-(2-fluorophenyl)thiophene-3-carboxamide (72.5 mg, 0.307 mmol) as the starting materials.

Calc'd for $C_{19}H_{19}FN_3O_2S$ [M+H]$^+$: 372. Found: 372.

Example 3

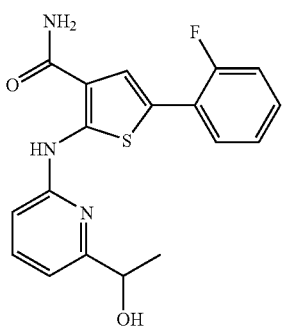 [SMILES: CC(O)c1cccc(Nc2sc(-c3ccccc3F)cc2C(N)=O)n1]

5-(2-Fluorophenyl)-2-{[6-(1-hydroxyethyl)pyridin-2-yl]amino}thiophene-3-carboxamide

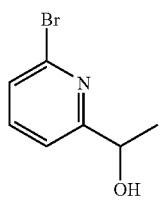

Step 1: 1-(6-Bromopyridin-2-yl)ethanol

A solution of 1-(6-bromopyridin-2-yl)ethanone (2.9636 g, 14.82 mmol) in methanol (40 mL) at 0° C. was charged with sodium borohydride (1.682 g, 44.4 mmol) and then allowed to warm to room temperature. After 2.5 hours, the reaction mixture was diluted with dichloromethane (60 mL) and water (60 mL) and the layers were separated. The organic layer was dried over sodium sulfate, filtered, and concentrated to yield the title compound.

Calc'd for $C_7H_9BrNO$ [M+H]$^+$: 204. Found: 204.

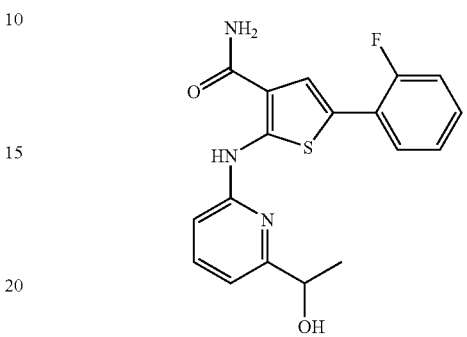

Step 2: 5-(2-Fluorophenyl)-2-{[6-(1-hydroxyethyl)pyridin-2-yl]amino}thiophene-3-carboxamide The title compound was prepared according to the general procedure in Example 1 using 1-(6-bromopyridin-2-yl)ethanol (65.0 mg, 0.322 mmol) and 2-amino-5-(2-fluorophenyl)thiophene-3-carboxamide (78.0 mg, 0.330 mmol) as the starting materials.

Calc'd for $C_{18}H_{16}FN_3O_2S$ [M+H]$^+$: 358. Found: 358.

Example 4

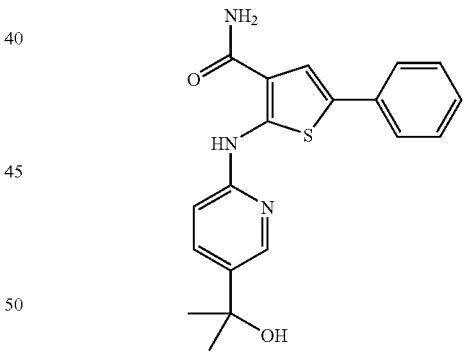

2-{[5-(1-Hydroxy-1-methylethyl)pyridin-2-yl]amino}-5-phenylthiophene-3-carboxamide 2-{[5-(1-Hydroxy-1-methylethyl)pyridin-2-yl]amino}-5-phenylthiophene-3-carboxamide was prepared using 2-(6-bromopyridin-3-yl)propan-2-ol (79.3 mg, 0.367 mmol) (for preparation, see WO 2004/050024 A2 Example 120 Step A) and 2-amino-5-phenylthiophene-3-carboxamide (80 mg, 0.367 mmol) as the starting materials according the general procedure in Example 1.

Calc'd for $C_{19}H_{20}N_3OS$ [M+H]$^+$: 354. Found: 354.

The following examples in Table 3 were prepared using procedures similar to those described in the above examples.

TABLE 3

| Example # | Structure | Compound Name | Characterization [M + H]+ |
|---|---|---|---|
| 5 | 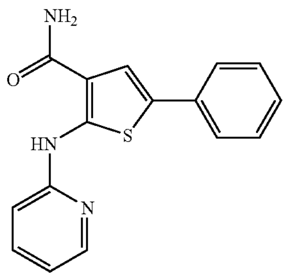 [SMILES: NC(=O)c1cc(-c2ccccc2)sc1Nc1ccccn1] | 5-phenyl-2-(pyridin-2-ylamino)thiophene-3-carboxamide | Calc'd: 296, Found: 296 |
| 6 | 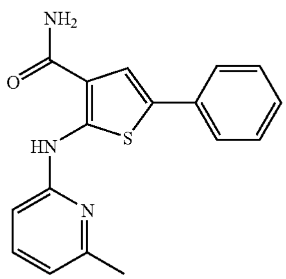 [SMILES: Cc1cccc(Nc2sc(-c3ccccc3)cc2C(N)=O)n1] | 2-[(6-methylpyridin-2-yl)amino]-5-phenylthiophene-3-carboxamide | Calc'd: 310, Found: 310 |
| 7 | 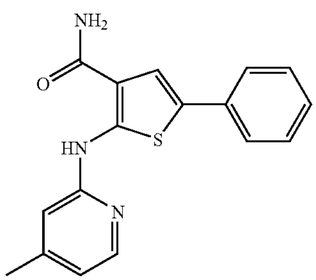 [SMILES: Cc1ccnc(Nc2sc(-c3ccccc3)cc2C(N)=O)c1] | 2-[(4-methylpyridin-2-yl)amino]-5-phenylthiophene-3-carboxamide | Calc'd: 310, Found: 310 |
| 8 | 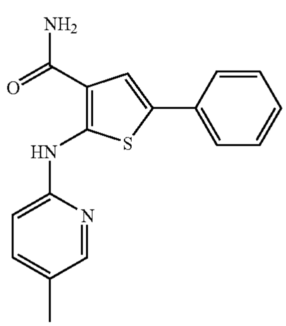 [SMILES: Cc1ccc(Nc2sc(-c3ccccc3)cc2C(N)=O)nc1] | 2-[(5-methylpyridin-2-yl)amino]-5-phenylthiophene-3-carboxamide | Calc'd: 310, Found: 310 |
| 9 | 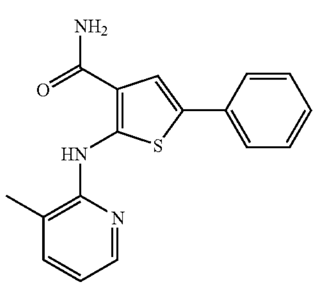 [SMILES: Cc1cccnc1Nc1sc(-c2ccccc2)cc1C(N)=O] | 2-[(3-methylpyridin-2-yl)amino]-5-phenylthiophene-3-carboxamide | Calc'd: 310, Found: 310 |

TABLE 3-continued

| Example # | Structure | Compound Name | Characterization [M + H]+ |
|---|---|---|---|
| 10 | 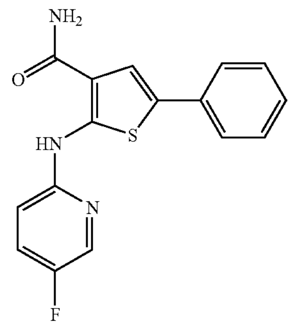 | 2-[(5-fluoropyridin-2-yl)amino]-5-phenylthiophene-3-carboxamide | Calc'd: 314, Found: 314 |
| 11 | 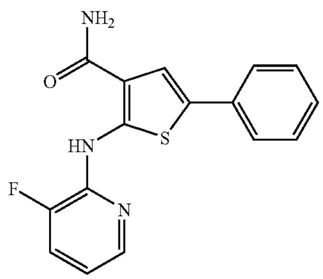 [SMILES: NC(=O)c1cc(-c2ccccc2)sc1Nc1ncccc1F] | 2-[(3-fluoropyridin-2-yl)amino]-5-phenylthiophene-3-carboxamide | Calc'd: 314, Found: 314 |
| 12 | 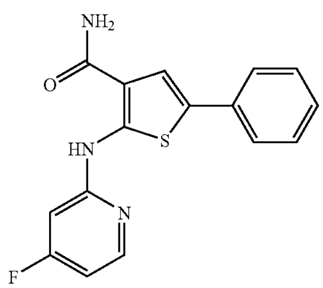 [SMILES: NC(=O)c1cc(-c2ccccc2)sc1Nc1cc(F)ccn1] | 2-[(4-fluoropyridin-2-yl)amino]-5-phenylthiophene-3-carboxamide | Calc'd: 314, Found: 314 |
| 13 | 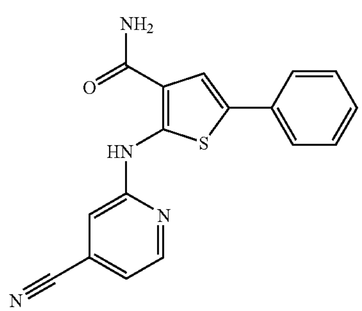 [SMILES: N#Cc1ccnc(Nc2sc(-c3ccccc3)cc2C(N)=O)c1] | 2-[(4-cyanopyridin-2-yl)amino]-5-phenylthiophene-3-carboxamide | Calc'd: 321, Found: 321 |
| 14 | 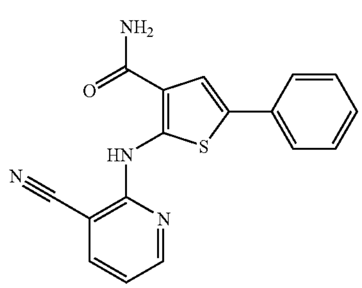 [SMILES: N#Cc1cccnc1Nc1sc(-c2ccccc2)cc1C(N)=O] | 2-[(3-cyanopyridin-2-yl)amino]-5-phenylthiophene-3-carboxamide | Calc'd: 321, Found: 321 |

TABLE 3-continued

| Example # | Structure | Compound Name | Characterization [M + H]+ |
|---|---|---|---|
| 15 | 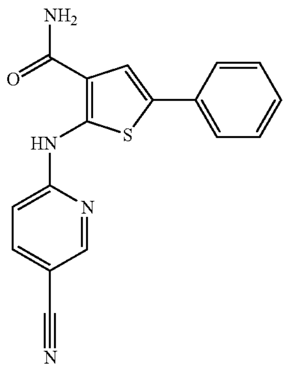 [SMILES: N#Cc1ccc(Nc2sc(-c3ccccc3)cc2C(N)=O)nc1] | 2-[(5-cyanopyridin-2-yl)amino]-5-phenylthiophene-3-carboxamide | Calc'd: 321, Found: 321 |
| 16 | 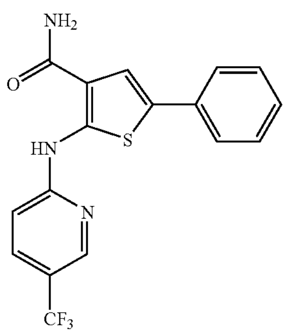 [SMILES: NC(=O)c1cc(-c2ccccc2)sc1Nc1ccc(C(F)(F)F)cn1] | 5-phenyl-2-{[5-(trifluoromethyl)pyridin-2-yl]amino}thiophene-3-carboxamide | Calc'd: 364, Found: 364 |
| 17 | 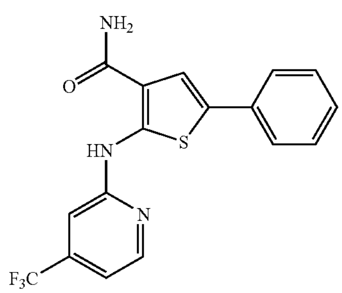 [SMILES: NC(=O)c1cc(-c2ccccc2)sc1Nc1cc(C(F)(F)F)ccn1] | 5-phenyl-2-{[4-(trifluoromethyl)pyridin-2-yl]amino}thiophene-3-carboxamide | Calc'd: 364, Found: 364 |
| 18 | 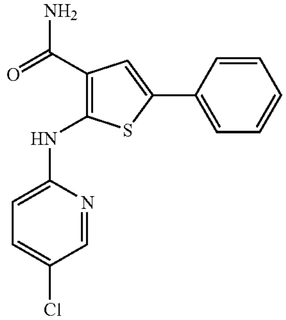 [SMILES: NC(=O)c1cc(-c2ccccc2)sc1Nc1ccc(Cl)cn1] | 2-[(5-chloropyridin-2-yl)amino]-5-phenylthiophene-3-carboxamide | Calc'd: 329, Found: 329 |

TABLE 3-continued

| Example # | Structure | Compound Name | Characterization [M + H]+ |
|---|---|---|---|
| 19 | 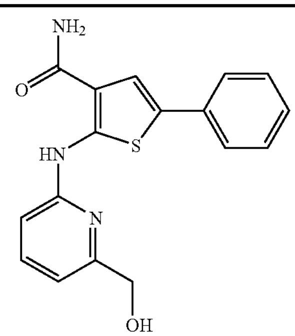 | 2-{[6-(hydroxymethyl)pyridin-2-yl]amino}-5-phenylthiophene-3-carboxamide | Calc'd: 326, Found: 326 |
| 20 | 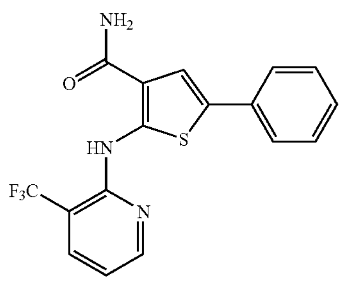 [SMILES: NC(=O)c1cc(-c2ccccc2)sc1Nc1ncccc1C(F)(F)F] | 5-phenyl-2-{[3-(trifluoromethyl)pyridin-2-yl]amino}thiophene-3-carboxamide | Calc'd: 364, Found: 364 |
| 21 | 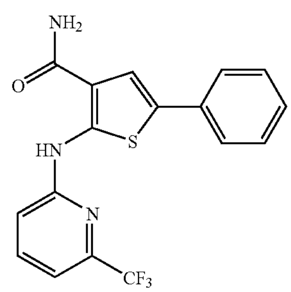 [SMILES: NC(=O)c1cc(-c2ccccc2)sc1Nc1cccc(C(F)(F)F)n1] | 5-phenyl-2-{[6-(trifluoromethyl)pyridin-2-yl]amino}thiophene-3-carboxamide | Calc'd: 364, Found: 364 |
| 22 | 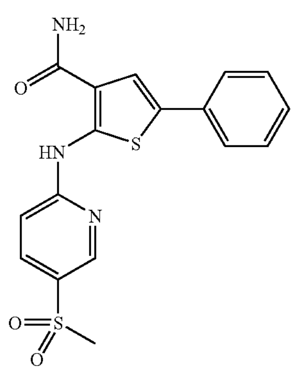 [SMILES: CS(=O)(=O)c1ccc(Nc2sc(-c3ccccc3)cc2C(N)=O)nc1] | 2-{[5-(methylsulfonyl)pyridin-2-yl]amino}-5-phenylthiophene-3-carboxamide | Calc'd: 374, Found: 374 |
| 23 | 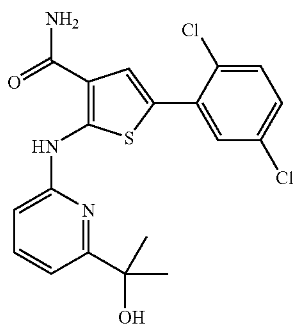 [SMILES: CC(C)(O)c1cccc(Nc2sc(-c3cc(Cl)ccc3Cl)cc2C(N)=O)n1] | 5-(2,5-dichlorophenyl)-2-{[6-(1-hydroxy-1-methylethyl)pyridin-2-yl]amino}thiophene-3-carboxamide | Calc'd: 422, Found: 422 |

TABLE 3-continued

| Example # | Structure | Compound Name | Characterization [M + H]+ |
|---|---|---|---|
| 24 | 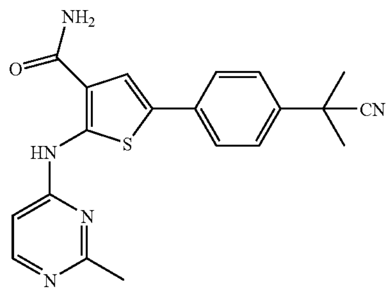 [SMILES: Cc1nccc(Nc2sc(-c3ccc(C(C)(C)C#N)cc3)cc2C(N)=O)n1] | 5-[4-(1-cyano-1-methylethyl)phenyl]-2-[(2-methylpyrimidin-4-yl)amino]thiophene-3-carboxamide | Calc'd: 378, Found: 378 |
| 25 | 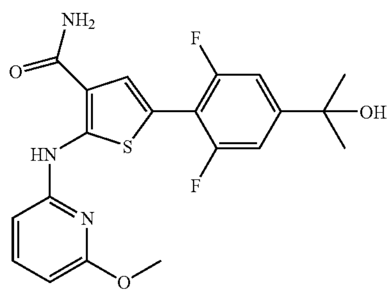 [SMILES: COc1cccc(Nc2sc(-c3c(F)cc(C(C)(C)O)cc3F)cc2C(N)=O)n1] | 5[2,6-difluoro-4-(1-hydroxy-1-methylethyl)phenyl]-2-[(6-methoxypyridin-2-yl)amino]thiophene-3-carboxamide | Calc'd: 420, Found: 420 |
| 26 | 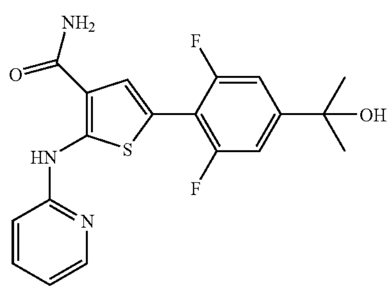 [SMILES: CC(C)(O)c1cc(F)c(-c2cc(C(N)=O)c(Nc3ccccn3)s2)c(F)c1] | 5-[2,6-difluoro-4-(1-hydroxy-1-methylethyl)phenyl]-2-(pyridin-2-ylamino)thiophene-3-carboxamide | Calc'd: 390, Found: 390 |
| 27 | 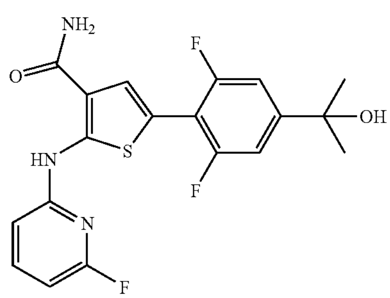 [SMILES: CC(C)(O)c1cc(F)c(-c2cc(C(N)=O)c(Nc3cccc(F)n3)s2)c(F)c1] | 5-[2,6-difluoro-4-(1-hydroxy-1-methylethyl)phenyl]-2-[(6-fluoropyridin-2-yl)amino]thiophene-3-carboxamide | Calc'd: 408, Found: 408 |
| 28 | 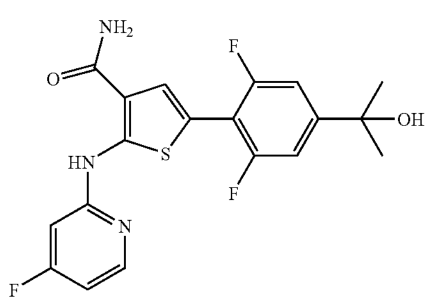 [SMILES: CC(C)(O)c1cc(F)c(-c2cc(C(N)=O)c(Nc3cc(F)ccn3)s2)c(F)c1] | 5-[2,6-difluoro-4-(1-hydroxy-1-methylethyl)phenyl]-2-[(4-fluoropyridin-2-yl)amino]thiophene-3-carboxamide | Calc'd: 408, Found: 408 |

TABLE 3-continued

| Example # | Structure | Compound Name | Characterization [M + H]+ |
|---|---|---|---|
| 29 | 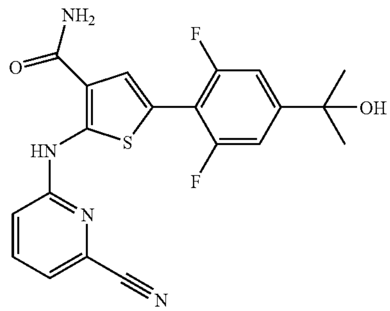 [SMILES: CC(C)(O)c1cc(F)c(-c2cc(C(N)=O)c(Nc3cccc(C#N)n3)s2)c(F)c1] | 2-[(6-cyanopyridin-2-yl)amino]-5-[2,6-difluoro-4-(1-hydroxy-1-methylethyl)phenyl]thiophene-3-carboxamide | Calc'd: 415, Found: 415 |
| 30 | 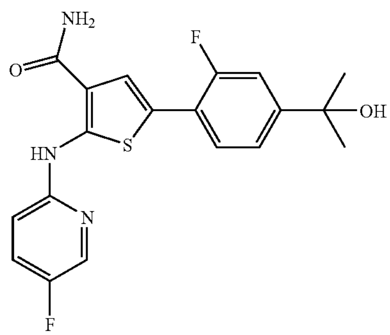 [SMILES: CC(C)(O)c1ccc(-c2cc(C(N)=O)c(Nc3ccc(F)cn3)s2)c(F)c1] | 5-[2-fluoro-4-(1-hydroxy-1-methylethyl)phenyl]-2-[(5-fluoropyridin-2-yl)amino]thiophene-3-carboxamide | Calc'd: 390, Found: 390 |
| 31 | 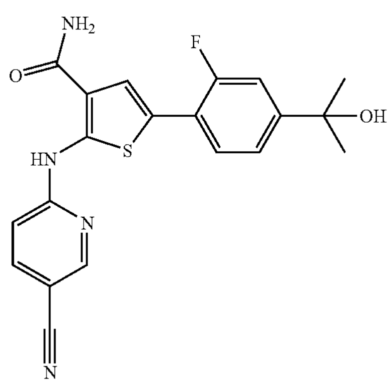 [SMILES: CC(C)(O)c1ccc(-c2cc(C(N)=O)c(Nc3ccc(C#N)cn3)s2)c(F)c1] | 2-[(5-cyanopyridin-2-yl)amino]-5-[2-fluoro-4-(1-hydroxy-1-methylethyl)phenyl]thiophene-3-carboxamide | Calc'd: 397, Found: 397 |
| 32 | 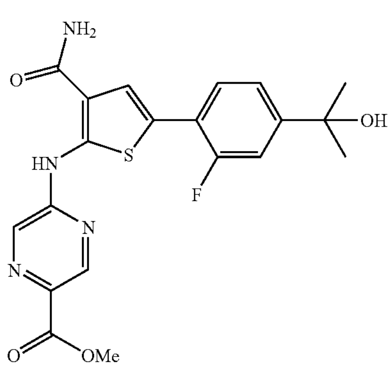 [SMILES: COC(=O)c1cnc(Nc2sc(-c3ccc(C(C)(C)O)cc3F)cc2C(N)=O)cn1] | methyl 5-({3-(aminocarbonyl)-5-[2-fluoro-4-(1-hydroxy-1-methylethyl)phenyl]-2-thienyl}amino)pyrazine-2-carboxylate | Calc'd: 431, Found: 431 |

TABLE 3-continued

| Example # | Structure | Compound Name | Characterization [M + H]+ |
|---|---|---|---|
| 33 | 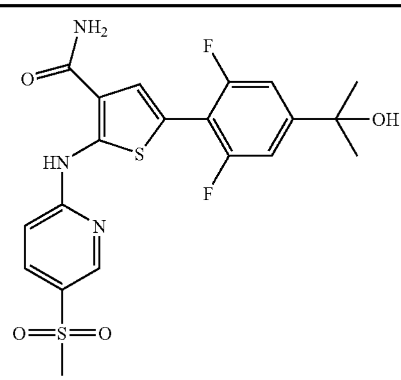 | 5-[2,6-Difluoro-4-(1-hydroxy-1-methylethyl)phenyl]-2-{[5-(methylsulfonyl)pyridin-2-yl]amino}thiophene-3-carboxamide | Calc'd: 468, Found: 468 |
| 34 | 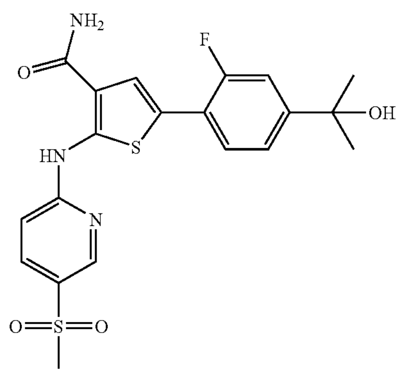 [SMILES: CC(C)(O)c1ccc(-c2cc(C(N)=O)c(Nc3ccc(S(C)(=O)=O)cn3)s2)c(F)c1] | 5-[2-Fluoro-4-(1-hydroxy-1-methylethyl)phenyl]-2-{[5-(methylsulfonyl)pyridin-2-yl]amino}thiophene-3-carboxamide | Calc'd: 450, Found: 450 |
| 35 | 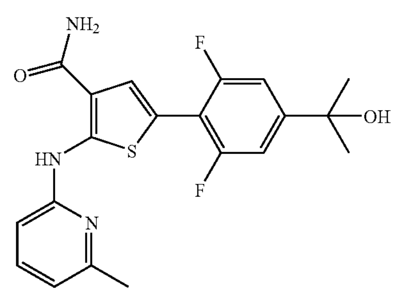 [SMILES: Cc1cccc(Nc2sc(-c3c(F)cc(C(C)(C)O)cc3F)cc2C(N)=O)n1] | 5-[2,6-Difluoro-4-(1-hydroxy-1-methylethyl)phenyl]-2-[(6-methylpyridin-2-yl)amino]thiophene-3-carboxamide | Calc'd: 404, Found: 404 |
| 36 | 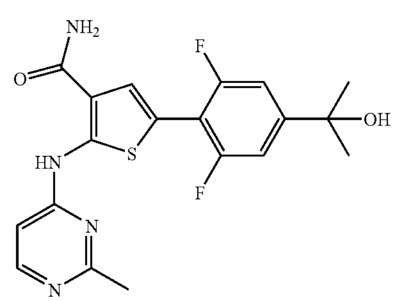 [SMILES: Cc1nccc(Nc2sc(-c3c(F)cc(C(C)(C)O)cc3F)cc2C(N)=O)n1] | 5-[2,6-Difluoro-4-(1-hydroxy-1-methylethyl)phenyl]-2-[(2-methylpyrimidin-4-yl)amino]thiophene-3-carboxamide | Calc'd: 405, Found: 405 |

TABLE 3-continued

| Example # | Structure | Compound Name | Characterization [M + H]⁺ |
|---|---|---|---|
| 37 | 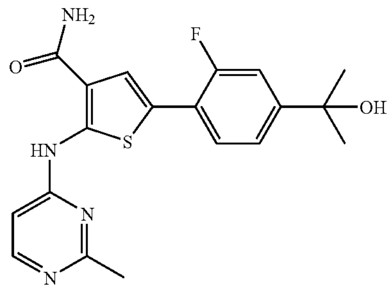 [SMILES: Cc1nccc(Nc2sc(-c3ccc(C(C)(C)O)cc3F)cc2C(N)=O)n1] | 5-[2-Fluoro-4-(1-hydroxy-1-methylethyl)phenyl]-2-[(2-methylpyrimidin-4-yl)amino]thiophene-3-carboxamide | Calc'd: 387, Found: 387 |
| 38 | 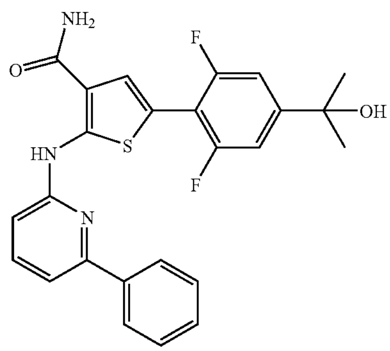 [SMILES: CC(C)(O)c1cc(F)c(-c2cc(C(N)=O)c(Nc3cccc(-c4ccccc4)n3)s2)c(F)c1] | 5-[2,6-difluoro-4-(1-hydroxy-1-methylethyl)phenyl]-2-[(6-phenylpyridin-2-yl)amino]thiophene-3-carboxamide | Calc'd: 466, Found: 466 |
| 39 | 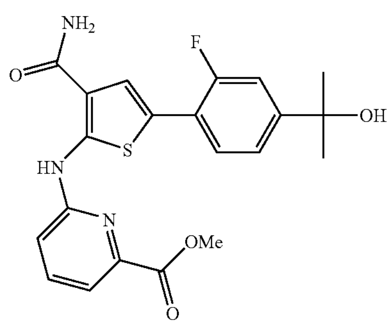 [SMILES: COC(=O)c1cccc(Nc2sc(-c3ccc(C(C)(C)O)cc3F)cc2C(N)=O)n1] | methyl 6-({3-(aminocarbonyl)-5-[2-fluoro-4-(1-hydroxy-1-methylethyl)phenyl]-2-thienyl}amino)pyridine-2-carboxylate | Calc'd: 430, Found: 430 |
| 40 | 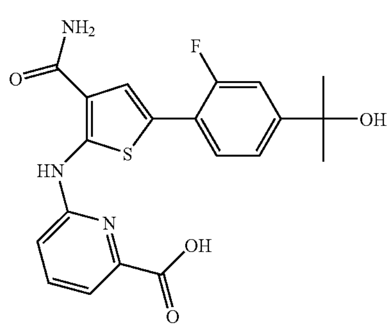 [SMILES: CC(C)(O)c1ccc(-c2cc(C(N)=O)c(Nc3cccc(C(=O)O)n3)s2)c(F)c1] | 6-({3-(aminocarbonyl)-5-[2-fluoro-4-(1-hydroxy-1-methylethyl)phenyl]-2-thienyl}amino)pyridine-2-carboxylic acid | Calc'd: 416, Found: 416 |

TABLE 3-continued

| Example # | Structure | Compound Name | Characterization [M + H]+ |
|---|---|---|---|
| 41 | 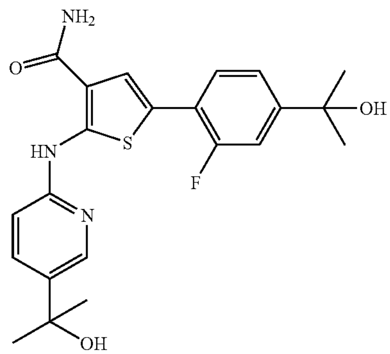 [SMILES: CC(C)(O)c1ccc(Nc2sc(-c3ccc(C(C)(C)O)cc3F)cc2C(N)=O)nc1] | 5-[2-fluoro-4-(1-hydroxy-1-methylethyl)phenyl]-2-{[5-(1-hydroxy-1-methylethyl)pyridin-2-yl]amino}thiophene-3-carboxamide | Calc'd: 430, Found: 430 |
| 42 | 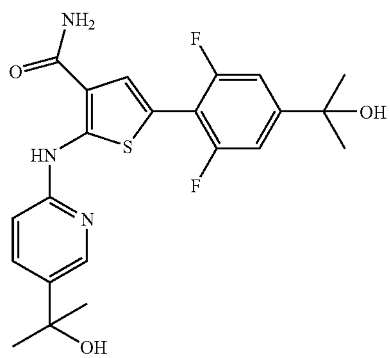 [SMILES: CC(C)(O)c1ccc(Nc2sc(-c3c(F)cc(C(C)(C)O)cc3F)cc2C(N)=O)nc1] | 5-[2,6-difluoro-4-(1-hydroxy-1-methylethyl)phenyl]-2-{[5-(1-hydroxy-1-methylethyl)pyridin-2-yl]amino}thiophene-3-carboxamide | Calc'd: 448, Found: 448 |
| 43 | 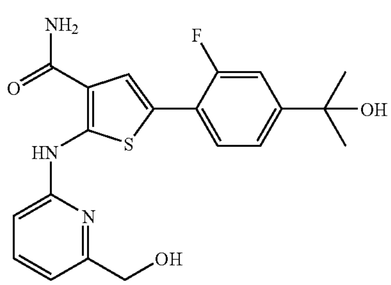 | 5-[2-fluoro-4-(1-hydroxy-1-methylethyl)phenyl]-2-{[6-(hydroxymethyl)pyridin-2-yl]amino}thiophene-3-carboxamide | Calc'd: 402, Found: 402 |
| 44 | 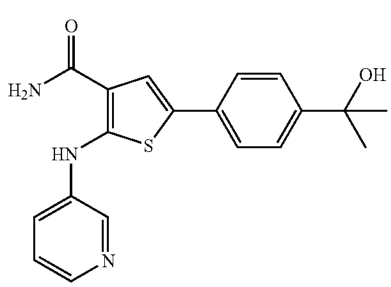 [SMILES: CC(C)(O)c1ccc(-c2cc(C(N)=O)c(Nc3cccnc3)s2)cc1] | 5-(4-(1-hydroxy-1-methylethyl)phenyl]-2-(3-pyridinylamino)-3-thiophenecarboxamide | Calc'd: 477, Found: 477 |

Example 45

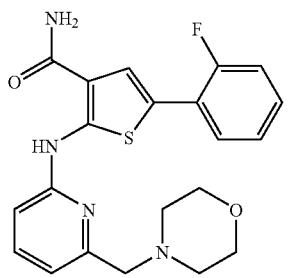 [SMILES: NC(=O)c1cc(-c2ccccc2F)sc1Nc1cccc(CN2CCOCC2)n1]

5-(2-Fluorophenyl)-2-{[6-(morpholin-4-ylmethyl)pyridin-2-yl]amino}thiophene-3-carboxamide

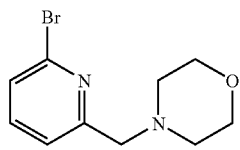

Step 1: 4-[(6-Bromopyridin-2-yl)methyl]morpholine

Reductive Amination Method A: A solution of 6-bromopyridine-2-carbaldehyde (3 g, 16.13 mmol) and morpholine (1.41 mL, 16.13 mmol) in 1,2-dichloroethane (22 mL) under argon was charged with sodium triacetoxyborohydride (4.79 g, 22.58 mmol) and allowed to stir for 14 hours. The reaction mixture was then diluted with ethyl acetate (100 mL), saturated aqueous sodium bicarbonate (60 mL), and saturated aqueous sodium carbonate (90 mL). The layers were separated and the organic layer was washed with saturated aqueous sodium bicarbonate (2×50 mL) and brine (2×50 mL), dried over sodium sulfate, filtered, and concentrated. The resulting material was purified by silica gel chromatography (30-100% ethyl acetate/hexanes) to afford the title compound as a white solid.

Calc'd for $C_{10}H_{14}BrN_2O$ [M+H]$^+$: 257. Found: 257.

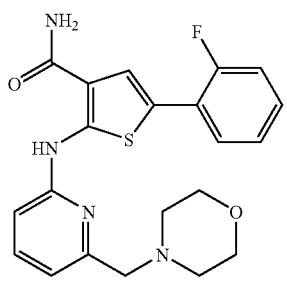 [SMILES: NC(=O)c1cc(-c2ccccc2F)sc1Nc1cccc(CN2CCOCC2)n1]

Step 2: 5-(2-Fluorophenyl)-2-{[6-(morpholin-4-ylmethyl)pyridin-2-yl]-amino}thiophene-3-carboxamide The title compound was prepared according to the general procedure in Example 1 using 4-[(6-bromopyridin-2-yl)methyl]morpholine (53 mg, 0.206 mmol) and 2-amino-5-(2-fluorophenyl)thiophene-3-carboxamide (49.6 mg, 0.210 mmol) as the starting materials.

Calc'd for $C_{21}H_{22}FN_4O_2S$ [M+H]$^+$: 413. Found: 413.

Example 46

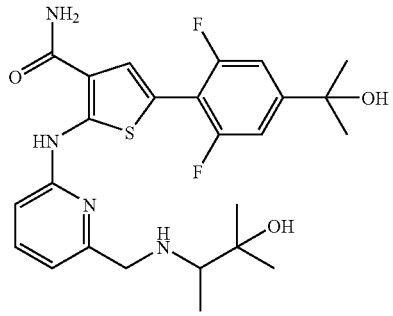 [SMILES: CC(NCc1cccc(Nc2sc(-c3c(F)cc(C(C)(C)O)cc3F)cc2C(N)=O)n1)C(C)(C)O]

5-[2,6-Difluoro-4-(1-hydroxy-1-methylethyl)phenyl]-2-[(6-{[(2-hydroxy-1,2-dimethylpropyl)amino]methyl}pyridin-2-yl)amino]thiophene-3-carboxamide

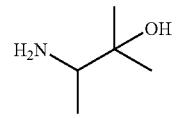

Step 1: 3-Amino-2-methylbutan-2-ol

Ammonia in methanol (7 M, 200 mL, 1400 mmol) was added to 2,2,3-trimethyloxirane (35 mL, 332 mmol) in a pressure flask. The flask was sealed and the reaction was stirred at 58° C. for 7 days. The reaction was then cooled to ambient temperature and concentrated in vacuo to afford the title compound which was used without purification.

$^1$H NMR (600 MHz, CDCl$_3$): 2.73 (q, 1H), 1.15 (s, 3H), 1.06 (s, 3H), 1.04 (d, 3H).

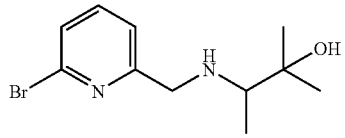

Step 2: 3-{[(6-Bromopyridin-2-yl)methyl]amino}-2-methylbutan-2-ol

The title compound was prepared according to the procedure in Example 45, Step 1 using 6-bromopyridine-2-carbaldehyde (0.20 g, 1.08 mmol) and 3-amino-2-methylbutan-2-ol (0.11 g, 1.08 mmol) as the starting materials.

Calc'd for $C_{11}H_{18}BrN_2O$ [M+H]$^+$: 273. Found: 273.

131

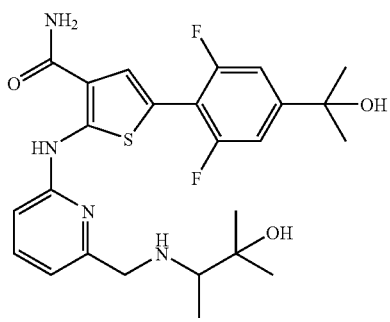 [SMILES: CC(NCc1cccc(Nc2sc(-c3c(F)cc(C(C)(C)O)cc3F)cc2C(N)=O)n1)C(C)(C)O]

Step 3: 5-[2,6-Difluoro-4-(1-hydroxy-1-methylethyl)phenyl]-2-[(6-{[(2-hydroxy-1,2-dimethylpropyl)amino]methyl}pyridin-2-yl)amino]thiophene-3-carboxamide The title compound was prepared by using the procedure listed in Example 1 with 2-amino-5-[2,6-difluoro-4-(1-hydroxy-1-methylethyl)phenyl]thiophene-3-carboxamide (0.080 g, 0.26 mmol) and 3-{[(6-bromopyridin-2-yl)methyl]amino}-2-methylbutan-2-ol (0.070 g, 0.26 mmol) as the starting materials.

Calc'd for $C_{25}H_{31}F_2N_4O_3S$ [M+H]$^+$: 505. Found: 505.

Example 47

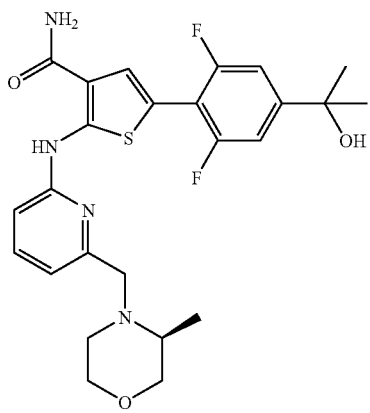 [SMILES: C[C@H]1COCCN1Cc1cccc(Nc2sc(-c3c(F)cc(C(C)(C)O)cc3F)cc2C(N)=O)n1]

5-[2,6-Difluoro-4-(1-hydroxy-1-methylethyl)phenyl]-2-[(6-{[(3S)-3-methylmorpholin-4-yl]methyl}pyridin-2-yl)amino]thiophene-3-carboxamide

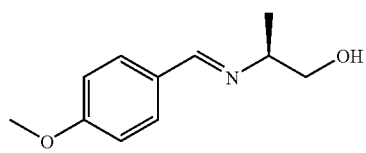

132

Step 1: (2S)-2-{[(1E)-(4-Methoxyphenyl)methylene]amino}propan-1-ol

Into a 10000 mL 4-necked, round bottomed flask purged and maintained with an inert atmosphere of nitrogen was placed 4-methoxybenzaldehyde (500 g, 3.67 mol), (S)-2-aminopropan-1-ol (276 g, 3.68 mol), 4-methylbenzenesulfonic acid (31.7 g, 184.09 mmol) and toluene (5000 mL). The resulting solution was maintained at reflux overnight. The reaction mixture was cooled and concentrated under vacuum. The residue was washed with 3000 mL of hexane and filtered to afford the title compound as a yellow solid.

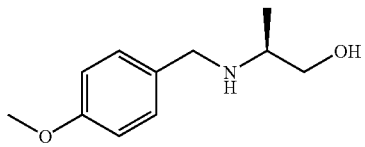

Step 2:
(2S)-2-[(4-Methoxybenzyl)amino]propan-1-ol

Into a 10000 mL 4-necked, round bottomed flask was placed a solution of (S)-2-(4-methoxybenzylideneamino)propan-1-ol (693 g, 3.59 mol) in CH$_3$OH (7000 mL). sodium borohydride (271.2 g, 7.17 mol) was added in several batches. The reaction mixture was cooled –10° C. After 2 hours at –10° C., the reaction was warmed to room temperature and concentrated under vacuum. The residual solution was diluted with 2000 mL of water and extracted three times with 3000 mL of ethyl acetate. The combined organic layer was dried over MgSO$_4$, filtered, and concentrated under vacuum. The residue was purified by flash chromatography (silica, 1:4 ethyl acetate/petroleum ether) to afford the title compound as a yellow solid.

$^1$H NMR (400 MHz, CDCl$_3$): δ 1.09-1.10 (d, 3H), 2.01 (m, 2H), 2.82-2.86 (m, 1H), 3.25-3.30 (m, 1H), 3.59-3.61 (m, 1H), 3.62-3.70 (m, 1H), 3.81-3.84 (m, 4H), 6.86-6.88 (d, 2H), 7.24-7.27 (m, 21-1).

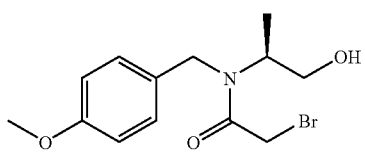 [SMILES: COc1ccc(CN(C(=O)CBr)[C@@H](C)CO)cc1]

Step 3: 2-Bromo-N-[(1S)-2-hydroxy-1-methylethyl]-N-(4-methoxybenzyl)acetamide

Into a 20000 mL 4-necked, round bottomed flask purged and maintained with an inert atmosphere of nitrogen was placed a solution of (S)-2-(4-methoxybenzylamino)propan-1-ol (300 g, 1.54 mol) in dichloromethane (12000 mL) and triethylamine (155.8 g, 1.54 mol). 2-Bromoacetyl bromide (310.8 g, 1.54 mol) was added dropwise, while cooling to a temperature of –17 to –25° C. and maintained at this temperature for 4 hours. The reaction mixture was warmed to room temperature and washed three times with 2000 mL of water, dried over MgSO$_4$, filtered, and concentrated under vacuum to afford the title compound as a yellow oil.

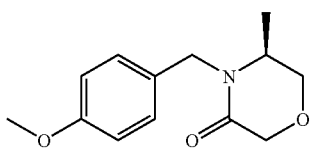 [SMILES: COc1ccc(CN2C(=O)COC[C@@H]2C)cc1]

Step 4: (5S)-4-(4-Methoxybenzyl)-5-methylmorpholin-3-one

Into a 10000 mL 4-necked, round bottomed flask purged and maintained with an inert atmosphere of nitrogen was placed a suspension of sodium hydride (125.6 g, 3.14 mol, 60%) in THF (5000 mL) and cooled to 25° C., followed by the addition of a solution of N-(4-methoxybenzyl)-2-bromo-N-(1-hydroxypropan-2-yl)acetamide (498 g, 1.57 mol) in THF (500 mL) dropwise over 30 minutes at 25° C. The resulting solution was allowed to stir overnight at 25° C. Upon completion, the reaction mixture was quenched by adding 1000 mL of ethanol and 250 mL of water. The resulting solution was further diluted with 1500 mL of dichloromethane and then washed three times with 2000 mL of water. The organic layer was dried over magnesium sulfate, filtered, and concentrated under vacuum to afford the title compound as a yellow oil.

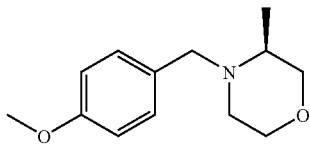 [SMILES: COc1ccc(CN2CCOC[C@@H]2C)cc1]

Step 5: (3S)-4-(4-Methoxybenzyl)-3-methylmorpholine

Into a 5000 mL 4-necked, round bottomed flask purged and maintained with an inert atmosphere of nitrogen was placed a suspension of lithium aluminum hydride (60.04 g, 1.58 mol) in THF (2000 mL), followed by the dropwise addition of a solution of (S)-4-(4-methoxybenzyl)-5-methylmorpholin-3-one (186 g, 790.48 mmol) in THF (300 mL). The resulting solution was heated to reflux for 1 hour. The reaction mixture was cooled to 0° C., quenched by adding 500 mL of ethyl acetate and then 500 mL of water, the resulting solution was extracted three times with 2000 mL of ethyl acetate. The combined organic layer was dried over MgSO$_4$, filtered, and concentrated under vacuum. The residue was purified by flash chromatography (silica, 1:30 ethyl acetate/petroleum ether) to afford the title compound as a yellow oil.

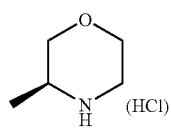

Step 6: (3S)-3-Methylmorpholine hydrochloride

A 2 L high pressure reactor was flushed and maintained with a hydrogen atmosphere, to which was added a solution of (S)-4-(4-methoxybenzyl)-3-methylmorpholine (90 g, 406.69 mmol) in CH$_3$OH (900 mL) and Pd/C (13.59 g, 66%). The resulting mixture was allowed to stir for 2 days while the temperature was maintained at 50° C. and under 20 atm of hydrogen. Upon completion, the spent catalyst was removed by filtration. The filtrate was concentrated under vacuum to afford the title compound as the free base. The above procedure was repeated with 65.3 g of (S)-4-(4-methoxybenzyl)-3-methylmorpholine. Product from the two batches was combined and dissolved in 150 mL of 10% HCl. The resulting solution was stirred for 2 hours at room temperature, then washed 3 times with 100 mL of ether. The aqueous layer was concentrated under vacuum to afford the title compound as a white solid.

$^1$H NMR (400 MHz, D$_2$O): 1.14-1.15 (d, 3H), 3.14-3.17 (m, 1H), 3.24-3.28 (m, 1H), 3.36-3.43 (m, 2H), 3.66-3.69 (m, 1H), 3.91-3.95 (m, 2H). Calc'd for C$_5$H$_{12}$NO [M+1]: 102. found 102.

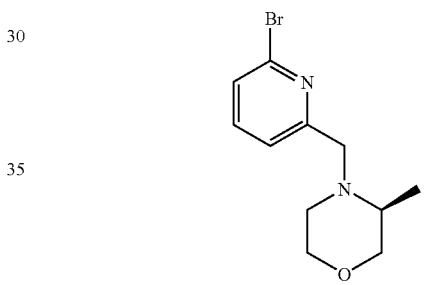

Step 7: (3S)-4-[(6-Bromopyridin-2-yl)methyl]-3-methylmorpholine

Reductive Amination Method B: 6-Bromopyridine-2-carbaldehyde (1.3 g, 7.0 mmol) was added to a 200 ml, round bottom under argon. Dichloroethane (28.0 ml) was added followed by (3S)-3-methylmorpholine (HCl salt) (1 g, 7.3 mmol) and triethylamine (1.0 ml, 7.3 mmol). The mixture was stirred for 0.5 hours at room temperature followed by the addition of sodium triacetoxyborohydride (2.07 g, 9.8 mmol) and the resulting slurry was maintained at room temperature overnight. The reaction was quenched by the careful addition of saturated aqueous sodium bicarbonate and was extracted once with DCM and once with ethyl acetate. The combined organics were dried over magnesium sulfate, filtered, and concentrated in vacuo. The resulting oily residue was purified via flash chromatography (silica, 0-10% methanol/ethyl acetate) to afford the title compound as a colorless oil.

$^1$H NMR (600 MHz, d6-DMSO): δ 7.69 (m, 1H), 7.47 (m, 2H), 3.92 (d, 1H), 3.60 (m, 2H), 3.42 (m, 1H), 3.33 (d, 1H), 3.10 (dd, 1H), 2.52 (d, 1H), 2.40 (m, 1H), 2.21 (m, 1H), 0.92 (d, 3H).

Step 8: 5-[2,6-Difluoro-4-(1-hydroxy-1-methylethyl)phenyl]-2-[(6-{[(3S)-3-methylmorpholin-4-yl]methyl}pyridin-2-yl)amino]thiophene-3-carboxamide

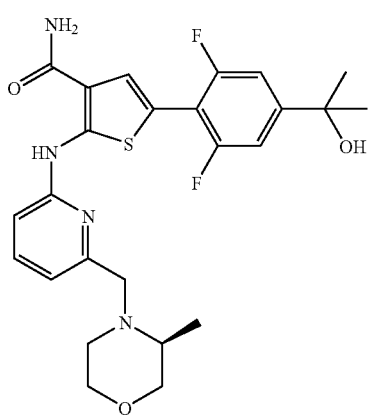 [SMILES: C[C@H]1COCCN1Cc1cccc(Nc2sc(-c3c(F)cc(C(C)(C)O)cc3F)cc2C(N)=O)n1]

The title compound was prepared as described in Example 1 using 2-amino-5-[2,6-difluoro-4-(1-hydroxy-1-methylethyl)phenyl]thiophene-3-carboxamide (150 mg, 0.48 mmol) and (3S)-4-[(6-bromopyridin-2-yl)methyl]-3-methylmorpholine (133 mg, 0.49 mmol) as starting materials.

$^1$H NMR (600 MHz, d6-DMSO): δ 12.07 (s, 1H), 7.85 (s, 1H), 7.74 (s, 1H), 7.65 (t, 1H), 7.33 (s, 1H), 7.24 (d, 2H), 6.95 (d, 1H), 6.92 (d, 1H), 5.27 (s, 1H), 3.95 (d, 1H), 3.59 (m, 2H), 3.43 (m, 1H), 3.37 (d, 1H), 3.10 (dd, 1H), 2.65 (m, 1H), 2.42 (m, 1H), 2.28 (m, 1H), 1.40 (s, 6H), 0.99 (d, 3H). Calc'd $C_{25}H_{29}F_2N_4O_3S$ [M+H]$^+$: 503. found 503.

Additional examples were prepared using procedures similar to those described in the above examples.

TABLE 4

| Example | Structure | Name | Reductive Amination Method | Characterization [M + H] |
|---|---|---|---|---|
| 48 | 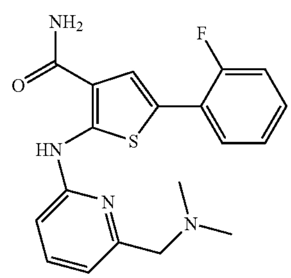 [SMILES: CN(C)Cc1cccc(Nc2sc(-c3ccccc3F)cc2C(N)=O)n1] | 2-({6-[(dimethylamino)methyl]pyridin-2-yl}amino)-5-(2-fluorophenyl)thiophene-3-carboxamide | A | Calc'd 371, Found 371 |
| 49 | 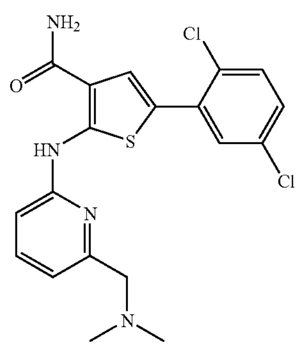 [SMILES: CN(C)Cc1cccc(Nc2sc(-c3cc(Cl)ccc3Cl)cc2C(N)=O)n1] | 5-(2,5-dichlorophenyl)-2-({6-[(dimethylamino)methyl]pyridin-2-yl}amino)thiophene-3-carboxamide | A | Calc'd 422, Found 422 |
| 50 | 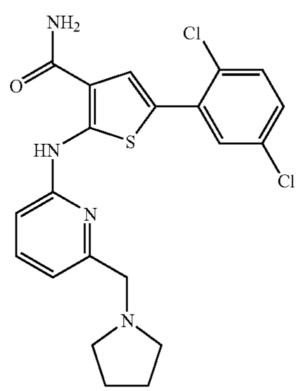 [SMILES: NC(=O)c1cc(-c2cc(Cl)ccc2Cl)sc1Nc1cccc(CN2CCCC2)n1] | 5-(2,5-dichlorophenyl)-2-{[6-(pyrrolidin-1-ylmethyl)pyridin-2-yl]amino}thiophene-3-carboxamide | A | Calc'd 488, Found 488 |

TABLE 4-continued

| Example | Structure | Name | Reductive Amination Method | Characterization [M + H] |
|---|---|---|---|---|
| 51 | 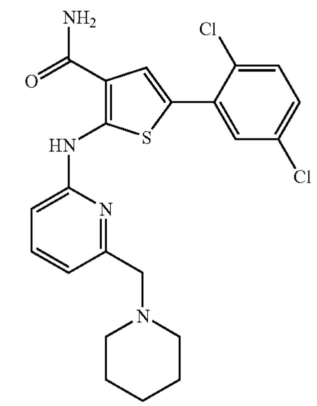 [SMILES: NC(=O)c1cc(-c2cc(Cl)ccc2Cl)sc1Nc1cccc(CN2CCCCC2)n1] | 5-(2,5-dichlorophenyl)-2-{[6-(piperidin-1-ylmethyl)pyridin-2-yl]amino}thiophene-3-carboxamide | A | Calc'd 462, Found 462 |
| 52 | 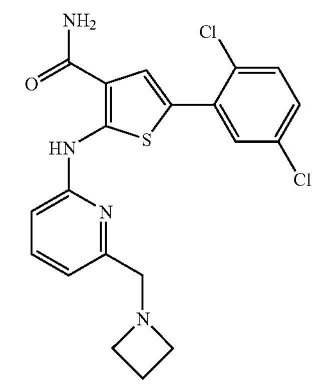 [SMILES: NC(=O)c1cc(-c2cc(Cl)ccc2Cl)sc1Nc1cccc(CN2CCC2)n1] | 2-{[6-(azetidin-1-ylmethyl)pyridin-2-yl]amino}-5-(2,5-dichlorophenyl)thiophene-3-carboxamide | A | Calc'd 434, Found 434 |
| 53 | 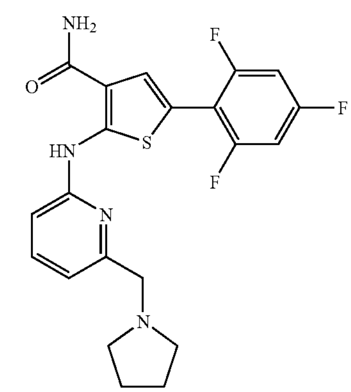 [SMILES: NC(=O)c1cc(-c2c(F)cc(F)cc2F)sc1Nc1cccc(CN2CCCC2)n1] | 2-{[6-(pyrrolidin-1-ylmethyl)pyridin-2-yl]amino}-5-(2,4,6-trifluorophenyl)thiophene-3-carboxamide | A | Calc'd 433, Found 433 |
| 54 | 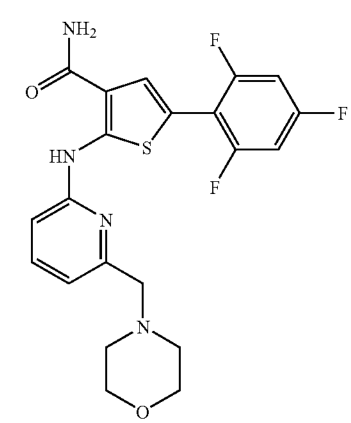 [SMILES: NC(=O)c1cc(-c2c(F)cc(F)cc2F)sc1Nc1cccc(CN2CCOCC2)n1] | 2-{[6-(morpholin-4-ylmethyl)pyridin-2-yl]amino}-5-(2,4,6-trifluorophenyl)thiophene-3-carboxamide | A | Calc'd 449, Found 449 |

TABLE 4-continued

| Example | Structure | Name | Reductive Amination Method | Characterization [M + H] |
|---|---|---|---|---|
| 55 | 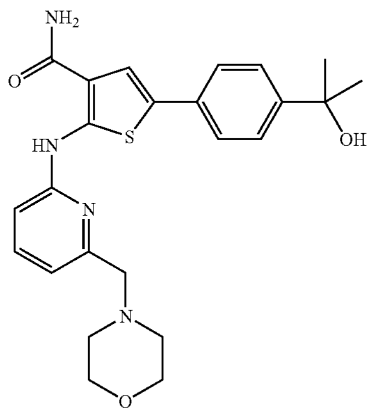 [SMILES: CC(C)(O)c1ccc(-c2cc(C(N)=O)c(Nc3cccc(CN4CCOCC4)n3)s2)cc1] | 5-[4-(1-hydroxy-1-methylethyl)phenyl]-2-{[6-(morpholin-4-ylmethyl)pyridin-2-yl]amino}thiophene-3-carboxamide | A | Calc'd 453, Found 453 |
| 56 | 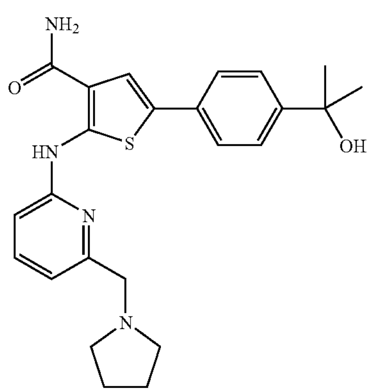 [SMILES: CC(C)(O)c1ccc(-c2cc(C(N)=O)c(Nc3cccc(CN4CCCC4)n3)s2)cc1] | 5-[4-(1-hydroxy-1-methylethyl)phenyl]-2-{[6-(pyrrolidin-1-ylmethyl)pyridin-2-yl]amino}thiophene-3-carboxamide | A | Calc'd 437, Found 437 |
| 57 | 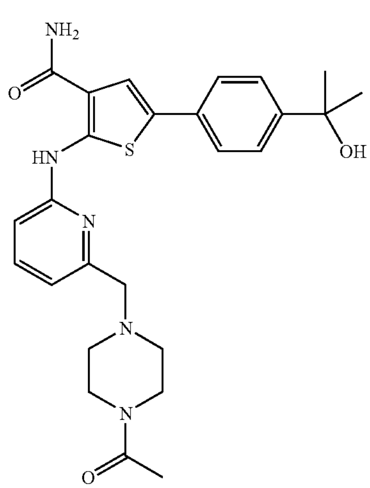 [SMILES: CC(=O)N1CCN(Cc2cccc(Nc3sc(-c4ccc(C(C)(C)O)cc4)cc3C(N)=O)n2)CC1] | 2-({6-[(4-acetylpiperazin-1-yl)methyl]pyridin-2-yl}amino)-5-[4-(1-hydroxy-1-methylethyl)phenyl]thiophene-3-carboxamide | A | Calc'd 494, Found 494 |

TABLE 4-continued

| Example | Structure | Name | Reductive Amination Method | Characterization [M + H] |
|---|---|---|---|---|
| 58 | 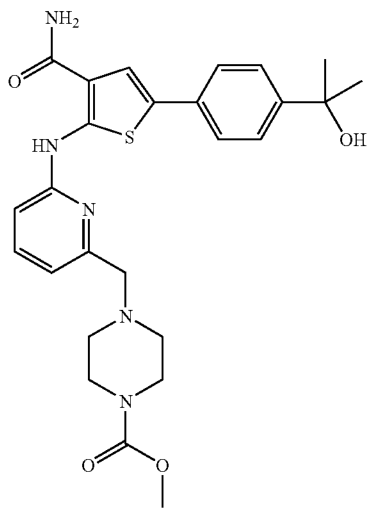 [SMILES: COC(=O)N1CCN(Cc2cccc(Nc3sc(-c4ccc(C(C)(C)O)cc4)cc3C(N)=O)n2)CC1] | methyl 4-{[6-({3-(aminocarbonyl)-5-[4-(1-hydroxy-1-methylethyl)phenyl]-2-thienyl}amino)pyridin-2-yl]methyl}piperazine-1-carboxylate | A | Calc'd 510, Found 510 |
| 59 | 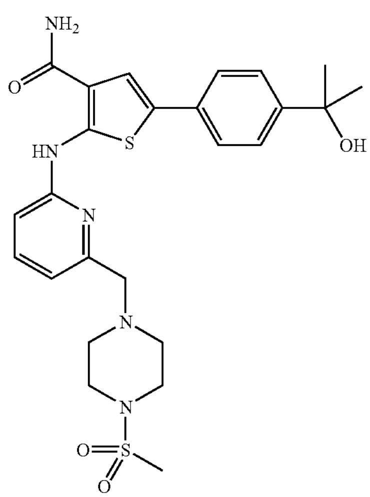 [SMILES: CC(C)(O)c1ccc(-c2cc(C(N)=O)c(Nc3cccc(CN4CCN(S(C)(=O)=O)CC4)n3)s2)cc1] | 5-[4-(1-hydroxy-1-methylethyl)phenyl]-2-[(6-{[4-(methylsulfonyl)piperazin-1-yl]methyl}pyridin-2-yl)amino]thiophene-3-carboxamide | A | Calc'd 530, Found 530 |
| 60 | 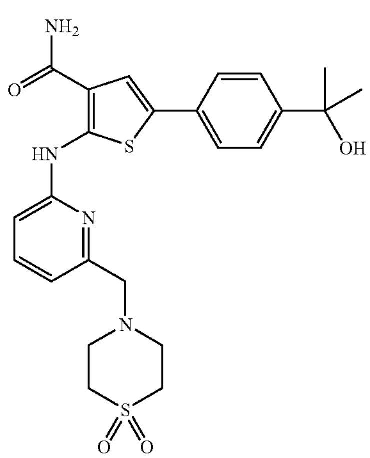 [SMILES: CC(C)(O)c1ccc(-c2cc(C(N)=O)c(Nc3cccc(CN4CCS(=O)(=O)CC4)n3)s2)cc1] | 2-({6-[(1,1-dioxidothiomorpholin-4-yl)methyl]pyridin-2-yl}amino)-5-[4-(1-hydroxy-1-methylethyl)phenyl]thiophene-3-carboxamide | A | Calc'd 501, Found 501 |

TABLE 4-continued

| Example | Structure | Name | Reductive Amination Method | Characterization [M + H] |
|---|---|---|---|---|
| 61 | 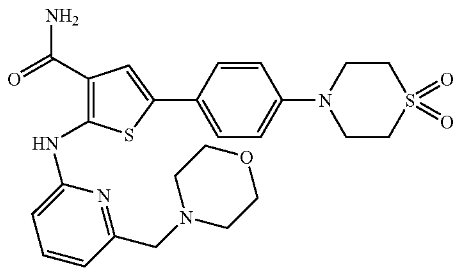 [SMILES: NC(=O)c1cc(-c2ccc(N3CCS(=O)(=O)CC3)cc2)sc1Nc1cccc(CN2CCOCC2)n1] | 5-[4-(1,1-dioxidothiomorpholin-4-yl)phenyl]-2-{[6-(morpholine-4-ylmethyl)pyridine-2-yl]amino}thiophene-3-carboxamide | A | Calc'd 528, Found 528 |
| 62 | 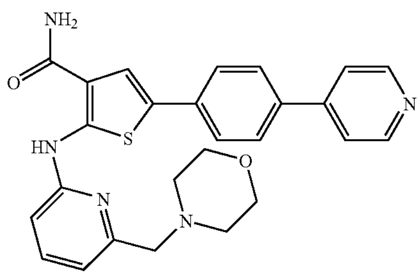 [SMILES: NC(=O)c1cc(-c2ccc(-c3ccncc3)cc2)sc1Nc1cccc(CN2CCOCC2)n1] | 2-{[6-(morpholin-4-ylmethyl)pyridin-2-yl]amino}-5-(4-pyridin-4-ylphenyl)thiophene-3-carboxamide | A | Calc'd 472, Found 472 |
| 63 | 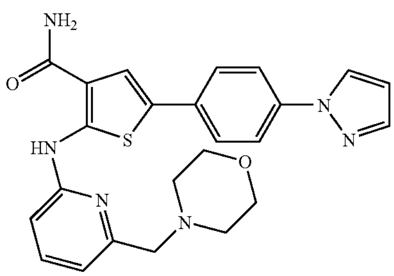 [SMILES: NC(=O)c1cc(-c2ccc(-n3cccn3)cc2)sc1Nc1cccc(CN2CCOCC2)n1] | 2-{[6-(morpholin-4-ylmethyl)pyridin-2-yl]amino}-5-[4-(1H-pyrazol-1-yl)phenyl]thiophene-3-carboxamide | A | Calc'd 461, Found 461 |
| 64 | 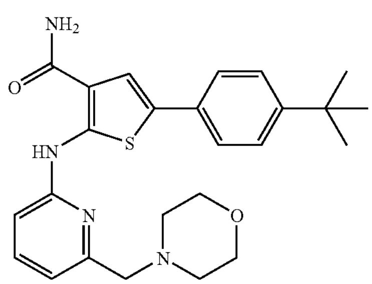 [SMILES: CC(C)(C)c1ccc(-c2cc(C(N)=O)c(Nc3cccc(CN4CCOCC4)n3)s2)cc1] | 5-(4-tert-butylphenyl)-2-{[6-(morpholin-4-ylmethyl)pyridin-2-yl]amino}thiophene-3-carboxamide | A | Calc'd 451, Found 451 |
| 65 | 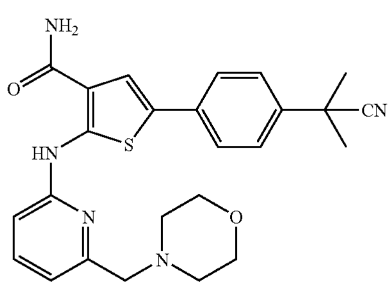 [SMILES: CC(C)(C#N)c1ccc(-c2cc(C(N)=O)c(Nc3cccc(CN4CCOCC4)n3)s2)cc1] | 5-[4-(1-cyano-1-methylethyl)phenyl]-2-{[6-(morpholin-4-ylmethyl)pyridin-2-yl]amino}thiophene-3-carboxamide | A | Calc'd 462, Found 462 |

TABLE 4-continued

| Example | Structure | Name | Reductive Amination Method | Characterization [M + H] |
|---|---|---|---|---|
| 66 | 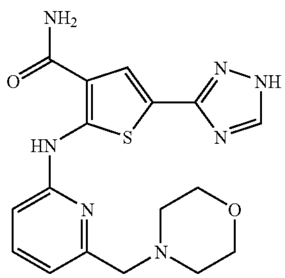 [SMILES: NC(=O)c1cc(-c2nc[nH]n2)sc1Nc1cccc(CN2CCOCC2)n1] | 2-{[6-(morpholin-4-ylmethyl)pyridin-2-yl]amino}-5-(1H-1,2,4-triazol-3-yl)thiophene-3-carboxamide | A | Calc'd 386, Found 386 |
| 67 | 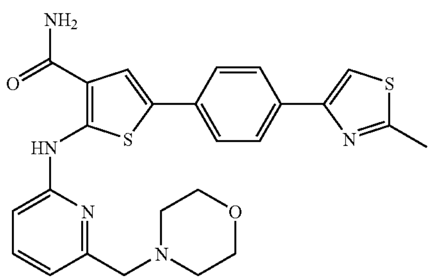 [SMILES: Cc1nc(-c2ccc(-c3cc(C(N)=O)c(Nc4cccc(CN5CCOCC5)n4)s3)cc2)cs1] | 5-[4-(2-methyl-1,3-thiazol-4-yl)phenyl]-2-{[6-(morpholin-4-ylmethyl)pyridin-2-yl]amino}thiophene-3-carboxamide | A | Calc'd 492, Found 492 |
| 68 | 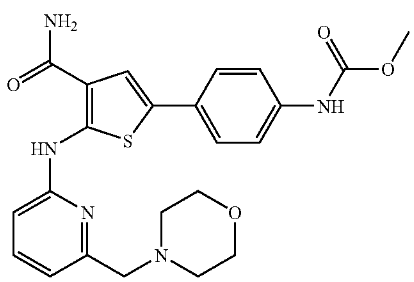 [SMILES: COC(=O)Nc1ccc(-c2cc(C(N)=O)c(Nc3cccc(CN4CCOCC4)n3)s2)cc1] | methyl [4-(4-(aminocarbonyl)-5-{[6-(morpholin-4-ylmethyl)pyridin-2-yl]amino}-2-thienyl)phenyl] carbamate | A | Calc'd 468, Found 468 |
| 69 | 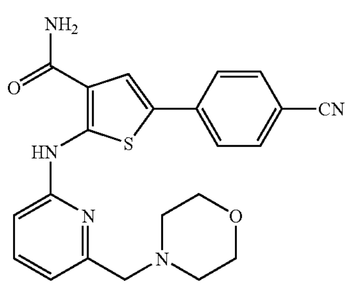 [SMILES: N#Cc1ccc(-c2cc(C(N)=O)c(Nc3cccc(CN4CCOCC4)n3)s2)cc1] | 5-(4-cyanophenyl)-2-{[6-(morpholin-4-ylmethyl)pyridin-2-yl]amino}thiophene-3-carboxamide | A | Calc'd 420, Found 420 |
| 70 | 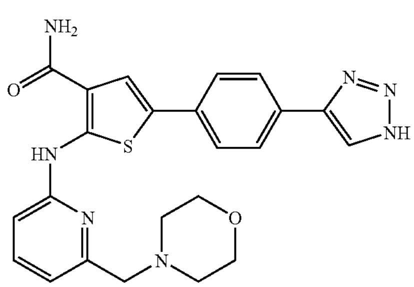 [SMILES: NC(=O)c1cc(-c2ccc(-c3c[nH]nn3)cc2)sc1Nc1cccc(CN2CCOCC2)n1] | 2-{[6-(morpholin-4-ylmethyl)pyridin-2-yl]amino}-5-[4-(1H-1,2,3-triazol-4-yl)phenyl]thiophene-3-carboxamide | A | Calc'd 462, Found 462 |

TABLE 4-continued

| Example | Structure | Name | Reductive Amination Method | Characterization [M + H] |
|---|---|---|---|---|
| 71 | 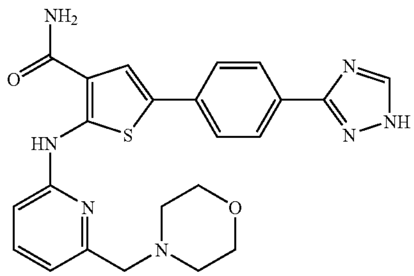 | 2-{[6-(morpholin-4-ylmethyl)pyridin-2-yl]amino}-5-[4-(1H-1,2,4-triazol-3-yl)phenyl]thiophene-3-carboxamide | A | Calc'd 462, Found 462 |
| 72 | 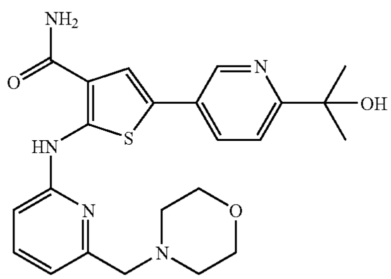 [SMILES: CC(C)(O)c1ccc(-c2cc(C(N)=O)c(Nc3cccc(CN4CCOCC4)n3)s2)cn1] | 5-[6-(1-hydroxy-1-methylethyl)pyridin-3-yl]-2-{[6-(morpholin-4-ylmethyl)pyridin-2-yl]amino}thiophene-3-carboxamide | A | Calc'd 454, Found 454 |
| 73 | 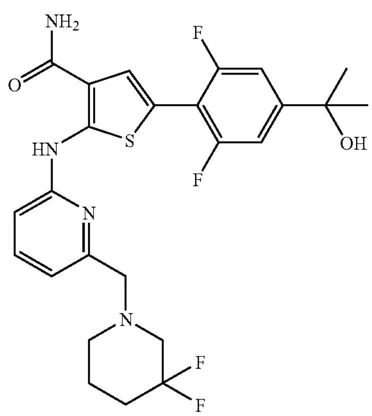 [SMILES: CC(C)(O)c1cc(F)c(-c2cc(C(N)=O)c(Nc3cccc(CN4CCCC(F)(F)C4)n3)s2)c(F)c1] | 5-[2,6-difluoro-4-(1-hydroxy-1-methylethyl)phenyl]-2-({6-[(3,3-difluoropiperidin-1-yl)methyl]pyridin-2-yl}amino)thiophene-3-carboxamide | A | Calc'd 523, Found 523 |
| 74 | 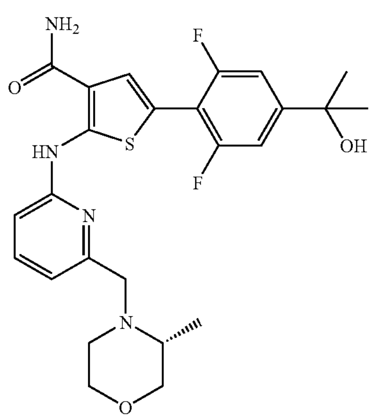 [SMILES: C[C@@H]1COCCN1Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-[(6-{[(3R)-3-methylmorpholin-4-yl]methyl}pyridin-2-yl)amino]thiophene-3-carboxamide | B | Calc'd 503, Found 503 |

TABLE 4-continued

| Example | Structure | Name | Reductive Amination Method | Characterization [M + H] |
|---|---|---|---|---|
| 75 | 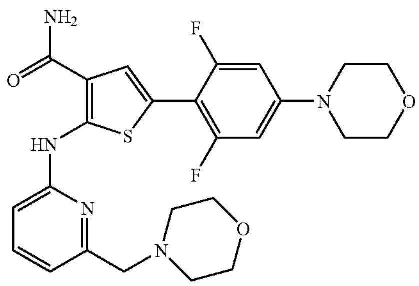 [SMILES: NC(=O)c1cc(-c2c(F)cc(N3CCOCC3)cc2F)sc1Nc1cccc(CN2CCOCC2)n1] | 5-(2,6-difluoro-4-morpholin-4-ylphenyl)-2-{[6-(morpholin-4-ylmethyl)pyridin-2-yl]amino}thiophene-3-carboxamide | A | Calc'd 516, Found 516 |
| 76 | 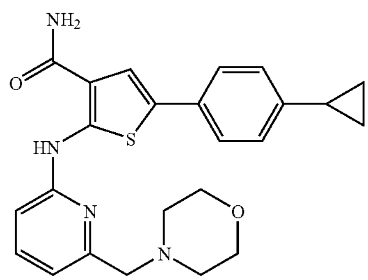 [SMILES: NC(=O)c1cc(-c2ccc(C3CC3)cc2)sc1Nc1cccc(CN2CCOCC2)n1] | 5-(4-cyclopropylphenyl)-2-{[6-(morpholin-4-ylmethyl)pyridin-2-yl]amino}thiophene-3-carboxamide | A | Calc'd 435, Found 435 |
| 77 | 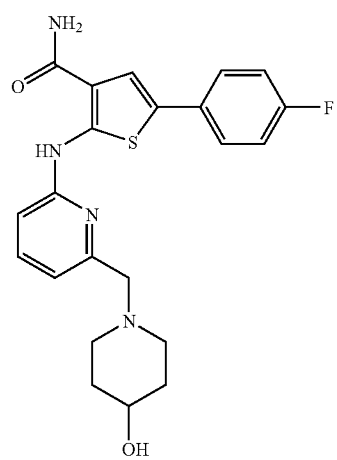 [SMILES: NC(=O)c1cc(-c2ccc(F)cc2)sc1Nc1cccc(CN2CCC(O)CC2)n1] | 5-(4-Fluorophenyl)-2-({6-[(4-hydroxypiperidin-1-yl)methyl]pyridin-2-yl}amino)thiophene-3-carboxamide | A | Calc'd 427, Found 427 |
| 78 | 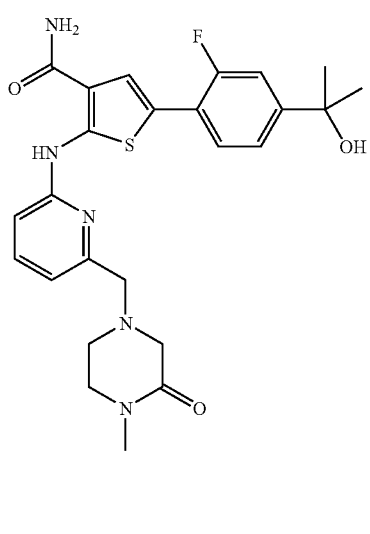 [SMILES: CN1CCN(Cc2cccc(Nc3sc(-c4ccc(C(C)(C)O)cc4F)cc3C(N)=O)n2)CC1=O] | 5-[2-fluoro-4-(1-hydroxy-1-methylethyl)phenyl]-2-({6-[(4-methyl-3-oxopiperazin-1-yl)methyl]pyridin-2-yl}amino)thiophene-3-carboxamide | A | Calc'd [M + 1]: 498, Found: 498 |

TABLE 4-continued

| Example | Structure | Name | Reductive Amination Method | Characterization [M + H] |
|---|---|---|---|---|
| 79 | 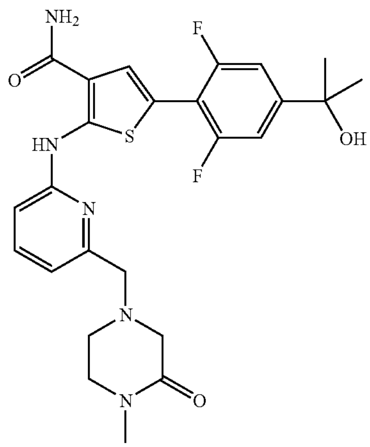 [SMILES: CN1CCN(Cc2cccc(Nc3sc(-c4c(F)cc(C(C)(C)O)cc4F)cc3C(N)=O)n2)CC1=O] | 5-[2,6-difluoro-4-(1-hydroxy-1-methylethyl)phenyl]-2-({6-[(4-methyl-3-oxopiperazin-1-yl)methyl]pyridin-2-yl}amino)thiophene-3-carboxamide | A | Calc'd [M + 1]: 516, Found: 516 |
| 80 | 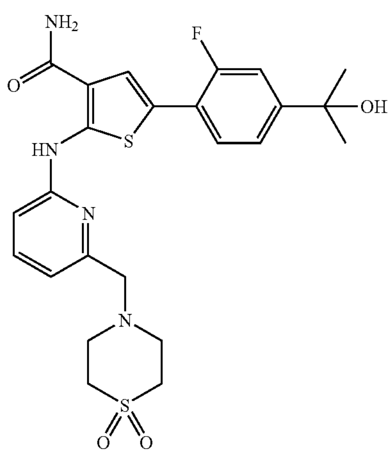 [SMILES: CC(C)(O)c1ccc(-c2cc(C(N)=O)c(Nc3cccc(CN4CCS(=O)(=O)CC4)n3)s2)c(F)c1] | 2-({6-[(1,1-dioxidothiomorpholin-4-yl)methyl]pyridin-2-yl}amino)-5-[2-fluoro-4-(1-hydroxy-1-methylethyl)phenyl]thiophene-3-carboxamide | A | Calc'd [M + 1]: 519, Found: 519 |
| 81 | 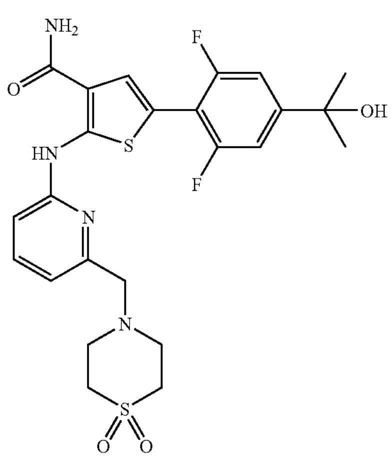 [SMILES: CC(C)(O)c1cc(F)c(-c2cc(C(N)=O)c(Nc3cccc(CN4CCS(=O)(=O)CC4)n3)s2)c(F)c1] | 5-[2,6-difluoro-4-(1-hydroxy-1-methylethyl)phenyl]-2-({6-[(1,1-dioxidothiomorpholin-4-yl)methyl]pyridin-2-yl}amino)thiophene-3-carboxamide | A | Calc'd [M + 1]: 537, Found: 537 |

TABLE 4-continued

| Example | Structure | Name | Reductive Amination Method | Characterization [M + H] |
|---|---|---|---|---|
| 82 | 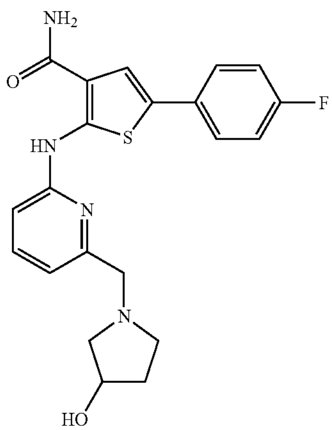 [SMILES: NC(=O)c1cc(-c2ccc(F)cc2)sc1Nc1cccc(CN2CCC(O)C2)n1] | 5-(4-fluorophenyl)-2-({6-[(3-hydroxypyrrolidin-1-yl)methyl]pyridin-2-yl}amino)thiophene-3-carboxamide | A | Calc'd 413, Found 413 |
| 83 | 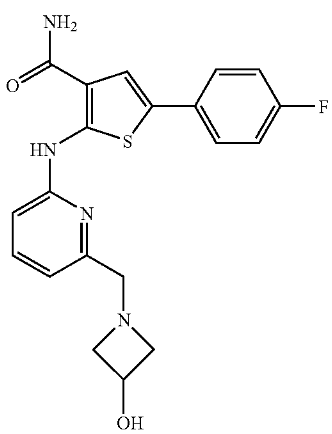 [SMILES: NC(=O)c1cc(-c2ccc(F)cc2)sc1Nc1cccc(CN2CC(O)C2)n1] | 5-(4-fluorophenyl)-2-({6-[(3-hydroxyazetidin-1-yl)methyl]pyridin-2-yl}amino)thiophene-3-carboxamide | B | Calc'd 399, Found 399 |
| 84 | 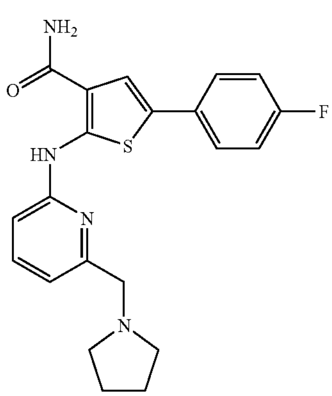 [SMILES: NC(=O)c1cc(-c2ccc(F)cc2)sc1Nc1cccc(CN2CCCC2)n1] | 5-(4-fluorophenyl)-2-{[6-(pyrrolidin-1-ylmethyl)pyridin-2-yl]amino}thiophene-3-carboxamide | A | Calc'd 397, Found 397 |

TABLE 4-continued

| Example | Structure | Name | Reductive Amination Method | Characterization [M + H] |
|---|---|---|---|---|
| 85 | 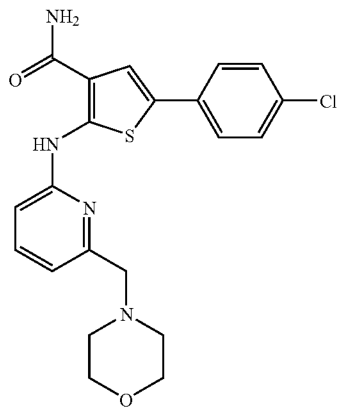 [SMILES: NC(=O)c1cc(-c2ccc(Cl)cc2)sc1Nc1cccc(CN2CCOCC2)n1] | 5-(4-chlorophenyl)-2-{[6-(morpholin-4-ylmethyl)pyridin-2-yl]amino}thiophene-3-carboxamide | A | Calc'd 429, Found 429 |
| 86 | 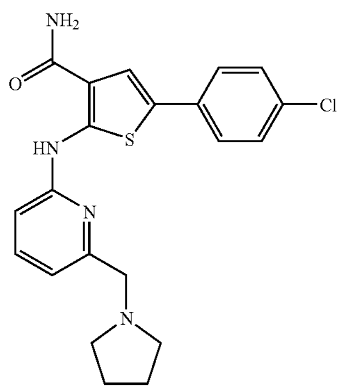 [SMILES: NC(=O)c1cc(-c2ccc(Cl)cc2)sc1Nc1cccc(CN2CCCC2)n1] | 5-(4-chlorophenyl)-2-{[6-(pyrrolidin-1-ylmethyl)pyridin-2-yl]amino}thiophene-3-carboxamide | A | Calc'd 413, Found 413 |
| 87 | 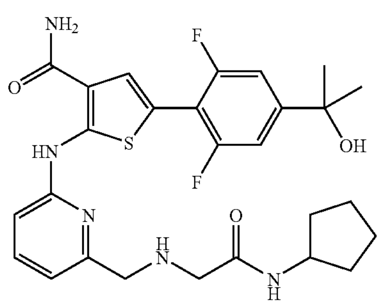 [SMILES: CC(C)(O)c1cc(F)c(-c2cc(C(N)=O)c(Nc3cccc(CNCC(=O)NC4CCCC4)n3)s2)c(F)c1] | 2-{6-({[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide | A | Calc'd 544, Found 544 |
| 88 | 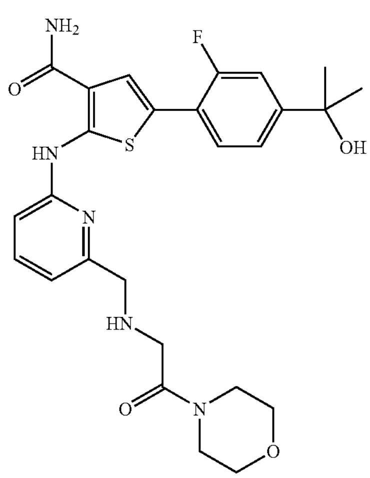 [SMILES: CC(C)(O)c1ccc(-c2cc(C(N)=O)c(Nc3cccc(CNCC(=O)N4CCOCC4)n3)s2)c(F)c1] | 5-[2-fluoro-4-(1-hydroxy-1-methylethyl)phenyl]-2-[(6-{[(2-morpholin-4-yl-2-oxoethyl)amino]methyl}pyridin-2-yl)amino]thiophene-3-carboxamide | A | Calc'd 528, Found 528 |

TABLE 4-continued

| Example | Structure | Name | Reductive Amination Method | Characterization [M + H] |
|---|---|---|---|---|
| 89 | 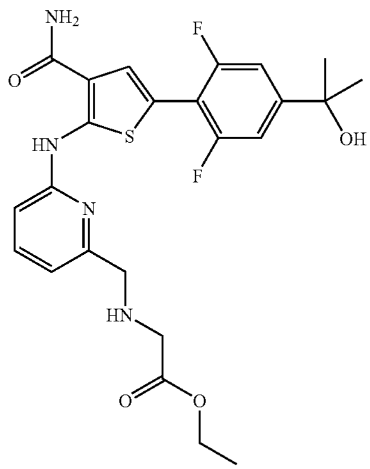 [SMILES: CCOC(=O)CNCc1cccc(Nc2sc(-c3c(F)cc(C(C)(C)O)cc3F)cc2C(N)=O)n1] | ethyl N-{[6-({3-(aminocarbonyl)-5-[2,6-difluoro-4-(1-hydroxy-1-methylethyl)phenyl]-2-thienyl}amino)pyridin-2-yl]methyl}glycinate | A | Calc'd 487, Found 487 |
| 90 | 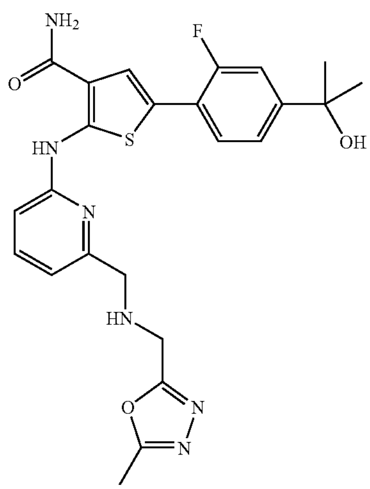 [SMILES: Cc1nnc(CNCc2cccc(Nc3sc(-c4ccc(C(C)(C)O)cc4F)cc3C(N)=O)n2)o1] | 5-[2-fluoro-4-(1-hydroxy-1-methylethyl)phenyl]-2-{[6-({[(5-methyl-1,3,4-oxadiazol-2-yl)methyl]amino}methyl)pyridin-2-yl]amino}thiophene-3-carboxamide | A | Calc'd 497, Found 497 |
| 91 | 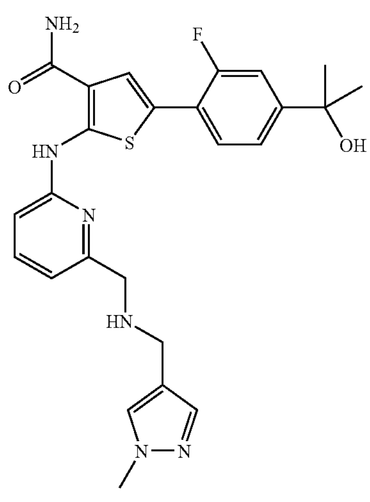 [SMILES: Cn1cc(CNCc2cccc(Nc3sc(-c4ccc(C(C)(C)O)cc4F)cc3C(N)=O)n2)cn1] | 5-[2-fluoro-4-(1-hydroxy-1-methylethyl)phenyl]-2-{[6-({[(1-methyl-1H-pyrazol-4-yl)methyl]amino}methyl)pyridin-2-yl]amino}thiophene-3-carboxamide | A | Calc'd 495, Found 495 |

TABLE 4-continued

| Example | Structure | Name | Reductive Amination Method | Characterization [M + H] |
|---|---|---|---|---|
| 92 | 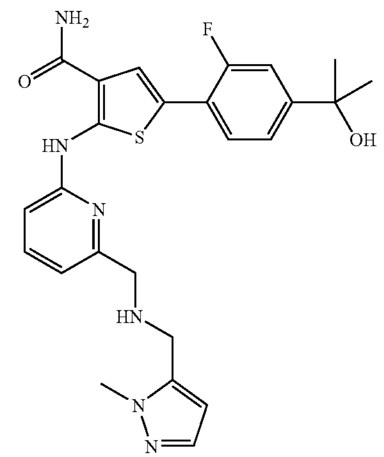 [SMILES: Cn1nccc1CNCc1cccc(Nc2sc(-c3ccc(C(C)(C)O)cc3F)cc2C(N)=O)n1] | 5-[2-fluoro-4-(1-hydroxy-1-methylethyl)phenyl]-2-{[6-({[(1-methyl-1H-pyrazol-5-yl)methyl]amino}methyl)pyridin-2-yl]amino}thiophene-3-carboxamide | A | Calc'd 495, Found 495 |
| 93 | 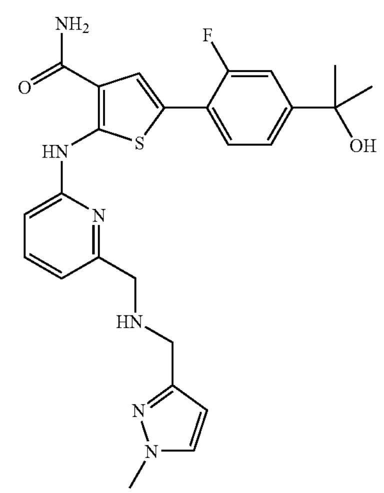 [SMILES: Cn1ccc(CNCc2cccc(Nc3sc(-c4ccc(C(C)(C)O)cc4F)cc3C(N)=O)n2)n1] | 5-[2-fluoro-4-(1-hydroxy-1-methylethyl)phenyl]-2-{[6-({[(1-methyl-1H-pyrazol-3-yl)methyl]amino}methyl)pyridin-2-yl]amino}thiophene-3-carboxamide | A | Calc'd 495, Found 495 |
| 94 | 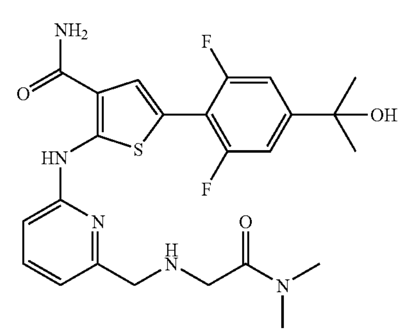 [SMILES: CN(C)C(=O)CNCc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-({[2-(dimethylamino)-2-oxoethyl]amino}methyl)pyridin-2-yl]amino}thiophene-3-carboxamide | A | Calc'd 504, Found 504 |

TABLE 4-continued

| Example | Structure | Name | Reductive Amination Method | Characterization [M + H] |
|---|---|---|---|---|
| 95 | 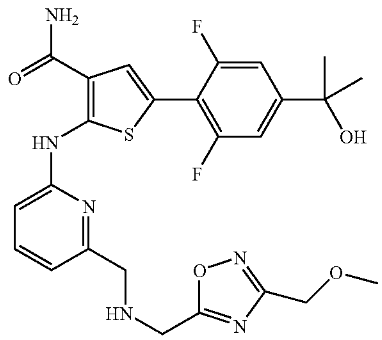 [SMILES: COCc1noc(CNCc2cccc(Nc3sc(-c4c(F)cc(C(C)(C)O)cc4F)cc3C(N)=O)n2)n1] | 5-[2,6-difluoro-4-(1-hydroxy-1-methylethyl)phenyl]-2-({6-[({3-(methoxymethyl)-1,2,4-oxadiazol-5-yl]methyl}amino)methyl]pyridin-2-yl}amino)thiophene-3-carboxamide | A | Calc'd 545, Found 545 |
| 96 | 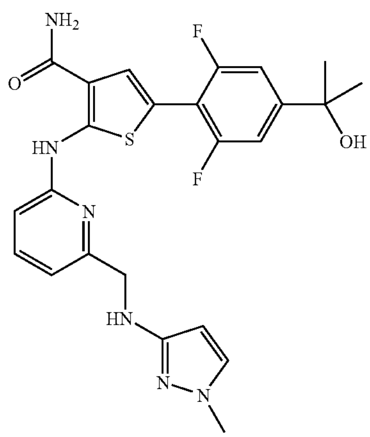 [SMILES: Cn1ccc(NCc2cccc(Nc3sc(-c4c(F)cc(C(C)(C)O)cc4F)cc3C(N)=O)n2)n1] | 5-[2,6-difluoro-4-(1-hydroxy-1-methylethyl)phenyl]-2-[(6-{[(1-methyl-1H-pyrazol-3-yl)amino]methyl}pyridin-2-yl)amino]thiophene-3-carboxamide | A | Calc'd 499, Found 499 |
| 97 | 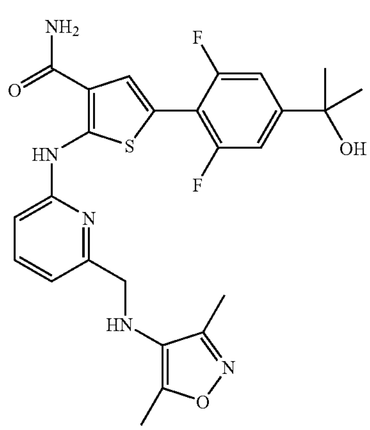 [SMILES: Cc1noc(C)c1NCc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-[(6-{[(3,5-dimethylisoxazol-4-yl)amino]methyl}pyridin-2-yl)amino]thiophene-3-carboxamide | A | Calc'd 514, Found 514 |

TABLE 4-continued

| Example | Structure | Name | Reductive Amination Method | Characterization [M + H] |
|---|---|---|---|---|
| 98 | 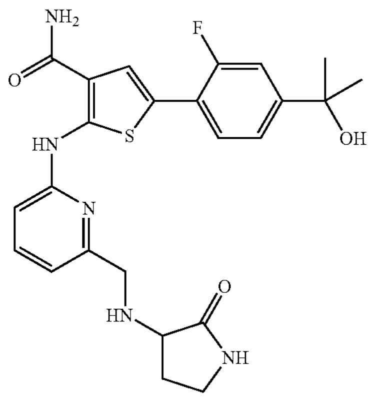 [SMILES: CC(C)(O)c1ccc(-c2cc(C(N)=O)c(Nc3cccc(CNC4CCNC4=O)n3)s2)c(F)c1] | 5-[2-fluoro-4-(1-hydroxy-1-methylethyl)phenyl]-2-[(6-{[(2-oxopyrrolidin-3-yl)amino]methyl}pyridin-2-yl)amino]thiophene-3-carboxamide | A | Calc'd 484, Found 484 |
| 99 | 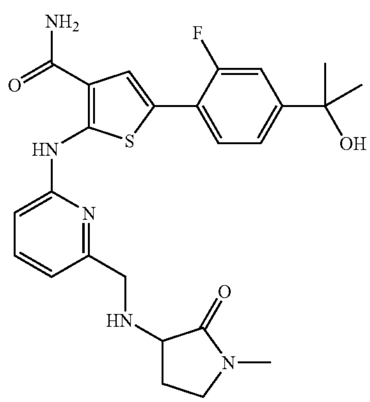 [SMILES: CN1CCC(NCc2cccc(Nc3sc(-c4ccc(C(C)(C)O)cc4F)cc3C(N)=O)n2)C1=O] | 5-[2-fluoro-4-(1-hydroxy-1-methylethyl)phenyl]-2-[(6-{[(1-methyl-2-oxopyrrolidin-3-yl)amino]methyl}pyridin-2-yl)amino]thiophene-3-carboxamide | A | Calc'd 498, Found 498 |
| 100 | 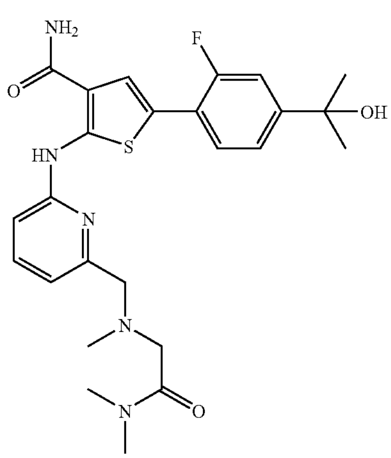 [SMILES: CN(CC(=O)N(C)C)Cc1cccc(Nc2sc(-c3ccc(C(C)(C)O)cc3F)cc2C(N)=O)n1] | 2-[(6-{[[2-(dimethylamino)-2-oxoethyl](methyl)amino]methyl}pyridin-2-yl)amino]-5-[2-fluoro-4-(1-hydroxy-1-methylethyl)phenyl]thiophene-3-carboxamide | A | Calc'd 500, Found 500 |

TABLE 4-continued

| Example | Structure | Name | Reductive Amination Method | Characterization [M + H] |
|---|---|---|---|---|
| 101 | 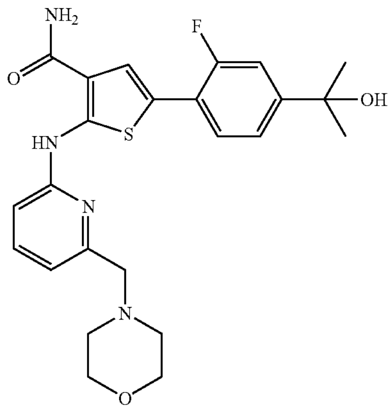 [SMILES: CC(C)(O)c1ccc(-c2cc(C(N)=O)c(Nc3cccc(CN4CCOCC4)n3)s2)c(F)c1] | 5-[2-fluoro-4-(1-hydroxy-1-methylethyl)phenyl]-2-{[6-(morpholin-4-ylmethyl)pyridin-2-yl]amino}thiophene-3-carboxamide | A | Calc'd 471, Found 471 |
| 102 | 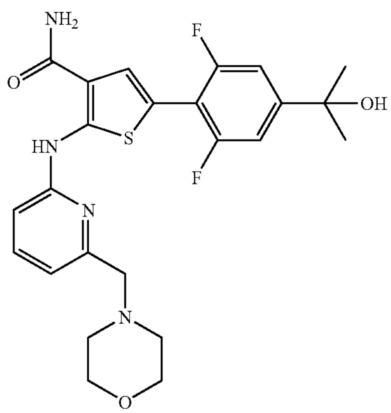 [SMILES: CC(C)(O)c1cc(F)c(-c2cc(C(N)=O)c(Nc3cccc(CN4CCOCC4)n3)s2)c(F)c1] | 5-[2,6-difluoro-4-(1-hydroxy-1-methylethyl)phenyl]-2-{[6-(morpholin-4-ylmethyl)pyridin-2-yl]amino}thiophene-3-carboxamide | A | Calc'd 489, Found 489 |
| 103 | 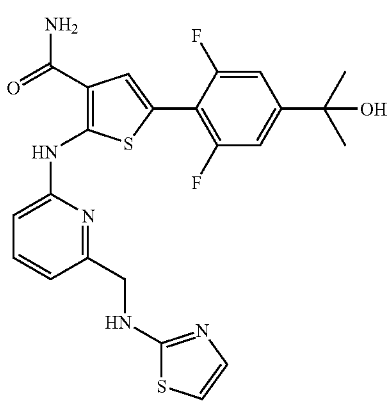 [SMILES: CC(C)(O)c1cc(F)c(-c2cc(C(N)=O)c(Nc3cccc(CNc4nccs4)n3)s2)c(F)c1] | 5-[2,6-difluoro-4-(1-hydroxy-1-methylethyl)phenyl]-2-({6-[(1,3-thiazol-2-ylamino)methyl]pyridin-2-yl}amino)thiophene-3-carboxamide | A | Calc'd 502, Found 502 |

Reductive Amination Method A: Using procedure described in Example 45 Step 1.
Reductive Amination Method B: Using procedure described in Example 47 Step 7.

Example 104

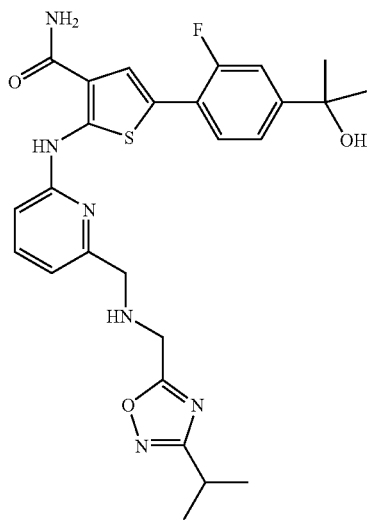 [SMILES: CC(C)c1noc(CNCc2cccc(Nc3sc(-c4ccc(C(C)(C)O)cc4F)cc3C(N)=O)n2)n1]

5-[2-Fluoro-4-(1-hydroxy-1-methylethyl)phenyl]-2-{[6-({[(3-isopropyl-1,2,4-oxadiazol-5-yl)methyl]amino}methyl)pyridin-2-yl]amino}thiophene-3-carboxamide

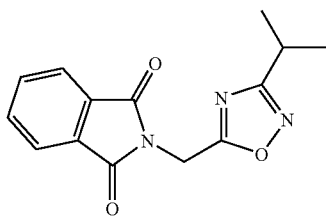 [SMILES: CC(C)c1noc(CN2C(=O)c3ccccc3C2=O)n1]

Step 1: 2-[(3-Isopropyl-1,2,4-oxadiazol-5-yl)methyl]-1H-isoindole-1,3(2H)-dione

To a solution of potassium phthalimide (72 g, 0.39 mol) in dry N,N-dimethylformamide (300 mL) was added 5-(chloromethyl)-3-isopropyl-1,2,4-oxadiazole (50 g, 0.31 mol) gradually with stirring. The reaction mixture was maintained at ambient temperature for 2 h and then poured into cold water (1.2 L). The resulting yellow precipitate was collected by filtration, washed with water, and dried in the air to yield the title compound.

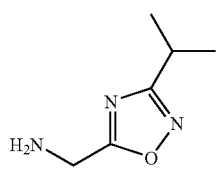

Step 2: 1-(3-Isopropyl-1,2,4-oxadiazol-5-yl)methanamine

To a vigorously stirred suspension of compound 2-[(3-isopropyl-1,2,4-oxadiazol-5-yl)methyl]-1H-isoindole-1,3 (2H)-dione (79 g, 0.29 mol) in ethanol (500 mL), hydrazine hydrate (16 g, 0.32 mol) was added. After the precipitate was completely dissolved, the reaction mixture was heated to reflux for 4 h. The precipitate was removed by filtration. The mother liquor was evaporated. The residue was dissolved in ether (200 mL). The precipitate was removed by filtration. The filtrate was evaporated. The residue was redistilled under high vacuum collecting the fraction boiling at 62-65° C./0.02 mmHg to yield the title compound.

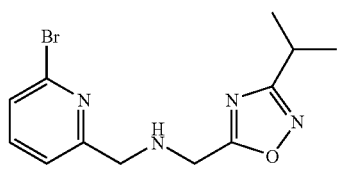 [SMILES: CC(C)c1noc(CNCc2cccc(Br)n2)n1]

Step 3: 1-(6-Bromopyridin-2-yl)-N-[(3-isopropyl-1,2,4-oxadiazol-5-yl)methyl]methanamine 6-Bromopyridine-2-carbaldehyde (1.18 g, 6.34 mmol) and 1-(3-isopropyl-1,2,4-oxadiazol-5-yl)methanamine (0.90 g, 6.34 mmol) were combined and dissolved in dichloroethane (26.0 ml), reacted for 45 minutes, at which time sodium triacetoxyborohydride (1.88 g, 8.88 mmol) was added and the reaction was maintained at room temperature overnight. The reaction was diluted with ethyl acetate followed by the addition of saturated sodium bicarbonate and saturated sodium carbonate to make sure the pH was basic. The organic layer was separated and washed with brine. The organic layer was dried over magnesium sulfate, filtered and concentrated. The crude reaction mixture was purified by silica gel chromatography to yield the title compound.

Calc'd for $C_{12}H_{16}BrN_4O$ [M+1]: 311. Found: 311.

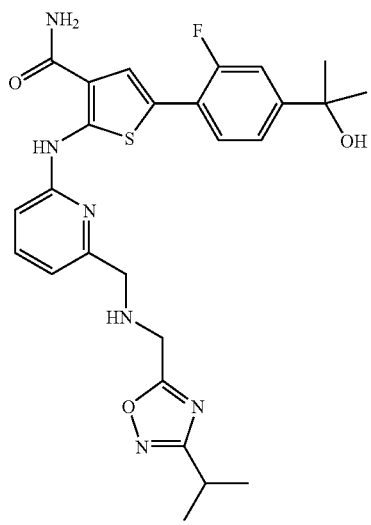 [SMILES: CC(C)c1noc(CNCc2cccc(Nc3sc(-c4ccc(C(C)(C)O)cc4F)cc3C(N)=O)n2)n1]

Step 4: 5-[2-Fluoro-4-(1-hydroxy-1-methylethyl)phenyl]-2-{[6-({[(3-isopropyl-1,2,4-oxadiazol-5-yl)methyl]amino}methyl)pyridin-2-yl]amino}thiophene-3-carboxamide The title compound was prepared according to the general procedure in Example 1 using 2-amino-5-[2-fluoro-4-(1-hydroxy-1-methylethyl)phenyl]thiophene-3-carboxamide (116 mg, 0.393 mmol) and 1-(6-bromopyridin-2-yl)-N-[(3-isopropyl-1,2,4-oxadiazol-5-yl)methyl]methanamine (120 mg, 0.39 mmol) as the starting materials.

Calc'd for $C_{26}H_{30}FN_6O_3S$ [M+H]$^+$: 525. Found: 525

Example 105

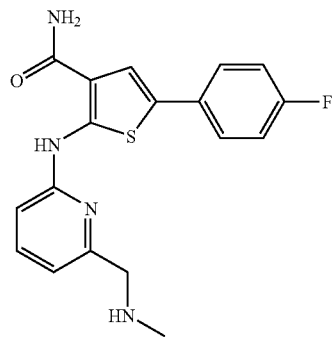 [SMILES: CNCc1cccc(Nc2sc(-c3ccc(F)cc3)cc2C(N)=O)n1]

5-(4-Fluorophenyl)-2-({6-[(methylamino)methyl]pyridin-2-yl}amino)thiophene-3-carboxamide

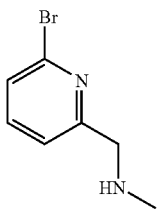

Step 1:
1-(6-Bromopyridin-2-yl)-N-methylmethanamine

The title compound was prepared according to the procedure in Example 45 Step 1 using 6-bromopyridine-2-carbaldehyde (0.50 g, 2.69 mmol) and methylamine (0.253 mg, 2.69 mmol) as the starting materials Calc'd for $C_7H_{10}BrN_2$ [M+H]$^+$: 201. Found: 201.

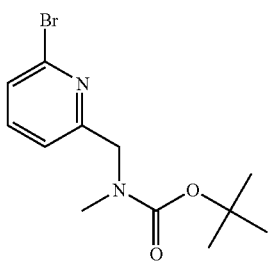 [SMILES: CN(Cc1cccc(Br)n1)C(=O)OC(C)(C)C]

Step 2: tert-Butyl[(6-bromopyridin-2-yl)methyl]methylcarbamate

A solution of 1-(6-bromopyridin-2-yl)-N-methylmethanamine (300 mg, 1.49 mmol) in dimethylformamide (4.2 mL) was charged with di-tert-butyl-dicarbonate (488 mg, 2.24 mmol). The reaction mixture was maintained at ambient temperature for 16 hours and then partitioned between ethyl acetate (15 mL) and saturated aqueous sodium bicarbonate (15 mL). The layers were separated and the organic layer was washed with saturated aqueous sodium bicarbonate (15 mL) and brine (2×15 mL), dried over sodium sulfate, filtered, and concentrated. The crude product was purified by silica gel chromatography using a 5-40% ethyl acetate/hexanes gradient to afford the title compound.

Calc'd for $C_{12}H_{18}BrN_2O_2$ [M+H]$^+$: 301. Found: 301.

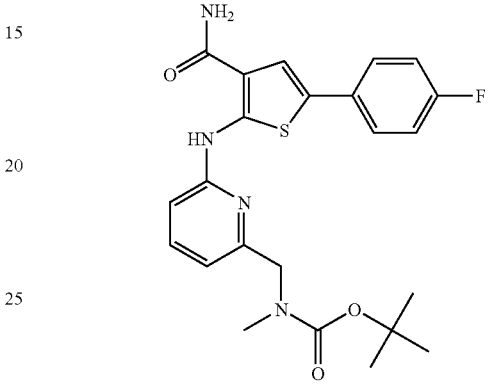

Step 3: tert-Butyl[(6-{[3-(aminocarbonyl)-5-(4-fluorophenyl)-2-thienyl]amino}pyridin-2-yl)methyl]methylcarbamate The title compound was prepared according to the general procedure in Example 1 using tert-butyl[(6-bromopyridin-2-yl)methyl]methylcarbamate (90.0 mg, 0.299 mmol) and 2-amino-5-(4-fluorophenyl)thiophene-3-carboxamide (78.0 mg, 0.329 mmol) as the starting materials.

Calc'd for $C_{23}H_{26}FN_4O_3S$ [M+H]$^+$: 457. Found: 457.

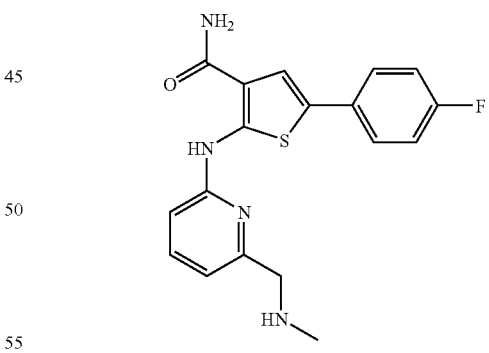

Step 4: 5-(4-Fluorophenyl)-2-({6-[(methylamino)methyl]pyridin-2-yl}amino)thiophene-3-carboxamide To a solution of tert-butyl[(6-{[3-(aminocarbonyl)-5-(4-fluorophenyl)-2-thienyl]amino}pyridin-2-yl)methyl]methylcarbamate (90 mg, 0.197 mmol) in dichloromethane (0.4 mL) was added trifluoroacetic acid (0.4 mL) and the reaction was maintained at room temperature for 1 hour. The volatiles were removed in vacuo and the crude product was purified by reverse phase HPLC (20-90% acetonitrile/water with 0.05% trifluoroacetic acid). The appropriate fractions were diluted with ethyl acetate (50 mL) and saturated aqueous sodium bicarbonate (40 mL). The layers were separated and the organic layer was washed with saturated aqueous sodium bicarbonate (40 mL) and water (2×40 mL), dried over sodium sulfate, filtered and concentrated to yield the title compound.

Calc'd for $C_{18}H_{18}FN_4OS$ [M+H]$^+$: 357. Found: 357.

Example 106

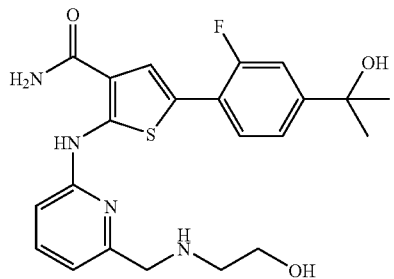 [SMILES: CC(C)(O)c1ccc(-c2cc(C(N)=O)c(Nc3cccc(CNCCO)n3)s2)c(F)c1]

5-(2-Fluoro-4-(1-hydroxy-1-methylethyl)phenyl)-2-((6-((2-hydroxyethyl)amino)methyl)-2-pyridinyl)amino)-3-thiophenecarboxamide

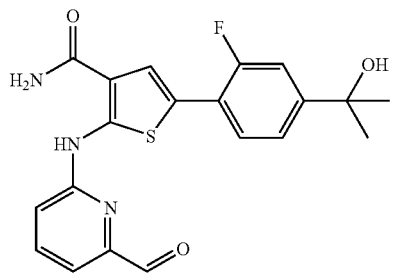 [SMILES: CC(C)(O)c1ccc(-c2cc(C(N)=O)c(Nc3cccc(C=O)n3)s2)c(F)c1]

Step 1: 5-[2-Fluoro-4-(1-hydroxy-1-methylethyl)phenyl]-2-[(6-formylpyridin-2-yl)amino]thiophene-3-carboxamide To a solution of 5-(2-fluoro-4-(1-hydroxy-1-methylethyl)phenyl)-2-((6-(hydroxymethyl)-2-pyridinyl)amino)-3-thiophenecarboxamide (Example 43) (513 mg, 1.28 mmol) in DMSO (83 ml) was added IBX polystyrene (2.9 g, 3.19 mmol). The reaction mixture was shaken at room temperature overnight. The reaction mixture was filtered and washed with DMSO (1 ml). Water was added to the eluent and a yellow precipitate was filtered, washed with water and dried in vacuo to afford the title compound.

Calc'd for $C_{20}H_{19}FN_3O_3S$ [M+H]$^+$: 400. Found: 400.

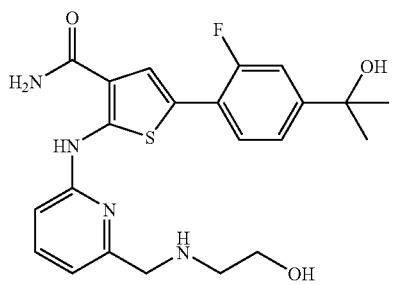

Step 2: 5-(2-Fluoro-4-(1-hydroxy-1-methylethyl)phenyl)-2-((6-((2-hydroxyethyl)amino)methyl)-2-pyridinyl)amino)-3-thiophenecarboxamide To a solution of 5-(2-fluoro-4-(1-hydroxy-1-methylethyl)phenyl)-2-((6-formyl-2-pyridinyl)amino)-3-thiophenecarboxamide (39 mg, 0.0976 mmol) in THF (900 µl) was added 2-aminoethanol (5.88 µl, 0.0976 mmol) and acetic acid (100 µl). The reaction mixture was stirred at room temperature overnight at which time silica-supported cyanoborohydride (202.1 mg, 0.192 mmol) was added. After 4 hours the reaction mixture was filtered, washed with THF (1 ml), and the solvent removed in vacuo. Analytically pure material was obtained by purification by preparative HPLC Reverse phase (C-18), eluting with acetonitrile/water+0.05% TFA. Lyophilizing afforded the title compound as the trifluoroacetic acid salt.

Calc'd for $C_{22}H_{26}FN_4O_3S$ [M+H]$^+$: 459. Found: 459.

Additional examples were prepared using procedures similar to those described in the above example and are illustrated in the following table.

TABLE 5

| Example # | Structure | Compound Name | Characterization |
|---|---|---|---|
| 107 | 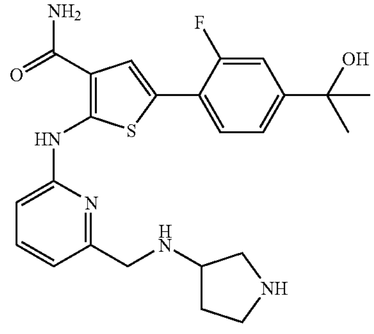 | 5-[2-fluoro-4-(1-hydroxy-1-methylethyl)phenyl]-2-((6-((3-pyrrolidinylamino)methyl)-2-pyridinyl)amino)-3-thiophenecarboxamide | Calc'd [M + H]$^+$: 570, Found: 570 |

TABLE 5-continued

| Example # | Structure | Compound Name | Characterization |
|---|---|---|---|
| 108 | 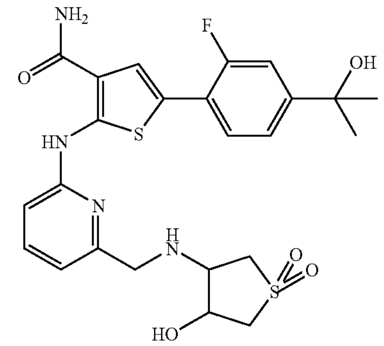 [SMILES: CC(C)(O)c1ccc(-c2cc(C(N)=O)c(Nc3cccc(CNC4CS(=O)(=O)CC4O)n3)s2)c(F)c1] | 5-(2-fluoro-4-(1-hydroxy-1-methylethyl)phenyl)-2-((6-(((4-hydroxy-1,1-dioxidotetrahydro-3-thienyl)amino)methyl)-2-pyridinyl)amino)-3-thiophenecarboxamide | Calc'd [M + H]$^+$: 535, Found: 535 |
| 109 | 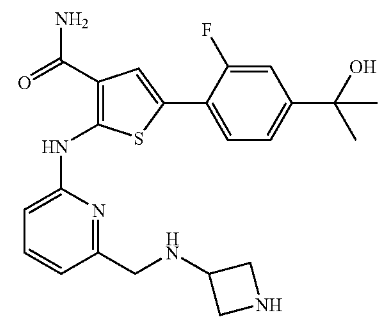 | 2-((6-((3-azetidinylamino)-2-pyridinyl)amino)-5-(2-fluoro-4-(1-hydroxy-1-methylethyl)phenyl)- -3-thiophenecarboxamide | Calc'd [M + H]$^+$: 556, Found: 556 |
| 110 | 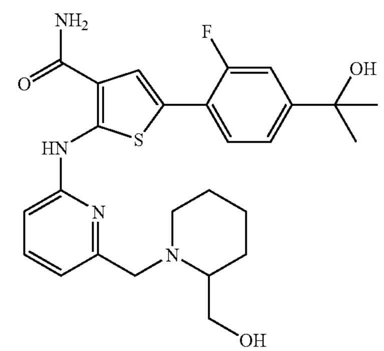 [SMILES: CC(C)(O)c1ccc(-c2cc(C(N)=O)c(Nc3cccc(CN4CCCCC4CO)n3)s2)c(F)c1] | 5-(2-fluoro-4-(1-hydroxy-1-methylethyl)phenyl)-2-((6-((2-hydroxymethyl)-1-piperidinyl)methyl)-2-pyridinyl)amino)-3-thiophenecarboxamide | Calc'd [M + H]$^+$: 499, Found: 499 |
| 111 | 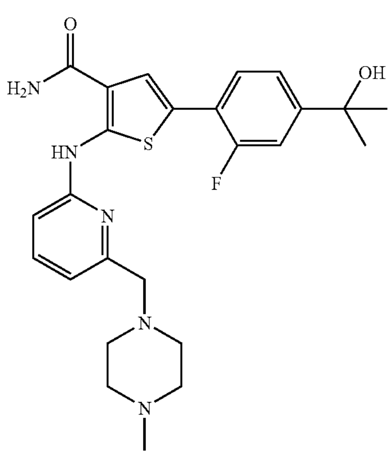 [SMILES: CN1CCN(Cc2cccc(Nc3sc(-c4ccc(C(C)(C)O)cc4F)cc3C(N)=O)n2)CC1] | 5-[2-fluoro-4-(1-hydroxy-1-methylethyl)phenyl]-2-({6-[(4-methylpiperazin-1-yl)methyl]pyridin-2-yl}amino)thiophene-3-carboxamide | Calc'd [M + H]$^+$: 484, Found: 484 |

TABLE 5-continued

| Example # | Structure | Compound Name | Characterization |
|---|---|---|---|
| 112 | 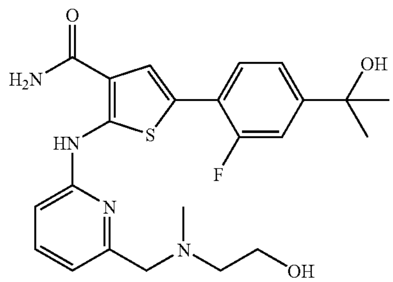 [SMILES: CN(CCO)Cc1cccc(Nc2sc(-c3ccc(C(C)(C)O)cc3F)cc2C(N)=O)n1] | 5-[2-fluoro-4-(1-hydroxy-1-methylethyl)phenyl]-2-[(6-{[(2-hydroxyethyl)(methyl)amino]methyl}pyridin-2-yl)amino]thiophene-3-carboxamide | Calc'd [M + H]⁺: 459, Found: 459 |
| 113 | 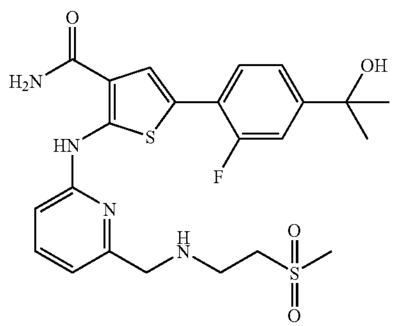 [SMILES: CC(C)(O)c1ccc(-c2cc(C(N)=O)c(Nc3cccc(CNCCS(C)(=O)=O)n3)s2)c(F)c1] | 5-[2-fluoro-4-(1-hydroxy-1-methylethyl)phenyl]-2-{[6-({[2-(methylsulfonyl)ethyl]amino}methyl)pyridin-2-yl]amino}thiophene-3-carboxamide | Calc'd [M + H]⁺: 507, Found: 507 |
| 114 | 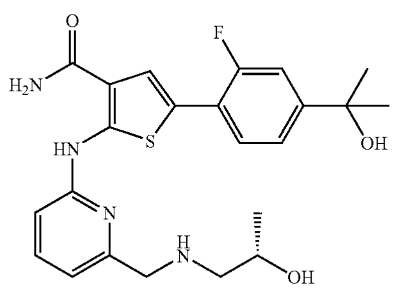 [SMILES: C[C@H](O)CNCc1cccc(Nc2sc(-c3ccc(C(C)(C)O)cc3F)cc2C(N)=O)n1] | 5-[2-fluoro-4-(1-hydroxy-1-methylethyl)phenyl]-2-{[6-({[(2S)-2-hydroxypropyl]amino}methyl)pyridin-2-yl]amino}thiophene-3-carboxamide | Calc'd [M + H]⁺: 459, Found: 459 |
| 115 | 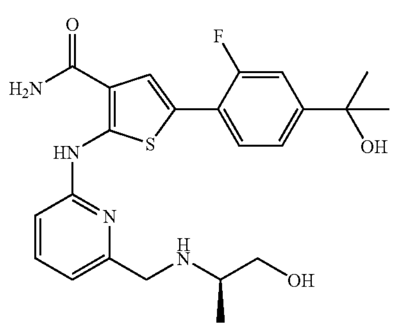 [SMILES: C[C@H](CO)NCc1cccc(Nc2sc(-c3ccc(C(C)(C)O)cc3F)cc2C(N)=O)n1] | 5-[2-fluoro-4-(1-hydroxy-1-methylethyl)phenyl]-2-{[6-({[(1R)-2-hydroxy-1-methylethyl]amino}methyl)pyridin-2-yl]amino}thiophene-3-carboxamide | Calc'd [M + H]⁺: 459, Found: 459 |
| 116 | 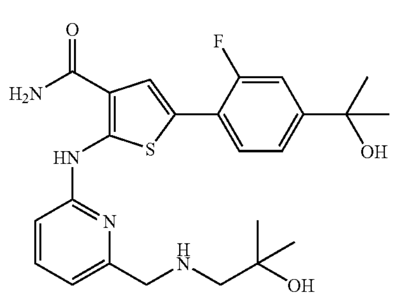 [SMILES: CC(C)(O)CNCc1cccc(Nc2sc(-c3ccc(C(C)(C)O)cc3F)cc2C(N)=O)n1] | 5-[2-fluoro-4-(1-hydroxy-1-methylethyl)phenyl]-2-[(6-{[(2-hydroxy-2-methylpropyl)amino]methyl}pyridin-2-yl)amino]thiophene-3-carboxamide | Calc'd [M + H]⁺: 473, Found: 473 |

Note: $[M + H]^+$ values as shown.

TABLE 5-continued

| Example # | Structure | Compound Name | Characterization |
|---|---|---|---|
| 117 | 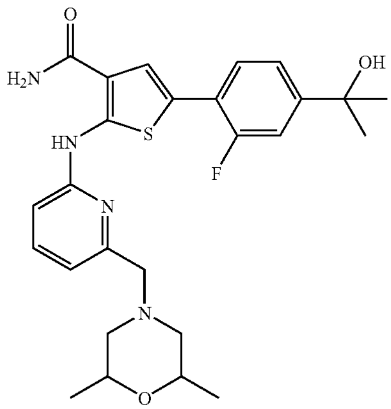 [SMILES: CC1CN(Cc2cccc(Nc3sc(-c4ccc(C(C)(C)O)cc4F)cc3C(N)=O)n2)CC(C)O1] | 2-({6-[(2,6-dimethylmorpholin-4-yl)methyl]pyridin-2-yl}amino)-5-[2-fluoro-4-(1-hydroxy-1-methylethyl)phenyl]thiophene-3-carboxamide | Calc'd [M + H]⁺: 499, Found: 499 |
| 118 | 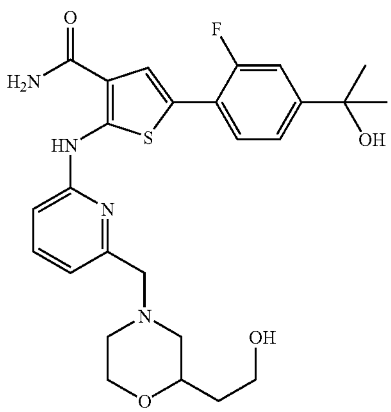 [SMILES: CC(C)(O)c1ccc(-c2cc(C(N)=O)c(Nc3cccc(CN4CCOC(CCO)C4)n3)s2)c(F)c1] | 5-[2-fluoro-4-(1-hydroxy-1-methylethyl)phenyl]-2-[(6-{[2-(2-hydroxyethyl)morpholin-4-ylmethyl}pyridin-2-yl)amino]thiophene-3-carboxamide | Calc'd [M + H]⁺: 515, Found: 515 |
| 119 | 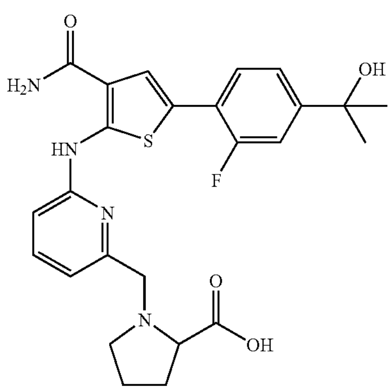 [SMILES: CC(C)(O)c1ccc(-c2cc(C(N)=O)c(Nc3cccc(CN4CCCC4C(=O)O)n3)s2)c(F)c1] | 1-{[6-({3-(aminocarbonyl)-5-[2-fluoro-4-(1-hydroxy-1-methylethyl)phenyl]-2-thienyl}amino)pyridine-2-yl]methyl}proline | Calc'd [M + H]⁺: 499, Found: 499 |
| 120 | 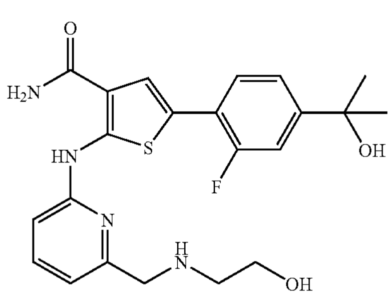 [SMILES: CC(C)(O)c1ccc(-c2cc(C(N)=O)c(Nc3cccc(CNCCO)n3)s2)c(F)c1] | 5-[2-fluoro-4-(1-hydroxy-1-methylethyl)phenyl]-2-[(6-{[(2-hydroxyethyl)amino]methyl}pyridin-2-yl)amino]thiophene-3-carboxamide | Calc'd [M + H]⁺: 445, Found: 445 |

TABLE 5-continued

| Example # | Structure | Compound Name | Characterization |
|---|---|---|---|
| 121 | 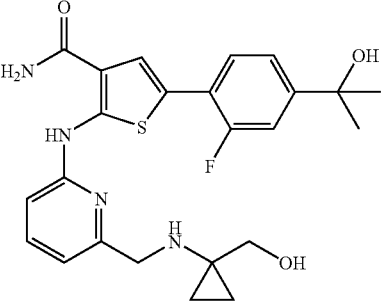 [SMILES: CC(C)(O)c1ccc(-c2cc(C(N)=O)c(Nc3cccc(CNC4(CO)CC4)n3)s2)c(F)c1] | 5-[2-fluoro-4-(1-hydroxy-1-methylethyl)phenyl]-2-{[6-({[1-(hydroxymethyl)cyclopropyl]amino}methyl)pyridin-2-yl]amino}thiophene-3-carboxamide | Calc'd [M + H]⁺: 471, Found: 471 |
| 122 | 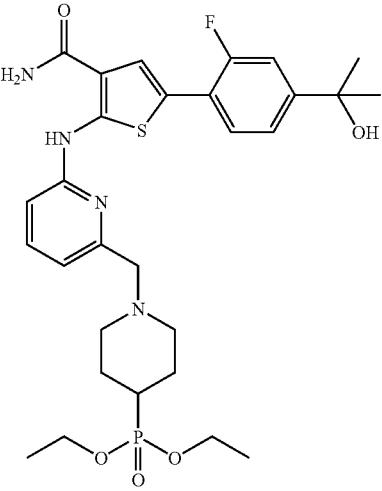 [SMILES: CCOP(=O)(OCC)C1CCN(Cc2cccc(Nc3sc(-c4ccc(C(C)(C)O)cc4F)cc3C(N)=O)n2)CC1] | diethyl (1-{[6-({3-(aminocarbonyl)-5-[2-fluoro-4-(1-hydroxy-1-methylethyl)phenyl]-2-thienyl}amino)pyridin-2-yl]methyl}piperidin-4-yl)phosphonate | Calc'd [M + H]⁺: 605, Found: 605 |
| 123 | 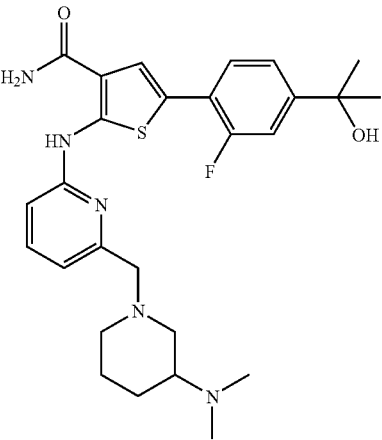 [SMILES: CN(C)C1CCCN(Cc2cccc(Nc3sc(-c4ccc(C(C)(C)O)cc4F)cc3C(N)=O)n2)C1] | 2-[(6-{[3-(dimethylamino)piperidin-1-yl]methyl}pyridin-2-yl)amino]-5-[2-fluoro-4-(1-hydroxy-1-methylethyl)phenyl]thiophene-3-carboxamide | Calc'd [M + H]⁺: 512, Found: 512 |

TABLE 5-continued

| Example # | Structure | Compound Name | Characterization |
|---|---|---|---|
| 124 | 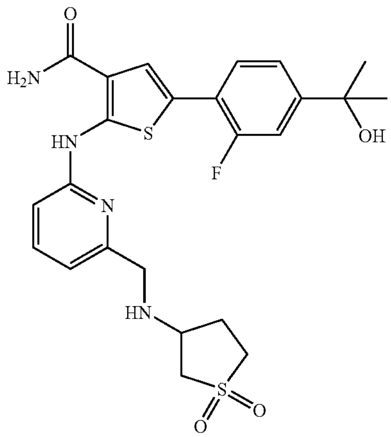 [SMILES: CC(C)(O)c1ccc(-c2cc(C(N)=O)c(Nc3cccc(CNC4CCS(=O)(=O)C4)n3)s2)c(F)c1] | 2-[(6-{[(1,1-dioxidotetrahydro-3-thienyl)amino]methyl}pyridin-2-yl)amino]-5-[2-fluoro-4-(1-hydroxy-1-methylethyl)phenyl]thiophene-3-carboxamide | Calc'd [M + H]⁺: 519, Found: 519 |
| 125 | 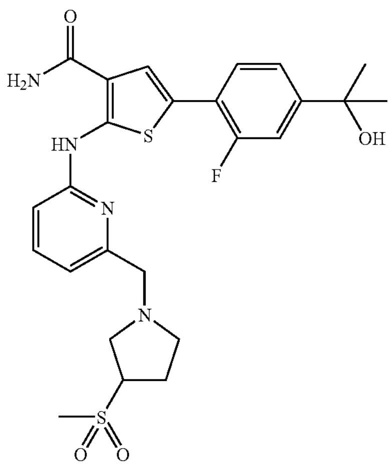 [SMILES: CC(C)(O)c1ccc(-c2cc(C(N)=O)c(Nc3cccc(CN4CCC(S(C)(=O)=O)C4)n3)s2)c(F)c1] | 5-[2-fluoro-4-(1-hydroxy-1-methylethyl)phenyl]-2-[(6-{[3-(methylsulfonyl)pyrrolidin-1-yl]methyl}pyridin-2-yl)amino]thiophene-3-carboxamide | Calc'd [M + H]⁺: 533, Found: 533 |
| 126 | 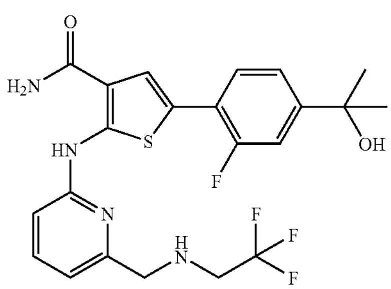 [SMILES: CC(C)(O)c1ccc(-c2cc(C(N)=O)c(Nc3cccc(CNCC(F)(F)F)n3)s2)c(F)c1] | 5-[2-fluoro-4-(1-hydroxy-1-methylethyl)phenyl]-2-[(6-{[(2,2,2-trifluoroethyl)amino]methyl}pyridin-2-yl)amino]thiophene-3-carboxamide | Calc'd [M + H]⁺: 483, Found: 483 |
| 127 | 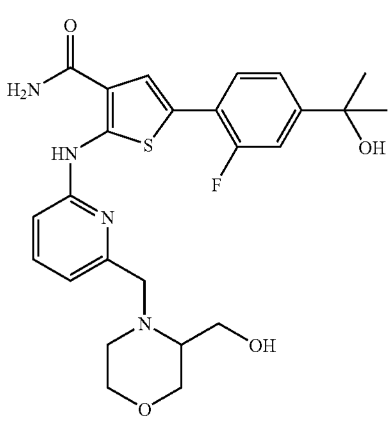 [SMILES: CC(C)(O)c1ccc(-c2cc(C(N)=O)c(Nc3cccc(CN4CCOCC4CO)n3)s2)c(F)c1] | 5-[2-fluoro-4-(1-hydroxy-1-methylethyl)phenyl]-2-[(6-{[3-(hydroxymethyl)morpholin-4-yl]methyl}pyridin-2-yl)amino]thiophene-3-carboxamide | Calc'd [M + H]⁺: 501, Found: 501 |

TABLE 5-continued

| Example # | Structure | Compound Name | Characterization |
|---|---|---|---|
| 128 | 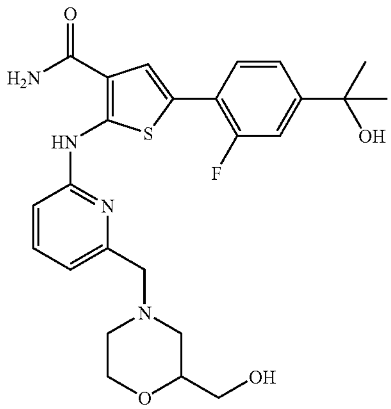 [SMILES: CC(C)(O)c1ccc(-c2cc(C(N)=O)c(Nc3cccc(CN4CCOC(CO)C4)n3)s2)c(F)c1] | 5-[2-fluoro-4-(1-hydroxy-1-methylethyl)phenyl]-2-[(6-{[2-(hydroxymethyl)morpholin-4-yl]methyl}pyridin-2-yl)amino]thiophene-3-carboxamide | Calc'd [M + H]⁺: 501, Found: 501 |
| 129 | 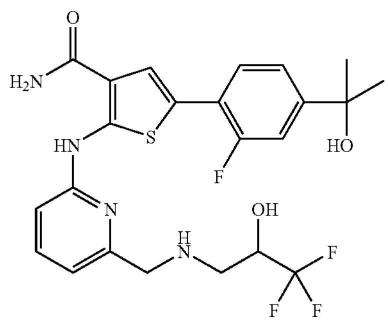 [SMILES: CC(C)(O)c1ccc(-c2cc(C(N)=O)c(Nc3cccc(CNCC(O)C(F)(F)F)n3)s2)c(F)c1] | 5-[2-fluoro-4-(1-hydroxy-1-methylethyl)phenyl]-2-[(6-{[(3,3,3-trifluoro-2-hydroxypropyl)amino]methyl}pyridin-2-yl)amino]thiophene-3-carboxamide | Calc'd [M + H]⁺: 513, Found: 513 |
| 130 | 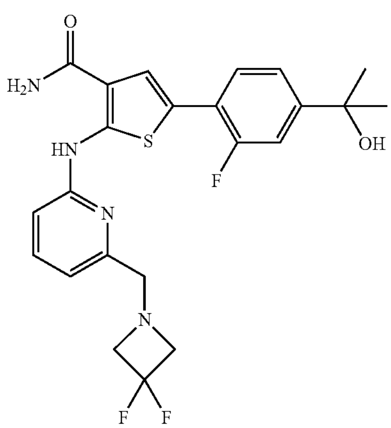 [SMILES: CC(C)(O)c1ccc(-c2cc(C(N)=O)c(Nc3cccc(CN4CC(F)(F)C4)n3)s2)c(F)c1] | 2-({6-[(3,3-difluoroazetidin-1-yl)methyl]pyridin-2-yl}amino)-5-[2-fluoro-4-(1-hydroxy-1-methylethyl)phenyl]thiophene-3-carboxamide | Calc'd [M + H]⁺: 477, Found: 477 |
| 131 | 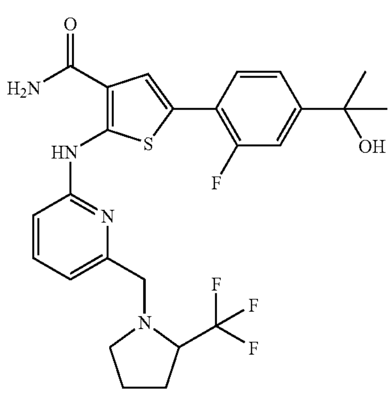 [SMILES: CC(C)(O)c1ccc(-c2cc(C(N)=O)c(Nc3cccc(CN4CCCC4C(F)(F)F)n3)s2)c(F)c1] | 5-[2-fluoro-4-(1-hydroxy-1-methylethyl)phenyl]-2-[6-{[2-(trifluoromethyl)pyrrolidin-1-yl]methyl}pyridin-2-yl)amino]thiophene-3-carboxamide | Calc'd [M + H]⁺: 523, Found: 523 |

TABLE 5-continued

| Example # | Structure | Compound Name | Characterization |
|---|---|---|---|
| 132 | 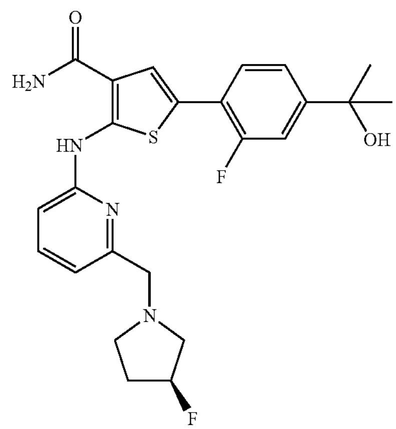 [SMILES: CC(C)(O)c1ccc(-c2cc(C(N)=O)c(Nc3cccc(CN4CC[C@H](F)C4)n3)s2)c(F)c1] | 5-[2-fluoro-4-(1-hydroxy-1-methylethyl)phenyl]-2-[(6-{[(3S)-3-fluoropyrrolidin-1-yl]methyl}pyridin-2-yl)amino]thiophene-3-carboxamide | Calc'd [M + H]⁺: 473, Found: 473 |
| 133 | 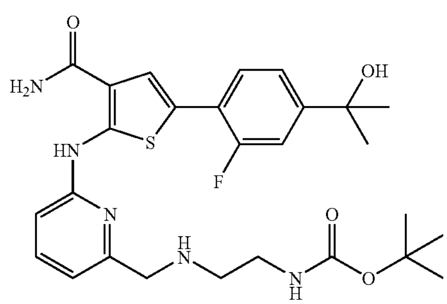 [SMILES: CC(C)(C)OC(=O)NCCNCc1cccc(Nc2sc(-c3ccc(C(C)(C)O)cc3F)cc2C(N)=O)n1] | Tert-butyl [2-({[6-({3-(aminocarbonyl)-5-[2-fluoro-4-(1-hydroxy-1-methylethyl)phenyl]-2-thienyl}amino)pyridin-2-yl]methyl}amino)ethyl] carbamate | Calc'd [M + H]⁺: 544, Found: 544 |

Example 134

5-[2-Fluoro-4-(1-hydroxy-1-methylethyl)phenyl]-2-({6-[(2-oxo-3-oxa-1,8-diazaspiro[4.5]dec-8-yl)methyl]pyridin-2-yl}amino)thiophene-3-carboxamide

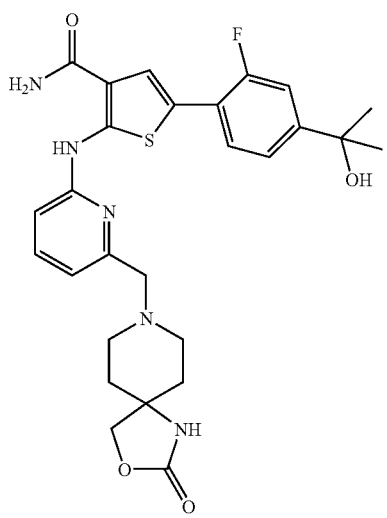 [SMILES: CC(C)(O)c1ccc(-c2cc(C(N)=O)c(Nc3cccc(CN4CCC5(CC4)COC(=O)N5)n3)s2)c(F)c1]

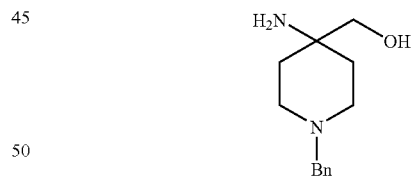

Step 1: (4-Amino-1-benzylpiperidin-4-yl)methanol

To a 1 L 4-neck round bottom flask was added LAH (9.42 g, 248 mmol) in dry THF (1000 mL) and the reaction mixture was cooled to 0° C. A solution of methyl 4-amino-1-benzylpiperidine-4-carboxylate (47.0 g, 165 mmol) in dry THF (250 ml) was added and the reaction mixture was allowed to warm to room temperature. The reaction mixture was cooled to 0° C. and quenched with water and filtered. The solid was washed with 50 ml of ethyl acetate. The organic layer of the filtrate was separated, washed with 2×200 ml portions of water and 200 ml of brine, dried over anhydrous sodium sulfate, filtered, and concentrated under reduced pressure to afford the title compound.

¹H NMR (400 MHz, DMSO-d₆): δ 1.62-1.67 (m, 4H), 2.50 (br s, 2H), 3.44-3.54 (m, 4H), 3.61-3.68 (m, 2H), 7.26-7.36 (m, 5H); Calc'd for $C_{13}H_{21}N_2O$: [M+1]: 221 found 221.

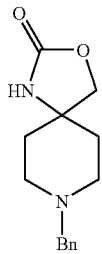

Step 2: 8-Benzyl-3-oxa-1,8-diazaspiro[4.5]decan-2-one

To a 1 L 4-neck round bottom flask was added (4-amino-1-benzylpiperidin-4-yl)methanol (21.86 g, 99 mmol) and diisopropyl amine (23.0 g, 249 mmol) in dry toluene (300 ml). The reaction mixture was cooled to 0° C. and a solution of triphosgene (35.57 g, 119 mmol) in toluene (100 ml) was added. The reaction mixture was heated to 60° C. for 1.5 h. After cooling to room temperature, the reaction mixture was diluted with water (200 ml), basified with aqueous NH₄OH, and extracted with ethyl acetate (3×200 ml). The organic layers were combined and washed with two 200 ml portions of water and 200 ml of brine, dried over anhydrous sodium sulfate, filtered, and concentrated. The solid was stirred in hexanes for 1.5 hours and filtered again to afford the title compound.

¹H NMR (400 MHz, DMSO-d₆): δ 1.59-1.67 (m, 4H), 2.19 (br s, 2H), 2.49-2.50 (m, 2H), 3.47 (s, 2H), 4.06 (s, 2H), 7.21-7.33 (m, 5H), 7.96 (br s, 1H). Calc'd for $C_{14}H_{19}N_2O_2$ [M+H]⁺: 247 found 247.

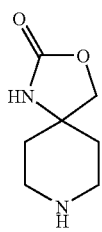

Step 3: 3-Oxa-1,8-diazaspiro[4.5]decan-2-one

To a 250 ml round bottom flask was purged with nitrogen was added a solution of 8-benzyl-3-oxa-1,8-diazaspiro[4.5]decan-2-one (12.5 g, 51 mmol) in MeOH (70 ml) and 1.0 g of activated 10% Pd/C. The reaction mixture was placed under H₂ (60 psi) for 5 h. The reaction mixture was filtered through celite, and the filtrate was evaporated under vacuum to yield the title compound as a solid.

¹H NMR (400 MHz, DMSO-d₆): δ 1.48-1.58 (m, 4H), 2.53-2.58 (m, 2H), 2.77-2.80 (m, 2H), 4.04 (s, 2H), 8.00 (br. s, 1H). Calc'd for $C_7H_{13}N_2O_2$ [M+H]⁺: 157 found 157.

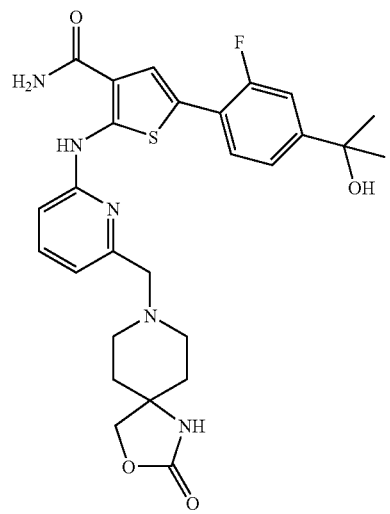 [SMILES: CC(C)(O)c1ccc(-c2cc(C(N)=O)c(Nc3cccc(CN4CCC5(CC4)COC(=O)N5)n3)s2)c(F)c1]

Step 4: 5-[2-Fluoro-4-(1-hydroxy-1-methylethyl)phenyl]-2-({6-[(2-oxo-3-oxa-1,8-diazaspiro[4.5]dec-8-yl)methyl]pyridin-2-yl}amino)thiophene-3-carboxamide The title compound was prepared according to Example 106 Step 2 using 5-(2-fluoro-4-(1-hydroxy-1-methylethyl)phenyl)-2-((6-formyl-2-pyridinyl)amino)-3-thiophenecarboxamide (19.5 mg, 0.05 mmol) and 8-[(6-bromopyridin-2-yl)methyl]-3-oxa-1,8-diazaspiro[4.5]decan-2-one (7.6 mg, 0.05 mmol) as the starting materials.

Calc'd for $C_{27}H_{31}FN_5O_4S$ [M+H]⁺: 540 found 540.

Example 135

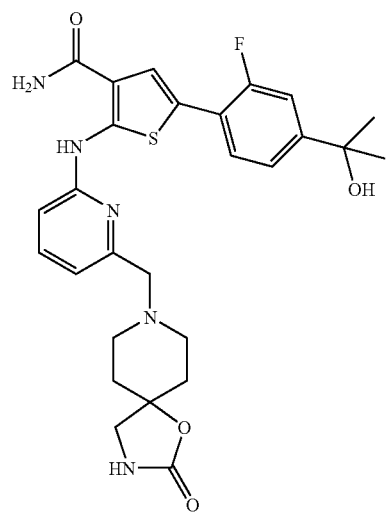 [SMILES: CC(C)(O)c1ccc(-c2cc(C(N)=O)c(Nc3cccc(CN4CCC5(CC4)CNC(=O)O5)n3)s2)c(F)c1]

5-[2-Fluoro-4-(1-hydroxy-1-methylethyl)phenyl]-2-({6-[(2-oxo-1-oxa-3,8-diazaspiro[4.5]dec-8-yl)methyl]pyridin-2-yl}amino)thiophene-3-carboxamide

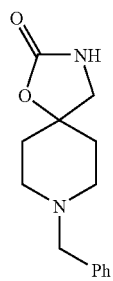

Step 1: 8-Benzyl-1-oxa-3,8-diaza-spiro[4.5]decan-2-one

The title compound was prepared according to Example 134 Step 2 using 4-(aminomethyl)-1-benzylpiperidin-4-ol (26.53 g, 121 mmol) as the starting material.

$^1$H NMR (400 MHz, DMSO-d$_6$): δ 1.84 (br s, 2H), 1.96-2.03 (m, 2H), 2.57 (br s, 4H), 3.32 (s, 2H), 3.55 (s, 2H), 5.42 (s, 1H), 7.26-7.32 (m, 5H). Calc'd for C$_{14}$H$_{19}$N$_2$O$_2$ [M+H]$^+$: 247 found 247.

Step 2: 1-Oxa-3,8-diaza-spiro[4.5]decan-2-one

The title compound was prepared according to Example 134 Step 3 using 8-benzyl-1-oxa-3,8-diazaspiro[4.5]decan-2-one (16.1 g, 65 mmol) as the starting material.

$^1$H NMR (400 MHz, DMSO-d$_6$): δ 1.51-1.79 (m 4H), 2.62-2.65 (m, 2H), 2.77-2.79 (m, 2H), 3.16-3.12 (m, 2H), 4.46 (br s, 1H), 7.49 (br s, 1H). Calc'd for C$_7$H$_{13}$N$_2$O$_2$ [M+H]$^+$: 157 found 157.

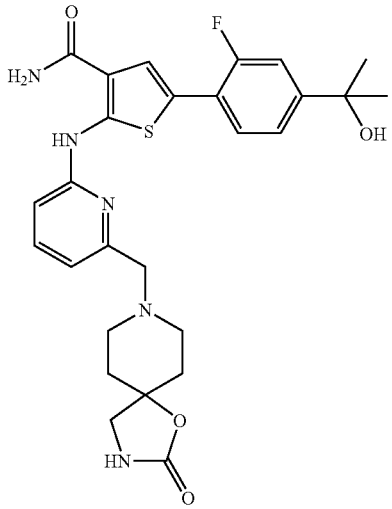 [SMILES: CC(C)(O)c1ccc(-c2cc(C(N)=O)c(Nc3cccc(CN4CCC5(CC4)CNC(=O)O5)n3)s2)c(F)c1]

Step 3: 5-[2-Fluoro-4-(1-hydroxy-1-methylethyl)phenyl]-2-({6-[(2-oxo-1-oxa-3,8-diazaspiro[4.5]dec-8-yl)methyl]pyridin-2-yl}amino)thiophene-3-carboxamide The title compound was prepared according to Example 106 Step 2 using 5-(2-fluoro-4-(1-hydroxy-1-methylethyl)phenyl)-2-((6-formyl-2-pyridinyl)amino)-3-thiophenecarboxamide (19.5 mg, 0.05 mmol) and 1-oxa-3,8-diaza-spiro[4.5]decan-2-one (7.6 mg, 0.05 mmol) as the starting materials.

Calc'd for C$_{27}$H$_{31}$FN$_5$O$_4$S [M+H]$^+$: 540 found 540.

Example 136

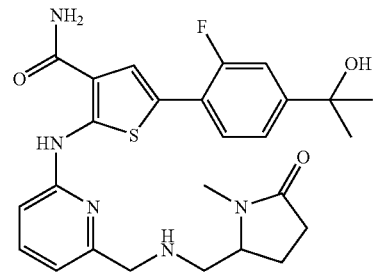 [SMILES: CN1C(=O)CCC1CNCc1cccc(Nc2sc(-c3ccc(C(C)(C)O)cc3F)cc2C(N)=O)n1]

5-[2-Fluoro-4-(1-hydroxy-1-methylethyl)phenyl]-2-{[6-({[(1-methyl-5-oxopyrrolidin-2-yl)methyl]amino}methyl)pyridin-2-yl]amino}thiophene-3-carboxamide

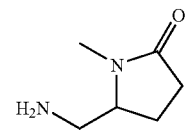

Step 1: 5-(Aminomethyl)-1-methylpyrrolidin-2-one

A mixture of (1-methyl-5-oxopyrrolidin-2-yl)methyl 4-methylbenzenesulfonate (196 g, 0.73 mol), sodium azide (142 g, 2.19 mol) and N-methyl-2-pyrrolidinone (800 ml) was heated to 80° C. for two hours, cooled, diluted with diethyl ether (3 L) and filtered through a pad of silica gel. The silica gel pad was washed with 1 L of a mixture of methanol:diethyl ether (5:1). The combined filtrates were concentrated in vacuo. The residue was subsequently treated with a suspension of sodium hydride in mineral oil (60%, 44 g, 1.1 mol) at 10-15° C. under rapid stirring for two hours followed by the addition of lithium iodide (155 g, 1.1 mol). The reaction mixture was allowed to warm to 25° C. for 3 hours. The unreacted sodium hydride was quenched with water. The mixture was diluted with dioxane (1.5 L) and diethyl ether (5 L) and filtered through a plug of silica gel. The silica gel plug was then washed with ether. The combined filtrates were concentrated, the residue was dissolved in dioxane (2 L), cooled to 0° C., and triphenylphosphine (191 g, 0.73 mol) was added at 0° C. for 1 hour. The reaction mixture was stirred at 25° C. for 10 hours, then water (25 mL) and aqueous ammonia (1 mL, 25%) were added, and the mixture was refluxed for two hours, cooled, and evaporated. The residue was dissolved in isopropanol (2.5 L), and to the solution was added a solution of oxalic acid (88 g, 0.7 mol) in isopropanol (1 L). The precipitate that formed was filtered, washed with isopropanol (1 L), and dried to give the title compound as the oxalate salt.

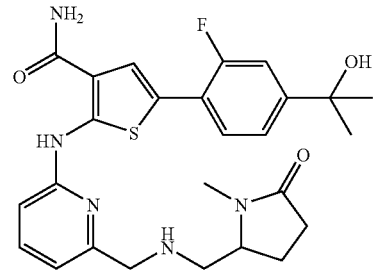 [SMILES: CN1C(=O)CCC1CNCc1cccc(Nc2sc(-c3ccc(C(C)(C)O)cc3F)cc2C(N)=O)n1]

Step 2: 5-[2-Fluoro-4-(1-hydroxy-1-methylethyl) phenyl]-2-{[6-({[(1-methyl-5-oxopyrrolidin-2-yl) methyl]amino}methyl)pyridin-2-yl] amino}thiophene-3-carboxamide The title compound was prepared as described in Example 106, Step 2 using the oxalate salt of 5-(aminomethyl)-1-methylpyrrolidin-2-one (21 mg, 0.096 mmol) and 5-[2-fluoro-4-(1-hydroxy-1-methylethyl)phenyl]-2-[(6-formylpyridin-2-yl)amino]thiophene-3-carboxamide (39 mg, 0.096 mmol) as starting materials.

Calc'd for $C_{26}H_{31}FN_5O_3S$ [M+H]$^+$: 512. found 512.

Example 137

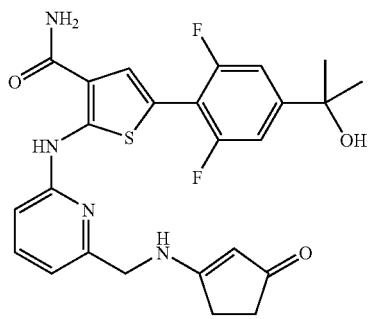 [SMILES: CC(C)(O)c1cc(F)c(-c2cc(C(N)=O)c(Nc3cccc(CNC4=CC(=O)CC4)n3)s2)c(F)c1]

5-[2,6-Difluoro-4-(1-hydroxy-1-methylethyl)phenyl]-2-[(6-{[(3-oxocyclopent-1-en-1-yl)amino]methyl}yridine-2-yl)amino]thiophene-3-carboxamide

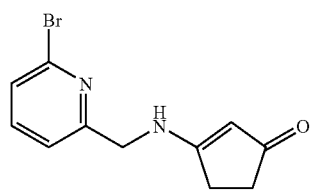 [SMILES: O=C1C=C(NCc2cccc(Br)n2)CC1]

Step 1: 3-{[(6-Bromopyridin-2-yl)methyl]amino}cyclopent-2-en-1-one

A solution of 1-(6-bromopyridin-2-yl)methanamine hydrochloride (500 mg, 2.24 mmol) in toluene (10 ml) was charged with triethylamine (0.31 ml, 2.24 mmol). The reaction was stirred for 5 minutes after which cyclopentane-1,3-dione (330 mg, 3.36 mmol) and p-toluenesulfonic acid monohydrate (43 mg, 0.022 mmol) were added. The reaction mixture was heated to reflux at 95° C. for 45 minutes. The reaction mixture was cooled to ambient temperature and diluted with ethyl acetate (15 ml), 2N sodium hydroxide (10 ml) and brine (10 ml). The layers were separated and the organic layer was then dried over sodium sulfate, filtered and concentrated to yield the title compound.

Calc'd for $C_{11}H_{12}BrN_2O$ [M+H]$^+$: 267. Found: 267.

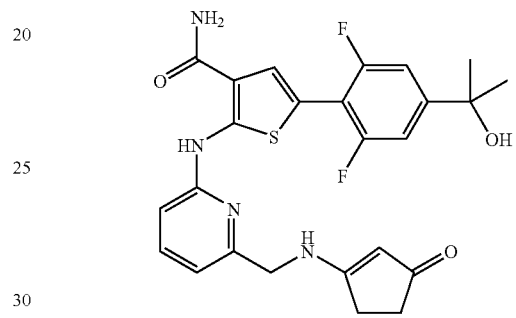

Step 2: 5-[2,6-Difluoro-4-(1-hydroxy-1-methylethyl) phenyl]-2-[(6-{[(3-oxocyclopent-1-en-1-yl)amino] methyl}yridine-2-yl)amino]thiophene-3-carboxamide The title compound was prepared according to the general procedure in Example 1 using 3-{[(6-bromopyridin-2-yl)methyl]amino}cyclopent-2-en-1-one (128 mg, 0.48 mmol) and 2-amino-5-[2,6-difluoro-4-(1-hydroxy-1-methylethyl)phenyl]thiophene-3-carboxamide (150 mg, 0.48 mmol) as the starting materials.

Calc'd for $C_{25}H_{25}F_2N_4O_3S$ [M+H]$^+$: 499. Found: 499.

An additional example was prepared using procedures similar to those described in the above example and is illustrated in the following table.

TABLE 6

| Example # | Structure | Compound Name | Characterization |
|---|---|---|---|
| 138 | 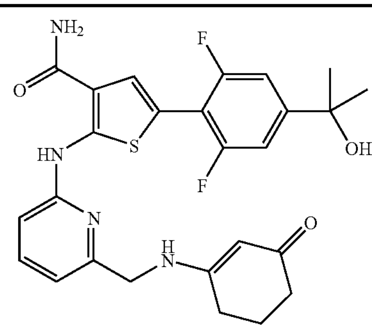 | 5-[2,6-difluoro-4-(1-hydroxy-1-methylethyl)phenyl]-2-[(6-{[(3-oxocyclohex-1-en-1-yl)amino]methyl}pyridin-2-yl)amino]thiophene-3-carboxamide | Calc'd [M + H]$^+$: 513, Found: 513 |

Example 139

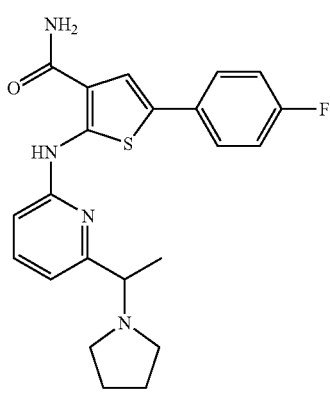 [SMILES: CC(c1cccc(Nc2sc(-c3ccc(F)cc3)cc2C(N)=O)n1)N1CCCC1]

5-(4-Fluorophenyl)-2-{[6-(1-pyrrolidin-1-ylethyl)pyridin-2-yl]amino}thiophene-3-carboxamide

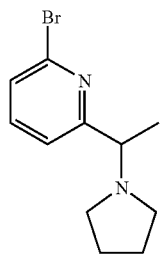

Step 1: 2-Bromo-6-(1-pyrrolidin-1-ylethyl)pyridine

A solution of 1-(6-bromopyridin-2-yl)ethanol (Example 3, Step 1) (0.5 g, 2.48 mmol) in tetrahydrofuran (4 mL) at 0° C. was charged with triethyl amine (1.04 mL, 7.42 mmol), and then a solution of methanesulfonic anhydride (0.56 g, 3.22 mmol) in tetrahydrofuran (6 mL) added over 30 minutes. The reaction mixture was stirred at 0° C. for 2 hrs and then pyrrolidine (0.21 mL, 2.48 mmol) was added and the mixture was warmed to room temperature. After sixteen days the reaction mixture was poured into aqueous hydrogen chloride (1 M, 10 mL) and dichloromethane (10 mL) The layers were separated and the organic layer was extracted with aqueous hydrogen chloride (1 M, 10 mL). The combined aqueous layers were neutralized with aqueous sodium hydroxide (2 M) until pH=10 and then extracted with dichloromethane (3×20 mL). The combined organic layers were dried over sodium sulfate, filtered, and concentrated to afford the title compound.
Calc'd for $C_{11}H_{16}BrN_2$ [M+H]$^+$: 255. Found: 255.

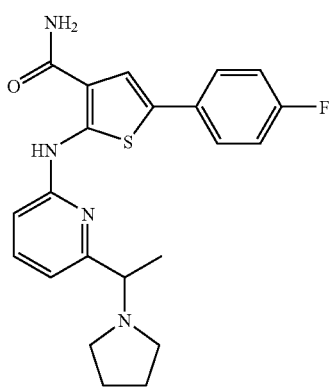 [SMILES: CC(c1cccc(Nc2sc(-c3ccc(F)cc3)cc2C(N)=O)n1)N1CCCC1]

Step 2: 5-(4-Fluorophenyl)-2-{[6-(1-pyrrolidin-1-ylethyl)pyridin-2-yl]amino}thiophene-3-carboxamide The title compound was prepared according to the general procedure in Example 1 using 2-bromo-6-(1-pyrrolidin-1-ylethyl)pyridine (200 mg, 0.78 mmol) and 2-amino-5-(4-fluorophenyl)thiophene-3-carboxamide (204 mg, 0.86 mmol) as the starting materials.
Calc'd for $C_{22}H_{24}FN_4OS$ [M+H]$^+$: 411. Found: 411.

Example 140

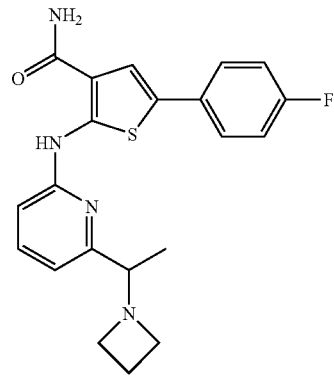 [SMILES: CC(c1cccc(Nc2sc(-c3ccc(F)cc3)cc2C(N)=O)n1)N1CCC1]

5-(4-Fluorophenyl)-2-{[6-(1-pyrrolidin-1-ylethyl)pyridin-2-yl]amino}thiophene-3-carboxamide

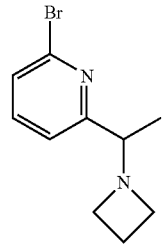

Step 1: 2-(1-Azetidin-1-ylethyl)-6-bromopyridine

The title compound was prepared according to the procedure in Example 139 Step 1 using azetidine (0.141 g, 2.48 mmol) and 1-(6-bromopyridin-2-yl)ethanol (0.500 g, 2.48 mmol) as the starting materials.
Calc'd for $C_{10}H_{14}BrN_2$ [M+H]$^+$: 241. Found: 241.

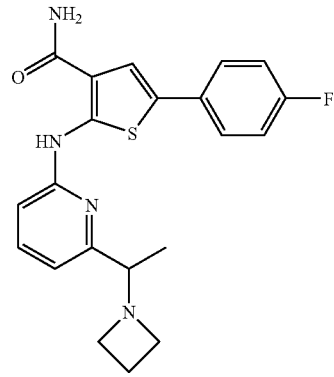 [SMILES: CC(c1cccc(Nc2sc(-c3ccc(F)cc3)cc2C(N)=O)n1)N1CCC1]

Step 2: 2-{[6-(1-Azetidin-1-ylethyl)pyridin-2-yl]amino}-5-(4-fluorophenyl)thiophene-3-carboxamide The title compound was prepared according to the general procedure in Example 1 using 2-(1-azetidin-1-ylethyl)-6-bromopyridine (200 mg, 0.83 mmol) and 2-amino-5-(4-fluorophenyl)thiophene-3-carboxamide (216 mg, 0.91 mmol) as the starting materials.

Calc'd for $C_{21}H_{22}FN_4OS$ [M+H]$^+$: 397. Found: 397.

Example 141

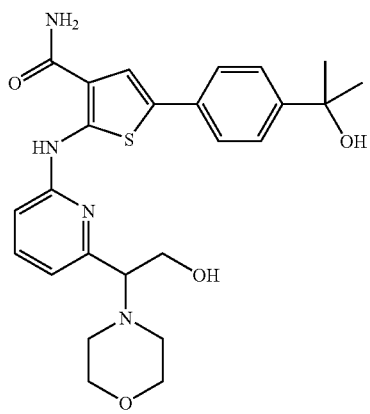 [SMILES: CC(C)(O)c1ccc(-c2cc(C(N)=O)c(Nc3cccc(C(CO)N4CCOCC4)n3)s2)cc1]

5-[4-(1-Hydroxy-1-methylethyl)phenyl]-2-{[6-(2-hydroxy-1-morpholin-4-ylethyl)pyridin-2-yl]amino}thiophene-3-carboxamide

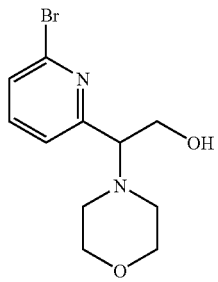 [SMILES: OCC(c1cccc(Br)n1)N1CCOCC1]

Step 1:
2-(6-Bromopyridin-2-yl)-2-morpholin-4-methanol

To a solution of 4-[(6-bromopyridin-2-yl)methyl]morpholine (Example 45 Step 1) (500 mg, 1.945 mmol) in tetrahydrofuran at −78° C. was added a solution of LDA (1.8 M in tetrahydrofuran/heptane/ethylbenzene, 3.24 mL, 5.83 mmol) over 15 minutes. The resulting red solution was stirred at −78° C. for one hour and then a solution of 1H-1,2,3-benzotriazol-1-ylmethanol (580 mg, 3.89 mmol) in 14 mL tetrahydrofuran was added. After 2.5 hours, a saturated aqueous ammonium chloride solution (5 mL) was added and the reaction mixture was allowed to warm to room temperature. The layers were separated and the organic layer was washed with saturated aqueous sodium bicarbonate (10 mL) and brine (10 mL), dried with sodium sulfate, filtered, and concentrated. The resulting oil was dissolved in tetrahydrofuran (15 mL) and diethyl ether (30 mL), and this solution was washed with aqueous sodium hydroxide (5 M, 15 mL), brine (15 mL), saturated aqueous sodium carbonate (10 mL), and brine (10 mL). The organic layer was dried over magnesium sulfate, filtered, and concentrated and the crude residue was purified by silica gel chromatography (0.2-10% methanol/ethyl acetate) to yield the title compound.

Calc'd for $C_{11}H_{16}BrN_2O_2$ [M+H]$^+$: 287. Found: 287.

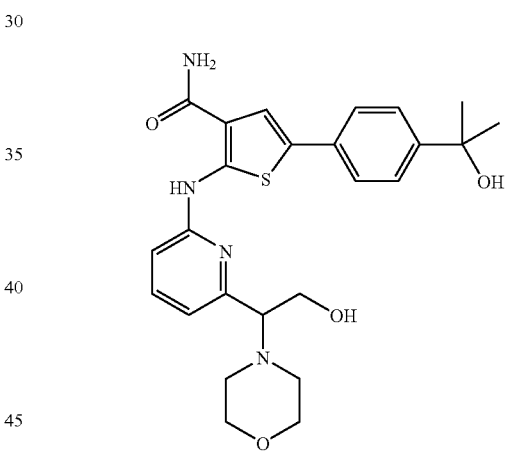

Step 2: 5-[4-(1-Hydroxy-1-methylethyl)phenyl]-2-{[6-(2-hydroxy-1-morpholin-4-ylethyl)pyridin-2-yl]amino}thiophene-3-carboxamide The title compound was prepared according to the general procedure in Example 1 using 2-(6-bromopyridin-2-yl)-2-morpholin-4-ylethanol (194 mg, 0.68 mmol) and 2-amino-5-[4-(1-hydroxy-1-methylethyl)phenyl]thiophene-3-carboxamide (190 mg, 0.69 mmol) as the starting materials.

Calc'd for $C_{25}H_{31}N_4O_4S$ [M+H]$^+$: 483. Found: 483.

Additional examples were prepared using procedures similar to those described in the above example and are illustrated in the following table.

TABLE 7

| Example # | Structure | Compound Name | Characterization |
|---|---|---|---|
| 142 | 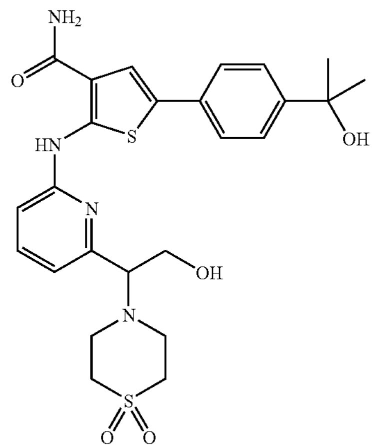 [SMILES: CC(C)(O)c1ccc(-c2cc(C(N)=O)c(Nc3cccc(C(CO)N4CCS(=O)(=O)CC4)n3)s2)cc1] | 2-({6-[1-(1,1-dioxidothiomoholin-4-yl)-2-hydroxyethyl]pyridine-2-yl}amino)-5-[4-(1-hydroxy-1-methylethyl)phenyl]thiophene-3-carboxamide | Calc'd [M + H]$^+$: 531, Found: 531 |
| 143 | 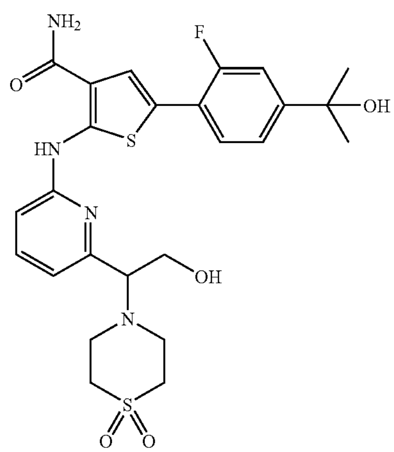 [SMILES: CC(C)(O)c1ccc(-c2cc(C(N)=O)c(Nc3cccc(C(CO)N4CCS(=O)(=O)CC4)n3)s2)c(F)c1] | 2-({6-[1-(1,1-dioxidothiomorpholin-4-yl)-2-hydroxyethyl]pyridin-2-yl}amino)-5-[2-fluoro-4-(1-hydroxy-1-methylethyl)phenyl]thiophene-3-carboxamide | Calc'd [M + H]$^+$: 549, Found: 549 |
| 144 | 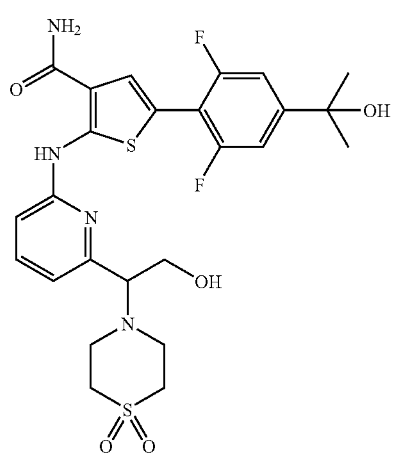 [SMILES: CC(C)(O)c1cc(F)c(-c2cc(C(N)=O)c(Nc3cccc(C(CO)N4CCS(=O)(=O)CC4)n3)s2)c(F)c1] | 5-[2,6-difluoro-4-(1-hydroxy-1-methylethyl)phenyl]-2-({6-[1-(1,1-dioxidothiomorpholin-4-yl)-2-hydroxyethyl]pyridin-2-yl}amino)thiophene-3-carboxamide | Calc'd [M + H]$^+$: 567, Found: 567 |

TABLE 7-continued

| Example # | Structure | Compound Name | Characterization |
|---|---|---|---|
| 145 | 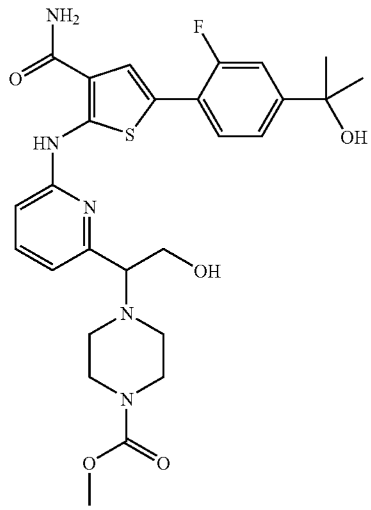 [SMILES: COC(=O)N1CCN(C(CO)c2cccc(Nc3sc(-c4ccc(C(C)(C)O)cc4F)cc3C(N)=O)n2)CC1] | Methyl-4-{1-[6-({3-aminocarbonyl)-5-[2-fluoro-4-(1-hydroxy-1-methylethyl)phenyl]-2-thienyl}amino)pyridine-2-yl]-2-hydroxyethyl}piperazine-1-carboxylate | Calc'd [M + H]+: 558, Found: 558 |
| 146 | 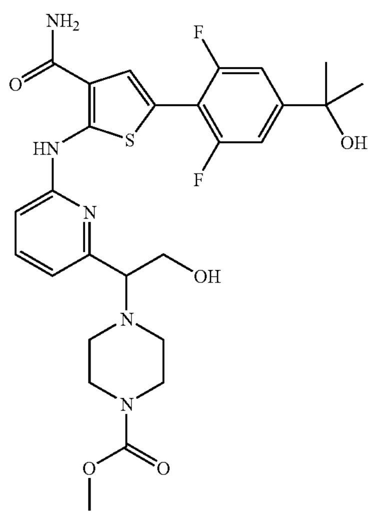 [SMILES: COC(=O)N1CCN(C(CO)c2cccc(Nc3sc(-c4c(F)cc(C(C)(C)O)cc4F)cc3C(N)=O)n2)CC1] | Methyl-4-{1-[6-({3-aminocarbonyl)-5-[2,6-difluoro-4-(1-hydroxy-1-methylethyl)phenyl]-2-thienyl}amino)pyridine-2-yl]-2-hydroxyethyl}piperazine-1-carboxylate | Calc'd [M + H]+: 576, Found: 576 |
| 147 | 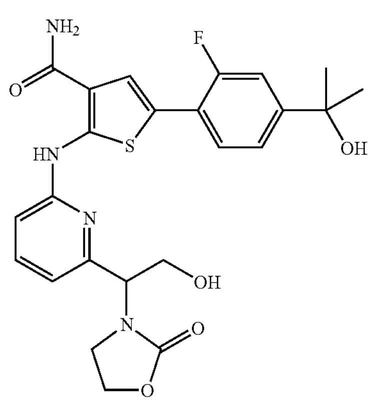 [SMILES: CC(C)(O)c1ccc(-c2cc(C(N)=O)c(Nc3cccc(C(CO)N4CCOC4=O)n3)s2)c(F)c1] | 5-[2-fluoro-4-(1-hydroxy-1-methylethyl)phenyl]-2-({6-[2-hydroxy-1-(2-oxo-1,3-oxazolidin-3-yl)ethyl]pyridin-2-yl}amino)thiophene-3-carboxamide | Calc'd [M + H]+: 501, Found: 502 |

TABLE 7-continued

| Example # | Structure | Compound Name | Characterization |
|---|---|---|---|
| 148 | 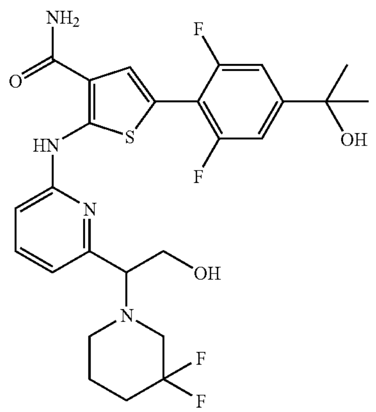 [SMILES: CC(C)(O)c1cc(F)c(-c2cc(C(N)=O)c(Nc3cccc(C(CO)N4CCCC(F)(F)C4)n3)s2)c(F)c1] | 5-[2,6-difluoro-4-(1-hydroxy-1-methylethyl)phenyl]-2-({6-[1-(3,3-difluoropiperidin-1-yl)-2-hydroxyethyl]pyridin-2-yl}amino)thiophene-3-carboxamide | Calc'd [M + H]$^+$: 553, Found: 553 |
| 149 | 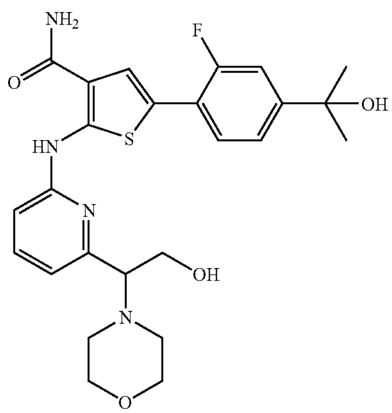 | 5-[2-fluoro-4-(1-hydroxy-1-methylethyl)phenyl]-2-{[6-(2-hydroxy-1-morpholin-4-ylethyl)pyridin-2-yl]amino}thiophene-3-carboxamide | Calc'd [M + H]$^+$: 501, Found: 501 |
| 150 | 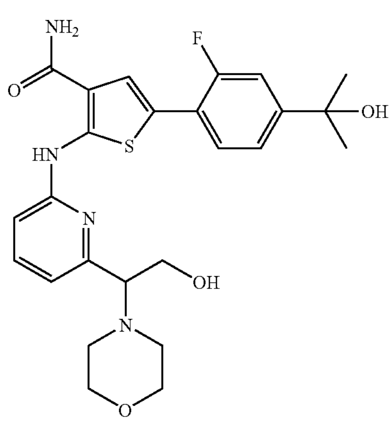 | 5-[2-fluoro-4-(1-hydroxy-1-methylethyl)phenyl]-2-({6-[(1S)-2-hydroxy-1-morpholin-4-ylethyl]pyridin-2-yl}amino)thiophene-3-carboxamide (Enantiomer A) | Calc'd [M + H]$^+$: 501, Found: 501 |

TABLE 7-continued

| Example # | Structure | Compound Name | Characterization |
|---|---|---|---|
| 151 | 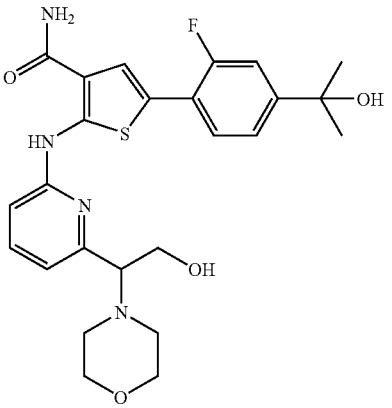 | 5-[2-fluoro-4-(1-hydroxy-1-methylethyl)phenyl]-2-({6-[(1R)-2-hydroxy-1-morpholin-4-ylethyl]pyridin-2-yl}amino)thiophene-3-carboxamide (Enantiomer B) | Calc'd [M + H]$^+$: 501, Found: 501 |
| 152 | 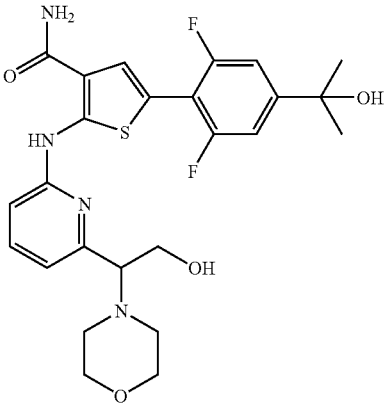 [SMILES: CC(C)(O)c1cc(F)c(-c2cc(C(N)=O)c(Nc3cccc(C(CO)N4CCOCC4)n3)s2)c(F)c1] | 5-[2,6-difluoro-4-(1-hydroxy-1-methylethyl)phenyl]-2-{[6-(2-hydroxy-1-morpholin-4-ylethyl)pyridin-2-yl]amino}thiophene-3-carboxamide | Calc'd [M + H]$^+$: 519, Found: 519 |
| 153 | 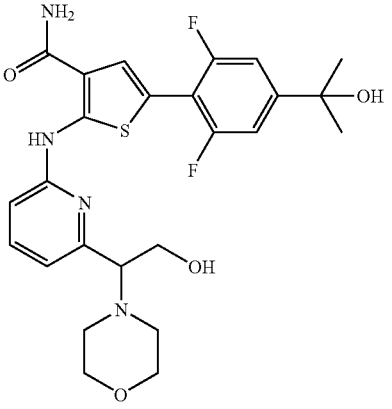 | 5-[2,6-difluoro-4-(1-hydroxy-1-methylethyl)phenyl]-2-({6-[(1S)-2-hydroxy-1-morpholin-4-ylethyl]pyridin-2-yl}amino)thiophene-3-carboxamide (Enantiomer A) | Calc'd [M + H]$^+$: 519, Found: 519 |

TABLE 7-continued

| Example # | Structure | Compound Name | Characterization |
|---|---|---|---|
| 154 | 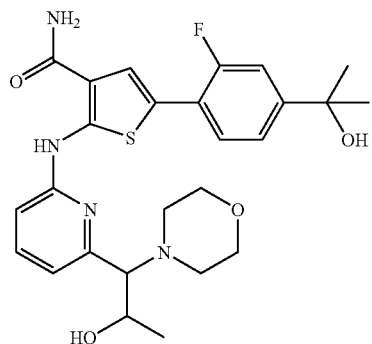 (Enantiomer B) | 5-[2,6-difluoro-4-(1-hydroxy-1-methylethyl)phenyl]-2-({6-[(1R)-2-hydroxy-1-morpholin-4-ylethyl]pyridin-2-yl}amino)thiophene-3-carboxamide (Enantiomer B) | Calc'd [M + H]$^+$: 519, Found: 519 |

Example 155

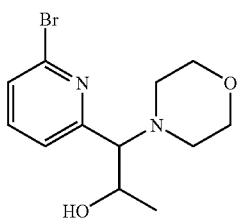 [SMILES: CC(O)C(c1cccc(Br)n1)N1CCOCC1]

5-[2-Fluoro-4-(1-hydroxy-1-methylethyl)phenyl]-2-{[6-(2-hydroxy-1-morpholin-4-ylpropyl)pyridin-2-yl]amino}thiophene-3-carboxamide

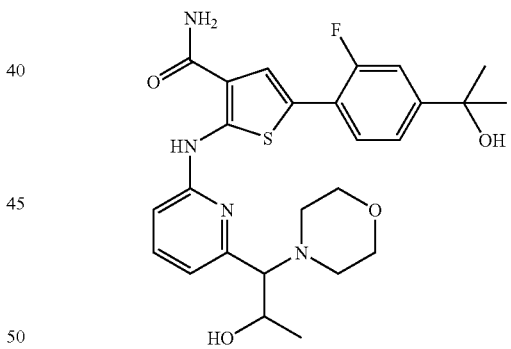

Step 1. 1-(6-Bromopyridin-2-yl)-1-morpholin-4-ylpropan-2-ol

4-[(6-Bromopyridin-2-yl)methyl]morpholine (Example 45, step 1) (200 mg, 0.78 mmol) was placed under argon and then taken up in tetrahydrofuran (8 mL). The solution was cooled to −78° C. followed by the addition of LDA (0.65 mL of 1.8 M, 1.17 mmol) over 30 minutes. The reaction was maintained at −78° C. for one hour. Acetaldehyde (0.1 mL, 7.8 mmol) was then added and the reaction was then stirred at −78° C. for 2 hours. An additional portion of acetaldehyde (0.1 mL, 7.8 mmol) was then added and the reaction was then stirred an additional 2 hrs at −78° C. The reaction was quenched with water and extracted with ethyl acetate. The organic layer was dried over magnesium sulfate, filtered, and concentrated in vacuo. Purification of the crude mixture via flash chromatography (silica, 0-5% methanol/ethyl acetate) afforded the title compound as a white solid.

Calc'd for $C_{12}H_{18}BrN_2O_2$ [M+H]$^+$: 301. found 301.

Step 2. 5-[2-Fluoro-4-(1-hydroxy-1-methylethyl)phenyl]-2-{[6-(2-hydroxy-1-morpholin-4-ylpropyl)pyridin-2-yl]amino}thiophene-3-carboxamide The title compound was prepared as described in Example 1 using 2-amino-5-[2-fluoro-4-(1-hydroxy-1-methylethyl)phenyl]thiophene-3-carboxamide (150 mg, 0.510 mmol) and 1-(6-bromopyridin-2-yl)-1-morpholin-4-ylpropan-2-ol (168 mg, 0.510 mmol) as starting materials. $^1$H NMR (600 MHz, d6-DMSO): δ 11.96 (s, 1H), 7.84 (s, 1H), 7.81 (s, 1H), 7.66 (t, 1H), 7.54 (m, 1H), 7.36 (s, 1H), 7.32 (d, 1H), 7.31 (s, 1H), 7.95 (d, 1H), 6.78 (d, 1H), 5.13 (s, 1H), 4.55 (m, 1H), 4.18 (s, 1H), 3.54 (m, 4H), 3.31 (d, 1H), 2.61 (m, 2H), 2.33 (m, 2H), 1.40 (s, 6H), 0.89 (d, 3H). Calc'd for $C_{26}H_{32}FN_4O_4S$ [M+H]$^+$: 515. found 515.

Example 156

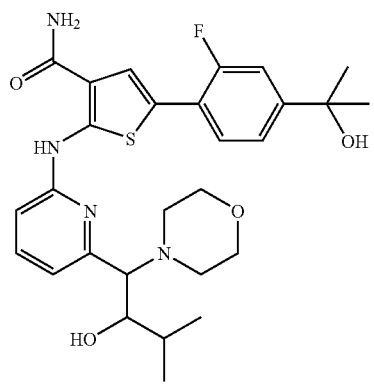 [SMILES: CC(C)C(O)C(c1cccc(Nc2sc(-c3ccc(C(C)(C)O)cc3F)cc2C(N)=O)n1)N1CCOCC1]

5-[2-Fluoro-4-(1-hydroxy-1-methylethyl)phenyl]-2-{[6-(2-hydroxy-3-methyl-1-morpholin-4-ylbutyl)pyridin-2-yl]amino}thiophene-3-carboxamide

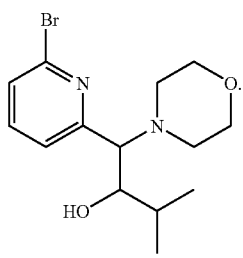 [SMILES: CC(C)C(O)C(c1cccc(Br)n1)N1CCOCC1]

Step 1. 1-(6-Bromopyridin-2-yl)-3-methyl-1-morpholin-4-ylbutan-2-ol

4-[(6-Bromopyridin-2-yl)methyl]morpholine (Example 45, Step 1) (500 mg, 1.95 mmol) was placed under argon and then taken up in tetrahydrofuran (19.5 mL). The solution was cooled to −78° C. LDA (1.62 mL of 1.8 M, 2.92 mmol) was added dropwise over 30 minutes. The mixture was stirred at −78° C. for one hour. Isobutyraldehyde (0.71 mL, 7.8 mmol) was then added and the reaction was then stirred at −78° C. for 2 hours. The reaction was quenched with water and extracted with ethyl acetate. The organic layer was dried over magnesium sulfate, filtered, and concentrated in vacuo. Purification via flash chromatography (silica, 50-100% ethyl acetate/hexanes) afforded the title compound as a white solid.

Calc'd for $C_{14}H_{22}BrN_2O_2$ [M+H]$^+$: 329. found 329.

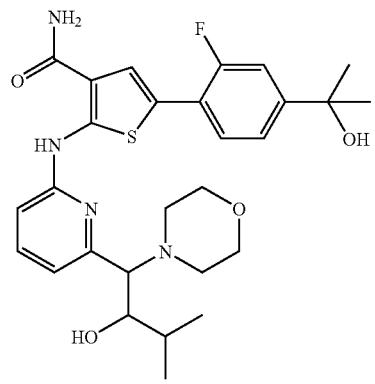 [SMILES: CC(C)C(O)C(c1cccc(Nc2sc(-c3ccc(C(C)(C)O)cc3F)cc2C(N)=O)n1)N1CCOCC1]

Step 2. 5-[2-Fluoro-4-(1-hydroxy-1-methylethyl)phenyl]-2-{[6-(2-hydroxy-3-methyl-1-morpholin-4-ylbutyl)pyridin-2-yl]amino}thiophene-3-carboxamide The title compound was prepared as described in Example 1 using 2-amino-5-[2-fluoro-4-(1-hydroxy-1-methylethyl)phenyl]thiophene-3-carboxamide (150 mg, 0.510 mmol) and 1-(6-bromopyridin-2-yl)-3-methyl-1-morpholin-4-ylbutan-2-ol (168 mg, 0.51 mmol) as starting materials.

$^1$H NMR (600 MHz, d6-DMSO): δ 11.99 (s, 1H), 7.84 (s, 1H), 7.81 (s, 1H), 7.66 (m, 1H), 7.54 (t, 1H), 7.34 (s, 1H), 7.31 (m, 2H), 6.94 (d, 1H), 6.81 (d, 1H), 5.12 (s, 1H), 4.38 (d, 1H), 3.96 (s, 1H), 3.53 (m, 4H), 3.49 (d, 1H), 2.62 (m, 2H), 2.30 (m, 2H), 1.40 (s, 6H), 1.33 (m, 1H), 0.89 (d, 3H), 0.70 (d, 3H). Calc'd for $C_{28}H_{36}FN_4O_4S$ [M+H]$^+$: 543. found 543.

Example 157

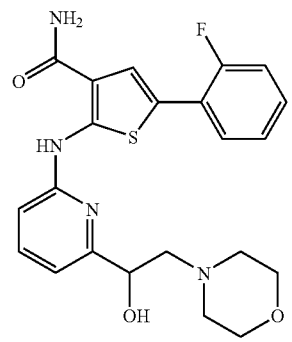 [SMILES: NC(=O)c1cc(-c2ccccc2F)sc1Nc1cccc(C(O)CN2CCOCC2)n1]

5-(2-Fluorophenyl)-2-{[6-(1-hydroxy-2-morpholin-4-ylethyl)pyridin-2-yl]amino}thiophene-3-carboxamide

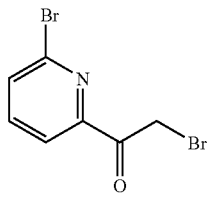 [SMILES: O=C(CBr)c1cccc(Br)n1]

Step 1: 2-Bromo-1-(6-bromopyridin-2-yl)ethanone

A solution of 1-(6-bromopyridin-2-yl)ethanone (9.2 g, 46.0 mmol) in acetic acid (25 mL) was heated to 70° C. and bromine (2.4 mL, 46.0 mmol) was added dropwise over 30 minutes. After 75 minutes, the solution was cooled to room temperature and a yellow solid precipitated which was collected by filtration and washed with acetic acid (3×10 mL) The solid was then dissolved in a mixture of ethyl acetate (150 mL), hexanes (50 mL), and saturated aqueous sodium bicarbonate (75 mL). The layers were separated and the organic layer was washed with brine (30 mL), dried over sodium sulfate, filtered, and concentrated. The crude residue was purified by silica gel chromatography (10-50% dichloromethane/hexanes) to give the title compound as a white solid.

Calc'd for $C_7H_6Br_2NO$ [M+H]$^+$: 278. Found: 278.

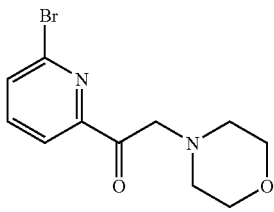 [SMILES: O=C(CN1CCOCC1)c1cccc(Br)n1]

Step 2: 1-(6-Bromopyridin-2-yl)-2-morpholin-4-ylethanone

To a solution of 2-bromo-1-(6-bromopyridin-2-yl)ethanone (250 mg, 0.90 mmol) in tetrahydrofuran (1 mL) and dimethylformamide (1 mL) was added morpholine (0.18 mL, 2.0 mmol). After 45 minutes, the reaction mixture was diluted with ethyl acetate (30 mL) and washed with saturated aqueous sodium bicarbonate (15 mL) and brine (15 mL). The organic layer was dried over sodium sulfate, filtered, and concentrated to afford the title compound.

Calc'd for $C_{11}H_{14}BrN_2O_2$ [M+H]$^+$: 285. Found: 285.

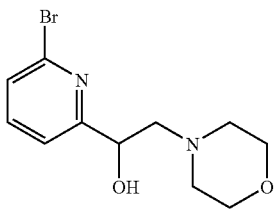 [SMILES: OC(CN1CCOCC1)c1cccc(Br)n1]

Step 3: 1-(6-Bromopyridin-2-yl)-2-morpholin-4-ylethanol

To a solution of 1-(6-bromopyridin-2-yl)-2-morpholin-4-ylethanone (234 mg, 0.82 mmol) in methanol at 0° C. was added sodium borohydride (31.0 mg, 0.82 mmol). After 30 minutes, formic acid (0.1 mL) was added and then the reaction mixture was diluted with ethyl acetate (40 mL), saturated aqueous sodium bicarbonate (10 mL), and water (10 mL). The layers were separated and the organic layer was washed with brine (10 mL), dried over sodium sulfate, filtered, and concentrated to give the title compound.

Calc'd for $C_{11}H_{16}BrN_2O_2$ [M+H]$^+$: 287. Found: 287

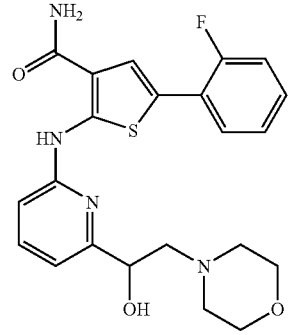 [SMILES: NC(=O)c1cc(-c2ccccc2F)sc1Nc1cccc(C(O)CN2CCOCC2)n1]

Step 4: 5-(2-Fluorophenyl)-2-{[6-(1-hydroxy-2-morpholin-4-ylethyl)pyridin-2-yl]amino}thiophene-3-carboxamide The title compound was prepared according to the general procedure in Example 1 using 1-(6-bromopyridin-2-yl)-2-morpholin-4-ylethanol (86 mg, 0.30 mmol) and 2-amino-5-(2-fluorophenyl)thiophene-3-carboxamide (72 mg, 0.31 mmol) as the starting materials.

Calc'd for $C_{22}H_{24}FN_4O_3S$ [M+H]$^+$: 443. Found: 443.

Example 158

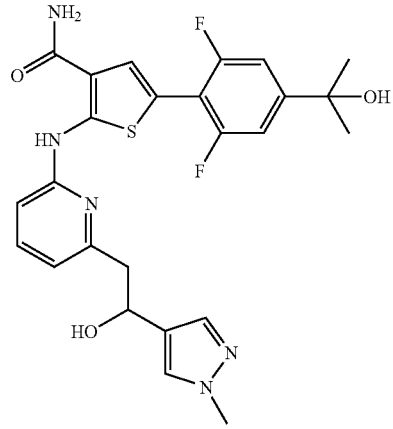 [SMILES: Cn1cc(C(O)Cc2cccc(Nc3sc(-c4c(F)cc(C(C)(C)O)cc4F)cc3C(N)=O)n2)cn1]

5-[2,6-Difluoro-4-(1-hydroxy-1-methylethyl)phenyl]-2-({6-[2-hydroxy-2-(1-methyl-1H-pyrazol-4-yl)ethyl]pyridin-2-yl}amino)thiophene-3-carboxamide

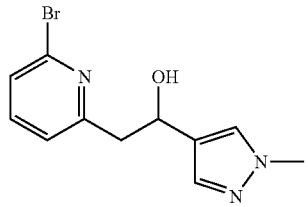 [SMILES: Cn1cc(C(O)Cc2cccc(Br)n2)cn1]

Step 1. 2-(6-Bromopyridin-2-yl)-1-(1-methyl-1H-pyrazol-4-yl)ethanol

Diisopropylamine (0.73 mL, 5.09 mmol) was taken up in THF (10 mL) and cooled to −78° C. n-BuLi (2.04 mL, 5.09 mmol) was added dropwise and the resulting mixture stirred at −78° C. for 90 minutes. The resulting LDA solution was transferred by cannula to a solution of 2-bromo-6-methylpyridine (500 mg, 2.91 mmol) in THF (20 mL) at −78° C. After stirring for 1 hour at −78° C., a solution of 1-methyl-1H-pyrazole-4-carbaldehyde (640 mg, 5.81 mmol) in THF (3 mL) was added and stirring continued for 30 minutes. Saturated NH$_4$Cl was added and the products extracted into EtOAc (2×). The combined organic extracts were washed with brine, dried over MgSO$_4$, filtered, and concentrated in vacuo. Purification of the residue by flash column chromatography on silica gel (12-100% EtOAc-hexanes followed by 0-10% MeOH-EtOAc) gave the title compound as a white solid.

Calc'd for C$_{11}$H$_{13}$BrN$_3$O [M+H]$^+$: 282, 284. Found: 282, 284.

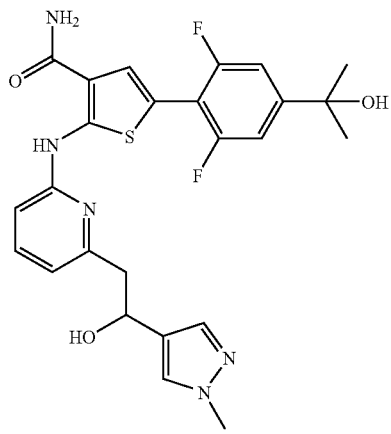 [SMILES: Cn1cc(C(O)Cc2cccc(Nc3sc(-c4c(F)cc(C(C)(C)O)cc4F)cc3C(N)=O)n2)cn1]

Step 2. 5-[2,6-Difluoro-4-(1-hydroxy-1-methylethyl)phenyl]-2-({6-[2-hydroxy-2-(1-methyl-1H-pyrazol-4-yl)ethyl]pyridin-2-yl}amino)thiophene-3-carboxamide The title compound was prepared according to the general procedure in Example 1 using (2-(6-bromopyridin-2-yl)-1-(1-methyl-1H-pyrazol-4-yl)ethanol (0.090 g, 0.32 mmol) and 2-amino-5-[2,6-difluoro-4-(1-hydroxy-1-methylethyl)phenyl]thiophene-3-carboxamide (0.10 g, 0.32 mmol) as the starting materials.

Calc'd for C$_{25}$H$_{26}$F$_2$N$_5$O$_3$S [M+H]$^+$: 514. Found: 514.

Additional examples were prepared using procedures similar to those described in the above examples and are illustrated in the following table.

TABLE 8

| Example # | Structure | Compound Name | Characterization |
|---|---|---|---|
| 159 | 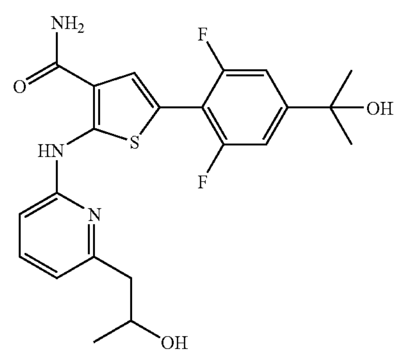 [SMILES: CC(O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-(2-hydroxypropyl)pyridin-2-yl]amino}thiophene-3-carboxamide | Calc'd [M + H]$^+$: 448, Found: 448 |
| 160 | 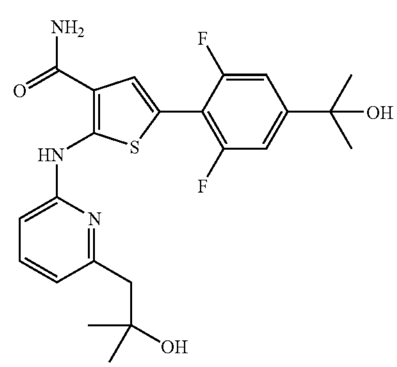 [SMILES: CC(C)(O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-(2-hydroxy-2-methylpropyl)pyridin-2-yl]amino}thiophene-3-carboxamide | Calc'd [M + H]$^+$: 462, Found: 462 |

Example 161

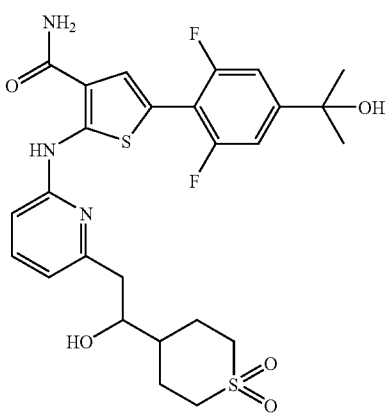 [SMILES: CC(C)(O)c1cc(F)c(-c2cc(C(N)=O)c(Nc3cccc(CC(O)C4CCS(=O)(=O)CC4)n3)s2)c(F)c1]

5-[2,6-Difluoro-4-(1-hydroxy-1-methylethyl)phenyl]-2-({6-[2-(1,1-dioxidotetrahydro-2H-thiopyran-4-yl)-2-hydroxyethyl]pyridin-2-yl}amino)thiophene-3-carboxamide

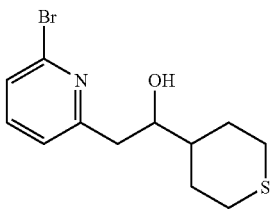 [SMILES: OC(Cc1cccc(Br)n1)C1CCSCC1]

Step 1: 2-(6-Bromopyridin-2-yl)-1-(tetrahydro-2H-thiopyran-4-yl)ethanol

The title compound was prepared according to the procedure in Example 158 Step 1 using 2-bromo-6-methylpyridine (1.5 g, 8.72 mmol) and tetrahydro-2H-thiopyran-4-carbaldehyde (2.27 g, 17.4 mmol) as the starting materials.

Calc'd for $C_{12}H_{17}BrNOS$ [M+H]$^+$: 302, 304. Found: 302, 304.

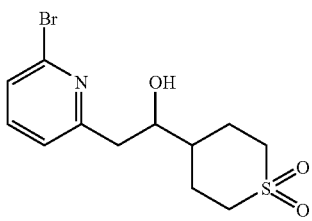 [SMILES: O=S1(=O)CCC(C(O)Cc2cccc(Br)n2)CC1]

Step 2: 2-(6-Bromopyridin-2-yl)-1-(1,1-dioxidotetrahydro-2H-thiopyran-4-yl)ethanol 2-(6-Bromopyridin-2-yl)-1-(tetrahydro-2H-thiopyran-4-yl)ethanol (1.90 g, 6.27 mmol) was take up in DCM (60 mL) and cooled to 0° C. m-CPBA (3.09 g, 13.8 mmol) was added and the resulting mixture stirred at 0° C. for 30 minutes before warming to room temperature and stirring overnight. The reaction mixture was purified directly by MPLC (40-100% EtOAc-hexanes) to give the title compound as a white solid.

Calc'd for $C_{12}H_{17}BrNO_3S$ [M+H]$^+$: 334, 336. Found: 334, 336.

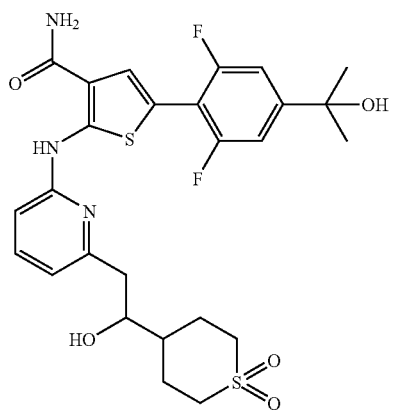 [SMILES: CC(C)(O)c1cc(F)c(-c2cc(C(N)=O)c(Nc3cccc(CC(O)C4CCS(=O)(=O)CC4)n3)s2)c(F)c1]

Step 3. 5-[2,6-Difluoro-4-(1-hydroxy-1-methylethyl)phenyl]-2-({6-[2-(1,1-dioxidotetrahydro-2H-thiopyran-4-yl)-2-hydroxyethyl]pyridin-2-yl}amino)thiophene-3-carboxamide The title compound was prepared according to the general procedure in Example 1 using 2-(6-bromopyridin-2-yl)-1-(1,1-dioxidotetrahydro-2H-thiopyran-4-yl)ethanol (0.11 g, 0.32 mmol) and 2-amino-5-[2,6-difluoro-4-(1-hydroxy-1-methylethyl)phenyl]thiophene-3-carboxamide (0.10 g, 0.32 mmol) as the starting materials.

Calc'd for $C_{26}H_{30}F_2N_3O_5S_2$ [M+H]$^+$: 566. Found: 566.

Example 162

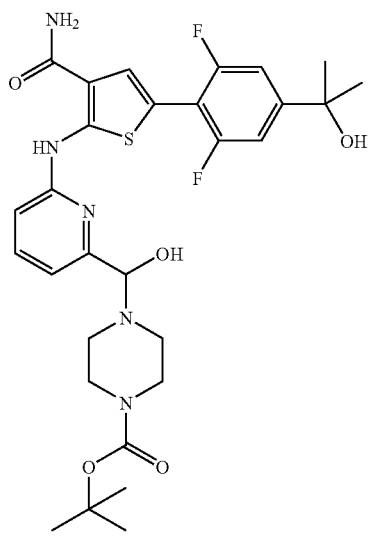 [SMILES: CC(C)(C)OC(=O)N1CCN(C(O)c2cccc(Nc3sc(-c4c(F)cc(C(C)(C)O)cc4F)cc3C(N)=O)n2)CC1]

215 tert-Butyl 4-[[6-({3-(aminocarbonyl)-5-[2,6-difluoro-4-(1-hydroxy-1-methylethyl)phenyl]-2-thienyl}amino)pyridin-2-yl](hydroxy)methyl]piperazine-1-carboxylate

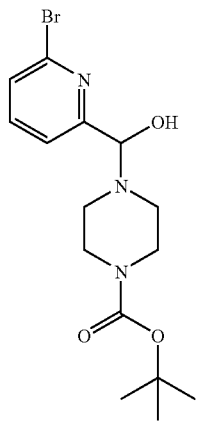 [SMILES: CC(C)(C)OC(=O)N1CCN(C(O)c2cccc(Br)n2)CC1]

Step 1: tert-Butyl 4-[(6-bromopyridin-2-yl)(hydroxy)methyl]piperazine-1-carboxylate 2,6-Dibromopyridine (5.45 g, 23.01 mmol) was dissolved in tetrahydrofuran (27.3 mL) and cooled to −78° C. under argon after which n-butyllithium (10.40 mL, 26.0 mmol) was added and the solution was stirred for thirty minutes. A solution of tert-butyl 4-formylpiperazine-1-carboxylate (5.00 g, 23.47 mmol) in tetrahydrofuran (8 mL) was added and the solution was stirred at −78° C. for one hour and then for one hour at ambient temperature. The reaction was quenched with saturated sodium bicarbonate (10 mL) and stirred for ten minutes. The product was extracted with ether, dried over magnesium sulfate, filtered and concentrated. The crude material was purified by silica gel chromatography to give the title compound.

Calc'd for $C_{16}H_{23}BrN_2O_3$ [M+H]$^+$: 372. Found: 372.

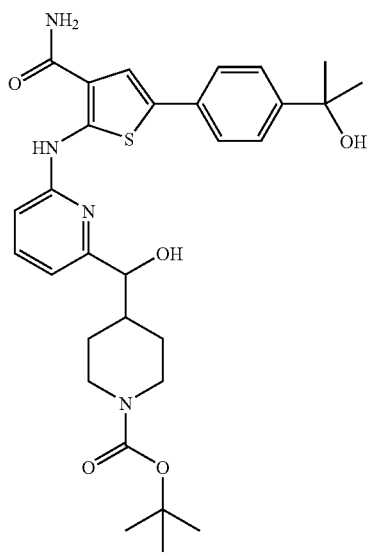 [SMILES: CC(C)(C)OC(=O)N1CCC(C(O)c2cccc(Nc3sc(-c4ccc(C(C)(C)O)cc4)cc3C(N)=O)n2)CC1]

216

Step 2: tert-Butyl 4-[[6-({3-(aminocarbonyl)-5-[4-(1-hydroxy-1-methylethyl)phenyl]-2-thienyl}amino)pyridin-2-yl](hydroxy)methyl]piperidine-1-carboxylate The title compound was prepared as described in Example 1 with 2-amino-5-[4-(1-hydroxy-1-methylethyl)phenyl]thiophene-3-carboxamide (0.20 g, 0.73 mmol) and tert-butyl 4-[(6-bromopyridin-2-yl)(hydroxy)methyl]piperidine-1-carboxylate (0.27 g, 0.71 mmol) as the starting materials.

Calc'd for $C_{30}H_{39}N_4O_5S$ [M+H]$^+$: 567. Found: 567.

Example 163

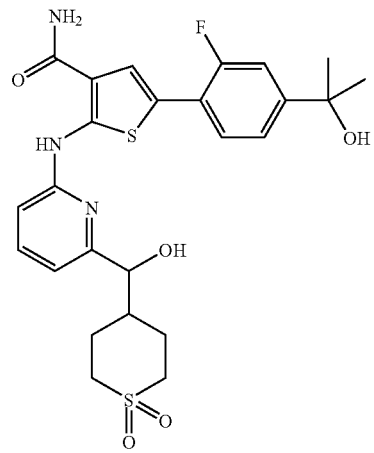 [SMILES: CC(C)(O)c1ccc(-c2cc(C(N)=O)c(Nc3cccc(C(O)C4CCS(=O)(=O)CC4)n3)s2)c(F)c1]

2-({6-[(1,1-Dioxidotetrahydro-2H-thiopyran-4-yl)(hydroxy)methyl]pyridin-2-yl}amino)-5-[2-fluoro-4-(1-hydroxy-1-methylethyl)phenyl]thiophene-3-carboxamide

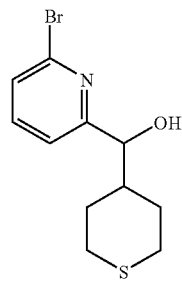 [SMILES: OC(c1cccc(Br)n1)C1CCSCC1]

Step 1: (6-Bromopyridin-2-yl)(tetrahydro-2H-thiopyran-4-yl)methanol

The title compound was prepared as described in Example 162, Step 1 with 2,6-dibromopyridine (3.64 g, 15.36 mmol) and tetrahydro-2H-thiopyran-4-carbaldehyde (2.00 g, 15.36 mmol) as the starting materials.

Calc'd for $C_{11}H_{15}NOS$ [M+H]$^+$: 289. Found: 289.

217

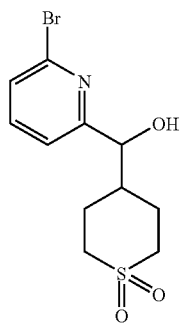

Step 2: (6-Bromopyridin-2-yl)(1,1-dioxidotetrahydro-2H-thiopyran-4-yl)methanol

(6-Bromopyridin-2-yl)(tetrahydro-2H-thiopyran-4-yl)methanol (0.10 g, 0.35 mmol) was dissolved in dichloromethane (2.5 mL) and cooled to 0° C. 3-Chloroperoxybenzoic acid (0.18 g, 0.80 mmol) was added and the reaction mixture was allowed to warm to room temperature. The reaction was quenched with saturated sodium bicarbonate and diluted with dichloromethane. After separation of the layers, the organic layer was dried over magnesium sulfate, filtered, and concentrated. The crude mixture was purified by silica gel chromatography to yield the title compound.

Calc'd for $C_{11}H_{15}NO_3S$ [M+H]$^+$: 321. Found: 321.

218

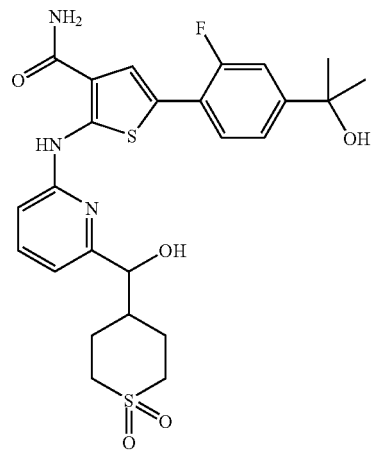 [SMILES: CC(C)(O)c1ccc(-c2cc(C(N)=O)c(Nc3cccc(C(O)C4CCS(=O)(=O)CC4)n3)s2)c(F)c1]

Step 3: 2-({6-[(1,1-Dioxidotetrahydro-2H-thiopyran-4-yl)(hydroxy)methyl]pyridin-2-yl}amino)-5-[2-fluoro-4-(1-hydroxy-1-methylethyl)phenyl]thiophene-3-carboxamide

The title compound was prepared as described in Example 1 with 2-amino-5-[2-fluoro-4-(1-hydroxy-1-methylethyl)phenyl]thiophene-3-carboxamide (0.14 g, 0.47 mmol) and (6-bromopyridin-2-yl)(1,1-dioxidotetrahydro-2H-thiopyran-4-yl)methanol (0.15 g, 0.46 mmol) as the starting materials.

Calc'd for $C_{25}H_{29}N_3O_5S_2$ [M+H]$^+$: 534. Found: 534.

Additional examples were prepared using procedures similar to those described in the above examples and are illustrated in the following table.

TABLE 9

| Example | Structure | Compound Name | Characterization |
|---|---|---|---|
| 164 | 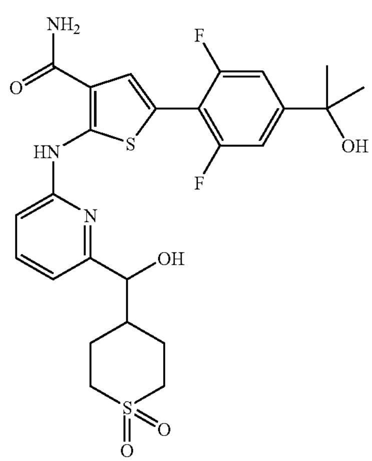 [SMILES: CC(C)(O)c1cc(F)c(-c2cc(C(N)=O)c(Nc3cccc(C(O)C4CCS(=O)(=O)CC4)n3)s2)c(F)c1] | 2-({6-[(1,1-dioxidotetrahydro-2H-thiopyran-4-yl)(hydroxy)methyl]pyridin-2-yl}amino)-5-[2,6-difluoro-4-(1-hydroxy-1-methylethyl)phenyl]thiophene-3-carboxamide | Calc'd [M + H]$^+$: 552, Found: 552 |

TABLE 9-continued

| Example | Structure | Compound Name | Characterization |
| --- | --- | --- | --- |
| 165 | 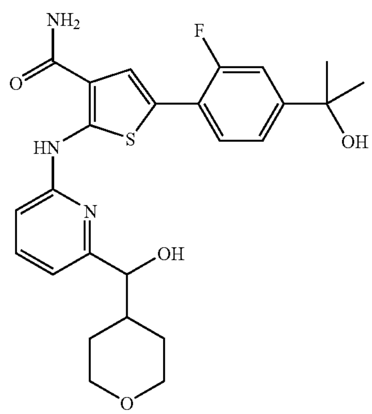 [SMILES: CC(C)(O)c1ccc(-c2cc(C(N)=O)c(Nc3cccc(C(O)C4CCOCC4)n3)s2)c(F)c1] | 5-[2-fluoro-4-(1-hydroxy-1-methylethyl)phenyl]-2-({6-[hydroxy(tetrahydro-2H-pyran-4-yl)methyl]pyridin-2-yl}amino)thiophene-3-carboxamide | Calc'd [M + H]⁺: 486, Found: 486 |
| 166 | 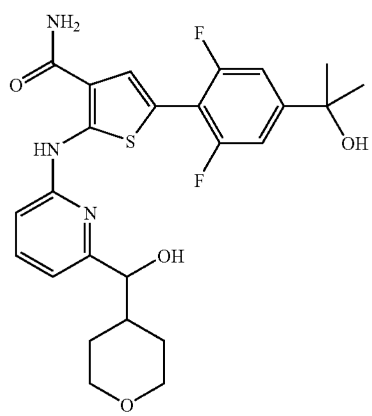 [SMILES: CC(C)(O)c1cc(F)c(-c2cc(C(N)=O)c(Nc3cccc(C(O)C4CCOCC4)n3)s2)c(F)c1] | 5-[2,6-difluoro-4-(1-hydroxy-1-methylethyl)phenyl]-2-({6-[hydroxy(tetrahydro-2H-pyran-4-yl)methyl]pyridin-2-yl}amino)thiophene-3-carboxamide | Calc'd [M + H]⁺: 504, Found: 504 |
| 167 | 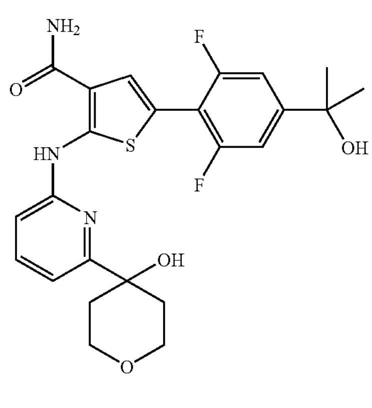 [SMILES: CC(C)(O)c1cc(F)c(-c2cc(C(N)=O)c(Nc3cccc(C4(O)CCOCC4)n3)s2)c(F)c1] | 5-[2,6-difluoro-4-(1-hydroxy-1-methylethyl)phenyl]-2-{[6-(4-hydroxytetrahydro-2H-pyran-4-yl)pyridin-2-yl]amino}thiophene-3-carboxamide | Calc'd [M + H]⁺: 490, Found: 490 |

TABLE 9-continued

| Example | Structure | Compound Name | Characterization |
|---------|-----------|---------------|------------------|
| 168 | 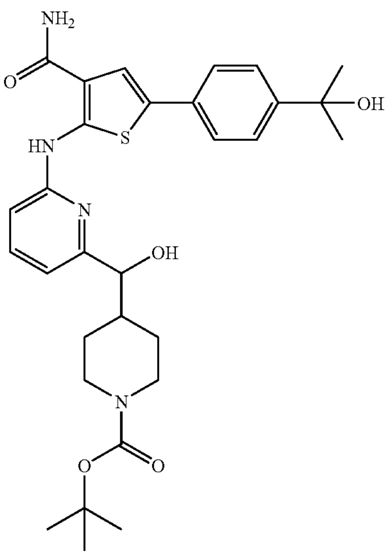 [SMILES: CC(C)(C)OC(=O)N1CCC(C(O)c2cccc(Nc3sc(-c4ccc(C(C)(C)O)cc4)cc3C(N)=O)n2)CC1] | tert-butyl 4-[[6-({3-(aminocarbonyl)-5-[4-(1-hydroxy-1-methylethyl)phenyl]-2-thienyl}amino)pyridin-2-yl](hydroxy)methyl]piperidine-1-carboxylate | Calc'd [M + H]⁺: 567, Found: 567 |

Example 169

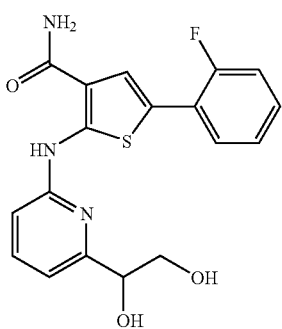 [SMILES: NC(=O)c1cc(-c2ccccc2F)sc1Nc1cccc(C(O)CO)n1]

2-{[6-(1,2-Dihydroxyethyl)pyridin-2-yl]amino}-5-(2-fluorophenyl)thiophene-3-carboxamide

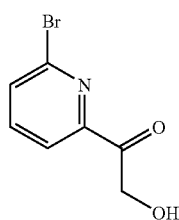 [SMILES: O=C(CO)c1cccc(Br)n1]

Step 1: 1-(6-Bromopyridin-2-yl)-2-hydroxyethanone

To a solution of 2-bromo-1-(6-bromopyridin-2-yl)ethanone (500 mg, 1.79 mmol) in dimethylformamide (11.5 mL) was added sodium nitrite (124 mg, 1.79 mmol). After 14 hours, the reaction was diluted with ethyl acetate (200 mL) and washed with saturated aqueous sodium bicarbonate (100 mL), water (2×100 mL), and brine (100 mL). The organic layer was dried over sodium sulfate, filtered, and concentrated to give the title compound. ¹H NMR (600 MHz, DMSO): δ 7.94 (m, 2H), 7.91 (m, 1H), 5.07 (t, J=5.9 Hz, 1H), 4.85 (d, J=5.9 Hz, 2H).

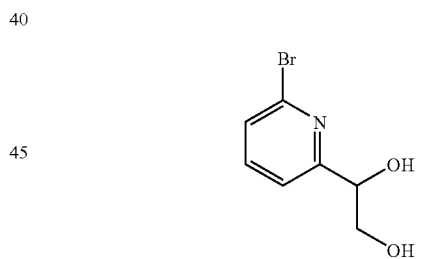

Step 2: 1-(6-Bromopyridin-2-yl)ethane-1,2-diol

A solution of 1-(6-bromopyridin-2-yl)-2-hydroxyethanone (2.2 g, 10.18 mmol) in ethanol (127 mL) was charged with sodium borohydride (0.385 g, 10.18 mmol). After 30 minutes, the reaction was concentrated to dryness and then partitioned between ethyl acetate (50 mL) and 3:1 saturated aqueous sodium bicarbonate:water (25 mL). The layers were separated and the organic layer was washed with brine (25 mL), dried over sodium sulfate, filtered, and concentrated to afford the title compound. ¹H NMR (600 MHz, DMSO): δ 7.69 (m, 1H), 7.46 (m, 2H), 5.50 (d, J=5.0 Hz, 1H), 4.69 (m, 1H), 4.49 (m, 1H), 3.61 (m, 1H), 3.46 (m, 1H).

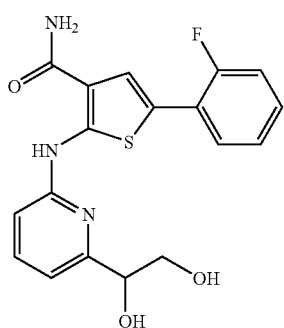 [SMILES: NC(=O)c1cc(-c2ccccc2F)sc1Nc1cccc(C(O)CO)n1]

Step 3: 2-{[6-(1,2-Dihydroxyethyl)pyridin-2-yl]amino}-5-(2-fluorophenyl)thiophene-3-carboxamide The title compound was prepared according to the general procedure in Example 1 using 1-(6-bromopyridin-2-yl)ethane-1,2-diol (71 mg, 0.33 mmol) and 2-amino-5-(2-fluorophenyl)thiophene-3-carboxamide (78 mg, 0.33 mmol) as the starting materials.
Calc'd for $C_{18}H_{17}FN_3O_3S$ [M+H]$^+$: 374. Found: 374.

Example 170

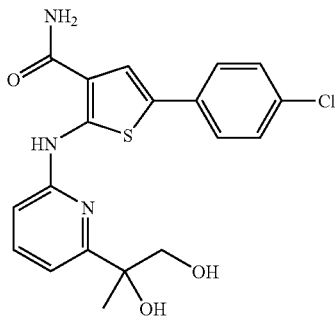 [SMILES: CC(O)(CO)c1cccc(Nc2sc(-c3ccc(Cl)cc3)cc2C(N)=O)n1]

5-(4-Chlorophenyl)-2-{[6-(1,2-dihydroxy-1-methylethyl)pyridin-2-yl]amino}thiophene-3-carboxamide

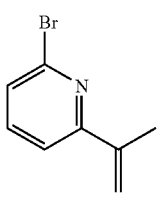

Step 1: 2-Bromo-6-isopropenylpyridine

To a solution of 2-(6-bromopyridin-2-yl)propan-2-ol (Example 2, Step 1) (2.44 g, 11.29 mmol) and methansulfonic anhydride (5.90 g, 33.9 mmol) in dichloromethane (35 mL) was added triethylamine (6.26 mL, 45.2 mmol). After three hours, the reaction mixture was partitioned between ethyl acetate (50 mL) and saturated aqueous sodium bicarbonate (25 mL). The layers were separated and the organic layer was washed with saturated aqueous sodium bicarbonate (25 mL) and brine (2×25 mL), dried over sodium sulfate, filtered, and concentrated. The resulting yellow liquid was purified by silica gel chromatography (2-20% ethyl acetate/hexanes) to afford the title compound.
$^1$H NMR (600 MHz, DMSO): δ 7.70 (t, 1H), 7.61 (d, 1H), 7.49 (d, 1H), 5.89 (s, 1H), 5.33 (s, 1H), 2.06 (s, 3H).

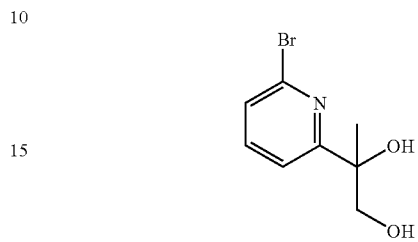

Step 2: 2-(6-Bromopyridin-2-yl)propane-1,2-diol

To a solution of 2-bromo-6-isopropenylpyridine (0.510 g, 2.57 mmol) in acetone (1 mL) and water (2 mL) was added N-methylmorpholine N-oxide (0.317 g, 2.70 mmol) followed by osmium tetroxide (0.257 mL, 0.013 mmol). After 16 hours, dithionite (0.05 g) and water (1.5 mL) were added. After an additional 15 minutes, the reaction mixture was filtered though a pad of Celite. The filter was rinsed with acetone (3×1.5 mL), and the filtrate was concentrated under vacuo to remove the acetone. The remaining liquid was diluted with 9:1 chloroform:isopropanol (4 mL) and aqueous hydrogen chloride (2 M) was added until the aqueous layer was acidic. The layers were separated, and the acidic (pH=1) aqueous layer was extracted with 9:1 chloroform:isopropanol (2×4 mL). The combined organic layers were washed with 3:1 water:brine (2.5 mL), saturated aqueous sodium bicarbonate (4 mL), and brine (4 mL), dried over sodium sulfate, filtered, and concentrated to afford the title compound.
Calc'd for $C_8H_{11}BrNO_2$ [M+H]$^+$: 232. Found: 232.

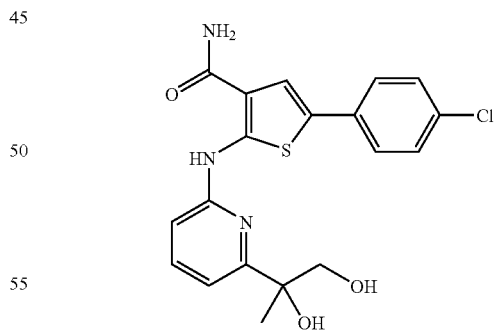

Step 3: 5-(4-Chlorophenyl)-2-{[6-(1,2-dihydroxy-1-methylethyl)pyridin-2-yl]amino}thiophene-3-carboxamide The title compound was prepared by using the procedure described in Example 1 with 2-amino-5-(4-chlorophenyl)thiophene-3-carboxamide (240 mg, 0.95 mmol) and 2-(6- bromopyridin-2-yl)propane-1,2-diol (200 mg, 0.86 mmol) as the starting materials.

Calc'd for $C_{19}H_{19}ClN_3O_3S$ [M+H]⁺: 404. Found: 404.

Example 171

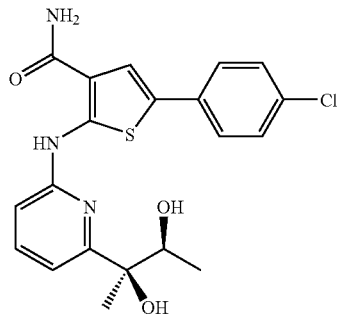 [SMILES: C[C@H](O)[C@@](C)(O)c1cccc(Nc2sc(-c3ccc(Cl)cc3)cc2C(N)=O)n1]

5-(4-Chlorophenyl)-2-({6-[(cis)-1,2-dihydroxy-1-methylpropyl]pyridin-2-yl}amino)thiophene-3-carboxamide

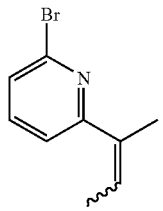

Step 1: 2-Bromo-6-[(1E)-1-methylprop-1-en-1-yl]pyridine and 2-Bromo-6-[(1Z)-1-methylprop-1-en-1-yl]pyridine To a solution of 2,6-dibromopyridine (3 g, 12.66 mmol) in tetrahydrofuran (25 mL) under argon at 0° C. was added 1,1'-bis(diphenylphosphino)ferrocene (0.07 g, 0.13 mmol) and dibenyzlideneacetone bis(triphenylphosphine) (0.116 g, 0.13 mmol), and then 4 vacuum/argon flush cycles were performed. Bromo[(1E)-1-methylprop-1-en-1-yl]magnesium in tetrahydrofuran (0.5 M, 25.3 mL, 12.66 mmol) was then added over 5 minutes and the reaction was allowed to reach room temperature. After six days, the reaction mixture was partitioned between diethyl ether (50 mL) and saturated aqueous ammonium chloride (50 mL). The layers were separated and the aqueous layer was extracted with diethyl ether (50 mL). The combined organic layers were filtered through a Buchner funnel and then washed with saturated aqueous sodium bicarbonate (30 mL) and brine (30 mL), dried over magnesium sulfate, filtered, and concentrated. The crude material was purified by silica gel chromatography (15-75% dichloromethane/hexanes) to give a mixture of 2-bromo-6-[(1E)-1-methylprop-1-en-1-yl]pyridine and 2-bromo-6-[(1Z)-1-methylprop-1-en-1-yl]pyridine as a white solid.

Calc'd for $C_9H_{11}BrN$ [M+H]⁺: 212. Found: 212.

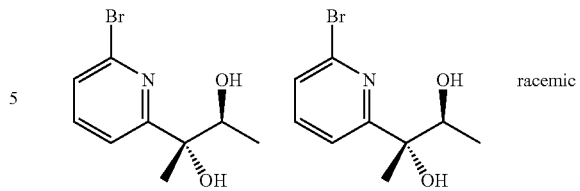

Step 2: trans-2-(6-Bromopyridin-2-yl)butane-2,3-diol and cis-2-(6-Bromopyridin-2-yl)butane-2,3-diol A mixture of 2-bromo-6-[(1E)-1-methylprop-1-en-1-yl]pyridine and 2-bromo-6-[(1Z)-1-methylprop-1-en-1-yl]pyridine (2.69 g, 12.66 mmol) was dissolved in acetone (10 mL) followed by addition of water (10 mL), N-methylmorpholine N-oxide (1.56 g, 13.29 mmol), and osmium tetroxide (1.27 mL, 0.063 mmol). After 48 hours, dithionite (0.15 g), florisil (1.5 g), and water (8 mL) were added. After an additional 15 minutes, the reaction mixture was filtered though a pad of Celite. The filter was rinsed with acetone (2×5 mL, then 2×10 mL), and the filtrate was concentrated in vacuo to remove the acetone. The remaining liquid was diluted with 9:1 chloroform:isopropanol (20 mL) and aqueous hydrogen chloride (1 M, 20 mL). The layers were separated, and the acidic (pH=1) aqueous layer was extracted with 9:1 chloroform:isopropanol (2×20 mL) The combined organic layers were washed with 3:1 water:brine (12 mL), saturated aqueous sodium bicarbonate (10 mL), and brine (10 mL), dried over sodium sulfate, filtered, and concentrated. The crude residue was purified by silica gel chromatography (1-8% methanol/dichloromethane) to separately afford trans-2-(6-bromopyridin-2-yl)butane-2,3-diol and cis-2-(6-bromopyridin-2-yl)butane-2,3-diol.

Calc'd for $C_9H_{13}BrNO_2$ [M+H]⁺: 246. Found: 246.

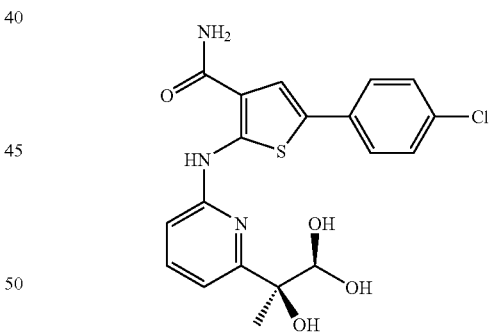

Step 3: 5-(4-Chlorophenyl)-2-({6-[(cis)-1,2-dihydroxy-1-methylpropyl]pyridin-2-yl}amino)thiophene-3-carboxamide The title compound was prepared by using the procedure in Example 1 with 2-amino-5-(4-chlorophenyl)thiophene-3-carboxamide (226 mg, 0.89 mmol) and cis-2-(6-bromopyridin-2-yl)butane-2,3-diol (200 mg, 0.81 mmol) as the starting materials.

Calc'd for $C_{20}H_{21}ClN_3O_3S$ [M+H]⁺: 418. Found: 418.

Additional examples were prepared using procedures similar to those described in the above examples and are illustrated in the following table.

TABLE 10

| Example # | Structure | Compound Name | Characterization |
|---|---|---|---|
| 172 | 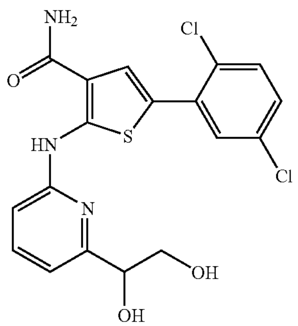 [SMILES: NC(=O)c1cc(-c2cc(Cl)ccc2Cl)sc1Nc1cccc(C(O)CO)n1] | 5-(2,5-dichlorophenyl)-2-{[6-(1,2-dihydroxyethyl)pyridin-2-yl]amino}thiophene-3-carboxamide | Calc'd [M + H]⁺: 424, Found: 424 |
| 173 | 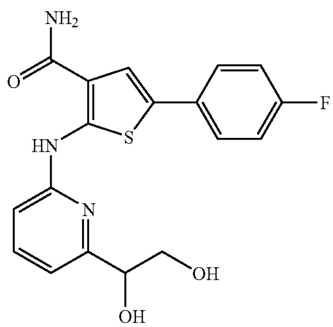 [SMILES: NC(=O)c1cc(-c2ccc(F)cc2)sc1Nc1cccc(C(O)CO)n1] | 2-{[6-(1,2-dihydroxyethyl)pyridin-2-yl]amino}-5-(4-fluorophenyl)thiophene-3-carboxamide | Calc'd [M + H]⁺: 374, Found: 374 |
| 174 | 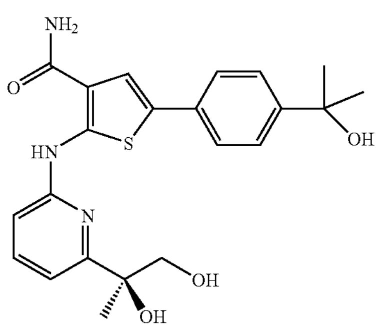 [SMILES: CC(C)(O)c1ccc(-c2cc(C(N)=O)c(Nc3cccc([C@](C)(O)CO)n3)s2)cc1] | 2-({6-[(1S)-1,2-dihydroxy-1-methylethyl]pyridin-2-yl}amino)-5-[4-(1-hydroxy-1-methylethyl)phenyl]thiophene-3-carboxamide | Calc'd [M + H]⁺: 428, Found: 428 |
| 175 | 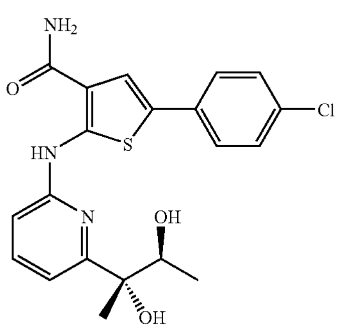 | 2-({6-[(1R)-1,2-dihydroxy-1-methylethyl]pyridin-2-yl}amino)-5-[4-(1-hydroxy-1-methylethyl)phenyl]thiophene-3-carboxamide | Calc'd [M + H]⁺: 428, Found: 428 |

TABLE 10-continued

| Example # | Structure | Compound Name | Characterization |
|---|---|---|---|
| 176 | 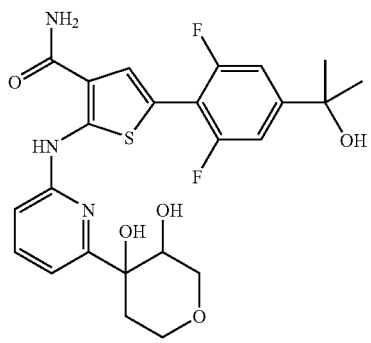 | 5-(4-chlorophenyl)-2-({6-[(trans)-1,2-dihydroxy-1-methylpropyl]pyridin-2-yl}amino)thiophene-3-carboxamide | Calc'd [M + H]⁺: 418, Found: 418 |

Example 177

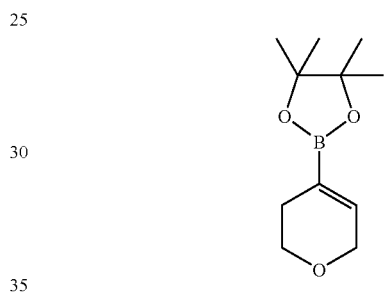

3-C-[6-({3-(Aminocarbonyl)-5-[2,6-difluoro-4-(1-hydroxy-1-methylethyl)phenyl]-2-thienyl}amino)pyridin-2-yl]-1,5-anhydro-2-deoxypentitol

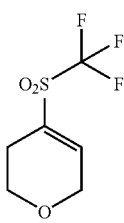

Step 1: 4-[(Trifluoromethyl)sulfonyl]-3,6-dihydro-2H-pyran

Tetrahydrofuran (46.0 mL) and LDA (1.8 M in THF) (6.10 mL, 10.99 mmol) were placed in a 3-neck flask that had been evacuated and flushed with argon. The solution was cooled to −78° C. and a solution of tetrahydro-4H-pyran-4-one (1 g, 9.99 mmol) in THF (10 mL) and added dropwise via an addition funnel over the span of 20 minutes. The solution was stirred at −78° C. for 25 minutes at which time 1,1,1-Trifluoro-N-phenyl-N-[(trifluoromethyl)sulfonyl]methanesulfonamide (3.82 g, 10.69 mmol) was added and the solution was warmed to zero degrees and the temperature was maintained for 3 hours. The reaction was concentrated in vacuo and filtered over a pad of alumina (hexanes/EtOAc 10:1) to give the title compound which was used in the next reaction without further purification.

¹H NMR (600 MHz, CDCl₃): δ 5.80 (m, 1H), 4.24 (q, 2H), 3.87 (t, 2H), 2.44 (m, 2H).

Step 2: 4-(4,4,5,5-Tetramethyl-1,3,2-dioxaborolan-2-yl)-3,6-dihydro-2H-pyran Dioxane (0.25 ml) was placed in a flask and argon was bubbled though it for several minutes. Bis(pinacolato)diboron (120 mg, 0.47 mmol), 1,1'-bis(diphenylphosphino)ferrocene (23.88 mg, 0.043 mmol), potassium acetate (127 mg, 1.29 mmol), 1,1'-bis(diphenylphosphino)ferrocenedichloro palladium(II) dichloromethane complex (31.5 mg, 0.043 mmol) were placed in a flask and argon was used to degas the flask. The degassed dioxane was used to transfer vinyl triflate (100 mg, 0.43 mmol) into the flask and the solution was heated overnight at 80° C. The reaction was cooled to ambient temperature, quenched with water, and diluted with dichloromethane. The organic layer was separated, dried over magnesium sulfate, filtered and concentrated. The crude residue was purified by column chromatography was used for purification to yield the title compound.

¹H NMR (600 MHz, CDCl₃): δ 6.50 (m, 1H), 4.17 (q, 2H), 3.73 (t, 2H), 2.20 (m, 2H), 1.24 (s, 12H).

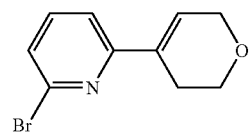

Step 3: 2-Bromo-6-(3,6-dihydro-2H-pyran-4-yl)pyridine 2,6-Dibromopyridine (710 mg, 3.00 mmol), potassium carbonate (1184 mg, 8.57 mmol), PdCl$_2$(dppf) (104 mg, 0.14 mmol) were placed in a flask and the flask was purged with argon. 4-(4,4,5,5-Tetramethyl-1,3,2-dioxaborolan-2-yl)-3,6-dihydro-2H-pyran (600 mg, 2.86 mmol) was dissolved in degassed DMF (19 mL), added to the reaction mixture and 5 argon/vacuum purge cycles were performed. The reaction was heated at 80° C. overnight. The reaction was cooled to room temperature, diluted with ethyl acetate, washed with water, dried over magnesium sulfate, filtered, and concentrated. The crude mixture was purified by silica gel chromatography to yield the title compound.

$^1$H NMR (600 MHz, CDCl$_3$): δ 7.47 (t, 1H), 7.30 (d, 1H), 7.26 (d, 1H), 6.75 (s, 1H), 4.34 (m, 2H), 3.90 (t, 2H), 2.56 (m, 2H).

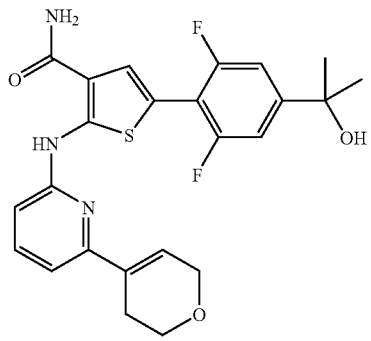 [SMILES: CC(C)(O)c1cc(F)c(-c2cc(C(N)=O)c(Nc3cccc(C4=CCOCC4)n3)s2)c(F)c1]

Step 4: 5-[2,6-Difluoro-4-(1-hydroxy-1-methylethyl)phenyl]-2-{[6-(3,6-dihydro-2H-pyran-4-yl)pyridin-2-yl]amino}thiophene-3-carboxamide The title compound was prepared by using the procedure listed in Example 1 with 2-amino-5-[2,6-difluoro-4-(1-hydroxy-1-methylethyl)phenyl]thiophene-3-carboxamide (0.24 g, 0.75 mmol) and 2-bromo-6-(3,6-dihydro-2H-pyran-4-yl)pyridine (0.18 g, 0.74 mmol) as the starting materials.

Calc'd for C$_{24}$H$_{24}$F$_2$N$_3$O$_3$S [M+H]$^+$: 472. Found: 472.

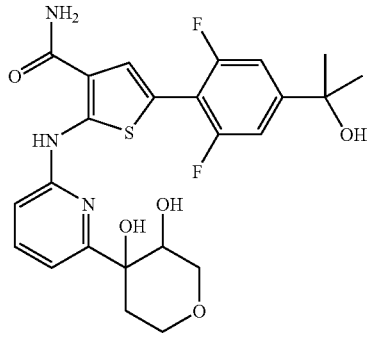 [SMILES: CC(C)(O)c1cc(F)c(-c2cc(C(N)=O)c(Nc3cccc(C4(O)CCOCC4O)n3)s2)c(F)c1]

Step 5: 3-C-[6-({3-(Aminocarbonyl)-5-[2,6-difluoro-4-(1-hydroxy-1-methylethyl)phenyl]-2-thienyl}amino)pyridin-2-yl]-1,5-anhydro-2-deoxy-pentitol 5-[2,6-Difluoro-4-(1-hydroxy-1-methylethyl)phenyl]-2-{[6-(3,6-dihydro-2H-pyran-4-yl)pyridin-2-yl] amino}thiophene-3-carboxamide (50 mg, 0.11 mmol) was dissolved in a mixture of tetrahydrofuran (1.40 mL) and water (0.68 mL). 4-Methylmorpholine N-oxide (14.91 mg, 0.13 mmol) and osmium tetroxide (3.33 μl 10.60 μmol) were added and the reaction was allowed to stir overnight. Saturated sodium thiosulfate was added and the reaction was stirred for ten minutes. The product was extracted with ethyl acetate, dried over magnesium sulfate, filtered and concentrated. Purification by reverse phase HPLC (10-100% acetonitrile/water+0.05% TFA modifier) afforded the title compound.

Calc'd for C$_{24}$H$_{26}$F$_2$N$_3$O$_5$S [M+H]$^+$: 506. Found: 506.

Example 178

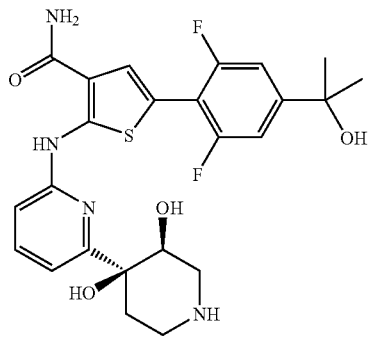 [SMILES: CC(C)(O)c1cc(F)c(-c2cc(C(N)=O)c(Nc3cccc([C@@]4(O)CCNC[C@@H]4O)n3)s2)c(F)c1]

5-[2,6-Difluoro-4-(1-hydroxy-1-methylethyl)phenyl]-2-({6-[(3S,4S)-3,4-dihydroxypiperidin-4-yl]pyridin-2-yl}amino)thiophene-3-carboxamide

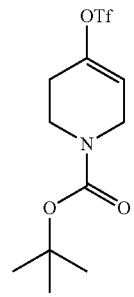 [SMILES: CC(C)(C)OC(=O)N1CC=C(OS(=O)(=O)C(F)(F)F)CC1]

Step 1: tert-Butyl 4-(trifluoromethylsulfonyloxy)-5,6-dihydropyridine-1(2H)-carboxylate Into a 250 mL 3-necked round bottom flask, was placed a solution of diisopropylamine (5.0 g, 49.5 mmol) in tetrahydrofuran (50 mL). The temperature was cooled to −78° C. To the above was added n-butyllithium (19.8 mL, 49.8 mmol, 2.5M) dropwise. The temperature was maintained at −78° C. for 30 min followed by the addition of a solution of tert-butyl 4-oxopiperidine-1-carboxylate (9.0 g, 45.2 mmol) in tetrahydrofuran (50 mL). After 2 hours at −78° C., a solution of n-phenyltrifluoromethanesulfonimide (17.7 g, 49.6 mmol) in tetrahydrofuran (50 mL) was added while warming to a temperature of −70° C. The resulting solution was allowed to react, with stirring, for an additional 2 hours while the temperature was maintained between −60 and −70° C. The mixture was concentrated by evaporation under vacuo. The residue was purified by eluting through a column with a 1/20 ethyl acetate/petroleum ether solvent system to yield the title compound as yellow oil.

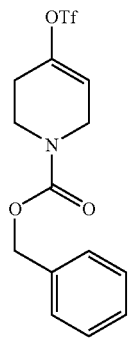 [SMILES: O=C(OCc1ccccc1)N1CC=C(OS(=O)(=O)C(F)(F)F)CC1]

Step 2: Benzyl 4-(trifluoromethylsulfonyloxy)-5,6-dihydropyridine-1(2H)-carboxylate Into a 50 mL roundbottom flask, was placed tert-butyl 4-(trifluoromethylsulfonyloxy)-5,6-dihydropyridine-1(2H)-carboxylate (3.5 g, 10.00 mmol). To this was added dichloromethane (20 mL) followed by the addition of trifluoroacetic acid (5 mL). The resulting solution was allowed to react, with stirring, overnight while the temperature was maintained at room temperature. The mixture was concentrated by evaporation under vacuum using a rotary evaporator. This was followed by the addition of dichloromethane (20 mL). This was followed by the addition of triethylamine (3.03 g, 29.94 mmol). To the mixture was added benzyl chloroformate (2.05 g, 12.02 mmol). The resulting solution was allowed to react overnight at room temperature. The reaction mixture was filtered and the filtrate was concentrated under vacuo. The crude mixture was purified by silica gel chromatography (1:40 EtOAc/petroleum ether) to yield the title compound as a yellow liquid.
Calc'd for $C_{14}H_{15}F_3NO_5S$ [M+H]$^+$: 366. Found: 366.

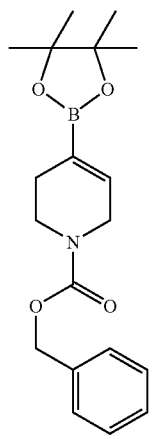 [SMILES: CC1(C)OB(C2=CCN(C(=O)OCc3ccccc3)CC2)OC1(C)C]

Step 3: Benzyl 4-(4,4,5,5-tetramethyl-1,3,2-dioxaborolan-2-yl)-5,6-dihydropyridine-1(2H)-carboxylate A 2000 mL 3-necked round bottom flask was purged with nitrogen, and a solution of benzyl 4-(trifluoromethylsulfonyloxy)-5,6-dihydropyridine-1(2H)-carboxylate (34.8 g, 95.26 mmol) in 1,4-dioxane (589 mL) was added followed by the sequential addition of 4,4,5,5-tetramethyl-2-(4,4,5,5-tetramethyl-1,3,2-dioxaborolan-2-yl)-1,3,2-dioxaborolane (26.62 g, 104.84 mmol), PdCl2(dppf) (2.73 g, 3.34 mmol) and potassium acetate (28 g, 285.42 mmol). The resulting solution was allowed to react overnight at 80° C. The solution was cooled and concentrated under reduced pressure. The filter cake was washed with ethyl acetate. The resulting mixture was washed one time with water (40 mL). The resulting solution was extracted three times with ethyl acetate and the organic layers combined and dried over magnesium sulfate. The crude mixture was purified by silica gel column (1:20 EtOAc/petroleum ether) to yield the title compound.
Calc'd for $C_{19}H_{27}BNO_4$ [M+H]$^+$: 344. Found: 344.

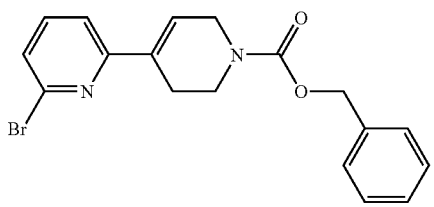 [SMILES: O=C(OCc1ccccc1)N1CC=C(c2cccc(Br)n2)CC1]

Step 4: Benzyl 6-bromo-3',6'-dihydro-2,4'-bipyridine-1'(2'H)-carboxylate

The title compound was prepared by using the procedure listed in Example 177 Step 3 with 2,6-dibromopyridine (0.77 g, 3.21 mmol) and benzyl 4-(4,4,5,5-tetramethyl-1,3,2-dioxaborolan-2-yl)-3,6-dihydropyridine-1(2H)-carboxylate (1.05 g, 3.06 mmol) as the starting materials.
Calc'd for $C_{18}H_{18}BrN_2O_2$ [M+H]$^+$: 374. Found: 374.

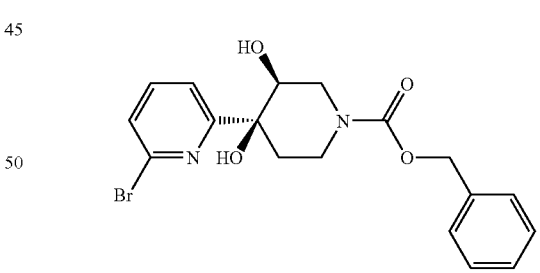

Step 5: Benzyl (3S,4S)-4-(6-bromopyridin-2-yl)-3,4-dihydroxypiperidine-1-carboxylate The title compound was prepared by using the procedure listed in Example 177 Step 5 with benzyl 6-bromo-3',6'-dihydro-2,4'-bipyridine-1'(2'H)-carboxylate (0.10 g, 0.27 mmol) as the starting material.
Calc'd for $C_{18}H_{20}BrN_2O_4$ [M+H]$^+$: 408. Found: 408.

235

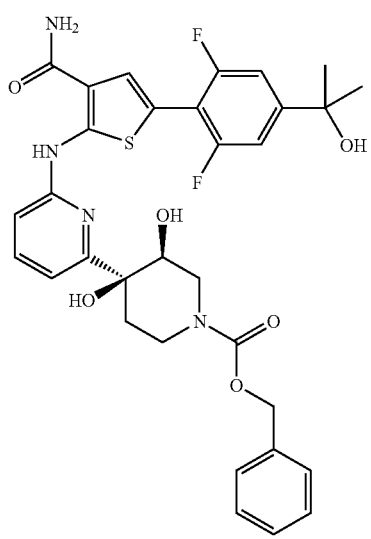 [SMILES: CC(C)(O)c1cc(F)c(-c2cc(C(N)=O)c(Nc3cccc([C@@]4(O)CCN(C(=O)OCc5ccccc5)C[C@@H]4O)n3)s2)c(F)c1]

Step 6: Benzyl (3S,4S)-4-[6-({3-(aminocarbonyl)-5-[2,6-difluoro-4-(1-hydroxy-1-methylethyl)phenyl]-2-thienyl}amino)pyridin-2-yl]-3,4-dihydroxypiperidine-1-carboxylate The title compound was prepared using the procedure listed in Example 1 with 2-amino-5-[2,6-difluoro-4-(1-hydroxy-1-methylethyl)phenyl]thiophene-3-carboxamide (0.11 g, 0.34 mmol) and benzyl (3S,4S)-4-(6-bromopyridin-2-yl)-3,4-dihydroxypiperidine-1-carboxylate (0.13 g, 0.33 mmol) as the starting materials.

Calc'd for $C_{32}H_{33}F_2N_4O_6S$ [M+H]$^+$: 639. Found: 639.

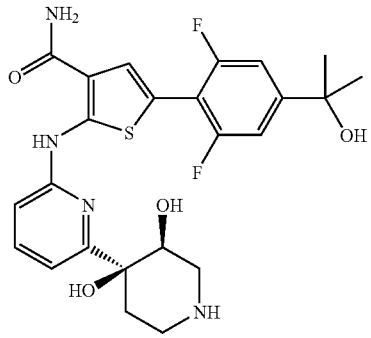 [SMILES: CC(C)(O)c1cc(F)c(-c2cc(C(N)=O)c(Nc3cccc([C@@]4(O)CCNC[C@@H]4O)n3)s2)c(F)c1]

Step 7: 5-[2,6-Difluoro-4-(1-hydroxy-1-methylethyl)phenyl]-2-({6-[(3S,4S)-3,4-dihydroxypiperidin-4-yl]pyridin-2-yl}amino)thiophene-3-carboxamide Benzyl (3S,4S)-4-[6-({3-(aminocarbonyl)-5-[2,6-difluoro-4-(1-hydroxy-1-methylethyl)phenyl]-2-thienyl}amino)pyridin-2-yl]-3,4-dihydroxypiperidine-1-carboxylate (100 mg, 0.16 mmol) was dissolved in methanol (4.6 mL) and subjected to the H-cube hydrogenator machine, where the solution passed through a palladium on carbon cartridge at 0.5 mL/min at a temperature of 35° C. and a hydrogen pressure of 40 PSI. Once complete, the solution was concentrated and the crude residue was purified by reverse phase HPLC to yield the title compound.

Calc'd for $C_{24}H_{26}F_2N_4O_4S$ [M+H]$^+$: 505. Found: 505.

Example 179

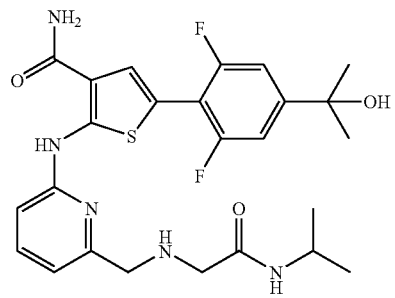 [SMILES: CC(C)NC(=O)CNCc1cccc(Nc2sc(-c3c(F)cc(C(C)(C)O)cc3F)cc2C(N)=O)n1]

5-[2,6-Difluoro-4-(1-hydroxy-1-methylethyl)phenyl]-2-{[6-({[2-(isopropylamino)-2-oxoethyl]amino}methyl)pyridin-2-yl]amino}thiophene-3-carboxamide

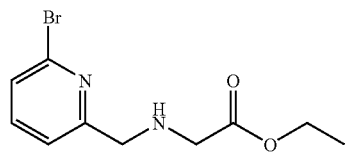

Step 1: Ethyl N-[(6-bromopyridin-2-yl)methyl]glycinate

6-Bromopyridine-2-carbaldehyde (10 g, 53.8 mmol) and glycine ethyl ester hydrochloride (7.50 g, 53.8 mmol) were placed in a flask. Dichloroethane (220 mL) and triethylamine (7.49 mL, 53.8 mmol) were added and the reaction was stirred for 45 minutes. Sodium triacetoxyborohydride (15.95 g, 75 mmol) was added and the reaction was stirred at ambient temperature overnight. The reaction was diluted with ethyl acetate, saturated sodium bicarbonate, and saturated sodium carbonate to make the pH basic. The organic layer was separated and washed with brine. The organic layer was dried over magnesium sulfate, filtered and concentrated. The crude mixture was purified by silica gel chromatography to yield the title compound.

Calc'd for $C_{10}H_{14}BrN_2O_2$ [M+H]$^+$: 274. Found: 274.

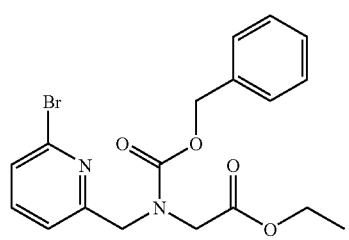 [SMILES: CCOC(=O)CN(Cc1cccc(Br)n1)C(=O)OCc1ccccc1]

Step 2: Ethyl N-[(benzyloxy)carbonyl]-N-[(6-bromopyridin-2-yl)methyl]glycinate Sodium hydride (88 mg, 2.20 mmol) was suspended in DMF (2.93 mL) and cooled to 0° C. Ethyl N-[(6-bromopyridin-2-yl)methyl]glycinate (200 mg, 0.73 mmol) was added and the solution was stirred for thirty minutes at 0° C. Benzyl chloroformate (0.11 mL, 0.73 mmol) was added and the solution was heated at 50° C. and allowed to stir until completion. The reaction was diluted with ethyl acetate, washed with water, dried over magnesium sulfate, filtered and concentrated. The crude mixture was purified by silica gel chromatography to yield the title compound.
Calc'd for $C_{18}H_{20}BrN_2O_4$ [M+H]$^+$: 407. Found: 407.

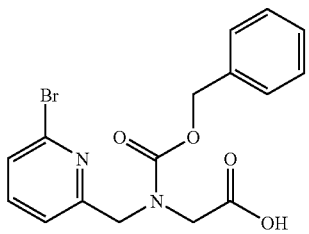 [SMILES: O=C(O)CN(Cc1cccc(Br)n1)C(=O)OCc1ccccc1]

Step 3: N-[(Benzyloxy)carbonyl]-N-[(6-bromopyridin-2-yl)methyl]glycine

Ethyl N-[(benzyloxy)carbonyl]-N-[(6-bromopyridin-2-yl)methyl]glycinate (0.21 g, 0.52 mmol) was dissolved in methanol (5.1 mL) and tert-butanol (5.1 mL). Potassium hydroxide (2.6 mL, 2.60 mmol) was added and the reaction was heated at 60° C. for two hours. The reaction was made acidic with 1M hydrochloric acid and the product extracted with ethyl acetate. The organic layer was then dried over magnesium sulfate, filtered and concentrated. The product was used without further purification to yield the title compound.

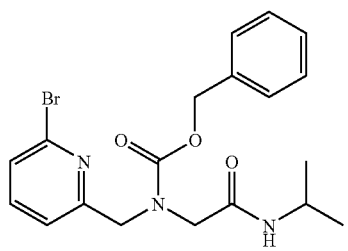 [SMILES: CC(C)NC(=O)CN(Cc1cccc(Br)n1)C(=O)OCc1ccccc1]

Step 4: Benzyl[(6-bromopyridin-2-yl)methyl][2-(isopropylamino)-2-oxoethyl]carbamate N-[(Benzyloxy)carbonyl]-N-[(6-bromopyridin-2-yl)methyl]glycine (0.16 g, 0.42 mmol) was dissolved in DMF (2.1 mL) and 1-(3-dimethylaminopropyl)-3-ethylcarbodiimide hydrochloride (0.081 g, 0.42 mmol) and 1-hydroxybenzotriazole hydrate (0.066 g, 0.43 mmol) were added. Isopropyl amine (0.025 g, 0.42 mmol) was added and the reaction was stirred overnight. The reaction was diluted with ethyl acetate, washed with water, dried over magnesium sulfate, filtered and concentrated. The crude residue was purified by reverse phase HPLC (10-100% acetonitrile/water+0.05% TFA modifier) to yield the title compound.
Calc'd for $C_{19}H_{23}BrN_3O_3$ [M+H]$^+$: 420. Found: 420.

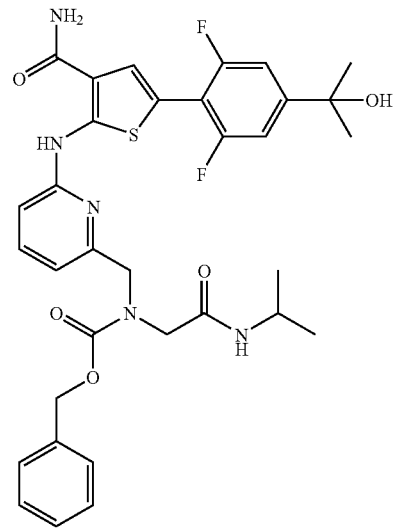 [SMILES: CC(C)NC(=O)CN(Cc1cccc(Nc2sc(-c3c(F)cc(C(C)(C)O)cc3F)cc2C(N)=O)n1)C(=O)OCc1ccccc1]

Step 5: Benzyl{[6-({3-(aminocarbonyl)-5-[2,6-difluoro-4-(1-hydroxy-1-methylethyl)phenyl]-2-thienyl}amino)pyridin-2-yl]methyl}[2-(isopropylamino)-2-oxoethyl]carbamate The title compound was prepared by using the procedure described in Example 1 with 2-amino-5-[2,6-difluoro-4-(1-hydroxy-1-methylethyl)phenyl]thiophene-3-carboxamide (0.92 g, 0.30 mmol) and benzyl[(6-bromopyridin-2-yl)methyl][2-(isopropylamino)-2-oxoethyl]carbamate (0.12 g, 0.30 mmol) as the starting materials.
Calc'd for $C_{33}H_{36}FN_5O_5S$ [M+H]$^+$: 652. Found: 652.

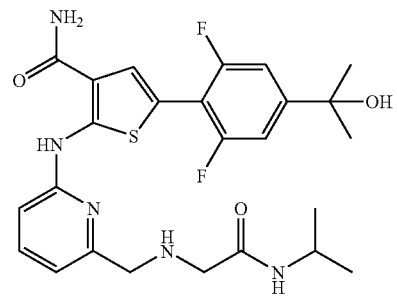 [SMILES: CC(C)NC(=O)CNCc1cccc(Nc2sc(-c3c(F)cc(C(C)(C)O)cc3F)cc2C(N)=O)n1]

Step 6: 5-[2,6-Difluoro-4-(1-hydroxy-1-methylethyl)phenyl]-2-{[6-({[2-(isopropylamino)-2-oxoethyl]amino}methyl)pyridin-2-yl]amino}thiophene-3-carboxamide Benzyl{[6-({3-(aminocarbonyl)-5-[2,6-difluoro-4-(1-hydroxy-1-methylethyl)phenyl]-2-thienyl}amino)pyridin-2-yl]methyl}[2-(isopropylamino)-2-oxoethyl]carbamate (83 mg, 0.13 mmol) was dissolved in methanol. Palladium on carbon (0.68 mg, 6.4 µmol) was added and a hydrogen balloon was placed on top. The solution was evacuated and then charged with hydrogen several times. The reaction was stirred for 3 hours. The solution was filtered through celite and concentrated. The crude residue was purified by reverse phase HPLC (10-100% acetonitrile/water+0.05% TFA modifier) to yield the title compound.
Calc'd for $C_{25}H_{30}F_2N_5O_3S$ [M+H]$^+$: 518. Found: 518.

Example 180

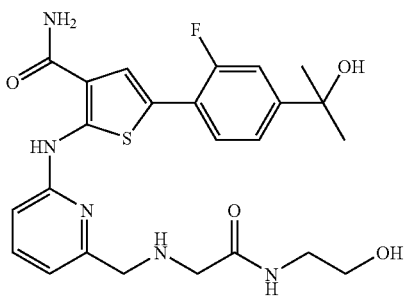 [SMILES: CC(C)(O)c1ccc(-c2cc(C(N)=O)c(Nc3cccc(CNCC(=O)NCCO)n3)s2)c(F)c1]

5-[2-Fluoro-4-(1-hydroxy-1-methylethyl)phenyl]-2-({6-[({2-[(2-hydroxyethyl)amino]-2-oxoethyl}amino)methyl]pyridin-2-yl}amino)thiophene-3-carboxamide

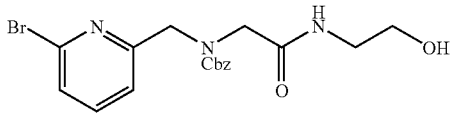 [SMILES: O=C(CN(Cc1cccc(Br)n1)C(=O)OCc1ccccc1)NCCO]

Step 1: Benzyl[(6-bromopyridin-2-yl)methyl]{2-[(2-hydroxyethyl)amino]-2-oxoethyl}carbamate A mixture of N-[(benzyloxy)carbonyl]-N-[(6-bromopyridin-2-yl)methyl]glycine (Example 179, Step 3) (112 mg, 0.295 mmol), 2-aminoethanol (18 μL, 0.295 mmol), HOBt (59 mg, 0.325 mmol) and PS-CDI (586 mg, 0.732 mmol) in DCM (4.0 mL) was irradiated in the microwave at 100° C. for 5 min. To this mixture, MP-isocyanate (967 mg, 1.22 mmol), PS-trisamine (393 mg, 1.34 mmol) and DCM (5.0 mL) were added and irradiated in the microwave at 100° C. for 10 min. The reaction mixture was filtered, washed with DCM and the filtrate was concentrated in vacuo to afford the title compound as a clear oil.

Calc'd for $C_{18}H_{21}BrN_3O_4$ [M+H]$^+$: 422. Found: 422.

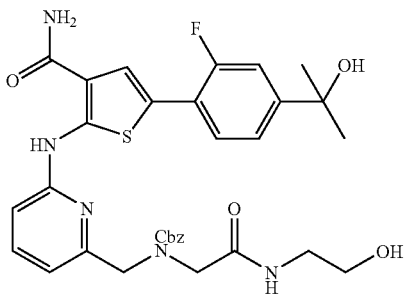 [SMILES: CC(C)(O)c1ccc(-c2cc(C(N)=O)c(Nc3cccc(CN(CC(=O)NCCO)C(=O)OCc4ccccc4)n3)s2)c(F)c1]

Step 2: Benzyl{[6-({3-(aminocarbonyl)-5-[2-fluoro-4-(1-hydroxy-1-methylethyl)phenyl]-2-thienyl}amino)pyridin-2-yl]methyl}{2-[(2-hydroxyethyl)amino]-2-oxoethyl}carbamate The title compound was prepared as described in Example 1 using 2-amino-5-[2-fluoro-4-(1-hydroxy-1-methylethyl) phenyl]thiophene-3-carboxamide (50 mg, 0.17 mmol) and benzyl[(6-bromopyridin-2-yl)methyl]{2-[(2-hydroxyethyl)amino]-2-oxoethyl}carbamate (110 mg, 0.26 mmol) as starting materials.

Calc'd for $C_{32}H_{35}FN_5O_6S$ [M+H]$^+$: 635. Found: 635.

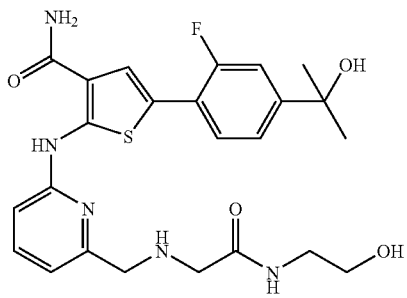 [SMILES: CC(C)(O)c1ccc(-c2cc(C(N)=O)c(Nc3cccc(CNCC(=O)NCCO)n3)s2)c(F)c1]

Step 3: 5-[2-Fluoro-4-(1-hydroxy-1-methylethyl)phenyl]-2-({6-[({2-[(2-hydroxyethyl)amino]-2-oxoethyl}amino)methyl]pyridin-2-yl}amino)thiophene-3-carboxamide The title compound was prepared as described in Example 179, Step 6 using benzyl{([6-({3-(aminocarbonyl)-5-[2-fluoro-4-(1-hydroxy-1-methylethyl)phenyl]-2-thienyl}amino)pyridin-2-yl]methyl}{2-[(2-hydroxyethyl)amino]-2-oxoethyl}carbamate (22 mg, 0.035 mmol) as starting material.

Calc'd for $C_{24}H_{29}FN_5O_4S$ [M+H]$^+$: 502. Found: 502.

Example 181

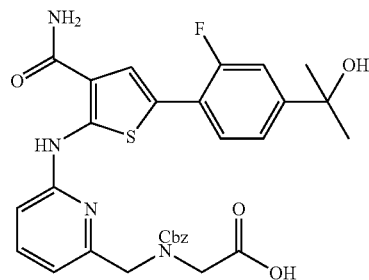 [SMILES: CC(C)(O)c1ccc(-c2cc(C(N)=O)c(Nc3cccc(CN(CC(=O)O)C(=O)OCc4ccccc4)n3)s2)c(F)c1]

Step 1: {{[6-({3-(Aminocarbonyl)-5-[2-fluoro-4-(1-hydroxy-1-methylethyl)phenyl]-2-thienyl}amino)pyridin-2-yl]methyl}[(benzyloxy)carbonyl]amino}acetic acid The title compound was prepared as described in Example 1 with 2-amino-5-[2-fluoro-4-(1-hydroxy-1-methylethyl)phenyl]thiophene-3-carboxamide (500 mg, 1.70 mmol) and N-[(benzyloxy)carbonyl]-N-[(6-bromopyridin-2-yl)methyl]glycine (Example 179, Step 3) (644 mg, 1.70 mmol).

Calc'd for $C_{30}H_{30}FN_4O_6S$ [M+H]$^+$: 593. Found: 593.

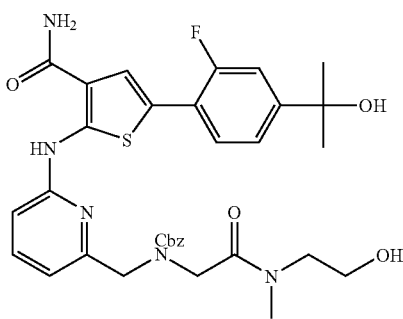 [SMILES: CN(CCO)C(=O)CN(Cc1cccc(Nc2sc(-c3ccc(C(C)(C)O)cc3F)cc2C(N)=O)n1)C(=O)OCc1ccccc1]

Step 2: Benzyl{[6-({3-(aminocarbonyl)-5-[2-fluoro-4-(1-hydroxy-1-methylethyl)phenyl]-2-thienyl}amino)pyridin-2-yl]methyl}{2-[(2-hydroxyethyl)(methyl)amino]-2-oxoethyl}carbamate A mixture of PS-CDI (152 mg, 0.19 mmol), HOBt (14 mg, 0.091 mmol), {{[6-({3-(Aminocarbonyl)-5-[2-fluoro-4-(1-hydroxy-1-methylethyl)phenyl]-2-thienyl}amino)pyridin-2-yl]methyl}[(benzyloxy)carbonyl]amino}acetic acid (45 mg, 0.076 mmol) and 2-(methylamino)ethanol (7.0 mg, 0.091 mmol) in 2:1 mixture of DCM (1.6 mL) and DMF (0.8 mL) was heated to 100° C. under the microwave irradiation for 5 min. Upon cooling, MP-isocyanate (241 mg, 0.30 mmol), PS-trisamine (89 mg, 0.30 mmol) and 1 mL DCM were added to a reaction mixture and heated to 100° C. under the microwave irradiation for 10 min. The reaction mixture was filtered, washed with DCM, and concentrated in vacuo to afford the title compound.

Calc'd for $C_{33}H_{37}FN_5O_6S$ [M+H]$^+$: 650. Found: 650.

Additional examples were prepared using procedures similar to those described in the above examples and are illustrated in the following table.

TABLE 11

| Example # | Structure | Compound Name | Characterization |
|---|---|---|---|
| 182 | 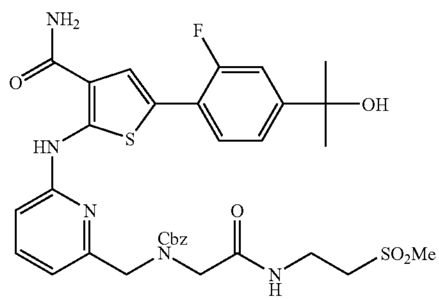 [SMILES: CC(C)(O)c1ccc(-c2cc(C(N)=O)c(Nc3cccc(CN(CC(=O)NCCS(C)(=O)=O)C(=O)OCc4ccccc4)n3)s2)c(F)c1] | benzyl{[6-({3-(aminocarbonyl)-5-[2-fluoro-4-(1-hydroxy-1-methylethyl)phenyl]-2-thienyl}amino)pydin-2-yl]methyl}(2-{[2-(methylsulfonyl)ethyl]amino}-2-oxoethyl)carbamate | Calc'd [M + H]$^+$: 698, Found: 698 |
| 183 | 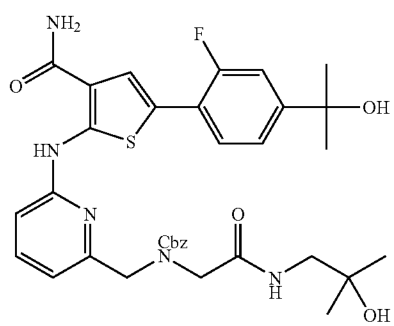 [SMILES: CC(C)(O)CNC(=O)CN(Cc1cccc(Nc2sc(-c3ccc(C(C)(C)O)cc3F)cc2C(N)=O)n1)C(=O)OCc1ccccc1] | benzyl{[6-({3-(aminocarbonyl)-5-[2-fluoro-4-(1-hydroxy-1-methylethyl)phenyl]-2-thienyl}amino)pyridin-2-yl]methyl}{2-[(2-hydroxy-2-methylpropyl)amino]-2-oxoethyl}carbamate | Calc'd [M + H]$^+$: 664, Found: 664 |
| 184 | 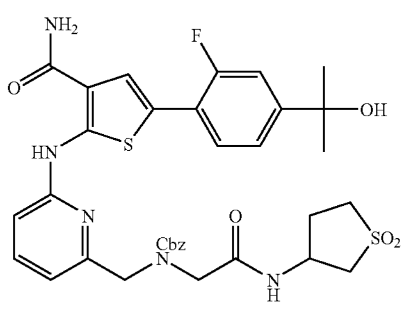 [SMILES: CC(C)(O)c1ccc(-c2cc(C(N)=O)c(Nc3cccc(CN(CC(=O)NC4CCS(=O)(=O)C4)C(=O)OCc4ccccc4)n3)s2)c(F)c1] | benzyl{[6-({3-(aminocarbonyl)-5-[2-fluoro-4-(1-hydroxy-1-methylethyl)phenyl]-2-thienyl}amino)pyridin-2-yl]methyl}{2-[(1,1-dioxidotetrahydro-3-thienyl)amino]-2-oxoethyl}carbamate | Calc'd [M + H]$^+$: 710, Found: 710 |

TABLE 11-continued

| Example # | Structure | Compound Name | Characterization |
|---|---|---|---|
| 185 | 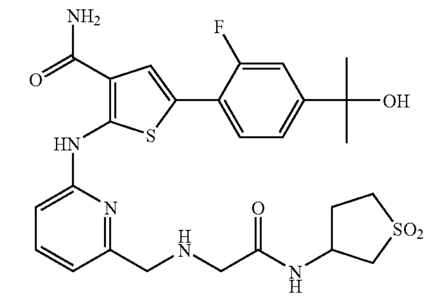 [SMILES: CC(C)(O)c1ccc(-c2cc(C(N)=O)c(Nc3cccc(CNCC(=O)NC4CCS(=O)(=O)C4)n3)s2)c(F)c1] | 2-({6-[({2-[(1,1-dioxidotetrahydro-3-thienyl)amino]-2-oxoethyl}amino)methyl]pyridin-2-yl}amino)-5-[2-fluoro-4-(1-hydroxy-1-methylethyl)phenyl]thiophene-3-carboxamide | Calc'd [M + H]⁺: 576, Found: 576 |
| 186 | 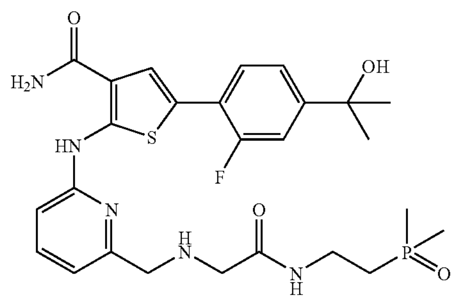 [SMILES: CC(C)(O)c1ccc(-c2cc(C(N)=O)c(Nc3cccc(CNCC(=O)NCCP(C)(C)=O)n3)s2)c(F)c1] | 2-[(6-{[(2-{[2-(dimethylphosphoryl)ethyl]amino}-2-oxoethyl)amino]methyl}pyridin-2-yl)amino]-5-[2-fluoro-4-(1-hydroxy-1-methylethyl)phenyl]thiophene-3-carboxamide | Calc'd [M + H]⁺: 562, Found: 562 |

Example 187

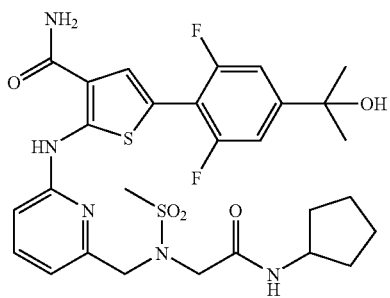 [SMILES: CC(C)(O)c1cc(F)c(-c2cc(C(N)=O)c(Nc3cccc(CN(CC(=O)NC4CCCC4)S(C)(=O)=O)n3)s2)c(F)c1]

2-[(6-{[[2-(Cyclopentylamino)-2-oxoethyl](methylsulfonyl)amino]methyl}pyridin-2-yl)amino]-5-[2,6-difluoro-4-(1-hydroxy-1-methylethyl)phenyl]thiophene-3-carboxamide

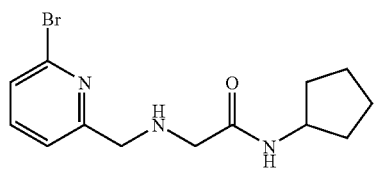 [SMILES: O=C(CNCc1cccc(Br)n1)NC1CCCC1]

Step 1: $N^2$-[(6-Bromopyridin-2-yl)methyl]-N-cyclopentylglycinamide

The title compound was prepared by using the procedure listed in Example 47, Step 7 with 6-bromopyridine-2-carbaldehyde (1.0 g, 5.38 mmol) and N-cyclopentylglycinamide hydrochloride (0.96 g, 5.38 mmol) as the starting materials.

$^1$H NMR (600 MHz, CDCl$_3$): δ 7.52 (t, J=9.6 Hz, 1H), 7.39 (d, J=9.6 Hz, 1H), 7.21 (bs, 1H), 7.17 (d, J=9.0 Hz, 1H), 4.23 (sext, J=8.4 Hz, 1H), 3.83 (s, 2H), 3.26 (s, 2H), 1.98 (sext, J=8.4 Hz, 1H), 1.65 (m, 6H), 1.41 (sext, J=6.0 Hz, 2H).

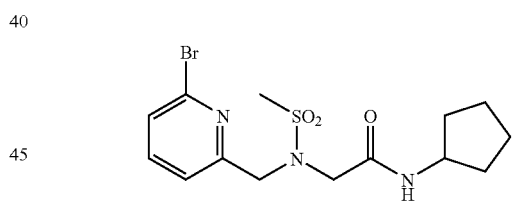

Step 2: $N^2$-[(6-Bromopyridin-2-yl)methyl]-N-cyclopentyl-$N^2$-(methylsulfonyl)glycinamide $N^2$-[(6-Bromopyridin-2-yl)methyl]-N-cyclopentylglycinamide (0.25 g, 0.80 mmol) was dissolved in dichloromethane (3.2 mL) and triethylamine (0.34 mL, 2.4 mmol) was added. The reaction was cooled to 0° C. and methanesulfonyl chloride (0.069 mL, 0.88 mmol) was added and the reaction was allowed to warm to room temperature. The solution was diluted with ethyl acetate, washed with water, dried over magnesium sulfate, filtered and concentrated. The crude mixture was purified by silica gel chromatography to yield the title compound.

Calc'd for C$_{14}$H$_{21}$BrN$_3$O$_3$S [M+H]⁺: 390. Found: 390.

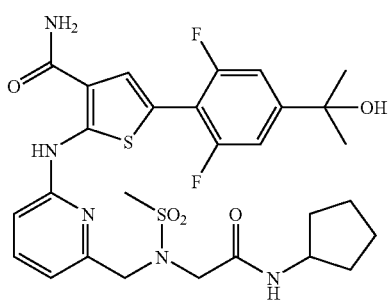 [SMILES: CC(C)(O)c1cc(F)c(-c2cc(C(N)=O)c(Nc3cccc(CN(CC(=O)NC4CCCC4)S(C)(=O)=O)n3)s2)c(F)c1]

Step 3: 2-[(6-{[[2-(Cyclopentylamino)-2-oxoethyl](methylsulfonyl)amino]methyl}pyridin-2-yl)amino]-5-[2,6-difluoro-4-(1-hydroxy-1-methylethyl)phenyl]thiophene-3-carboxamide The title compound was prepared as described in Example 1 using N²-[(6-bromopyridin-2-yl)methyl]-N-cyclopentyl-N²-(methylsulfonyl)glycinamide (0.15 g, 0.38 mmol) and 2-amino-5-[2,6-difluoro-4-(1-hydroxy-1-methylethyl)phenyl]thiophene-3-carboxamide (0.12 g, 0.38 mmol) as the starting materials.

Calc'd for $C_{28}H_{34}F_2N_5O_5S_2$ [M+H]⁺: 622. Found: 622.

Example 188

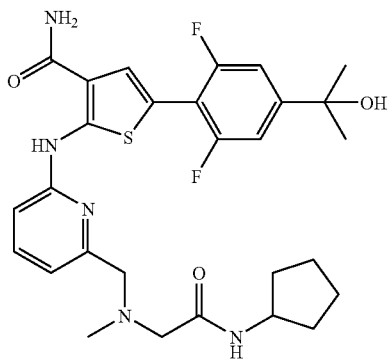 [SMILES: CN(CC(=O)NC1CCCC1)Cc1cccc(Nc2sc(-c3c(F)cc(C(C)(C)O)cc3F)cc2C(N)=O)n1]

2-[(6-{[[2-(Cyclopentylamino)-2-oxoethyl](methyl)amino]methyl}pyridin-2-yl)amino]-5-[2,6-difluoro-4-(1-hydroxy-1-methylethyl)phenyl]thiophene-3-carboxamide

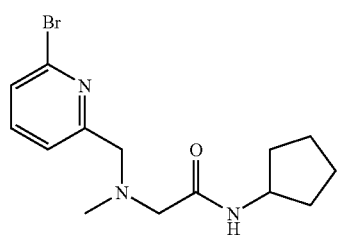 [SMILES: CN(CC(=O)NC1CCCC1)Cc1cccc(Br)n1]

Step 1: N²-[(6-Bromopyridin-2-yl)methyl]-N-cyclopentyl-N²-methylglycinamide

N²-[(6-Bromopyridin-2-yl)methyl]-N-cyclopentylglycinamide (Example 187, Step 1) (0.33 g, 1.06 mmol) was dissolved in dichloromethane (5.30 mL) and formaldehyde (0.087 mL, 1.17 mmol) and acetic acid (0.12 mL, 2.12 mmol) were added. The reaction was stirred for 45 minutes and sodium triacetoxyborohydride (0.36 g, 1.70 mmol) was added. Once complete, the reaction was then quenched with water and extracted with ethyl acetate. The organic layer was dried over magnesium sulfate, filtered and concentrated. The crude mixture was purified by silica gel chromatography to yield the title compound.

Calc'd for $C_{14}H_{21}BrN_3O$ [M+H]⁺: 326. Found: 326.

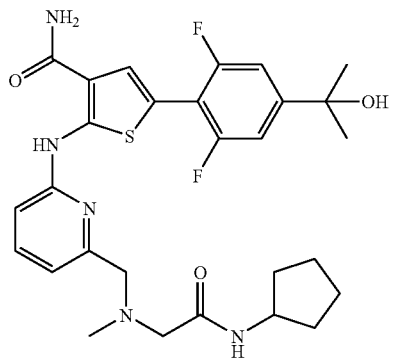 [SMILES: CN(CC(=O)NC1CCCC1)Cc1cccc(Nc2sc(-c3c(F)cc(C(C)(C)O)cc3F)cc2C(N)=O)n1]

Step 2: 2-[(6-{[[2-(Cyclopentylamino)-2-oxoethyl](methyl)amino]methyl}pyridin-2-yl)amino]-5-[2,6-difluoro-4-(1-hydroxy-1-methylethyl)phenyl]thiophene-3-carboxamide The title compound was prepared by using the procedure listed in Example 1 with 2-amino-5-[2,6-difluoro-4-(1-hydroxy-1-methylethyl)phenyl]thiophene-3-carboxamide (0.12 g, 0.38 mmol) and N²-[(6-bromopyridin-2-yl)methyl]-N-cyclopentyl-N²-methylglycinamide (0.11 g, 0.34 mmol) as the starting materials.

Calc'd for $C_{28}H_{34}FN_5O_3S$ [M+H]⁺: 558. Found: 558.

Example 189

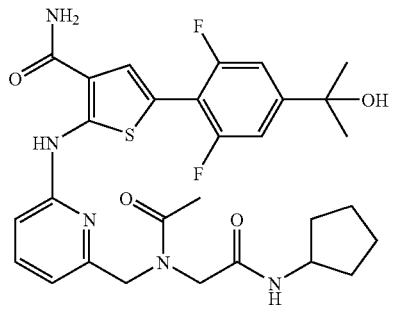 [SMILES: CC(=O)N(CC(=O)NC1CCCC1)Cc1cccc(Nc2sc(-c3c(F)cc(C(C)(C)O)cc3F)cc2C(N)=O)n1]

2-{[6-({Acetyl[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide

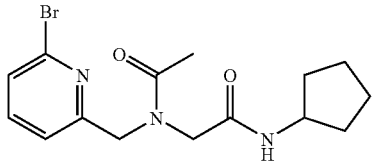 [SMILES: CC(=O)N(CC(=O)NC1CCCC1)Cc1cccc(Br)n1]

Step 1: N²-Acetyl-N²-[(6-bromopyridin-2-yl)methyl]-N-cyclopentylglycinamide

N²-[(6-Bromopyridin-2-yl)methyl]-N-cyclopentylglycinamide (Example 187, Step 1) (0.25 g, 0.80 mmol) was dissolved in dichloromethane (3.2 mL) and triethylamine (0.34 mL, 2.4 mmol) was added and the reaction was cooled to 0° C. Acetyl chloride (0.06 mL, 0.88 mmol) was added and the reaction was allowed to warm to room temperature and stir to completion. The solution was diluted with dichloromethane, washed with water, dried over magnesium sulfate, filtered and concentrated. The crude residue was purified by reverse phase HPLC to yield the title compound.

Calc'd for $C_{15}H_{21}BrN_3O_2$ [M+H]⁺: 354. Found: 354.

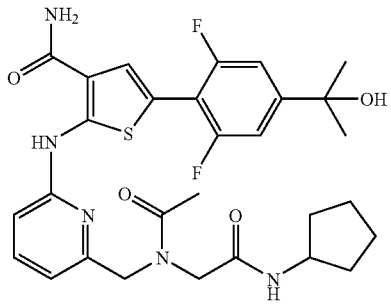 [SMILES: CC(=O)N(CC(=O)NC1CCCC1)Cc1cccc(Nc2sc(-c3c(F)cc(C(C)(C)O)cc3F)cc2C(N)=O)n1]

Step 2: 2-{[6-({Acetyl[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide The title compound was prepared using the procedure described in Example 1 with 2-amino-5-[2,6-difluoro-4-(1-hydroxy-1-methylethyl)phenyl]thiophene-3-carboxamide (0.12 g, 0.38 mmol) and N²-acetyl-N²-[(6-bromopyridin-2-yl)methyl]-N-cyclopentylglycinamide (0.14 g, 0.38 mmol) as the starting materials.

Calc'd for $C_{29}H_{34}FN_5O_4S$ [M+H]⁺: 586. Found: 586.

Example 190

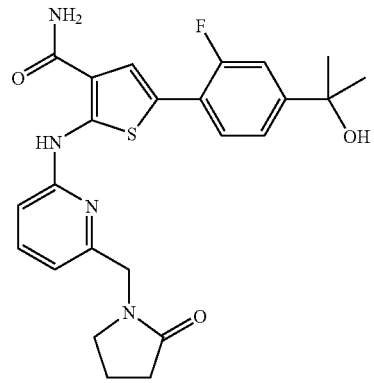 [SMILES: CC(C)(O)c1ccc(-c2cc(C(N)=O)c(Nc3cccc(CN4CCCC4=O)n3)s2)c(F)c1]

5-[2-Fluoro-4-(1-hydroxy-1-methylethyl)phenyl]-2-({6-[(2-oxopyrrolidin-1-yl)methyl]pyridine-2-yl}amino)thiophene-3-carboxamide

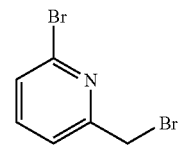

Step 1: 2-Bromo-6-(bromomethyl)pyridine

A solution of (6-bromopyridin-2-yl)methanol (25 g, 133 mmol) in dichloromethane (200 ml) was charged with triphenylphosphene (41.8 g, 160 mmol). The reaction was cooled to 0° C. and N-bromosuccinimide (26 g, 146 mmol) was added over one minute. After 1 hour, the reaction was concentrated in vacuo and directly purified via silica gel chromatography to afford the title compound.

¹H NMR (600 MHz, CDCl₃): δ 7.55 (t, 1H), 7.40 (dd, 2H), 4.48 (s, 2H).

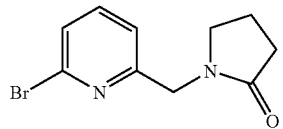 [SMILES: O=C1CCCN1Cc1cccc(Br)n1]

Step 2: 1-[(Bromopyridin-2-yl)methyl]pyrrolidin-2-one

Sodium hydride (199 mg, 4.98 mmol) was suspended in DMF (16.1 mL) and cooled to 0° C. 2-Pyrrolidone (0.17 g, 1.99 mmol) was added and the solution was stirred for 30 minutes, followed by the addition of 2-bromo-6-(bromomethyl)pyridine (0.50 mg, 1.99 mmol). The reaction was heated to 50° C. for two hours, cooled to room temperature, quenched with water and extracted multiple times with ethyl acetate. The combined organic layers were dried with magnesium sulfate, filtered and concentrated. The crude mixture was purified by silica gel chromatography to yield the title compound.

Calc'd for $C_{10}H_{12}BrN_2O$ [M+H]⁺: 256. Found: 256.

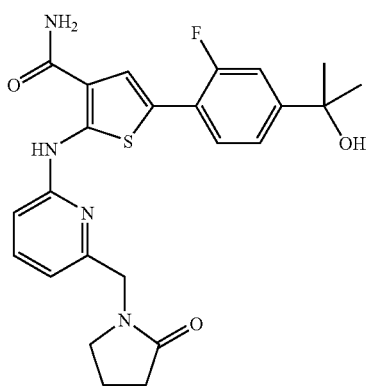 [SMILES: CC(C)(O)c1ccc(-c2cc(C(N)=O)c(Nc3cccc(CN4CCCC4=O)n3)s2)c(F)c1]

Step 3: 5-[2-Fluoro-4-(1-hydroxy-1-methylethyl)phenyl]-2-({6-[(2-oxopyrrolidin-1-yl)methyl]pyridine-2-yl}amino)thiophene-3-carboxamide The title compound was prepared by using the procedure listed in Example 1 with 2-amino-5-[2-fluoro-4-(1-hydroxy-1-methylethyl)phenyl]thiophene-3-carboxamide (0.14 g, 0.48 mmol) and 1-[(bromopyridin-2-yl)methyl]pyrrolidin-2-one (0.12 g, 0.47 mmol) as starting materials.

Calc'd for $C_{24}H_{26}FN_4O_3S$ [M+H]$^+$: 469. Found: 469.

Example 191

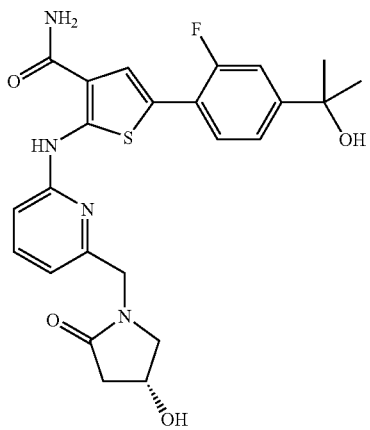 [SMILES: CC(C)(O)c1ccc(-c2cc(C(N)=O)c(Nc3cccc(CN4C[C@H](O)CC4=O)n3)s2)c(F)c1]

5-[2-Fluoro-4-(1-hydroxy-1-methylethyl)phenyl]-2-[(6-{[(4R)-4-hydroxy-2-oxopyrrolidin-1-yl]methyl}pyridin-2-yl)amino]thiophene-3-carboxamide

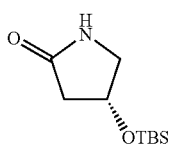 [SMILES: CC(C)(C)[Si](C)(C)O[C@H]1CNC(=O)C1]

Step 1: (4R)-4-{[tert-Butyl(dimethyl)silyl]oxy}pyrrolidin-2-one

4-Hydroxy-2-pyrrolidone (1.00 g, 9.89 mmol) was suspended in DMF (25 mL) and cooled to 0° C. Imidazole (1.01 g, 14.84 mmol) and TBS—Cl (1.57 g, 10.39 mmol) were added and the reaction was then warmed to room temperature. After 30 minutes the reaction was poured into water (~50 mL) and the resulting white precipitate was collected by filtration, dried in an oven, and used without further purification.

$^1$H NMR (600 MHz, CDCl$_3$): δ 5.80 (bs, 1H), 4.54 (sept, J=3.6 Hz, 1H), 3.57 (dd, J=9.6, 6.0 Hz, 1H), 3.22 (dd, J=10.2, 3.6 Hz, 1H), 2.52 (dd, J=16.8, 6.6 Hz, 1H), 2.25 (dd, J=16.8, 3.6 Hz, 1H), 0.86 (s, 9H), 0.49 (s, 6H).

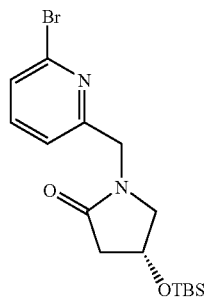 [SMILES: CC(C)(C)[Si](C)(C)O[C@@H]1CC(=O)N(Cc2cccc(Br)n2)C1]

Step 2: (4R)-1-[(6-Bromopyridin-2-yl)methyl]-4-{[tert-butyl(dimethyl)silyl]oxy}pyrrolidin-2-one (4R)-4-{[tert-Butyl(dimethyl)silyl]oxy}pyrrolidin-2-one (1.08 g, 5.02 mmol) was dissolved in tetrahydrofuran (21.13 mL) and cooled to 0° C. Sodium hydride (0.23 g, 5.86 mmol) was added and the solution was allowed to stir for 15 minutes. In a separate flask, 2-bromo-6-(bromomethyl)pyridine (Example 190, Step 1) (1.05 g, 4.18 mmol) was dissolved in THF (10.57 mL) and cooled to 0° C., and added dropwise to the reaction mixture. The solution was stirred for 15 minutes at 0° C. and then at room temperature. The reaction mixture was quenched with water, and the product extracted with ethyl acetate. The combined organic layers were dried over magnesium sulfate, filtered and concentrated to afford the title compound which was used without further purification.

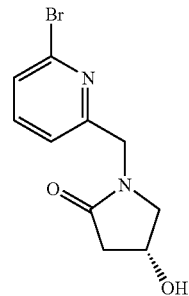 [SMILES: O=C1C[C@@H](O)CN1Cc1cccc(Br)n1]

Step 3: (4R)-1-[(6-Bromopyridin-2-yl)methyl]-4-hydroxypyrrolidin-2-one (4R)-1-[(6-Bromopyridin-2-yl)methyl]-4-{[tert-butyl(dimethyl)silyl]oxy}pyrrolidin-2-one was dissolved in tetrahydrofuran (33.4 mL), and tetrabutylammonium fluoride (5.84 mL, 5.84 mmol) was added dropwise and the solution stirred at ambient temperature for five minutes. The reaction mixture was concentrated and purified by silica gel chromatography to yield the title compound.

¹H NMR (600 MHz, CDCl₃): δ 7.52 (t, J=7.8 Hz, 1H), 7.38 (d, J=7.8 Hz, 1H), 7.22 (d, J=7.8 Hz, 1H), 4.83 (d, J=16.2 Hz, 1H), 4.51 (m, 1H), 4.35 (d, J=16.2 Hz, 1H), 3.72 (dd, J=10.8, 4.8 Hz, 1H), 3.38 (d, J=11.4 Hz, 1H), 3.31 (m, 1H).

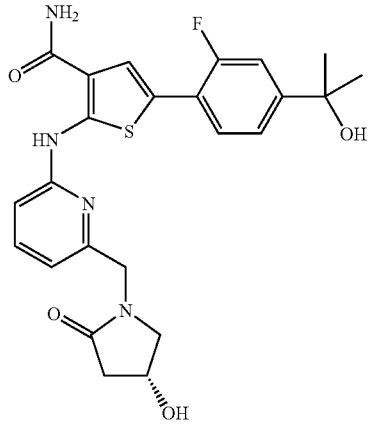 [SMILES: CC(C)(O)c1ccc(-c2cc(C(N)=O)c(Nc3cccc(CN4C[C@H](O)CC4=O)n3)s2)c(F)c1]

Step 4: 5-[2-Fluoro-4-(1-hydroxy-1-methylethyl)phenyl]-2-[(6-{[(4R)-4-hydroxy-2-oxopyrrolidin-1-yl]methyl}pyridin-2-yl)amino]thiophene-3-carboxamide The title compound was prepared as described in Example 1 using 2-amino-5-[2,6-difluoro-4-(1-hydroxy-1-methylethyl)phenyl]thiophene-3-carboxamide (0.16 g, 0.54 mmol) and (4R)-1-[(6-bromopyridin-2-yl)methyl]-4-hydroxypyrrolidin-2-one (0.14 g, 0.53 mmol) as the starting materials.

Calc'd for $C_{24}H_{26}FN_4O_4S$ [M+H]⁺: 485. Found: 485.

Additional examples were prepared using procedures similar to those described in the above examples and are illustrated in the following table.

TABLE 12

| Example # | Structure | Compound Name | Characterization |
|---|---|---|---|
| 192 | 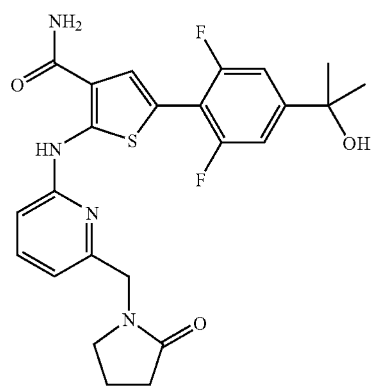 [SMILES: CC(C)(O)c1cc(F)c(-c2cc(C(N)=O)c(Nc3cccc(CN4CCCC4=O)n3)s2)c(F)c1] | 5-[2,6-Difluoro-4-(1-hydroxy-1-methylethyl)phenyl]-2-({6-[(2-oxopyrrolidin-1-yl)methyl]pyridine-2-yl}amino)thiophene-3-carboxamide | Calc'd [M + H]+: 487, Found: 487 |
| 193 | 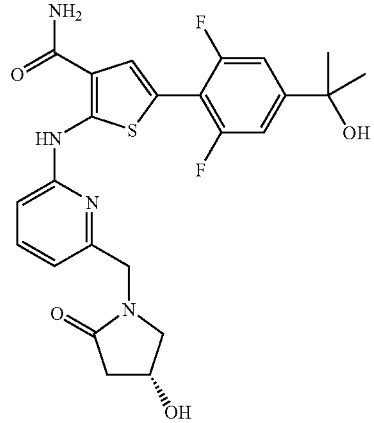 [SMILES: CC(C)(O)c1cc(F)c(-c2cc(C(N)=O)c(Nc3cccc(CN4C[C@H](O)CC4=O)n3)s2)c(F)c1] | 5-[2,6-difluoro-4-(1-hydroxy-1-methylethyl)phenyl]-2-[(6-{[(4R)-4-hydroxy-2-oxopyrrolidin-1-yl]methyl}pyridin-2-yl)amino]thiophene-3-carboxamide | Calc'd [M + H]+: 503, Found: 503 |

TABLE 12-continued

| Example # | Structure | Compound Name | Characterization |
|---|---|---|---|
| 194 | 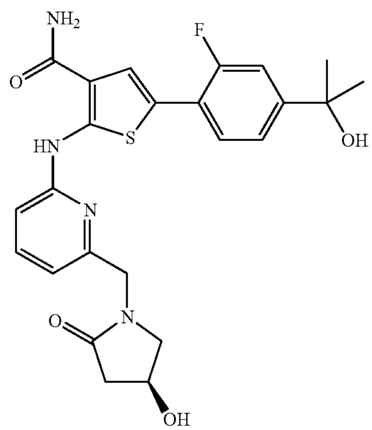 [SMILES: CC(C)(O)c1ccc(-c2cc(C(N)=O)c(Nc3cccc(CN4C[C@@H](O)CC4=O)n3)s2)c(F)c1] | 5-[2-fluoro-4-(1-hydroxy-1-methylethyl)phenyl]-2-[(6-{[(4S)-4-hydroxy-2-oxopyrrolidin-1-yl]methyl}pyridin-2-yl)amino]thiophene-3-carboxamide | Calc'd [M + H]+: 485, Found: 485 |
| 195 | 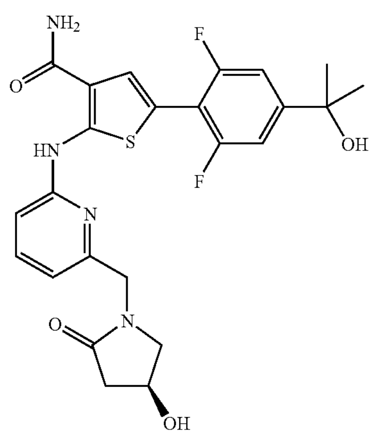 [SMILES: CC(C)(O)c1cc(F)c(-c2cc(C(N)=O)c(Nc3cccc(CN4C[C@@H](O)CC4=O)n3)s2)c(F)c1] | 5-[2,6-difluoro-4-(1-hydroxy-1-methylethyl)phenyl]-2-[(6-{[(4S)-4-hydroxy-2-oxopyrrolidin-1-yl]methyl}pyridin-2-yl)amino]thiophene-3-carboxamide | Calc'd [M + H]+: 503, Found: 503 |
| 196 | 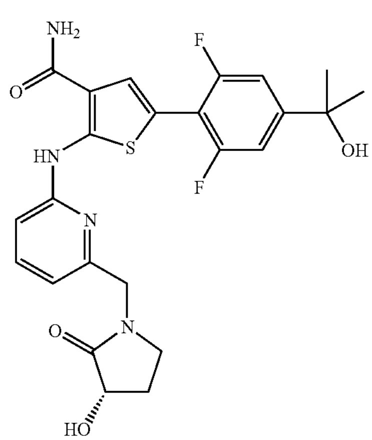 [SMILES: CC(C)(O)c1cc(F)c(-c2cc(C(N)=O)c(Nc3cccc(CN4CC[C@H](O)C4=O)n3)s2)c(F)c1] | 5-[2,6-difluoro-4-(1-hydroxy-1-methylethyl)phenyl]-2-[(6-{[(3S)-3-hydroxy-2-oxopyrrolidin-1-yl]methyl}pyridin-2-yl)amino]thiophene-3-carboxamide | Calc'd [M + H]+: 503, Found: 503 |

TABLE 12-continued

| Example # | Structure | Compound Name | Characterization |
|---|---|---|---|
| 197 | 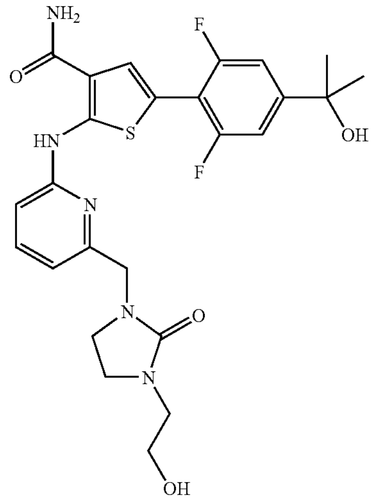 [SMILES: CC(C)(O)c1cc(F)c(-c2cc(C(N)=O)c(Nc3cccc(CN4CCN(CCO)C4=O)n3)s2)c(F)c1] | 5-[2,6-difluoro-4-(1-hydroxy-1-methylethyl)phenyl]-2-[(6-{[3-(2-hydroxyethyl)-2-oxoimidazolidin-1-yl]methyl}pyridin-2-yl)amino]thiophene-3-carboxamide | Calc'd [M + H]+: 532, Found: 532 |
| 198 | 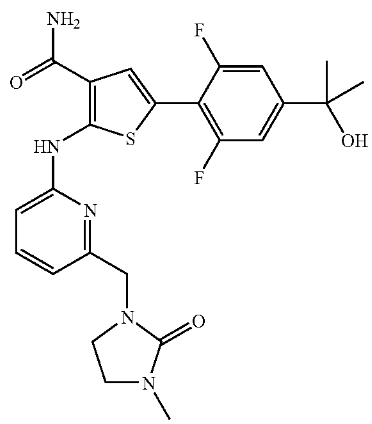 [SMILES: CN1CCN(Cc2cccc(Nc3sc(-c4c(F)cc(C(C)(C)O)cc4F)cc3C(N)=O)n2)C1=O] | 5-[2,6-difluoro-4-(1-hydroxy-1-methylethyl)phenyl]-2-({6-[(3-methyl-2-oxoimidazolidin-1-yl)methyl]pyridin-2-yl}amino)thiophene-3-carboxamide | Calc'd [M + H]+: 502, Found: 502 |
| 199 | 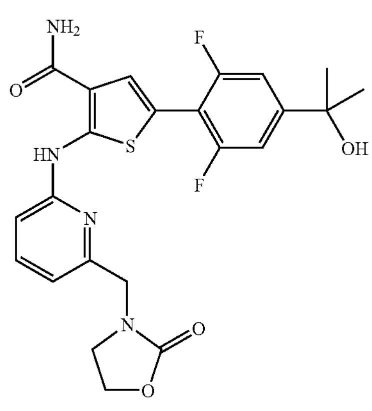 [SMILES: CC(C)(O)c1cc(F)c(-c2cc(C(N)=O)c(Nc3cccc(CN4CCOC4=O)n3)s2)c(F)c1] | 5-[2,6-difluoro-4-(1-hydroxy-1-methylethyl)phenyl]-2-({6-[(2-oxo-1,3-oxazolidin-3-yl)methyl]pyridin-2-yl}amino)thiophene-3-carboxamide | Calc'd [M + H]+: 489, Found: 489 |

TABLE 12-continued

| Example # | Structure | Compound Name | Characterization |
|---|---|---|---|
| 200 | 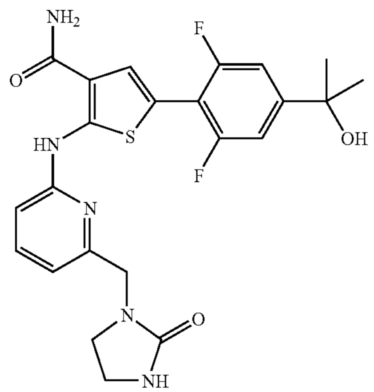 [SMILES: CC(C)(O)c1cc(F)c(-c2cc(C(N)=O)c(Nc3cccc(CN4CCNC4=O)n3)s2)c(F)c1] | 5-[2,6-difluoro-4-(1-hydroxy-1-methylethyl)phenyl]-2-({6-[(2-oxoimidazolidin-1-yl)methyl]pyridin-2-yl}amino)thiophene-3-carboxamide | Calc'd [M + H]+: 488, Found: 488 |
| 201 | 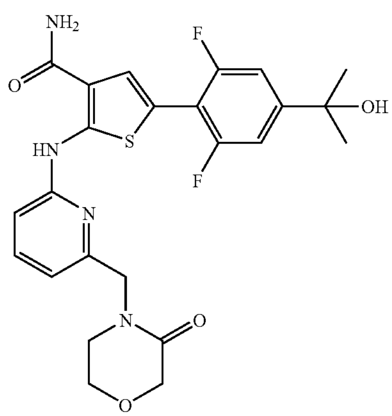 [SMILES: CC(C)(O)c1cc(F)c(-c2cc(C(N)=O)c(Nc3cccc(CN4CCOCC4=O)n3)s2)c(F)c1] | 5-[2,6-difluoro-4-(1-hydroxy-1-methylethyl)phenyl]-2-({6-[(3-oxomorpholin-4-yl)methyl]pyridin-2-yl}amino)thiophene-3-carboxamide | Calc'd [M + H]+: 503, Found: 503 |
| 202 | 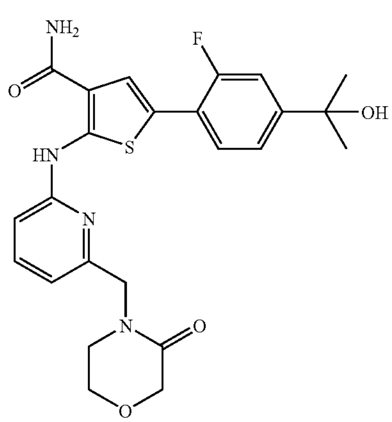 [SMILES: CC(C)(O)c1ccc(-c2cc(C(N)=O)c(Nc3cccc(CN4CCOCC4=O)n3)s2)c(F)c1] | 5-[2-fluoro-4-(1-hydroxy-1-methylethyl)phenyl]-2-({6-[(3-oxomorpholin-4-yl)methyl]pyridin-2-yl}amino)thiophene-3-carboxamide | Calc'd [M + H]+: 485, Found: 485 |

Example 203

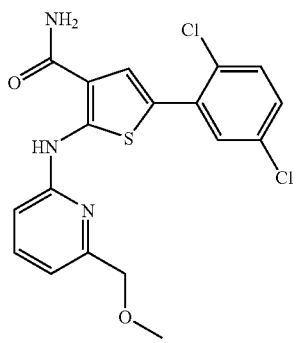 [SMILES: COCc1cccc(Nc2sc(-c3cc(Cl)ccc3Cl)cc2C(N)=O)n1]

5-(2,5-Dichlorophenyl)-2-{[6-(methoxymethyl)pyridin-2-yl]amino}thiophene-3-carboxamide The title compound was prepared as described in Example 1 using 2-bromo-6-(methoxymethyl)pyridine (105 mg, 0.520 mmol) (for preparation, see *Journal of Organic Chemistry* 1993, 58, 4389-97) and 2-amino-5-(2,5-dichlorophenyl)thiophene-3-carboxamide (152 mg, 0.530 mmol) as starting materials.

Calc'd for $C_{18}H_{16}N_3O_2S$ [M+H]$^+$: 408. Found: 408.

Example 204

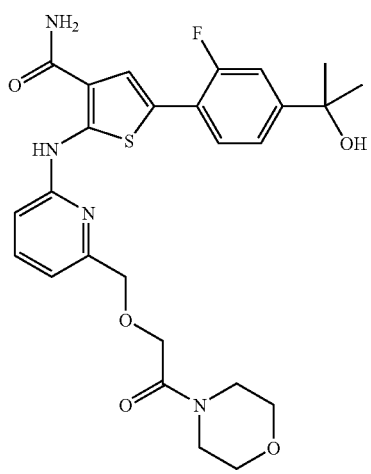 [SMILES: CC(C)(O)c1ccc(-c2cc(C(N)=O)c(Nc3cccc(COCC(=O)N4CCOCC4)n3)s2)c(F)c1]

5-[2-Fluoro-4-(1-hydroxy-1-methylethyl)phenyl]-2-({6-[(2-morpholin-4-yl-2-oxoethoxy)methyl]pyridin-2-yl}amino)thiophene-3-carboxamide

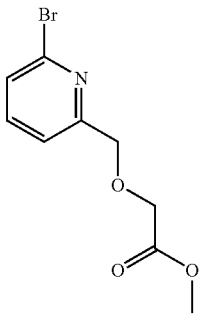

Step 1: Methyl[(6-bromopyridin-2-yl)methoxy]acetate

To a suspension of sodium hydride (0.50 g, 12.38 mmol) in N,N-dimethylformamide (20 mL) at 0° C. was added a mixture of methyl hydroxyacetate (1.0 g, 11.25 mmol) and 2-bromo-6-(bromomethyl)pyridine (Example 190, Step 1) (3.4 g, 13.5 mmol) dropwise. After stirring for 5 hours, the reaction was quenched with iso-propanol/methanol solution. The reaction mixture was poured onto iced water and extracted with ether. The organic phase was dried over MgSO$_4$, filtered and evaporated. The crude mixture was purified by silica gel column and eluted with ethyl acetate:petroleum ether (1:10) to afford the title compound. $^1$H NMR (400 MHz, CDCl$_3$): δ 7.55 (t, 1H), 7.48 (d, 1H), 7.39 (d, 1H), 4.71 (s, 2H), 4.22 (s, 2H), 3.77 (s, 3H).

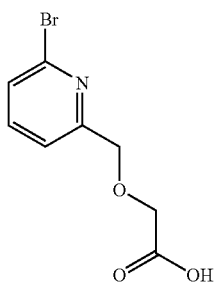 [SMILES: O=C(O)COCc1cccc(Br)n1]

Step 2: [(6-Bromopyridin-2-yl)methoxy]acetic acid

To a solution of methyl[(6-bromopyridin-2-yl)methoxy]acetate (2.5 g, 19.2 mmol) in methanol (50 mL) was added aqueous lithium hydroxide (1M) dropwise over 15 min at 0° C. The reaction mixture was allowed to warm to room temperature overnight. The organic solvent was removed in vacuum and the residual aqueous solution was extracted with Et$_2$O, and the aqueous phase was acidified to pH 2 with 1 N HCl. The aqueous phase was extracted with CH$_2$Cl$_2$ (3×100 mL). The combined organic extracts were dried and concentrated to afford the title compound.

$^1$H NMR (400 MHz CDCl$_3$): δ 7.59 (t, 1H), 7.44 (d, 1H), 7.38 (d, 1H), 4.76 (s, 2H), 4.29 (s, 2H).

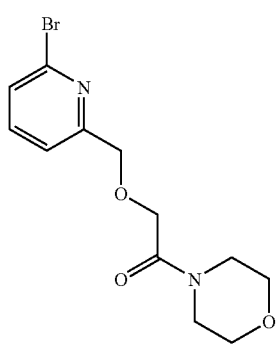 [SMILES: O=C(COCc1cccc(Br)n1)N1CCOCC1]

Step 3: 4-{[(6-Bromopyridin-2-yl)methoxy]acetyl}morpholine

To a solution of [(6-bromopyridin-2-yl)methoxy]acetic acid (1.6 g, 7.5 mmol) and morpholine (0.65 g, 7.5 mmol) in dichloromethane at 0° C. was added N-ethyl-N-isopropylpropan-2-amine (3.9 mL, 22.5 mmol), 1-hydroxybenzotriazole hydrate (1.5 g, 11.25 mmol) and 1-(3-dimethylaminopropyl)-3-ethylcarbodiimide hydrochloride (2.1 g, 11.25 mmol). The reaction mixture was stirred at room temperature overnight. The reaction solution was concentrated under reduced pressure, and the resulting residue was purified by silica gel column chromatography, eluting with ethyl acetate:hexanes (3:7) to afford the title compound.

$^1$H NMR (400 MHz CDCl$_3$): δ 7.58 (t, 1H), 7.44 (m, 1H), 7.42 (m, 1H), 4.68 (s, 2H), 4.30 (s, 2H), 3.69 (m, 4H), 3.63 (m, 2H), 3.52 (m, 2H).

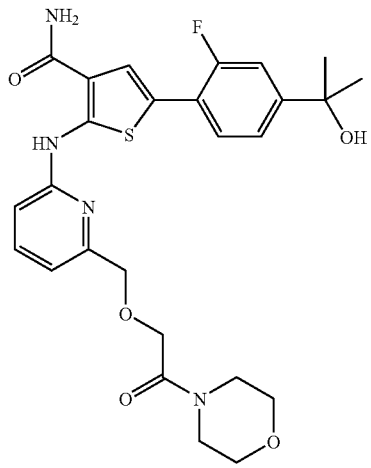 [SMILES: CC(C)(O)c1ccc(-c2cc(C(N)=O)c(Nc3cccc(COCC(=O)N4CCOCC4)n3)s2)c(F)c1]

Step 4: 5-[2-Fluoro-4-(1-hydroxy-1-methylethyl)phenyl]-2-({6-[(2-morpholin-4-yl-2-oxoethoxy)methyl]pyridin-2-yl}amino)thiophene-3-carboxamide The title compound was prepared as described in Example 1 with 2-amino-5-[2-fluoro-4-(1-hydroxy-1-methylethyl)phenyl]thiophene-3-carboxamide (0.12 g, 0.41 mmol) and 4-{[(6-bromopyridin-2-yl)methoxy]acetyl}morpholine (0.13 g, 0.40 mmol) as the starting materials.

Calc'd for C$_{26}$H$_{30}$FN$_4$O$_5$S [M+H]$^+$: 529. Found: 529.

Example 205

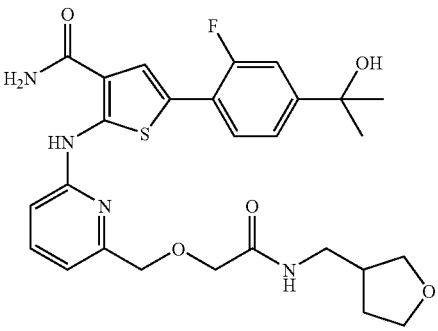 [SMILES: CC(C)(O)c1ccc(-c2cc(C(N)=O)c(Nc3cccc(COCC(=O)NCC4CCOC4)n3)s2)c(F)c1]

5-(2-Fluoro-4-(1-hydroxy-1-methylethyl)phenyl)-2-((6-((2-oxo-2-((tetrahydro-3-furanylmethyl)amino)ethoxy)methyl)-2-pyridinyl)amino)-3-thiophenecarboxamide

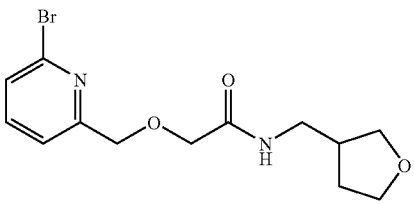 [SMILES: O=C(COCc1cccc(Br)n1)NCC1CCOC1]

Step 1: 2-((6-Bromo-2-pyridinyl)methoxy)-N-(tetrahydro-3-furanylmethyl)acetamide To a stirred solution of [(6-bromopyridin-2-yl)methoxy]acetic acid (Example 204, Step 2) (100 mg, 0.41 mmol) in THF (5 ml) was added (tetrahydrofuran-3-yl)methanamine (41 mg, 0.41 mmol), polystyrene-cyclohexylcarbodiimide (590 mg, 0.73 mmol) and 1-hydroxybenzatriazole monohydrate (69 mg, 0.45 mmol). After shaking overnight, macropourous-isocyanate (720 mg, 0.91 mmol) and polystyrene-trisamine (380 mg, 1.29 mmol) were added. After shaking overnight, the reaction mixture was filtered, washed with THF (1 ml), and dried in vacuo. Analytically pure material was obtained by purification by preparative HPLC Reverse phase (C-18), eluting with acetonitrile/water+0.05% TFA. Lyophilizing afforded the title compound as a TFA salt.

Calc'd for C$_{13}$H$_{18}$N$_2$O$_3$Br [M+H]$^+$: 330, 331. Found: 330, 331.

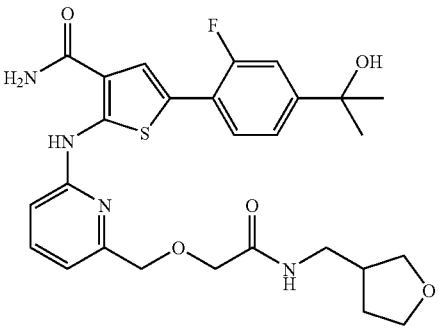 [SMILES: CC(C)(O)c1ccc(-c2cc(C(N)=O)c(Nc3cccc(COCC(=O)NCC4CCOC4)n3)s2)c(F)c1]

Step 2: 5-(2-Fluoro-4-(1-hydroxy-1-methylethyl) phenyl)-2-((6-((2-oxo-2-((tetrahydro-3-furanylmethyl)amino)ethoxy)methyl)-2-pyridinyl)amino)-3-thiophenecarboxamide To a solution of 2-((6-bromo-2-pyridinyl)methoxy)-N-(tetrahydro-3-furanylmethyl)acetamide (132 mg, 0.40 mmol) in t-amyl alcohol (1.3 ml) was added 2-amino-5-(2-fluoro-4-(1-hydroxy-1-methylethyl)phenyl)-3-thiophenecarboxamide (118 mg, 0.40 mmol), potassium carbonate (61 mg, 0.44 mmol), X-Phos (96 mg, 0.20 mmol) and tris(dibenzylideneacetone)dipalladium (37 mg, 0.04 mmol). The vial was capped, evacuated, and backfilled with argon. The reaction mixture was heated in a microwave at 120° C. for 20 min, cooled to ambient temperature, filtered, and concentrated in vacuo. Analytically pure material was obtained by preparative reverse phase HPLC(C-18), eluting with acetonitrile/water+0.05% TFA. Lyophilizing the desired fractions afforded the title compound as a TFA salt.

Calc'd for $C_{27}H_{32}FN_4O_5S$ [M+H]$^+$: 543. Found: 543.

Additional examples were prepared using procedures similar to those described in the above examples and are illustrated in the following table.

TABLE 13

| Example # | Structure | Compound Name | Characterization | Method |
|---|---|---|---|---|
| 206 | 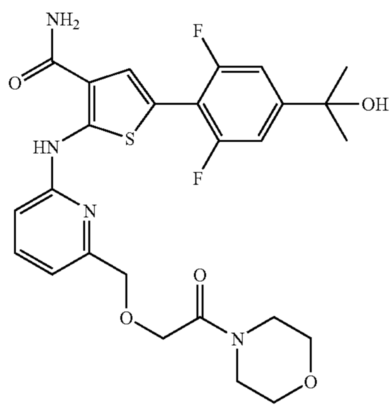 [SMILES: CC(C)(O)c1cc(F)c(-c2cc(C(N)=O)c(Nc3cccc(COCC(=O)N4CCOCC4)n3)s2)c(F)c1] | 5-[2,6-Difluoro-4-(1-hydroxy-1-methylethyl)phenyl]-2-({6-[(2-morpholin-4-yl-2-oxoethoxy)methyl]pyridin-2-yl}amino)thiophene-3-carboxamide | Calc'd [M + H]$^+$: 547, Found: 547 | A |
| 207 | 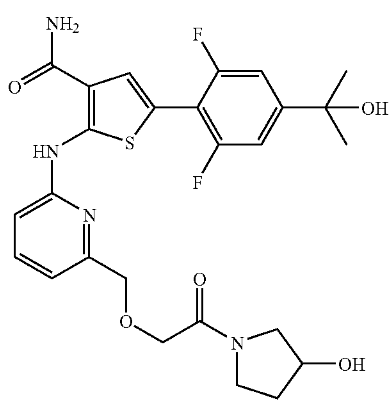 [SMILES: CC(C)(O)c1cc(F)c(-c2cc(C(N)=O)c(Nc3cccc(COCC(=O)N4CCC(O)C4)n3)s2)c(F)c1] | 5-[2,6-difluoro-4-(1-hydroxy-1-methylethyl)phenyl]-2-[(6-{[2-(3-hydroxypyrrolidin-1-yl)-2-oxoethoxy]methyl}pyridin-2-yl)amino]thiophene-3-carboxamide | Calc'd [M + H]$^+$: 547, Found: 547 | A |
| 208 | 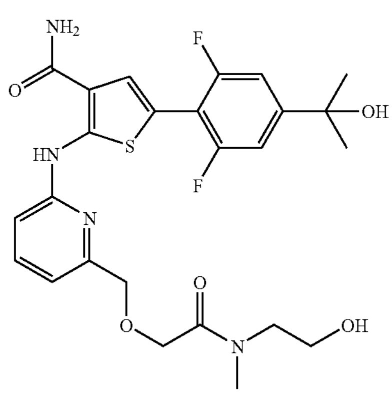 [SMILES: CN(CCO)C(=O)COCc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-({2-[(2-hydroxyethyl)(methyl)amino]-2-oxoethoxy}methyl)pyridin-2-yl]amino}thiophene-3-carboxamide | Calc'd [M + H]$^+$: 535, Found: 535 | A |

TABLE 13-continued

| Example # | Structure | Compound Name | Characterization | Method |
|---|---|---|---|---|
| 209 | 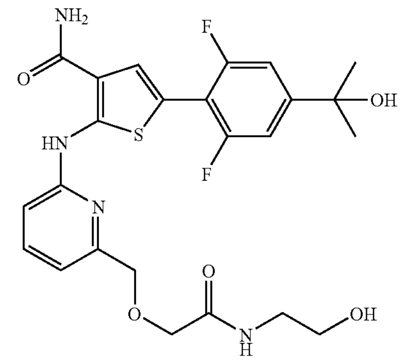 [SMILES: CC(C)(O)c1cc(F)c(-c2cc(C(N)=O)c(Nc3cccc(COCC(=O)NCCO)n3)s2)c(F)c1] | 5-[2,6-difluoro-4-(1-hydroxy-1-methylethyl)phenyl]-2-{[6-({2-[(2-hydroxyethyl)amino]-2-oxoethoxy}methyl)pyridin-2-yl]amino}thiophene-3-carboxamide | Calc'd [M + H]$^+$: 521, Found: 521 | A |
| 210 | 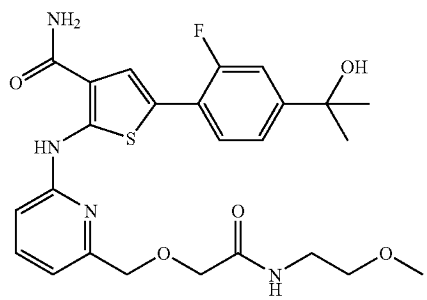 [SMILES: COCCNC(=O)COCc1cccc(Nc2sc(-c3ccc(C(C)(C)O)cc3F)cc2C(N)=O)n1] | 5-(2-fluoro-4-(1-hydroxy-1-methylethyl)phenyl)-2-((6-((2-oxo-2-methoxyethyl)amino)-2-oxoethoxy)methyl)-2-pyridinyl)amino)-3-thiophenecarboxamide | Calc'd [M + H]$^+$: 517, Found: 517 | B |
| 211 | 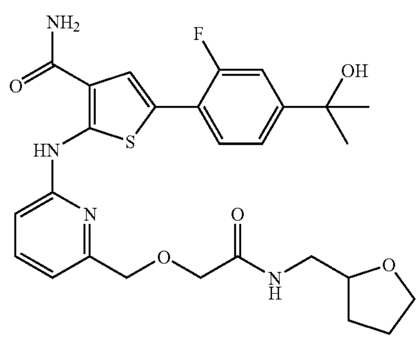 [SMILES: CC(C)(O)c1ccc(-c2cc(C(N)=O)c(Nc3cccc(COCC(=O)NCC4CCCO4)n3)s2)c(F)c1] | 5-(2-fluoro-4-(1-hydroxy-1-methylethyl)phenyl)-2-((6-((2-oxo-2-(tetrahydro-2-furanylmethyl)amino)ethoxy)methyl)-2-pyridinyl)amino)-3-thiophenecarboxamide | Calc'd [M + H]$^+$: 543, Found: 543 | B |
| 212 | 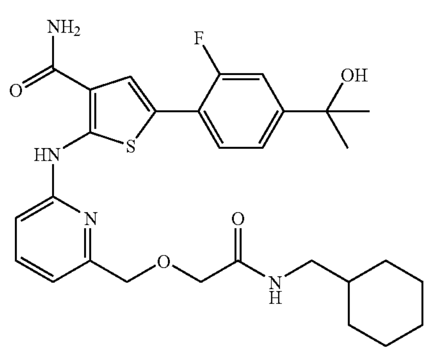 | 2-((6-((2-cyclohexylmethyl)amino)-2-oxoethoxy)methyl)-2-pyridinyl)amino)-5-(2-fluoro-4-(1-hydroxy-1-methylethyl)phenyl)-3-thiophenecarboxamide | Calc'd [M + H]$^+$: 541, Found: 541 | B |

TABLE 13-continued

| Example # | Structure | Compound Name | Characterization | Method |
|---|---|---|---|---|
| 213 | 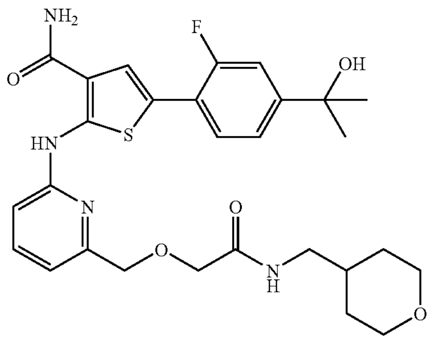 | 5-(2-fluoro-4-(1-hydroxy-1-methylethyl)phenyl)-2-((6-((2-(((2-oxo-2-(tetrahydro-2H-pyran-4-ylmethyl)amino)ethoxy)methyl)-2-pyridinyl)amino)-3-thiophenecarboxamide | Calc'd [M + H]⁺: 543, Found: 543 | B |
| 214 | 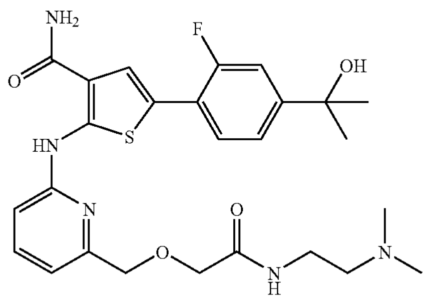 [SMILES: CN(C)CCNC(=O)COCc1cccc(Nc2sc(-c3ccc(C(C)(C)O)cc3F)cc2C(N)=O)n1] | 2-((6-((2-((2-dimethylamino)ethyl)amino)-2-oxoethoxy)methyl)-2-pyridinyl)amino)-5-(2-fluoro-4-(1-hydroxy-1-methylethyl)phenyl)-3-thiophenecarboxamide | Calc'd [M + H]⁺: 530, Found: 530 | B |
| 215 | 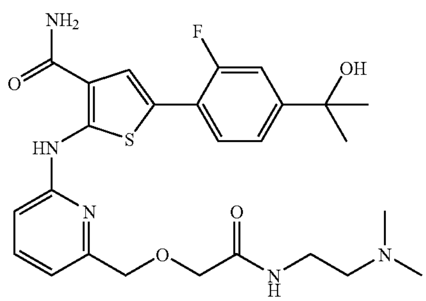 [SMILES: CN(C)CCNC(=O)COCc1cccc(Nc2sc(-c3ccc(C(C)(C)O)cc3F)cc2C(N)=O)n1] | 2-((6-((2-((2-dimethylamino)ethyl)amino)-2-oxoethoxy)methyl)-2-pyridinyl)amino)-5-(2-fluoro-4-(1-hydroxy-1-methylethyl)phenyl)-3-thiophenecarboxamide | Calc'd [M + H]⁺: 530, Found: 530 | B |

Method A: Using procedures described in Example 204
Method B: Using procedures described in Example 205

Example 216

[6-({3-(Aminocarbonyl)-5-[2,6-difluoro-4-(1-hydroxy-1-methylethyl)phenyl]-2-thienyl}amino)pyridin-2-yl]methyl methylcarbamate

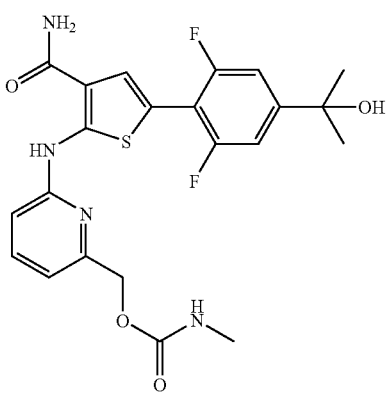 [SMILES: CNC(=O)OCc1cccc(Nc2sc(-c3c(F)cc(C(C)(C)O)cc3F)cc2C(N)=O)n1]

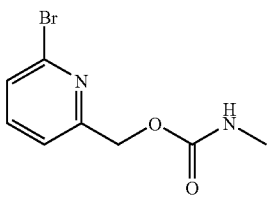

Step 1. (6-Bromopyridin-2-yl)methyl methylcarbamate (6-Bromopyridin-2-yl)methanol (1.5 g, 7.98 mmol) and DMAP (0.097 g, 0.798 mmol) were taken up in THF (20 mL) and cooled to 0° C. Methyl isocyanate (0.501 g, 8.78 mmol)

was added before warming to room temperature and stirring overnight. The reaction mixture was cooled to 0° C. and sodium hydride (0.319 g, 7.98 mmol) was added. After 30 minutes at 0° C., water was added followed by saturated NH₄Cl and the products extracted into EtOAc (2×). The combined organic extracts were washed with brine, dried over MgSO₄, filtered, and concentrated in vacuo. Purification of the residue by silica gel chromatography (6-50% EtOAc-hexanes) gave the title compound as a pale yellow solid.

Calc'd for $C_8H_{10}BrN_2O_2$ [M+H]⁺: 245, 247. Found: 245, 247.

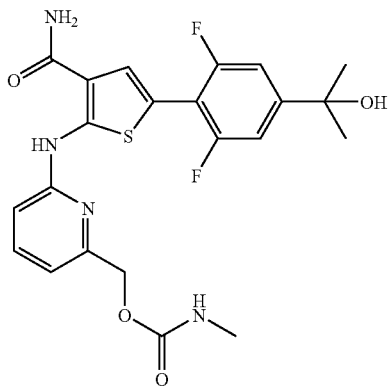 [SMILES: CNC(=O)OCc1cccc(Nc2sc(-c3c(F)cc(C(C)(C)O)cc3F)cc2C(N)=O)n1]

Step 2. [6-({3-(Aminocarbonyl)-5-[2,6-difluoro-4-(1-hydroxy-1-methylethyl)phenyl]-2-thienyl}amino)pyridin-2-yl]methyl methylcarbamate The title compound was prepared according to the general procedure in Example 1 using (6-bromopyridin-2-yl)methyl methylcarbamate (149 mg, 0.61 mmol) and 2-amino-5-[2,6-difluoro-4-(1-hydroxy-1-methylethyl)phenyl]thiophene-3-carboxamide (200 mg, 0.64 mmol) as the starting materials.

Calc'd for $C_{22}H_{23}F_2N_4O_4S$ [M+H]⁺: 477. Found: 477.

Example 217

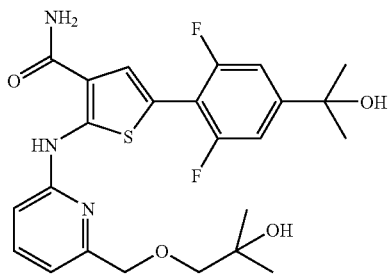 [SMILES: CC(C)(O)COCc1cccc(Nc2sc(-c3c(F)cc(C(C)(C)O)cc3F)cc2C(N)=O)n1]

5-[2,6-Difluoro-4-(1-hydroxy-1-methylethyl)phenyl]-2-({6-[(2-hydroxy-2-methylpropoxy)methyl]pyridin-2-yl}amino)thiophene-3-carboxamide

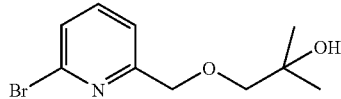

Step 1: 1-[(6-Bromopyridin-2-yl)methoxy]-2-methylpropan-2-ol

To a solution of methyl[(6-bromopyridin-2-yl)methoxy]acetate (Example 204, Step 1) (1.2 g, 5.0 mmol) in dichloromethane (30 mL) at room temperature was added methylmagnesium bromide (3.7 mL, 11 mmol). The reaction mixture was stirred at room temperature for one hour. Saturated aqueous ammonium chloride was added and the mixture was extracted with ether. The organic layer was concentrated under reduced pressure, and the resulting residue purified on silica gel to yield the title compound.

¹H NMR (400 MHz CDCl₃): δ 7.57 (t, 1H), 7.42 (m, 1H), 7.37 (m, 1H), 4.67 (s, 2H), 3.41 (s, 2H), 1.25 (s, 6H).

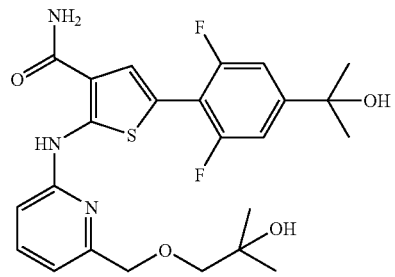 [SMILES: CC(C)(O)COCc1cccc(Nc2sc(-c3c(F)cc(C(C)(C)O)cc3F)cc2C(N)=O)n1]

Step 2: 5-[2,6-Difluoro-4-(1-hydroxy-1-methylethyl)phenyl]-2-({6-[(2-hydroxy-2-methylpropoxy)methyl]pyridin-2-yl}amino)thiophene-3-carboxamide t-Amyl alcohol (41 mL) was placed in a flask and argon was bubbled through it for several minutes. 2-Amino-5-[2,6-difluoro-4-(1-hydroxy-1-methylethyl)phenyl]thiophene-3-carboxamide (2.50 g, 8.0 mmol), dicyclohexyl(2',4',6'-triisopropylbiphenyl-2-yl)phosphine (1.90 g, 4 mmol), Pd₂(dba)₃ (0.73 g, 0.8 mmol), and potassium carbonate (1.22 g, 8.8 mmol) were placed in a reaction vessel that was purged with argon. Degassed t-amyl alcohol (10 mL) was used to transfer 1-[(6-bromopyridin-2-yl)methoxy]-2-methylpropan-2-ol (2.08 g, 8.0 mmol) to the reaction vessel and the remaining t-amyl alcohol was added. Seven argon/vacuum cycles were performed. The solution was heated at 105° C. overnight. The reaction was then cooled to ambient temperature, diluted with methanol, and silica gel was added. The resulting mixture was concentrated in vacuo and then purified by column chromatography (silica, 0-5% methanol/ethyl acetate). Purification via mass guided reverse phase HPLC (Agilent 1100 HPLC-MSD, Phenomenex Gemeni-C18, 10 μM, 250 mm×50 mm i.d. column, 20-95% acetonitrile/water+0.01% formic acid modifier, 75-100 mL/min flow rate) afforded the title compound.

¹H NMR (600 MHz, CDCl₃): δ 12.11 (s, 1H), 7.88 (bs, 1H), 7.74 (s, 1H), 7.72 (t, 1H), 7.37 (bs, 1H), 7.25 (d, 2H), 7.00 (d, 1H), 6.98 (d, 1H), 5.30 (s, 1H), 4.58 (s, 2H), 4.38 (s, 1H), 3.30 (s, 2H), 1.43 (s, 6H), 1.10 (s, 6H).

Calc'd for $C_{24}H_{28}F_2N_3O_4S$ [M+H]⁺: 492. Found: 492.

Example 218

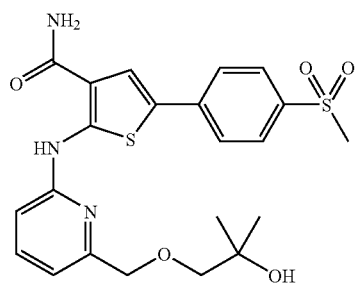 [SMILES: CC(C)(O)COCc1cccc(Nc2sc(-c3ccc(S(C)(=O)=O)cc3)cc2C(N)=O)n1]

2-({6-[(2-Hydroxy-2-methylpropoxy)methyl]pyridin-2-yl}amino)-5-[4-(methylsulfonyl)phenyl]thiophene-3-carboxamide 2-Amino-5-[4-(methylsulfonyl)phenyl]thiophene-3-carboxamide (150 mg, 0.51 mmol), 1-[(6-bromopyridin-2-yl)methoxy]-2-methylpropan-2-ol (Example 217 Step 1) (125 mg, 0.48 mmol), Pd₂dba₃ (46.3 mg, 0.051 mmol), K₂CO₃ (77 mg, 0.557 mmol) and X-Phos (120 mg, 0.25 mmol) were added to a 5 mL microwave vial. Degassed tert-amyl alcohol (1.2 mL) was added and the vial evacuated and back-filled with N₂ (3×). The resulting mixture was stirred at 100° C. overnight. After cooling to room temperature, the mixture was diluted with methanol, silica gel was added, and the solvent was removed in vacuo. Purification of the residue by flash chromatography (silica, 0-10% MeOH-DCM) gave the title compound as a yellow solid.

Calc'd for $C_{22}H_{26}N_3O_5S_2$ [M+H]⁺: 476. Found: 476.

Example 219

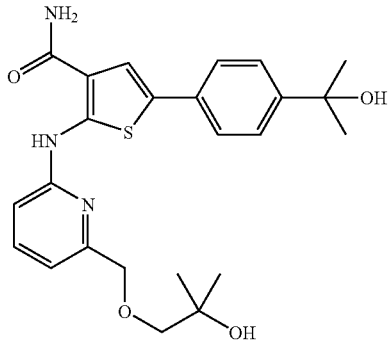 [SMILES: CC(C)(O)COCc1cccc(Nc2sc(-c3ccc(C(C)(C)O)cc3)cc2C(N)=O)n1]

5-[4-(1-Hydroxy-1-methylethyl)phenyl]-2-({6-[(2-hydroxy-2-methylpropoxy)methyl]pyridin-2-yl}amino)thiophene-3-carboxamide 2-Amino-5-[4-(1-hydroxy-1-methylethyl)phenyl]thiophene-3-carboxamide (0.1 g, 0.362 mmol), 1-[(6-bromopyridin-2-yl)methoxy]-2-methylpropan-2-ol (Example 217 Step 1) (0.085 g, 0.326 mmol), Pd₂dba₃ (0.017 g, 0.018 mmol), K₂CO₃ (0.055 g, 0.398 mmol) and X-Phos (0.043 g, 0.090 mmol) were added to a 5 mL microwave vial. Degassed EtOH (1 mL) was added and the vial evacuated and back-filled with N₂ (3×). The resulting mixture was stirred at 100° C. overnight. After cooling to room temperature, the mixture was diluted with methanol, silica gel was added, and the solvent was removed in vacuo. Purification of the residue by flash chromatography (silica, 0-10% MeOH—CHCl₃) gave the title compound as a beige solid after triturating in EtOAc.

Calc'd for $C_{24}H_{30}N_3O_4S$ [M+H]⁺: 456. Found: 456.

Example 220

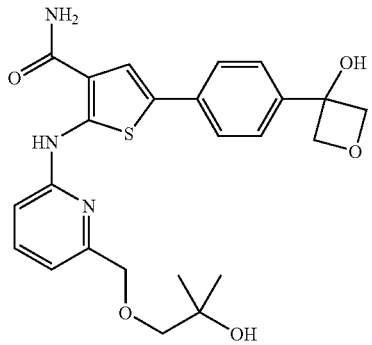 [SMILES: CC(C)(O)COCc1cccc(Nc2sc(-c3ccc(C4(O)COC4)cc3)cc2C(N)=O)n1]

2-({6-[(2-Hydroxy-2-methylpropoxy)methyl]pyridin-2-yl}amino)-5-[4-(methylsulfonyl)phenyl]thiophene-3-carboxamide 2-Amino-5-[4-(3-hydroxyoxetan-3-yl)phenyl]thiophene-3-carboxamide (150 mg, 0.517 mmol), 1-[(6-bromopyridin-2-yl)methoxy]-2-methylpropan-2-ol (Example 217 Step 1) (121 mg, 0.465 mmol), Pd₂dba₃ (23.65 mg, 0.026 mmol), K₂CO₃ (79 mg, 0.568 mmol) and X-Phos (61.6 mg, 0.129 mmol) were added to a 5 mL microwave vial. Degassed tert-amyl alcohol (1.2 mL) was added and the vial evacuated and back-filled with N₂ (3×). The resulting mixture was stirred at 100° C. overnight. After cooling to room temperature, the mixture was diluted with methanol, silica gel was added, and the solvent was removed in vacuo. Purification of the residue by flash chromatography (silica, 0-10% MeOH—CHCl₃) gave the title compound as a pale brown solid after triturating in EtOAc.

¹H NMR (600 MHz, DMSO): 11.98 (s, 1H), 7.82 (s, 1H), 7.74 (s, 1H), 7.69 (t, 1H), 7.60 (d, 2H), 7.56 (d, 2H), 7.35 (s, 1H), 6.97 (d, 1H), 6.93 (d, 1H), 6.34 (s, 1H), 4.74 (d, 2H), 4.67 (d, 2H), 4.62 (s, 2H), 4.39 (s, 1H), 3.33 (s, 2H), 1.12 (s, 6H). Calc'd for $C_{24}H_{28}N_3O_5S$ [M+H]⁺: 470. Found: 470.

Example 221

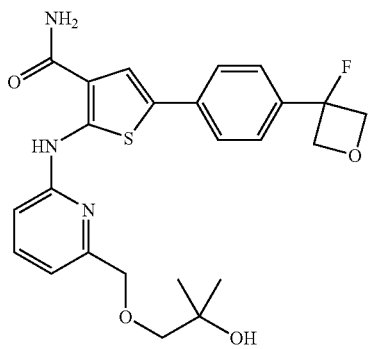 [SMILES: CC(C)(O)COCc1cccc(Nc2sc(-c3ccc(C4(F)COC4)cc3)cc2C(N)=O)n1]

5-[4-(3-Fluorooxetan-3-yl)phenyl]-2-({6-[(2-hydroxy-2-methylpropoxy)methyl]pyridin-2-yl}amino)thiophene-3-carboxamide 2-Amino-5-[4-(3-fluorooxetan-3-yl)phenyl]thiophene-3-carboxamide (88 mg, 0.301 mmol), 1-[(6-bromopyridin-2-yl)methoxy]-2-methylpropan-2-ol (Example 217 Step 1) (78 mg, 0.301 mmol), Pd$_2$dba$_3$ (27.6 mg, 0.030 mmol), K$_2$CO$_3$ (45.8 mg, 0.331 mmol) and X-Phos (71.8 mg, 0.151 mmol) were added to a 5 mL microwave vial. Degassed tert-amyl alcohol (0.6 mL) was added and the vial evacuated and back-filled with N$_2$ (3×). The resulting mixture was stirred at 100° C. overnight. After cooling to room temperature, the mixture was diluted with methanol, silica gel was added, and the solvent was removed in vacuo. Purification of the residue by flash chromatography (silica, 0-10% MeOH-DCM) followed by flash chromatography (silica, 12-100% EtOAc-hexanes) gave the title compound as a pale yellow solid.

Calc'd for C$_{24}$H$_{27}$FN$_3$O$_4$S [M+H]$^+$: 472. Found: 472.

Additional examples were prepared using procedures similar to those described in the above examples and are illustrated in the following table.

TABLE 14

| Example | Structure | Name | Characterization [M + H]$^+$ |
|---|---|---|---|
| 222 | 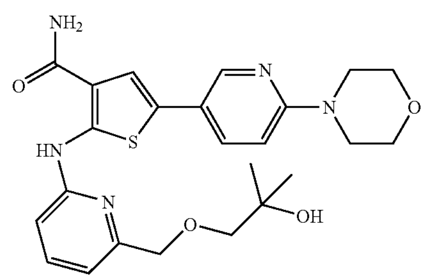 [SMILES: CC(C)(O)COCc1cccc(Nc2sc(-c3ccc(N4CCOCC4)nc3)cc2C(N)=O)n1] | 2-({6-[(2-hydroxy-2-methylpropoxy)methyl]pyridin-2-yl}amino)-5-(6-morpholin-4-ylpyridin-3-yl)thiophene-3-carboxamide | Calc'd 484; found 484 |
| 223 | 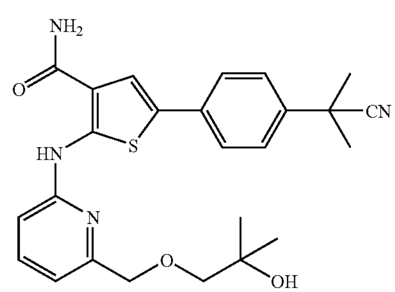 [SMILES: CC(C)(O)COCc1cccc(Nc2sc(-c3ccc(C(C)(C)C#N)cc3)cc2C(N)=O)n1] | 5-[4-(1-cyano-1-methylethyl)phenyl]-2-({6-[(2-hydroxy-2-methylpropoxy)methyl]pyridin-2-yl}amino)thiophene-3-carboxamide | Calc'd 465; found 465 |
| 224 | 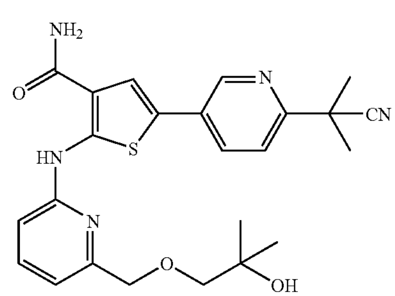 [SMILES: CC(C)(O)COCc1cccc(Nc2sc(-c3ccc(C(C)(C)C#N)nc3)cc2C(N)=O)n1] | 5-[6-(1-cyano-1-methylethyl)pyridin-3-yl]-2-({6-[(2-hydroxy-2-methylpropoxy)methyl]pyridin-2-yl}amino)thiophene-3-carboxamide | Calc'd 462; found 462 |

TABLE 14-continued

| Example | Name | Characterization [M + H]+ |
|---|---|---|
| 225 | 2-({6-[(2-hydroxy-2-methylpropoxy)methyl]pyridin-2-yl}amino)-5-(1-{[2-(trimethylsilyl)ethoxy]methyl}-1H-1,2,4-triazol-3-yl)thiophene-3-carboxamide | Calc'd 519; found 519 |
| 226 | 2-({6-[(2-hydroxy-2-methylpropoxy)methyl]pyridin-2-yl}amino)-5-(1H-1,2,4-triazol-3-yl)thiophene-3-carboxamide | Calc'd 389; found 389 |
| 227 | 2-({6-[(2-hydroxy-2-methylpropoxy)methyl]pyridin-2-yl}amino)-5-[4-(1H-1,2,4-triazol-4-yl)phenyl]thiophene-3-carboxamide | Calc'd 465; found 465 |
| 228 | 2-({6-[(2-hydroxy-2-methylpropoxy)methyl]pyridin-2-yl}amino)-5-[4-(1H-1,2,4-triazol-3-yl)phenyl]thiophene-3-carboxamide | Calc'd 465; found 465 |
| 229 | 2-({6-[(2-hydroxy-2-methylpropoxy)methyl]pyridin-2-yl}amino)-5-[4-(morpholin-4-ylmethyl)phenyl]thiophene-3-carboxamide | Calc'd 497; found 497 |

TABLE 14-continued

| Example | Structure | Name | Characterization [M + H]+ |
|---|---|---|---|
| 230 | 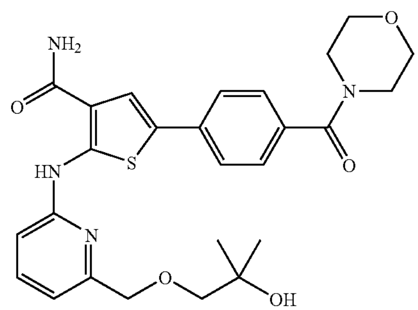 [SMILES: CC(C)(O)COCc1cccc(Nc2sc(-c3ccc(C(=O)N4CCOCC4)cc3)cc2C(N)=O)n1] | 2-({6-[(2-hydroxy-2-methylpropoxy)methyl]pyridin-2-yl}amino)-5-[4-(morpholin-4-ylcarbonyl)phenyl]thiophene-3-carboxamide | Calc'd 511; found 511 |
| 231 | 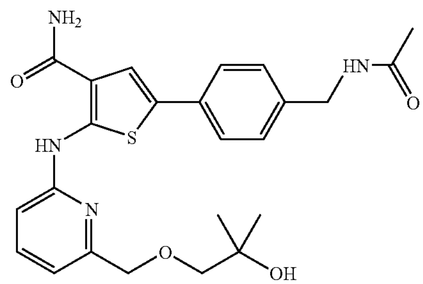 [SMILES: CC(=O)NCc1ccc(-c2cc(C(N)=O)c(Nc3cccc(COCC(C)(C)O)n3)s2)cc1] | 5-{4-[(acetylamino)methyl]phenyl}-2-({6-[(2-hydroxy-2-methylpropoxy)methyl]pyridin-2-yl}amino)thiophene-3-carboxamide | Calc'd 469; found 469 |
| 232 | 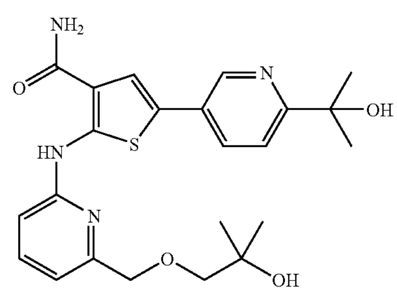 [SMILES: CC(C)(O)COCc1cccc(Nc2sc(-c3ccc(C(C)(C)O)nc3)cc2C(N)=O)n1] | 5-[6-(1-hydroxy-1-methylethyl)pyridin-3-yl]-2-({6-[(2-hydroxy-2-methylpropoxy)methyl]pyridin-2-yl}amino)thiophene-3-carboxamide | Calc'd 457; found 457 |
| 233 | 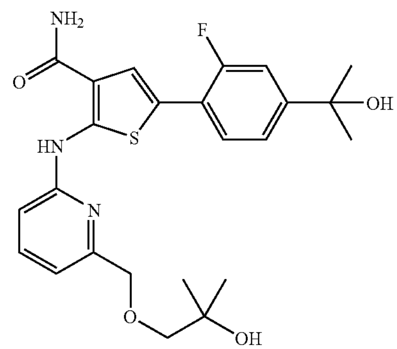 [SMILES: CC(C)(O)COCc1cccc(Nc2sc(-c3ccc(C(C)(C)O)cc3F)cc2C(N)=O)n1] | 5-[2-fluoro-4-(1-hydroxy-1-methylethyl)phenyl]-2-({6-[(2-hydroxy-2-methylpropoxy)methyl]pyridin-2-yl}amino)thiophene-3-carboxamide | Calc'd 474; found 474 |

Example 234

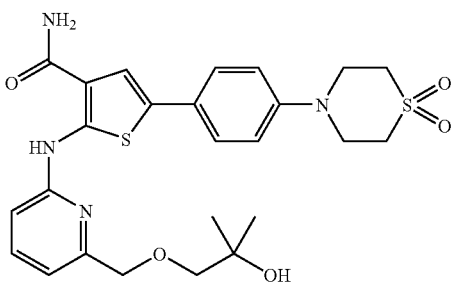 [SMILES: CC(C)(O)COCc1cccc(Nc2sc(-c3ccc(N4CCS(=O)(=O)CC4)cc3)cc2C(N)=O)n1]

5-[4-(1,1-Dioxidothiomorpholin-4-yl)phenyl]-2-({6-[(2-hydroxy-2-methylpropoxy)methyl]pyridin-2-yl}amino)thiophene-3-carboxamide 5-[4-(1,1-Dioxidothiomorpholin-4-yl)phenyl]-2-nitrothiophene-3-carboxamide (Intermediate 16) (525 mg, 1.376 mmol) and Pt/C, doped with V (90 mg, 0.014 mmol) were stirred at room temperature overnight in degassed MeOH (5 mL) under a balloon of $H_2$. The vial was then evacuated and back-filled with $N_2$ (4×) and 1-[(6-bromopyridin-2-yl)methoxy]-2-methylpropan-2-ol (Example 217 Step 1) (358 mg, 1.38 mmol), $Pd_2dba_3$ (126 mg, 0.138 mmol), X-Phos (328 mg, 0.69 mmol) and $K_2CO_3$ (209 mg, 1.51 mmol) were added. The vial was evacuated and back-filled with $N_2$ (3×) and the resulting mixture was stirred at 100° C. for 4 hours. After cooling to room temperature, the mixture was diluted with methanol, silica gel was added, and the solvent was removed in vacuo. Purification of the residue by silica gel chromatography (0-6% MeOH—$CHCl_3$) gave the title compound as a beige solid after triturating in DCM.

Calc'd for $C_{25}H_{31}N_4O_5S_2$ [M+H]$^+$: 531. Found: 531.

Example 235

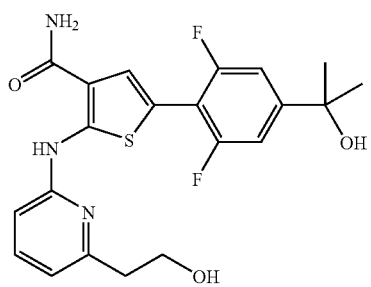 [SMILES: CC(C)(O)c1cc(F)c(-c2cc(C(N)=O)c(Nc3cccc(CCO)n3)s2)c(F)c1]

5-[2,6-Difluoro-4-(1-hydroxy-1-methylethyl)phenyl]-2-{[6-(2-hydroxyethyl)pyridin-2-yl]amino}thiophene-3-carboxamide

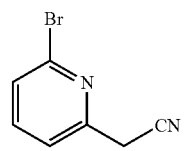

Step 1: (6-Bromopyridin-2-yl)acetonitrile

A solution of 2-bromo-6-(bromomethyl)pyridine (Example 190, Step 1) (5 g, 19.9 mmol) in dimethylsulfoxide (50 mL) was charged with sodium cyanide (2.93 g, 59.8 mmol). The reaction was heated to 50° C. overnight. Upon completion, the reaction was diluted with ethyl acetate (100 mL) and water (100 mL) and the layers were separated. The organic layer was then dried over sodium sulfate, filtered, concentrated, and purified by silica gel chromatography (hexane:ethyl acetate 7:3) followed by purification by reverse phase HPLC (10-100% acetonitrile/water+0.05% TFA modifier) to afford the title compound.

Calc'd for $C_7H_6BrN_2$ [M+H]$^+$: 196. Found: 196.

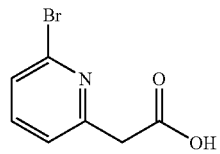 [SMILES: O=C(O)Cc1cccc(Br)n1]

Step 2: (6-Bromopyridin-2-yl)acetic acid (6-Bromopyridin-2-yl)acetonitrile (50 mg, 0.25 mmol) was taken up in methanol (2 mL) and 1 N aqueous sodium hydroxide (2 ml, 2 mmol) was added. The reaction was heated to 80° C. overnight. Upon completion, the reaction was cooled to ambient temperature, diluted with ethyl acetate (15 mL) and water (15 mL), and the layers were separated. The aqueous layer was acidified with 2N aqueous hydrochloric acid and extracted with ethyl acetate. The organic layer was dried over magnesium sulfate, filtered, and concentrated in vacuo to afford the title compound which was used without further purification.

Calc'd for $C_7H_7BrNO_2$ [M+H]$^+$: 216. Found: 216.

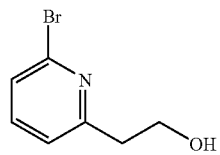

Step 3: 2-(6-Bromopyridin-2-yl)ethanol

A solution of (6-bromopyridin-2-yl)acetic acid (1.1 g, 5.09 mmol) in tetrahydrofuran (20 ml) was cooled to 0° C. Sodium borohydride (0.385 g, 10.18 mmol) was slowly added followed by the addition of boron trifluoride diethyl etherate (1.29 ml, 10.18 mmol). The reaction was allowed to come to room temperature. After 2 hrs, the reaction was diluted with brine, ammonium chloride and ethyl acetate. After layer separation, the organic layer was dried over sodium sulfate, filtered and concentrated. The crude residue was purification by silica gel chromatography (3:7 hexane:ethyl acetate) to yield the title compound.

Calc'd for $C_7H_9BrNO$ [M+H]$^+$: 202. Found: 202.

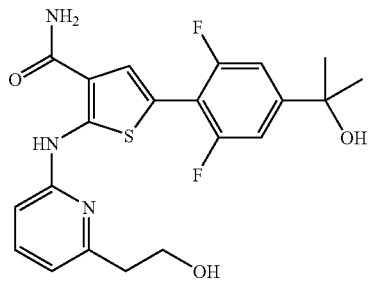 [SMILES: CC(C)(O)c1cc(F)c(-c2cc(C(N)=O)c(Nc3cccc(CCO)n3)s2)c(F)c1]

Step 4: 5-[2,6-Difluoro-4-(1-hydroxy-1-methylethyl)phenyl]-2-{[6-(2-hydroxyethyl)pyridin-2-yl]amino}thiophene-3-carboxamide The title compound was prepared as described in Example 1 using 2-(6-bromopyridin-2-yl)ethanol (48 mg, 0.24 mmol) and 2-amino-5-[2,6-difluoro-4-(1-hydroxy-1-methylethyl)phenyl]thiophene-3-carboxamide (75 mg, 0.24 mmol) as the starting materials.

Calc'd for $C_{21}H_{22}F_2N_3O_3S[M+H]^+$: 434. Found: 434.

Example 236

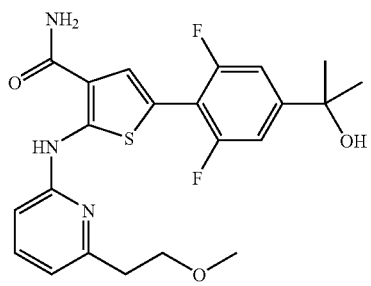 [SMILES: COCCc1cccc(Nc2sc(-c3c(F)cc(C(C)(C)O)cc3F)cc2C(N)=O)n1]

5-[2,6-Difluoro-4-(1-hydroxy-1-methylethyl)phenyl]-2-{[6-(2-methoxyethyl)pyridin-2-yl]amino}thiophene-3-carboxamide

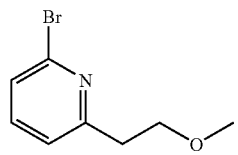

Step 1: 2-Bromo-6-(2-methoxyethyl)pyridine

A solution of sodium hydride (59 mg, 1.49 mmol) in tetrahydrofuran (2 ml) was cooled to 0° C. in an ice bath. 2-(6-Bromopyridin-2-yl)ethanol (Example 235 Step 3) (100 mg, 0.49 mmol) in tetrahydrofuran (2 ml) was added dropwise and the reaction was allowed to warm to room temperature. After 45 minutes at room temperature, the reaction was cooled to 0° C., followed by the addition of methyl iodide (0.09 ml, 1.49 mmol). The reaction was then allowed to warm to room temperature. Upon completion, the reaction was cooled to 0° C. and water was added dropwise. Ethyl acetate was then added and the layers were separated. The organic layer was then dried over sodium sulfate, filtered and concentrated. Purification of the crude residue by silica gel chromatography afforded the title compound.

Calc'd for $C_8H_{11}BrNO [M+H]^+$: 216. Found: 216.

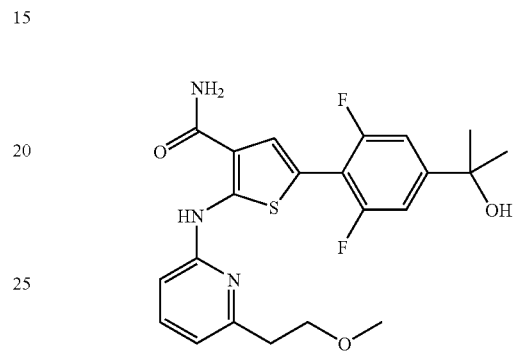

Step 2: 5-[2,6-Difluoro-4-(1-hydroxy-1-methylethyl)phenyl]-2-{[6-(2-methoxyethyl)pyridin-2-yl]amino}thiophene-3-carboxamide The title compound was prepared according to the general procedure in Example 1 using 2-bromo-6-(2-methoxyethyl)pyridine (42 mg, 0.19 mmol) and 2-amino-5-[2,6-difluoro-4-(1-hydroxy-1-methylethyl)phenyl]thiophene-3-carboxamide (60 mg, 0.19 mmol) as the starting materials.

Calc'd for $C_{22}H_{24}F_2N_3O_3S [M+H]^+$: 448. Found: 448.

Additional examples were prepared using procedures similar to those described in the above examples and are illustrated in the following table.

TABLE 15

| Example | Structure | Compound Name | Characterization |
| --- | --- | --- | --- |
| 237 | ![structure] | 5-[2,6-difluoro-4-(1-hydroxy-1-methylethyl)phenyl]-2-{[6-(2-ethoxyethyl)pyridin-2-yl]amino}thiophene-3-carboxamide | Calc'd $[M + H]^+$: 462, Found: 462 |

TABLE 15-continued

| Example | Structure | Compound Name | Characterization |
|---|---|---|---|
| 238 | 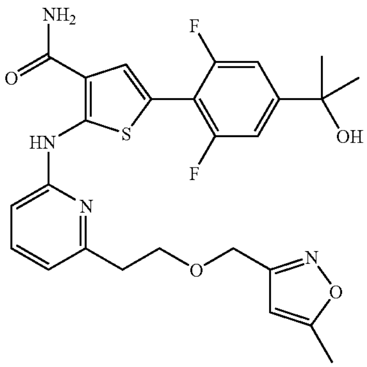 | 5-[2,6-Difluoro-4-(1-hydroxy-1-methylethyl)phenyl]-2-[(6-{2-[(5-methylisoxazol-3-yl)methoxy]ethyl}pyridin-2-yl)amino]thiophene-3-carboxamide | Calc'd [M + H]$^+$: 529, Found: 529 |
| 239 | 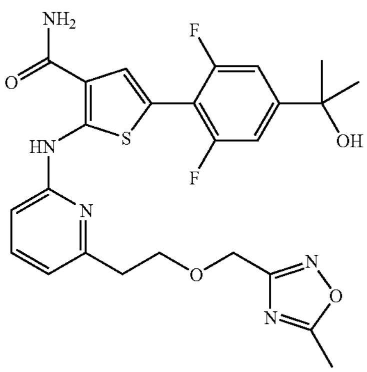 [SMILES: Cc1nc(COCCc2cccc(Nc3sc(-c4c(F)cc(C(C)(C)O)cc4F)cc3C(N)=O)n2)no1] | 5-[2,6-difluoro-4-(1-hydroxy-1-methylethyl)phenyl]-2-[(6-{2-[(5-methyl-1,2,4-oxadiazol-3-yl)methoxy]ethyl}pyridin-2-yl)amino]thiophene-3-carboxamide | Calc'd [M + H]$^+$: 530, Found: 530 |
| 240 | 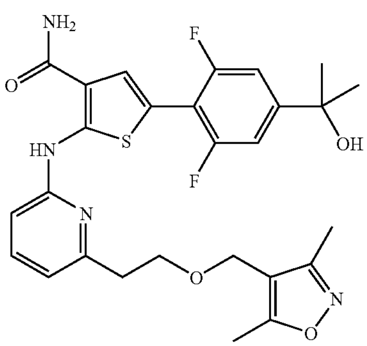 [SMILES: Cc1noc(C)c1COCCc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-[(6-{2-[(3,5-dimethylisoxazol-4-yl)methoxy]ethyl}pyridin-2-yl)amino]thiophene-3-carboxamide | Calc'd [M + H]$^+$: 543, Found: 543 |

Example 241

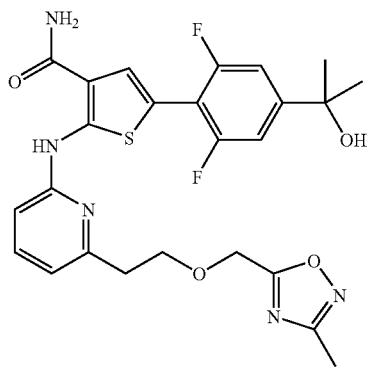 [SMILES: Cc1noc(COCCc2cccc(Nc3sc(-c4c(F)cc(C(C)(C)O)cc4F)cc3C(N)=O)n2)n1]

5-[2,6-Difluoro-4-(1-hydroxy-1-methylethyl)phenyl]-2-[(6-{2-[(3-methyl-1,2,4-oxadiazol-5-yl)methoxy]ethyl}pyridin-2-yl)amino]thiophene-3-carboxamide

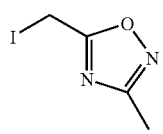

Step 1: 5-(Iodomethyl)-3-methyl-1,2,4-oxadiazole

A solution of 5-(chloromethyl)-3-methyl-1,2,4-oxadiazole (100 mg, 0.75 mmol) in acetone (3 ml) was charged with sodium iodide (170 mg, 1.13 mmol). The mixture was allowed to react at room temperature for 3 hrs, at which time

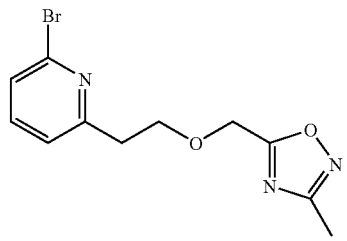 [SMILES: Cc1noc(COCCc2cccc(Br)n2)n1]

Step 2: 2-Bromo-6-{2-[(3-methyl-1,2,4-oxadiazol-5-yl)methoxy]ethyl}pyridine

The title compound was prepared as described in Example 236, Step 1 using 2-(6-bromopyridin-2-yl)ethanol (Example 235 Step 3) (50 mg, 0.25 mmol) and 5-(iodomethyl)-3-methyl-1,2,4-oxadiazole (110 mg, 0.50 mmol) as starting materials.

Calc'd for $C_{11}H_{13}BrN_3O_2$ [M+H]$^+$: 298. Found: 298.

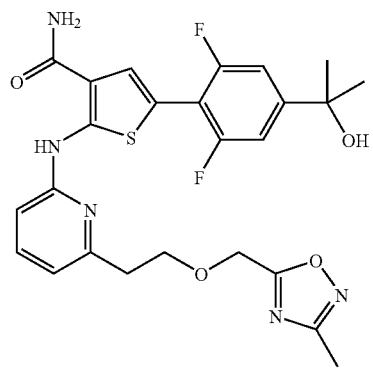 [SMILES: Cc1noc(COCCc2cccc(Nc3sc(-c4c(F)cc(C(C)(C)O)cc4F)cc3C(N)=O)n2)n1]

Step 3: 5-[2,6-Difluoro-4-(1-hydroxy-1-methylethyl)phenyl]-2-[(6-{2-[(3-methyl-1,2,4-oxadiazol-5-yl)methoxy]ethyl}pyridin-2-yl)amino]thiophene-3-carboxamide The title compound was as described in Example 1 using 2-bromo-6-{2-[(3-methyl-1,2,4-oxadiazol-5-yl)methoxy]ethyl}pyridine (29 mg, 0.01 mmol) and 2-amino-5-[2,6-difluoro-4-(1-hydroxy-1-methylethyl)phenyl]thiophene-3-carboxamide (30 mg, 0.01 mmol) as the starting materials.

Calc'd for $C_{25}H_{26}F_2N_5O_4S$ [M+H]$^+$: 530. Found: 530.

Example 242

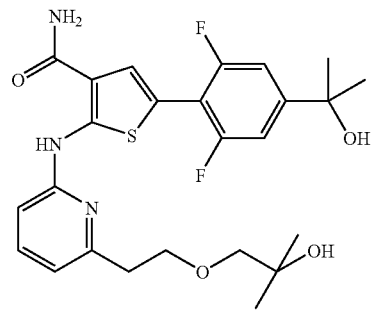 [SMILES: CC(C)(O)COCCc1cccc(Nc2sc(-c3c(F)cc(C(C)(C)O)cc3F)cc2C(N)=O)n1]

5-[2,6-Difluoro-4-(1-hydroxy-1-methylethyl)phenyl]-2-({6-[2-(2-hydroxy-2-methylpropoxy)ethyl]pyridin-2-yl}amino)thiophene-3-carboxamide

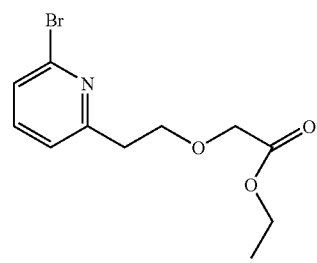 [SMILES: CCOC(=O)COCCc1cccc(Br)n1]

Step 1: Ethyl[2-(6-bromopyridin-2-yl)ethoxy]acetate

A solution of sodium hydride (74 mg, 1.87 mmol) in tetrahydrofuran (2 ml) was cooled to 0° C. 2-(6-Bromopyridin-2-yl)ethanol (Example 235, Step 3) (126 mg, 0.62 mmol) in tetrahydrofuran (2 ml) was added dropwise and the reaction was allowed to warm to room temperature. After 45 minutes at room temperature, the reaction was cooled to 0° C. and ethyl bromoacetate (0.14 ml, 1.25 mmol) was added. The reaction was allowed to warm to room temperature and then heated to 50° C. Upon completion, the reaction was cooled to 0° C. and water was added dropwise. Ethyl acetate was then added and the layers were separated. The organic layer was then dried over sodium sulfate, filtered and concentrated. Purification of the crude residue by silica gel chromatography afforded the title compound.

Calc'd for $C_{11}H_{15}BrNO_3$ [M+H]$^+$: 288. Found: 288.

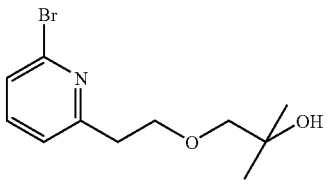

Step 2: 1-[2-(6-Bromopyridin-2-yl)ethoxy]-2-methylpropan-2-ol

A solution of ethyl[2-(6-bromopyridin-2-yl)ethoxy]acetate (76 mg, 0.26 mmol) in tetrahydrofuran (3 ml) was cooled to 0° C. Methylmagnesium bromide (0.26 ml, 0.79 mmol) was then added and the reaction was allowed to warm to room temperature. After 2 hrs, the reaction mixture was diluted with sodium bicarbonate and ethyl acetate and the layers were separated. The organic layer was dried over sodium sulfate, filtered and concentrated. Purification of the crude residue by silica gel chromatography afforded the title compound.

Calc'd for $C_{11}H_{17}BrNO_2$ $[M+H]^+$: 274. Found: 274.

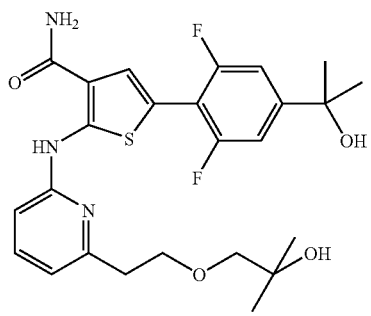 [SMILES: CC(C)(O)COCCc1cccc(Nc2sc(-c3c(F)cc(C(C)(C)O)cc3F)cc2C(N)=O)n1]

Step 3: 5-[2,6-Difluoro-4-(1-hydroxy-1-methylethyl)phenyl]-2-({6-[2-(2-hydroxy-2-methylpropoxy)ethyl]pyridin-2-yl}amino)thiophene-3-carboxamide The title compound was prepared according to the general procedure in Example 1 using 1-[2-(6-bromopyridin-2-yl)ethoxy]-2-methylpropan-2-ol (53 mg, 0.19 mmol) and 2-amino-5-[2,6-difluoro-4-(1-hydroxy-1-methylethyl)phenyl]thiophene-3-carboxamide (60 mg, 0.19 mmol) as the starting materials.

Calc'd for $C_{25}H_{30}F_2N_3O_4S$ $[M+H]^+$: 506. Found: 506

Example 243

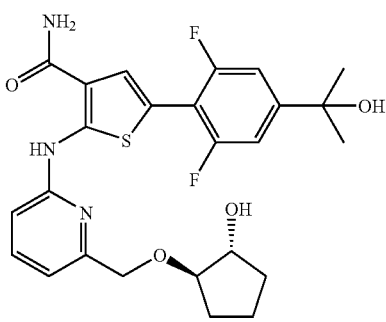 [SMILES: CC(C)(O)c1cc(F)c(-c2cc(C(N)=O)c(Nc3cccc(CO[C@@H]4CCC[C@H]4O)n3)s2)c(F)c1]

5-[2,6-Difluoro-4-(1-hydroxy-1-methylethyl)phenyl]-2-{[6-({[(1R,2R)-2-hydroxycyclopentyl]oxy}methyl)pyridin-2-yl]amino}thiophene-3-carboxamide

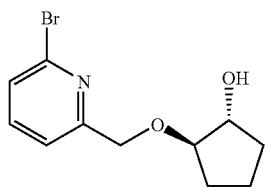 [SMILES: O[C@@H]1CCC[C@H]1OCc1cccc(Br)n1]

Step 1: (1R,2R)-2-[(6-Bromopyridin-2-yl)methoxy]cyclopentanol

Sodium hydride (0.48 mg, 11.96 mmol) was suspended in DMF (12.0 mL) and cooled to 0° C. (1R,2R)-Cyclopentane-1,2-diol (1.22 g, 11.96 mmol) was added and the reaction was stirred for 30 minutes. 2-Bromo-6-(bromomethyl)pyridine (Example 190, Step 1) (0.30 g, 1.20 mmol) was added and the reaction mixture was allowed to warm to room temperature overnight. The reaction was then diluted with ether and quenched with water. After layer separation, the organic layer was dried over magnesium sulfate, filtered and concentrated. Purification of the crude residue by silica gel chromatography afforded the title compound.

Calc'd for $C_{11}H_{15}BrNO_2$ $[M+H]^+$: 272. Found: 272.

Step 2: 5-[2,6-Difluoro-4-(1-hydroxy-1-methylethyl)phenyl]-2-{[6-({[(1R,2R)-2-hydroxycyclopentyl]oxy}methyl)pyridin-2-yl]amino}thiophene-3-carboxamide The title compound was prepared as described in Example 1 with 2-amino-5-[2,6-difluoro-4-(1-hydroxy-1-methylethyl)phenyl]thiophene-3-carboxamide (0.14 g, 0.43 mmol) and (1R,2R)-2-[(6-bromopyridin-2-yl)methoxy]cyclopentanol (0.12 g, 0.43 mmol) as the starting materials.

Calc'd for $C_{25}H_{28}F_2N_3O_4S$ $[M+H]^+$: 504. Found: 504.

Additional examples were prepared using procedures similar to those described in the above examples and are illustrated in the following table.

TABLE 16

| Example | Structure | Name | Characterization |
|---|---|---|---|
| 244 | 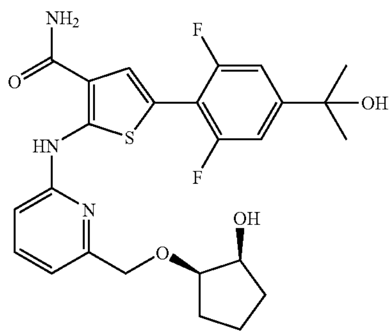 [SMILES: CC(C)(O)c1cc(F)c(-c2cc(C(N)=O)c(Nc3cccc(CO[C@@H]4CCC[C@@H]4O)n3)s2)c(F)c1] | 5-[2,6-difluoro-4-(1-hydroxy-1-methylethyl)phenyl]-2-{[6-({[(1R,2S)-2-hydroxycyclopentyl]oxy}methyl)pyridin-2-yl]amino}thiophene-3-carboxamide | Calc'd [M + H]+: 504, Found: 504 |
| 245 | 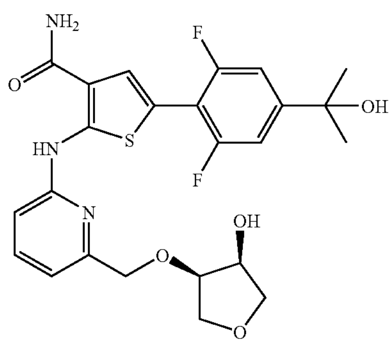 [SMILES: CC(C)(O)c1cc(F)c(-c2cc(C(N)=O)c(Nc3cccc(CO[C@@H]4COC[C@@H]4O)n3)s2)c(F)c1] | 5-[2,6-difluoro-4-(1-hydroxy-1-methylethyl)phenyl]-2-{[6-({[(3R,4S)-4-hydroxytetrahydrofuran-3-yl]oxy}methyl)pyridin-2-yl]amino}thiophene-3-carboxamide | Calc'd [M + H]+: 506, Found: 506 |
| 246 | 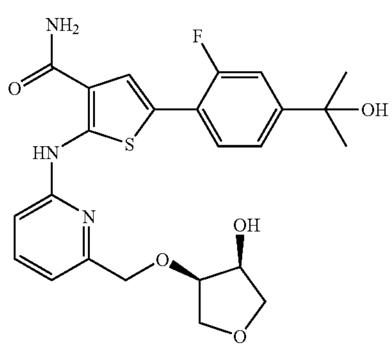 [SMILES: CC(C)(O)c1ccc(-c2cc(C(N)=O)c(Nc3cccc(CO[C@@H]4COC[C@@H]4O)n3)s2)c(F)c1] | 5-[2-fluoro-4-(1-hydroxy-1-methylethyl)phenyl]-2-{[6-({[(3R,4S)-4-hydroxytetrahydrofuran-3-yl]oxy}methyl)pyridin-2-yl]amino}thiophene-3-carboxamide | Calc'd [M + H]+: 488, Found: 488 |
| 247 | 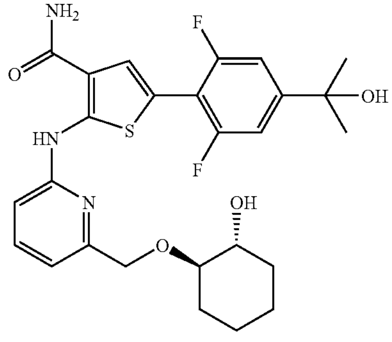 [SMILES: CC(C)(O)c1cc(F)c(-c2cc(C(N)=O)c(Nc3cccc(CO[C@@H]4CCCC[C@H]4O)n3)s2)c(F)c1] | 5-[2,6-difluoro-4-(1-hydroxy-1-methylethyl)phenyl]-2-{[6-({[(1R,2R)-2-hydroxycyclohexyl]oxy}methyl)pyridin-2-yl]amino}thiophene-3-carboxamide | Calc'd [M + H]+: 518, Found: 518 |

TABLE 16-continued

| Example | Structure | Name | Characterization |
|---|---|---|---|
| 248 | 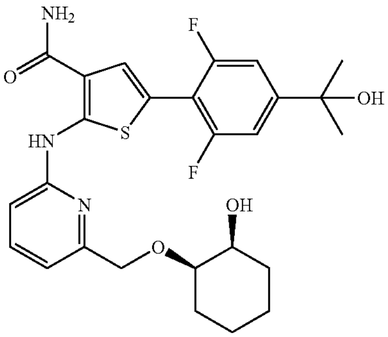 [SMILES: CC(C)(O)c1cc(F)c(-c2cc(C(N)=O)c(Nc3cccc(CO[C@@H]4CCCC[C@@H]4O)n3)s2)c(F)c1] | 5-[2,6-difluoro-4-(1-hydroxy-1-methylethyl)phenyl]-2-{[6-({[(1R,2S)-2-hydroxycyclohexyl]oxy}methyl)pyridin-2-yl]amino}thiophene-3-carboxamide | Calc'd [M + H]$^+$: 518, Found: 518 |
| 249 | 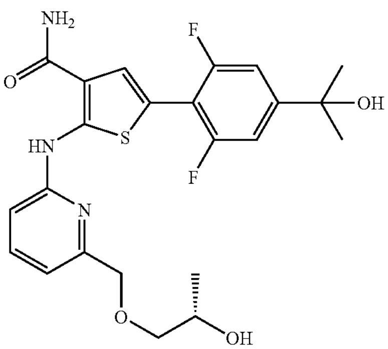 [SMILES: C[C@H](O)COCc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-({[(2S)-2-hydroxypropyl]oxy}methyl)pyridin-2-yl]amino}thiophene-3-carboxamide | Calc'd [M + H]$^+$: 478, Found: 478 |

Example 250

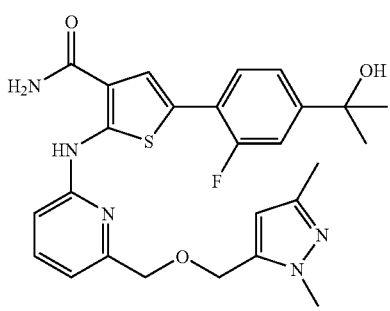 [SMILES: Cc1cc(COCc2cccc(Nc3sc(-c4ccc(C(C)(C)O)cc4F)cc3C(N)=O)n2)n(C)n1]

2-[(6-{[(1,3-Dimethyl-1H-pyrazol-5-yl)methoxy]methyl}pyridin-2-yl)amino]-5-[2-fluoro-4-(1-hydroxy-1-methylethyl)phenyl]thiophene-3-carboxamide Step 1: 2-Bromo-6-{[(1,3-dimethyl-1H-pyrazol-5-yl)methoxy]methyl}pyridine To a suspension of NaH (64 mg, 1.59 mmol) in THF (4 mL) at 0° C. under argon was added 5-(chloromethyl)-1,3-dimethyl-1H-pyrazole (230 mg, 1.59 mmol) and allowed to stir for 20 minutes. (6-Bromopyridin-2-yl)methanol (150 mg, 0.80 mmol) was then added and the mixture was allowed to warm to room temperature and then heated to 55° C. overnight. The reaction was then cooled to ambient temperature and quenched by the addition of water. The quenched reaction mixture was diluted with water (10 mL) and DCM (10 mL) and shaken. The suspensions were passed through disposable phase separators and the DCM eluent was captured and evaporated to dryness to afford the title compound which was used without further purification.

Calc'd for $C_{12}H_{15}BrN_3O$ [M+H]$^+$: 296. Found 296.

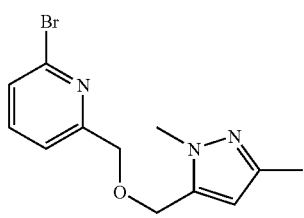 [SMILES: Cc1cc(COCc2cccc(Br)n2)n(C)n1]

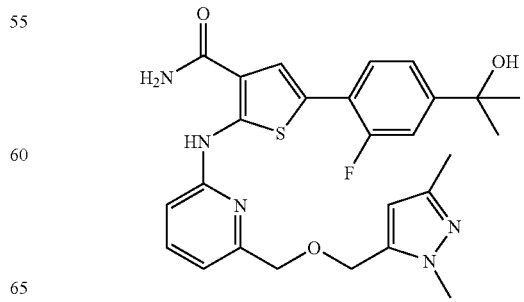

Step 2: 2-[(6-{[(1,3-Dimethyl-1H-pyrazol-5-yl)methoxy]methyl}pyridin-2-yl)amino]-5-[2-fluoro-4-(1-hydroxy-1-methylethyl)phenyl]thiophene-3-carboxamide The title compound was prepared as described Example 1 using 2-amino-5-[2-fluoro-4-(1-hydroxy-1-methylethyl)phenyl]thiophene-3-carboxamide (200 mg, 0.68 mmol) and 2-bromo-6-{[(1,3-dimethyl-1H-pyrazol-5-yl)methoxy]methyl}pyridine (205 mg, 0.68 mmol) as starting materials.
Calc'd for $C_{26}H_{29}FN_5O_3S$ [M+H]$^+$: 510. found 510.

Example 251

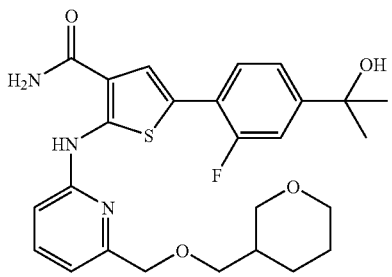 [SMILES: CC(C)(O)c1ccc(-c2cc(C(N)=O)c(Nc3cccc(COCC4CCCOC4)n3)s2)c(F)c1]

5-[2-Fluoro-4-(1-hydroxy-1-methylethyl)phenyl]-2-({6-[(tetrahydro-2H-pyran-3-ylmethoxy)methyl]pyridin-2-yl}amino)thiophene-3-carboxamide

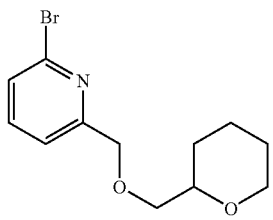 [SMILES: Brc1cccc(COCC2CCCCO2)n1]

Step 1: 2-Bromo-6-[(tetrahydro-2H-pyran-2-ylmethoxy)methyl]pyridine

To a suspension of NaH (63.8 mg, 1.59 mmol) in THF (4 mL) at 0° C. under argon was added tetrahydro-2H-pyran-2-ylmethanol (92.5 mg, 0.80 mmol). The mixture was maintained at 0° C. for 20 minutes, at which time 2-bromo-6-(bromomethyl)pyridine (Example 190, Step 1) (200 mg, 0.80 mmol) was added. The reaction allowed to warm to room temperature and then heated to 55° C. overnight. The reaction was then cooled to ambient temperature and quenched by the addition of water. The quenched reaction mixture was diluted with water (10 mL) and DCM (10 mL) and shaken. The suspensions were passed through disposable phase separators and the DCM eluent was captured and evaporated to dryness to afford the title compound which was used without further purification.
Calc'd for $C_{12}H_{17}BrNO_2$ [M+H]$^+$: 286. Found 286.

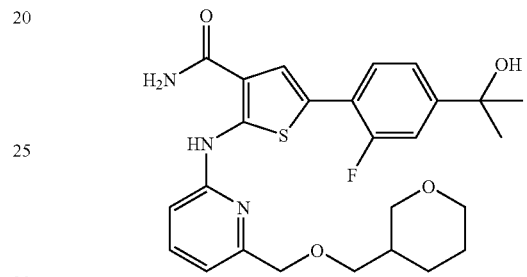

Step 2: 5-[2-Fluoro-4-(1-hydroxy-1-methylethyl)phenyl]-2-({6-[(tetrahydro-2H-pyran-3-ylmethoxy)methyl]pyridin-2-yl}amino)thiophene-3-carboxamide The title compound was prepared as described in Example 1 using 2-amino-5-[2-fluoro-4-(1-hydroxy-1-methylethyl)phenyl]thiophene-3-carboxamide (140 mg, 0.478 mmol) and 2-bromo-6-[(tetrahydro-2H-pyran-2-ylmethoxy)methyl]pyridine (136 mg, 0.478 mmol) as starting materials.
Calc'd for $C_{26}H_{31}FN_3O_4S$ [M+H]$^+$: 500. found 500.
Additional examples were prepared using procedures similar to those described in the above examples and are illustrated in the following table.

TABLE 17

| Example # | Structure | Compound Name | Characterization | Method |
|---|---|---|---|---|
| 252 | (structure shown) | 5-[2-fluoro-4-(1-hydroxy-1-methylethyl)phenyl]-2-({6-[(pyridin-4-ylmethoxy)methyl]pyridin-2-yl}amino)thiophene-3-carboxamide | Calc'd [M + H]$^+$: 493, Found: 493 | B |

TABLE 17-continued

| Example # | Structure | Compound Name | Characterization | Method |
|---|---|---|---|---|
| 253 | 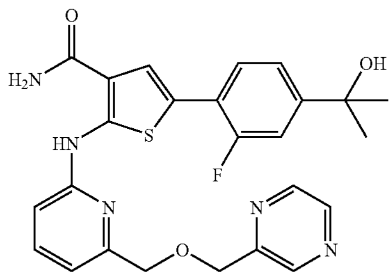 | 5-[2-fluoro-4-(1-hydroxy-1-methylethyl)phenyl]-2-({6-[(pyrazin-2-ylmethoxy)methyl]pyridin-2-yl}amino)thiophene-3-carboxamide | Calc'd [M + H]$^+$: 494, Found: 494 | B |
| 254 | 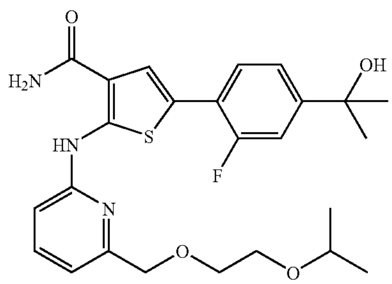 [SMILES: CC(C)OCCOCc1cccc(Nc2sc(-c3ccc(C(C)(C)O)cc3F)cc2C(N)=O)n1] | 5-[2-fluoro-4-(1-hydroxy-1-methylethyl)phenyl]-2-({6-[(2-isopropoxyethoxy)methyl]pyridin-2-yl}amino)thiophene-3-carboxamide | Calc'd [M + H]$^+$: 488, Found: 488 | B |
| 255 | 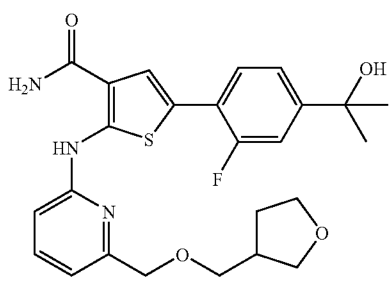 [SMILES: CC(C)(O)c1ccc(-c2cc(C(N)=O)c(Nc3cccc(COCC4CCOC4)n3)s2)c(F)c1] | 5-[2-fluoro-4-(1-hydroxy-1-methylethyl)phenyl]-2-({6-[(tetrahydrofuran-3-ylmethoxy)methyl]pyridin-2-yl}amino)thiophene-3-carboxamide | Calc'd [M + H]$^+$: 486, Found: 486 | B |
| 256 | 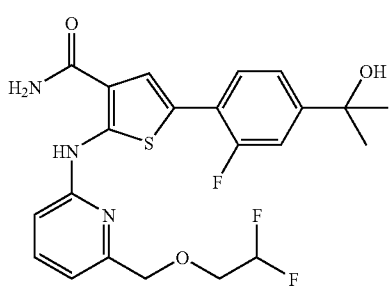 [SMILES: CC(C)(O)c1ccc(-c2cc(C(N)=O)c(Nc3cccc(COCC(F)F)n3)s2)c(F)c1] | 2-({6-[(2,2-difluoroethoxy)methyl]pyridin-2-yl}amino)-5-[2-fluoro-4-(1-hydroxy-1-methylethyl)phenyl]thiophene-3-carboxamide | Calc'd [M + H]$^+$: 466, Found: 466 | B |
| 257 | 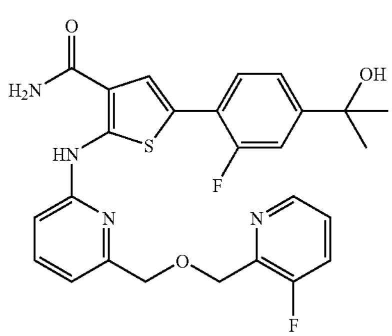 [SMILES: CC(C)(O)c1ccc(-c2cc(C(N)=O)c(Nc3cccc(COCc4ncccc4F)n3)s2)c(F)c1] | 5-[2-fluoro-4-(1-hydroxy-1-methylethyl)phenyl]-2-[(6-{[(3-fluoropyridin-2-yl)methoxy]methyl}pyridin-2-yl)amino]thiophene-3-carboxamide | Calc'd [M + H]$^+$: 511, Found: 511 | B |

TABLE 17-continued

| Example # | Structure | Compound Name | Characterization | Method |
|---|---|---|---|---|
| 258 | 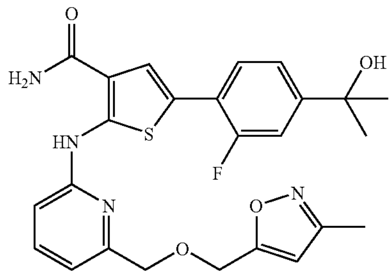 | 5-[2-fluoro-4-(1-hydroxy-1-methylethyl)phenyl]-2-[(6-{[(3-methylisoxazol-5-yl)methoxy]methyl}pyridin-2-yl)amino]thiophene-3-carboxamide | Calc'd [M + H]⁺: 497, Found: 497 | A |
| 259 | 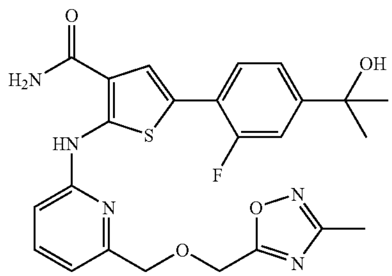 [SMILES: Cc1noc(COCc2cccc(Nc3sc(-c4ccc(C(C)(C)O)cc4F)cc3C(N)=O)n2)n1] | 5-[2-fluoro-4-(1-hydroxy-1-methylethyl)phenyl]-2-[(6-{[(3-methyl-1,2,4-oxadiazol-5-yl)methoxy]methyl}pyridin-2-yl)amino]thiophene-3-carboxamide | Calc'd [M + H]⁺: 498, Found: 498 | A |
| 260 | 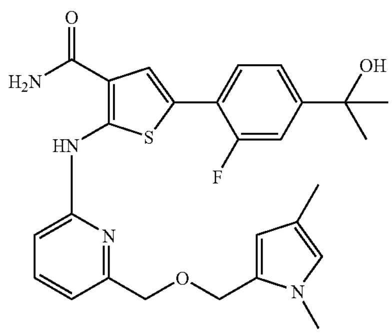 [SMILES: Cc1cc(COCc2cccc(Nc3sc(-c4ccc(C(C)(C)O)cc4F)cc3C(N)=O)n2)n(C)c1] | 2-[(6-{[(1,3-dimethyl-1H-pyrazol-5-yl)methoxy]methyl}pyridin-2-yl)amino]-5-[2-fluoro-4-(1-hydroxy-1-methylethyl)phenyl]thiophene-3-carboxamide | Calc'd [M + H]⁺: 510, Found: 510 | A |
| 261 | 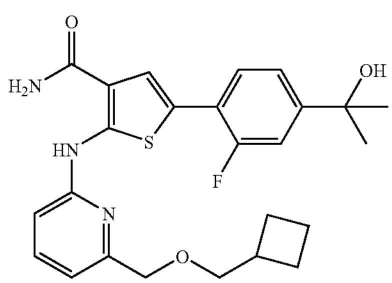 [SMILES: CC(C)(O)c1ccc(-c2cc(C(N)=O)c(Nc3cccc(COCC4CCC4)n3)s2)c(F)c1] | 2-({6-[(cyclobutylmethoxy)methyl]pyridin-2-yl}amino)-5-[2-fluoro-4-(1-hydroxy-1-methylethyl)phenyl]thiophene-3-carboxamide | Calc'd [M + H]⁺: 470, Found: 470 | B |
| 262 | 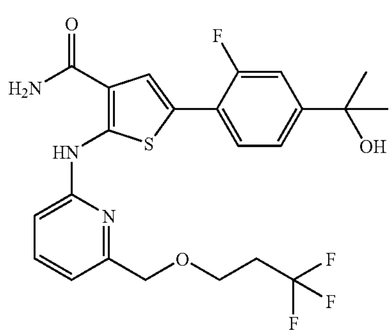 [SMILES: CC(C)(O)c1ccc(-c2cc(C(N)=O)c(Nc3cccc(COCCC(F)(F)F)n3)s2)c(F)c1] | 5-[2-fluoro-4-(1-hydroxy-1-methylethyl)phenyl]-2-({6-[(3,3,3-trifluoropropoxy)methyl]pyridin-2-yl}amino)thiophene-3-carboxamide | Calc'd [M + H]⁺: 498, Found: 498 | B |

TABLE 17-continued

| Example # | Structure | Compound Name | Characterization | Method |
|---|---|---|---|---|
| 263 | 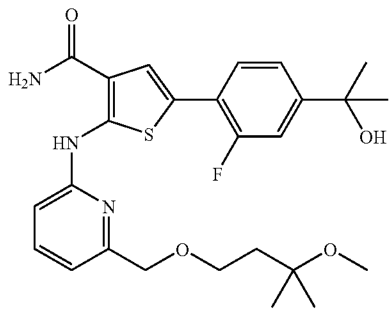 [SMILES: COC(C)(C)CCOCc1cccc(Nc2sc(-c3ccc(C(C)(C)O)cc3F)cc2C(N)=O)n1] | 5-[2-fluoro-4-(1-hydroxy-1-methylethyl)phenyl]-2-({6-[(3-methoxy-3-methylbutoxy)methyl]pyridin-2-yl}amino)thiophene-3-carboxamide | Calc'd [M + H]$^+$: 502, Found: 502 | B |
| 264 | 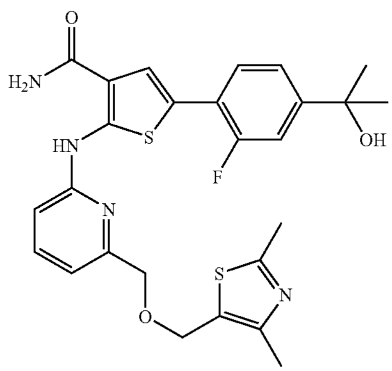 [SMILES: Cc1nc(C)c(COCc2cccc(Nc3sc(-c4ccc(C(C)(C)O)cc4F)cc3C(N)=O)n2)s1] | 2-[(6-{[(2,4-dimethyl-1,3-thiazol-5-yl)methoxy]methyl}pyridin-2-yl)amino]-5-[2-fluoro-4-(1-hydroxy-1-methylethyl)phenyl]thiophene-3-carboxamide | Calc'd [M + H]$^+$: 527, Found: 527 | B |
| 265 | 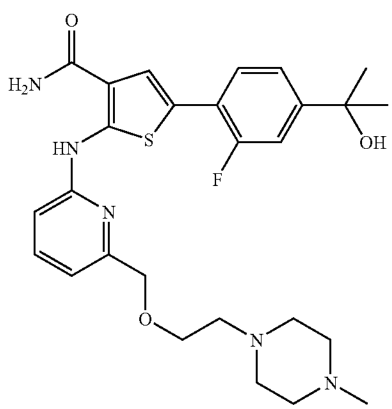 [SMILES: CN1CCN(CCOCc2cccc(Nc3sc(-c4ccc(C(C)(C)O)cc4F)cc3C(N)=O)n2)CC1] | 5-[2-fluoro-4-(1-hydroxy-1-methylethyl)phenyl]-2-[(6-{[2-(4-methylpiperazin-1-yl)ethoxy]methyl}pyridin-2-yl)amino]thiophene-3-carboxamide | Calc'd [M + H]$^+$: 528, Found: 528 | B |
| 266 | 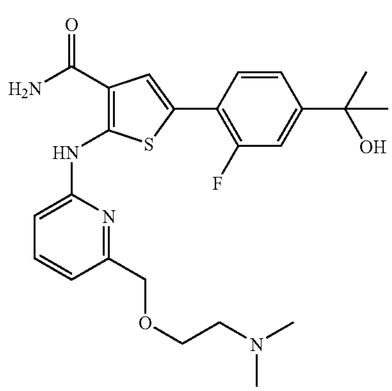 [SMILES: CN(C)CCOCc1cccc(Nc2sc(-c3ccc(C(C)(C)O)cc3F)cc2C(N)=O)n1] | 2-[(6-{[2-(dimethylamino)ethoxy]methyl}pyridin-2-yl)amino]-5-[2-fluoro-4-(1-hydroxy-1-methylethyl)phenyl]thiophene-3-carboxamide | Calc'd [M + H]$^+$: 473, Found: 473 | B |

| Example # | Structure | Compound Name | Characterization | Method |
|---|---|---|---|---|
| 267 | 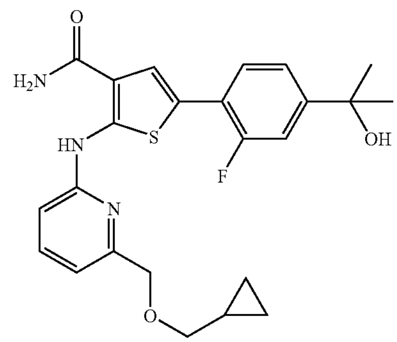 [SMILES: CC(C)(O)c1ccc(-c2cc(C(N)=O)c(Nc3cccc(COCC4CC4)n3)s2)c(F)c1] | 2-({6-[(cyclopropylmethoxy)methyl]pyridin-2-yl}amino)-5-[2-fluoro-4-(1-hydroxy-1-methylethyl)phenyl]thiophene-3-carboxamide | Calc'd [M + H]⁺: 456, Found: 456 | B |
| 268 | 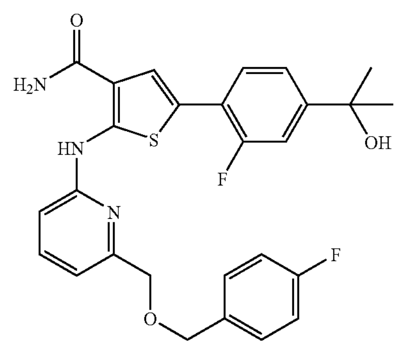 [SMILES: CC(C)(O)c1ccc(-c2cc(C(N)=O)c(Nc3cccc(COCc4ccc(F)cc4)n3)s2)c(F)c1] | 2-[(6-{[(4-fluorobenzyl)oxy]methyl}pyridin-2-yl)amino]-5-[2-fluoro-4-(1-hydroxy-1-methylethyl)phenyl]thiophene-3-carboxamide | Calc'd [M + H]⁺: 510, Found: 510 | B |
| 269 | 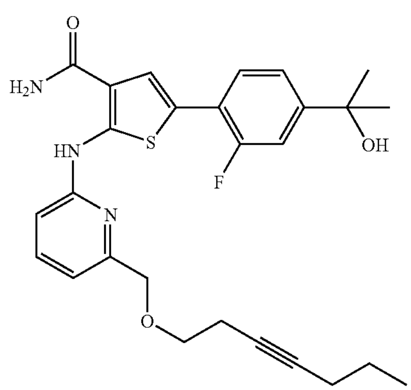 [SMILES: CCCC#CCCOCc1cccc(Nc2sc(-c3ccc(C(C)(C)O)cc3F)cc2C(N)=O)n1] | 5-[2-fluoro-4-(1-hydroxy-1-methylethyl)phenyl]-2-({6-[(hept-3-yn-1-yloxy)methyl]pyridin-2-yl}amino)thiophene-3-carboxamide | Calc'd [M + H]⁺: 496, Found: 496 | B |
| 270 | 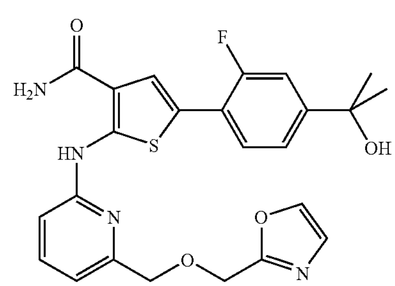 [SMILES: CC(C)(O)c1ccc(-c2cc(C(N)=O)c(Nc3cccc(COCc4ncco4)n3)s2)c(F)c1] | 5-[2-fluoro-4-(1-hydroxy-1-methylethyl)phenyl]-2-({6-[(1,3-oxazol-2-ylmethoxy)methyl]pyridin-2-yl}amino)thiophene-3-carboxamide | Calc'd [M + H]⁺: 483, Found: 483 | A |

| Example # | Structure | Compound Name | Characterization | Method |
|---|---|---|---|---|
| 271 | 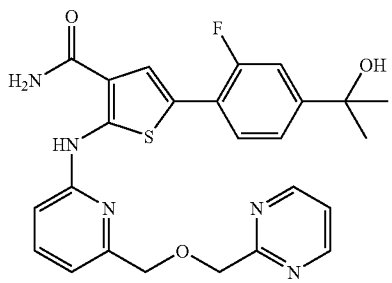 [SMILES: CC(C)(O)c1ccc(-c2cc(C(N)=O)c(Nc3cccc(COCc4ncccn4)n3)s2)c(F)c1] | 5-[2-fluoro-4-(1-hydroxy-1-methylethyl)phenyl]-2-({6-[(pyrimidin-2-ylmethoxy)methyl]pyridin-2-yl}amino)thiophene-3-carboxamide | Calc'd [M + H]$^+$: 494, Found: 494 | A |

Method A: Using procedures described in Example 250
Method B: Using procedures described in Example 251

Example 272

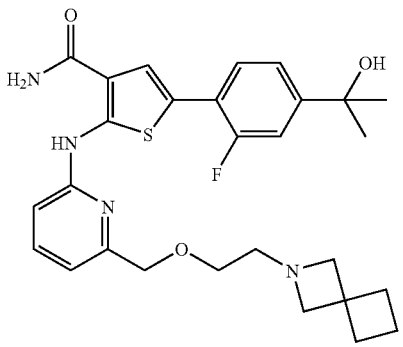 [SMILES: CC(C)(O)c1ccc(-c2cc(C(N)=O)c(Nc3cccc(COCCN4CC5(CCC5)C4)n3)s2)c(F)c1]

2-[(6-{[2-(2-Azaspiro[3.3]hept-2-yl)ethoxy]methyl}pyridin-2-yl)amino]-5-[2-fluoro-4-(1-hydroxy-1-methylethyl)phenyl]thiophene-3-carboxamide

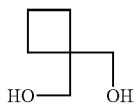

Step 1: Cyclobutane-1,1-diyldimethanol

To a 5 L two necked round bottom flask containing LAH (76 g, 2.0 mol) was added 1000 mL of cold diethyl ether. The reaction mixture was cooled to 0° C. and a solution of diethyl cyclobutane-1,1-dicarboxylate (100 g, 0.5 mol) in diethyl ether (500 mL) was added over a period of 2 h. After the addition was completed, the contents were stirred at 25-30° C. for 2 h. The reaction mixture was cooled to −10° C. and excess lithium aluminum hydride was quenched by slow addition of ice over a period of 3 h followed by addition of 20% aqueous sodium hydroxide solution. The reaction mixture was filtered and the precipitate was washed 3 times with 200 mL of diethyl ether. The combined organic layers were dried over anhydrous $Na_2SO_4$, filtered, and concentrated under reduced pressure to afford the title compound. $^1$H NMR (400 MHz, $CDCl_3$) δ 3.76 (s, 4H), 2.26 (br s, 2H), 1.95 (m, 2H), 1.81 (m, 4H).

Step 2: 1,1-Bis(bromomethyl)cyclobutane

To a three necked 2 L RB flask was added cyclobutane-1,1-diyldimethanol (100 g, 0.86 mol) and pyridine (300 mL). Phosphorus tribromide (300 mL, 3.19 mol) was added slowly over 30 min and the reaction mixture was heated to 80-85° C. and maintained for 2 h. The reaction was cooled to 5-10° C. and chloroform (300 mL) was added. The reaction was further cooled to 0-5° C. and quenched with ice water. The reaction was filtered and washed with chloroform (50 mL). The aqueous layer from the filtrate was extracted with 3×400 mL of chloroform. The combined layers were dried over $Na_2SO_4$, filtered, and concentrated. The crude residue was purified by column chromatography using petroleum ether to afford the title compound.

$^1$H NMR (400 MHz, $CDCl_3$) δ 3.68 (s, 4H) 1.97 (m, 4H), 1.90 (m, 2H).

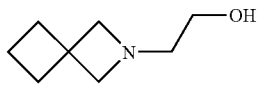

Step 3: 2-(2-Azaspiro[3.3]hept-2-yl)ethanol

To a three neck 3 L round bottom flask was added 1,1-bis(bromomethyl)cyclobutane (100 g, 0.43 mol), potassium carbonate (285 g, 2.06 mol), acetonitrile (1000 mL) and ethanolamine (37.8 g, 0.62 mol). The reaction mixture was heated to reflux for 2 days. The reaction mixture was concentrated to half volume and water was added (300 mL). The aqueous layer was extracted with dichloromethane (2×500 mL). The combined organic layers were washed with brine (200 mL), dried over sodium sulfate, filtered, and concentrated to afford the title compound.

$^1$H NMR (400 MHz, $CDCl_3$) δ 3.80 (br s, 1H), 3.45 (m, 2H), 3.16 (s, 4H), 2.49 (m, 2H), 2.05 (m, 4H), 2.75 (m, 2H). Calc'd for $C_8H_{16}NO$ [M+H]$^+$: 142. Found: 142.

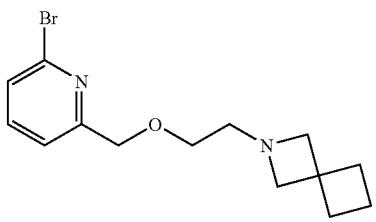 [SMILES: Brc1cccc(COCCN2CC3(CCC3)C2)n1]

Step 4: 2-{2-[(6-Bromopyridin-2-yl)methyoxy]ethyl}-2-azaspiro[3.3]heptane

The title compound was prepared according to Example 251, Step 1 using 2-bromo-6-(bromomethyl)pyridine (Example 190, Step 1) (200 mg, 0.80 mmol) and 2-(2-azaspiro[3.3]hept-2-yl)ethanol (112 mg, 0.80 mmol) as the starting materials.

Calc'd for $C_{14}H_{20}BrN_2O$ $[M+H]^+$: 311. Found: 311.

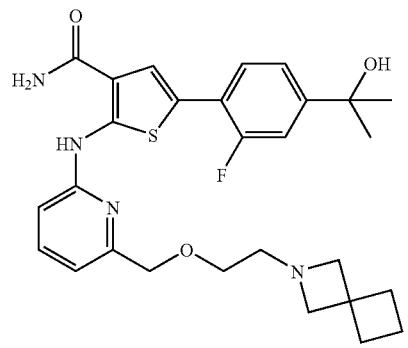

Step 5: 2-[(6-{[2-(2-Azaspiro[3.3]hept-2-yl)ethoxy]methyl}pyridin-2-yl)amino]-5-[2-fluoro-4-(1-hydroxy-1-methylethyl)phenyl]thiophene-3-carboxamide The title compound was prepared according to Example 251, Step 2 using 5-(2-fluoro-4-(1-hydroxy-1-methylethyl)phenyl)-2-((6-formyl-2-pyridinyl)amino)-3-thiophenecarboxamide (200 mg, 0.68 mmol) and 2-{2-[(6-bromopyridin-2-yl)methyoxy]ethyl}-2-azaspiro[3.3]heptane (211 mg, 0.68 mmol) as the starting materials.

Calc'd for $C_{28}H_{34}FN_4O_3S$ $[M+H]^+$: 525 found 525.

Example 273

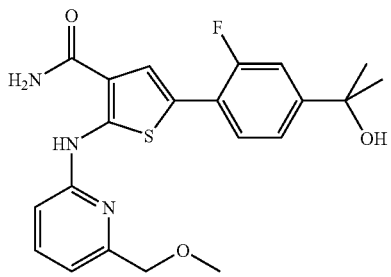 [SMILES: COCc1cccc(Nc2sc(-c3ccc(C(C)(C)O)cc3F)cc2C(N)=O)n1]

5-[2-Fluoro-4-(1-hydroxy-1-methylethyl)phenyl]-2-{[6-(methoxymethyl)pyridin-2-yl]amino}thiophene-3-carboxamide To a suspension of NaH (9.96 mg, 0.25 mmol) in DMF (1.25 mL) at 0° C. under argon was added 5-[2-fluoro-4-(1-hydroxy-1-methylethyl)phenyl]-2-{[6-(hydroxymethyl)pyridin-2-yl]amino}thiophene-3-carboxamide (Example 43) (50 mg, 0.125 mmol) and the mixture was stirred for 20 minutes. Iodomethane (26.6 mg, 0.187 mmol) was then added and the reaction was allowed to warm to room temperature and subsequently heated to 60° C. overnight. The reaction was cooled to ambient temperature, quenched by the addition of water, extracted with ethyl acetate and concentrated in vacuo. The crude residue was reverse phase HPLC (acteonitrile/water with formic acid as a modifier) to afford the title compound.

Calc'd for $C_{21}H_{23}FN_3O_3S$ $[M+H]^+$: 416. Found 416.

Example 274

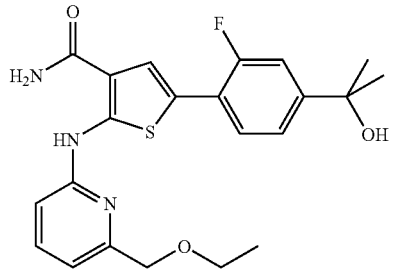 [SMILES: CCOCc1cccc(Nc2sc(-c3ccc(C(C)(C)O)cc3F)cc2C(N)=O)n1]

2-{[6-(Ethoxymethyl)pyridin-2-yl]amino}-5-[2-fluoro-4-(1-hydroxy-1-methylethyl)phenyl]thiophene-3-carboxamide To a suspension of NaH (10 mg, 0.25 mmol) in DMF (1.25 mL) at 0° C. under argon was added 5-[2-fluoro-4-(1-hydroxy-1-methylethyl)phenyl]-2-{[6-(hydroxymethyl)pyridin-2-yl]amino}thiophene-3-carboxamide (Example 48) (50 mg, 0.125 mmol) and the mixture was allowed to stir for 20 minutes. Iodoethane (29 mg, 0.19 mmol) was then added and the reaction was allowed to warm to room temperature and subsequently heated to 60° C. overnight. The reaction was cooled to ambient temperature, quenched by the addition of water, extracted with ethyl acetate and concentrated in vacuo. The crude residue was reverse phase HPLC (acteonitrile/water with formic acid as a modifier) to afford the title compound.

Calc'd for $C_{22}H_{25}FN_3O_3S$ $[M+H]^+$: 430. Found 430.

Example 275

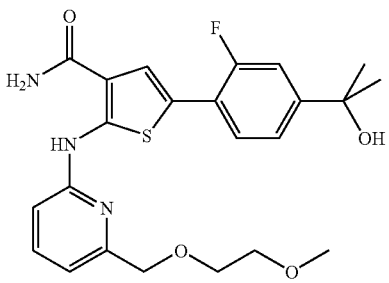 [SMILES: COCCOCc1cccc(Nc2sc(-c3ccc(C(C)(C)O)cc3F)cc2C(N)=O)n1]

5-[2-Fluoro-4-(1-hydroxy-1-methylethyl)phenyl]-2-({6-[(2-methoxyethoxy) methyl]pyridin-2-yl}amino)thiophene-3-carboxamide To a suspension of NaH (7.5 mg, 0.19 mmol) in DMF (1.25 mL) at 0° C. under argon was added 5-[2-fluoro-4-(1-hydroxy-1-methylethyl)phenyl]-2-{[6-(hydroxymethyl)pyridin-2-yl]amino}thiophene-3-carboxamide (Example 43) (50 mg, 0.13 mmol) and the mixture was allowed to stir for 10 minutes. 1-Bromo-2-methoxyethane (26 mg, 0.187 mmol) was then added and the reaction was allowed to warm to room temperature overnight. The reaction was then quenched by the addition of water, extracted with ethyl acetate and concentrated in vacuo. The crude residue was reverse phase HPLC (acteonitrile/water with formic acid as a modifier) to afford the title compound.

Calc'd for $C_{23}H_{27}FN_3O_4S$ [M+H]$^+$: 460. Found 460.

Example 276

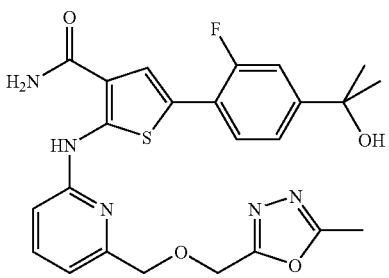 [SMILES: Cc1nnc(COCc2cccc(Nc3sc(-c4ccc(C(C)(C)O)cc4F)cc3C(N)=O)n2)o1]

5-[2-Fluoro-4-(1-hydroxy-1-methylethyl)phenyl]-2-[(6-{[(5-methyl-1,3,4-oxadiazol-2-yl)methoxy]methyl}pyridin-2-yl)amino]thiophene-3-carboxamide To a suspension of NaH (14 mg, 0.35 mmol) in DMF (1.75 mL) at 0° C. under argon was added 5-[2-fluoro-4-(1-hydroxy-1-methylethyl)phenyl]-2-{[6-(hydroxymethyl)pyridin-2-yl]amino}thiophene-3-carboxamide (Example 43) (70 mg, 0.17 mmol) and the mixture was allowed to stir for 10 minutes. 2-(Chloromethyl)-5-methyl-1,3,4-oxadiazole (35 mg, 0.26 mmol) was then added and the reaction was allowed to warm to room temperature overnight. The reaction was then quenched by the addition of water, extracted with ethyl acetate and concentrated in vacuo. The crude residue was reverse phase HPLC (acteonitrile/water with formic acid as a modifier) to afford the title compound.

Calc'd for $C_{24}H_{25}FN_5O_4S$ [M+H]$^+$: 498. Found 498.

Example 277

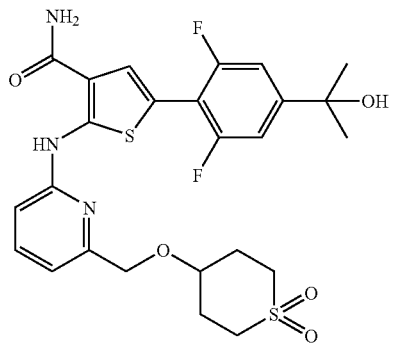 [SMILES: CC(C)(O)c1cc(F)c(-c2cc(C(N)=O)c(Nc3cccc(COC4CCS(=O)(=O)CC4)n3)s2)c(F)c1]

5-[2,6-Difluoro-4-(1-hydroxy-1-methylethyl)phenyl]-2-[(6-{[(1,1-dioxidotetrahydro-2H-thiopyran-4-yl)oxy]methyl}pyridin-2-yl)amino]thiophene-3-carboxamide

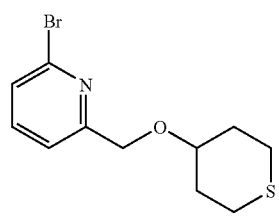 [SMILES: Brc1cccc(COC2CCSCC2)n1]

Step 1: 2-Bromo-6-[(tetrahydro-2H-thiopyran-4-yloxy)methyl]pyridine

Sodium hydride (0.24 g, 5.98 mmol) was suspended in tetrahydrofuran (19.9 mL) and cooled to 0° C. Tetrahydro-2H-thiopyran-4-ol (0.24 g, 1.99 mmol) was added and the reaction was stirred for 30 minutes. 2-Bromo-6-(bromomethyl)pyridine (Example 190, Step 1) (0.5 g, 1.99 mmol) was added and the reaction was warmed to and maintained at ambient temperature overnight. The reaction was diluted with ethyl acetate, quenched slowly with water, the layers were separated, and the aqueous layer was extracted with ethyl acetate. The combined organic layers were dried over magnesium sulfate, filtered and concentrated. The crude mixture was purified by silica gel chromatography to yield the title compound.

Calc'd for $C_{11}H_{15}BrNOS$ [M+H]$^+$: 288. Found: 288.

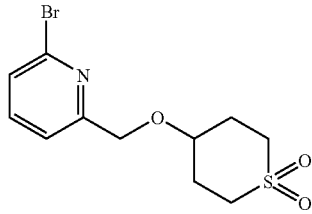 [SMILES: O=S1(=O)CCC(OCc2cccc(Br)n2)CC1]

Step 2: 2-Bromo-6-{[(1,1-dioxidotetrahydro-2H-thiopyran-4-yl)oxy]methyl}pyridine 2-Bromo-6-[(tetrahydro-2H-thiopyran-4-yloxy)methyl]pyridine (0.34 g, 1.19 mmol) was dissolved in dichloromethane (11.9 mL) and cooled to 0° C. 3-Chloroperoxybenzoic acid (450 mg, 2.63 mmol) was added and the reaction mixture was allowed to warm to room temperature. The reaction was diluted with dichloromethane, washed with saturated sodium bicarbonate, dried over magnesium sulfate, filtered and concentrated. The crude mixture was purified by silica gel chromatography to yield the title compound.

Calc'd for $C_{11}H_{15}BrNO_3S$ [M+H]$^+$: 320. Found: 320.

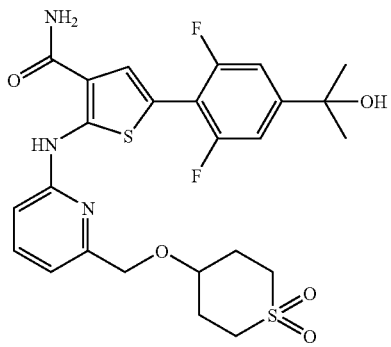 [SMILES: CC(C)(O)c1cc(F)c(-c2cc(C(N)=O)c(Nc3cccc(COC4CCS(=O)(=O)CC4)n3)s2)c(F)c1]

Step 3: 5-[2,6-Difluoro-4-(1-hydroxy-1-methylethyl)phenyl]-2-[(6-{[(1,1-dioxidotetrahydro-2H-thiopyran-4-yl)oxy]methyl}pyridin-2-yl)amino]thiophene-3-carboxamide The title compound was prepared as described in Example 1 with 2-amino-5-[2,6-difluoro-4-(1-hydroxy-1-methylethyl)phenyl]thiophene-3-carboxamide (0.10 g, 0.32 mmol) and 2-bromo-6-{[(1,1-dioxidotetrahydro-2H-thiopyran-4-yl)oxy]methyl}pyridine (0.10 g, 0.32 mmol) as the starting materials.

Calc'd for $C_{25}H_{28}F_2N_3O_5S_2$ [M+H]$^+$: 552. Found: 552.

The following example was prepared using procedures similar to those described in the above example.

TABLE 18

| Example | Structure | Name | Characterization |
|---|---|---|---|
| 278 | 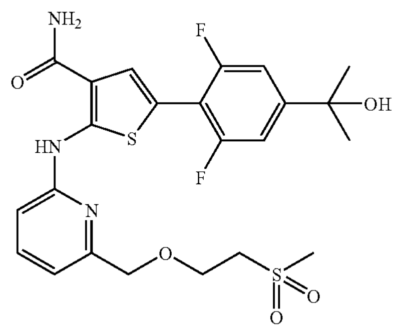 [SMILES: CC(C)(O)c1cc(F)c(-c2cc(C(N)=O)c(Nc3cccc(COCCS(C)(=O)=O)n3)s2)c(F)c1] | 5-[2,6-difluoro-4-(1-hydroxy-1-methylethyl)phenyl]-2-[(6-{2-(methylsulfonyl)ethoxy]methyl}pyridin-2-yl)amino]thiophene-3-carboxamide | Calc'd [M + H]$^+$: 526, Found: 526 |

Example 279

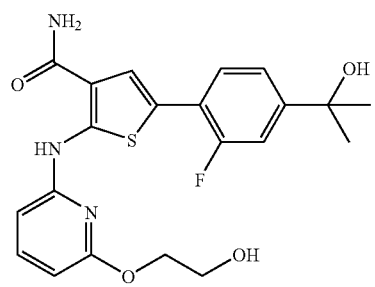 [SMILES: CC(C)(O)c1ccc(-c2cc(C(N)=O)c(Nc3cccc(OCCO)n3)s2)c(F)c1]

5-[2-Fluoro-4-(1-hydroxy-1-methylethyl)phenyl]-2-{[6-(2-hydroxyethoxy)pyridin-2-yl]amino}thiophene-3-carboxamide The title compound was prepared as described in Example 205, Step 2 using 2-amino-5-[2-fluoro-4-(1-hydroxy-1-methylethyl)phenyl]thiophene-3-carboxamide (60 mg, 0.20 mmol) and 2-[(6-bromopyridin-2-yl)oxy]ethanol (48.8 mg, 0.22 mmol) as starting materials.

Calc'd for $C_{21}H_{22}FN_3O_4S$ [M+H]$^+$: 432. found 432.

Additional examples were prepared using procedures similar to those described in the above example and are illustrated in the following table.

TABLE 19

| Example # | Structure | Name | Characterization |
|---|---|---|---|
| 280 | 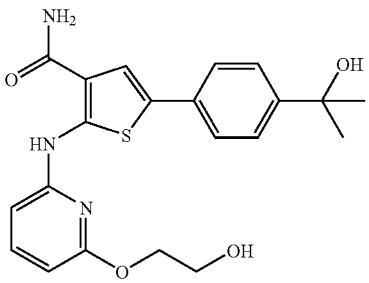 [SMILES: CC(C)(O)c1ccc(-c2cc(C(N)=O)c(Nc3cccc(OCCO)n3)s2)cc1] | 2-{[6-(2-hydroxyethoxy)pyridin-2-yl]amino}-5-[4-(1-hydroxy-1-methylethyl)phenyl]thiophene-3-carboxamide | Calc'd [M + H]$^+$: 414, Found: 414 |
| 281 | 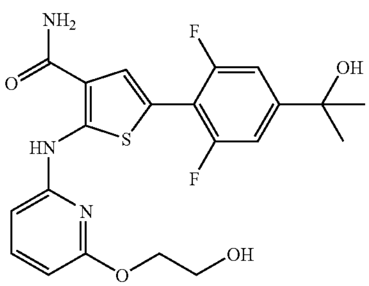 [SMILES: CC(C)(O)c1cc(F)c(-c2cc(C(N)=O)c(Nc3cccc(OCCO)n3)s2)c(F)c1] | 5-[2,6-difluoro-4-(1-hydroxy-1-methylethyl)phenyl]-2-{[6-(2-hydroxyethoxy)pyridin-2-yl]amino}thiophene-3-carboxamide | Calc'd [M + H]$^+$: 450, Found: 450 |

Example 282

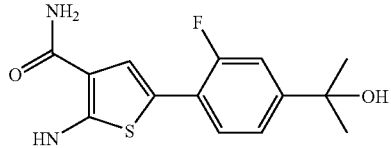

6-({3-(Aminocarbonyl)-5-[2-fluoro-4-(1-hydroxy-1-methylethyl)phenyl]-2-thienyl}amino)-N-(trans-4-hydroxycyclohexyl)pyridine-2-carboxamide

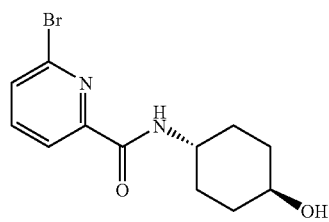 [SMILES: O=C(N[C@H]1CC[C@H](O)CC1)c1cccc(Br)n1]

Step 1: 6-Bromo-N-(trans-4-hydroxycyclohexyl)pyridine-2-carboxamide

Method A: 6-Bromopyridine-2-carboxylic acid (0.50 g, 2.48 mmol), trans-4-aminocyclohexanol hydrochloride (0.38 g, 2.48 mmol), 1-(3-dimethylaminopropyl)-3-ethylcarbodiimide hydrochloride (0.47 g, 2.48 mmol) 1-hydroxybenzotriazole hydrate (0.39 g, 2.52 mmol) were taken up DMF (12.40 mL) and triethylamine (1.04 mL, 7.43 mmol) and allowed to react overnight at room temperature. The reaction was then diluted with ethyl acetate, washed with water, dried over magnesium sulfate, filtered and concentrated. The crude residue was purified by reverse phase HPLC (10-100% acetonitrile/water+0.05% TFA modifier) to afford the title compound.

Calc'd for $C_{12}H_{16}BrN_2O_2$ [M+H]$^+$: 299. Found: 299.

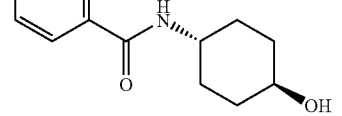

Step 2: 6-({3-(Aminocarbonyl)-5-[2-fluoro-4-(1-hydroxy-1-methylethyl)phenyl]-2-thienyl}amino)-N-(trans-4-hydroxycyclohexyl)pyridine-2-carboxamide The title compound was prepared as described in Example 1 with 2-amino-5-[2-fluoro-4-(1-hydroxy-1-methylethyl)phenyl]thiophene-3-carboxamide (0.11 g, 0.39 mmol) and 6-bromo-N-(trans-4-hydroxycyclohexyl)pyridine-2-carboxamide (0.11 g, 0.38 mmol) as the starting materials.

Calc'd for $C_{26}H_{30}FN_4O_4S$ [M+H]$^+$: 513. Found: 513.

Example 283

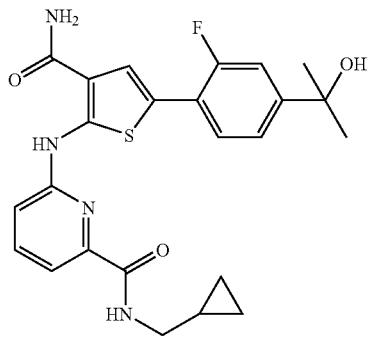 [SMILES: CC(C)(O)c1ccc(-c2cc(C(N)=O)c(Nc3cccc(C(=O)NCC4CC4)n3)s2)c(F)c1]

6-({3-(Aminocarbonyl)-5-[2-fluoro-4-(1-hydroxy-1-methylethyl)phenyl]-2-thienyl}amino)-N-(cyclopropylmethyl)pyridine-2-carboxamide

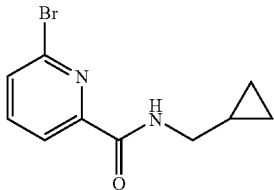 [SMILES: O=C(NCC1CC1)c1cccc(Br)n1]

Step 1: 6-Bromo-N-(cyclopropylmethyl)pyridine-2-carboxamide

Method B: A mixture of PS-CDI (1.3 g, 1.86 mmol) in DMF was shaken for 5 min prior to addition of 1-cyclopropylmethanamine (68 mg, 0.96 mmol), 6-bromopyridine-2-carboxylic acid (150 mg, 0.74 mmol) and DIEA (156 µL, 0.89 mmol). The reaction was heated to 100° C. under microwave irradiation for 7 min. Upon cooling to ambient temperature, Si-carbonate (2.7 g, 2.23 mmol) and DCM (3 mL) were added and the resulting mixture was shaken overnight at room temperature. The reaction mixture was then filtered, washed with DCM, concentrated in vacuo and purified by reverse phase HPLC (acetonitrile/water+formic acid modifier) to afford the title compound.

Calc'd for $C_{10}H_{12}BrN_2O$ [M+H]$^+$: 254. Found: 254.

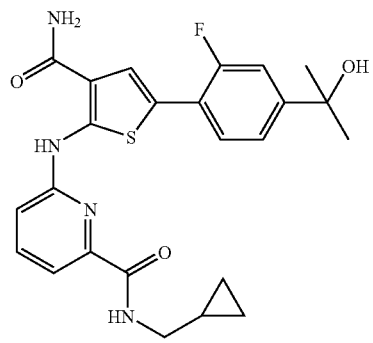 [SMILES: CC(C)(O)c1ccc(-c2cc(C(N)=O)c(Nc3cccc(C(=O)NCC4CC4)n3)s2)c(F)c1]

Step 2: 6-Bromo-N-(cyclopropylmethyl)pyridine-2

The title compound was prepared as described Example 1 using 6-bromo-N-(cyclopropylmethyl)pyridine-2-carboxamide (170 mg, 0.67 mmol) and 2-amino-5-[2-fluoro-4-(1-hydroxy-1-methylethyl)phenyl]thiophene-3-carboxamide (196 mg, 0.67 mmol) as the starting materials.

Calc'd for $C_{24}H_{26}FN_4O_3S$ [M+H]$^+$: 469. Found 469.

Example 284

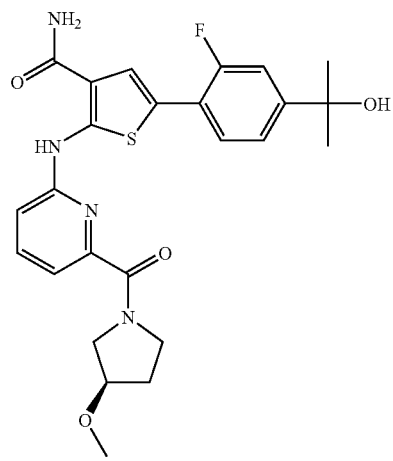 [SMILES: CO[C@@H]1CCN(C(=O)c2cccc(Nc3sc(-c4ccc(C(C)(C)O)cc4F)cc3C(N)=O)n2)C1]

5-[2-Fluoro-4-(1-hydroxy-1-methylethyl)phenyl]-2-[(6-{[(3R)-3-methoxypyrrolidin-1-yl]carbonyl}pyridin-2-yl)amino]thiophene-3-carboxamide

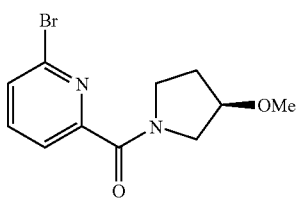 [SMILES: CO[C@@H]1CCN(C(=O)c2cccc(Br)n2)C1]

Step 1: 2-Bromo-6-{[(3R)-3-methoxypyrrolidin-1-yl]carbonyl}pyridine

Method C: A solution of (3R)-3-methoxypyrrolidine (90 mg, 0.89 mmol), 6-bromopyridine-2-carboxylic acid (150 mg, 0.74 mmol), TEA (124 µL, 0.89 mmol), EDC (142 mg, 0.74 mmol) and HOBt (171 mg, 1.11 mmol) in 1:1 mixture of DMF (1.9 mL) and DCM (1.9 mL) was allowed to react overnight at room temperature. Upon reaction completion, PS-trisamine (874 mg, 2.97 mmol) and DCM (3 mL) were added and the resulting mixture was shaken overnight at room temperature. The reaction mixture was then filtered, washed with DCM, concentrated in vacuo and purified by reverse phase HPLC (acetonitrile/water+formic acid modifier) to afford the title compound.

Calc'd for $C_{11}H_{14}BrN_2O_2$ [M+H]$^+$: 285. Found: 285.

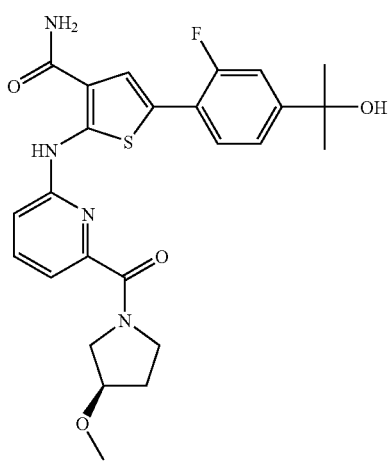 [SMILES: CO[C@@H]1CCN(C(=O)c2cccc(Nc3sc(-c4ccc(C(C)(C)O)cc4F)cc3C(N)=O)n2)C1]

Step 2: 5-[2-Fluoro-4-(1-hydroxy-1-methylethyl)phenyl]-2-[(6-{[(3R)-3-methoxypyrrolidin-1-yl]carbonyl}pyridin-2-yl)amino]thiophene-3-carboxamide The title compound was prepared as described Example 1 using 2-bromo-6-{[(3R)-3-methoxypyrrolidin-1-yl]carbonyl}pyridine (53 mg, 0.19 mmol) and 2-amino-5-[2-fluoro-4-(1-hydroxy-1-methylethyl)phenyl]thiophene-3-carboxamide (55 mg, 0.19 mmol) as starting materials.

Calc'd for $C_{25}H_{28}FN_4O_4S$ $[M+1]^+$: 499. Found 499.

Additional examples were prepared using procedures similar to those described in the above examples and are illustrated in the following table.

TABLE 20

| Example | Structure | Compound Name | Characterization [M + H]⁺ | Method |
|---|---|---|---|---|
| 285 | 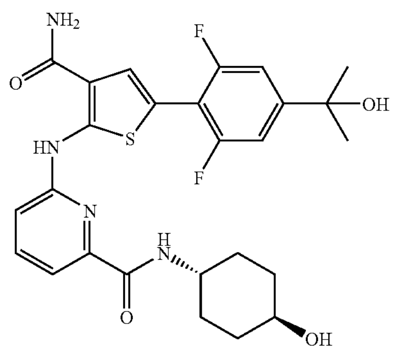 [SMILES: CC(C)(O)c1cc(F)c(-c2cc(C(N)=O)c(Nc3cccc(C(=O)N[C@H]4CC[C@H](O)CC4)n3)s2)c(F)c1] | 6-({3-(aminocarbonyl)-5-[2,6-difluoro-4-(1-hydroxy-1-methylethyl)phenyl]-2-thienyl}amino)-N-(trans-4-hydroxycyclohexyl)pyridine-2-carboxamide | Calc'd 531, Found: 531 | A |
| 286 | 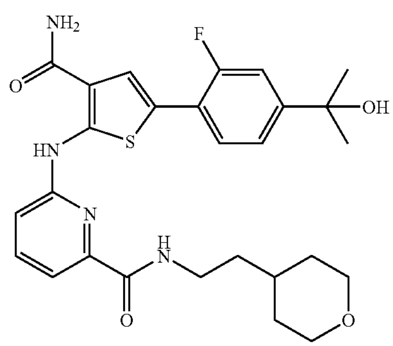 [SMILES: CC(C)(O)c1ccc(-c2cc(C(N)=O)c(Nc3cccc(C(=O)NCCC4CCOCC4)n3)s2)c(F)c1] | 6-({3-(aminocarbonyl)-5-[2-fluoro-4-(1-hydroxy-1-methylethyl)phenyl]-2-thienyl}amino)-N-[2-(tetrahydro-2H-pyran-4-yl)ethyl]pyridine-2-carboxamide | Calc'd 527, Found: 527 | A |
| 287 | 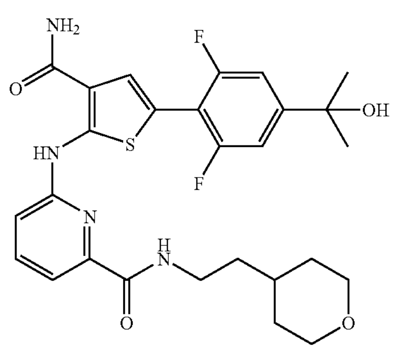 [SMILES: CC(C)(O)c1cc(F)c(-c2cc(C(N)=O)c(Nc3cccc(C(=O)NCCC4CCOCC4)n3)s2)c(F)c1] | 6-({3-(aminocarbonyl)-5-[2,6-difluoro-4-(1-hydroxy-1-methylethyl)phenyl]-2-thienyl}amino)-N-[2-(tetrahydro-2H-pyran-4-yl)ethyl]pyridine-2-carboxamide | Calc'd 545, Found: 545 | A |

TABLE 20-continued

| Example | Structure | Compound Name | Characterization [M + H]+ | Method |
|---|---|---|---|---|
| 288 | 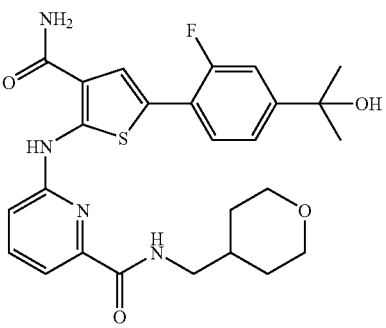 [SMILES: CC(C)(O)c1ccc(-c2cc(C(N)=O)c(Nc3cccc(C(=O)NCC4CCOCC4)n3)s2)c(F)c1] | 6-({3-(aminocarbonyl)-5-[2-fluoro-4-(1-hydroxy-1-methylethyl)phenyl]-2-thienyl}amino)-N-(tetrahydro-2H-pyran-4-ylmethyl)pyridine-2-carboxamide | Calc'd 513, Found: 513 | A |
| 289 | 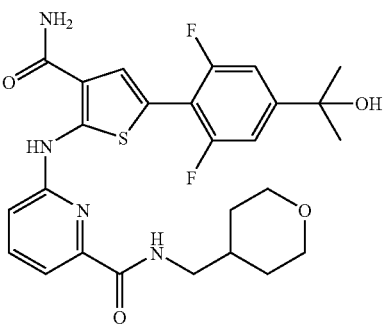 [SMILES: CC(C)(O)c1cc(F)c(-c2cc(C(N)=O)c(Nc3cccc(C(=O)NCC4CCOCC4)n3)s2)c(F)c1] | 6-({3-(aminocarbonyl)-5-[2,6-difluoro-4-(1-hydroxy-1-methylethyl)phenyl]-2-thienyl}amino)-N-(tetrahydro-2H-pyran-4-ylmethyl)pyridine-2-carboxamide | Calc'd 531, Found: 531 | A |
| 290 | 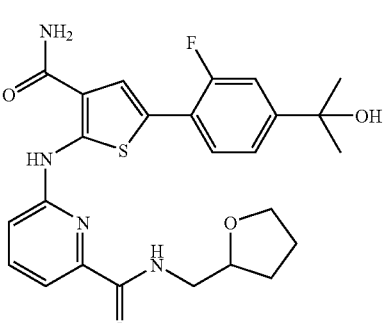 | 6-({3-(aminocarbonyl)-5-[2-fluoro-4-(1-hydroxy-1-methylethyl)phenyl]-2-thienyl}amino)-N-(tetrahydrofuran-2-ylmethyl)pyridine-2-carboxamide | Calc'd 499, Found: 499 | A |
| 291 | 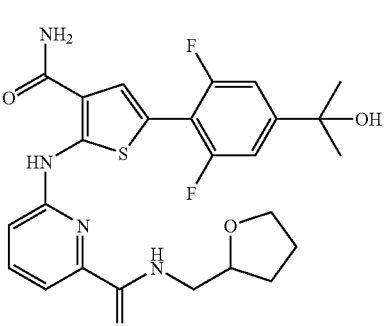 | 6-({3-(aminocarbonyl)-5-[2,6-difluoro-4-(1-hydroxy-1-methylethyl)phenyl]-2-thienyl}amino)-N-(tetrahydrofuran-2-ylmethyl)pyridine-2-carboxamide | Calc'd 517, Found: 517 | A |

TABLE 20-continued

| Example | Structure | Compound Name | Characterization [M + H]+ | Method |
|---|---|---|---|---|
| 292 | 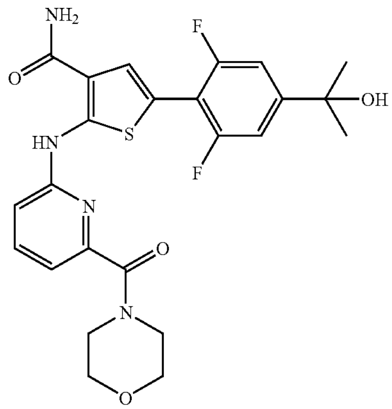 [SMILES: CC(C)(O)c1cc(F)c(-c2cc(C(N)=O)c(Nc3cccc(C(=O)N4CCOCC4)n3)s2)c(F)c1] | 5-[2,6-difluoro-4-(1-hydroxy-1-methylethyl)phenyl]-2-{[6-(morpholin-4-ylcarbonyl)pyridin-2-yl]amino}thiophene-3-carboxamide | Calc'd 503, Found: 503 | A |
| 293 | 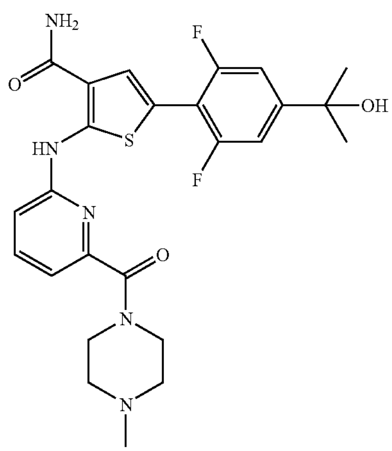 [SMILES: CN1CCN(C(=O)c2cccc(Nc3sc(-c4c(F)cc(C(C)(C)O)cc4F)cc3C(N)=O)n2)CC1] | 5-[2,6-difluoro-4-(1-hydroxy-1-methylethyl)phenyl]-2-({6-[(4-methylpiperazin-1-yl)carbonyl]pyridin-2-yl}amino)thiophene-3-carboxamide | Calc'd 516, Found: 516 | A |
| 294 | 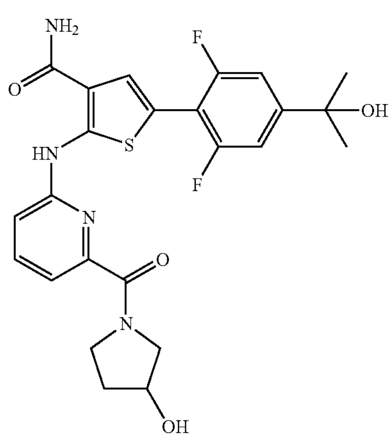 [SMILES: CC(C)(O)c1cc(F)c(-c2cc(C(N)=O)c(Nc3cccc(C(=O)N4CCC(O)C4)n3)s2)c(F)c1] | 5-[2,6-difluoro-4-(1-hydroxy-1-methylethyl)phenyl] -2-({6-[(3-hydroxypyrrolidin-1-yl)carbonyl]pyridin-2-yl}amino)thiophene-3-carboxamide | Calc'd [M + 1]: 503, Found: 503 | A |

TABLE 20-continued

| Example | Structure | Compound Name | Characterization [M + H]+ | Method |
|---|---|---|---|---|
| 295 | 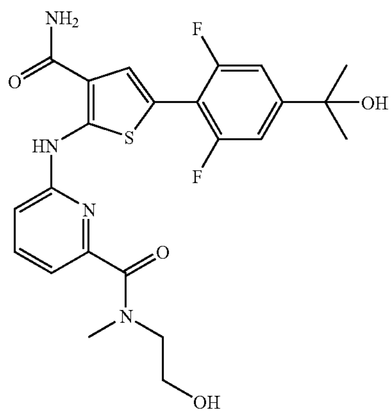 [SMILES: CN(CCO)C(=O)c1cccc(Nc2sc(-c3c(F)cc(C(C)(C)O)cc3F)cc2C(N)=O)n1] | 6-({3-(aminocarbonyl)-5-[2,6-difluoro-4-(1-hydroxy-1-methylethyl)phenyl]-2-thienyl}amino)-N-(2-hydroxyethyl)-N-methylpyridine-2-carboxamide | Calc'd 491, Found: 491 | A |
| 296 | 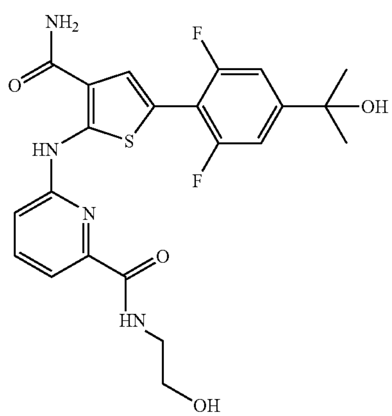 [SMILES: CC(C)(O)c1cc(F)c(-c2cc(C(N)=O)c(Nc3cccc(C(=O)NCCO)n3)s2)c(F)c1] | 6-({3-(aminocarbonyl)-5-[2,6-difluoro-4-(1-hydroxy-1-methylethyl)phenyl]-2-thienyl}amino)-N-(2-hydroxyethyl)pyridine-2-carboxamide | Calc'd 477, Found: 477 | A |
| 297 | 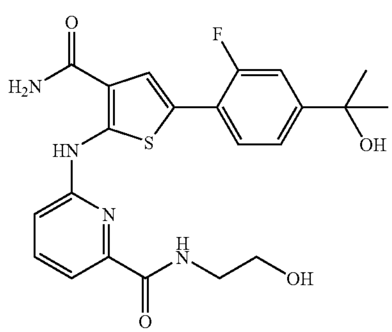 [SMILES: CC(C)(O)c1ccc(-c2cc(C(N)=O)c(Nc3cccc(C(=O)NCCO)n3)s2)c(F)c1] | 6-({3-(aminocarbonyl)-5-[2-fluoro-4-(1-hydroxy-1-methylethyl)phenyl]-2-thienyl}amino)-N-(2-hydroxyethyl)pyridine-2-carboxamide | Calc'd 459, Found: 459 | C |
| 298 | 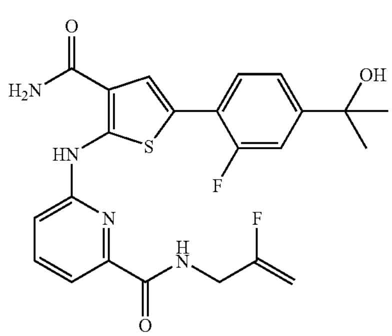 [SMILES: C=C(F)CNC(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-(2-fluoroprop-2-en-1-yl)pyridine-2-carboxamide | Calc'd 474, Found: 474 | B |

TABLE 20-continued

| Example | Structure | Compound Name | Characterization [M + H]+ | Method |
|---|---|---|---|---|
| 299 | 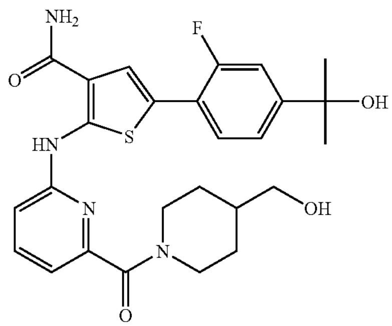 [SMILES: CC(C)(O)c1ccc(-c2cc(C(N)=O)c(Nc3cccc(C(=O)N4CCC(CO)CC4)n3)s2)c(F)c1] | 5-[2-fluoro-4-(1-hydroxy-1-methylethyl)phenyl]-2-[(6-{[4-(hydroxymethyl)piperidin-1-yl]carbonyl}pyridin-2-yl)amino]thiophene-3-carboxamide | Calc'd 513, Found: 513 | B |
| 300 | 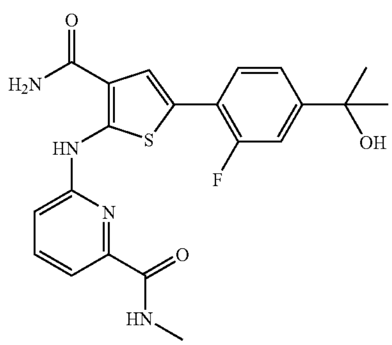 [SMILES: CNC(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-methylpyridine-2-carboxamide | Calc'd 429, Found: 429 | B |
| 301 | 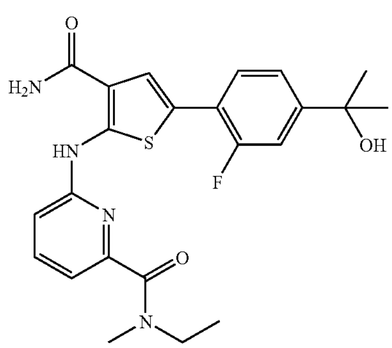 [SMILES: CCN(C)C(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-ethyl-N-methylpyridine-2-carboxamide | Calc'd 457, Found: 457 | B |
| 302 | 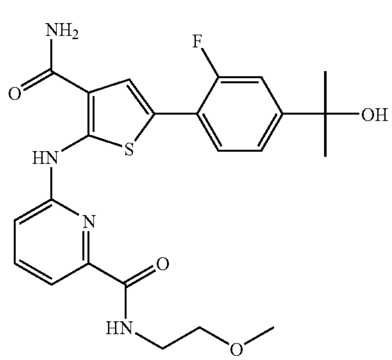 [SMILES: COCCNC(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-(2-methoxyethyl)pyridine-2-carboxamide | Calc'd 473, Found: 473 | B |

| Example | Structure | Compound Name | Characterization [M + H]+ | Method |
|---|---|---|---|---|
| 303 | 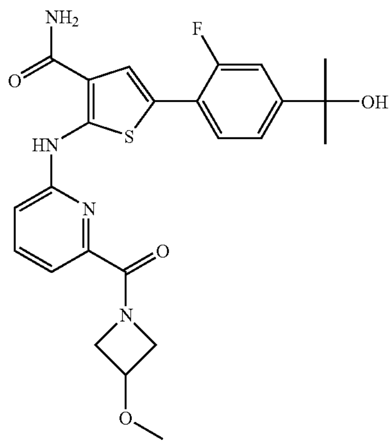 [SMILES: COC1CN(C(=O)c2cccc(Nc3sc(-c4ccc(C(C)(C)O)cc4F)cc3C(N)=O)n2)C1] | 5-[2-fluoro-4-(1-hydroxy-1-methylethyl)phenyl]-2-({6-[(3-methoxyazetidin-1-yl)carbonyl]pyridin-2-yl}amino)thiophene-3-carboxamide | Calc'd 485, Found: 485 | B |
| 304 | 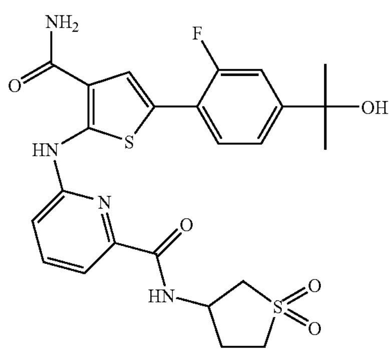 [SMILES: CC(C)(O)c1ccc(-c2cc(C(N)=O)c(Nc3cccc(C(=O)NC4CCS(=O)(=O)C4)n3)s2)c(F)c1] | 6-({3-(aminocarbonyl)-5-[2-fluoro-4-(1-hydroxy-1-methylethyl)phenyl]-2-thienyl}amino)-N-(1,1-dioxidotetrahydro-3-thienyl)pyridine-2-carboxamide | Calc'd 533, Found: 533 | B |
| 305 | 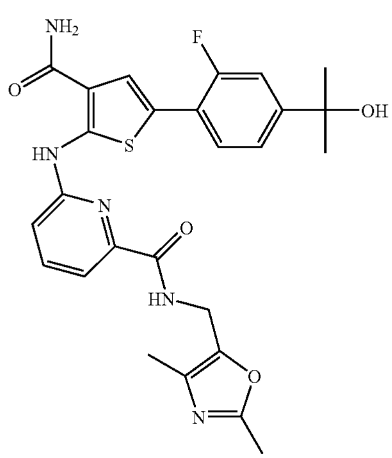 [SMILES: Cc1nc(C)c(CNC(=O)c2cccc(Nc3sc(-c4ccc(C(C)(C)O)cc4F)cc3C(N)=O)n2)o1] | 6-({3-(aminocarbonyl)-5-[2-fluoro-4-(1-hydroxy-1-methylethyl)phenyl]-2-thienyl}amino)-N-[(2,5-dimethyl-1,3-oxazol-4-yl)methyl]-N-methylpyridine-2-carboxamide | Calc'd 538, Found: 538 | C |

| Example | Structure | Compound Name | Characterization [M + H]+ | Method |
|---|---|---|---|---|
| 306 | 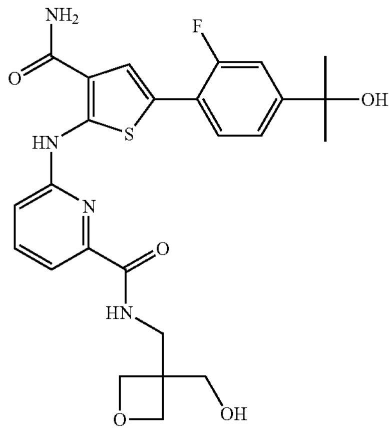 [SMILES: CC(C)(O)c1ccc(-c2cc(C(N)=O)c(Nc3cccc(C(=O)NCC4(CO)COC4)n3)s2)c(F)c1] | 6-({3-(aminocarbonyl)-5-[2-fluoro-4-(1-hydroxy-1-methylethyl)phenyl]-2-thienyl}amino)-N-{[3-(hydroxymethyl)oxetan-3-yl]methyl}pyridine-2-carboxamide | Calc'd 515, Found: 515 | C |
| 307 | 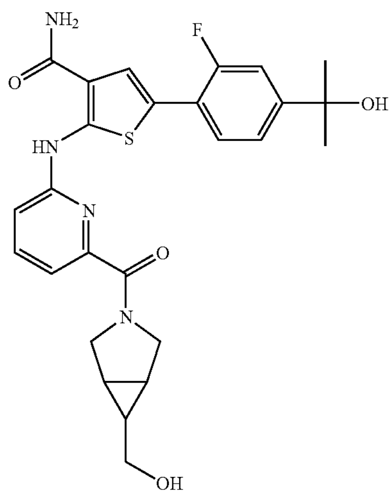 [SMILES: CC(C)(O)c1ccc(-c2cc(C(N)=O)c(Nc3cccc(C(=O)N4CC5C(CO)C5C4)n3)s2)c(F)c1] | 5-[2-fluoro-4-(1-hydroxy-1-methylethyl)phenyl]-2-[(6-{[6-(hydroxymethyl)-3-azabicyclo[3.1.0]hex-3-yl]carbonyl}pyridin-2-yl)amino]thiophene-3-carboxamide | Calc'd 511, Found: 511 | C |
| 308 | 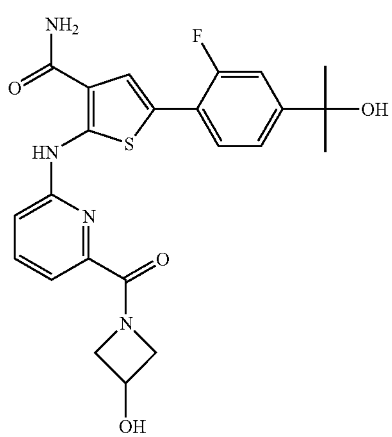 [SMILES: CC(C)(O)c1ccc(-c2cc(C(N)=O)c(Nc3cccc(C(=O)N4CC(O)C4)n3)s2)c(F)c1] | 5-[2-fluoro-4-(1-hydroxy-1-methylethyl)phenyl]-2-({6-[(3-hydroxyazetidin-1-yl)carbonyl]pyridin-2-yl}amino)thiophene-3-carboxamide | Calc'd 471, Found: 471 | C |

TABLE 20-continued

| Example | Structure | Compound Name | Characterization [M + H]+ | Method |
|---|---|---|---|---|
| 309 | 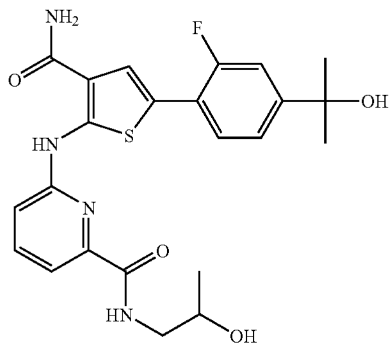 | 6-({3-(aminocarbonyl)-5-[2-fluoro-4-(1-hydroxy-1-methylethyl)phenyl]-2-thienyl}amino)-N-(2-hydroxypropyl)pyridine-2-carboxamide | Calc'd 473, Found: 473 | C |
| 310 | 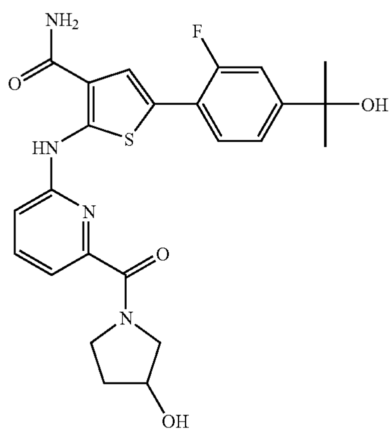 [SMILES: CC(C)(O)c1ccc(-c2cc(C(N)=O)c(Nc3cccc(C(=O)N4CCC(O)C4)n3)s2)c(F)c1] | 5-[2-fluoro-4-(1-hydroxy-1-methylethyl)phenyl]-2-({6-[(3-hydroxypyrrolidin-1-yl)carbonyl]pyridin-2-yl}amino)thiophene-3-carboxamide | Calc'd 485, Found: 485 | C |
| 311 | 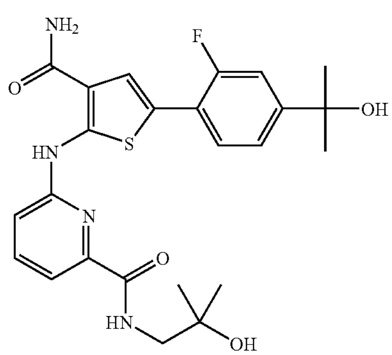 [SMILES: CC(C)(O)CNC(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-(2-hydroxy-2-methylpropyl)pyridine-2-carboxamide | Calc'd 487, Found: 487 | C |
| 312 | 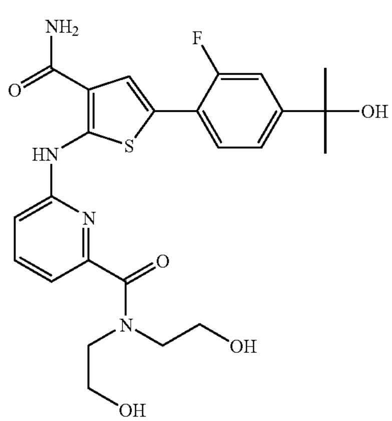 [SMILES: CC(C)(O)c1ccc(-c2cc(C(N)=O)c(Nc3cccc(C(=O)N(CCO)CCO)n3)s2)c(F)c1] | 6-({3-(aminocarbonyl)-5-[2-fluoro-4-(1-hydroxy-1-methylethyl)phenyl]-2-thienyl}amino)-N,N-bis(2-hydroxyethyl)pyridine-2-carboxamide | Calc'd 503, Found: 503 | C |

TABLE 20-continued

| Example | Structure | Compound Name | Characterization [M + H]+ | Method |
|---|---|---|---|---|
| 313 | 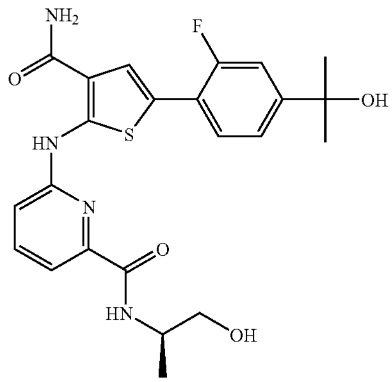 [SMILES: C[C@H](CO)NC(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-[(1R)-2-hydroxy-1-methylethyl]pyridine-2-carboxamide | Calc'd 473, Found: 473 | C |
| 314 | 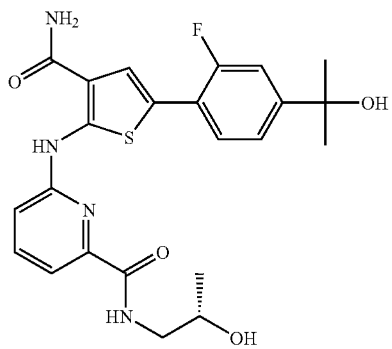 | 6-({3-(aminocarbonyl)-5-[2-fluoro-4-(1-hydroxy-1-methylethyl)phenyl]-2-thienyl}amino)-N-[(2S)-2-hydroxypropyl]pyridine-2-carboxamide | Calc'd 473, Found: 473 | C |
| 315 | 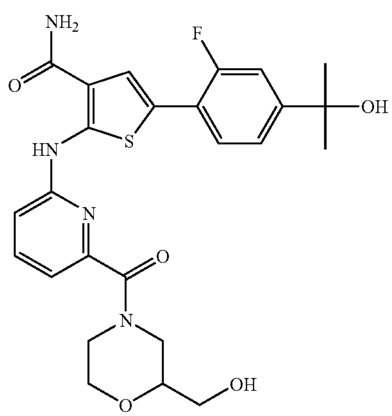 [SMILES: CC(C)(O)c1ccc(-c2cc(C(N)=O)c(Nc3cccc(C(=O)N4CCOC(CO)C4)n3)s2)c(F)c1] | 5-[2-fluoro-4-(1-hydroxy-1-methylethyl)phenyl]-2-[(6-{[2-(hydroxymethyl)morpholin-4-yl]carbonyl}pyridin-2-yl)amino]thiophene-3-carboxamide | Calc'd 515, Found: 515 | C |
| 316 | 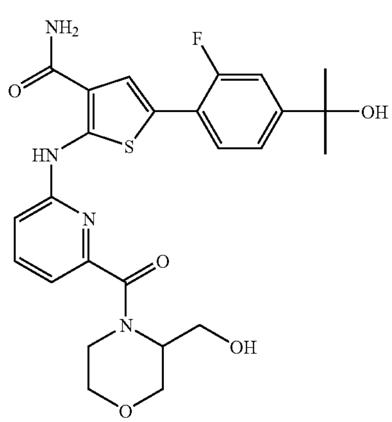 [SMILES: CC(C)(O)c1ccc(-c2cc(C(N)=O)c(Nc3cccc(C(=O)N4CCOCC4CO)n3)s2)c(F)c1] | 5-[2-fluoro-4-(1-hydroxy-1-methylethyl)phenyl]-2-[(6-{[3-(hydroxymethyl)morpholin-4-yl]carbonyl}pyridin-2-yl)amino]thiophene-3-carboxamide | Calc'd 515, Found: 515 | C |

TABLE 20-continued

| Example | Structure | Compound Name | Characterization [M + H]+ | Method |
|---|---|---|---|---|
| 317 | 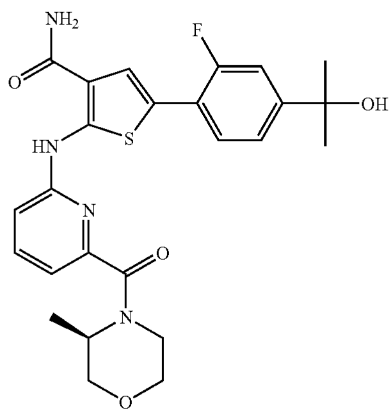 [SMILES: C[C@@H]1COCCN1C(=O)c1cccc(Nc2sc(-c3ccc(C(C)(C)O)cc3F)cc2C(N)=O)n1] | 5-[2-fluoro-4-(1-hydroxy-1-methylethyl)phenyl]-2-[(6-{[(3R)-3-methylmorpholin-4-yl]carbonyl}pyridin-2-yl)amino]thiophene-3-carboxamide | Calc'd 499, Found: 499 | C |
| 318 | 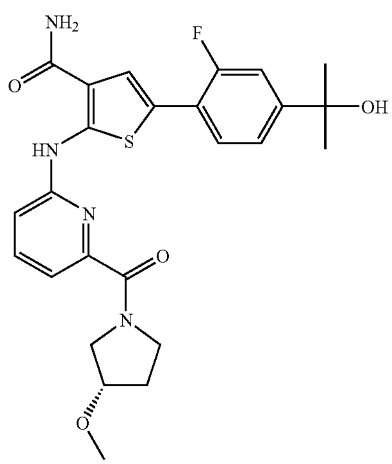 [SMILES: CO[C@H]1CCN(C(=O)c2cccc(Nc3sc(-c4ccc(C(C)(C)O)cc4F)cc3C(N)=O)n2)C1] | 5-[2-fluoro-4-(1-hydroxy-1-methylethyl)phenyl]-2-[(6-{[(3S)-3-methoxypyrrolidin-1-yl]carbonyl}pyridin-2-yl)amino]thiophene-3-carboxamide | Calc'd 499, Found: 499 | C |
| 319 | 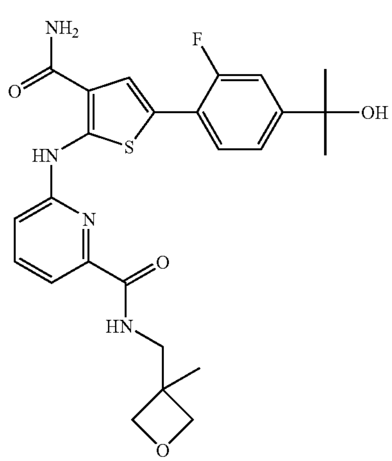 [SMILES: CC1(CNC(=O)c2cccc(Nc3sc(-c4ccc(C(C)(C)O)cc4F)cc3C(N)=O)n2)COC1] | 6-({3-(aminocarbonyl)-5-[2-fluoro-4-(1-hydroxy-1-methylethyl)phenyl]-2-thienyl}amino)-N-[(3-methyloxetan-3-yl)methyl]pyridine-2-carboxamide | Calc'd 499, Found: 499 | C |

TABLE 20-continued

| Example | Structure | Compound Name | Characterization [M + H]+ | Method |
|---|---|---|---|---|
| 320 | 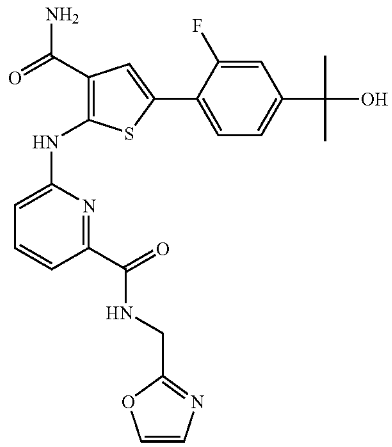 [SMILES: CC(C)(O)c1ccc(-c2cc(C(N)=O)c(Nc3cccc(C(=O)NCc4ncco4)n3)s2)c(F)c1] | 6-({3-(aminocarbonyl)-5-[2-fluoro-4-(1-hydroxy-1-methylethyl)phenyl]-2-thienyl}amino)-N-(1,3-oxazol-2-ylmethyl)pyridine-2-carboxamide | Calc'd 496, Found: 496 | C |
| 321 | 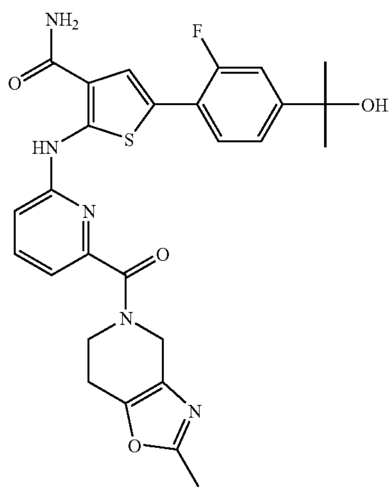 [SMILES: Cc1nc2c(o1)CCN(C(=O)c1cccc(Nc3sc(-c4ccc(C(C)(C)O)cc4F)cc3C(N)=O)n1)C2] | 5-[2-fluoro-4-(1-hydroxy-1-methylethyl)phenyl]-2-({6-[(2-methyl-6,7-dihydro[1,3]oxazolo[4,5-c]pyridin-5(4H)-yl)carbonyl]pyridin-2-yl}amino)thiophene-3-carboxamide | Calc'd [M + 2]: 537, Found 537 | C |
| 322 | 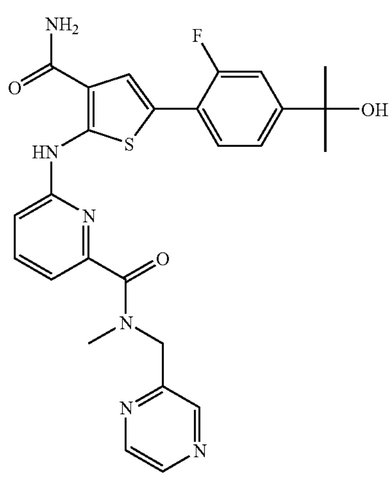 [SMILES: CN(Cc1cnccn1)C(=O)c1cccc(Nc2sc(-c3ccc(C(C)(C)O)cc3F)cc2C(N)=O)n1] | 6-({3-(aminocarbonyl)-5-[2-fluoro-4-(1-hydroxy-1-methylethyl)phenyl]-2-thienyl}amino)-N-methyl-N-(pyrazin-2-ylmethyl)pyridine-2-carboxamide | Calc'd [M + 2]: 522, Found 522 | C |

TABLE 20-continued

| Example | Structure | Compound Name | Characterization [M + H]+ | Method |
|---|---|---|---|---|
| 323 | 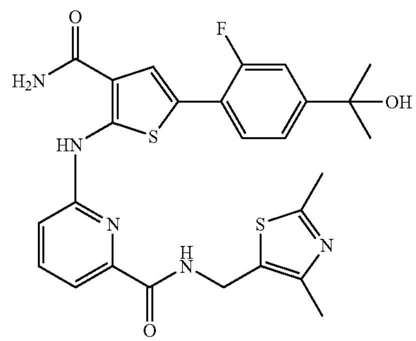 [SMILES: Cc1nc(C)c(CNC(=O)c2cccc(Nc3sc(-c4ccc(C(C)(C)O)cc4F)cc3C(N)=O)n2)s1] | 6-({3-(aminocarbonyl)-5-[2-fluoro-4-(1-hydroxy-1-methylethyl)phenyl]-2-thienyl}amino)-N-[(2,4-dimethyl-1,3-thiazol-5-yl)methyl]pyridine-2-carboxamide | Calc'd 540, Found: 540 | C |

Method A: Using procedures described in Example 282
Method B: Using procedures described in Example 283
Method C: Using procedures described in Example 284

Example 324

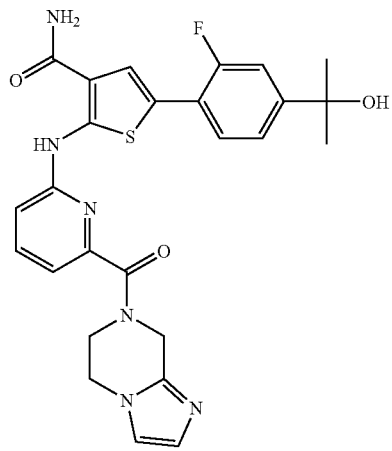 [SMILES: CC(C)(O)c1ccc(-c2cc(C(N)=O)c(Nc3cccc(C(=O)N4CCn5ccnc5C4)n3)s2)c(F)c1]

2-{[6-(5,6-Dihydroimidazo[1,2-a]pyrazin-7(8H)-ylcarbonyl)pyridin-2-yl]amino}-5-[2-fluoro-4-(1-hydroxy-1-methylethyl)phenyl]thiophene-3-carboxamide

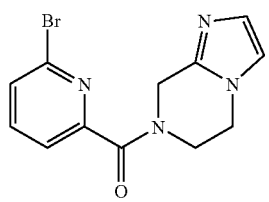 [SMILES: O=C(c1cccc(Br)n1)N1CCn2ccnc2C1]

Step 1: 2-Bromo-6-{[(3R)-3-methoxypyrrolidin-1-yl]carbonyl}pyridine

A solution of HOBt (148 mg, 0.97 mmol), DIEA (130 µL, 0.74 mmol), HATU (367 mg, 0.97 mmol), bromopyridine-2-carboxylic acid (150 mg, 0.74 mmol) and 5,6,7,8-tetrahydroimidazo[1,2-a]pyrazine (91 mg, 0.74 mmol) in DMF (2.5 mL) was stirred overnight at 65° C. Upon completion, Si-carbonate (2.8 g, 2.23 mmol) and DCM (3 mL) were added and the mixture was shaken overnight at room temperature. The resulting mixture was then filtered, washed with DCM, concentrated in vacuo and purified by reverse phase HPLC (acetonitrile/water+formic acid modifier) to afford the title compound.

Calc'd for $C_{12}H_{12}BrN_4O$ [M+H]+: 307. Found: 307.

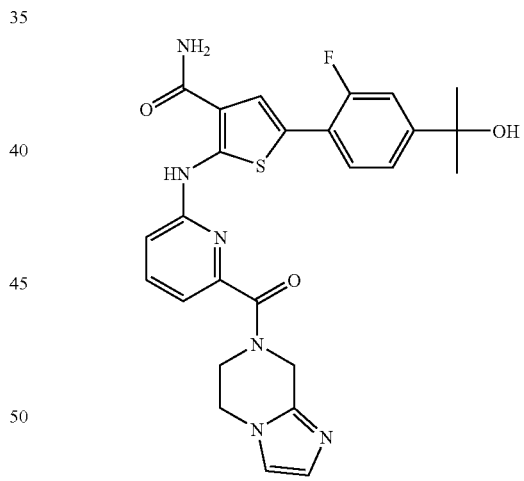

Step 2: 2-{[6-(5,6-Dihydroimidazo[1,2-a]pyrazin-7(8H)-ylcarbonyl)pyridin-2-yl]amino}-5-[2-fluoro-4-(1-hydroxy-1-methylethyl)phenyl]thiophene-3-carboxamide The title compound was prepared as described in Example 1 using 2-bromo-6-{[(3R)-3-methoxypyrrolidin-1-yl]carbonyl}pyridine (200 mg, 0.65 mmol) and 2-amino-5-[2-fluoro-4-(1-hydroxy-1-methylethyl)phenyl]thiophene-3-carboxamide (192 mg, 0.65 mmol) as starting materials.

Calc'd for $C_{26}H_{26}FN_6O_3S$ [M+H]+: 521. Found 521.

Example 325

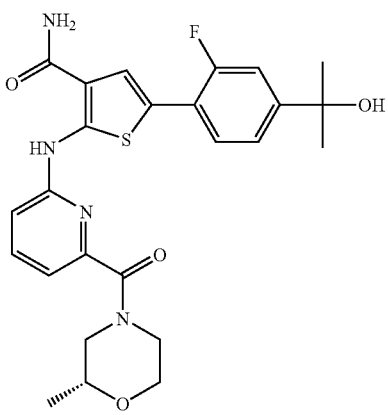 [SMILES: C[C@@H]1CN(C(=O)c2cccc(Nc3sc(-c4ccc(C(C)(C)O)cc4F)cc3C(N)=O)n2)CCO1]

5-[2-Fluoro-4-(1-hydroxy-1-methylethyl)phenyl]-2-[(6-{[(2R)-2-methylmorpholin-4-yl]carbonyl}pyridin-2-yl)amino]thiophene-3-carboxamide

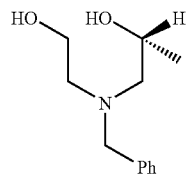

Step 1: (2R)-1-[Benzyl(2-hydroxyethyl)amino]propan-2-ol

To a solution of (2S)-2-hydroxypropyl 4-methylbenzenesulfonate (540 g, 2.34 mol) in EtOH (3 L) at 0° C. was added a solution of KOH (160 g, 2.5 mol) in ethanol (2 L). The mixture was maintained at room temperature overnight. Upon completion, 2-benzylamino-ethanol (500 g, 3.3 mol) was added to the reaction, and the resulting mixture was stirred at room temperature for two days. Boc$_2$O (500 g, 2.29 mol) was then added and the mixture was stirred for another day. The mixture was then filtered, the filter cake washed with ethanol (500 mL), and the filtrate concentrated in vacuo. The residue was dissolved in EtOAc (3.5 L), washed with water (500 mL) and brine (500 mL), and concentrated in vacuo. The resulting crude residue was purified by silica gel chromatography (1:2 EtOAc:petroleum ether) to afford the title compound as a brown oil.

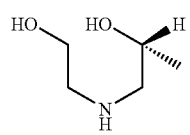

Step 2: (2R)-1-[(2-Hydroxyethyl)amino]propan-2-ol

A solution of (2R)-1-[benzyl(2-hydroxyethyl)amino]propan-2-ol (120 g, 0.57 mol) in ethanol (1.5 L) was hydrogenated at 50° C. in the presence of 10% Pd/C (12 g) at 50 psi of H$_2$. Upon completion, the reaction mixture was passed through a celite pad eluting with ethanol (200 mL). The filtrate was concentrated to yield the title compound as brown oil.

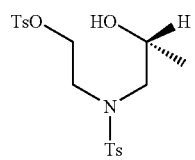 [SMILES: Cc1ccc(S(=O)(=O)OCCN(C[C@@H](C)O)S(=O)(=O)c2ccc(C)cc2)cc1]

Step 3: 2-{[(2R)-2-Hydroxypropyl][(4-methylphenyl)sulfonyl]amino}ethyl 4-methylbenzenesulfonate To a solution of (2R)-1-[(2-hydroxyethyl)amino]propan-2-ol (130.0 g, 1.09 mol) in CH$_2$Cl$_2$ (2 L) and Et$_3$N (304 mL, 2.18 mol) was added TsCl (305 g, 1.60 mol) portion-wise at 0° C. The mixture was maintained at room temperature overnight, then washed with water (800 mL) and brine (500 mL), dried over Na$_2$SO$_4$, filtered and concentrated in vacuo. The resulting residue was purified by silica gel chromatography, eluting with ethyl acetate/petroleum ether to give the title compound as a white solid.

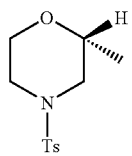

Step 4: (2R)-2-Methyl-4-[(4-methylphenyl)sulfonyl]morpholine

To a solution of 2-{[(2R)-2-hydroxypropyl][(4-methylphenyl)sulfonyl]amino}ethyl 4-methylbenzenesulfonate (340 g, 0.80 mol) in dry THF (3 L) at 0° C. was added NaH (60%, 120 g, 3.00 mol) portion wise. The reaction mixture was warmed to room temperature and stirred for 14 h. The reaction was then cooled to 0° C., and water (100 mL) was added to quench the reaction. The mixture was completely quenched by pouring into water (1 L) and the phases were separated. The aqueous phase was extracted with EtOAc (3×500 mL) and the combined organic layers were washed with brine (500 mL), dried over Na$_2$SO$_4$, filtered, and concentrated in vacuo. The crude residue was purified by silica gel chromatography (8:1 petroleum ether:EtOAc) to yield the title compound as an oil.

$^1$H NMR (600 MHz, CDCl$_3$): δ 7.63 (d, 2H), 7.35 (d, 2H), 3.88 (dd, 1H), 3.85-3.49 (m, 4H), 2.45 (s, 3H), 2.43-2.32 (m, 1H), 2.03 (t, 1H), 1.13 (d, 3H).

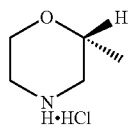

Step 5: (2R)-2-Methylmorpholine hydrochloride

Freshly-cut Na (133 g, 5.8 mol) was added piece by piece to a solution of (2R)-2-methyl-4-[(4-methylphenyl)sulfonyl]morpholine (145 g, 0.58 mol) in n-amyl alcohol (1.5 L) at 60° C. The mixture was refluxed for 4 h and cooled to 0° C., at which time a solution of HCl in MeOH (2 L, 4 N) was added. The organics were evaporated in vacuo and the resulting aqueous phase extracted with $CHCl_3$ (3 L) and filtered. The organic layer was concentrated in vacuo and the crude residue was recrystallized from dry ether (500 mL) to afford the title compound as a white solid. Calc'd for $C_5H_{13}ClNO$ [M+H]$^+$: 102. Found: 102.

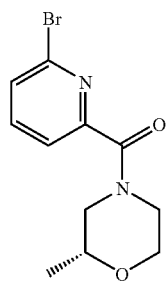 [SMILES: C[C@@H]1CN(C(=O)c2cccc(Br)n2)CCO1]

Step 6: (2R)-4-[(6-Bromopyridin-2-yl)carbonyl]-2-methylmorpholine

The title compound was prepared as described in Example 283, Step 1 using (2R)-2-methylmorpholine hydrochloride (124 mg, 0.90 mmol) and 6-bromopyridine-2-carboxylic acid (150 mg, 0.74 mmol) as starting materials.

Calc'd for $C_{11}H_{14}BrN_2O_2$ [M+1]$^+$: 285. found 285.

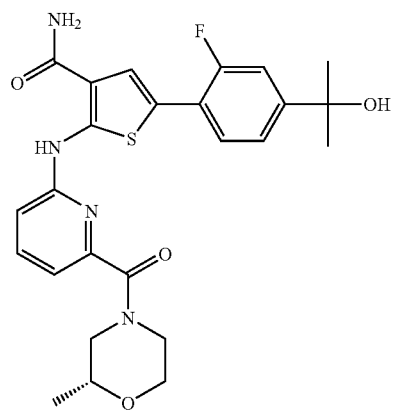 [SMILES: C[C@@H]1CN(C(=O)c2cccc(Nc3sc(-c4ccc(C(C)(C)O)cc4F)cc3C(N)=O)n2)CCO1]

Step 7: 5-[2-Fluoro-4-(1-hydroxy-1-methylethyl)phenyl]-2-[(6-{[(2R)-2-methylmorpholin-4-yl]carbonyl}pyridin-2-yl)amino]thiophene-3-carboxamide The title compound was prepared as described Example 1 using (2R)-4-[(6-bromopyridin-2-yl)carbonyl]-2-methylmorpholine (133 mg, 0.47 mmol) and 2-amino-5-[2-fluoro-4-(1-hydroxy-1-methylethyl)phenyl]thiophene-3-carboxamide (137 mg, 0.47 mmol) as starting materials Calc'd for $C_{25}H_{28}FN_4O_4S$ [M+H]$^+$: 499. Found 499.

The following example was prepared using procedures similar to those described in the above example.

TABLE 21

| Example | Structure | Compound Name | Characterization |
|---|---|---|---|
| 326 | 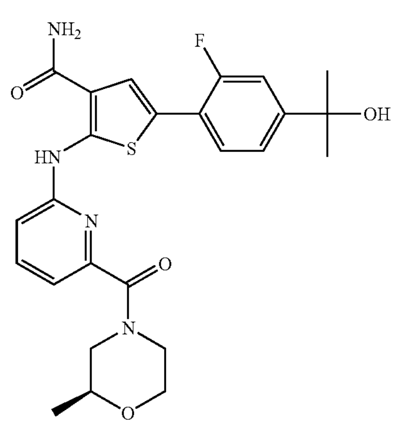 [SMILES: C[C@H]1CN(C(=O)c2cccc(Nc3sc(-c4ccc(C(C)(C)O)cc4F)cc3C(N)=O)n2)CCO1] | 5-[2-Fluoro-4-(1-hydroxy-1-methylethyl)phenyl]-2-[(6-{[(2S)-2-methylmorpholin-4-yl]carbonyl}pyridin-2-yl)amino]thiophene-3-carboxamide | Calc'd [M + H]$^+$: 499, Found: 499 |

Example 327

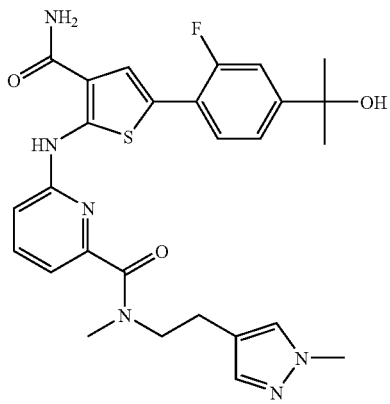 [SMILES: CN(CCc1cnn(C)c1)C(=O)c1cccc(Nc2sc(-c3ccc(C(C)(C)O)cc3F)cc2C(N)=O)n1]

6-({3-(Aminocarbonyl)-5-[2-fluoro-4-(1-hydroxy-1-methylethyl)phenyl]-2-thienyl}amino)-N-methyl-N-[2-(1-methyl-1H-pyrazol-4-yl)ethyl]pyridine-2-carboxamide

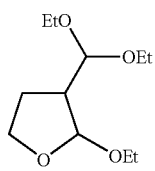

Step 1: 3-(Diethoxymethyl)-2-ethoxytetrahydrofuran

To a solution of ethyl orthoformate (63 g, 0.425 mol) and boron trifluoride diethyl ether complex (8.1 g) at 0° C. was added dihydrofuran (9 g, 0.129 mol). The reaction mixture was maintained at room temperature for 30 minutes, followed by the addition of diethanolamine (1 g). Upon completion, the reaction mixture was purified by distillation to afford the title compound.

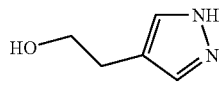

Step 2: 2-(1H-Pyrazol-4-yl)ethanol

To a cooled (0° C.) solution of hydrazine dihydrochloride (20 g, 0.19 mol) in water (50 mL) was added 3-(diethoxymethyl)-2-ethoxytetrahydrofuran (32 g, 0.15 mol). The reaction mixture was stirred for 5 min followed by the addition of sodium carbonate (30 g). Upon completion, the reaction mixture was extracted with ether (50 mL×4), the combined organic layers were concentrated in vacuo and purified by fractional distillation (b.p. 140-145 0° C.) to afford the title compound.

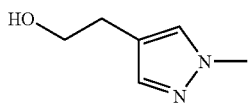

Step 3: 2-(1-methyl-1H-pyrazol-4-yl)ethanol

To a solution cooled (0° C.) of 2-(1H-pyrazol-4-yl)ethanol (93 g, 0.83 mol) and potassium hydroxide (48.8 g, 0.87 mol) in absolute ethanol (9.25 L) was added methyl iodide (178 g, 1.25 mol) dropwise. The mixture was allowed to react for 30 min, at which time it was poured into water (400 mL) and extracted with diethyl ether (4×100 mL). The combined organic layers were dried (Na$_2$SO$_4$), filtered, concentrated in vacuo, and purified by vacuum distillation to afford the title compound.

b.p. 130-135° C./8-9-mm Hg.

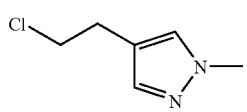

Step 4: 4-(2-Chloroethyl)-1-methyl-1H-pyrazole

To excess thionyl chloride (250 mL) at 0° C. was added 2-(1-methyl-1H-pyrazol-4-yl)ethanol (82 g, 0.651 mol). The reaction mixture was heated to reflux for 15 minutes. The excess thionyl chloride was removed in vacuo and the crude product was purified by recrystallization from EtOH to afford the title compound.

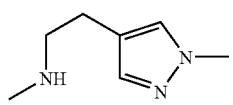

Step 5: N-Methyl-2-(1-methyl-1H-pyrazol-4-yl)ethanamine

To neat 4-(2-chloroethyl)-1-methyl-1H-pyrazole (50 g, 0.24 mol) was added a 25% aqueous solution of methylamine (1.15 L, 7.21 mol). The mixture was placed into an autoclave at 60° C. for 15 h. The resulting mixture was concentrated in vacuo, treated with aqueous solution of NaOH and extracted with DCM. The combined organic layers were concentrated in vacuo and purified by vacuum distillation to afford the title compound. b.p. 89-90° C./2 mm Hg.

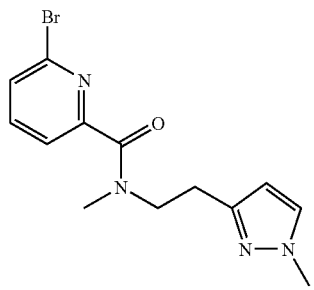 [SMILES: CN(CCc1ccn(C)n1)C(=O)c1cccc(Br)n1]

Step 6: 6-Bromo-N-methyl-N-[2-(1-methyl-1H-pyrazol-3-yl)ethyl]pyridine-2-carboxamide The title compound was prepared as described in Example 283, Step 1 using N-methyl-2-(1-methyl-1H-pyrazol-4-yl)

ethanamine (125 mg, 0.90 mmol) and 6-bromopyridine-2-carboxylic acid (150 mg, 0.74 mmol) as starting materials.

Calc'd for $C_{13}H_{16}BrN_4O$ [M+H]⁺: 323. found 323.

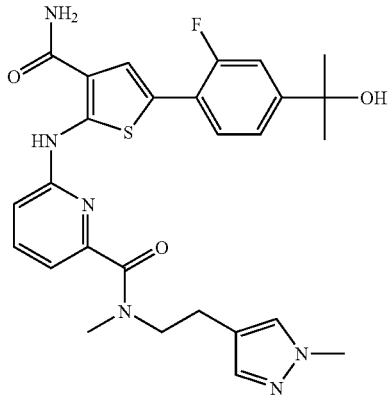 [SMILES: CN(CCc1cnn(C)c1)C(=O)c1cccc(Nc2sc(-c3ccc(C(C)(C)O)cc3F)cc2C(N)=O)n1]

Step 7: 6-({3-(Aminocarbonyl)-5-[2-fluoro-4-(1-hydroxy-1-methylethyl)phenyl]-2-thienyl}amino)-N-methyl-N-[2-(1-methyl-1H-pyrazol-4-yl)ethyl]pyridine-2-carboxamide The title compound was prepared as described Example 1 using 6-bromo-N-methyl-N-[2-(1-methyl-1H-pyrazol-3-yl)ethyl]pyridine-2-carboxamide (94 mg, 0.29 mmol) and 2-amino-5-[2-fluoro-4-(1-hydroxy-1-methylethyl)phenyl]thiophene-3-carboxamide (86 mg, 0.29 mmol) as starting materials.

Calc'd for $C_{27}H_{30}FN_6O_3S$ [M+H]⁺: 537. Found 537.

Example 328

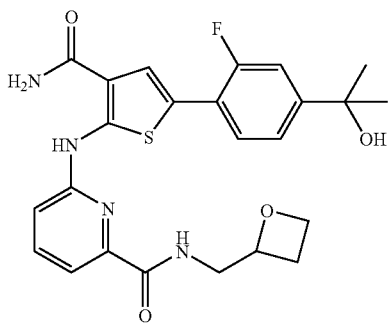 [SMILES: CC(C)(O)c1ccc(-c2cc(C(N)=O)c(Nc3cccc(C(=O)NCC4CCO4)n3)s2)c(F)c1]

6-({3-(Aminocarbonyl)-5-[2-fluoro-4-(1-hydroxy-1-methylethyl)phenyl]-2-thienyl}amino)-N-(oxetan-2-ylmethyl)pyridine-2-carboxamide

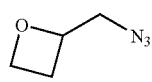

Step 1: 2-(Azidomethyl)oxetaneoxetan-2-ylmethyl azide

To a solution of oxetan-2-ylmethyl 4-methylbenzenesulfonate (16.8 g, 0.069 mol) in DMF (100 mL) was added NaN₃ (6.70 g, 0.10 mol). The reaction mixture was stirred at 80° C. overnight. Upon completion, the mixture was cooled to ambient temperature, diluted with ice water (200 mL) and extracted with diethyl ether (3×60 mL) The combined organic layers were washed with brine, dried and concentrated in vacuo to afford the title compound.

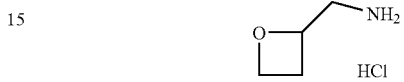

Step 2: 1-Oxetan-2-ylmethanamine hydrochloride

A suspension of 2-(azidomethyl)oxetaneoxetan-2-ylmethyl azide (8.0 g, 0.07 mol) and 10% Pd—C (5 wt % t) in methanol was stirred at room temperature overnight under a hydrogen atmosphere. Upon completion, the mixture was filtered through celite. The filtrate was cooled to 0° C., diluted with a solution of hydrogen chloride in ether, concentrated under reduced pressure, dissolved in EtOAc (30 mL) and stirred at 0° C. for 20 min. The heterogeneous mixture was filtered and the solid was washed with diethyl ether to afford the title compound as a white solid.

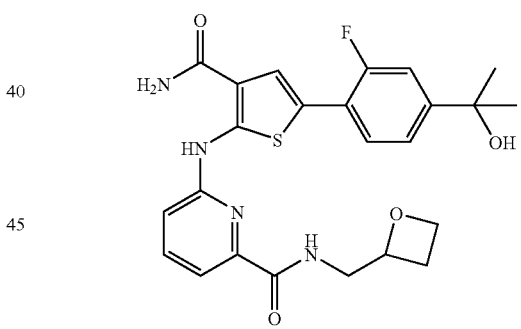

Step 3: 6-({3-(Aminocarbonyl)-5-[2-fluoro-4-(1-hydroxy-1-methylethyl)phenyl]-2-thienyl}amino)-N-(oxetan-2-ylmethyl)pyridine-2-carboxamide A mixture of 6-({3-(aminocarbonyl)-5-[2-fluoro-4-(1-hydroxy-1-methylethyl)phenyl]-2-thienyl}amino)pyridine-2-carboxylic acid (Table 3, Example 40) (50 mg, 0.12 mmol), 1-oxetan-2-ylmethanamine (11 mg, 0.12 mmol), 1-hydroxybenzotriazole hydrate (22 mg, 0.14 mmol), and PS-Carbodiimide (240 mg, 0.30 mmol, 1.25 mmol/g) in DMF (4 mL) was irradiated in a microwave at 100° C. for 10 minutes. Upon completion, the crude reaction was filtered, concentrated, and purified by silica gel chromatography (0-7% methanol/ethyl acetate) to afford the title compound.

Calc'd for $C_{24}H_{26}FN_4O_4S$ [M+H]⁺: 485. Found 485.

Example 329

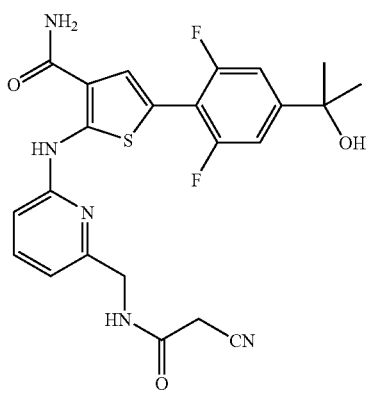 [SMILES: CC(C)(O)c1cc(F)c(-c2cc(C(N)=O)c(Nc3cccc(CNC(=O)CC#N)n3)s2)c(F)c1]

2-[(6-{[(Cyanoacetyl)amino]methyl}pyridin-2-yl)
amino]-5-[2,6-difluoro-4-(1-hydroxy-1-methylethyl)
phenyl]thiophene-3-carboxamide

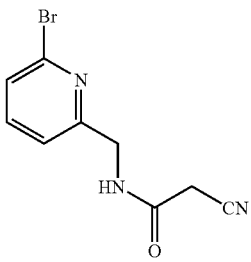 [SMILES: N#CCC(=O)NCc1cccc(Br)n1]

Step 1:
N-[(6-Bromopyridin-2-yl)methyl]-2-cyanoacetamide

6-Bromo-2-pyridinemethanamine hydrochloride (0.25 g, 1.12 mmol) was taken up in DMF (8.4 mL) and triethylamine (0.31 mL, 2.24 mmol) was added. After five minutes, cyanoacetic acid (0.095 g, 1.12 mmol), 1-(3-dimethylaminopropyl)-3-ethylcarbodiimide hydrochloride (0.21 g, 1.12 mmol), 1-hydroxybenzotriazole hydrate (0.18 g, 1.14 mmol) were added and the reaction was maintained at room temperature overnight. Upon completion the mixture was diluted with ethyl acetate, washed with water, dried over magnesium sulfate, filtered and concentrated. The crude material was purified by silica gel chromatography to yield the title compound.
Calc'd for $C_9H_9BrN_3O$ [M+H]$^+$: 255. Found: 255.

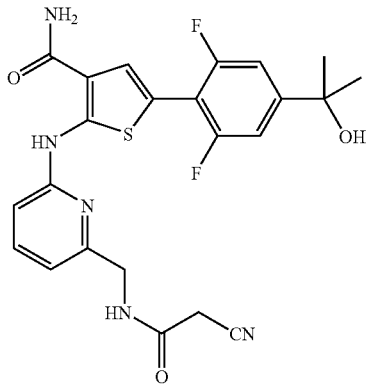 [SMILES: CC(C)(O)c1cc(F)c(-c2cc(C(N)=O)c(Nc3cccc(CNC(=O)CC#N)n3)s2)c(F)c1]

Step 2: 2-[(6-{[(Cyanoacetyl)amino]methyl}pyridin-2-yl)amino]-5-[2,6-difluoro-4-(1-hydroxy-1-methyl-ethyl)phenyl]thiophene-3-carboxamide The title compound was prepared using the procedure described in Example 1 with 2-amino-5-[2,6-difluoro-4-(1-hydroxy-1-methylethyl)phenyl]thiophene-3-carboxamide (0.12 g, 0.38 mmol) and N-[(6-bromopyridin-2-yl)methyl]-2-cyanoacetamide (0.96 g, 0.38 mmol) as starting materials.
Calc'd for $C_{23}H_{22}F_2N_5O_3S$ [M+H]$^+$: 255. Found: 255.

Example 330

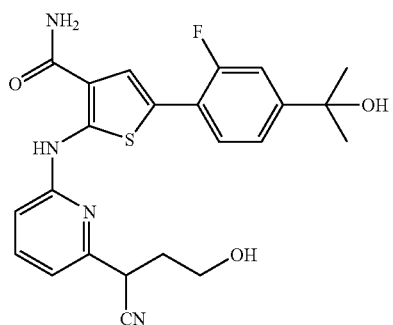 [SMILES: CC(C)(O)c1ccc(-c2cc(C(N)=O)c(Nc3cccc(C(C#N)CCO)n3)s2)c(F)c1]

2-{[6-(1-Cyano-3-hydroxypropyl)pyridin-2-yl]
amino}-5-[2-fluoro-4-(1-hydroxy-1-methyl ethyl)
phenyl]thiophene-3-carboxamide

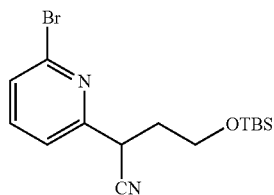 [SMILES: CC(C)(C)[Si](C)(C)OCCC(C#N)c1cccc(Br)n1]

Step 1: 2-(6-Bromopyridin-2-yl)-4-{[tert-butyl(dimethyl)silyl]oxy}butanenitrile (6-Bromopyridin-2-yl)acetonitrile (Example 235, Step 1) (500 mg, 2.54 mmol) was dissolved in THF (10 mL) and cooled to −78° C. LHMDS (1.0 M in THF, 3.05 ml, 3.05 mmol) was added dropwise, and the solution was maintained at −78° C. for 20 minutes. A solution of (2-bromoethoxy)-tert-butyldimethylsilane (600 μL, 2.79 mmol) in THF (5.0 mL) was added dropwise over 5 minutes. The resulting mixture was maintained at −78° C. for 2 hours and warmed to room temperature overnight. The solution was then diluted with water and extracted with EtOAc (2×). The combined organic layers were washed with brine, dried over MgSO$_4$, filtered and evaporated. Silica gel chromatography (0-15% EtOAc/hexanes) afforded the title compound as a colorless oil.
Calc'd for $C_{15}H_{24}BrN_2OSi$ [M+H]$^+$ 355. found 355.

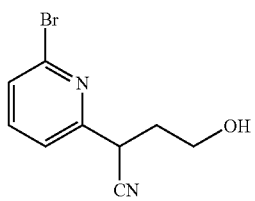 [SMILES: N#CC(CCO)c1cccc(Br)n1]

Step 2:
2-(6-Bromopyridin-2-yl)-4-hydroxybutanenitrile

To a solution of 2-(6-bromopyridin-2-yl)-4-{[tert-butyl (dimethyl)silyl]oxy}butanenitrile (470 mg, 1.32 mmol) in THF (4.0 mL) was added HCl (2.0 M, 4.00 mL, 8.00 mmol). The solution was stirred at room temperature for 1 hour. It was then diluted with water and extracted with EtOAc (2×). The combined organic layers were washed with brine, dried over MgSO$_4$, filtered, and concentrated. Silica gel chromatography (15-100% EtOAc/hexanes) afforded the title compound as a colorless oil.

Calc'd for C$_9$H$_{10}$BrN$_2$O [M+H]$^+$ 241. found 241.

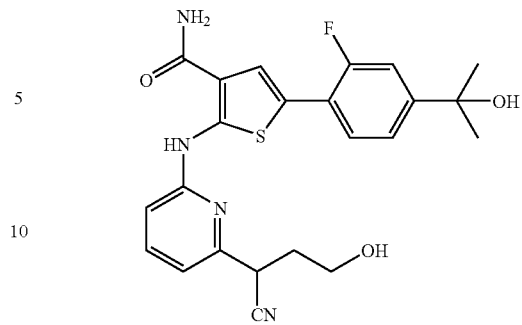

Step 3: 2-{[6-(1-Cyano-3-hydroxypropyl)pyridin-2-yl]amino}-5-[2-fluoro-4-(1-hydroxy-1-methylethyl) phenyl]thiophene-3-carboxamide The title compound was prepared according to the procedure described in Example 1 using 2-(6-bromopyridin-2-yl)-4-hydroxybutanenitrile (97 mg, 0.40 mmol) and 2-amino-5-[2-fluoro-4-(1-hydroxy-1-methylethyl)phenyl]thiophene-3-carboxamide (118 mg, 0.40 mmol) as starting materials.

Calc'd for C$_{23}$H$_{24}$FN$_4$O$_3$S [M+H]$^+$ 455. found 455.

Additional examples were prepared using procedures similar to those described in the above examples and are illustrated in the following table.

TABLE 22

| Example # | Structure | Name | MS [M + H]$^+$ |
|---|---|---|---|
| 331 | 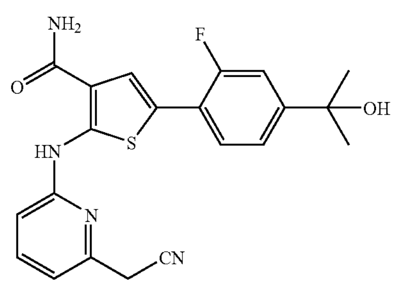 [SMILES: CC(C)(O)c1ccc(-c2cc(C(N)=O)c(Nc3cccc(CC#N)n3)s2)c(F)c1] | 2-{[6-(cyanomethyl)pyridin-2-yl]amino}-5-[2-fluoro-4-(1-hydroxy-1-methylethyl)phenyl]thiophene-3-carboxamide | Calc'd 411, found 411 |
| 332 | 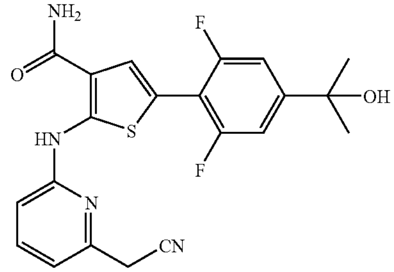 [SMILES: CC(C)(O)c1cc(F)c(-c2cc(C(N)=O)c(Nc3cccc(CC#N)n3)s2)c(F)c1] | 2-{[6-(cyanomethyl)pyridin-2-yl]amino}-5-[2,6-difluoro-4-(1-hydroxy-1-methylethyl)phenyl]thiophene-3-carboxamide | Calc'd 429, found 429 |

Example 355

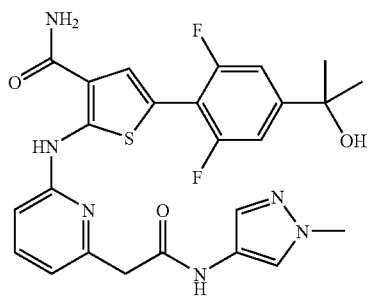

5-[2,6-Difluoro-4-(1-hydroxy-1-methylethyl)phenyl]-2-[(6-{2-[(1-methyl-1H-pyrazol-4-yl)amino]-2-oxoethyl}pyridin-2-yl)amino]thiophene-3-carboxamide

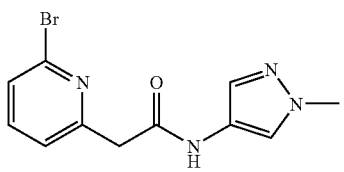 [SMILES: Cn1cc(NC(=O)Cc2cccc(Br)n2)cn1]

Step 1: 2-(6-Bromopyridin-2-yl)-N-(1-methyl-1-H-pyrazol-4-yl)acetamide

A solution of (6-bromopyridin-2-yl)acetic acid (Example 235, Step 2) (30 mg, 0.39 mmol) in dimethylformamide (3 mL) was charged with carbonyldiimidazole (338 mg, 2.08 mmol) and maintained at room temperature for 1 hour. A solution of 1-methyl-1H-pyrazol-4-amine (175 mg, 1.81 mmol) in dimethylformamide (2 mL) was added and the reaction was stirred overnight at room temperature. The reaction was then directly purified by reverse phase HPLC (10-100% acetonitrile/water+0.05% TFA modifier) to yield the title compound.

Calc'd for $C_{11}H_{12}BrN_4O$ [M+H]$^+$: 295. Found: 295.

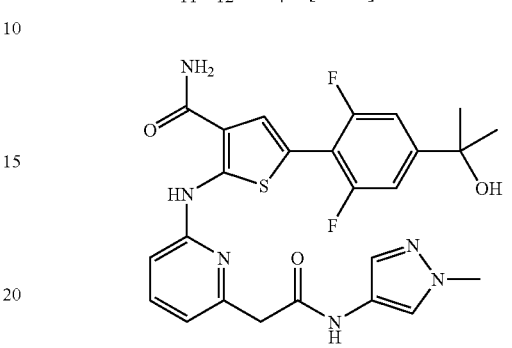

Step 2: 5-[2,6-Difluoro-4-(1-hydroxy-1-methylethyl) phenyl]-2-[(6-{2-[(1-methyl-1H-pyrazol-4-yl) amino]-2-oxoethyl}pyridin-2-yl)amino]thiophene-3-carboxamide The title compound was prepared according to the procedure described in Example 1 using 2-(6-bromopyridin-2-yl)-N-(1-methyl-1-H-pyrazol-4-yl)acetamide (217 mg, 0.74 mmol) and 2-amino-5-[2,6-difluoro-4-(1-hydroxy-1-methylethyl)phenyl]thiophene-3-carboxamide (230 mg, 0.74 mmol) as starting materials.

Calc'd for $C_{25}H_{25}F_2N_6O_3S$ [M+H]$^+$: 527. Found: 527.

Additional examples were prepared using procedures similar to those described in the above examples and are illustrated in the following table.

TABLE 28

| Example | Structure | Name | Characterization |
|---|---|---|---|
| 356 | (structure) | 5-[2,6-difluoro-4-(1-hydroxy-1-methylethyl)phenyl]-2-[(6-{2-[(1-methyl-1H-pyrazol-3-yl)amino]-2-oxoethyl}pyridin-2-yl)amino]thiophene-3-carboxamide | Calc'd [M + H]$^+$: 527, Found: 527 |
| 357 | (structure) | 5-[2,6-difluoro-4-(1-hydroxy-1-methylethyl)phenyl]-2-[(6-{2-[(1-methyl-1H-pyrazol-5-yl)amino-2-oxoethyl}pyridin-2-yl)amino]thiophene-3-carboxamide | Calc'd [M + H]$^+$: 527, Found: 527 |

TABLE 28-continued

| Example | Structure | Name | Characterization |
|---|---|---|---|
| 358 | 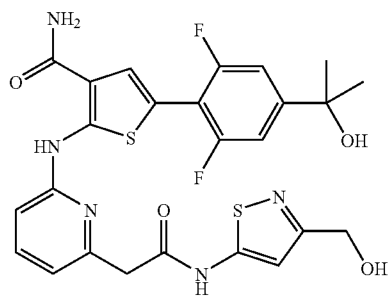 [SMILES: CC(C)(O)c1cc(F)c(-c2cc(C(N)=O)c(Nc3cccc(CC(=O)Nc4cc(CO)ns4)n3)s2)c(F)c1] | 5-[2,6-difluoro-4-(1-hydroxy-1-methylethyl)phenyl]-2-{[6-(2-{[3-(hydroxymethyl)isothiazol-5-yl]amino}-2-oxoethyl)pyridin-2-yl]amino}thiophene-3-carboxamide | Calc'd [M + H]$^+$: 560, Found: 560 |
| 359 | 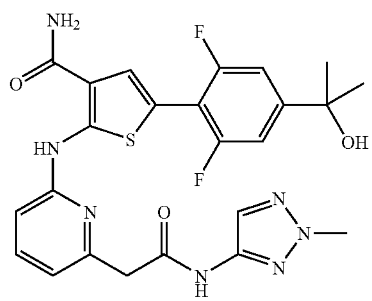 [SMILES: Cn1ncc(NC(=O)Cc2cccc(Nc3sc(-c4c(F)cc(C(C)(C)O)cc4F)cc3C(N)=O)n2)n1] | 5-[2,6-difluoro-4-(1-hydroxy-1-methylethyl)phenyl]-2-[(6-{2-[(2-methyl-2H-1,2,3-triazol-4-yl)amino]-2-oxoethyl}pyridin-2-yl)amino]thiophene-3-carboxamide | Calc'd [M + H]$^+$: 528, Found: 528 |

Example 360

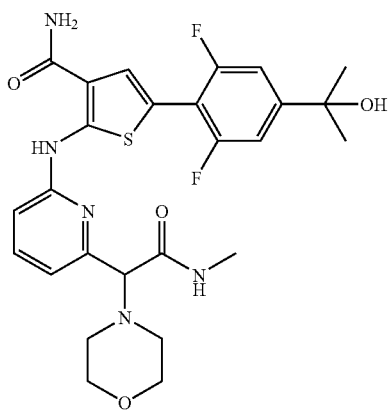 [SMILES: CNC(=O)C(c1cccc(Nc2sc(-c3c(F)cc(C(C)(C)O)cc3F)cc2C(N)=O)n1)N1CCOCC1]

5-[2,6-Difluoro-4-(1-hydroxy-1-methylethyl)phenyl]-2-({6-[2-(methylamino)-1-morpholin-4-yl-2-oxoethyl]pyridin-2-yl}amino)thiophene-3-carboxamide

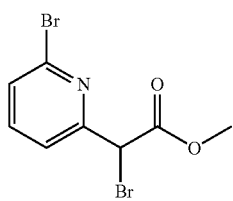

Step 1: Methyl bromo(6-bromopyridin-2-yl)acetate

To a solution of methyl (6-bromopyridin-2-yl)acetate (Example 350, Step 1) (6.00 g, 26.1 mmol) in CCl$_4$ (100 mL) were added NBS (4.87 g, 27.4 mmol) and benzoyl peroxide (474 mg, 1.96 mmol). The reaction was heated at reflux overnight. The solution was then cooled to room temperature, filtered, and evaporated. Silica gel chromatography (0-40% EtOAc/hexanes) afforded the title compound as a yellow oil.

Calc'd for C$_8$H$_8$Br$_2$NO$_2$ [M+H]$^+$ 310. found 310.

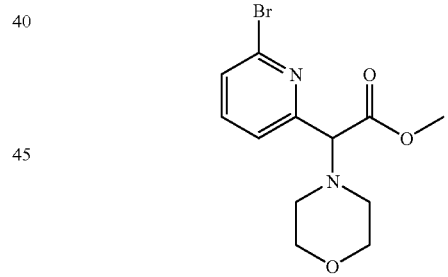

Step 2: Methyl (6-bromopyridin-2-yl)(morpholin-4-yl)acetate

Methyl bromo(6-bromopyridin-2-yl)acetate (1.00 g, 3.24 mmol) was taken up in DMF (10 mL) and morpholine (367 µL, 4.21 mmol) and DIEA (848 µL, 4.86 mmol) were added. After maintaining the reaction at room temperature overnight, the reaction was diluted with water and extracted with EtOAc (2×). The combined organic layers were washed with brine, dried over MgSO$_4$, filtered, and evaporated. Silica gel chromatography (0-100% EtOAc/hexanes) afforded the title compound as a yellow oil.

Calc'd for C$_{12}$H$_{16}$BrN$_2$O$_3$ [M+H]$^+$ 315. found 315.

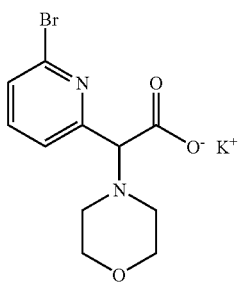 [SMILES: O=C([O-])C(c1cccc(Br)n1)N1CCOCC1 ; [K+]]

Step 3: Potassium (6-bromopyridin-2-yl)(morpholin-4-yl)acetate

To a solution of methyl (6-bromopyridin-2-yl)(morpholin-4-yl)acetate (1.98 g, 6.28 mmol) in THF (21 mL) and MeOH (7 mL) was added aqueous KOH (1.0 M, 6.91 mL, 6.91 mmol). The reaction was maintained at room temperature overnight and then concentrated to dryness to afford the title compound which was carried forward without purification.

Calcd for $C_{11}H_{13}BrN_2O_3$ $[M+H]^+$ 301. found 301.

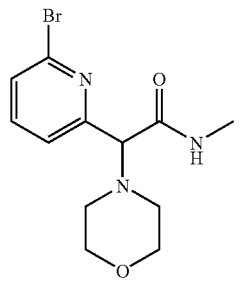 [SMILES: CNC(=O)C(c1cccc(Br)n1)N1CCOCC1]

Step 4: 2-(6-Bromopyridin-2-yl)-N-methyl-2-morpholin-4-ylacetamide

Potassium (6-bromopyridin-2-yl)(morpholin-4-yl)acetate (533 mg, 1.57 mmol), HOBT (361 mg, 2.36 mmol), EDC (452 mg, 2.36 mmol), and methylamine hydrochloride (318 mg, 4.71 mmol) were taken up in DMF (5.0 mL) and DIEA (0.41 mL, 2.36 mmol) was added. The reaction was maintained at room temperature overnight, then diluted with water, and extracted with 5:1 $CH_2Cl_2$:MeOH (2×). The combined organic layers were dried over $MgSO_4$, filtered, and evaporated. Silica gel chromatography (0-10% MeOH/$CH_2Cl_2$) yielded the title compound as a colorless solid.

Calc'd for $C_{12}H_{17}BrN_3O_2$ $[M+H]^+$ 314. found 314.

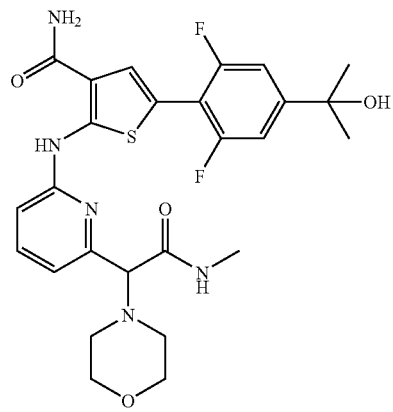 [SMILES: CNC(=O)C(c1cccc(Nc2sc(-c3c(F)cc(C(C)(C)O)cc3F)cc2C(N)=O)n1)N1CCOCC1]

Step 5: 5-[2,6-Difluoro-4-(1-hydroxy-1-methylethyl)phenyl]-2-({6-[2-(methylamino)-1-morpholin-4-yl-2-oxoethyl]pyridin-2-yl}amino)thiophene-3-carboxamide The title compound was synthesized from 2-(6-bromopyridin-2-yl)-N-methyl-2-morpholin-4-ylacetamide (120 mg, 0.38 mmol) and 2-amino-5-[2,6-difluoro-4-(1-hydroxy-1-methylethyl)phenyl]thiophene-3-carboxamide (125 mg, 0.40 mmol) according to the procedure described in Example 1.

Calc'd for $C_{26}H_{30}F_2N_5O_4S$ $[M+H]^+$ 546. found 546.

Additional examples were prepared using procedures similar to those described in the above examples and are illustrated in the following table.

TABLE 29

| Example # | Structure | Name | Characterization $[M + H]^+$ |
|---|---|---|---|
| 361 | 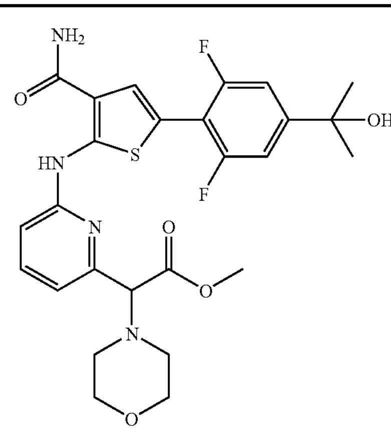 | methyl [6-({3-(aminocarbonyl)-5-[2,6-difluoro-4-(1-hydroxy-1-methylethyl)phenyl]-2-thienyl}amino)pyridin-2-yl](morpholin-4-yl)acetate | Calc'd 547, found 547 |

TABLE 29-continued

| Example # | Structure | Name | Characterization [M + H]+ |
|---|---|---|---|
| 362 | 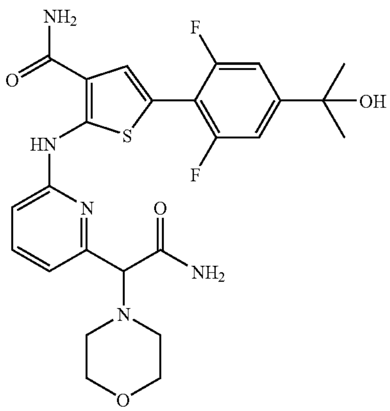 [SMILES: CC(C)(O)c1cc(F)c(-c2cc(C(N)=O)c(Nc3cccc(C(C(N)=O)N4CCOCC4)n3)s2)c(F)c1] | 2-{[6-(2-amino-1-morpholin-4-yl-2-oxoethyl)pyridin-2-yl]amino}-5-[2,6-difluoro-4-(1-hydroxy-1-methylethyl)phenyl]thiophene-3-carboxamide | Calc'd 532, found 532 |
| 363 | 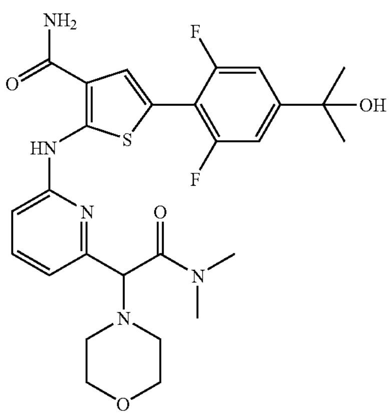 [SMILES: CN(C)C(=O)C(c1cccc(Nc2sc(-c3c(F)cc(C(C)(C)O)cc3F)cc2C(N)=O)n1)N1CCOCC1] | 5-[2,6-difluoro-4-(1-hydroxy-1-methylethyl)phenyl]-2-({6-[2-(dimethylamino)-1-morpholin-4-yl-2-oxoethyl]pyridin-2-yl}amino)thiophene-3-carboxamide | Calc'd 560, found 560 |

Example 364

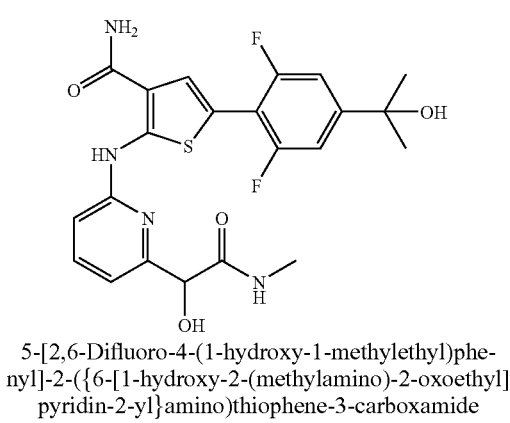

5-[2,6-Difluoro-4-(1-hydroxy-1-methylethyl)phenyl]-2-({6-[1-hydroxy-2-(methylamino)-2-oxoethyl]pyridin-2-yl}amino)thiophene-3-carboxamide

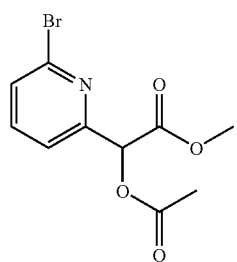 [SMILES: COC(=O)C(OC(C)=O)c1cccc(Br)n1]

Step 1:
Methyl(acetyloxy)(6-bromopyridin-2-yl)acetate

Methyl bromo(6-bromopyridin-2-yl)acetate (Example 360, Step 1) (500 mg, 1.62 mmol) and KOAc (635 mg, 6.47 mmol) were taken up in DMF (3.0 mL) and heated to 120° C. for 20 minutes in a microwave. The reaction mixture was diluted with water and extracted with EtOAc (2×). The combined organic layers were washed with brine, dried over MgSO$_4$, filtered, and evaporated. Silica gel chromatography (0-40% EtOAc/hexanes) afforded the title compound as a pale yellow solid.

Calc'd for $C_{10}H_{11}BrNO_4$ [M+H]+ 288. found 288.

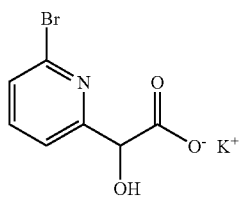 [SMILES: O=C([O-])C(O)c1cccc(Br)n1 ; [K+]]

Step 2: Potassium (6-bromopyridin-2-yl)(hydroxy)acetate

To a solution of methyl(acetyloxy)(6-bromopyridin-2-yl)acetate (1.36 g, 4.70 mmol) in THF (20 mL) and MeOH (10 mL) was added aqueous KOH (1.0 M, 9.88 mL, 9.88 mmol). The solution was stirred at room temperature for 2 hours and then the solvent was evaporated to give the title compound as a colorless solid which was carried on without purification.

Calcd for $C_7H_7BrNO_3$ [M+H]$^+$ 232. found 232.

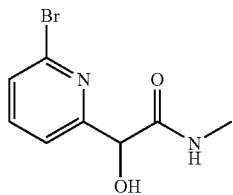

Step 3: 2-(6-Bromopyridin-2-yl)-2-hydroxy-N-methylacetamide

Potassium (6-bromopyridin-2-yl)(hydroxy)acetate (423 mg, 1.57 mmol), HOBT (600 mg, 3.91 mmol), EDC (750 mg, 3.91 mmol), and methylamine hydrochloride (529 mg, 7.83 mmol) were taken up in DMF (5.0 mL), and DIEA (684 µL, 3.91 mmol) was added. The reaction was stirred at room temperature for 6 hours, diluted with water, and extracted with 5:1 $CH_2Cl_2$:MeOH (2×). The combined organic layers were dried over $MgSO_4$, filtered, and evaporated. Silica gel chromatography (40-100% EtOAc/hexanes) provided the title compound as a colorless solid.

Calc'd for $C_8H_{10}N_2O_2$ [M+H]$^+$ 245. found 245.

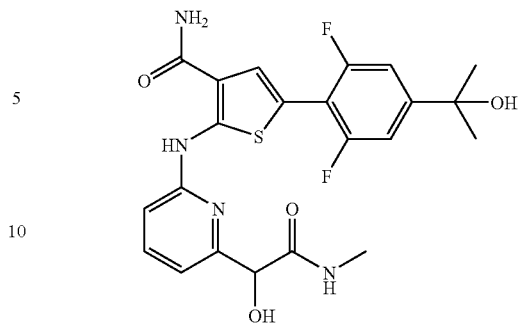

Step 4: 5-[2,6-Difluoro-4-(1-hydroxy-1-methylethyl) phenyl]-2-({6-[1-hydroxy-2-(methylamino)-2-oxoethyl]pyridin-2-yl}amino)thiophene-3-carboxamide The title compound was prepared according to the procedure described in Example 1 using 2-(6-bromopyridin-2-yl)-2-hydroxy-N-methylacetamide (94 mg, 0.38 mmol) and 2-amino-5-[2,6-difluoro-4-(1-hydroxy-1-methylethyl)phenyl]thiophene-3-carboxamide (126 mg, 0.40 mmol) as starting materials.

Calc'd for $C_{22}H_{23}F_2N_4O_4S$ [M+H]$^+$: 477. found 477.

Additional examples were prepared by procedures similar to those described in the above examples and are illustrated in the following table.

TABLE 30

| Example # | Structure | Name | Characterization [M + H]$^+$: |
|---|---|---|---|
| 365 | 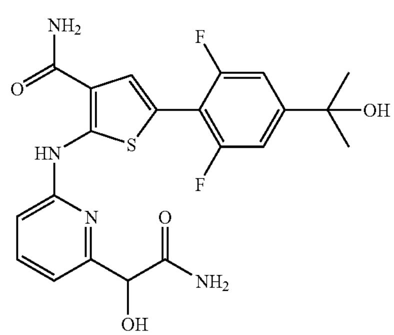 [SMILES: CC(C)(O)c1cc(F)c(-c2cc(C(N)=O)c(Nc3cccc(C(O)C(N)=O)n3)s2)c(F)c1] | 2-{[6-(2-amino-1-hydroxy-2-oxoethyl)pyridin-2-yl]amino}-5-[2,6-difluoro-4-(1-hydroxy-1-methylethyl)phenyl]thiophene-3-carboxamide | Calc'd 463, found 463 |
| 366 | 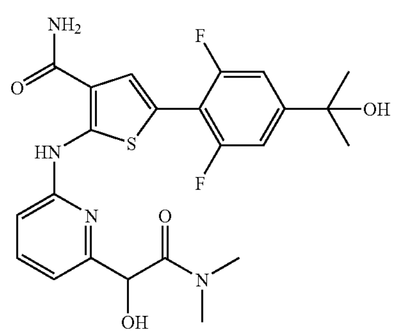 [SMILES: CN(C)C(=O)C(O)c1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-({6-[2-(dimethylamino)-1-hydroxy-2-oxoethyl]pyridin-2-yl}amino)thiophene-3-carboxamide | Calc'd 491, found 491 |

Example 367

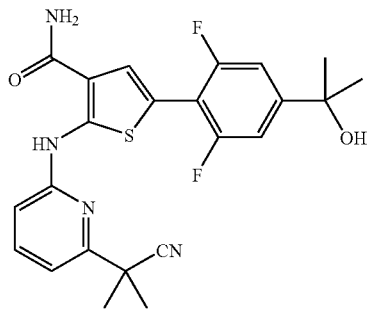 [SMILES: CC(C)(O)c1cc(F)c(-c2cc(C(N)=O)c(Nc3cccc(C(C)(C)C#N)n3)s2)c(F)c1]

2-{[6-(1-Cyano-1-methylethyl)pyridin-2-yl]amino}-
5-[2,6-difluoro-4-(1-hydroxy-1-methylethyl)phenyl]
thiophene-3-carboxamide

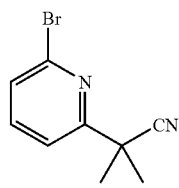

Step 1:
2-(6-Bromopyridin-2-yl)-2-methylpropanenitrile n-Butyllithium (6.48 ml, 10.4 mmol) was added to a cooled (0° C.) solution of diisopropylamine (1.48 ml, 10.4 mmol) in THF (10 mL). The reaction was maintained at 0° C. for 30 minutes, at which time it was cooled to −78° C. and a solution of (6-bromopyridin-2-yl)acetonitrile (Example 235, Step 1) (930 mg, 4.71 mmol) in THF (10 mL) was added dropwise. The reaction was then maintained at −78° C. for 1 hour and then methyl iodide (0.65 ml, 10.4 mmol) was added. The reaction was allowed warm to room temperature slowly overnight. The mixture was then diluted with water and ethyl acetate and the layers were separated. The organic layer was then dried over sodium sulfate, filtered and concentrated to yield the title compound.

Calc'd for $C_9H_{10}BrN_2$ [M+H]$^+$: 225. Found: 225.

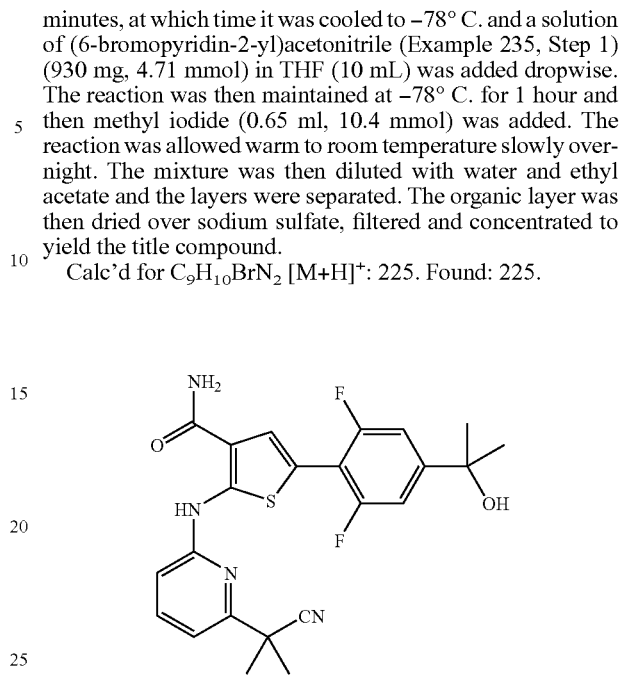

Step 2: 2-{[6-(1-Cyano-1-methylethyl)pyridin-2-yl]
amino}-5-[2,6-difluoro-4-(1-hydroxy-1-methylethyl)
phenyl]thiophene-3-carboxamide The title compound was prepared according to the general procedure in Example 1 using 2-(6-bromopyridin-2-yl)-2-methylpropanenitrile (108 mg, 0.48 mmol) and 2-amino-5-[2,6-difluoro-4-(1-hydroxy-1-methylethyl)phenyl]
thiophene-3-carboxamide (150 mg, 0.48 mmol) as the starting materials.

Calc'd for $C_{23}H_{23}F_2N_4O_2S$ [M+H]$^+$: 457. Found: 457.

The following example was prepared using procedures similar to the above examples and is illustrated in the following table.

TABLE 31

| Example # | Structure | Name | Characterization [M + H]$^+$ |
|---|---|---|---|
| 368 | ![structure] | 2-{[6-(1-cyanoethyl)pyridin-2-yl]amino}-5-[2,6-difluoro-4-(1-hydroxy-1-methylethyl)phenyl]thiophene-3-carboxamide | Calc'd 443, found 443 |

Example 369

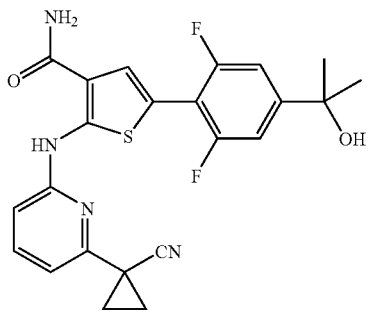 [SMILES: CC(C)(O)c1cc(F)c(-c2cc(C(N)=O)c(Nc3cccc(C4(C#N)CC4)n3)s2)c(F)c1]

2-{[6-(1-Cyanocyclopropyl)pyridin-2-yl]amino}-5-[2,6-difluoro-4-(1-hydroxy-1-methylethyl)phenyl]thiophene-3-carboxamide

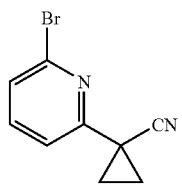 [SMILES: N#CC1(c2cccc(Br)n2)CC1]

Step 1:
1-(6-Bromopyridin-2-yl)cyclopropanecarbonitrile n-Butyllithium (6.66 ml, 10.7 mmol) was added to a cooled (0° C.) solution of diisopropylamine (1.52 ml, 10.7 mmol) in THF (10 mL) and maintained at 0° C. for 30 minutes. The reaction was then cooled to −78° C. and a solution of (6-bromopyridin-2-yl)acetonitrile (Example 235, Step 1) (1 g, 5.08 mmol) in tetrahydrofuran (10 mL) was added dropwise. The reaction was maintained at −78° C. for 1 hour, and then 1,2-dibromoethane (0.92 ml, 10.7 mmol) was added. The reaction was allowed to warm to room temperature and maintained at room temperature for 3 days. The mixture was then diluted with water and ethyl acetate and the layers were separated. The organic layer was dried over sodium sulfate, filtered and concentrated. Purification by silica gel chromatography afforded the title compound.

Calc'd for $C_9H_8BrN_2$ [M+H]$^+$: 223. Found: 223.

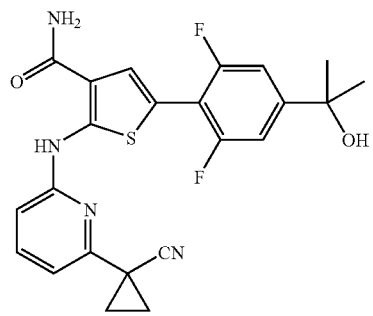 [SMILES: CC(C)(O)c1cc(F)c(-c2cc(C(N)=O)c(Nc3cccc(C4(C#N)CC4)n3)s2)c(F)c1]

Step 2: 2-{[6-(1-Cyanocyclopropyl)pyridin-2-yl]amino}-5-[2,6-difluoro-4-(1-hydroxy-1-methylethyl)phenyl]thiophene-3-carboxamide The title compound was prepared according to the procedure described in Example 1 using 1-(6-bromopyridin-2-yl)cyclopropanecarbonitrile (107 mg, 0.48 mmol) and 2-amino-5-[2,6-difluoro-4-(1-hydroxy-1-methylethyl)phenyl]thiophene-3-carboxamide (150 mg, 0.48 mmol) as starting materials.

Calc'd for $C_{23}H_{21}F_2N_4O_2S$ [M+H]$^+$: 455. Found: 455.

Example 370

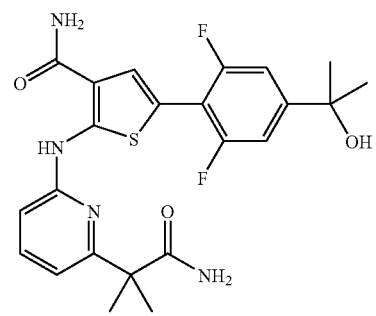 [SMILES: CC(C)(O)c1cc(F)c(-c2cc(C(N)=O)c(Nc3cccc(C(C)(C)C(N)=O)n3)s2)c(F)c1]

2-{[6-(2-Amino-1,1-dimethyl-2-oxoethyl)pyridin-2-yl]amino}-5-[2,6-difluoro-4-(1-hydroxy-1-methylethyl)phenyl]thiophene-3-carboxamide

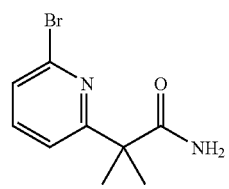

Step 1:
2-(6-Bromopyridin-2-yl)-2-methylpropanamide

To a solution of 2-(6-bromopyridin-2-yl)-2-methylpropanenitrile (Example 367, Step 1) (200 mg, 0.89 mmol) in dimethylsulfoxide (4 mL) was added hydrogen peroxide (0.42 mL, 4.8 mmol) and potassium carbonate (1.23 g, 8.89 mmol). The reaction was then stirred overnight at 70° C. The resulting slurry was cooled to ambient temperature, filtered and directly purified by reverse phase HPLC (10-100% acteonitrile/water+0.05% TFA modifier) to yield the title compound.

$^1$H NMR (600 MHz, DMSO): δ 7.68 (t, 1H), 7.47 (d, 1H), 7.37 (d, 1H), 6.97 (d, 2H), 1.42 (s, 6H).

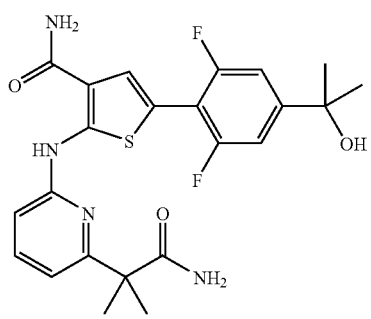 [SMILES: CC(C)(O)c1cc(F)c(-c2cc(C(N)=O)c(Nc3cccc(C(C)(C)C(N)=O)n3)s2)c(F)c1]

Step 2: 2-{[6-(2-Amino-1,1-dimethyl-2-oxoethyl)pyridin-2-yl]amino}-5-[2,6-difluoro-4-(1-hydroxy-1-methylethyl)phenyl]thiophene-3-carboxamide The title compound was prepared according to the procedure described in Example 1 using 2-(6-bromopyridin-2-yl)-2-methylpropanamide (117 mg, 0.48 mmol) and 2-amino-5-[2,6-difluoro-4-(1-hydroxy-1-methylethyl)phenyl]thiophene-3-carboxamide (150 mg, 0.48 mmol) as starting materials.

Calc'd for $C_{23}H_{25}F_2N_4O_3S$ [M+H]$^+$: 475. Found: 475.

Example 371

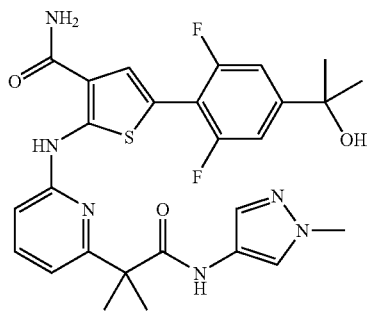

5-[2,6-Difluoro-4-(1-hydroxy-1-methylethyl)phenyl]-2-[(6-{1,1-dimethyl-2-[(1-methyl-1H-pyrazol-4-yl)amino]-2-oxoethyl}pyridin-2-yl)amino]thiophene-3-carboxamide

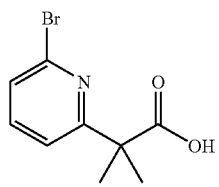

Step 1: 2-(6-Bromopyridin-2-yl)-2-methylpropanoic acid

To a solution of 2-(6-bromopyridin-2-yl)-2-methylpropanenitrile (Example 367, Step 1) (50 mg, 0.22 mmol) in methanol (2 mL) was added 1 N aqueous sodium hydroxide (2 mL) and the mixture was heated to 80° C. overnight. The reaction was then cooled to ambient temperature, diluted with ethyl acetate (15 mL) and water (15 mL), and the layers were separated. The aqueous layer was acidified with 2 N hydrochloric acid solution and extracted with ethyl acetate (15 mL). The organic layer was dried over sodium sulfate, filtered and concentrated to yield the title compound.

Calc'd for $C_9H_{11}BrNO_2$ [M+H]$^+$: 244. Found: 244.

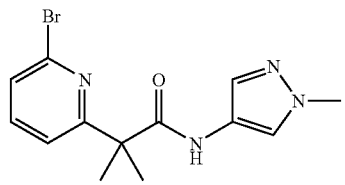 [SMILES: Cn1cc(NC(=O)C(C)(C)c2cccc(Br)n2)cn1]

Step 2: 2-(6-Bromopyridin-2-yl)-2-methyl-N-(1-methyl-1-H-pyrazol-4-yl)propanamide A solution of 2-(6-bromopyridin-2-yl)-2-methylpropanoic acid (120 mg, 0.49 mmol) in dimethylformamide (3 mL) was charged with 1-methyl-1H-pyrazol-4-amine (48 mg, 0.49 mmol). Dimethylaminopyridine (60 mg, 0.49 mmol) and 1-(3-dimethylaminopropyl)-3-ethylcarbodiimide hydrochloride (94 mg, 0.49 mmol) were added and the reaction was stirred overnight at room temperature. The reaction was purified by reverse phase HPLC (10-100% acetonitrile/water+ 0.05% TFA modifier) to afford the title compound.

Calc'd for $C_{13}H_{16}BrN_4O$ [M+H]$^+$: 323. Found: 323.

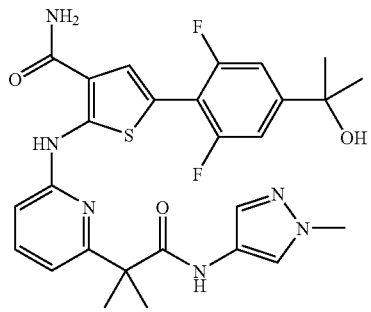 [SMILES: Cn1cc(NC(=O)C(C)(C)c2cccc(Nc3sc(-c4c(F)cc(C(C)(C)O)cc4F)cc3C(N)=O)n2)cn1]

Step 3: 5-[2,6-Difluoro-4-(1-hydroxy-1-methylethyl)phenyl]-2-[(6-{1,1-dimethyl-2-[(1-methyl-1H-pyrazol-4-yl)amino]-2-oxoethyl}pyridin-2-yl)amino]thiophene-3-carboxamide The title compound was prepared according to the procedure described in Example 1 using 2-(6-bromopyridin-2-yl)-2-methyl-N-(1-methyl-1-H-pyrazol-4-yl)propanamide (47 mg, 0.14 mmol) and 2-amino-5-[2,6-difluoro-4-(1-hydroxy-1-methylethyl)phenyl]thiophene-3-carboxamide (45 mg, 0.14 mmol) as starting materials.

Calc'd for $C_{27}H_{29}F_2N_6O_3S$ [M+H]$^+$: 555. Found: 555.

Example 372

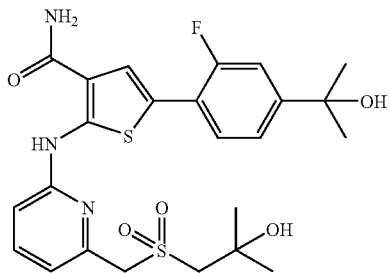 [SMILES: CC(C)(O)CS(=O)(=O)Cc1cccc(Nc2sc(-c3ccc(C(C)(C)O)cc3F)cc2C(N)=O)n1]

5-[2-Fluoro-4-(1-hydroxy-1-methylethyl)phenyl]-2-
[(6-{[(2-hydroxy-2-methylpropyl)sulfonyl]
methyl}pyridin-2-yl)amino]thiophene-3-carboxamide

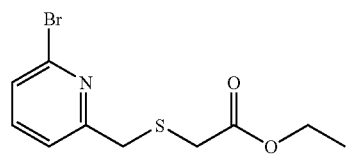

Step 1: Ethyl{[(6-bromopyridin-2-yl)methyl]
thio}acetate

Sodium hydride (0.48 g, 11.96 mmol) was suspended in tetrahydrofuran (52.4 mL) and cooled to 0° C. Ethyl mercaptoacetate (0.48 mg, 3.99 mmol) was added and the solution was stirred for 30 minutes at 0° C. 2-Bromo-6-(bromomethyl)pyridine (Example 190, Step 1) (1.0 g, 3.99 mmol) was added and the solution was allowed to stir until completion. The reaction mixture was then diluted with water and extracted with ethyl acetate (2×). The combined organics were dried over magnesium sulfate, filtered, concentrated, and purified by silica gel chromatography to yield the title compound.
Calc'd for $C_{10}H_{13}BrNO_2S$ [M+H]$^+$: 290. Found: 290.

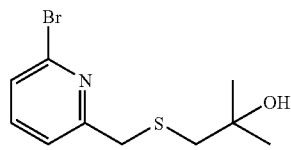

Step 2: 1-{[(6-Bromopyridin-2-yl)methyl]thio}-2-methylpropan-2-ol

Ethyl{[(6-bromopyridin-2-yl)methyl]thio}acetate (0.40 g, 1.38 mmol) was taken up in THF (6.8 mL) and cooled to 0° C. Methylmagnesium bromide (1.48 mL, 4.14 mmol) was added dropwise, the reaction was warmed to room temperature, and maintained at room temperature for 3 hours. The mixture was then quenched with aqueous saturated ammonium chloride and diluted with ethyl acetate. The organic layer was separated, dried over magnesium sulfate, filtered and concentrated. The crude residue was purified by silica gel chromatography to yield the title compound.
Calc'd for $C_{10}H_{15}BrNOS$ [M+H]$^+$: 276. Found: 276.

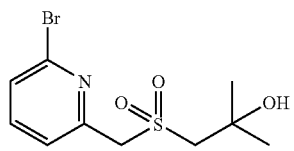 [SMILES: CC(C)(O)CS(=O)(=O)Cc1cccc(Br)n1]

Step 3: 1-{[(6-Bromopyridin-2-yl)methyl]sulfonyl}-2-methylpropan-2-ol

1-{[(6-Bromopyridin-2-yl)methyl]thio}-2-methylpropan-2-ol (0.29 g, 1.03 mmol) was taken up in DCM (5 mL) and cooled to 0° C. 3-Chloroperoxybenzoic acid (0.46 g, 2.06 mmol) was added and the reaction was allowed to stir for 30 minutes. The mixture was then diluted with ethyl acetate, washed with water, dried over magnesium sulfate, filtered and concentrated. The crude residue was purified by silica gel chromatography to yield the title compound.
Calc'd for $C_{10}H_{15}BrNO_3S$ [M+H]$^+$: 308. Found: 308.

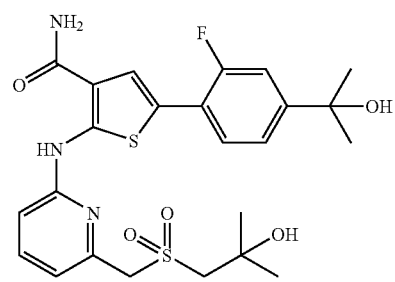 [SMILES: CC(C)(O)CS(=O)(=O)Cc1cccc(Nc2sc(-c3ccc(C(C)(C)O)cc3F)cc2C(N)=O)n1]

Step 4: 5-[2-Fluoro-4-(1-hydroxy-1-methylethyl)phenyl]-2-[(6-{[(2-hydroxy-2-methylpropyl)sulfonyl]methyl}pyridin-2-yl)amino]thiophene-3-carboxamide The title compound was prepared using the procedure described in Example 1 with 2-amino-5-[2-fluoro-4-(1-hydroxy-1-methylethyl)phenyl]thiophene-3-carboxamide (0.097 g, 0.33 mmol) and 1-{[(6-bromopyridin-2-yl)methyl]sulfonyl}-2-methylpropan-2-ol (0.10 g, 0.32 mmol) as starting materials.
Calc'd for $C_{24}H_{29}FN_3O_5S_2$ [M+H]$^+$: 522. Found: 522.

Additional examples were prepared using procedures similar to the above examples and are illustrated in the following table.

TABLE 32

| Example # | Structure | Name | Characterization |
|---|---|---|---|
| 373 | 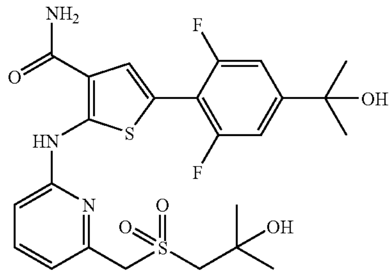 [SMILES: CC(C)(O)CS(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-[(6-{[(2-hydroxy-2-methylpropyl)sulfonyl]methyl}pyridin-2-yl)amino]thiophene-3-carboxamide | Calc'd [M + H]⁺: 540, Found: 540 |
| 374 | 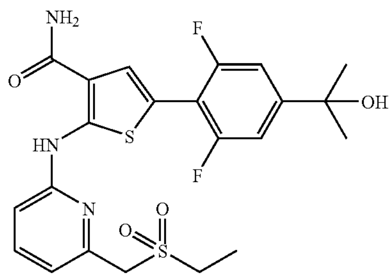 [SMILES: CCS(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-({6-[(ethylsulfonyl)methyl]pyridin-2-yl}amino)thiophene-3-carboxamide | Calc'd [M + H]⁺: 496, Found: 496 |
| 375 | 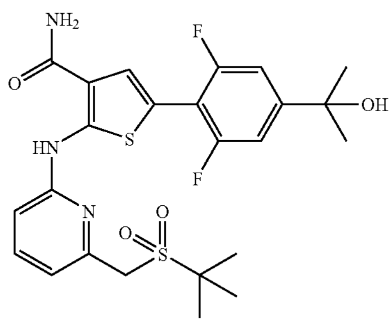 [SMILES: CC(C)(O)c1cc(F)c(-c2cc(C(N)=O)c(Nc3cccc(CS(=O)(=O)C(C)(C)C)n3)s2)c(F)c1] | 2-({6-[(tert-butylsulfonyl)methyl]pyridin-2-yl}amino)-5-[2,6-difluoro-4-(1-hydroxy-1-methylethyl)phenyl]thiophene-3-carboxamide | Calc'd [M + H]⁺: 524, Found: 524 |
| 376 | 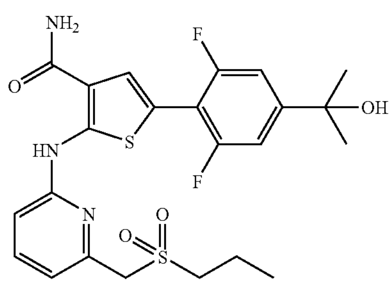 [SMILES: CCCS(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-({6-[(propylsulfonyl)methyl]pyridin-2-yl}amino)thiophene-3-carboxamide | Calc'd [M + H]⁺: 510, Found: 510 |
| 377 | 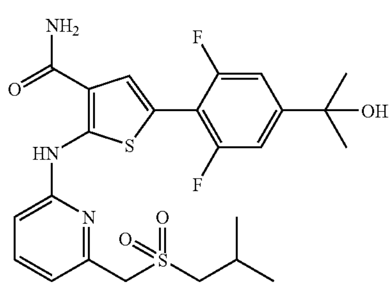 [SMILES: CC(C)CS(=O)(=O)Cc1cccc(Nc2sc(-c3c(F)cc(C(C)(C)O)cc3F)cc2C(N)=O)n1] | 5-[2,6-difluoro-4-(l-hydroxy-1-methylethyl)phenyl]-2-({6-[(isobutylsulfonyl)methyl]pyridin-2-yl}amino)thiophene-3-carboxamide | Calc'd [M + H]⁺: 524, Found: 524 |

TABLE 32-continued

| Example # | Structure | Name | Characterization |
|---|---|---|---|
| 378 | 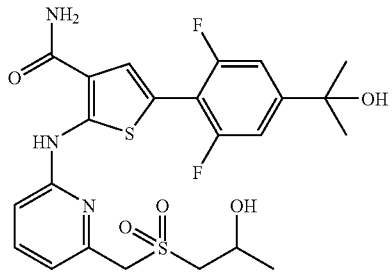 [SMILES: CC(O)CS(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-[(6-{[(2-hydroxypropyl)sulfonyl]methyl}pyridin-2-yl)amino]thiophene-3-carboxamide | Calc'd [M + H]+: 526, Found: 526 |
| 379 | 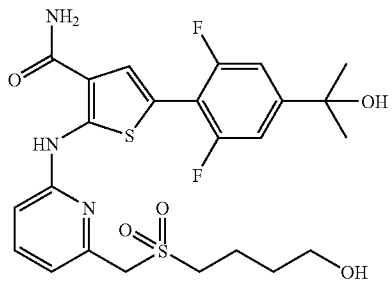 [SMILES: CC(C)(O)c1cc(F)c(-c2cc(C(N)=O)c(Nc3cccc(CS(=O)(=O)CCCCO)n3)s2)c(F)c1] | 5-[2,6-difluoro-4-(1-hydroxy-1-methylethyl)phenyl]-2-[(6-{[(4-hydroxybutyl)sulfonyl]methyl}pyridin-2-yl)amino]thiophene-3-carboxamide | Calc'd [M + H]+: 540, Found: 540 |
| 380 | 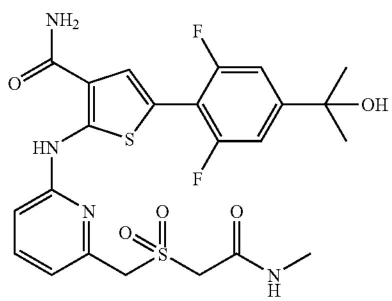 [SMILES: CNC(=O)CS(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-({[2-(methylamino)-2-oxoethyl]sulfonyl}methyl)pyridin-2-yl]amino}thiophene-3-carboxamide | Calc'd [M + H]+: 539, Found: 539 |
| 381 | 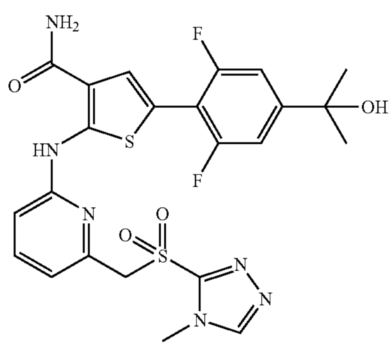 [SMILES: Cn1cnnc1S(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-[(6-{[(4-methyl-4H-1,2,4-triazol-3-yl)sulfonyl]methyl}pyridin-2-yl)amino]thiophene-3-carboxamide | Calc'd [M + H]+: 549, Found: 549 |
| 382 | 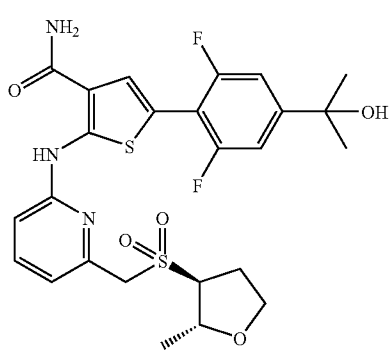 [SMILES: C[C@H]1OCC[C@@H]1S(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-({[(2S,3S)-2-methyltetrahydrofuran-3-yl]sulfonyl}methyl)pyridin-2-yl]amino}thiophene-3-carboxamide | Calc'd [M + H]+: 552, Found: 552 |

TABLE 32-continued

| Example # | Structure | Name | Characterization |
|---|---|---|---|
| 383 | 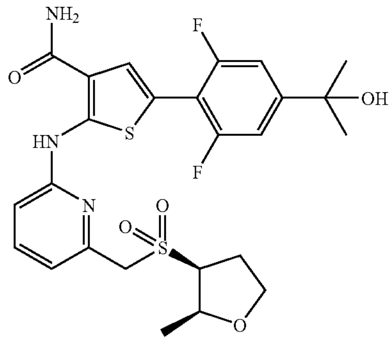 [SMILES: C[C@@H]1OCC[C@@H]1S(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-({[(2S,3S)-2-methyltetrahydrofuran-3-yl]sulfonyl}methyl)pyridin-2-yl]amino}thiophene-3-carboxamide | Calc'd [M + H]⁺: 552, Found: 552 |
| 384 | 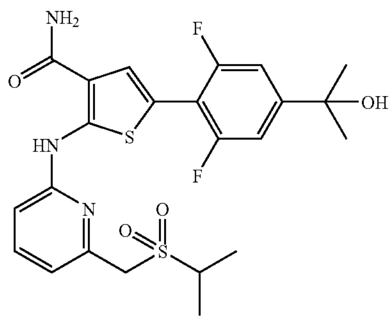 [SMILES: CC(C)S(=O)(=O)Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-({6-[(isopropylsulfonyl)methyl]pyridin-2-yl}amino)thiophene-3-carboxamide | Calc'd [M + H]⁺: 510, Found: 510 |
| 385 | 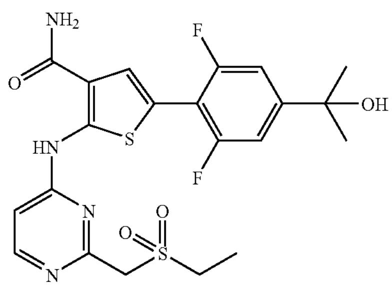 [SMILES: CCS(=O)(=O)Cc1nccc(Nc2sc(-c3c(F)cc(C(C)(C)O)cc3F)cc2C(N)=O)n1] | 5-[2,6-Difluoro-4-(1-hydroxy-1-methylethyl)phenyl]-2-({2-[(ethylsulfonyl)methyl]pyrimidin-4-yl}amino)thiophene-3-carboxamide | Calc'd [M + H]⁺: 497, Found: 497 |
| 386 | 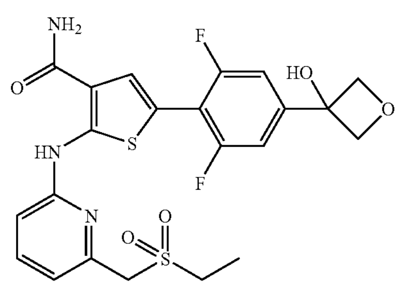 | 5-[2,6-difluoro-4-(3-hydroxyoxetan-3-yl)phenyl]-2-({6-[(ethylsulfonyl)methyl]pyridin-2-yl}amino)thiophene-3-carboxamide | Calc'd [M + H]⁺: 474, Found: 474 |
| 387 | 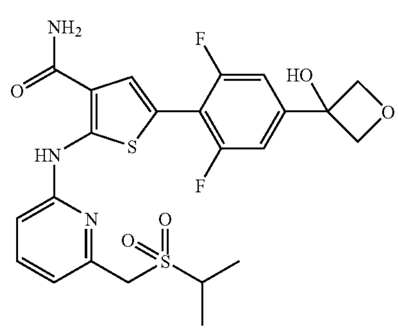 | 5-[2,6-difluoro-4-(3-hydroxyoxetan-3-yl)phenyl]-2-({6-[(isopropylsulfonyl)methyl]pyrimidin-2-yl}amino)thiophene-3-carboxamide | Calc'd [M + H]⁺: 488, Found: 488 |

Example 388

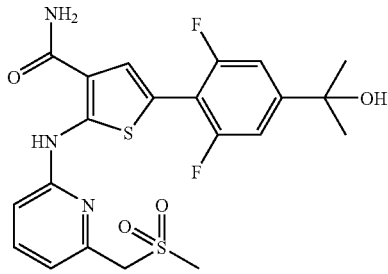 [SMILES: CC(C)(O)c1cc(F)c(-c2cc(C(N)=O)c(Nc3cccc(CS(C)(=O)=O)n3)s2)c(F)c1]

5-[2,6-Difluoro-4-(1-hydroxy-1-methylethyl)phenyl]-2-({6-[(methylsulfonyl)methyl]pyridin-2-yl}amino)thiophene-3-carboxamide

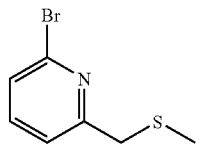

Step 1: 2-Bromo-6-[(methylthio)methyl]pyridine

2-Bromo-6-(bromomethyl)pyridine (Example 190, Step 1) (0.20 g, 0.80 mmol) and sodium thiomethoxide (0.072 g, 1.04 mmol) were taken up in DMF (12.1 mL) heated at 80° C. for 3 hours. The reaction was then cooled to ambient temperature, diluted with ethyl acetate, washed with water, dried over magnesium sulfate, filtered and concentrated. The crude residue was purified by silica gel chromatography to yield the title compound. $^1$H NMR (600 MHz, CDCl$_3$): 7.53 (t, J=9.0 Hz, 1H), 7.37 (d, J=9.0 Hz, 1H), 7.36 (d, J=9.0 Hz, 1H), 3.77 (s, 2H), 2.08 (2, 3H).

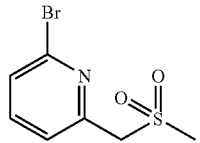

Step 2: 2-Bromo-6-[(methylsulfonyl)methyl]pyridine

2-Bromo-6-[(methylsulfonyl)methyl]pyridine was prepared using the procedure described in Example 372 Step 3 using 2-bromo-6-[(methylthio)methyl]pyridine (0.15 g, 0.67 mmol) as the starting material.

Calc'd for C$_7$H$_9$BrNO$_2$S [M+H]$^+$: 250. Found: 250.

Step 3: 5-[2,6-Difluoro-4-(1-hydroxy-1-methylethyl)phenyl]-2-({6-[(methylsulfonyl)methyl]pyridin-2-yl}amino)thiophene-3-carboxamide The title compound was prepared using the procedure described in Example 1 with 2-amino-5-[2,6-difluoro-4-(1-hydroxy-1-methylethyl)phenyl]thiophene-3-carboxamide (0.075 g, 0.24 mmol) and 2-bromo-6-[(methylsulfonyl)methyl]pyridine (0.060 g, 0.24 mmol) as starting materials.

Calc'd for C$_{21}$H$_{22}$FN$_3$O$_4$S$_2$ [M+H]$^+$: 482. Found: 482.

The following example was prepared using procedures similar to those described in the above examples and is illustrated in the following table.

TABLE 33

| Example # | Name | Structure | Characterization |
|---|---|---|---|
| 389 | 5-[2-fluoro-4-(1-hydroxy-1-methylethyl)phenyl]-2-({6-[(methylsulfonyl)methyl]pyridin-2-yl}amino)thiophene-3-carboxamide | 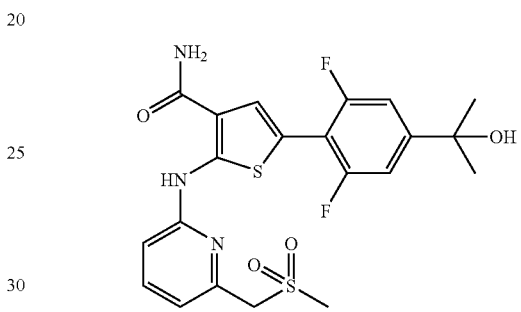 | Calc'd [M + H]$^+$: 464, Found: 464 |

Example 390

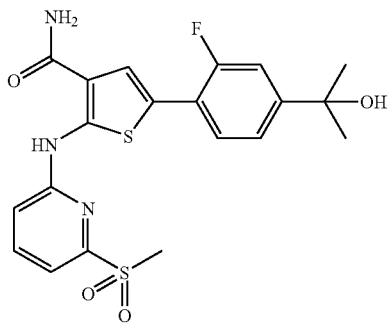 [SMILES: CC(C)(O)c1ccc(-c2cc(C(N)=O)c(Nc3cccc(S(C)(=O)=O)n3)s2)c(F)c1]

5-[2-Fluoro-4-(1-hydroxy-1-methylethyl)phenyl]-2-{[6-(methylsulfonyl)pyridin-2-yl]amino}thiophene-3-carboxamide

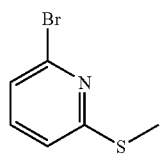

Step 1: 2-Bromo-6-(methylthio)pyridine

To a solution of 2,6-dibromopyridine (0.50 g, 2.11 mmol) in DMF (21 mL) was added sodium thiomethoxide (0.16 g, 2.32 mmol) and the solution was allowed to react overnight. The solution was then diluted with ethyl ether, washed with water, dried over magnesium sulfate, filtered and concentrated. The crude residue was purified by silica gel chromatography to yield the title compound. $^1$H NMR (600 MHz, CDCl$_3$): 7.32 (t, J=7.3 Hz, 1H), 7.15 (dd, J=9.6, 1.2 Hz, 1H), 7.12 (dd, J=9.0, 0.6 Hz, 1H), 2.55 (s, 1H).

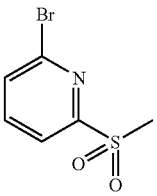

Step 2: 2-Bromo-6-(methylsulfonyl)pyridine

The title compound was prepared using the procedure described in Example 372 Step 3 with 2-bromo-6-(methylthio)pyridine (0.39 g, 1.92 mmol) as the starting material.
Calc'd for C$_6$H$_7$BrNO$_2$S [M+H]$^+$: 236. Found: 236.

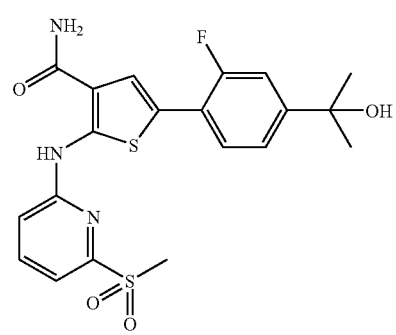 [SMILES: CC(C)(O)c1ccc(-c2cc(C(N)=O)c(Nc3cccc(S(C)(=O)=O)n3)s2)c(F)c1]

Step 3: 5-[2-Fluoro-4-(1-hydroxy-1-methylethyl)phenyl]-2-{[6-(methylsulfonyl)pyridin-2-yl]amino}thiophene-3-carboxamide The title compound was prepared using the procedure described in Example 1 using 2-amino-5-[2-fluoro-4-(1-hydroxy-1-methylethyl)phenyl]thiophene-3-carboxamide (0.13 g, 0.44 mmol) and 2-bromo-6-(methylsulfonyl)pyridine (0.10 g, 0.44 mmol) as the starting materials.
Calc'd for C$_{20}$H$_{21}$FN$_3$O$_4$S$_2$ [M+1]$^+$: 450. Found: 450.

The following example was prepared using procedures similar to those described in the above examples and is illustrated in the following table.

TABLE 34

| Example # | Structure | Name | Characterization |
|---|---|---|---|
| 391 | (structure shown) | 5-[2,6-difluoro-4-(1-hydroxy-1-methylethyl)phenyl]-2-{[6-(methylsulfonyl)pyridin-2-yl]amino}thiophene-3-carboxamide | Calc'd [M + H]$^+$: 468, Found: 468 |

Example 392

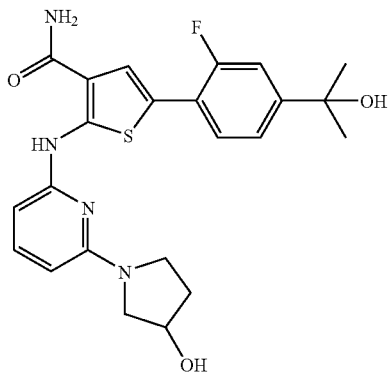 [SMILES: CC(C)(O)c1ccc(-c2cc(C(N)=O)c(Nc3cccc(N4CCC(O)C4)n3)s2)c(F)c1]

5-[2,6-Difluoro-4-(1-hydroxy-1-methylethyl)phenyl]-2-{[6-(3-hydroxypyrrolidin-1-yl)pyridin-2-yl]amino}thiophene-3-carboxamide

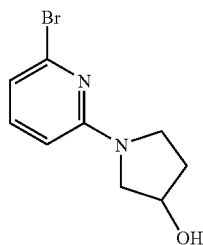 [SMILES: OC1CCN(c2cccc(Br)n2)C1]

Step 1. 1-(6-Bromopyridin-2-yl)pyrrolidin-3-ol

A mixture of 2,6-dibromopyridine (2.37 g, 0.01 mol), pyrrolidin-3-ol (1.0 g, 0.01 mol), 1,8-diazabicclo[5.4.0]-7-undecene (1.5 mL) in 10 mL of THF was heated at 70° C. under a nitrogen atmosphere for 11 hours. The reaction mixture was then cooled to room temperature, diluted with ethyl acetate (30 mL). The resulting solution was washed with water and brine, dried over anhydrous magnesium sulfate, filtered and concentrated. The residue was purified by silica gel chromatography (10-30% ethyl acetate/hexane) to give the title compound.

$^1$H NMR (400 MHz, CDCl$_3$): δ 7.25 (t, 1H), 6.68 (d, 1H), 6.40 (d, 1H), 3.81 (t, 2H), 3.68 (t, 2H), 3.04 (s, 4H).

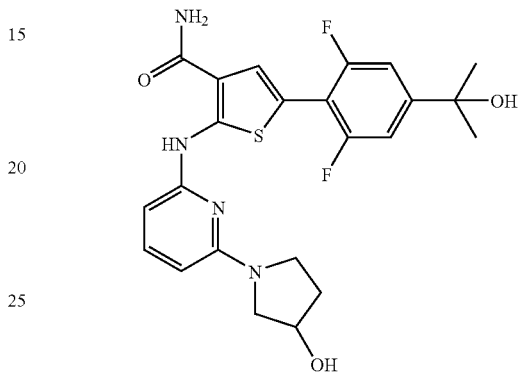

Step 2. 5-[2,6-Difluoro-4-(1-hydroxy-1-methylethyl)phenyl]-2-{[6-(3-hydroxypyrrolidin-1-yl)pyridin-2-yl]amino}thiophene-3-carboxamide The title compound was prepared according to the procedure described in Example 1 using 2-amino-5-[2,6-difluoro-4-(1-hydroxy-1-methylethyl)phenyl]thiophene-3-carboxamide (200 mg, 0.64 mmol) and 1-(6-bromopyridin-2-yl)pyrrolidin-3-ol (132 mg, 0.54 mmol) as the starting materials.

Calc'd for C$_{23}$H$_{25}$F$_2$N$_4$O$_3$S [M+H]$^+$: 475. Found: 475.

Additional examples were prepared using procedures similar to those described in the above examples and are illustrated in the following table.

TABLE 35

| Example # | Structure | Name | Characterization |
|---|---|---|---|
| 393 | ![structure] | 5-[2,6-Difluoro-4-(1-hydroxy-1-methylethyl)phenyl]-2-({6-[(2-hydroxyethyl)(methyl)amino]pyridin-2-yl}amino)thiophene-3-carboxamide | Calc'd [M + H]$^+$: 463, Found: 463 |

TABLE 35-continued

| Example # | Structure | Name | Characterization |
|---|---|---|---|
| 394 | 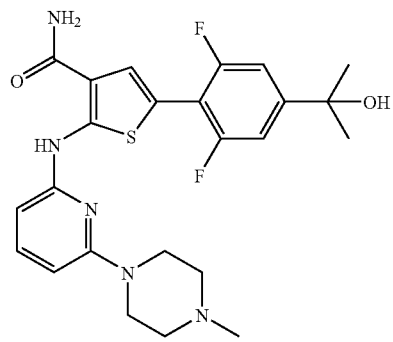 | 5-[2,6-Difluoro-4-(1-hydroxy-1-methylethyl)phenyl]-2-[(6-pyrrolidin-1-ylpyridin-2-yl)amino]thiophene-3-carboxamide | Calc'd [M + H]$^+$: 459, Found: 459 |

Example 395

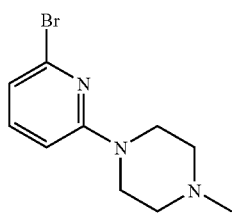

5-[2,6-Difluoro-4-(1-hydroxy-1-methylethyl)phenyl]-2-{[6-(4-methylpiperazin-1-yl)pyridin-2-yl]amino}thiophene-3-carboxamide

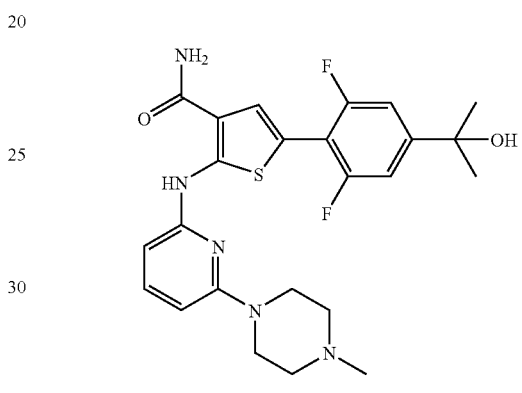

Step 1. 1-(6-Bromopyridin-2-yl)-4-methylpiperazine

A mixture of 2,6-dibromopyridine (4.74 g, 0.02 mol), anhydrous K$_2$CO$_3$ (2.8 g, 0.02 mol) and N-methylpiperazine (2.2 mL) in 30 mL of DMSO was stirred at 80° C. for 4 hours. The mixture was cooled to ambient temperature, poured into ice-water, and extracted with ethyl acetate (2×). The combined organics were dried over Na$_2$SO$_4$, filtered, and evaporated. The residue was then acidified with aqueous HCl to form a white solid, which was filtered and then re-crystallized in 95% ethanol to give the title compound as the HCl salt.

$^1$H NMR (400 MHz, CDCl$_3$): 7.36 (t, 1H), 6.89 (d, 1H), 6.57 (d, 1H), 4.32~4.36 (m, 2H), 3.75~3.82 (m, 2H), 3.52~3.55 (m, 2H), 2.86~2.93 (m, 2H), 2.83 (s, 3H).

Step 2. 5-[2,6-Difluoro-4-(1-hydroxy-1-methylethyl)phenyl]-2-{[6-(4-methylpiperazin-1-yl)pyridin-2-yl]amino}thiophene-3-carboxamide The title compound was prepared according to the procedure described in Example 1 using 2-amino-5-[2,6-difluoro-4-(1-hydroxy-1-methylethyl)phenyl]thiophene-3-carboxamide and 1-(6-bromopyridin-2-yl)-4-methylpiperazine as the starting materials.

Calc'd for C$_{24}$H$_{28}$F$_2$N$_5$O$_2$S [M+H]$^+$: 488. Found: 488.

Example 396

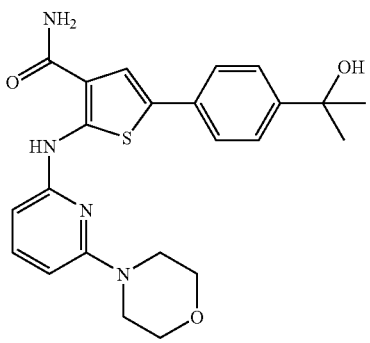 [SMILES: CC(C)(O)c1ccc(-c2cc(C(N)=O)c(Nc3cccc(N4CCOCC4)n3)s2)cc1]

5-(4-(1-hydroxy-1-methylethyl)phenyl-2((6-(4-morpholinyl)-2-pyridinyl)amino)-3-thiophenecarboxamide The title compound was prepared as described in Example 205, Step 2 using 2-amino-5-[4-(1-hydroxy-1-methylethyl)phenyl]thiophene-3-carboxamide (60 mg, 0.22 mmol) and 4-(6-bromopyridin-2-yl)morpholine (53 mg, 0.22 mmol) as starting materials.

Calc'd for $C_{23}H_{27}N_4O_3S$ [M+H]$^+$ 440. found 440.

An additional example was prepared using procedures similar to those described in the above example and is illustrated in the following table.

TABLE 36

| Example # | Structure | Name | Characterization |
|---|---|---|---|
| 397 | 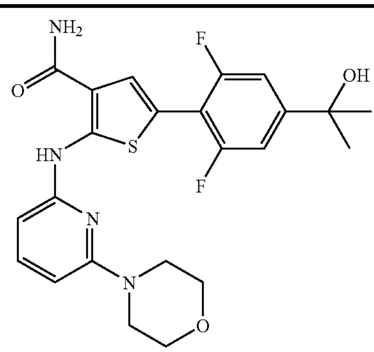 | 5-(2,6-difluoro-4-(1-hydroxy-1-methylethyl)phenyl)-2-((6-(4-morpholinyl)-2-pyridinyl)amino)-3-thiophenecarboxamide | Calc'd [M + H]$^+$: 475, Found: 475 |

Example 398

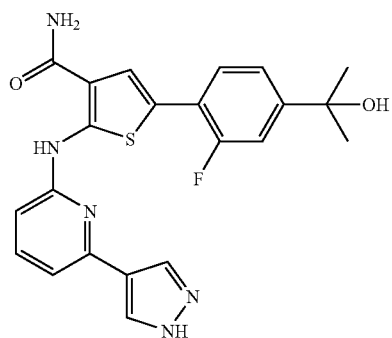 [SMILES: CC(C)(O)c1ccc(-c2cc(C(N)=O)c(Nc3cccc(-c4cn[nH]c4)n3)s2)c(F)c1]

5-[2-Fluoro-4-(1-hydroxy-1-methylethyl)phenyl]-2-{[6-(1H-pyrazol-4-yl)pyridin-2-yl]amino}thiophene-3-carboxamide

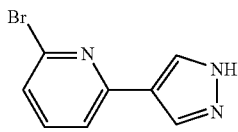 [SMILES: Brc1cccc(-c2cn[nH]c2)n1]

Step 1: 2-Bromo-6-(1H-pyrazol-4-yl)pyridine

Method A: A vial was charged with 2,6-dibromopyridine (169 mg, 0.71 mmol), potassium carbonate (282 mg, 2.04 mmol), and 1,1-bis(diphenylphosphino)ferrocenedichloropalladium(II) (25 mg, 0.034 mmol) and evacuated and back-filled with argon three times. 4-(4,4,5,5-Tetramethyl-1,3,2-dioxoborolan-2-yl)-1H-pyrazole-1-carboxylic acid tert-butyl ester (200 mg, 0.68 mmol) was dissolved in degassed dimethylformamide (4.7 mL) in a separate vial and then and transferred to the vial containing 2,6-dibromopyridine. The reaction was heated to 80° C. and allowed to stir for 14 hours. It was then cooled to room temperature, diluted with water, and extracted with ethyl acetate (2×). The organic layers were combined, dried over magnesium sulfate, filtered, and concentrated under reduced pressure. The resulting mixture was purified via silica gel chromatography (0-5% methanol in ethyl acetate) to afford the title compound.

Calc'd for $C_8H_7BrN_3$ [M+H]$^+$: 223. Found: 223.

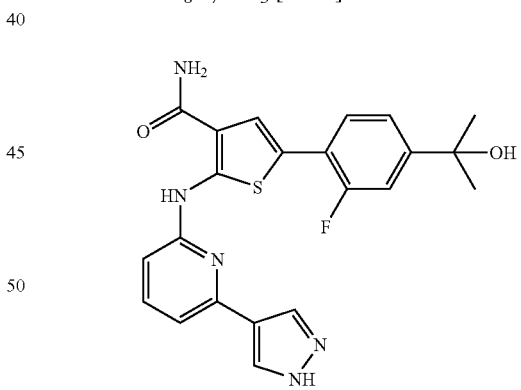

Step 2: 5-[2-Fluoro-4-(1-hydroxy-1-methylethyl)phenyl]-2-{[6-(1H-pyrazol-4-yl)pyridin-2-yl]amino}thiophene-3-carboxamide The title compound was prepared as described in Example 1 using 2-amino-5-[2-fluoro-4-(1-hydroxy-1-methylethyl)phenyl]thiophene-3-carboxamide (77 mg, 0.26 mmol) and 2-bromo-6-(1H-pyrazol-4-yl)pyridine (59 mg, 0.262 mmol) as starting materials.

$^1$H NMR (600 MHz, d6-DMSO): δ 13.12 (s, 1H), 11.99 (s, 1H), 8.7 (s, 1H), 8.20 (s, 1H), 7.89 (s, 1H), 7.82 (s, 1H), 7.65

(m, 2H), 7.33 (m, 3H), 7.25 (d, 1H), 6.83 (d, 1H), 5.16 (s, 1H), 1.42 (s, 6H). Calc'd for $C_{22}H_{21}F_4N_5O_2S$ [M+H]$^+$: 438. Found: 438.

Example 399

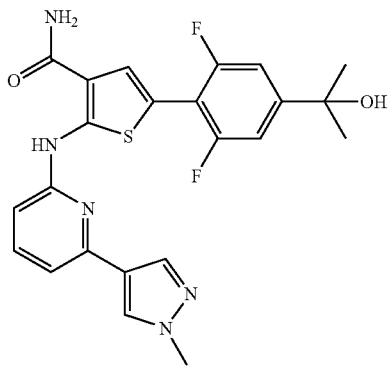 [SMILES: Cn1cc(-c2cccc(Nc3sc(-c4c(F)cc(C(C)(C)O)cc4F)cc3C(N)=O)n2)cn1]

5-[2,6-Difluoro-4-(1-hydroxy-1-methylethyl)phenyl]-2-{[6-(1-methyl-1H-pyrazol-4-yl)pyridin-2-yl]amino}thiophene-3-carboxamide

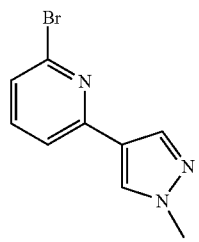

Step 1:
2-Bromo-6-(1-methyl-1H-pyrazol-4-yl)pyridine

Method B: To a solution of 1-methyl-4-(4,4,5,5-tetramethyl-1,3,2-dioxaborolan-2-yl)-1H-pyrazole (1.8 g, 8.6 mmol) and 2,6-dibromopyridine (3.05 g, 13 mmol) in dioxane (18 mL) and 2M $Na_2CO_3$ (15 mL) was added Pd(PPh$_3$)$_4$ (0.2 g). The mixture was degassed by bubbling nitrogen through the mixture for 5 min, sealed, and heated to 100° C. overnight. The reaction solution was cooled, filtered, and extracted with ethyl acetate (2×). The organic layers were dried over $Na_2SO_4$, filtered, concentrated, and purified by silica gel chromatography to yield the title compound.

$^1$H NMR (400 MHz d6-DMSO) δ 8.27 (s, 1H), 7.96 (s, 1H), 7.69-7.63 (m, 2H), 7.37-7.35 (dd, 1H). Calc'd for $C_9H_9BrN_3$ [M+H]$^+$: 238. Found: 238.

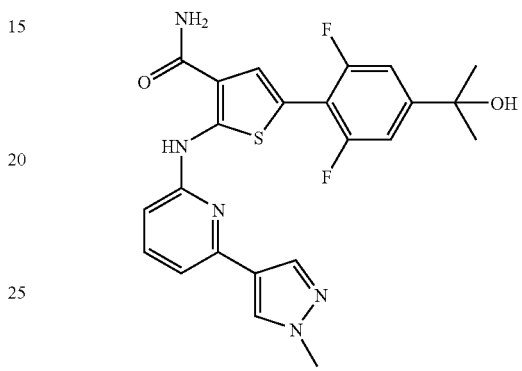

Step 2: 5-[2,6-Difluoro-4-(1-hydroxy-1-methylethyl)phenyl]-2-{[6-(1-methyl-1H-pyrazol-4-yl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 2-bromo-6-(1-methyl-1H-pyrazol-4-yl)pyridine (114 mg, 0.48 mmol) as starting materials.

Calc'd for $C_{23}H_{22}F_2N_5O_2S$ [M+H]$^+$: 470. found: 470.

Additional examples were prepared using procedures similar to those described in the above examples and are illustrated in the following table.

TABLE 37

| Example # | Structure | Name | Method | Characterization [M + H]$^+$ |
|---|---|---|---|---|
| 400 | ![structure] | 5-[2-fluoro-4-(1-hydroxy-1-methylethyl)phenyl]-2-({6-[3-(methylsulfonyl)phenyl]pyridin-2-yl}amino)thiophene-3-carboxamide | A | Calc'd 526, found 526 |

TABLE 37-continued

| Example # | Structure | Name | Method | Characterization [M + H]+ |
|---|---|---|---|---|
| 401 | 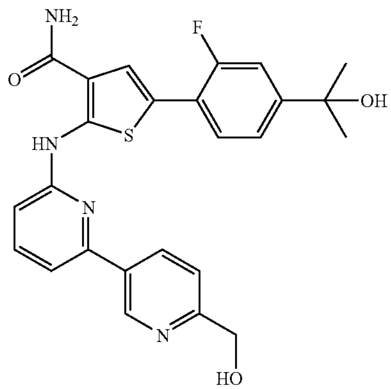 [SMILES: CC(C)(O)c1ccc(-c2cc(C(N)=O)c(Nc3cccc(-c4ccc(CO)nc4)n3)s2)c(F)c1] | 5-[2-fluoro-4-(1-hydroxy-1-methylethyl)phenyl]-2-{[6'-(hydroxymethyl)-2,3'-bipyridin-6-yl]amino}thiophene-3-carboxamide | A | Calc'd 479, found 479 |
| 402 | 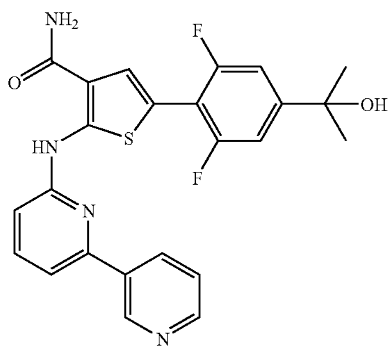 [SMILES: CC(C)(O)c1cc(F)c(-c2cc(C(N)=O)c(Nc3cccc(-c4cccnc4)n3)s2)c(F)c1] | 2-(2,3'-bipyridin-6-ylamino)-5-[2,6-difluoro-4-(1-hydroxy-1-methylethyl)phenyl]thiophene-3-carboxamide | B | Calc'd 467, found 467 |

Method A: Using the procedures described in Example 398
Method B: Using the procedures described in Example 399

Example 403

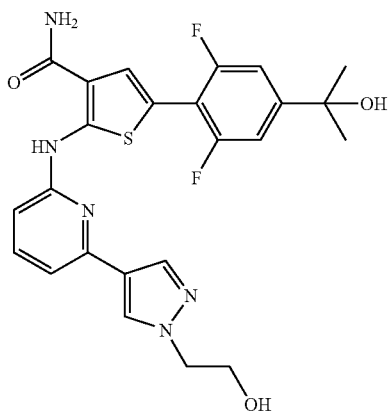 [SMILES: CC(C)(O)c1cc(F)c(-c2cc(C(N)=O)c(Nc3cccc(-c4cnn(CCO)c4)n3)s2)c(F)c1]

5-[2,6-Difluoro-4-(1-hydroxy-1-methylethyl)phenyl]-2-({6-[1-(2-hydroxyethyl)-1H-pyrazol-4-yl]pyridin-2-yl}amino)thiophene-3-carboxamide

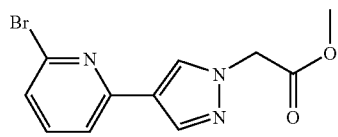 [SMILES: COC(=O)Cn1cc(-c2cccc(Br)n2)cn1]

Step 1: Methyl[4-(6-bromopyridin-2-yl)-1H-pyrazol-1-yl]acetate

Potassium Carbonate (740 mg, 5.36 mmol), methyl bromoacetate (0.37 mL, 4.02 mmol) and 2-bromo-6-(1H-pyrazol-4-yl)pyridine (Example 398, Step 1) were taken up in acetonitrile. The mixture was heated at 70° C. for 72 hours. It was then poured into 300 mL diethyl ether and 50 mL water. The organic layer was separated, dried over magnesium sulfate, filtered, and concentrated to yield the title compound.
Calc'd for $C_{11}H_{11}BrN_3O_2$ [M+H]+: 296. Found: 296.

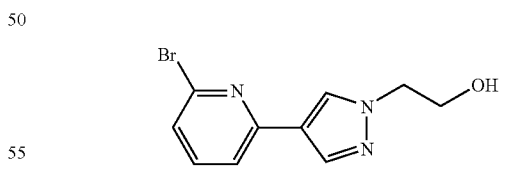

Step 2: 2-[4-(6-Bromopyridin-2-yl)-1H-pyrazol-1-yl]ethanol

To a cooled (0° C.) solution of methyl[4-(6-bromopyridin-2-yl)-1H-pyrazol-1-yl]acetate (196 mg, 0.66 mmol) in tetrahydrofuran (3.4 mL) was added diisobutylaluminum hydride (1.0M in hexane, 1.99 mL, 1.99 mmol) dropwise. The solution was allowed to warm to room temperature and maintained at room temperature overnight. Additional diisobutylaluminum hydride (0.66 mL, 0.66 mmol) was then added and the reaction was stirred for another 24 hours. Saturated aqueous potassium sodium tartrate (20 mL) was then added and the solution was vigorously stirred for three hours. Ethyl acetate (7 mL) was added to the solution, and it was stirred another 60 minutes. The organic layer was separated and the aqueous layer was extracted three times with ethyl acetate. The combined organic layers were dried over magnesium sulfate, filtered, and concentrated in vacuo. Purification via silica gel chromatography (0-5% methanol in ethyl acetate) afforded the title compound.

Calc'd for $C_{10}H_{11}BrN_3O$ [M+H]$^+$: 268. Found: 268.

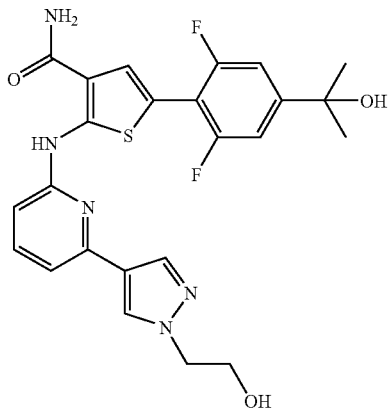 [SMILES: CC(C)(O)c1cc(F)c(-c2cc(C(N)=O)c(Nc3cccc(-c4cnn(CCO)c4)n3)s2)c(F)c1]

Step 3: 5-[2,6-Difluoro-4-(1-hydroxy-1-methylethyl)phenyl]-2-({6-[1-(2-hydroxyethyl)-1H-pyrazol-4-yl]pyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (35 mg, 0.11 mmol) and 5-(6-chloro-2-methylpyridin-3-yl)-1,3,4-oxadiazol-2(3H)-one (30 mg, 0.11 mmol) as starting materials.

$^1$H NMR (600 MHz, d6-DMSO): δ 12.11 (s, 1H), 8.35 (s, 1H), 8.16 (s, 1H), 7.94 (s, 1H), 7.88 (s, 1H), 7.69 (t, 1H), 7.39 (s, 1H), 7.30 (d, 2H), 7.23 (d, 1H), 6.88 (d, 1H), 5.31 (s, 1H), 4.95 (t, H), 4.12 (t, 2H), 3.78 (q, 2H), 1.44 (s, 6H). Calc'd for $C_{24}H_{24}F_2N_5O_3S$ [M+H]$^+$: 500. Found: 500.

Example 404

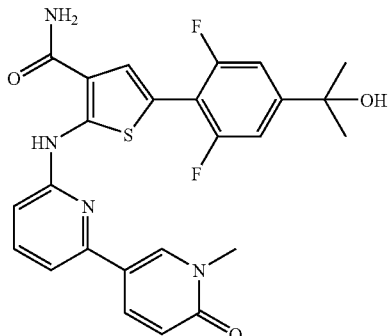

5-[2,6-Difluoro-4-(1-hydroxy-1-methylethyl)phenyl]-2-[(1'-methyl-6'-oxo-1',6'-dihydro-2,3'-bipyridin-6-yl)amino]thiophene-3-carboxamide

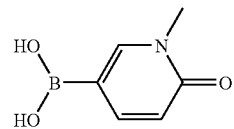

Step 1: (1-Methyl-6-oxo-1,6-dihydropyridin-3-yl)boronic acid

5-Bromo-1-methylpyridin-2(1H)-one (400 mg, 2.17 mmol), tricyclohexylphosphine (72 mg, 0.26 mmol), 4,4,4',4',5,5,5',5'-octamethyl-2,2'-bi-1,3,2-dioxaborolane (540 mg, 2.17 mmol), potassium acetate (522 mg, 5.32 mmol) and Pd$_2$(dba)$_3$ (97 mg, 0.11 mmol) were added to a flask. The flask was evacuated and purged with argon three times. Fully degassed dioxane (9.5 mL) was added and the reaction was sealed and heated at 90° C. overnight. The mixture was then cooled to room temperature, filtered over a thin layer of celite, eluting with dichloromethane. The majority of the dichloromethane was evaporated under reduced pressure and hexane was added until a precipitate formed. The slurry was filtered and the filtrate was concentrated. The resulting residue was dissolved in dioxane, 10 equivalents of 1 N hydrochloric acid were added, and the mixture was stirred overnight. Removal of the solvent under reduced pressure and purification of the resulting residue via reverse phase HPLC (10-100% acetonitrile/water+0.05% TFA modifier) afforded the title compound.

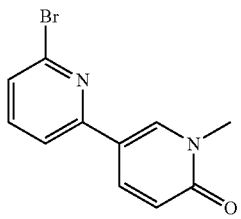

Step 2: 6-Bromo-1'-methyl-2,3'-bipyridin-6'(1'H)-one

A flask was charged with (1-methyl-6-oxo-1,6-dihydropyridin-3-yl)boronic acid (80 mg, 0.52 mmol), potassium carbonate (217 mg, 1.57 mmol), and 1,1-bis(diphenylphosphino)ferrocenedichloropalladium(II) (19 mg, 0.026 mmol) and evacuated and purged with argon (5×). 2,6-Dibromopyridine (130 mg, 0.55 mmol) was placed into a separate flask and evacuated and backfilled with argon (3×). Degassed dimethylformamide (3.6 mL) was added to the vial containing 2,6-dibromopyridine and the solution was transferred to the flask containing the remainder of the reactants. The mixture was heated at 80° C. overnight, then cooled to room temperature, taken up in water, and extracted with ethyl acetate (2×). The ethyl acetate layers were combined, dried over magnesium sulfate, filtered, and concentrated under reduced pressure. The resulting mixture was purified via silica gel chromatography (0-5% methanol in ethyl acetate) to afford the title compound.

Calc'd for $C_{11}H_{10}BrN_2O$ $[M+H]^+$: 264. Found: 264.

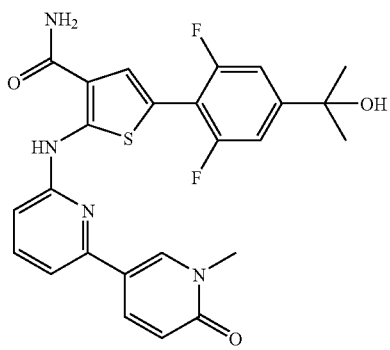 [SMILES: Cn1cc(-c2cccc(Nc3sc(-c4c(F)cc(C(C)(C)O)cc4F)cc3C(N)=O)n2)ccc1=O]

Step 3: 5-[2,6-Difluoro-4-(1-hydroxy-1-methylethyl) phenyl]-2-[(1'-methyl-6'-oxo-1',6'-dihydro-2,3'-bipyridin-6-yl)amino]thiophene-3-carboxamide The title compound was prepared as described in Example 1 using 2-amino-5-[2,6-difluoro-4-(1-hydroxy-1-methylethyl)phenyl]thiophene-3-carboxamide (38 mg, 0.12 mmol) and 6-bromo-1'-methyl-2,3'-bipyridin-6'(1'H)-one (33 mg, 0.12 mmol) as starting materials.

$^1$H NMR (600 MHz, d4-methanol): δ 8.65 (d, 1H), 8.34 (dd, 1H), 7.82 (s, 1H), 7.70 (t, 1H), 7.28 (d, 1H), 7.21 (d, 2H), 6.83 (d, 1H), 6.64 (d, 1H), 3.71 (s, 3H), 1.55 (s, 6H). Calc'd for $C_{25}H_{23}F_2N_4O_3S$ $[M+H]^+$: 497. Found: 497.

Example 405

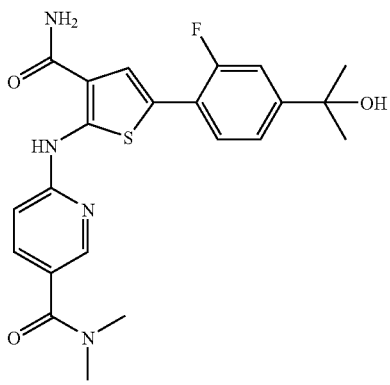 [SMILES: CN(C)C(=O)c1ccc(Nc2sc(-c3ccc(C(C)(C)O)cc3F)cc2C(N)=O)nc1]

6-({3-(Aminocarbonyl)-5-[2-fluoro-4-(1-hydroxy-1-methylethyl)phenyl]-2-thienyl}amino)-N,N-dimethylnicotinamide

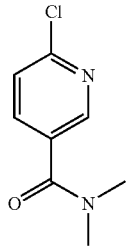

Step 1: 6-Chloro-N,N-dimethylnicotinamide

6-Chloronicotinoyl chloride (500 mg, 2.76 mmol) and triethylamine (0.576 ml, 4.13 mmol) were taken-up in THF (13.8 ml) under argon and cooled to 0° C. Dimethylamine hydrochloride (337 mg, 4.13 mmol) was dissolved in THF (2 ml) and added dropwise to the reaction mixture over 15 minutes. The mixture was maintained at 0° C. for 1 hour, warmed to room temperature, and stirred for 15 minutes. The reaction was then diluted with ethyl acetate and washed twice with brine. The aqueous layers were combined and back-extracted twice with ethyl acetate. The organic layers were combined, dried over anhydrous magnesium sulfate, filtered, and concentrated to afford the title compound.

Calc'd for $C_8H_{10}ClN_2O$ $[M+H]^+$: 185. Found: 185.

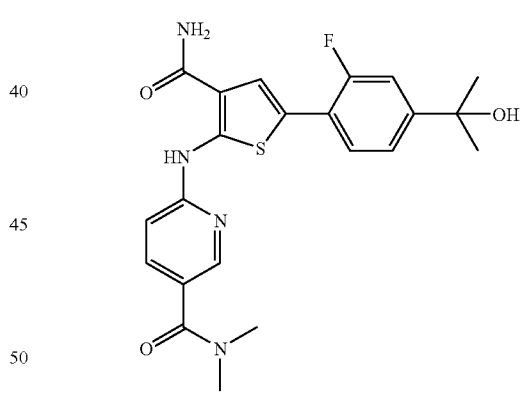

Step 2: 6-({3-(Aminocarbonyl)-5-[2-fluoro-4-(1-hydroxy-1-methylethyl)phenyl]-2-thienyl}amino)-N,N-dimethylnicotinamide The title compound was prepared as described in Example 1 using 2-amino-5-[2-fluoro-4-(1-hydroxy-1-methylethyl)phenyl]thiophene-3-carboxamide (150 mg, 0.510 mmol) and 6-chloro-N,N-dimethylnicotinamide (94 mg, 0.510 mmol) as starting materials.

Calc'd for $C_{22}H_{24}FN_4O_3S$ $[M+H]^+$: 443. Found: 443.

Additional examples were prepared using procedures similar to those described in the above examples and are illustrated in the following table.

TABLE 38

| Example # | Structure | Name | Characterization |
|---|---|---|---|
| 406 | 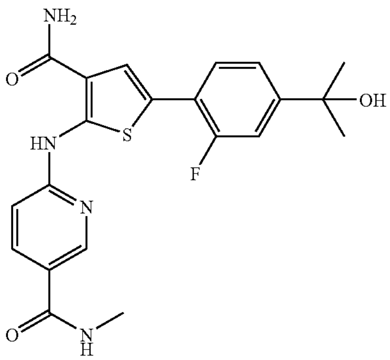 [SMILES: CNC(=O)c1ccc(Nc2sc(-c3ccc(C(C)(C)O)cc3F)cc2C(N)=O)nc1] | 6-({3-(aminocarbonyl)-5-[2-fluoro-4-(1-hydroxy-1-methylethyl)phenyl]-2-thienyl}amino)-N-methylnicotinamide | Calc'd 429, found 429 |
| 407 | 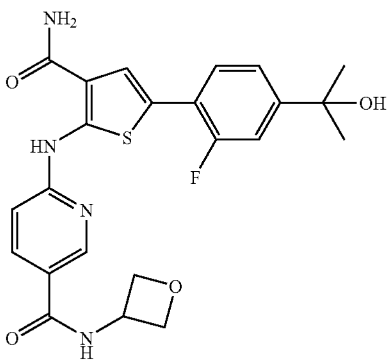 [SMILES: CC(C)(O)c1ccc(-c2cc(C(N)=O)c(Nc3ccc(C(=O)NC4COC4)cn3)s2)c(F)c1] | 6-({3-(aminocarbonyl)-5-[2-fluoro-4-(1-hydroxy-1-methylethyl)phenyl]-2-thienyl}amino)-N oxetan-3-ylnicotinamide | Calc'd 471, found 471 |

Example 408

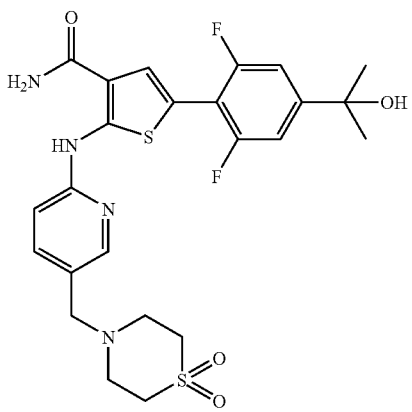 [SMILES: CC(C)(O)c1cc(F)c(-c2cc(C(N)=O)c(Nc3ccc(CN4CCS(=O)(=O)CC4)cn3)s2)c(F)c1]

5-[2,6-Difluoro-4-(1-hydroxy-1-methylethyl)phenyl]-2-({5-[(1,1-dioxidothiomorpholin-4-yl)methyl]pyridin-2-yl}amino)thiophene-3-carboxamide

Step 1: 4-[(6-Chloropyridin-3-yl)methyl]thiomorpholine 1,1-dioxide

Method A: 6-Chloronicotinaldehyde (500 mg, 3.53 mmol) and thiomorpholine 1,1-dioxide (477 mg, 3.53 mmol) were taken up in dichloroethane (14 mL) and allowed to react at room temperature for 1 hour. Sodium triacetoxyborhydride (1.12 g, 5.3 mmol) was then added and the resulting mixture was stirred overnight at room temperature. The reaction was then diluted with dichloromethane and saturated aqueous sodium bicarbonate. The organic layer was separated, and the aqueous layer was extracted with ethyl acetate (3×). The organic layers were combined, dried over magnesium sulfate, filtered, and concentrated under reduced pressure. Purification via reverse phase HPLC (10-100% acetonitrile/water+ 0.05% TFA modifier) afforded the title compound.

Calc'd for $C_{10}H_{13}ClN_2O_2S$ [M+H]⁺: 261. Found: 261.

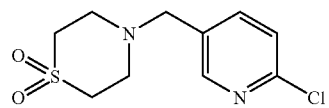 [SMILES: O=S1(=O)CCN(Cc2ccc(Cl)nc2)CC1]

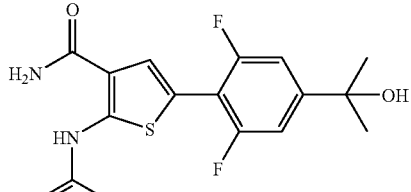

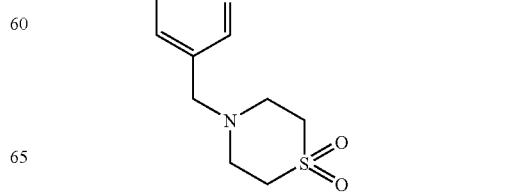

Step 2: 5-[2,6-Difluoro-4-(1-hydroxy-1-methylethyl) phenyl]-2-({5-[(1,1-dioxidothiomorpholin-4-yl)methyl]pyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (41 mg, 0.13 mmol) and 4-[(6-chloropyridin-3-yl)methyl]thiomorpholine 1,1-dioxide (34 mg, 0.13 mmol) as starting materials.
Calc'd for $C_{24}H_{27}F_2N_4O_4S_2$ [M+H]$^+$: 537. Found: 537.

Example 409

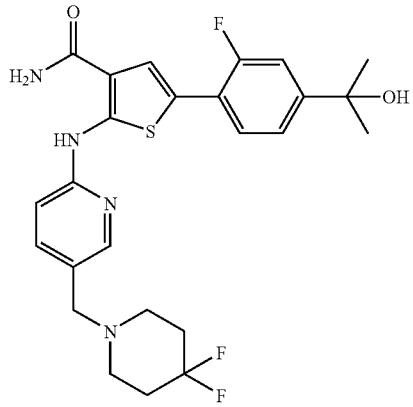 [SMILES: CC(C)(O)c1ccc(-c2cc(C(N)=O)c(Nc3ccc(CN4CCC(F)(F)CC4)cn3)s2)c(F)c1]

5-[2,6-Difluoro-4-(1-hydroxy-1-methylethyl)phenyl]-2-({5-[(4,4-difluoro piperidin-1-yl)methyl]pyridin-2-yl}amino)thiophene-3-carboxamide

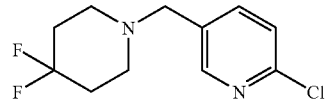 [SMILES: FC1(F)CCN(Cc2ccc(Cl)nc2)CC1]

Step 1: 2-Chloro-5-[(4,4-difluoropiperidin-1-yl)methyl]pyridine

Method B: 6-Chloronicotinaldehyde (500 mg, 3.5 mmol) and the hydrochloric acid salt of 4,4-difluoropiperidine (428 mg, 3.5 mmol) were taken up in dichloroethane (14 mL) and triethylamine (0.49 mL, 3.5 mmol). The mixture was aged for 1 hour at room temperature. Sodium triacetoxyborhydride (1.123 g, 5.30 mmol) was then added and the reaction was stirred overnight at room temperature. The mixture was then diluted with dichloromethane and quenched with saturated aqueous sodium bicarbonate. The organic layer was separated, and the aqueous layer was extracted with ethyl acetate three times. The organic layers were combined, dried over magnesium sulfate, filtered, and concentrated under reduced pressure. The resulting solid was dissolved in acetonitrile, water, and DMSO and purified via reverse phase HPLC (10-100% acetonitrile/water+0.05% TFA modifier, monitoring at 267 nm) to afford the title compound.
Calc'd for $C_{11}H_{14}ClF_2N_2$ [M+H]$^+$: 247. Found: 247.

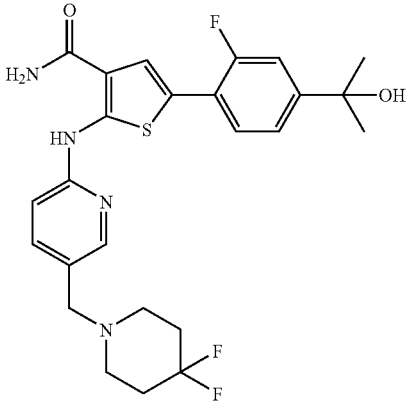 [SMILES: CC(C)(O)c1ccc(-c2cc(C(N)=O)c(Nc3ccc(CN4CCC(F)(F)CC4)cn3)s2)c(F)c1]

Step 2: 5-[2,6-Difluoro-4-(1-hydroxy-1-methylethyl) phenyl]-2-({5-[(4,4-difluoro piperidin-1-yl)methyl] pyridin-2-yl}amino)thiophene-3-carboxamide The title compound was prepared as described in Example 1 using 2-amino-5-[2-fluoro-4-(1-hydroxy-1-methylethyl) phenyl]thiophene-3-carboxamide (150 mg, 0.51 mmol) and 2-chloro-5-[(4,4-difluoropiperidin-1-yl)methyl]pyridine (126 mg, 0.51 mmol) as starting materials.
Calc'd for $C_{25}H_{28}F_3N_4O_2S$ [M+H]$^+$: 505. Found: 505.
Additional analogues were prepared using procedures similar to those described in the above examples.

TABLE 39

| Example # | Structure | Name | Method | Characterization [M + H]$^+$ |
|---|---|---|---|---|
| 410 | (structure shown) | 5-[2,6-difluoro-4-(1-hydroxy-1-methylethyl)phenyl]-2-({5-[(dimethylamino)methyl]pyridin-2-yl}amino)thiophene-3-carboxamide | B | Calc'd: 447<br>Found: 447 |

TABLE 39-continued

| Example # | Structure | Name | Method | Characterization [M + H]+ |
|---|---|---|---|---|
| 411 | 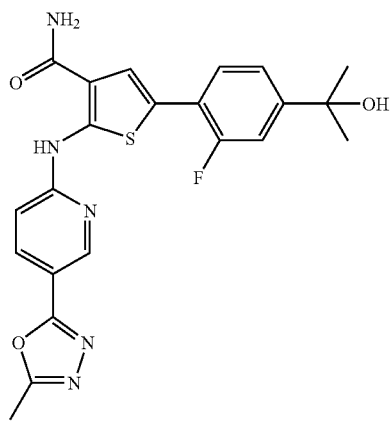 [SMILES: Cc1nnc(-c2ccc(Nc3sc(-c4ccc(C(C)(C)O)cc4F)cc3C(N)=O)nc2)o1] | 5-[2,6-Difluoro-4-(1-hydroxy-1-methylethyl)phenyl]-2-{[5-pyrrolidin-1-ylmethyl)pyridin-2-yl]amino}thiophene-3-carboxamide | A | Calc'd: 473<br>Found: 473 |

Method A: Using the procedures described in Example 408
Method B: Using the procedures described in Example 409

Example 412

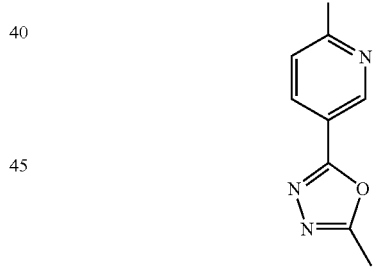

5-[2-Fluoro-4-(1-hydroxy-1-methylethyl)phenyl]-2-{[5-(5-methyl-1,3,4-oxadiazol-2-yl)pyridin-2-yl]amino}thiophene-3-carboxamide

Step 1: N'-Acetyl-6-chloronicotinohydrazide

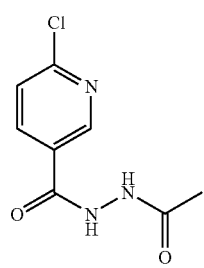

6-Chloronicotinoyl chloride (500 mg, 2.84 mmol) and acetohydrazide (232 mg, 3.12 mmol) were added to dimethylformamide (14.2 mL) at 0° C. The mixture was allowed to warm to room temperature and maintained at room temperature overnight. The reaction was then slightly concentrated in vacuo and diluted in acetonitrile. This mixture was directly purified via reverse phase HPLC (10-100% acetonitrile/water+0.05% TFA modifier). Fractions containing the desired product were lyophilized and free based using bicarbonate resin to afford the title compound.

$^1$H NMR (600 MHz, d6-DMSO): δ 10.58 (s, 1H), 10.00 (s, 1H), 8.83 (s, 1H), 8.24 (d, 1H), 7.68 (d, 1H), 1.91 (s, 3H).

Step 2: 2-Chloro-5-(5-methyl-1,3,4-oxadiazol-2-yl)pyridine

N'-Acetyl-6-chloronicotinohydrazide (95 mg, 0.45 mml) and 3,3,3-triethyl-1-(methoxycarbonyl)diazathian-3-ium-1-ide 2,2-dioxide (159 mg, 0.67 mmol) were taken up in tetrahydrofuran (4.5 mL) and heated in a microwave at 120° C. for 30 minutes. The reaction was then diluted with ethyl acetate and washed with saturated aqueous ammonium chloride, water, and brine. The organic layer was dried over magnesium sulfate, filtered, and concentrated in vacuo to afford the title compound.

$^1$H NMR (600 MHz, d6-DMSO): δ 8.96 (d, 1H), 8.37 (dd, 1H), 7.75 (d, 1H), 2.59 (s, 1H).

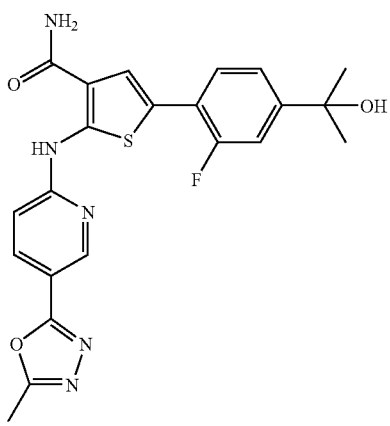 [SMILES: Cc1nnc(-c2ccc(Nc3sc(-c4ccc(C(C)(C)O)cc4F)cc3C(N)=O)nc2)o1]

Step 3: 5-[2-Fluoro-4-(1-hydroxy-1-methylethyl)phenyl]-2-{[5-(5-methyl-1,3,4-oxadiazol-2-yl)pyridin-2-yl]amino}thiophene-3-carboxamide The title compound was prepared as described in Example 1 using 2-amino-5-[2-fluoro-4-(1-hydroxy-1-methylethyl)phenyl]thiophene-3-carboxamide (90 mg, 0.31 mmol) and 2-chloro-5-(5-methyl-1,3,4-oxadiazol-2-yl)pyridine (60 mg, 0.31 mmol) as starting materials.

$^1$H NMR (600 MHz, d6-DMSO): δ 12.42 (s, 1H), 8.82 (s, 1H), 8.17 (dd, 1H), 7.96 (s, 1H), 7.90 (s, 1H), 7.61 (t, 1H), 7.53 (s, 1H), 7.35 (m, 2H), 7.27 (d, 1H), 5.18 (s, 1H), 2.57 (s, 3H), 1.43 (s, 6H). Calc'd for $C_{22}H_{21}FN_5O_3S$ [M+H]$^+$: 454. Found: 454.

Example 413

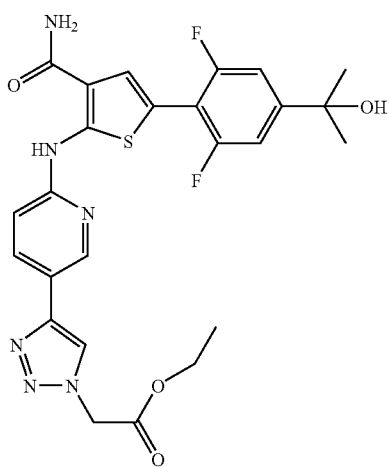 [SMILES: CCOC(=O)Cn1cc(-c2ccc(Nc3sc(-c4c(F)cc(C(C)(C)O)cc4F)cc3C(N)=O)nc2)nn1]

400

Ethyl{4-[6-({3-(aminocarbonyl)-5-[2,6-difluoro-4-(1-hydroxy-1-methylethyl)phenyl]-2-thienyl}amino)pyridin-3-yl]-1H-1,2,3-triazol-1-yl}acetate

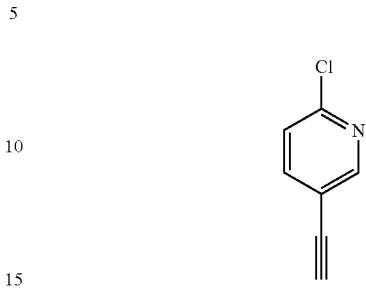

Step 1: 2-Chloro-5-ethynylpyridine

2-Chloro-5-trimethylsilanylethynyl-pyridine (1.00 g, 4.77 mmol) was taken up in THF (23.8 ml) under argon at 0° C. Tetrabutylammonium fluoride (5.72 ml of 1.0 M in THF, 5.72 mmol) was added dropwise over 5 minutes. The mixture was then allowed to warm to room temperature and maintained at room temperature for 1.5 hours. The reaction was quenched with saturated aqueous ammonium chloride, and extracted three times with ethyl acetate. The organic fractions were combined, dried over anhydrous magnesium sulfate, filtered, and concentrated. The resulting crude product was purified by silica gel chromatography (0-65% ethyl acetate/hexanes) to afford the title compound.

Calc'd for $C_7H_5ClN$ [M+H]$^+$: 138. Found: 138.

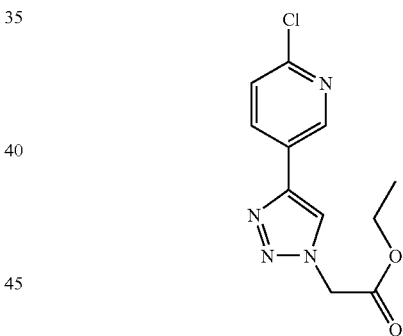

Step 2: Ethyl[4-(6-chloropyridin-3-yl)-1H-1,2,3-triazol-1-yl]acetate

2-Chloro-5-ethynylpyridine (100 mg, 0.73 mmol) and ethylazidoacetate (0.41 ml, 0.73 mmol) were taken up in water (1.5 ml) and 2-methylpropan-2-ol (1.5 ml) at room temperature. Aqueous solutions of copper(II) sulfate pentahydrate (9.08 mg, 0.036 mmol) in 1 mL of water and L-sodium ascorbate (28.8 mg, 0.145 mmol) in 1 mL of water were sequentially added, and the reaction was stirred at room temperature for 18 hours. The reaction was then quenched with saturated aqueous sodium bicarbonate, and extracted three times with ethyl acetate. The organic layers were combined, dried over anhydrous magnesium sulfate, filtered, and concentrated. The resulting crude product was purified by silica gel chromatography (0-65% ethyl acetate/hexanes) to afford the title compound.

Calc'd for $C_{11}H_{12}ClN_4O_2$ [M+H]$^+$: 267. Found: 267.

401

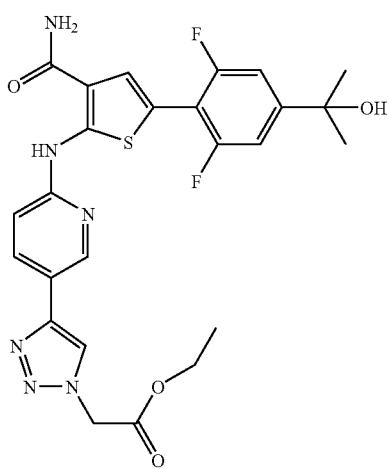 [SMILES: CCOC(=O)Cn1cc(-c2ccc(Nc3sc(-c4c(F)cc(C(C)(C)O)cc4F)cc3C(N)=O)nc2)nn1]

Step 3: Ethyl{4-[6-({3-(aminocarbonyl)-5-[2,6-difluoro-4-(1-hydroxy-1-methylethyl)phenyl]-2-thienyl}amino)pyridin-3-yl]-1H-1,2,3-triazol-1-yl}acetate The title compound was prepared as described in Example 1 using 2-amino-5-[2,6-difluoro-4-(1-hydroxy-1-methylethyl)phenyl]thiophene-3-carboxamide (150 mg, 0.48 mmol) and ethyl[4-(6-chloropyridin-3-yl)-1H-1,2,3-triazol-1-yl]acetate (128 mg, 0.48 mmol) as starting materials.

Calc'd for $C_{25}H_{25}F_2N_6O_4S$ [M+H]$^+$: 543. Found: 543.

Example 414

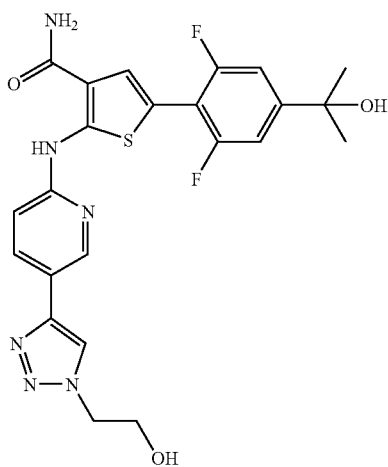 [SMILES: CC(C)(O)c1cc(F)c(-c2cc(C(N)=O)c(Nc3ccc(-c4cn(CCO)nn4)cn3)s2)c(F)c1]

402

5-[2,6-Difluoro-4-(1-hydroxy-1-methylethyl)phenyl]-2-({5-[1-(2-hydroxyethyl)-1H-1,2,3-triazol-4-yl]pyridin-2-yl}amino)thiophene-3-carboxamide

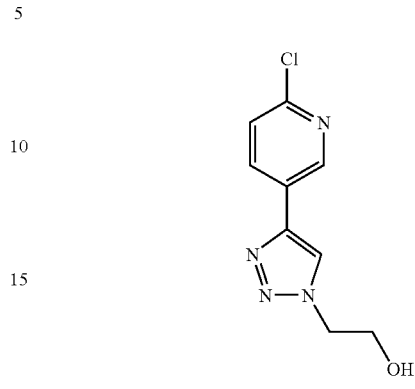

Step 1: 2-[4-(6-Chloropyridin-3-yl)-1H-1,2,3-triazol-1-yl]ethanol

Ethyl[4-(6-chloropyridin-3-yl)-1H-1,2,3-triazol-1-yl]acetate (150 mg, 0.56 mmol) (Example 413, Step 2) was taken up in THF (2.8 ml) and cooled to 0° C. Diisobutyl aluminum hydride (1.7 ml of 1.0M in hexanes, 1.7 mmol) was added dropwise over 15 minutes, and the reaction was maintained at 0° C. for 30 minutes. The reaction was allowed to warm to room temperature and maintained at room temperature for 20 hours. The mixture was then quenched with saturated aqueous potassium sodium tartrate and stirred for 2 hours. Ethyl acetate (10 mL) was added, and the mixture was stirred for 1 hour, after which product was extracted three times with ethyl acetate. The organic layers were combined, dried over anhydrous magnesium sulfate, filtered, and concentrated. The resulting crude product was purified by silica gel chromatography (0-5% methanol/ethyl acetate) to afford the title compound.

Calc'd for $C_9H_{10}ClN_4O$ [M+H]$^+$: 225. Found: 225.

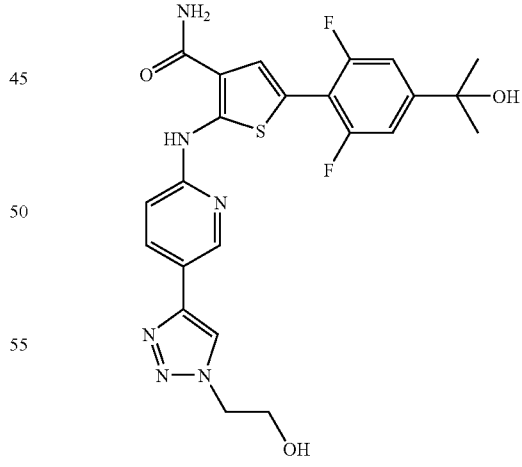

Step 2: 5-[2,6-Difluoro-4-(1-hydroxy-1-methylethyl)phenyl]-2-({5-[1-(2-hydroxyethyl)-1H-1,2,3-triazol-4-yl]pyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (100 mg, 0.32 mmol) and 2-[4-(6-chloropyridin-3-yl)-1H-1,2,3-triazol-1-yl]ethanol (72 mg, 0.32 mmol) as starting materials.

Calc'd for $C_{23}H_{23}F_2N_6O_3S$ [M+H]$^+$: 501. Found: 501.

Example 415

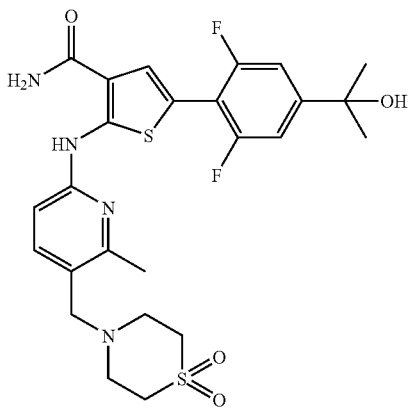 [SMILES: Cc1nc(Nc2sc(-c3c(F)cc(C(C)(C)O)cc3F)cc2C(N)=O)ccc1CN1CCS(=O)(=O)CC1]

5-[2,6-Difluoro-4-(1-hydroxy-1-methylethyl)phenyl]-2-({5-[(1,1-dioxidothiomorpholin-4-yl)methyl]-6-methylpyridin-2-yl}amino)thiophene-3-carboxamide

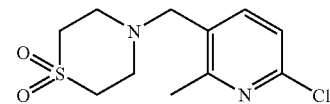 [SMILES: Cc1nc(Cl)ccc1CN1CCS(=O)(=O)CC1]

Step 1: 4-[(6-Chloro-2-methylpyridin-3-yl)methyl]thiomorpholine 1,1-dioxide

Method A: 6-Chloro-2-methylnicotinaldehyde (500 mg, 3.2 mmol) and thiomorpholine 1,1-dioxide (434 mg, 3.2 mmol) were taken up in dichloroethane (13 mL) and the reaction was aged for 1 hour. Sodium triacetoxyborhydride (1.0 g, 4.8 mmol) was then added and the mixture was stirred overnight at room temperature. The reaction was then diluted with dichloromethane and aqueous sodium bicarbonate. The organic layer was separated, and the aqueous layer was extracted with ethyl acetate (3×). The organic layers were combined, dried over magnesium sulfate, filtered, and concentrated under reduced pressure. The resulting solid was dissolved in acetonitrile, water, and DMSO and purified via reverse phase HPLC (10-100% acetonitrile/water+0.05% TFA modifier) to afford the title compound.

$^1$H NMR (600 MHz, d6-DMSO): δ 7.71 (d, 1H), 7.29 (d, 1H), 3.63 (s, 2H), 3.09 (t, 4H), 2.86 (t, 4H), 2.46 (s, 3H).

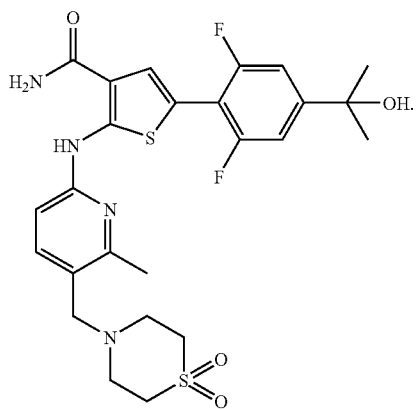

Step 2: 5-[2,6-Difluoro-4-(1-hydroxy-1-methylethyl)phenyl]-2-({5-[(1,1-dioxidothiomorpholin-4-yl)methyl]-6-methylpyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 4-[(6-chloro-2-methylpyridin-3-yl)methyl]thiomorpholine 1,1-dioxide (132 mg, 0.48 mmol) as starting materials.

$^1$H NMR (600 MHz, d6-DMSO): δ 12.03 (s, 1H), 7.86 (s, 1H), 7.75 (s, 1H), 7.57 (d, 1H), 7.34 (s, 1H), 7.25 (d, 2H), 6.88 (d, 1H), 5.29 (s, 1H), 3.58 (s, 2H), 3.09 (m, 4H), 2.86 (m, 4H), 2.51 (s, 3H), 1.43 (s, 6H). Calc'd for $C_{25}H_{29}F_2N_4O_4S_2$ [M+H]$^+$: 551. Found: 551.

Example 416

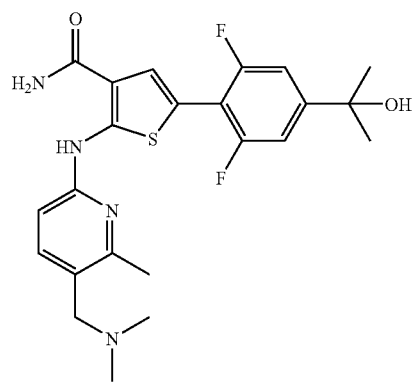 [SMILES: Cc1nc(Nc2sc(-c3c(F)cc(C(C)(C)O)cc3F)cc2C(N)=O)ccc1CN(C)C]

405

5-[2,6-Difluoro-4-(1-hydroxy-1-methylethyl)phenyl]-2-[(5-{[(2-hydroxy-1,2-dimethylpropyl)amino]methyl}-6-methylpyridin-2-yl)amino]thiophene-3-carboxamide

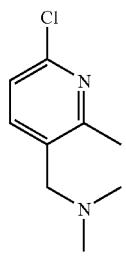

Step 1: 1-(6-Chloro-2-methylpyridin-3-yl)-N,N-dimethylmethanamine

Method B: 6-Chloro-2-methylnicotinaldehyde (200 mg, 1.29 mmol) and dimethylamine hydrochloride (105 mg, 1.29 mmol) were taken up in dichloroethane (5 ml) and triethylamine (0.18 ml, 1.29 mmol) and the reaction was aged for 1 hour. Sodium triacetoxyborohydride (410 mg, 1.93 mmol) was then added and the reaction was stirred at room temperature overnight. The mixture was then diluted with dichloromethane and saturated aqueous sodium bicarbonate. The layers were separated and the aqueous layer was extracted with ethyl acetate (3×). The organic layers were combined, dried over magnesium sulfate, filtered, and concentrated under reduced pressure. Purification via silica gel chromatography afforded the title compound.

Calc'd for $C_9H_{14}ClN_2$ [M+H]$^+$: 185. Found: 185.

406

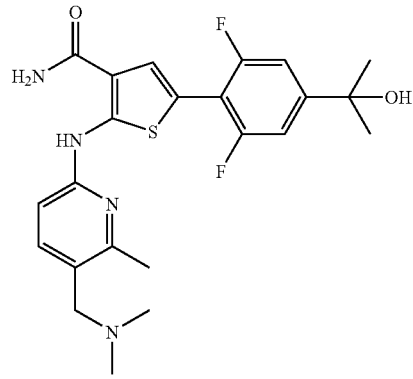 [SMILES: Cc1nc(Nc2sc(-c3c(F)cc(C(C)(C)O)cc3F)cc2C(N)=O)ccc1CN(C)C]

Step 2: 5-[2,6-Difluoro-4-(1-hydroxy-1-methylethyl)phenyl]-2-[(5-{[(2-hydroxy-1,2-dimethylpropyl)amino]methyl}-6-methylpyridin-2-yl)amino]thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 1-(6-chloro-2-methylpyridin-3-yl)-N,N-dimethylmethanamine (89 mg, 0.48 mmol) as starting materials.

Calc'd for $C_{25}H_{27}F_2N_4O_4S$ [M+H]$^+$: 461. Found: 461.

Additional examples were prepared using procedures similar to those described in the above examples and are illustrated in the following table.

TABLE 40

| Example # | Structure | Name | Method | Characterization [M + H]$^+$ |
|---|---|---|---|---|
| 417 | 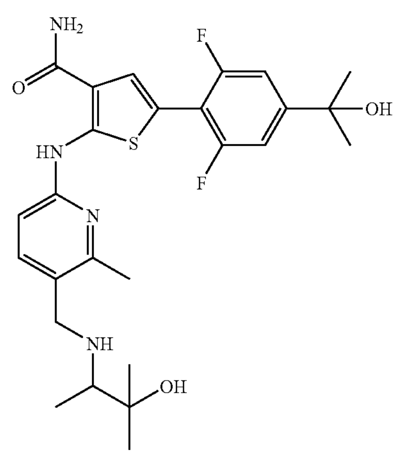 [SMILES: Cc1nc(Nc2sc(-c3c(F)cc(C(C)(C)O)cc3F)cc2C(N)=O)ccc1CNC(C)C(C)(C)O] | 5-[2,6-difluoro-4-(1-hydroxy-1-methylethyl)phenyl]-2-[(5-{[(2-hydroxy-1,2-dimethylpropyl)amino]methyl}-6-methylpyridin-2-yl)amino]thiophene-3-carboxamide | A | Calc'd 519, found 519 |

TABLE 40-continued

| Example # | Structure | Name | Method | Characterization [M + H]⁺ |
|---|---|---|---|---|
| 418 | 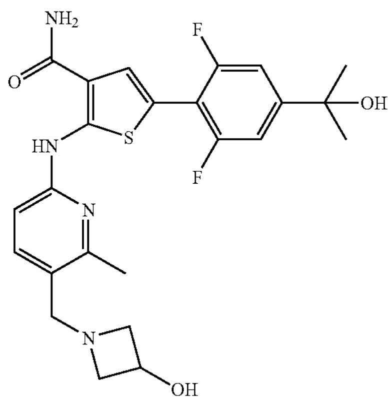 [SMILES: Cc1nc(Nc2sc(-c3c(F)cc(C(C)(C)O)cc3F)cc2C(N)=O)ccc1CN1CC(O)C1] | 5-[2,6-difluoro-4-(1-hydroxy-1-methylethyl)phenyl]-2-({5-[(3-hydroxyazetidin-1-yl)methyl]-6-methylpyridin-2-yl}amino)thiophene-3-carboxamide | B | Calc'd 489, found 489 |
| 419 | 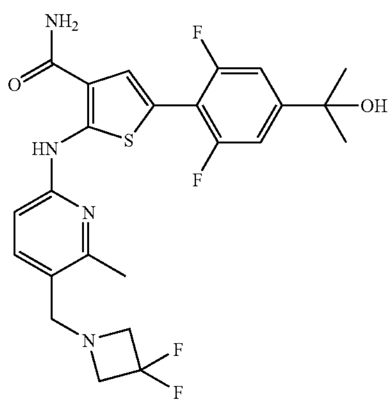 [SMILES: Cc1nc(Nc2sc(-c3c(F)cc(C(C)(C)O)cc3F)cc2C(N)=O)ccc1CN1CC(F)(F)C1] | 2-({5-[(3,3-difluoroazetidin-1-yl)methyl]-6-methylpyridin-2-yl}amino)-5-[2,6-difluoro-4-(1-hydroxy-1-methylethyl)phenyl]thiophene-3-carboxamide | B | Calc'd 509, found 509 |
| 420 | 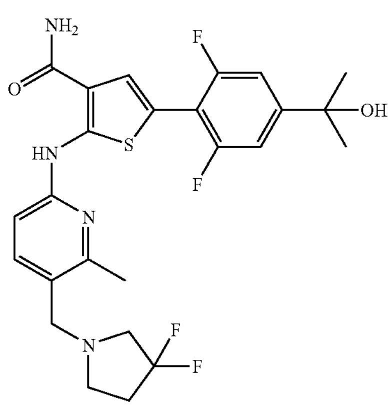 [SMILES: Cc1nc(Nc2sc(-c3c(F)cc(C(C)(C)O)cc3F)cc2C(N)=O)ccc1CN1CCC(F)(F)C1] | 5-[2,6-difluoro-4-(1-hydroxy-1-methylethyl)phenyl]-2-({5-[(3,3-difluoropyrrolidin-1-yl)methyl]-6-methylpyridin-2-yl}amino)thiophene-3-carboxamide | B | Calc'd 523, found 523 |

Method A: Using procedures described in Example 415
Method B: Using procedures described in Example 416

Example 421

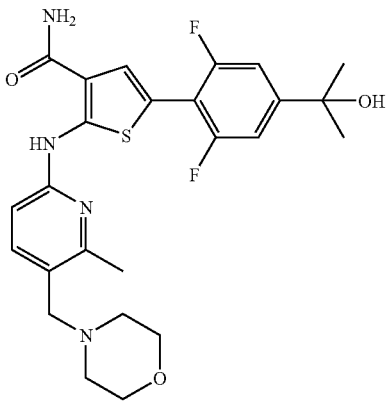 [SMILES: Cc1nc(Nc2sc(-c3c(F)cc(C(C)(C)O)cc3F)cc2C(N)=O)ccc1CN1CCOCC1]

5-[2,6-Difluoro-4-(1-hydroxy-1-methylethyl)phenyl]-2-{[6-methyl-5-(morpholin-4-ylmethyl)pyridin-2-yl]amino}thiophene-3-carboxamide

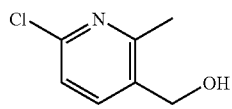

Step 1: (6-Chloro-2-methylpyridin-3-yl)methanol

Sodium borohydride (0.73 g, 19.28 mmol) was added to a solution of 6-chloro-2-methylnicotinaldehyde (1.5 g, 9.64 mmol) in methanol (38.6 mL) at room temperature. The mixture was stirred for 2 hours, then quenched with water and saturated aqueous sodium bicarbonate, and extracted three times with ethyl acetate. The organic layers were combined, dried over magnesium sulfate, filtered, and concentrated under reduced pressure to afford the title compound.

Calc'd for $C_7H_9ClNO$ [M+H]$^+$: 158. Found: 158.

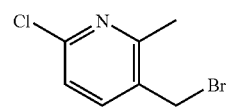

Step 2: 3-(Bromomethyl)-6-chloro-2-methylpyridine (6-Chloro-2-methylpyridin-3-yl)methanol (500 mg, 3.17 mmol) was taken up in dichloromethane (9.1 mL) and cooled to 0° C. Phosphorus tribromide (0.6 mL, 6.35 mmol) was added dropwise, and the reaction was allowed to warm to room temperature overnight. The reaction was then quenched by slow addition of saturated aqueous sodium bicarbonate, followed by solid sodium carbonate to obtain pH>7. The mixture was extracted with dichloromethane two times. The combined organic layers were dried over magnesium sulfate, filtered, and concentrated under reduced pressure. Purification was performed via silica gel chromatography (0-40% ethyl acetate in hexane) to yield the title compound.

Calc'd for $C_7H_8BrClN$ [M+H]$^+$: 220. Found: 220.

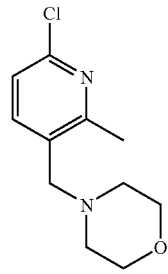

Step 3: 4-[(6-Chloro-2-methylpyridin-3-yl)methyl]morpholine 3-(Bromomethyl)-6-chloro-2-methylpyridine (500 mg, 2.27 mmol) was taken up in $CH_2Cl_2$ (5.0 mL) and morpholine (257 µL, 2.95 mmol) and DIEA (594 µL, 3.40 mmol) were added. After stirring at room temperature overnight, the reaction was diluted with water and extracted with $CH_2Cl_2$ (2×). The combined organic layers were dried over MgSO$_4$, filtered, and evaporated. Flash chromatography (0-10% MeOH (w/2 M NH$_3$)/$CH_2Cl_2$) provided the title compound as a colorless oil.

Calc'd for $C_{11}H_{16}ClN_2O$ [M+H]$^+$ 227. found 227.

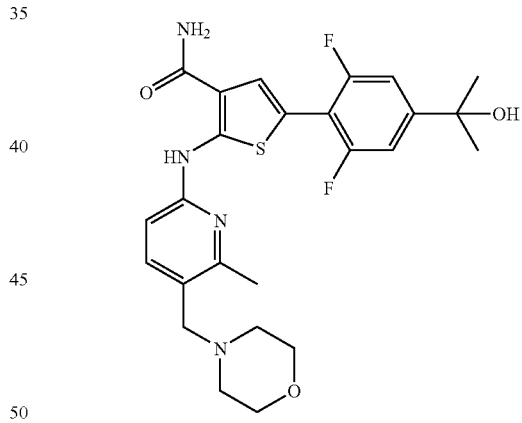

Step 4: 5-[2,6-Difluoro-4-(1-hydroxy-1-methylethyl)phenyl]-2-{[6-methyl-5-(morpholin-4-ylmethyl)pyridin-2-yl]amino}thiophene-3-carboxamide The title compound was synthesized from 4-[(6-chloro-2-methylpyridin-3-yl)methyl]morpholine (90 mg, 0.40 mmol) and 2-amino-5-[2,6-difluoro-4-(1-hydroxy-1-methylethyl)phenyl]thiophene-3-carboxamide (130 mg, 0.42 mmol) according to the procedure described in Example 1.

Calc'd for $C_{25}H_{29}F_2N_4O_3S$ [M+H]$^+$ 503. found 503.

An additional example was prepared by procedures similar to those described above and is illustrated in the following table.

TABLE 41

| Example # | Structure | Name | Characterization |
|---|---|---|---|
| 422 | 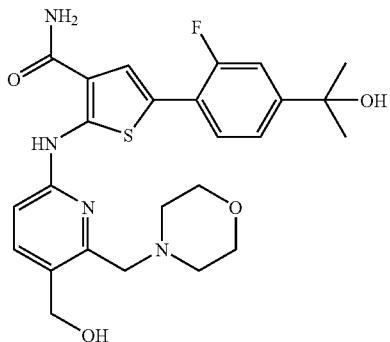 | 5-[2,6-difluoro-4-(1-hydroxy-1-methylethyl)phenyl-2-{[5-(morpholin-4-ylmethyl)pyridin-2-yl]amino}thiophene-3-carboxamide | Calc'd [M + H]⁺: 489, found 489 |

Example 423

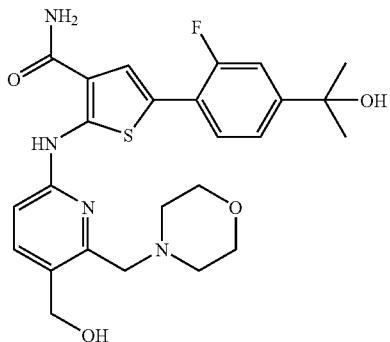 [SMILES: CC(C)(O)c1ccc(-c2cc(C(N)=O)c(Nc3ccc(CO)c(CN4CCOCC4)n3)s2)c(F)c1]

5-[2-Fluoro-4-(1-hydroxy-1-methylethyl)phenyl]-2-{[5-(hydroxymethyl)-6-(morpholin-4-ylmethyl)pyridin-2-yl]amino}thiophene-3-carboxamide

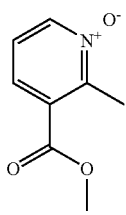

Step 1. Methyl 2-methylpyridine-3-carboxylate 1-oxide

Methyl 2-methylpyridine-3-carboxylate (10 g, 66.2 mmol) was taken up in DCM (140 mL) and mCPBA (16.31 g, 72.8 mmol) was added. The resulting mixture was allowed to react at room temperature overnight and then purified directly by silica gel chromatography (0-20% MeOH-EtOAc) to afford the title compound as a beige solid.

$^1$H NMR (600 MHz, CDCl$_3$): δ 8.56 (dd, J=4.8 and 1.8 Hz, 1H), 8.14 (dd, J=8.4 and 1.8 Hz, 1H), 7.16 (dd, J=8.4 and 4.8 Hz, 1H), 3.87 (s, 3H), 2.79 (s, 3H).

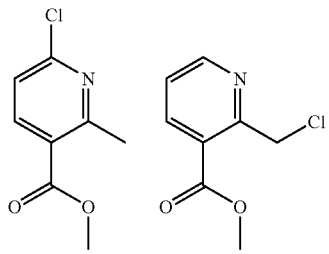

Step 2. Methyl 6-chloro-2-methylpyridine-3-carboxylate and methyl 2-(chloromethyl)pyridine-3-carboxylate Methyl 2-methylpyridine-3-carboxylate 1-oxide (2.93 g, 17.53 mmol) was taken up in POCl$_3$ (17 mL, 182 mmol) and heated to reflux for 3 hours. The mixture was then cooled to room temperature and poured into ice-water. The resulting dark solution was neutralised with solid Na$_2$CO$_3$ and the products extracted into EtOAc (×3). The combined organic extracts were washed with brine, dried over MgSO$_4$, filtered, and concentrated in vacuo. Purification of the residue by silica gel chromatography (2-30% EtOAc-hexanes) gave methyl 6-chloro-2-methylpyridine-3-carboxylate as a pale yellow oil (A) and methyl 2-(chloromethyl)pyridine-3-carboxylate (B) as an orange oil.

A—$^1$H NMR (600 MHz, CDCl$_3$): δ 8.13 (d, J=8.4 Hz, 1H), 7.21 (d, J=8.4 Hz, 1H), 3.89 (s, 3H), 2.79 (s, 3H).

B—$^1$H NMR (600 MHz, CDCl$_3$): δ 8.70 (dd, J=5.4 and 1.8 Hz, 1H), 8.26 (dd, J=7.8 and 1.8 Hz, 1H), 7.34 (dd, J=7.8 and 5.4 Hz, 1H), 3.87 (s, 3H), 2.79 (s, 3H).

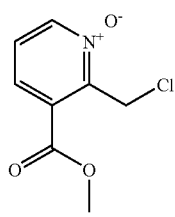

Step 3. Methyl 2-(chloromethyl)pyridine-3-carboxylate 1-oxide

Methyl 2-(chloromethyl)pyridine-3-carboxylate (4.45 g, 23.98 mmol) was taken up in DCM (50 mL) and mCPBA (5.91 g, 26.4 mmol) was added. The resulting solution was allowed to react at room temperature overnight and then purified directly by silica gel chromatography (0-20% MeOH-EtOAc) to afford the title compound as a white solid.
$^1$H NMR (600 MHz, CDCl$_3$): δ 8.22 (d, J=8.4 Hz, 1H), 7.37 (d, J=8.4 Hz, 1H), 5.03 (s, 2H), 3.95 (s, 3H).

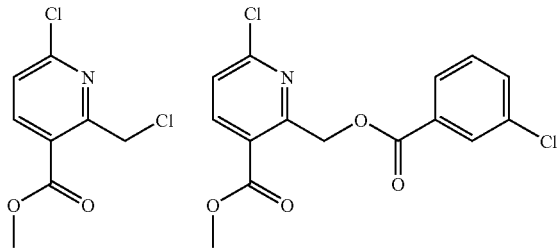

Step 4. Methyl 6-chloro-2-(chloromethyl)pyridine-3-carboxylate and methyl 6-chloro-2-({[(3-chlorophenyl)carbonyl]oxy}methyl)pyridine-3-carboxylate Methyl 2-(chloromethyl)pyridine-3-carboxylate 1-oxide (17.85 g, 89 mmol) was taken up in POCl$_3$ (80 mL, 858 mmol) and heated to reflux for 3 hours. The reaction was then cooled to room temperature and poured into ice-water. The resulting beige precipitate was collected by filtration and purified by silica gel chromatography (2-20% EtOAc-hexanes) to give methyl 6-chloro-2-(chloromethyl)pyridine-3-carboxylate (A) as a white solid and methyl 6-chloro-2-({[(3-chlorophenyl)carbonyl]oxy}methyl)pyridine-3-carboxylate (B) as a yellow solid.
A—Calc'd for C$_8$H$_8$Cl$_2$NO$_2$ [M+H]$^+$: 220, 222. Found: 220, 222.
B—Calc'd for C$_{15}$H$_{12}$Cl$_2$NO$_4$ [M+H]$^+$: 340, 342. Found: 340, 342.

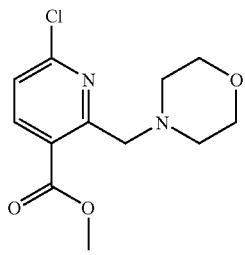 [SMILES: COC(=O)c1ccc(Cl)nc1CN1CCOCC1]

Step 5. Methyl 6-chloro-2-(morpholin-4-ylmethyl)pyridine-3-carboxylate

Methyl 6-chloro-2-(chloromethyl)pyridine-3-carboxylate (1.5 g, 6.82 mmol) and potassium carbonate (1.13 g, 8.18 mmol) were taken up in DMF (13 mL) and morpholine (0.59 mL, 6.82 mmol) was added. The mixture was allowed to react at room temperature overnight, at which time water was added and the products extracted into EtOAc (2×). The combined organic extracts were washed with brine, dried over MgSO$_4$, filtered, and concentrated in vacuo to give the title compound as an orange oil.
Calc'd for C$_{12}$H$_{16}$ClN$_2$O$_3$ [M+H]$^+$: 271, 273. Found: 271, 273.

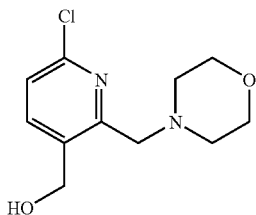

Step 6. [6-Chloro-2-(morpholin-4-ylmethyl)pyridin-3-yl]methanol

Methyl 6-chloro-2-(morpholin-4-ylmethyl)pyridine-3-carboxylate (0.5 g, 1.847 mmol) was take up in THF (9 mL) and cooled to 0° C. LiAlH$_4$, 2 M in THF (1.847 mL, 3.69 mmol) was added dropwise and the resulting mixture maintained at 0° C. for 5 hours. Saturated aqueous NH$_4$Cl was added and the products extracted into EtOAc (3×). The combined organic extracts were washed with brine, dried over MgSO$_4$, filtered, and concentrated in vacuo. Purification of the residue by silica gel chromatography (12-100% EtOAc-hexanes followed by 0-10% MeOH-EtOAc) gave the title compound as a pale yellow oil.
Calc'd for C$_{11}$H$_{16}$ClN$_2$O$_2$ [M+H]$^+$: 243, 245. Found: 243, 245.

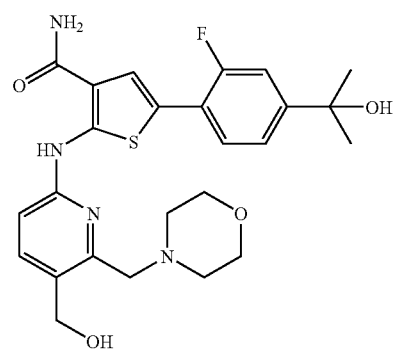 [SMILES: CC(C)(O)c1ccc(-c2cc(C(N)=O)c(Nc3ccc(CO)c(CN4CCOCC4)n3)s2)c(F)c1]

Step 7. 5-[2-Fluoro-4-(1-hydroxy-1-methylethyl)phenyl]-2-{[5-(hydroxymethyl)-6-(morpholin-4-ylmethyl)pyridin-2-yl]amino}thiophene-3-carboxamide The title compound was prepared according to the procedure described in Example 1 using [6-chloro-2-(morpholin-4-ylmethyl)pyridin-3-yl]methanol (66.0 mg, 0.27 mmol) and 2-amino-5-[2-fluoro-4-(1-hydroxy-1-methylethyl)phenyl]thiophene-3-carboxamide (80 mg, 0.27 mmol) as the starting materials.
Calc'd for C$_{25}$H$_{30}$FN$_4$O$_4$S [M+H]$^+$: 501. Found: 501.

Example 424

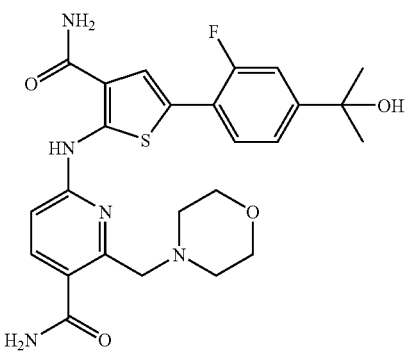 [SMILES: CC(C)(O)c1ccc(-c2cc(C(N)=O)c(Nc3ccc(C(N)=O)c(CN4CCOCC4)n3)s2)c(F)c1]

6-({3-(Aminocarbonyl)-5-[2-fluoro-4-(1-hydroxy-1-methylethyl)phenyl]-2-thienyl}amino)-2-(morpholin-4-ylmethyl)nicotinamide

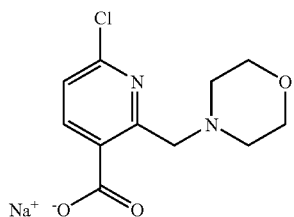

Step 1. 6-Chloro-2-(morpholin-4-ylmethyl)pyridine-3-carboxamide

Methyl 6-chloro-2-(morpholin-4-ylmethyl)pyridine-3-carboxylate (Example 423, Step 5) (1 g, 3.69 mmol) was taken up in THF (8 mL) and 2 N sodium hydroxide (1.85 mL, 3.69 mmol) was added. The mixture was stirred at room temperature for 4 hours and then the solvent was removed in vacuo to afford the title compound as a yellow solid.

Calc'd for $C_{11}H_{14}ClN_2O_3$ [M+H]$^+$: 257, 259. Found: 257, 259.

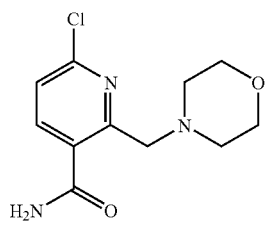 [SMILES: NC(=O)c1ccc(Cl)nc1CN1CCOCC1]

Step 2. 6-Chloro-2-(morpholin-4-ylmethyl)pyridine-3-carboxamide

Sodium 6-chloro-2-(morpholin-4-ylmethyl)pyridine-3-carboxylate (0.3 g, 1.077 mmol), EDC (0.619 g, 3.23 mmol), HOBt (0.495 g, 3.23 mmol), ammonium chloride (0.173 g, 3.23 mmol) and DIPEA (1.128 mL, 6.46 mmol) were stirred in DMF (10 mL) at room temperature overnight. Additional EDC (0.619 g, 3.23 mmol), HOBt (0.495 g, 3.23 mmol), ammonium chloride (0.173 g, 3.23 mmol) and DIPEA (1.128 mL, 6.46 mmol) were then added and stirring continued at room temperature for 24 hours. Saturated aqueous NaHCO$_3$ was added and the products were extracted into EtOAc (2×). The combined organic extracts were washed with brine, dried over MgSO$_4$, filtered, and concentrated in vacuo to give the title compound as a yellow solid.

Calc'd for $C_{11}H_{15}ClN_3O_2$ [M+H]$^+$: 256, 258. Found: 256, 258.

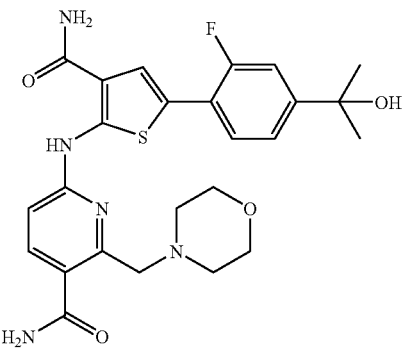

Step 3. 6-({3-(Aminocarbonyl)-5-[2-fluoro-4-(1-hydroxy-1-methylethyl)phenyl]-2-thienyl}amino)-2-(morpholin-4-ylmethyl)nicotinamide The title compound was prepared according to the general procedure in Example 1 using 6-chloro-2-(morpholin-4-ylmethyl)pyridine-3-carboxamide (87 mg, 0.34 mmol) and 2-amino-5-[2-fluoro-4-(1-hydroxy-1-methylethyl)phenyl]thiophene-3-carboxamide (100 mg, 0.34 mmol) as the starting materials.

Calc'd for $C_{25}H_{29}FN_5O_4S$ [M+H]$^+$: 514. Found: 514.

Example 425

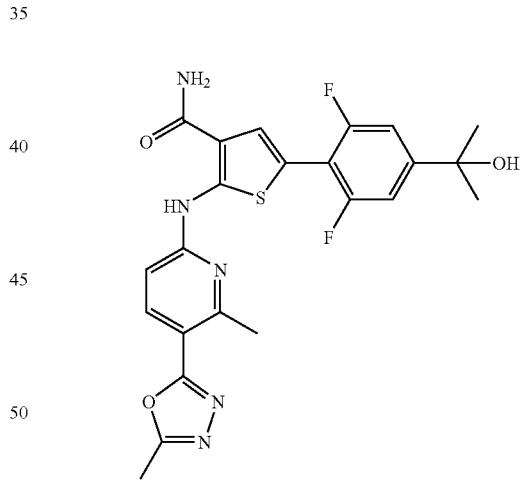

5-[2,6-Difluoro-4-(1-hydroxy-1-methylethyl)phenyl]-2-{[6-methyl-5-(5-methyl-1,3,4-oxadiazol-2-yl)pyridin-2-yl]amino}thiophene-3-carboxamide

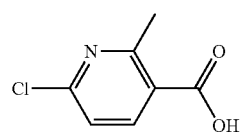

Step 1: 6-Chloro-2-methylnicotinic acid

Methyl 6-chloro-2-methylnicotinate (Example 423, Step 2) (900 mg, 4.85 mmol) was taken up in 2-methylpropan-2-ol (48.5 ml) and methanol (48.5 ml) and aqueous 1 molar potassium hydroxide (24.2 ml, 24.2 mmol) was added. The resulting slurry was heated at 60° C. for 4 hours, cooled to room temperature, and hydrochloric acid (1 M in water, 24.2 mL, 24.2 mmol) was added dropwise. The solution was then concentrated under reduced pressure until to afford a white solid, which was taken up in methanol and concentrated under reduced pressure. Water and ethyl acetate were added and the layers were separated. The aqueous layer was extracted with ethyl acetate three times. The combined organic layers were concentrated under reduced pressure to afford the title compound.

$^1$H NMR (600 MHz, d6-DMSO): δ (8.18 (d, 1H), 7.45 (d, 1H), 2.68 (s, 3H).

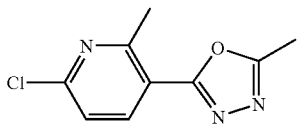

Step 2: 6-Chloro-2-methyl-3-(5-methyl-1,3,4-oxadiazol-2-yl)pyridine

6-Chloro-2-methylnicotinic acid (200 mg, 1.2 mmol), acetohydrazide (95 mg, 1.3 mmol), solid supported triphenylphosphine on polystyrene (1.88 mmol/g loading, 1.94 g, 3.5 mmol) were placed in a microwave vial. Dry acetonitrile (16.7 ml) followed by trichloroacetonitrile (0.23 ml, 2.33 mmol) were added and the vial was heated in a microwave at 150° C. for 20 minutes. It was allowed to cool to room temperature, filtered, and the filter cake was washed with acetonitrile. The filtrate was concentrated under reduced pressure to afford the title compound.

$^1$H NMR (600 MHz, d6-DMSO): δ 8.25 (d, 1H), 7.57 (d, 1H), 2.78 (s, 3H).

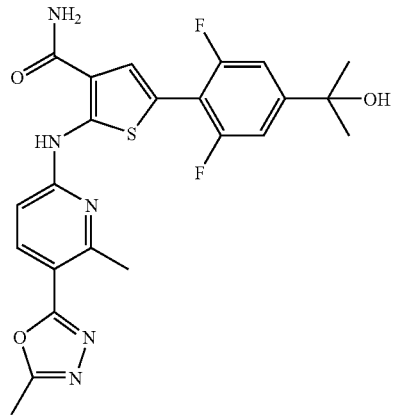 [SMILES: Cc1nnc(-c2ccc(Nc3sc(-c4c(F)cc(C(C)(C)O)cc4F)cc3C(N)=O)nc2C)o1]

Step 3: 5-[2,6-Difluoro-4-(1-hydroxy-1-methylethyl)phenyl]-2-{[6-methyl-5-(5-methyl-1,3,4-oxadiazol-2-yl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 6-chloro-2-methyl-3-(5-methyl-1,3,4-oxadiazol-2-yl)pyridine (101 mg, 0.48 mmol) as starting materials.

$^1$H NMR (600 MHz, d6-DMSO): δ 12.4 (s, 1H), 8.10 (d, 1H), 7.99 (s, 1H), 7.81 (s, 1H), 7.50 (s, 1H), 7.28 (, 2H), 7.13 (d, 1H), 5.31 (s, 1H), 2.82 (s, 3H), 2.56 (s, 3H), 1.43 (s, 6H). Calc'd for $C_{23}H_{22}F_2N_5O_3S$ [M+H]$^+$: 486. Found: 486.

Additional examples were prepared using procedures similar to those described above and are illustrated in the following table.

TABLE 42

| Example # | Structure | Name | Characterization [M + H]$^+$ |
|---|---|---|---|
| 426 | 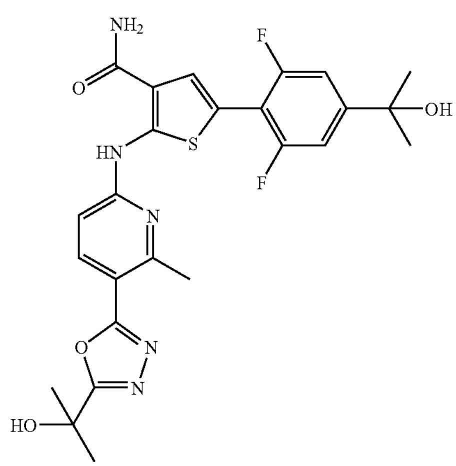 [SMILES: Cc1nc(Nc2sc(-c3c(F)cc(C(C)(C)O)cc3F)cc2C(N)=O)ccc1-c1nnc(C(C)(C)O)o1] | 5-[2,6-difluoro-4-(1-hydroxy-1-methylethyl)phenyl]-2-({5-[5-(1-hydroxy-1-methylethyl)-1,3,4-oxadiazol-2-yl]-6-methylpyridin-2-yl}amino)thiophene-3-carboxamide | Calc'd 530, found 530 |

TABLE 42-continued

| Example # | Structure | Name | Characterization [M + H]+ |
|---|---|---|---|
| 427 | 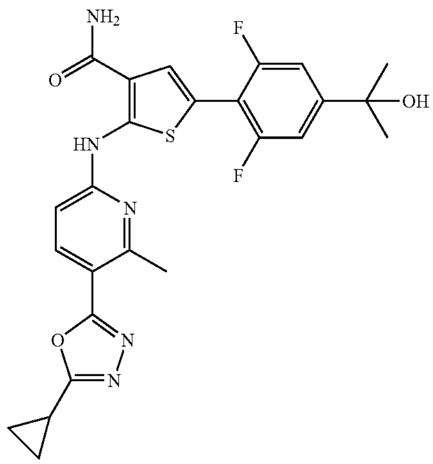 [SMILES: Cc1nc(Nc2sc(-c3c(F)cc(C(C)(C)O)cc3F)cc2C(N)=O)ccc1-c1nnc(C2CC2)o1] | 2-{[5-(5-cyclopropyl-1,3,4-oxadiazol-2-yl)-6-methylpyridin-2-yl]amino-5-[2,6-difluoro-4-(1-hydroxy-1-methylethyl)phenyl]thiophene-3-carboxamide | Calc'd 512, found 512 |
| 428 | 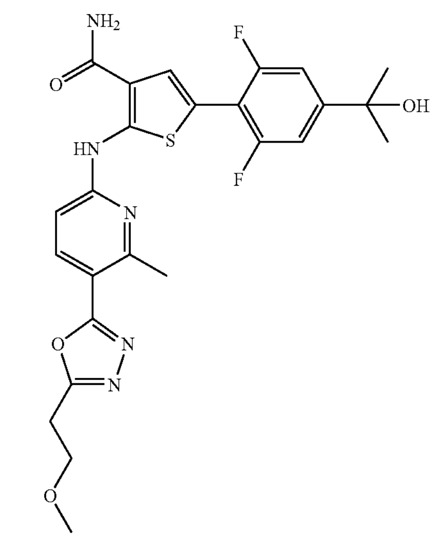 [SMILES: COCCc1nnc(-c2ccc(Nc3sc(-c4c(F)cc(C(C)(C)O)cc4F)cc3C(N)=O)nc2C)o1] | 5-[2,6-Difluoro-4-(1-hydroxy-1-methylethyl)phenyl]-2-({5-[5-(2-methoxyethyl)-1,3,4-oxadiazol-5-yl]-6-methylpyridin-2-yl}amino)thiophene-3-carboxamide | Calc'd 530, found 530 |
| 429 | 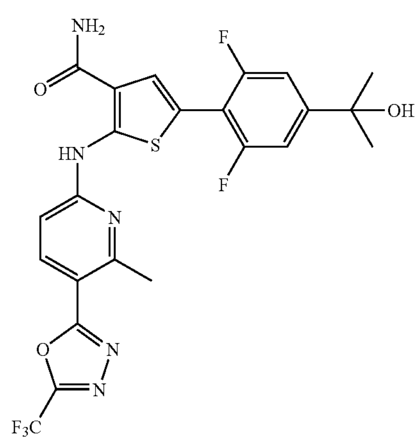 [SMILES: Cc1nc(Nc2sc(-c3c(F)cc(C(C)(C)O)cc3F)cc2C(N)=O)ccc1-c1nnc(C(F)(F)F)o1] | 5-[2,6-difluoro-4-(1-hydroxy-1-methylethyl)phenyl]-2-({6-methyl-5-[5-(trifluoromethyl)-1,3,4-oxadiazol-2-yl]pyridin-2-yl}amino)thiophene-3-carboxamide | Calc'd 540, found 540 |

Example 430

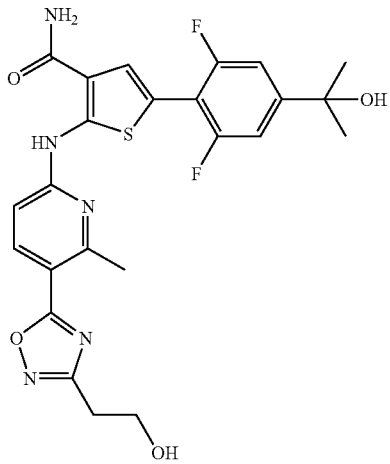 [SMILES: Cc1nc(Nc2sc(-c3c(F)cc(C(C)(C)O)cc3F)cc2C(N)=O)ccc1-c1nc(CCO)no1]

5-[2,6-Difluoro-4-(1-hydroxy-1-methylethyl)phenyl]-2-({5-[3-(2-hydroxyethyl)-1,2,4-oxadiazol-5-yl]-6-methylpyridin-2-yl}amino)thiophene-3-carboxamide

Step 1: 3-{[tert-Butyl(diphenyl)silyl]oxy}propanenitrile

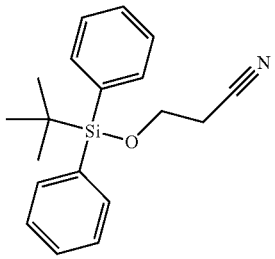 [SMILES: CC(C)(C)[Si](OCCC#N)(c1ccccc1)c1ccccc1]

To a solution of 3-hydroxypropanenitrile (1 g, 14.1 mmol), dimethylaminopyridine (0.34 g, 2.8 mmol), and triethylamine (2.9 ml, 21 mmol) in tetrahydrofuran (38 ml) was added tert-butyl(chloro)diphenylsilane (4.3 ml, 16.9 mmol). The mixture was stirred at room temperature overnight. The resulting white slurry was quenched with saturated aqueous ammonium chloride and extracted with ethyl acetate. The combined organics were dried over magnesium sulfate, filtered, and concentrated in vacuo. The resulting residue was purified via flash chromatography (silica, 0-17% ethyl acetate in hexane) to afford the title compound. $^1$H NMR (600 MHz, d6-DMSO): δ 7.65 (dd, 4H), 7.43 (dt, 2H), 7.40 (d, 4H), 3.82 (t, 2H), 2.52 (t, 2H), 1.10 (s, 9H).

Step 2: (1Z)-3-{[tert-Butyl(diphenyl)silyl]oxy}-N'-hydroxypropanimidamide

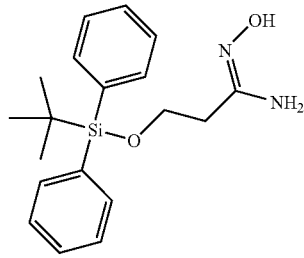 [SMILES: CC(C)(C)[Si](OCC/C(N)=N/O)(c1ccccc1)c1ccccc1]

To a solution of 3-{[tert-butyl(diphenyl)silyl]oxy}propanenitrile (4.4 g, 14.2 mmol) in methanol (40 ml) was added hydroxylamine hydrochloride (8.9 g, 128 mmol) and sodium bicarbonate (11.9 g, 142 mmol). The mixture was heated at reflux for 48 hours. The mixture was then cooled to room temperature, the solvent was evaporated, ice water was added, and the resulting solution was extracted with ethyl acetate (2×). The combined organic layers were dried over magnesium sulfate, filtered, and concentrated in vacuo. The resulting residue was purified via silica gel chromatography (50-100% ethyl acetate in hexanes) to afford the title compound.

Calc'd for $C_{19}H_{27}N_2O_2Si$ [M+H]$^+$: 343. Found: 343

Step 3: 3-[3-(2-{[tert-Butyl(diphenyl)silyl]oxy}ethyl)-1,2,4-oxadiazol-5-yl]-6-chloro-2-methylpyridine

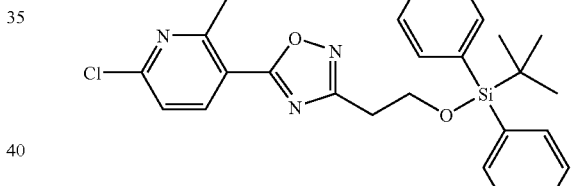

6-Chloro-2-methylnicotinic acid (Example 425, Step 1) (150 mg, 0.87 mmol) trichloroacetonitrile (0.13 ml, 1.31 mmol) and solid supported triphenylphosphine on polystyrene (1.88 mmol/g, 1.5 g, 2.62 mmol) were taken up in tetrahydrofuran (10.9 ml). The mixture was heated in the microwave at 100° C. for 5 minutes and cooled to room temperature. (1Z)-3-{[tert-Butyl(diphenyl)silyl]oxy}-N'-hydroxypropanimidamide (329 mg, 0.96 mmol), THF (5 mL), and N-ethyl-N-isopropylpropan-2-amine (0.15 ml, 0.87 mmol) were added. The resulting mixture was heated in the microwave at 150° C. for 15 minutes, cooled to room temperature and filtered. The filtrate was concentrated under reduced pressure and purified via silica gel chromatography (0-35% ethyl acetate in hexane) to afford the title compound.

$^1$H NMR (600 MHz, d6-DMSO): δ 8.38 (d, 1H), 7.62 (d, 1H), 7.54 (m, 4H), 7.40 (m, 2H), 7.37 (m, 4H), 4.06 (t, 2H), 3.06 (t, 2H), 0.93 (s, 3H), 0.90 (s, 9H).

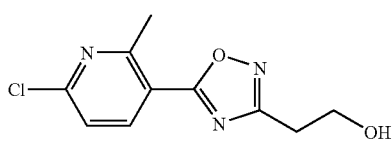 [SMILES: Cc1nc(Cl)ccc1-c1nc(CCO)no1]

Step 4: 2-[5-(6-Chloro-2-methylpyridin-3-yl)-1,2,4-oxadiazol-3-yl]ethanol

3-[3-(2-{[tert-Butyl(diphenyl)silyl]oxy}ethyl)-1,2,4-oxadiazol-5-yl]-6-chloro-2-methylpyridine (210 mg, 0.44 mmol) was taken up in tetrahydrofuran (2.2 ml) and tetrabutylammonium fluoride (0.44 ml of 1.0 M in THF, 0.44 mmol) was added. The solution was heated to 50° C. for 2 hours, cooled to room temperature, concentrated under reduced pressure, and directly purified via silica gel chromatography (0-100% ethyl acetate in hexane) to afford the title compound.

$^1$H NMR (600 MHz, d6-DMSO): δ 8.41 (d, 1H), 7.60 (d, 1H), 4.83 (t, 1H), 3.80 (q, 2H), 2.92 (t, 2H), 2.81 (s, 3H).

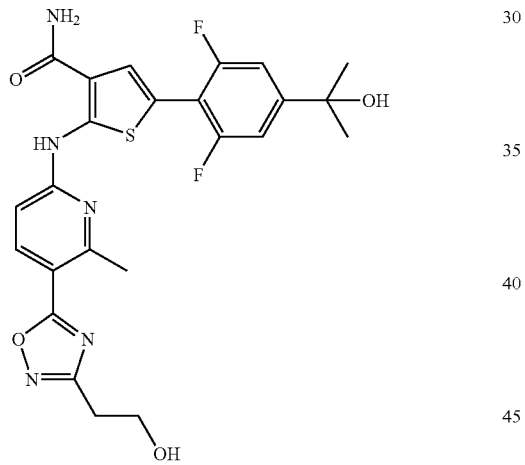

Step 5: 5-[2,6-Difluoro-4-(1-hydroxy-1-methylethyl)phenyl]-2-({5-[3-(2-hydroxyethyl)-1,2,4-oxadiazol-5-yl]-6-methylpyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (51 mg, 0.17 mmol) and 2-[5-(6-chloro-2-methylpyridin-3-yl)-1,2,4-oxadiazol-3-yl]ethanol (40 mg, 0.17 mmol) as starting materials.

$^1$H NMR (600 MHz, d6-DMSI): δ 12.48 (s, 1H), 8.26 (d, 1H), 8.01 (s, 1H), 7.82 (s, 1H), 7.53 (s, 1H), 7.28 (d, 2H), 7.15 (d, 1H), 5.31 (s, 1H), 4.82 (t, 1H), 3.80 (q, 2H), 2.90 (t, 2H), 2.86 (s, 3H), 1.43 (s, 6H). Calc'd for $C_{24}H_{24}F_2N_5O_4S$ [M+H]$^+$: 516. Found: 516.

Example 431

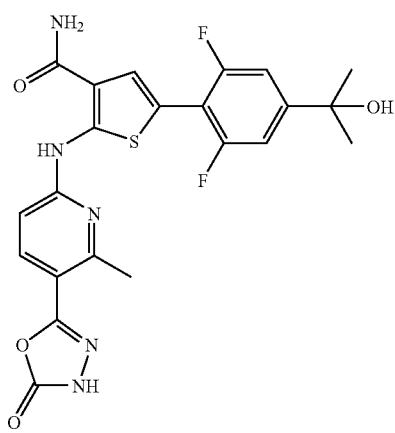 [SMILES: Cc1nc(Nc2sc(-c3c(F)cc(C(C)(C)O)cc3F)cc2C(N)=O)ccc1-c1n[nH]c(=O)o1]

5-[2,6-Difluoro-4-(1-hydroxy-1-methylethyl)phenyl]-2-{[6-methyl-5-(5-oxo-4,5-dihydro-1,3,4-oxadiazol-2-yl)pyridin-2-yl]amino}thiophene-3-carboxamide

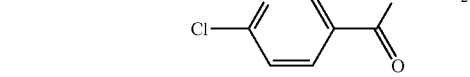

Step 1: 6-Chloro-2-methylnicotinohydrazide

6-Chloro-2-methylnicotinic acid (Example 425, Step 1) (480 mg, 2.59 mmol) was taken up in ethanol (5.2 ml). Hydrazine (0.8 ml, 12.93 mmol) was added and the reaction was heated to 80° C. overnight. It was then concentrated under reduced pressure and purified via silica gel chromatography (0-3% methanol in ethyl acetate) to yield the title compound.

Calc'd for $C_7H_9ClN_3O$ [M+H]$^+$: 186. Found: 186.

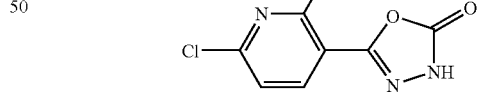

Step 2: 5-(6-Chloro-2-methylpyridin-3-yl)-1,3,4-oxadiazol-2(3H)-one

6-Chloro-2-methylnicotinohydrazide (60 mg, 0.32 mmol) and 1,1'-carbonylbis(1H-imidazole) (58 mg, 0.36 mmol) were taken up in dimethylformamide (1.6 ml). The reaction was heated overnight to 60° C. It was then allowed to cool to room temperature, taken up in ethyl acetate, and washed with water. The organic layer was concentrated under reduced pressure to afford the title compound.

Calc'd for $C_8H_7ClN_3O_2$ [M+H]$^+$: 212. Found: 212.

425

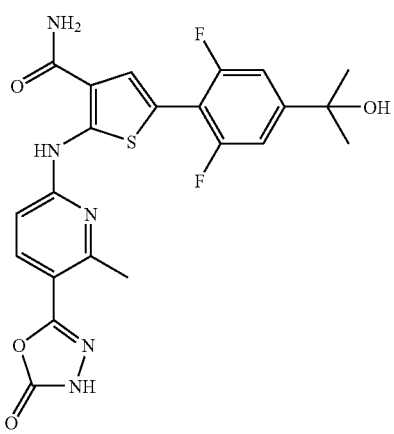 [SMILES: Cc1nc(Nc2sc(-c3c(F)cc(C(C)(C)O)cc3F)cc2C(N)=O)ccc1-c1n[nH]c(=O)o1]

Step 3: 5-[2,6-Difluoro-4-(1-hydroxy-1-methylethyl) phenyl]-2-{[6-methyl-5-(5-oxo-4,5-dihydro-1,3,4-oxadiazol-2-yl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 5-(6-chloro-2-methylpyridin-3-yl)-1,3,4-oxadiazol-2(3H)-one (101 mg, 0.48 mmol) as starting materials.

$^1$H NMR (600 MHz, d6-DMSO): δ 12.36 (s, 1H), 7.98 (s, 1H), 7.94 (d, 1H), 7.81 (s, 1H), 7.48 (s, 1H), 7.27 (d, 2H), 7.09 (d, 1H), 5.30 (s, 1H), 2.73 (s, 3H), 1.43 (s, 6H).

Calc'd for $C_{22}H_{20}F_2N_5O_4S$ [M+H]$^+$: 488 Found: 488.

Example 432

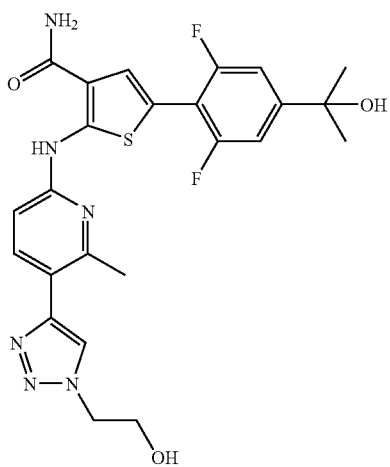

426

5-[2,6-Difluoro-4-(1-hydroxy-1-methylethyl)phenyl]-2-({5-[1-(2-hydroxyethyl)-1H-1,2,3-triazol-4-yl]-6-methylpyridin-2-yl}amino)thiophene-3-carboxamide

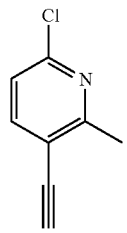

Step 1: 6-Chloro-3-ethynyl-2-methylpyridine

A 4.37 M sodium methoxide solution was prepared by dissolving sodium metal (2.10 g, 91.4 mmol) in dry methanol (20 ml). In a separate flask, Bestmann's reagent (2.11 ml, 13.5 mmol) was taken up in THF (44.3 ml) and cooled to −78° C. The sodium methoxide solution (3.09 ml, 13.50 mmol) was added dropwise to the reaction mixture over 30 minutes. A solution of 6-chloro-2-methylnicotinaldehyde (1.00 g, 6.43 mmol) in THF (20 ml) and then added dropwise to the reaction over 30 minutes and the reaction was allowed to warm slowly to −10° C. and maintained at −10° C. for 90 minutes. Saturated aqueous ammonium chloride was added, the layers were separated and the aqueous layer was extracted three times with ethyl acetate. The combined organic layers were dried over anhydrous magnesium sulfate, filtered, concentrated, and purified by silica gel chromatography (0-50% ethyl acetate/hexanes) to afford the title compound.

Calc'd for $C_8H_7ClN$ [M+H]$^+$: 152. Found: 152.

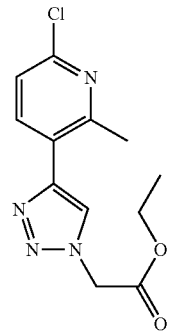 [SMILES: CCOC(=O)Cn1cc(-c2ccc(Cl)nc2C)nn1]

Step 2: Ethyl[4-(6-chloro-2-methylpyridin-3-yl)-1H-1,2,3-triazol-1-yl]acetate

The title compound was prepared as described in Example 413, Step 2 using 6-chloro-3-ethynyl-2-methylpyridine (250 mg, 1.65 mmol) and ethylazidoacetate (0.93 ml, 1.65 mmol) as starting materials Calc'd for $C_{12}H_{14}ClN_4O_2$ [M+H]$^+$: 281. Found: 281.

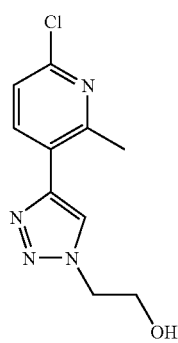 [SMILES: Cc1nc(Cl)ccc1-c1cn(CCO)nn1]

Step 3: 2-[4-(6-Chloro-2-methylpyridin-3-yl)-1H-1,2,3-triazol-1-yl]ethanol

The title compound was prepared as described in Example 414, Step 1 using ethyl[4-(6-chloro-2-methylpyridin-3-yl)-1H-1,2,3-triazol-1-yl]acetate (200 mg, 0.71 mmol) as the starting material.

Calc'd for $C_{10}H_{12}ClN_4O$ [M+H]$^+$: 239. Found: 239.

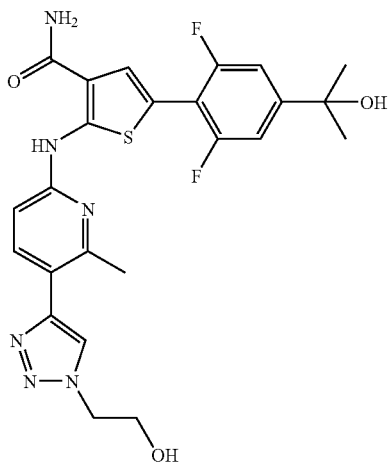 [SMILES: Cc1nc(Nc2sc(-c3c(F)cc(C(C)(C)O)cc3F)cc2C(N)=O)ccc1-c1cn(CCO)nn1]

Step 4: 5-[2,6-Difluoro-4-(1-hydroxy-1-methylethyl)phenyl]-2-({5-[1-(2-hydroxyethyl)-1H-1,2,3-triazol-4-yl]-6-methylpyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (100 mg, 0.32 mmol) and 2-[4-(6-chloro-2-methylpyridin-3-yl)-1H-1,2,3-triazol-1-yl]ethanol (76 mg, 0.32 mmol) as starting materials.

Calc'd for $C_{24}H_{25}F_2N_6O_3S$ [M+H]$^+$: 515. Found: 515.

Example 433

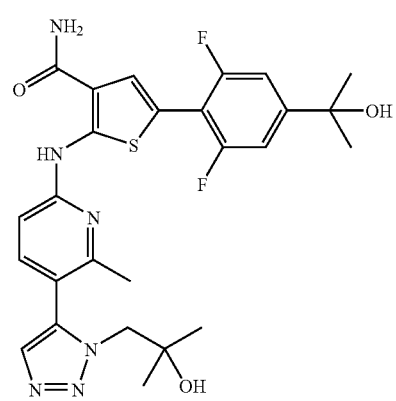 [SMILES: Cc1nc(Nc2sc(-c3c(F)cc(C(C)(C)O)cc3F)cc2C(N)=O)ccc1-c1cnnn1CC(C)(C)O]

5-[2,6-Difluoro-4-(1-hydroxy-1-methylethyl)phenyl]-2-({5-[1-(2-hydroxy-2-methylpropyl)-1H-1,2,3-triazol-5-yl]-6-methylpyridin-2-yl}amino)thiophene-3-carboxamide

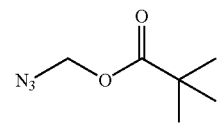

Step 1: Azidomethyl pivalate

Chloromethyl pivalate (1.93 ml, 12.9 mmol) and sodium azide (1.27 g, 19.3 mmol) were taken up in water (52 ml). The reaction mixture was heated to 90° C. for 22 hours. The reaction mixture was cooled to ambient temperature, and extracted with ethyl acetate three times. The organic layers were combined, washed with brine, dried over anhydrous magnesium sulfate, filtered, and concentrated in vacuo to afford the title compound.

$^1$H NMR (500 MHz, d6-DMSO): δ 5.12 (s, 2H), 1.23 (s, 9H).

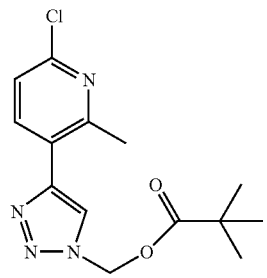 [SMILES: Cc1nc(Cl)ccc1-c1cn(COC(=O)C(C)(C)C)nn1]

Step 2: [4-(6-Chloro-2-methylpyridin-3-yl)-1H-1,2,3-triazol-1-yl]methyl pivalate The title compound was prepared as described in Example 413 Step 2 using 6-chloro-3-ethynyl-2-methylpyridine (Example 432, Step 1) (315 mg, 2.08 mmol) and azidomethyl pivalate (327 mg, 2.08 mmol) as starting materials.

Calc'd for $C_{14}H_{18}ClN_4O_2$ [M+H]⁺: 309. Found: 309.

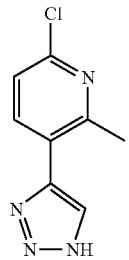

Step 3: 6-Chloro-2-methyl-3-(1H-1,2,3-triazol-4-yl)pyridine

[4-(6-Chloro-2-methylpyridin-3-yl)-1H-1,2,3-triazol-1-yl]methyl pivalate (350 mg, 0.96 mmol) was taken up in methanol (3.9 ml) at room temperature. Aqueous sodium hydroxide (1.0M, 4.8 ml, 4.8 mmol) was added, and the mixture was allowed to react for 2 hours. The reaction was then extracted three times with diethyl ether. The combined organic fractions were washed with water. The combined aqueous layers were adjusted to pH 7.0 via dropwise addition of 6 M aqueous hydrochloric acid. The neutralized mixture was saturated with solid sodium chloride and extracted three times with ethyl acetate. All the organic layers were combined, dried over anhydrous magnesium sulfate, filtered, and concentrated to afford the title compound.

Calc'd for $C_8H_8ClN_4$ [M+H]⁺: 195. Found: 195.

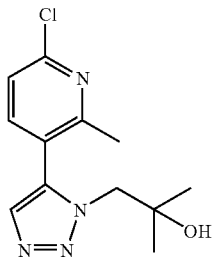 [SMILES: Cc1nc(Cl)ccc1-c1cnnn1CC(C)(C)O]

Step 4: 1-[5-(6-Chloro-2-methylpyridin-3-yl)-1H-1,2,3-triazol-1-yl]-2-methylpropan-2-ol 6-Chloro-2-methyl-3-(1H-1,2,3-triazol-4-yl)pyridine (131 mg, 0.68 mmol) and 1,2-epoxy-2-methylpropane (65 μl, 0.71 mmol) were taken-up in DMF (2.7 ml). Potassium 2-methylpropan-2-olate (114 mg, 1.01 mmol) was added, and the mixture was heated to 60° C. for seven hours. Saturated aqueous ammonium chloride was added and the resulting mixture was extracted three times with ethyl acetate. The combined organic layers were dried over anhydrous magnesium sulfate, filtered, concentrated, purified by reverse-phase HPLC (10-100% acetonitrile/water with 0.05% trifluoroacetic acid modifier). The appropriate fractions were neutralized with aqueous sodium bicarbonate and extracted twice with ethyl acetate. The organic layers were combined, dried over anhydrous magnesium sulfate, filtered, and concentrated to afford the title compound.

Calc'd for $C_{12}H_{16}ClN_4O$ [M+H]⁺: 267. Found: 267.

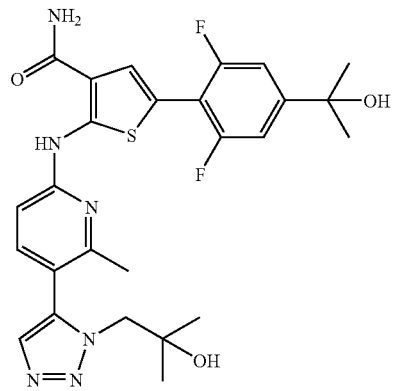 [SMILES: Cc1nc(Nc2sc(-c3c(F)cc(C(C)(C)O)cc3F)cc2C(N)=O)ccc1-c1cnnn1CC(C)(C)O]

Step 5: 5-[2,6-Difluoro-4-(1-hydroxy-1-methylethyl)phenyl]-2-({5-[1-(2-hydroxy-2-methylpropyl)-1H-1,2,3-triazol-5-yl]-6-methylpyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (70 mg, 0.22 mmol) and 1-[5-(6-chloro-2-methylpyridin-3-yl)-1H-1,2,3-triazol-1-yl]-2-methylpropan-2-ol (60 mg, 0.22 mmol) as starting materials.

Calc'd for $C_{26}H_{29}F_2N_6O_3S$ [M+H]⁺: 543. Found: 543.

Example 434

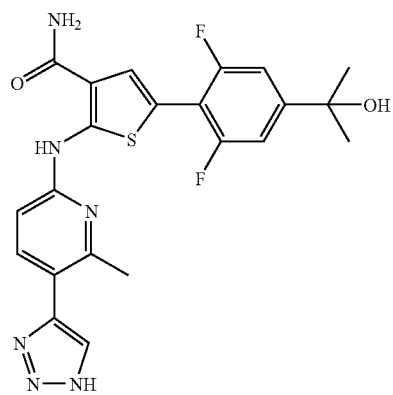 [SMILES: Cc1nc(Nc2sc(-c3c(F)cc(C(C)(C)O)cc3F)cc2C(N)=O)ccc1-c1c[nH]nn1]

5-[2,6-Difluoro-4-(1-hydroxy-1-methylethyl)phenyl]-2-{[6-methyl-5-(1H-1,2,3-triazol-4-yl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (60 mg, 0.19 mmol) and 6-chloro-2-methyl-3-(1H-1,2,3-triazol-4-yl)pyridine (Example 433, Step 3) (59 mg, 0.19 mmol) as starting materials.

Calc'd for $C_{22}H_{21}F_2N_6O_2S$ [M+H]⁺: 471. Found: 471.

Example 435

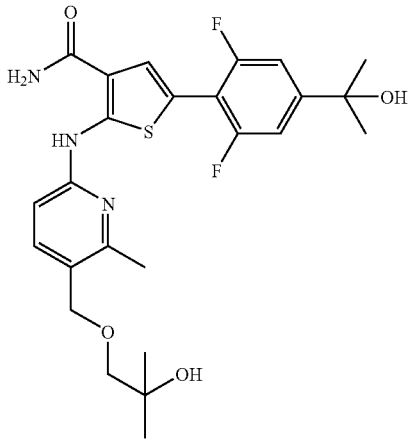 [SMILES: Cc1nc(Nc2sc(-c3c(F)cc(C(C)(C)O)cc3F)cc2C(N)=O)ccc1COCC(C)(C)O]

5-[2,6-Difluoro-4-(1-hydroxy-1-methylethyl)phenyl]-2-({5-[(2-hydroxy-2-methylpropoxy)methyl]-6-methylpyridin-2-yl}amino)thiophene-3-carboxamide

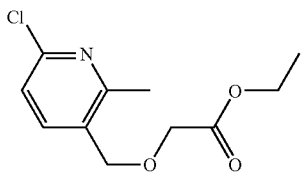 [SMILES: CCOC(=O)COCc1ccc(Cl)nc1C]

Step 1: Ethyl[(6-chloro-2-methylpyridin-3-yl)methoxy]acetate

Sodium hydride (266 mg of 60%, 6.66 mol) was suspended in tetrahydrofuran (14.8 mL) and cooled to 0° C. (6-Chloro-2-methylpyridin-3-yl)methanol (Example 421 Step 1) (350 mg, 2.22 mmol) was added and the mixture was stirred for 30 minutes at 0° C. Ethyl bromoacetate (0.25 mL, 2.22 mmol) was added and the solution was heated to 50° C. for 4 hours. The reaction mixture was then cooled to ambient temperature, diluted with water, and extracted with ethyl acetate. The aqueous layer was acidified with 1N HCl and extracted with ethyl acetate three times. All the organic layers were combined, dried over magnesium sulfate, filtered, concentrated, and purified via silica gel chromatography (0-100% ethyl acetate in hexane) to afford the title compound.

Calc'd for $C_{11}H_{15}ClNO_3$ [M+H]$^+$: 244. Found: 244.

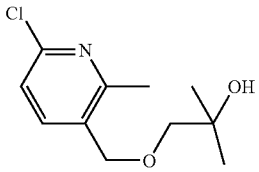

Step 2: 1-[(6-Chloro-2-methylpyridin-3-yl)methoxy]-2-methylpropan-2-ol solution of ethyl[(6-chloro-2-methylpyridin-3-yl)methoxy]acetate (500 mg, 2.05 mmol) was taken up in tetrahydrofuran (10.3 mL) and cooled to 0° C. Methylmagnesium bromide (2.1 mL of 3 M in diethyl ether, 6.2 mmol) was added dropwise and the reaction was maintained at 0° C. for 30 minutes. It was then allowed to warm to room temperature overnight. The reaction was quenched with water and extracted with ethyl acetate three times. The organic layers were combined, dried over magnesium sulfate, filtered, concentrated, and purification by silica gel chromatography (0-70% ethyl acetate in hexane). This material was then taken up in tetrahydrofuran (10.3 mL) and cooled to 0° C. Methylmagnesium bromide (2.1 mL of 3 M in diethyl ether, 6.2 mmol) was added dropwise and the reaction was maintained at 0° C. for 30 minutes. It was then allowed to warm to room temperature overnight. The reaction was quenched with water and extracted with ethyl acetate three times. The organic layers were combined, dried over magnesium sulfate, filtered, and concentrated to afford the title compound.

Calc'd for $C_{11}H_{17}ClNO_2$ [M+H]$^+$: 230. Found: 230.

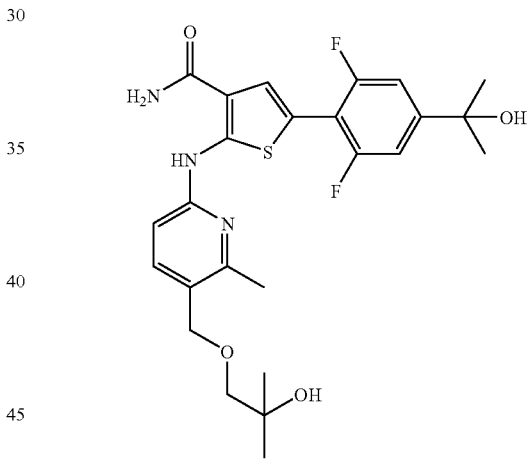

Step 3: 5-[2,6-Difluoro-4-(1-hydroxy-1-methylethyl)phenyl]-2-({5-[(2-hydroxy-2-methylpropoxy)methyl]-6-methylpyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 1-[(6-chloro-2-methylpyridin-3-yl)methoxy]-2-methylpropan-2-ol (110 mg, 0.48 mmol) as starting materials.

$^1$H NMR (600 MHz, d6-DMSO): δ 12.05 (s, 1H), 7.86 (s, 1H), 7.75 (s, 1H), 7.62 (d, 1H), 7.35 (s, 1H), 7.25 (d, 2H), 6.89 (d, 1H), 5.30 (s, 1H), 4.45 (s, 2H), 4.36 (s, 1H), 3.18 (s, 2H), 2.48 (s, 3H), 2.06 (s, 2H, 1.42 (s, 6H), 1.07 (s, 6H). Calc'd for $C_{25}H_{30}F_2N_3O_4S$ [M+H]$^+$: 506. Found: 506.

Example 436

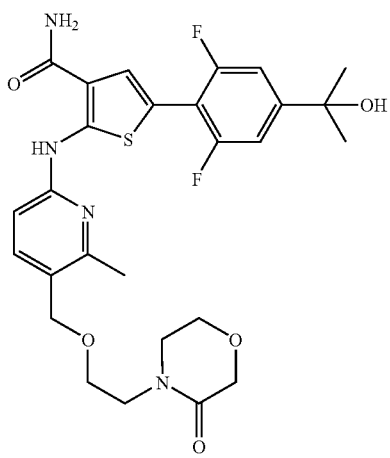 [SMILES: Cc1nc(Nc2sc(-c3c(F)cc(C(C)(C)O)cc3F)cc2C(N)=O)ccc1COCCN1CCOCC1=O]

5-[2,6-Difluoro-4-(1-hydroxy-1-methylethyl)phenyl]-2-[(6-methyl-5-{[2-(3-oxomorpholin-4-yl)ethoxy]methyl}pyridin-2-yl)amino]thiophene-3-carboxamide

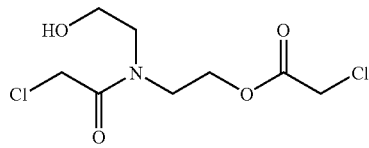 [SMILES: O=C(CCl)OCCN(CCO)C(=O)CCl]

Step 1: 2-[(Chloroacetyl)(2-hydroxyethyl)amino]ethyl chloroacetate

Triethylamine (1045 g, 10.35 mol) was added to a solution of diethanolamine (542.5 g, 5.17 mol) in THF (10 L). The mixture was cooled to −20° C. and 2-chloroacetyl chloride (1165.5 g, 10.32 mol) was added dropwise with stirring, followed by the addition of THF (7 L). The resulting solution was maintained at room temperature overnight, followed by maintaining the temperature at 15° C. for an additional 12 hours. The resulting mixture was filtered, and the filtrate was concentrated under reduced pressure. The resulting residue was diluted with dichloromethane, washed five times with brine, dried over $Na_2SO_4$, filtered, and concentrated to afford the title compound.

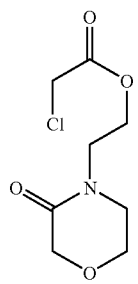

Step 2: 2-(3-Oxomorpholin-4-yl)ethyl chloroacetate

A solution of 2-(2-chloro-N-(2-hydroxyethyl)acetamido) ethyl 2-chloroacetate (269 g, 1.05 mol) in tetrahydrofuran (250 ml) was added dropwise to a cooled (5° C.) slurry of sodium hydride (50.4 g, 2.10 mol) in tetrahydrofuran (250 ml). To the mixture was then added tetrahydrofuran (3 L). The resulting mixture was allowed to react overnight while the temperature was maintained at 15° C. The mixture was then filtered, and the filtrate was diluted with dichloromethane, washed one time with 500 ml of water, dried over sodium sulfate, filtered, and concentrated under reduced pressure to afford the title compound.

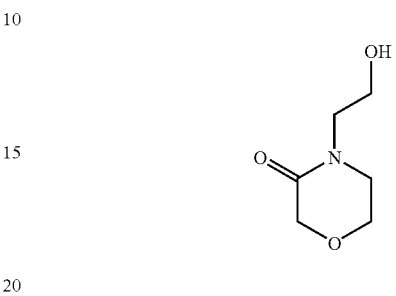

Step 3: 4-(2-Hydroxyethyl)morpholin-3-one

A solution of 2-(3-oxomorpholino)ethyl 2-chloroacetate (400 g, 1.81 mol) in methanol (2 L) was added dropwise to a cooled (15° C.) solution of potassium hydroxide (203 g, 3.62 mol) in methanol (10 L). This was followed by the addition methanol (3 L). The resulting solution was allowed to react overnight while the temperature was maintained at room temperature. The mixture was then filtered, and the filtrate was concentrated under reduced pressure. The resulting residue taken up in 1 L of dichloromethane, washed with 250 ml of water, dried over sodium sulfate, filtered and concentrated under reduced pressure. Purification was performed by distillation under reduced pressure (0.08 mm Hg) collecting the fraction that came over at 140° C. to afford the title compound.

Calc'd for $C_6H_{12}NO_3$ $[M+H]^+$: 146. Found: 146.

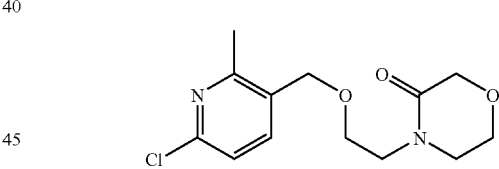

Step 4: 4-{2-[(6-Chloro-2-methylpyridin-3-yl)methoxy]ethyl}morpholin-3-one

Sodium hydride (190 mg of a 60%, 4.76 mmol) was suspended in THF (12.2 mL) and cooled to 0° C. 4-(2-Hydroxyethyl)morpholin-3-one (230 mg, 1.59 mmol) was added and the slurry was stirred for thirty minutes at 0° C. 3-(Bromomethyl)-6-chloro-2-methylpyridine (Example 421 Step 2) (350 mg, 1.59 mmol) was added and the solution was heated to 50° C. overnight. The reaction mixture was then cooled to ambient temperature, diluted with water, acidified using 1 N aqueous hydrochloric acid, and extracted with ethyl acetate (2×). The combined organic layers were dried over magnesium sulfate, filtered, concentrated, and purified by silica gel chromatography (0-2% methanol in ethyl acetate) to afford the title compound.

$^1$H NMR (600 MHz, d6-DMSO): δ 7.70 (d, 1H), 7.31 (d, 1H), 4.49 (s, 2H), 4.00 (s, 2H), 3.77 (t, 2H), 3.61 (t, 2H), 3.52 (t, 2H), 3.38 (t, 2H), 2.40 (s, 3H).

435

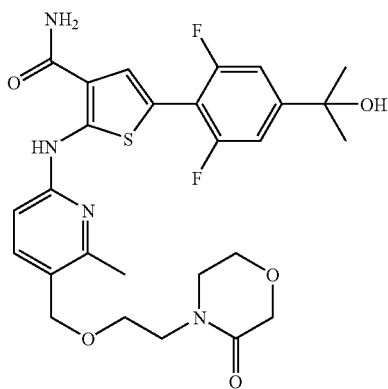 [SMILES: Cc1nc(Nc2sc(-c3c(F)cc(C(C)(C)O)cc3F)cc2C(N)=O)ccc1COCCN1CCOCC1=O]

Step 5: 5-[2,6-Difluoro-4-(1-hydroxy-1-methylethyl)phenyl]-2-[(6-methyl-5-{[2-(3-oxomorpholin-4-yl)ethoxy]methyl}pyridin-2-yl)amino]thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 4-{2-[(6-chloro-2-methylpyridin-3-yl)methoxy]ethyl}morpholin-3-one (137 mg, 0.48 mmol) as starting materials.

$^1$H NMR (600 MHz, d-6 DMSO): δ 12.06 (s, 1H), 7.86 (s, 1H), 7.75 (s, 1H), 7.58 (d, 1H), 7.34 (s, 1H), 7.25 (d, 2H), 6.89 (d, 1H), 5.29 (s, 1H), 4.44 (s, 2H), 3.99 (s, 2H), 3.77 (t, 2H), 3.58 (t, 2H), 3.51 (t, 2H), 2.46 (s, 3H), 1.43 (s, 6H). Calc'd for $C_{27}H_{31}F_2N_4O_5S$ [M+H]$^+$: 561. Found: 561.

Example 437

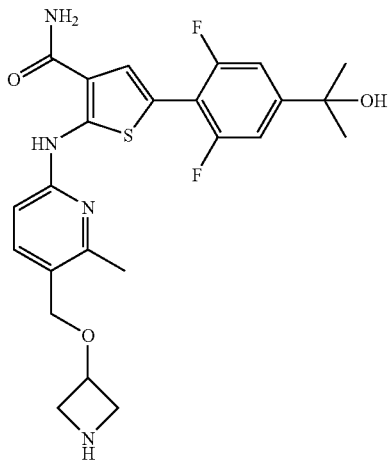 [SMILES: Cc1nc(Nc2sc(-c3c(F)cc(C(C)(C)O)cc3F)cc2C(N)=O)ccc1COC1CNC1]

436

2-({5-[(Azetidin-3-yloxy)methyl]-6-methylpyridin-2-yl}amino)-5-[2,6-difluoro-4-(1-hydroxy-1-methylethyl)phenyl]thiophene-3-carboxamide

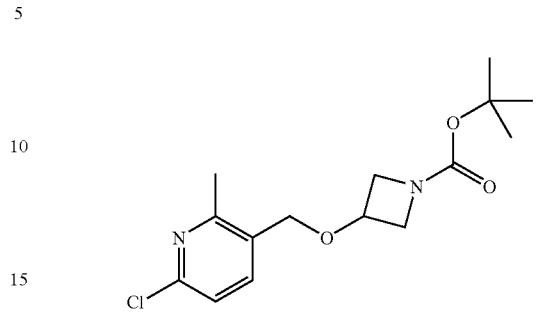

Step 1: tert-Butyl 3-[(6-chloro-2-methylpyridin-3-yl)methoxy]azetidine-1-carboxylate Sodium hydride (170 mg of 60%, 4.26 mmol) was suspended in tetrahydrofuran (12 mL) and cooled to 0° C. tert-Butyl 3-hydroxyazetidine-1-carboxylate (246 mg, 1.420 mmol) was added and the slurry was stirred for 30 minutes at 0° C. 3-(Bromomethyl)-6-chloro-2-methylpyridine (Example 421, Step 2) (313 mg, 1.420 mmol) was added and the solution was heated to 50° C. overnight. The reaction mixture was cooled to ambient temperature, diluted with water, acidified with 1 N hydrochloric acid, and extracted with ethyl acetate (2×). The combined organic layers were dried over magnesium sulfate, filtered, concentrated and purified via silica gel chromatography (0-2% methanol in ethyl acetate) to afford the title compound.

$^1$H NMR (600 MHz, d6-DMSO): δ 7.75 (d, 1H), 7.32 (d, 1H), 4.44 (s, 2H), 4.34 (m, 1H), 4.01 (m, 2H), 3.69 (s, 2H), 2.41 (s, 3H), 1.35 (s, 9H).

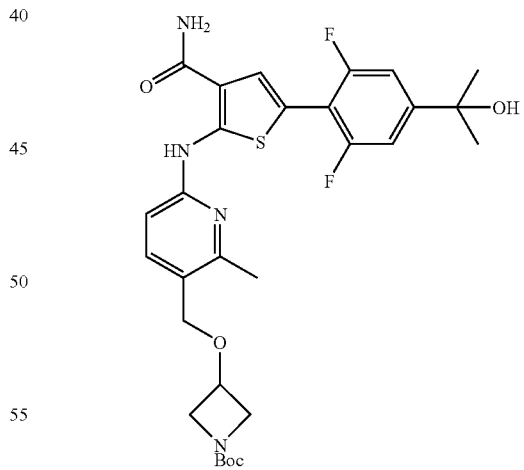

Step 2: tert-Butyl 3-{[6-({3-(aminocarbonyl)-5-[2,6-difluoro-4-(1-hydroxy-1-methylethyl)phenyl]-2-thienyl}amino)-2-methylpyridin-3-yl]methoxy}azetidine-1-carboxylate The title compound was prepared as described in Example 1 using 2-amino-5-[2,6-difluoro-4-(1-hydroxy-1-methylethyl)phenyl]thiophene-3-carboxamide (150 mg, 0.48 mmol) and tert-butyl 3-[(6-chloro-2-methylpyridin-3-yl)methoxy]azetidine-1-carboxylate (150 mg, 0.48 mmol) as starting materials.

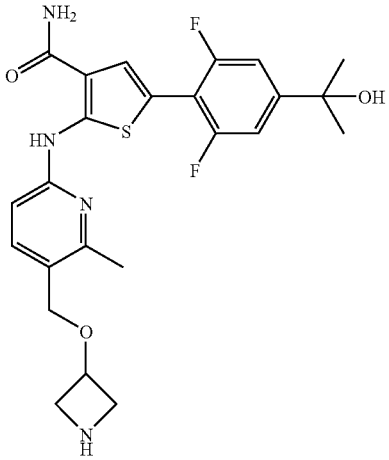 [SMILES: Cc1nc(Nc2sc(-c3c(F)cc(C(C)(C)O)cc3F)cc2C(N)=O)ccc1COC1CNC1]

Step 3: 2-({5-[(Azetidin-3-yloxy)methyl]-6-methylpyridin-2-yl}amino)-5-[2,6-difluoro-4-(1-hydroxy-1-methylethyl)phenyl]thiophene-3-carboxamide tert-Butyl 3-{[6-({3-(aminocarbonyl)-5-[2,6-difluoro-(1-hydroxy-1-methylethyl)phenyl]-2-thienyl}amino)-2-methylpyridin-3-yl]methoxy}azetidine-1-carboxylate (146 mg, 0.248 mmol) was suspended in acetonitrile (4 mL). Aqueous hydrochloric acid (3.7 mL of 1N, 3.7 mmol) was added, and the reaction was allowed to react at room temperature overnight. It was then heated to 50° C. for 5 hours. The mixture was cooled to room temperature, neutralized with 1 N aqueous sodium hydroxide and extracted with ethyl acetate (3×). The combined organic layers were dried over magnesium sulfate, filtered, and concentrated under reduced pressure to afford the title compound.

$^1$H NMR (600 MHz, d6-DMSO): δ 12.07 (s, 1H), 7.89 (s, 1H), 7.75 (s, 1H), 7.60 (d, 1H), 7.36 (d, 1H), 7.25 (d, 2H), 6.89 (d, 1H), 5.29 (s, 1H), 4.36 (s, 2H), 4.32 (m, 1H), 3.60 (m, 2H), 3.46 (m, 2H), 1.426 (s, 6H). Calc'd for $C_2H_{27}F_2N_4O_3S$ [M+H]$^+$: 489. Found: 489.

Example 438

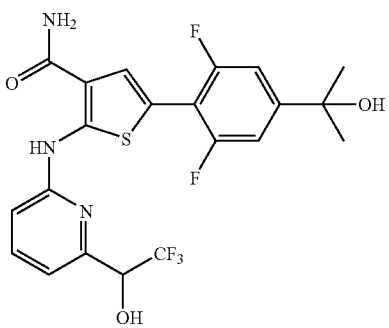 [SMILES: CC(C)(O)c1cc(F)c(-c2cc(C(N)=O)c(Nc3cccc(C(O)C(F)(F)F)n3)s2)c(F)c1]

5-[2,6-Difluoro-4-(1-hydroxy-1-methylethyl)phenyl]-2-{[6-(2,2,2-trifluoro-1-hydroxyethyl)pyridin-2-yl]amino}thiophene-3-carboxamide

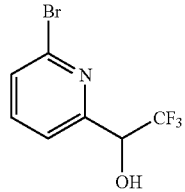 [SMILES: OC(c1cccc(Br)n1)C(F)(F)F]

Step 1: 1-(6-Bromopyridin-2-yl)-2,2,2-trifluoroethanol

6-Bromopyridine-2-carbaldehyde (1.0 g, 5.38 mmol) was taken up in 35 mL THF and cooled to 0° C. TMSCF$_3$ (1.0 mL, 6.45 mmol) was added followed by tetrabutylammonium fluoride (6.45 mL of 1.0M in THF). The reaction was stirred allowed to warm to room temperature and maintained at that temperature for 4.5 hours. The mixture was then diluted with water and brine, and extracted with ethyl acetate (3×). The organic layers were combined and dried over magnesium sulfate, filtered, and concentrated under reduced pressure. Purification by silica gel chromatography (0-40% ethyl acetate/hexanes) afforded the title compound.

$^1$H NMR (600 MHz, d6-DMSO) δ 7.83 (m, 1H), 7.67 (d, 1H), 7.63 (d, 1H), 7.15 (d, 1H), 5.11 (m, 1H).

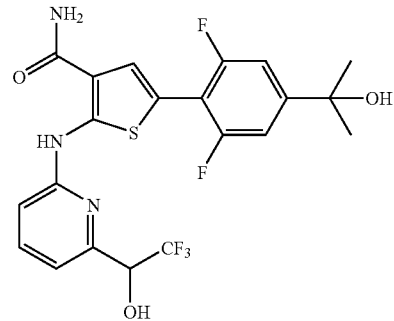 [SMILES: CC(C)(O)c1cc(F)c(-c2cc(C(N)=O)c(Nc3cccc(C(O)C(F)(F)F)n3)s2)c(F)c1]

Step 2: 5-[2,6-Difluoro-4-(1-hydroxy-1-methylethyl)phenyl]-2-{[6-(2,2,2-trifluoro-1-hydroxyethyl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 1-(6-bromopyridin-2-yl)-2,2,2-trifluoroethanol (123 mg, 0.48 mmol) as starting materials.

$^1$H NMR (600 MHz, d6-DMSO): δ 12.15 (s, 1H), 7.89 (s, 1H), 7.77 (t, 1H), 7.75 (s, 1H), 7.37 (s, 1H), 7.24 (d, 2H), 7.14 (d, 1H), 7.10 (d, 1H), 6.96 (d, 1H), 5.26 (s, 1H), 5.03 (p, 1H), 1.40 (s, 6H). Calc'd for $C_{22}H_{21}F_4N_5O_2S$ [M+H]$^+$: 488. Found: 488.

Chiral Separation:

Chiral separation of 5-[2,6-difluoro-4-(1-hydroxy-1-methylethyl)phenyl]-2-{[6-(2,2,2-trifluoro-1-hydroxyethyl)pyridin-2-yl]amino}thiophene-3-carboxamide was performed using chiral HPLC (ethanol in heptane) through a Chiral Tachnology AD-H column (2×25 cm, 5 uM column, isochratic, 15% ethanol in heptane, flow rate=10 mL/min). Enantiomer A had a retention time of 12.4 minutes, and enantiomer B had a retention time of 16.2 minutes.

Enantiomer A: ¹H NMR (600 MHz, d6-DMSO): δ 12.17 (s, 1H), 7.91 (s, 1H), 7.81 (t, 1H), 7.78 (s, 1H), 7.40 (s, 1H), 7.26 (d, 2H), 7.16 (d, 1H), 7.12 (d, 1H), 6.99 (d, 1H), 5.29 (s, 1H), 5.05 (m, 1H), 1.42 (s, 6H). $\tau_R$=12.4 min.

Enantiomer B: ¹H NMR (600 MHz, d6-DMSO): δ 12.17 (s, 1H), 7.92 (s, 1H), 7.79 (t, 1H), 7.78 (s, 1H), 7.40 (s, 1H), 7.26 (d, 2H), 7.16 (d, 1H), 7.12 (d, 1H), 6.99 (d, 1H), 5.29 (s, 1H), 5.05 (m, 1H), 1.43 (s, 6H). $\tau_R$=16.2 min.

The following example was prepared using procedures similar to those described in the above example and is illustrated in the following table.

TABLE 43

| Example # | Structure | Name | Characterization [M + H]⁺ |
|---|---|---|---|
| 439 | 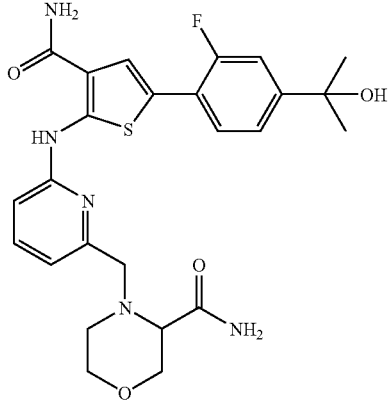 [SMILES: CC(C)(O)c1ccc(-c2cc(C(N)=O)c(Nc3cccc(CN4CCOCC4C(N)=O)n3)s2)c(F)c1] | 5-[2-fluoro-4-(1-hydroxy-1-methylethyl)phenyl]-2-{[6-(2,2,2-trifluoro-1-hydroxyethyl)pyridin-2-yl]amino}thiophene-3-carboxamide | Calc'd 470, found 470 |

Example 440

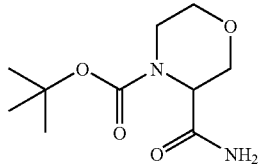

4-{[6-({3-(Aminocarbonyl)-5-[2-fluoro-4-(1-hydroxy-1-methylethyl)phenyl]-2-thienyl}amino)pyridin-2-yl]methyl}morpholine-3-carboxamide

Step 1: 1,1-Dimethylethyl 3-(aminocarbonyl)morpholine-4-carboxylate

4-{[(1,1-Dimethylethyl)oxy]carbonyl}morpholine-3-carboxylic acid (0.5 g, 2.162 mmol), ammonium chloride (0.347 g, 6.49 mmol), EDC (0.622 g, 3.24 mmol), HOBt (0.993 g, 6.49 mmol) and DIPEA (1.699 mL, 9.73 mmol) were stirred in DMF (10 mL) at room temperature overnight. Saturated NaHCO₃ was then added and the mixture was extracted with EtOAc (2×). The combined organic extracts were washed with brine, dried over MgSO₄, filtered, and concentrated in vacuo to give the title compound as a yellow gum.

Step 2: Morpholine-3-carboxamide hydrochloride 1,1-Dimethylethyl 3-(aminocarbonyl)morpholine-4-carboxylate (0.48 g, 2.085 mmol) was taken up in 4 M HCl in dioxane (5 mL, 10.00 mmol) and maintained at room temperature overnight. The solvent was removed in vacuo to afford the title compound as a pale yellow solid.

Step 3: 4-[(6-Bromopyridin-2-yl)methyl]morpholine-3-carboxamide

2-Bromo-6-(bromomethyl)pyridine (Example 190, Step 1) (150 mg, 0.60 mmol), morpholine-3-carboxamide hydrochloride (100 mg, 0.560 mmol) and potassium carbonate (207 mg, 1.50 mmol) were taken up in DMF (3 mL) and the reaction was maintained at room temperature overnight.

Water was then added and the mixture was extracted with EtOAc (2×). The combined organic extracts were washed with brine, dried over MgSO₄, filtered, and concentrated in vacuo to give the title compound as an orange oil.

Calc'd for $C_{11}H_{15}BrN_3O_2$ [M+H]⁺: 300, 302. Found: 300, 302.

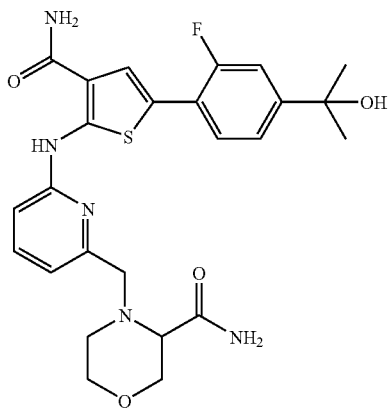 [SMILES: CC(C)(O)c1ccc(-c2cc(C(N)=O)c(Nc3cccc(CN4CCOCC4C(N)=O)n3)s2)c(F)c1]

Step 4. 4-{[6-({3-(Aminocarbonyl)-5-[2-fluoro-4-(1-hydroxy-1-methylethyl)phenyl]-2-thienyl}amino)pyridin-2-yl]methyl}morpholine-3-carboxamide The title compound was prepared as described in Example 1 using 2-amino-5-[2-fluoro-4-(1-hydroxy-1-methylethyl)phenyl]thiophene-3-carboxamide (80 mg, 0.27 mmol) and 4-[(6-bromopyridin-2-yl)methyl]morpholine-3-carboxamide (82 mg, 0.27 mmol) as starting materials.

Calc'd for $C_{25}H_{29}FN_5O_4S$ [M+H]⁺: 514. Found: 514.

Example 441

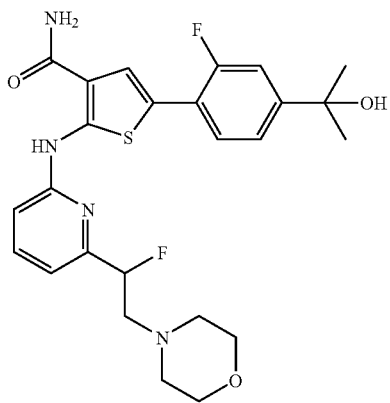 [SMILES: CC(C)(O)c1ccc(-c2cc(C(N)=O)c(Nc3cccc(C(F)CN4CCOCC4)n3)s2)c(F)c1]

5-[2-Fluoro-4-(1-hydroxy-1-methylethyl)phenyl]-2-{[6-(1-fluoro-2-morpholin-4-ylethyl)pyridin-2-yl]amino}thiophene-3-carboxamide

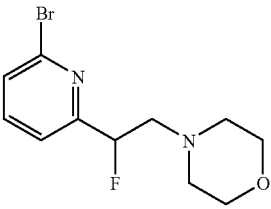

Step 1. 4-[2-(6-Bromopyridin-2-yl)-2-fluoroethyl]morpholine 2-(6-Bromopyridin-2-yl)-2-morpholin-4-ylethanol (Example 141, Step 1) (0.53 g, 1.86 mmol) was taken up in DCM (10 mL) and cooled to 0° C. DAST (0.27 mL, 2.04 mmol) was added and the resulting solution was allowed to react at 0° C. for 90 minutes. Saturated aqueous NaHCO₃ was added and the resulting mixture was extracted with DCM (2×). The combined organic extracts were washed with brine, dried over MgSO₄, filtered, concentrated in vacuo, and purified by silica gel chromatography (12-100% EtOAc-hexanes) to afford the title compound as a pale yellow solid.

Calc'd for $C_{11}H_{15}BrFN_2O$ [M+H]⁺: 289, 291. Found: 289, 291.

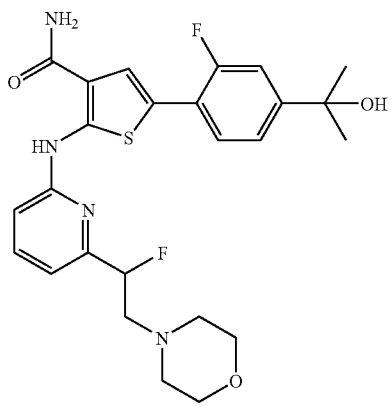 [SMILES: CC(C)(O)c1ccc(-c2cc(C(N)=O)c(Nc3cccc(C(F)CN4CCOCC4)n3)s2)c(F)c1]

Step 2. 5-[2-Fluoro-4-(1-hydroxy-1-methylethyl)phenyl]-2-{[6-(1-fluoro-2-morpholin-4-ylethyl)pyridin-2-yl]amino}thiophene-3-carboxamide The title compound was prepared according to the general procedure in Example 1 using 4-[2-(6-bromopyridin-2-yl)-2-fluoroethyl]morpholine (80 mg, 0.28 mmol) and 2-amino-5-[2-fluoro-4-(1-hydroxy-1-methylethyl)phenyl]thiophene-3-carboxamide (81 mg, 0.28 mmol) as the starting materials.

Calc'd for $C_{25}H_{29}F_2N_4O_3S$ [M+H]⁺: 503. Found: 503.

Example 442

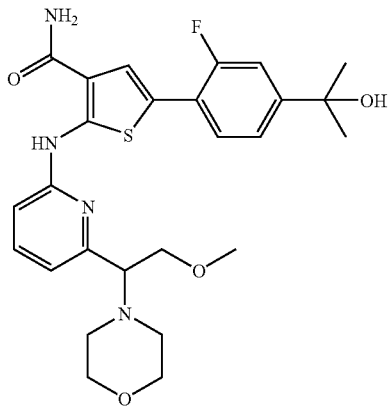 [SMILES: COCC(c1cccc(Nc2sc(-c3ccc(C(C)(C)O)cc3F)cc2C(N)=O)n1)N1CCOCC1]

5-[2-Fluoro-4-(1-hydroxy-1-methylethyl)phenyl]-
2-{[6-(2-methoxy-1-morpholin-4-ylethyl)pyridin-2-
yl]amino}thiophene-3-carboxamide

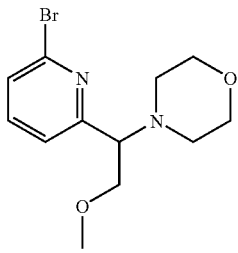 [SMILES: COCC(c1cccc(Br)n1)N1CCOCC1]

Step 1. 4-[1-(6-Bromopyridin-2-yl)-2-methoxyethyl]
morpholine 2-(6-Bromopyridin-2-yl)-2-morpholin-4-ylethanol (Example 141, Step 1) (1 g, 3.48 mmol) was taken up in THF (7 mL) and cooled to 0° C. Sodium hydride (0.153 g, 3.83 mmol) was added and the suspension stirred at 0° C. for 5 minutes. A solution of iodomethane (0.240 mL, 3.83 mmol) in THF (3 mL) was added and the reaction mixture stirred at 0° C. for 30 minutes. Saturated NH$_4$Cl was added and the reaction mixture was extracted with EtOAc (2×). The combined organic extracts were dried over MgSO$_4$, filtered, and concentrated in vacuo. Purification of the residue by silica gel column chromatography (40-100% EtOAc-hexanes) gave the title compound as a yellow oil.

Calc'd for C$_{12}$H$_{18}$BrN$_2$O$_2$ [M+H]$^+$: 301, 303. Found: 301, 303.

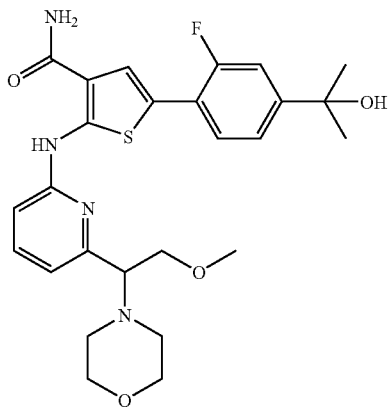 [SMILES: COCC(c1cccc(Nc2sc(-c3ccc(C(C)(C)O)cc3F)cc2C(N)=O)n1)N1CCOCC1]

Step 2. 5-[2-Fluoro-4-(1-hydroxy-1-methyl ethyl)
phenyl]-2-{[6-(2-methoxy-1-morpholin-4-ylethyl)
pyridin-2-yl]amino}thiophene-3-carboxamide The title compound was prepared according to the general procedure in Example 1 using 4-[1-(6-bromopyridin-2-yl)-2-methoxyethyl]morpholine (111 mg, 0.37 mmol) and 2-amino-5-[2-fluoro-4-(1-hydroxy-1-methylethyl)phenyl]thiophene-3-carboxamide (108 mg, 0.37 mmol) as the starting materials.

Calc'd for C$_{26}$H$_{32}$FN$_4$O$_4$S [M+H]$^+$: 515. Found: 515.

Example 443

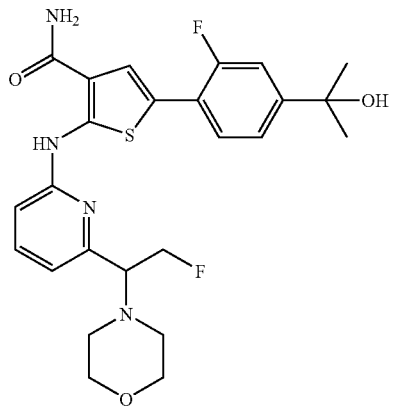 [SMILES: CC(C)(O)c1ccc(-c2cc(C(N)=O)c(Nc3cccc(C(CF)N4CCOCC4)n3)s2)c(F)c1]

5-[2-Fluoro-4-(1-hydroxy-1-methylethyl)phenyl]-
2-{[6-(2-fluoro-1-morpholin-4-ylethyl)pyridin-2-yl]
amino}thiophene-3-carboxamide

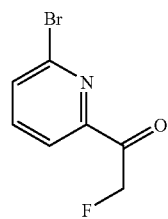 [SMILES: O=C(CF)c1cccc(Br)n1]

Step 1. 1-(6-Bromopyridin-2-yl)-2-fluoroethanone 1-(6-Bromopyridin-2-yl)ethanone (2 g, 10.0 mmol) and 1-fluoro-4-hydroxy-1,4-diazoniabicyclo[2.2.2]octane bis (tetrafluoroborate) (9.65 g, 15.0 mmol) were combined in MeOH (100 mL) and heated to reflux for 3 days. After cooling to room temperature, the white solid (alumina) was removed by filtration and filtrate was concentrated in vacuo. The residue was taken up in EtOAc and water and extracted with EtOAc (2×). The combined organic extracts were washed with brine, dried over MgSO$_4$, filtered, and concentrated in vacuo. The residue was stirred in a combination of 6 N HCl and Et$_2$O overnight. The organic phase was separated and the aqueous phase extracted with Et$_2$O. The combined organic extracts were washed with brine, dried over MgSO$_4$, filtered, and concentrated in vacuo. Purification of the residue by silica gel column chromatography (0-20% EtOAc-hexanes) gave the title compound as a white solid.

$^1$H NMR (600 MHz, DMSO): 8.01 (dd, 1H), 7.72 (m, 2H), 5.81 (d, 2H).

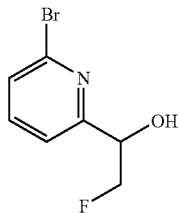 [SMILES: OC(CF)c1cccc(Br)n1]

Step 2: 1-(6-Bromopyridin-2-yl)-2-fluoroethanol 1-(6-Bromopyridin-2-yl)-2-fluoroethanone (0.53 g, 2.43 mmol) was taken up in MeOH (12 mL) and cooled to 0° C. Sodium borohydride (0.092 g, 2.43 mmol) was added and the mixture stirred at 0° C. for 1 hour. Water was added and the reaction mixture was extracted with EtOAc (2×). The combined organic extracts were washed with brine, dried over MgSO$_4$, filtered, and concentrated in vacuo to give the title compound as a colorless oil.

Calc'd for C$_7$H$_8$BrFNO [M+H]$^+$: 220, 222. Found: 220, 222.

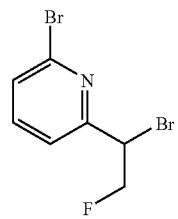 [SMILES: FCC(Br)c1cccc(Br)n1]

Step 3. 2-Bromo-6-(1-bromo-2-fluoroethyl)pyridine 1-(6-Bromopyridin-2-yl)-2-fluoroethanol (0.525 g, 2.39 mmol) and triphenylphosphine (1.252 g, 4.77 mmol) were taken up in DCM (25 mL). A solution of carbon tetrabromide (1.582 g, 4.77 mmol) in DCM (10 mL) was added and the resulting mixture stirred at room temperature overnight. The precipitate was removed by filtration and the filtrate concentrated in vacuo. Purification of the residue by silica gel column chromatography (0-10% EtOAc-hexanes) gave the title compound as a colorless oil.

Calc'd for C$_7$H$_7$Br$_2$FN [M+H]$^+$: 282, 284, 286. Found: 282, 284, 286.

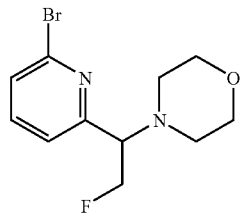 [SMILES: FCC(c1cccc(Br)n1)N1CCOCC1]

Step 4. 4-[1-(6-Bromopyridin-2-yl)-2-fluoroethyl]morpholine

2-Bromo-6-(1-bromo-2-fluoroethyl)pyridine (70 mg, 0.25 mmol), morpholine (0.022 mL, 0.25 mmol) and DIPEA (0.048 mL, 0.27 mmol) were stirred in DMF (1 mL) at room temperature for 4 hours. Additional morpholine (10.78 µL, 0.12 mmol) and DIPEA (0.024 mL, 0.14 mmol) were added and the resulting solution stirred at room temperature overnight. Water was added and the reaction mixture was extracted with EtOAc (2×). The combined organic extracts were washed with brine, dried over MgSO$_4$, filtered, and concentrated in vacuo. Purification of the residue by silica gel column chromatography (6-50% EtOAc-hexanes) gave the title compound as a pale yellow oil.

Calc'd for C$_{11}$H$_{15}$BrFN$_2$O [M+H]$^+$: 289, 291. Found: 289, 291.

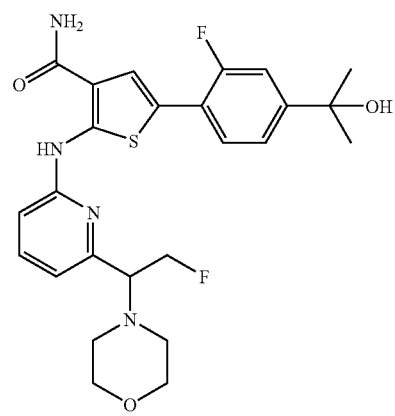

Step 5. 5-[2-Fluoro-4-(1-hydroxy-1-methylethyl)phenyl]-2-{[6-(2-fluoro-1-morpholin-4-ylethyl)pyridin-2-yl]amino}thiophene-3-carboxamide The title compound was prepared according to the general procedure in Example 1 using 4-[1-(6-bromopyridin-2-yl)-2-fluoroethyl]morpholine (36.3 mg, 0.13 mmol) and 2-amino-5-[2-fluoro-4-(1-hydroxy-1-methylethyl)phenyl]thiophene-3-carboxamide (37 mg, 0.13 mmol) as the starting materials.

Calc'd for C$_{25}$H$_{29}$F$_2$N$_4$O$_3$S [M+H]: 503. Found: 503.

Example 444

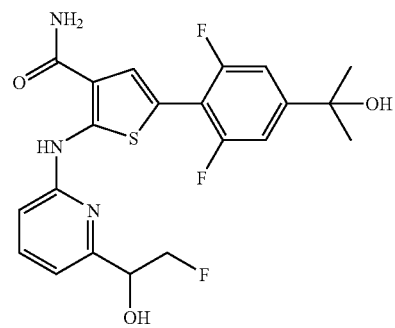 [SMILES: CC(C)(O)c1cc(F)c(-c2cc(C(N)=O)c(Nc3cccc(C(O)CF)n3)s2)c(F)c1]

447

5-[2,6-Difluoro-4-(1-hydroxy-1-methylethyl)phenyl]-2-{[6-(2-fluoro-1-hydroxyethyl)pyridin-2-yl]amino}thiophene-3-carboxamide

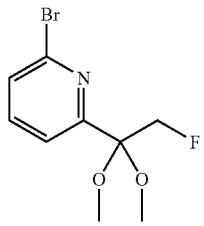

Step 1:
2-Bromo-6-(2-fluoro-1,1-dimethoxyethyl)pyridine 1-(6-Bromopyridin-2-yl)ethanone (Example 443, Step 1) (1 g, 5.0 mmol) and 1-fluoro-4-hydroxy-1,4-diazoniabicyclo[2.2.2]octane bis(tetrafluoroborate) (3.38 g, 5.25 mmol) were combined in MeOH (50 mL) and the reaction mixture was heated to reflux for 8 hours. Additional 1-fluoro-4-hydroxy-1,4-diazoniabicyclo[2.2.2]octane bis(tetrafluoroborate) (3.38 g, 5.25 mmol) was added before heating to reflux for 8 hours. After cooling to room temperature, the white solid (alumina) was removed by filtration and the solvent removed in vacuo. Water was added and the reaction mixture was extracted with ethyl acetate (×2). The combined organic extracts were washed with brine, dried over MgSO$_4$, filtered, and concentrated in vacuo to give the title compound.

$^1$H NMR (600 MHz, CDCl$_3$): 7.71 (dd, 1H), 7.56 (t, 1H), 7.43 (dd, 1H), 4.73 (d, 2H), 3.24 (s, 6H).

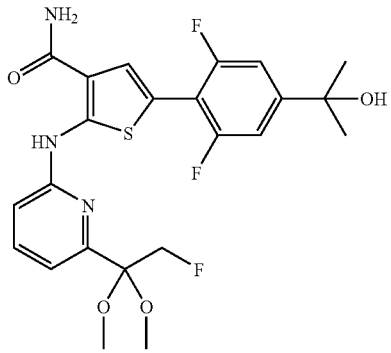 [SMILES: COC(CF)(OC)c1cccc(Nc2sc(-c3c(F)cc(C(C)(C)O)cc3F)cc2C(N)=O)n1]

Step 2: 5-[2,6-Difluoro-4-(1-hydroxy-1-methylethyl)phenyl]-2-{[6-(2-fluoro-1,1-dimethoxyethyl)pyridin-2-yl]amino}thiophene-3-carboxamide The title compound was prepared in the same manner described in Example 1 using 2-amino-5-[2,6-difluoro-4-(1-hydroxy-1-methylethyl)phenyl]thiophene-3-carboxamide (100 mg, 0.32 mmol) and 2-bromo-6-(2-fluoro-1,1-dimethoxyethyl)pyridine (85 mg, 0.32 mmol) as starting materials.

Calc'd for C$_{23}$H$_{25}$F$_3$N$_3$O$_4$S [M+H]$^+$: 496. Found: 496.

448

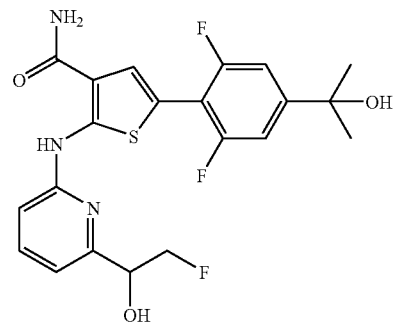 [SMILES: CC(C)(O)c1cc(F)c(-c2cc(C(N)=O)c(Nc3cccc(C(O)CF)n3)s2)c(F)c1]

Step 3: 5-[2,6-Difluoro-4-(1-hydroxy-1-methylethyl)phenyl]-2-{[6-(fluoroacetyl)pyridin-2-yl]amino}thiophene-3-carboxamide 5-[2,6-Difluoro-4-(1-hydroxy-1-methylethyl)phenyl]-2-{[6-(2-fluoro-1,1-dimethoxyethyl)pyridin-2-yl]amino}thiophene-3-carboxamide (61 mg, 0.12 mmol) was taken up in acetonitrile (1.2 ml) at room temperature. Hydrochloric acid (0.31 ml, 0.62 mmol) was added in one portion, and the reaction mixture was stirred overnight at room temperature. The reaction was quenched with saturated aqueous sodium bicarbonate and extracted three times with ethyl acetate. All organic layers were combined, dried over anhydrous magnesium sulfate, filtered, and concentrated to afford the title compound. Calc'd for C$_{21}$H$_{19}$F$_3$N$_3$O$_3$S [M+H]$^+$: 450. Found: 450.

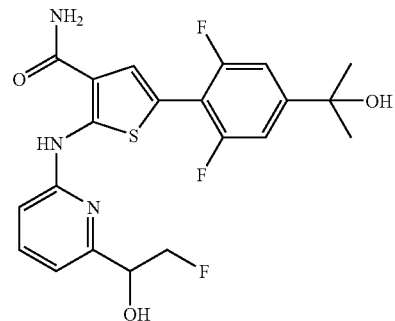 [SMILES: CC(C)(O)c1cc(F)c(-c2cc(C(N)=O)c(Nc3cccc(C(O)CF)n3)s2)c(F)c1]

Step 4: 5-[2,6-Difluoro-4-(1-hydroxy-1-methylethyl)phenyl]-2-{[6-(2-fluoro-1-hydroxyethyl)pyridin-2-yl]amino}thiophene-3-carboxamide In a dry flask, 5-[2,6-difluoro-4-(1-hydroxy-1-methylethyl)phenyl]-2-{[6-(fluoroacetyl)pyridin-2-yl]amino}thiophene-3-carboxamide (33.6 mg, 0.08 mmol) was taken up in methanol (0.75 ml) at room temperature. Sodium borohydride (6 mg, 0.15 mmol) was added in small portions and the reaction mixture was stirred at room temperature overnight. The reaction was quenched with aqueous sodium bicarbonate and extracted three times with ethyl acetate. All organic layers were combined, dried over anhydrous magnesium sulfate, filtered, and concentrated. The crude residue was purified by silica gel chromatography (0-100% ethyl acetate/hexanes) to afford the title compound.

Calc'd for C$_{21}$H$_{21}$F$_3$N$_3$O$_3$S [M+H]$^+$: 452. Found: 452.

Example 445

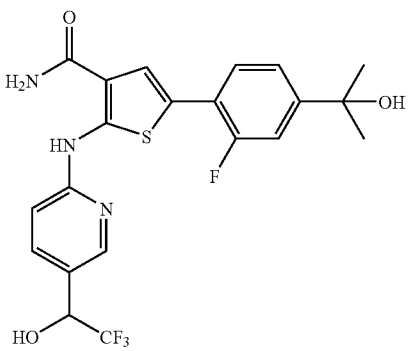 [SMILES: CC(C)(O)c1ccc(-c2cc(C(N)=O)c(Nc3ccc(C(O)C(F)(F)F)cn3)s2)c(F)c1]

5-[2-Fluoro-4-(1-hydroxy-1-methylethyl)phenyl]-2-{[5-(2,2,2-trifluoro-1-hydroxyethyl)pyridin-2-yl]amino}thiophene-3-carboxamide

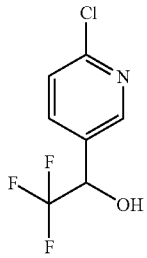

Step 1: 1-(6-Chloropyridin-3-yl)-2,2,2-trifluoroethanol

6-Chloronicotinaldehyde (500 mg, 3.53 mmol) was added to tetrahydrofuran (23 mL) and cooled to 0° C. Trimethyl (trifluoromethyl)silane (0.66 mL, 4.24 mmol) was added followed by 1 M tetra-n-butylammonium fluoride in tetrahydrofuran (4.24 mL, 4.24 mmol). The reaction mixture was allowed to warm to room temperature over 1 hour. The reaction was then diluted with water and brine and extracted with ethyl acetate three times. The organic layers were combined and dried over magnesium sulfate, filtered, and concentrated in vacuo. The concentrated material was purified via silica gel chromatography (0-40% ethyl acetate in hexanes) to afford the title compound.

Calc'd for $C_7H_5ClF_3NO$ $[M+H]^+$: 211. Found: 211.

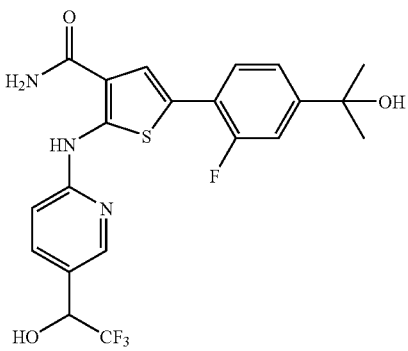 [SMILES: CC(C)(O)c1ccc(-c2cc(C(N)=O)c(Nc3ccc(C(O)C(F)(F)F)cn3)s2)c(F)c1]

Step 2: 5-[2-Fluoro-4-(1-hydroxy-1-methylethyl)phenyl]-2-{[5-(2,2,2-trifluoro-1-hydroxyethyl)pyridin-2-yl]amino}thiophene-3-carboxamide The title compound was prepared as described in Example 1 using 2-amino-5-[2-fluoro-4-(1-hydroxy-1-methylethyl)phenyl]thiophene-3-carboxamide (150 mg, 0.51 mmol) and 1-(6-chloropyridin-3-yl)-2,2,2-trifluoroethanol (108 mg, 0.51 mmol) as starting materials.

$^1$H NMR (600 MHz, d6-DMSO): δ 12.14 (s, 1H), 8.41 (s, 1H), 7.88 (s, 1H), 7.86 (s, 1H), 7.78 (d, 1H), 7.60 (t, 1H), 7.42 (s, 1H), 7.33 (m, 2H), 7.12 (d, 1H), 6.90 (d, 1H), 5.20 (p, 1H), 5.17 (s, 1H), 1.42 (s, 6H). Calc'd for $C_{21}H_{20}F_4N_3O_3S$ $[M+H]^+$: 470. Found: 470.

Example 446

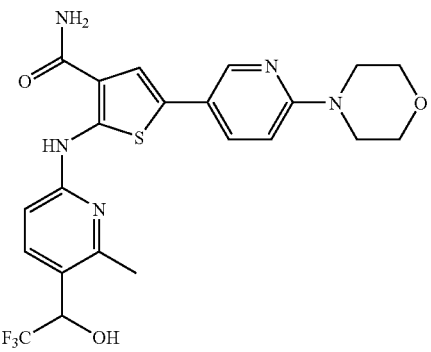 [SMILES: Cc1nc(Nc2sc(-c3ccc(N4CCOCC4)nc3)cc2C(N)=O)ccc1C(O)C(F)(F)F]

2-{[6-Methyl-5-(2,2,2-trifluoro-1-hydroxyethyl)pyridin-2-yl]amino}-5-(6-morpholin-4-ylpyridin-3-yl)thiophene-3-carboxamide

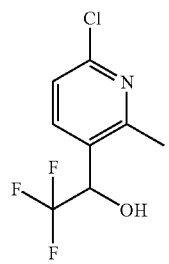

Step 1: 1-(6-Chloro-2-methylpyridin-3-yl)-2,2,2-trifluoroethanol

6-Chloro-2-methylnicotinaldehyde (250 mg, 1.6 mmol) was added to tetrahydrofuran (10.7 ml) and cooled to 0° C. Trimethyl(trifluoromethyl)silane (0.3 ml, 1.9 mmol) was added followed by tetrabutylammonium fluoride (1.9 ml, 1.0M in THF, 1.9 mmol). The reaction mixture was allowed to warm to room temperature over 1 hour. The reaction was then diluted with water and brine and extracted with ethyl acetate (3×). The organic layers were combined and dried over magnesium sulfate, filtered, and concentrated in vacuo to yield the title compound as a solid.

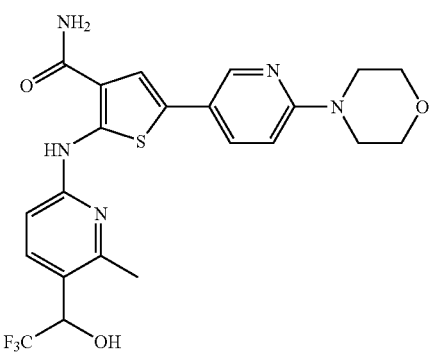

Step 2: 2-{[6-Methyl-5-(2,2,2-trifluoro-1-hydroxyethyl)pyridin-2-yl]amino}-5-(6-morpholin-4-ylpyridin-3-yl)thiophene-3-carboxamide The title compound was prepared as described in Example 1 using 2-amino-5-(6-morpholin-4-ylpyridin-3-yl)thiophene-3-carboxamide (150 mg, 0.49 mmol) and 1-(6-chloro-2-methylpyridin-3-yl)-2,2,2-trifluoroethanol (111 mg, 0.49 mmol) as starting materials.

$^1$H NMR (600 MHz, d6-DMSO): δ 11.96 (s, 1H), 8.34 (d, 1H), 7.75 (d, 1H), 7.72 (m, 2H), 7.64 (s, 1H), 7.39 (s, 1H), 6.93 (dd, 2H), 6.80 (d, 1H), 5.31 (m, 1H), 3.70 (t, 4H), 3.45 (t, 4H), 2.55 (s, 3H). Calc'd for $C_{22}H_{23}F_3N_5O_3S$ [M+H]$^+$: 494. Found: 494.

Example 447

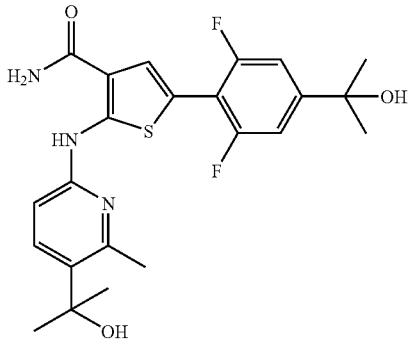 [SMILES: Cc1nc(Nc2sc(-c3c(F)cc(C(C)(C)O)cc3F)cc2C(N)=O)ccc1C(C)(C)O]

5-[2,6-Difluoro-4-(1-hydroxy-1-methylethyl)phenyl]-2-{[5-(1-hydroxy-1-methylethyl)-6-methylpyridin-2-yl]amino}thiophene-3-carboxamide

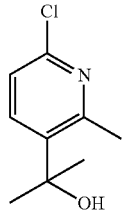

Step 1.
2-(6-Chloro-2-methylpyridin-3-yl)propan-2-ol

Methyl 6-chloro-2-methylnicotinate (Example 423 Step 2) (0.50 g, 2.7 mmol) was taken up in tetrahydrofuran (13.5 mL) and cooled to 0° C. Methyl magnesium bromide (1.0 mL of 3.0 M solution in tetrahydrofuran) was added dropwise and the reaction solution was stirred at 0° C. for 30 minutes and then allowed to warm to room temperature overnight. The reaction was quenched with water and extracted with ethyl acetate (3×). Organic layers were combined, dried over magnesium sulfate, filtered, and concentrated under reduced pressure. Purification via flash chromatography (silica, 0-70% ethyl acetate/hexanes) afforded the title compound.

Calc'd for $C_9H_{13}ClNO$ [M+H]$^+$: 186. found 186.

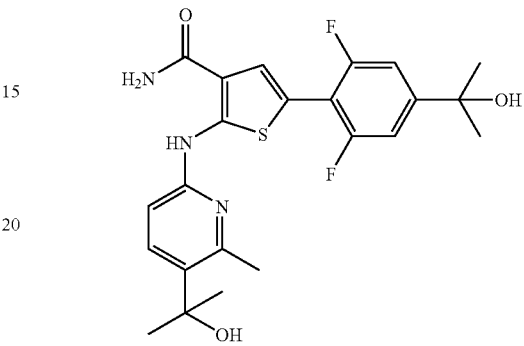

Step 2: 5-[2,6-difluoro-4-(1-hydroxy-1-methylethyl)phenyl]-2-{[5-(1-hydroxy-1-methylethyl)-6-methylpyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 2-(6-chloro-2-methylpyridin-3-yl)propan-2-ol (89 mg, 0.48 mmol) as starting materials.

$^1$H NMR (600 MHz, d6-DMSO): δ 11.96 (s, 1H), 7.84 (s, 1H), 7.74 (s, 1H0, 7.71 (d, 1H), 7.33 (s, 1H), 7.25 (d, 2H), 6.84 (d, 1H), 5.29 (s, 1H), 4.99 (s, 1H), 2.69 (s, 3H), 1.48 (s, 6H), 1.42 (s, 6H). Calc'd for $C_{23}H_{25}F_2N_3O_3S$ [M+H]$^+$: 462. Found: 462.

Example 448

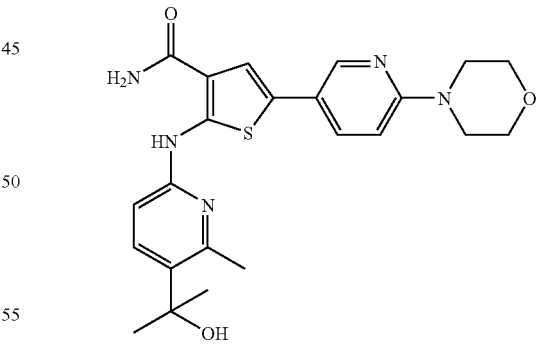

2-{[5-(1-Hydroxy-1-methylethyl)-6-methylpyridin-2-yl]amino}-5-(6-morpholin-4-ylpyridin-3-yl)thiophene-3-carboxamide The title compound was prepared as described in Example 1 using 2-amino-5-(6-morpholin-4-ylpyridin-3-yl)thiophene-3-carboxamide (91 mg, 0.49 mmol) 2-(6-chloro-2-methylpyridin-3-yl)propan-2-ol (89 mg, 0.48 mmol) (Example 447, Step 1) (150 mg, 0.49 mmol) as starting materials.

¹H NMR (600 MHz, d6-DMSO): δ 11.78 (s, 1H), 8.32 (s, 1H), 7.68 (m, 3H), 7.62 (s, 1H), 7.31 (s, 1H), 6.91 (d, 1H), 6.79 (d, 1H), 4.99 (s, 1H), 3.70 (m, 4H), 3.45 (m, 4H), 2.72 (s, 3H), 1.49 (s, 6H).

Example 449

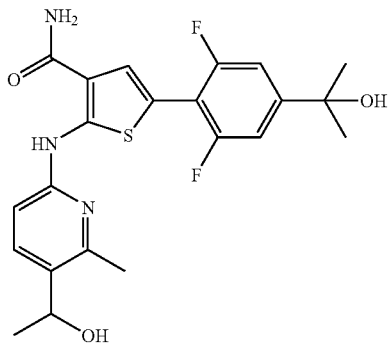

5-[2,6-Difluoro-4-(1-hydroxy-1-methylethyl)phenyl]-2-{[5-(1-hydroxyethyl)-6-methylpyridin-2-yl]amino}thiophene-3-carboxamide

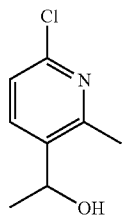

Step 1: 1-(6-Chloro-2-methylpyridin-3-yl)ethanol

6-Chloro-2-methylnicotinaldehyde (300 mg, 1.93 mmol) was taken up in THF (9.6 ml) under argon and cooled to –78° C. Methylmagnesium bromide (1.29 ml, 3.86 mmol) was added dropwise over 5 minutes. The reaction temperature was maintained at –78° C. for 20 minutes, then was allowed to warm to 0° C. over 2 hours. The reaction was quenched with saturated aqueous ammonium chloride and allowed to warm to room temperature. The reaction mixture was extracted three times with ethyl acetate, dried over anhydrous magnesium sulfate, filtered, and concentrated. The crude residue was purified by silica gel chromatography (10-75% ethyl acetate/hexanes) to afford the title compound.

Calc'd for $C_8H_{11}ClNO$ [M+H]⁺: 172. Found: 172.

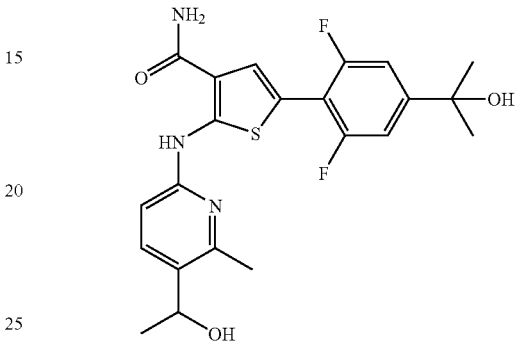

Step 2: 5-[2,6-Difluoro-4-(1-hydroxy-1-methylethyl)phenyl]-2-{[5-(1-hydroxyethyl)-6-methylpyridin-2-yl]amino}thiophene-3-carboxamide The title compound was prepared in the same manner described in Example 1 using 2-amino-5-[2,6-difluoro-4-(1-hydroxy-1-methylethyl)phenyl]thiophene-3-carboxamide (150 mg, 0.48 mmol) and 1-(6-chloro-2-methylpyridin 3-yl) ethanol (82 mg, 0.48 mmol) as starting materials.

Calc'd for $C_{22}H_{24}F_2N_3O_3S$ [M+H]⁺: 448. Found: 448.

Additional examples were prepared by using procedures similar to those described above and are illustrated in the following table.

TABLE 44

| Example # | Structure | Compound Name | Characterization [M + H]⁺ |
|---|---|---|---|
| 450 | 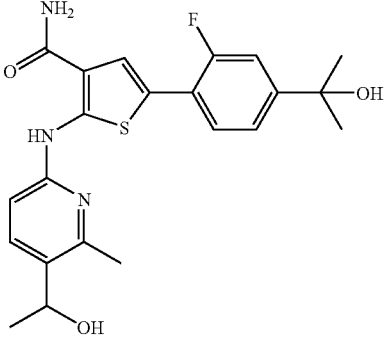 [SMILES: Cc1nc(Nc2sc(-c3ccc(C(C)(C)O)cc3F)cc2C(N)=O)ccc1C(C)O] | 5-[2-fluoro-4-(1-hydroxy-1-methylethyl)phenyl]-2-{[5-(l-hydroxyethyl)-6-methylpyridin-2-yl]amino}thiophene-3-carboxamide | Calc'd 430, found 430 |

TABLE 44-continued

| Example # | Structure | Compound Name | Characterization [M + H]+ |
|---|---|---|---|
| 451 | 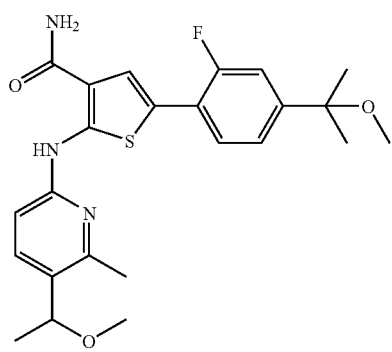 [SMILES: COC(C)c1ccc(Nc2sc(-c3ccc(C(C)(C)OC)cc3F)cc2C(N)=O)nc1C] | 2-{[5-(1-hydroxyethyl)-6-methylpyridin-2-yl]amino}-5-(6-morpholin-4-ylpyridin-3-yl)thiophene-3-carboxamide | Calc'd 440, found 440 |

Example 452

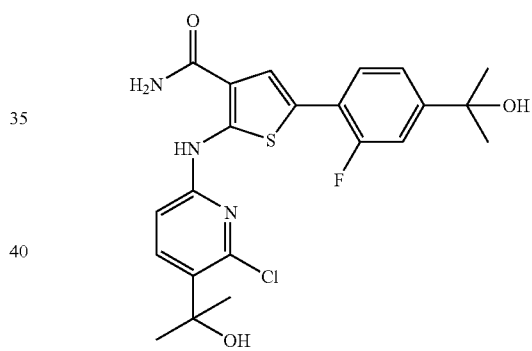

5-[2-Fluoro-4-(1-methoxy-1-methylethyl)phenyl]-2-{[5-(1-methoxyethyl)-6-methylpyridin-2-yl]amino}thiophene-3-carboxamide 5-[2-Fluoro-4-(1-hydroxy-1-methylethyl)phenyl]-2-{[5-(1-hydroxyethyl)-6-methylpyridin-2-yl]amino}thiophene-3-carboxamide (105 mg, 0.24 mmol) was taken-up in methanol (20 ml) and treated with trifluoroacetic acid (2.00 ml, 26.0 mmol). The reaction mixture was stirred at 60° C. for two hours. After cooling to room temperature, the reaction mixture was concentrated and the crude residue was purified by silica gel chromatography (15-75% ethyl acetate/hexanes) to afford the title compound.

Calc'd for $C_{22}H_{29}FN_3O_3S$ [M+H]+: 458. Found: 458.

Chiral separation of 5-[2-fluoro-4-(1-methoxy-1-methylethyl)phenyl]-2-{[5-(1-methoxyethyl)-6-methylpyridin-2-yl]amino}thiophene-3-carboxamide using chiral HPLC (AD column (2×25 cm, 10 uM), isochratic, 15% isopropanol/heptane, 10 mL/min, 254 nM) afforded the two enantiomers of the title compound with retention times of 26.75 min and 28.46 min.

Enantiomer A: $^1$H NMR (500 MHz, d6-DMSO) δ 11.98 (s, 1H), 7.86 (s, 1H), 7.83 (s, 1H), 7.63 (t, 1H), 7.58 (d, 1H), 7.36 (s, 1H), 7.26 (m, 1H), 7.24 (m, 1H), 6.92 (d, 1H), 4.51 (m, 1H), 3.11 (s, 3H), 3.00 (s, 3H), 2.51 (s, 3H), 1.45 (s, 6H), 1.31 (s, 3H). Calc'd for $C_{22}H_{29}FN_3O_3S$ [M+1]+: 458. Found: 458. $\tau_r$=26.75.

Enantiomer B: $^1$H NMR (500 MHz, d6-DMSO) δ 11.98 (s, 1H), 7.86 (s, 1H), 7.83 (s, 1H), 7.63 (t, 1H), 7.58 (d, 1H), 7.36 (s, 1H), 7.26 (m, 1H), 7.24 (m, 1H), 6.92 (d, 1H), 4.51 (m, 1H), 3.11 (s, 3H), 3.00 (s, 3H), 2.51 (s, 3H), 1.45 (s, 6H), 1.31 (s, 3H). $\tau_r$=28.46 min.

Example 453

2-{[6-Chloro-5-(1-hydroxy-1-methylethyl)pyridin-2-yl]amino}-5-[2-fluoro-4-(1-hydroxy-1-methylethyl)phenyl]thiophene-3-carboxamide

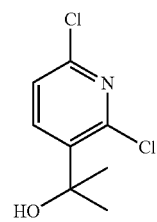

Step 1: 2-(2,6-Dichloropyridin-3-yl)propan-2-ol

A 0.2 M solution of methyl 2,6-dichloronicotinate (500 mg, 2.43 mmol) in tetrahydrofuran (12 mL) was added to a dry flask and cooled to 0° C. A 3 M solution of bromo(methyl)

magnesium in tetrahydrofuran (2.43 mL, 7.28 mmol) was added dropwise and the reaction solution was stirred at 0° C. for 30 minutes. It was then allowed to warm to room temperature overnight. The reaction was quenched with water and extracted with ethyl acetate. The organic layer was washed with water (2×). The organic layer was dried over magnesium sulfate, filtered, and concentrated in vacuo to afford the title compound.

Calc'd for $C_8H_{10}C_{12}NO$ [M+H]$^+$: 205. Found: 205.

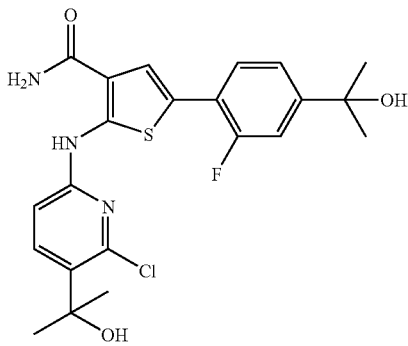 [SMILES: CC(C)(O)c1ccc(-c2cc(C(N)=O)c(Nc3ccc(C(C)(C)O)c(Cl)n3)s2)c(F)c1]

Step 2: 2-{[6-Chloro-5-(1-hydroxy-1-methylethyl) pyridin-2-yl]amino}-5-[2-fluoro-4-(1-hydroxy-1-methylethyl)phenyl]thiophene-3-carboxamide The title compound was prepared as described in Example 1 using 2-amino-5-[2-fluoro-4-(1-hydroxy-1-methylethyl) phenyl]thiophene-3-carboxamide (300 mg, 1.02 mmol) and 2-(2,6-dichloropyridin-3-yl)propan-2-ol (210 mg, 1.02 mmol) as starting materials.

$^1$H NMR (600 MHz, d6-DMSO): δ 12.1 (s, 1H), 8.08 (d, 1H), 7.88 (s, 1H), 7.85 (s, 1H), 7.56 (t, 1H), 7.43 (s, 1H), 7.34 (m, 2H), 7.09 (d, 1H), 5.37 (s, 1H), 5.17 (s, 1H), 1.58 (s, 6H), 1.42 (s, 6H). Calc'd for $C_{22}H_{24}ClFN_3O_3S$ [M+H]$^+$: 464. Found: 464.

Example 454

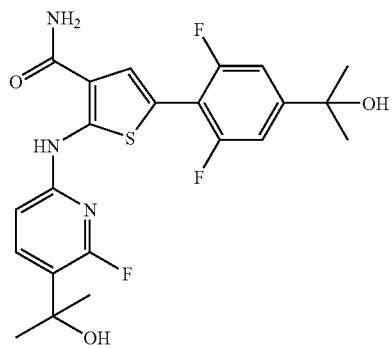

5-[2,6-Difluoro-4-(1-hydroxy-1-methylethyl)phenyl]-2-{[6-fluoro-5-(1-hydroxy-1-methylethyl)pyridin-2-yl]amino}thiophene-3-carboxamide

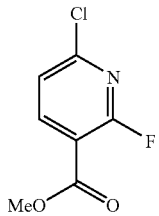 [SMILES: COC(=O)c1ccc(Cl)nc1F]

Step 1. Methyl 6-chloro-2-fluoronicotinate

2-Chloro-6-fluoropyridine (298 mg, 2.3 mmol) was taken up in tetrahydrofuran (11.4 mL) and cooled to −78° C. n-Butyllithium (1.42 mL of 1.6 M in hexanes, 2.3 mmol) was added dropwise over 5 min. The solution was stirred for 30 minutes and methyl chloroformate (0.3 mL, 3.9 mmol) was added dropwise over 15 minutes. The resulting mixture was stirred at −78° C. for 2 hrs and then warmed to 0° C. and stirred for 3 hours. The reaction was then quenched with saturated aqueous ammonium chloride and extracted with ethyl acetate. The combined organics were dried over magnesium sulfate, filtered, and concentrated in vacuo. The crude residue was purified by flash chromatography (silica, 0-17% ethyl acetate/hexanes) to afford the title compound as a white solid.

$^1$H NMR (500 MHz, d6-DMSO): δ 8.45 (dd, 1H), 7.65 (d, 1H), 3.86 (s, 3H).

Step 2. 2-(6-Chloro-2-fluoropyridin-3-yl)propan-2-ol

Methyl 6-chloro-2-fluoronicotinate (60 mg, 0.32 mmol) was taken up in tetrahydrofuran (1.6 ml) and cooled to 0° C. Methylmagnesium bromide (0.26 ml of 3.0 M in diethyl ether, 0.78 mmol) was added dropwise. The reaction was stirred for two hours at 0° C. and then warmed to room temperature and stirred for an additional three hours. The reaction was quenched with saturated aqueous ammonium chloride and extracted with ethyl acetate (2×). The combined organics were dried over magnesium sulfate, filtered, and concentrated in vacuo. Purification via flash chromatography (silica, 0-60% ethyl acetate/hexanes) afforded the title compound as a light yellow oil.

$^1$H NMR (500 MHz, d6-DMSO): δ 8.11 (dd, 1H), 7.48 (d, 1H), 5.55 (s, 1H), 1.45 (s, 6H).

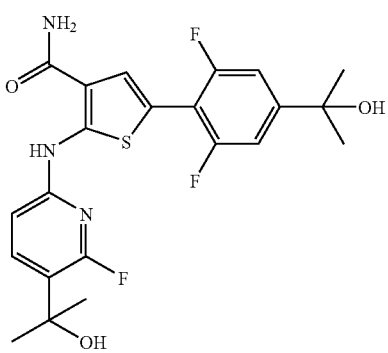 [SMILES: CC(C)(O)c1cc(F)c(-c2cc(C(N)=O)c(Nc3ccc(C(C)(C)O)c(F)n3)s2)c(F)c1]

Step 3. 5-[2,6-difluoro-4-(1-hydroxy-1-methylethyl)phenyl]-2-{[6-fluoro-5-(1-hydroxy-1-methylethyl)pyridin-2-yl]amino}thiophene-3-carboxamide The title compound was prepared as described in Example 1 using, 2-amino-5-[2,6-difluoro-4-(1-hydroxy-1-methylethyl)phenyl]thiophene-3-carboxamide (52 mg, 0.17 mmol) and 2-(6-chloro-2-fluoropyridin-3-yl)propan-2-ol (32 mg, 0.17 mmol) as starting materials.

$^1$H NMR (500 MHz, d6-DMSO): δ 12.21 (s, 1H), 7.99 (dd, 1H), 7.95 (s, 1H), 7.80 (s, 1H), 7.45 (s, 1H), 7.27 (d, 2H), 6.99 (d, 1H), 5.33 (s, 1H), 5.30 (s, 1H), 1.46 (s, 6H), 1.43 (s, 6H). Calc'd for $C_{22}H_{23}F_3N_3O_3S$ [M+H]$^+$: 466. found 466.

Example 455

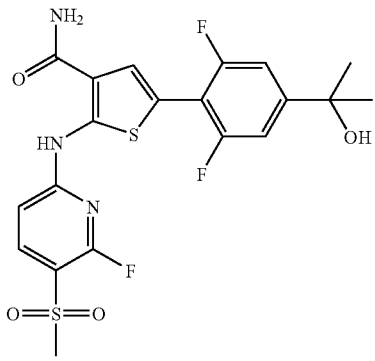 [SMILES: CC(C)(O)c1cc(F)c(-c2cc(C(N)=O)c(Nc3ccc(S(C)(=O)=O)c(F)n3)s2)c(F)c1]

5-[2,6-Difluoro-4-(1-hydroxy-1-methylethyl)phenyl]-2-{[6-fluoro-5-(methylsulfonyl)pyridin-2-yl]amino}thiophene-3-carboxamide

Step 1:
6-Chloro-2-fluoro-3-(methylsulfonyl)pyridine

2-Chloro-6-fluoropyridine (500 mg, 3.8 mmol) was taken up in tetrahydrofuran (19 mL) and cooled to −78° C. n-Butyllithium (2.4 mL, 3.8 mmol) was added dropwise over 10 minutes. The solution was stirred for 30 minutes and methanesulfonyl chloride (0.3 mL, 3.8 mmol) was added dropwise over 15 minutes. The resulting mixture was stirred at −78° C. for 2 hours and then warmed to 0° C. and stirred for 2 hours followed by an additional 2 hours at room temperature. The reaction was quenched with saturated aqueous ammonium chloride and extracted with ethyl acetate (2×). The combined organics were dried over magnesium sulfate, filtered, and concentrated in vacuo. The crude residue was purified by flash chromatography (silica, 0-75% ethyl acetate/hexanes) to afford the title compound as a light yellow oil.

Calc'd for $C_6H_6ClFNO_2S$ [M+H]$^+$: 210. found 210.

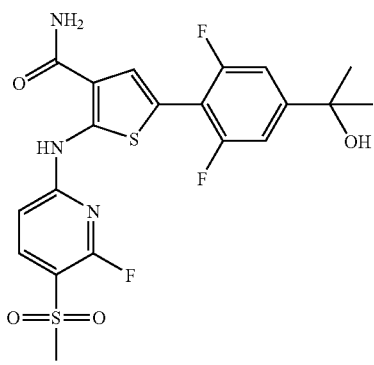 [SMILES: CC(C)(O)c1cc(F)c(-c2cc(C(N)=O)c(Nc3ccc(S(C)(=O)=O)c(F)n3)s2)c(F)c1]

Step 2. 5-[2,6-Difluoro-4-(1-hydroxy-1-methylethyl)phenyl]-2-{[6-fluoro-5-(methylsulfonyl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (45 mg, 0.14 mmol) and 6-chloro-2-fluoro-3-(methylsulfonyl)pyridine (30 mg, 0.14 mmol) as starting materials.

$^1$H NMR (500 MHz, d6-DMSO): δ 12.75 (s, 1H), 8.10 (m, 2H), 7.87 (s, 1H), 7.67 (s, 1H), 7.29 (d, 2H), 7.21 (d, 1H), 5.33 (s, 1H), 3.29 (s, 3H), 1.43 (s, 6H). Calc'd for $C_{20}H_{19}F_3N_3O_4S_2$ [M+H]$^+$: 486. found 486.

Example 456

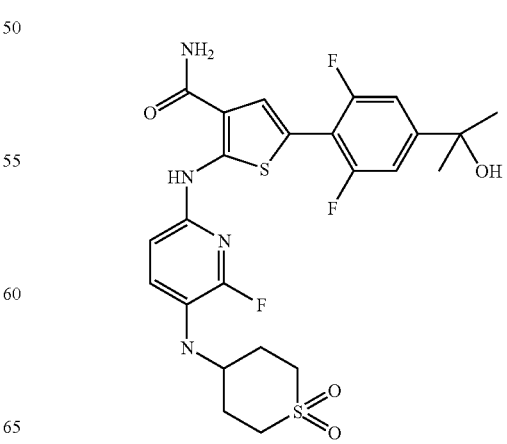

5-[2,6-Difluoro-4-(1-hydroxy-1-methylethyl)phenyl]-2-({5-[(1,1-dioxidothiomorpholin-4-yl)methyl]-6-fluoropyridin-2-yl}amino)thiophene-3-carboxamide

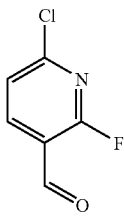

Step 1. 6-Chloro-2-fluoronicotinaldehyde

Diisopropylamine (1.14 ml, 8.0 mmol) was taken up in 8 mL tetrahydrofuran and cooled to −78° C. n-Buyllithium (4.8 ml, 7.6 mmol) was added dropwise. The flask was then warmed to 0° C. in an ice bath and stirred for 30 minutes. The reaction mixture was then added dropwise to a cooled (−78° C.) solution of 2-chloro-6-fluoropyridine (1.0 g, 7.60 mmol) in tetrahydrofuran (25.3 ml). The reaction mixture was stirred at −78° C. for one hour. Dimethylformamide (0.88 ml, 11.4 mmol) was added dropwise and the mixture was stirred an additional 2 hours at −78° C. The reaction was quenched via the addition of 1N aqueous hydrochloric acid and allowed to warm to room temperature. The resulting biphasic mixture was extracted twice with ethyl acetate. The combined organics were dried over magnesium sulfate, filtered, and concentrated in vacuo. The crude residue was purified by flash chromatography (silica, 0-17% ethyl acetate/hexanes) to afford the title compound.

$^1$H NMR (500 MHz, CDCl$_3$): δ 10.27 (s, 1H), 8.26 (dd, 1H), 7.41 (d, 1H).

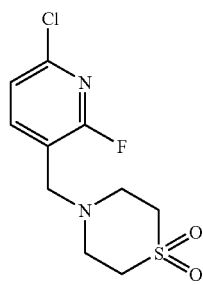 [SMILES: O=S1(=O)CCN(Cc2ccc(Cl)nc2F)CC1]

Step 2. 4-[(6-Chloro-2-fluoropyridin-3-yl)methyl]thiomorpholine 1,1-dioxide

6-Chloro-2-fluoronicotinaldehyde (116 mg, 0.73 mmol) was added to a 200 mL round bottom under argon. Dichloroethane (2.9 ml) was added followed by thiomorpholine 1,1-dioxide (98 mg, 0.73 mmol). The mixture was stirred for 45 min at room temperature, at which time sodium triacetoxyborohydride (216 mg, 1.02 mmol) was added. The resulting slurry was stirred for 72 hours at room temperature. Saturated aqueous sodium bicarbonate was added and the resulting mixture was extracted twice with ethyl acetate. The combined organics were dried over magnesium sulfate, filtered, and concentrated in vacuo. The crude residue was purified by flash chromatography (silica, 0-100% ethyl acetate/hexanes) to afford the title compound.

Calc'd for C$_{10}$H$_{13}$ClFN$_2$O$_2$S [M+H]$^+$: 279. found 279.

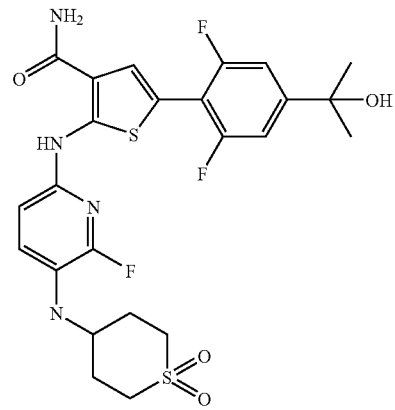 [SMILES: CC(C)(O)c1cc(F)c(-c2cc(C(N)=O)c(Nc3ccc(NC4CCS(=O)(=O)CC4)c(F)n3)s2)c(F)c1]

Step 3. 5-[2,6-Difluoro-4-(1-hydroxy-1-methylethyl)phenyl]-2-({5-[(1,1-dioxidothiomorpholin-4-yl)methyl]-6-fluoropyridin-2-yl}amino)thiophene-3-carboxamide The title compound was prepared as described in Example 1 using 2-amino-5-[2,6-difluoro-4-(1-hydroxy-1-methylethyl)phenyl]thiophene-3-carboxamide (25 mg, 0.08 mmol) and 4-[(6-chloro-2-fluoropyridin-3-yl)methyl]thiomorpholine 1,1-dioxide (22 mg, 0.08 mmol) as starting materials.

$^1$H NMR (500 MHz, d6-DMSO): δ 12.28 (s, 1H), 7.97 (s, 1H), 7.85 (m, 1H), 7.80 (s, 1H), 7.47 (s, 1H), 7.27 (d, 2H), 7.04 (d, 1H), 5.31 (s, 1H), 3.64 (s, 2H), 3.09 (m, 4H), 2.87 (m, 4H), 1.43 (s, 6H). Calc'd for C$_{24}$H$_{25}$F$_3$N$_4$O$_4$S$_2$Na [M+Na]: 577. found 577.

Example 457

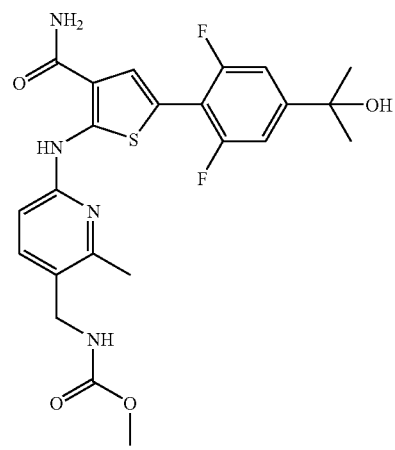 [SMILES: COC(=O)NCc1ccc(Nc2sc(-c3c(F)cc(C(C)(C)O)cc3F)cc2C(N)=O)nc1C]

463

Methyl{[6-({3-(aminocarbonyl)-5-[2,6-difluoro-4-(1-hydroxy-1-methylethyl)phenyl]-2-thienyl}amino)-2-methylpyridin-3-yl]methyl}carbamate

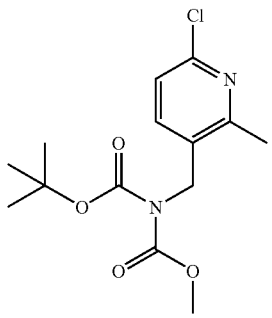 [SMILES: COC(=O)N(Cc1ccc(Cl)nc1C)C(=O)OC(C)(C)C]

Step 1: ten-Butyl methyl[(6-chloro-2-methylpyridin-3-yl)methyl]imidodicarbonate 3-(Bromomethyl)-6-chloro-2-methylpyridine (Example 421 Step 2) (625 mg, 2.83 mmol), iminodicarboxylic acid tert-butyl methyl ester (596 mg, 3.40 mmol), and $K_2CO_3$ (783 mg, 5.67 mmol) were combined in DMF (10 mL) and stirred at 50° C. for 2 h. The mixture was diluted with water and extracted with EtOAc (2×). The combined organic layers were washed with brine, dried ($MgSO_4$), filtered, and evaporated. Flash chromatography (0-40% EtOAc/hexanes) yielded the title compound as a colorless oil.

Calc'd for $C_{14}H_{20}ClN_2O_4$ [M+H]$^+$ 315. found 315.

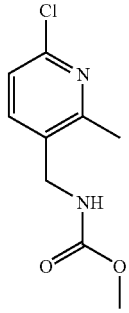

Step 2: Methyl[(6-chloro-2-methylpyridin-3-yl)methyl]carbamate tert-Butyl methyl[(6-chloro-2-methylpyridin-3-yl)methyl]imidodicarbonate (830 mg, 2.64 mmol) was taken up in a mixture of $CH_2Cl_2$ (8.0 ml) and TFA (2.0 ml) and stirred at room temperature for 1 h. The solution was concentrated, diluted with EtOAc, and washed with saturated $NaHCO_3$. The organic layer was washed with brine, dried ($MgSO_4$), filtered, and evaporated. Flash chromatography (25-100% EtOAc/hexanes) afforded the title compound as a colorless solid.

MS calcd for $C_9H_{12}ClN_2O_2$[M+H]$^+$ 215. found 215.

464

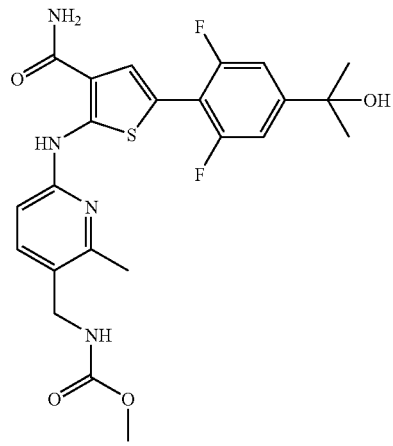 [SMILES: COC(=O)NCc1ccc(Nc2sc(-c3c(F)cc(C(C)(C)O)cc3F)cc2C(N)=O)nc1C]

Step 3: Methyl{[6-({3-(aminocarbonyl)-5-[2,6-difluoro-4-(1-hydroxy-1-methylethyl)phenyl]-2-thienyl}amino)-2-methylpyridin-3-yl]methyl}carbamate The title compound was synthesized from methyl[(6-chloro-2-methylpyridin-3-yl)methyl]carbamate (85 mg, 0.40 mmol) and 2-amino-5-[2,6-difluoro-4-(1-hydroxy-1-methylethyl)phenyl]thiophene-3-carboxamide (130 mg, 0.42 mmol) according to the general procedure in Example 1.

MS calcd for $C_{23}H_{24}F_2N_4O_4S$ [M+H]$^+$ 491. found 491.

Example 458

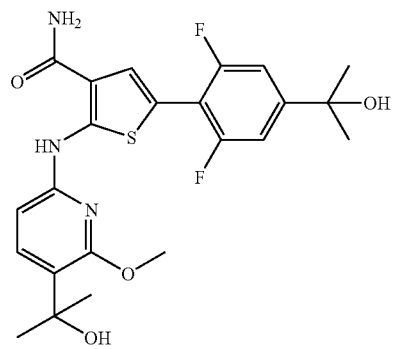 [SMILES: COc1nc(Nc2sc(-c3c(F)cc(C(C)(C)O)cc3F)cc2C(N)=O)ccc1C(C)(C)O]

5-[2,6-Difluoro-4-(1-hydroxy-1-methylethyl)phenyl]-2-{[5-(1-hydroxy-1-methylethyl)-6-methoxypyridin-2-yl]amino}thiophene-3-carboxamide

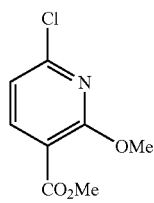 [SMILES: COC(=O)c1ccc(Cl)nc1OC]

Step 1: Methyl 6-chloro-2-methoxynicotinate

Methyl 6-chloro-2-fluoronicotinate (Example 454, Step 1) (76 mg, 0.40 mmol) was taken up in a 0.5 M solution of sodium methoxide in methanol (0.80 ml, 0.40 mmol) and stirred at room temperature for 3 hours. The mixture was quenched with saturated aqueous ammonium chloride and extracted twice with ethyl acetate. The combined organics were dried over magnesium sulfate, filtered, and concentrated in vacuo. The resulting residue was purified via flash chromatography (silica, 0-17% ethyl acetate/hexanes) to afford the title compound as a white solid.

Calc'd for $C_8H_9ClNO_3$ $[M+H]^+$: 202. found 202.

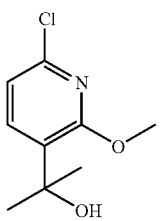

Step 2: 2-(6-Chloro-2-methoxypyridin-3-yl)propan-2-ol

Methyl 6-chloro-2-methoxynicotinate (50 mg, 0.25 mmol) was taken up in tetrahydrofuran (1.2 mL) and cooled to 0° C. Methylmagnesium bromide (0.29 mL of 3.0 M in diethyl ether, 0.74 mmol) was added dropwise. The reaction was stirred for two hours, then allowed to reach room temperature and left to stir for an additional three hours. The reaction was quenched with saturated aqueous ammonium chloride and extracted with ethyl acetate (2×). The combined organics were dried over magnesium sulfate, filtered and concentrated in vacuo. Purification via flash chromatography (silica, 0-60% ethyl acetate/hexanes) afforded the title compound as a light yellow oil.

$^1$H NMR (500 MHz, CDCl$_3$): δ 7.58 (d, 1H), 6.91 (d, 1H), 4.04 (s, 3H), 3.41 (s, 1H), 1.58 (s, 6H).

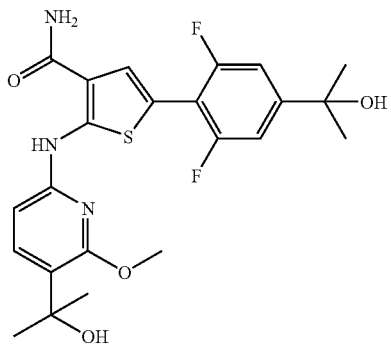 [SMILES: COc1nc(Nc2sc(-c3c(F)cc(C(C)(C)O)cc3F)cc2C(N)=O)ccc1C(C)(C)O]

Step 3: 5-[2,6-Difluoro-4-(1-hydroxy-1-methylethyl)phenyl]-2-{[5-(1-hydroxy-1-methylethyl)-6-methoxypyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (60 mg, 0.19 mmol) and 2-(6-chloro-2-methoxypyridin-3-yl)propan-2-ol (39 mg, 0.19 mmol) as starting materials.

$^1$H NMR (500 MHz, d6-DMSO): δ 12.00 (s, 1H), 7.89 (s, 1H), 7.83 (d, 1H), 7.81 (s, 1H), 7.37 (s, 1H), 7.25 (d, 2H), 6.58 (d, 1H), 5.27 (s, 1H), 5.02 (s, 1H), 4.07 (s, 3H), 1.44 (s, 6H), 1.42 (s, 6H). Calc'd for $C_{23}H_{26}F_2N_3O_4S$ $[M+H]^+$: 478. found 478.

Example 459

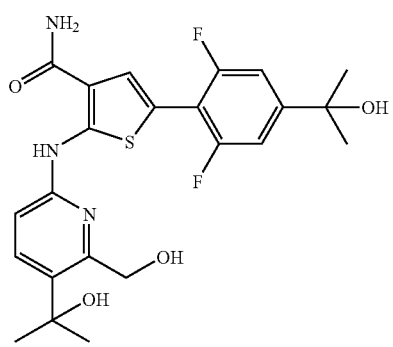 [SMILES: CC(C)(O)c1cc(F)c(-c2cc(C(N)=O)c(Nc3ccc(C(C)(C)O)c(CO)n3)s2)c(F)c1]

5-[2,6-Difluoro-4-(1-hydroxy-1-methylethyl)phenyl]-2-{[6-(hydroxymethyl)-5-(1-hydroxy-1-methylethyl)pyridin-2-yl]amino}thiophene-3-carboxamide

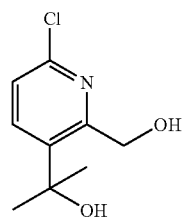

Step 1: 2-[6-Chloro-2-(hydroxymethyl)pyridin-3-yl]propan-2-ol

Methyl 6-chloro-2-{[(3-chlorobenzoyl)oxy]methyl} nicotinate (Example 423, Step 4) (1 g, 2.94 mmol) was taken up in tetrahydrofuran (14.7 ml) and cooled to 0° C. Methylmagnesium bromide (5.9 ml of 3.0M in diethyl ether, 17.6 mmol) was added dropwise. The reaction was stirred for two hours, then allowed to reach room temperature and left to stir overnight. The reaction was quenched with saturated aqueous ammonium chloride and extracted with ethyl acetate (2×). The combined organics were dried over anhydrous magnesium sulfate, filtered, and concentrated in vacuo. Purification via flash chromatography (silica, 0-60% ethyl acetate/hexanes) afforded the title compound as a light orange oil.

$^1$H NMR (500 MHz, CDCl$_3$): δ 7.64 (d, 1H), 7.21 (d, 1H), 4.97 (s, 2H), 4.30 (s, 1H), 2.02 (s, 1H), 1.63 (s, 6H).

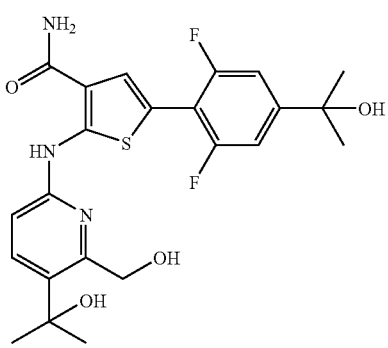 [SMILES: CC(C)(O)c1cc(F)c(-c2cc(C(N)=O)c(Nc3ccc(C(C)(C)O)c(CO)n3)s2)c(F)c1]

Step 2: 5-[2,6-Difluoro-4-(1-hydroxy-1-methylethyl)
phenyl]-2-{[6-(hydroxymethyl)-5-(1-hydroxy-1-
methylethyl)pyridin-2-yl]amino}thiophene-3-car-
boxamide The title compound was prepared as described in Example 1 using 2-amino-5-[2,6-difluoro-4-(1-hydroxy-1-methylethyl)phenyl]thiophene-3-carboxamide (105 mg, 0.34 mmol) and 2-[6-chloro-2-(hydroxymethyl)pyridin-3-yl]propan-2-ol (71 mg, 0.35 mmol) as starting materials.

$^1$H NMR (500 MHz, d6-DMSO): δ 12.05 (s, 1H), 7.90 (s, 1H), 7.78 (s, 1H), 7.72 (d, 1H), 7.38 (s, 1H), 7.26 (d, 2H), 6.97 (d, 1H), 5.35 (s, 1H), 5.29 (s, 1H), 4.86 (m, 2H), 4.81 (m, 1H), 1.49 (s, 6H), 1.43 (s, 6H). Calc'd for $C_{23}H_{26}F_2N_3O_4S$ [M+H]$^+$: 478. found 478.

Example 460

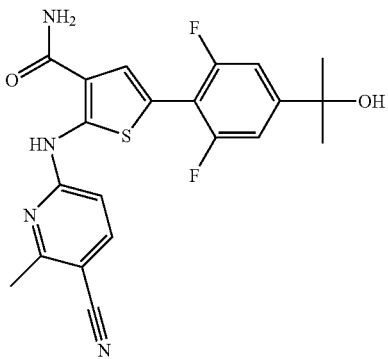 [SMILES: Cc1nc(Nc2sc(-c3c(F)cc(C(C)(C)O)cc3F)cc2C(N)=O)ccc1C#N]

2-[(5-Cyano-6-methylpyridin-2-yl)amino]-5-[2,6-
difluoro-4-(1-hydroxy-1-methylethyl)phenyl]
thiophene-3-carboxamide

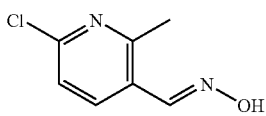

Step 1: 6-Chloro-2-methylnicotinaldehyde oxime

6-Chloro-2-methylnicotinaldehyde (1 g, 6.43 mmol), hydroxylamine hydrochloride (0.45 g, 6.43 mmol), and sodium acetate (0.53 g, 6.43 mmol) were dissolved in dry ethanol (32 ml) and transferred to a flame-dried round bottom flask. The reaction was allowed to stir at room temperature for 20 minutes. It was then concentrated under reduced pressure, re-dissolved in ethyl acetate, and washed with water. The aqueous layer was extracted with ethyl acetate two times. The organic layers were combined, dried over magnesium sulfate, filtered, and concentrated under reduced pressure. Purification was performed via silica gel chromatography (0-100% ethyl acetate in hexane) to afford the title compound.

$^1$H NMR (600 MHz, d6-DMSO): δ 8.30 (s, 1H), 7.99 (d, 1H), 7.36 (d, 1H), 2.53 (s, 3H).

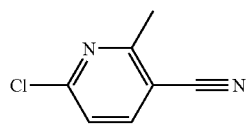

Step 2: 6-Chloro-2-methylnicotinonitrile

6-Chloro-2-methylnicotinaldehyde oxime (800 mg, 4.69 mmol) was placed in a flask which was then evacuated and backfilled with argon three times. Dry dichloromethane (27.3 ml) was then added and the solution was stirred at room temperature. 3,3,3-Triethyl-1-(methoxycarbonyl)diazathian-3-ium-1-ide 2,2-dioxide (3.91 g, 16.4 mmol) was added in 5 portions over 2 hours. The reaction was allowed to stir at room temperature-overnight. It was directly purified via silica gel chromatography (0-100% ethyl acetate in hexane) to afford the title compound.

$^1$H NMR (600 MHz, d6-DMSO): δ 8.30 (d, 1H), 7.59 (d, 1H), 2.64 (s, 3H).

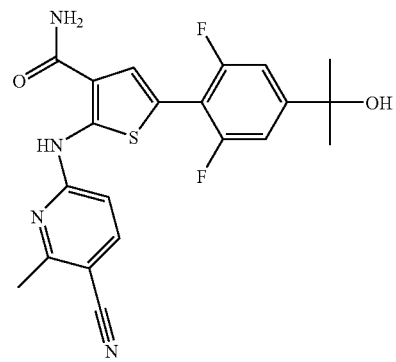 [SMILES: Cc1nc(Nc2sc(-c3c(F)cc(C(C)(C)O)cc3F)cc2C(N)=O)ccc1C#N]

Step 3: 2-[(5-Cyano-6-methylpyridin-2-yl)amino]-5-
[2,6-difluoro-4-(1-hydroxy-1-methylethyl)phenyl]
thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 6-chloro-2-methylnicotinonitrile (73 mg, 0.48 mmol) as starting materials.

¹H NMR (600 MHz, d6-DMSO): δ 12.47 (s, 1H), 8.02 (s, 1H), 7.99 (d, 1H), 7.82 (s, 1H), 7.54 (s, 1H), 7.27 (d, 2H), 7.11 (d, 1H), 5.31 (s, 1H), 2.63 (s, 3H), 1.43 (s, 6H). Calc'd for $C_{21}H_{19}F_2N_4O_2S$ [M+H]⁺: 429. Found: 429.

Example 461

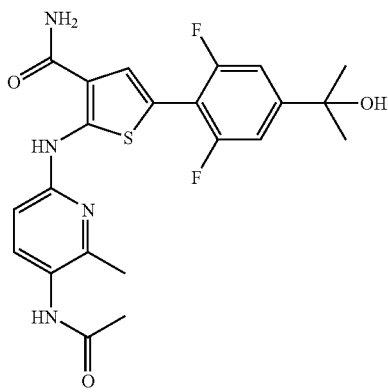 [SMILES: CC(=O)Nc1ccc(Nc2sc(-c3c(F)cc(C(C)(C)O)cc3F)cc2C(N)=O)nc1C]

2-{[5-(Acetylamino)-6-methylpyridin-2-yl]amino}-5-[2,6-difluoro-4-(1-hydroxy-1-methylethyl)phenyl]thiophene-3-carboxamide

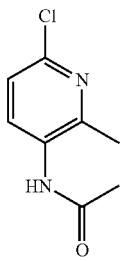

Step 1: N-(6-Chloro-2-methylpyridin-3-yl)acetamide

In a dry flask, 6-chloro-2-methylpyridin-3-amine (200 mg, 1.40 mmol) and triethylamine (217 μl, 1.56 mmol) were taken up in dichloromethane (7.0 ml) under argon. The solution was cooled to 0° C. and stirred for 20 minutes. Acetic anhydride (134 μl, 1.42 mmol) was added dropwise over 15 minutes. The mixture was allowed to warm to room temperature and left to stir for 22 hours. The reaction was quenched with aqueous sodium bicarbonate and washed with ethyl acetate three times. The organic layers were combined, dried over anhydrous magnesium sulfate, filtered, and concentrated. The resulting crude product was purified by silica gel chromatography (0-100% ethyl acetate/hexanes) to afford the title compound.

Calc'd for $C_8H_{10}ClN_2O$ [M+H]⁺: 185. Found: 185.

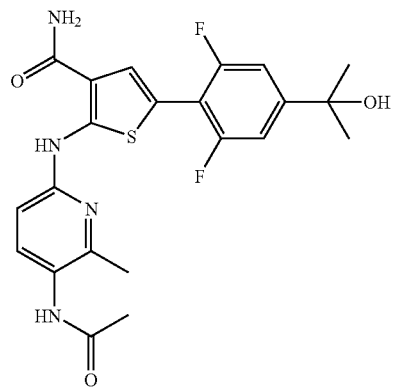 [SMILES: CC(=O)Nc1ccc(Nc2sc(-c3c(F)cc(C(C)(C)O)cc3F)cc2C(N)=O)nc1C]

Step 2: 2-{[5-(Acetylamino)-6-methylpyridin-2-yl]amino}-5-[2,6-difluoro-4-(1-hydroxy-1-methylethyl)phenyl]thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and N-(6-chloro-2-methylpyridin-3-yl)acetamide (89 mg, 0.48 mmol) as starting materials.

Calc'd for $C_{22}H_{23}F_2N_4O_3S$ [M+H]⁺: 461. Found: 461.

Example 462

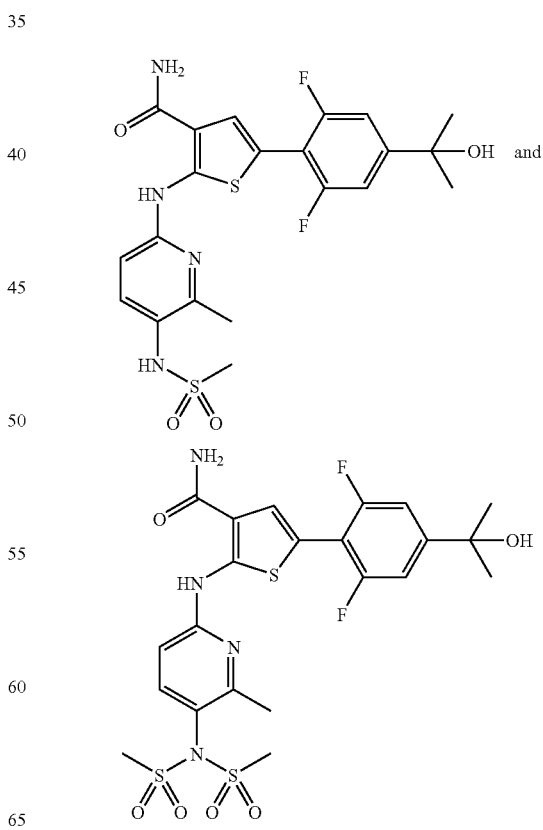

5-[2,6-Difluoro-4-(1-hydroxy-1-methylethyl)phenyl]-2-({6-methyl-5-[(methylsulfonyl)amino]pyridin-2-yl}amino)thiophene-3-carboxamide and

2-({5-[bis(Methylsulfonyl)amino]-6-methylpyridin-2-yl}amino)-5-[2,6-difluoro-4-(1-hydroxy-1-methylethyl)phenyl]thiophene-3-carboxamide

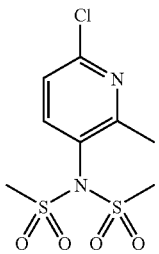

Step 1: N-(6-Chloro-2-methylpyridin-3-yl)-N-(methylsulfonyl)methanesulfonamide In a dry flask, 6-chloro-2-methylpyridin-3-amine (160 mg, 1.12 mmol) and triethylamine (470 µl, 3.37 mmol) were taken up in dichloromethane (5.6 ml) under argon. The solution was cooled to 0° C. and stirred for 20 minutes. Methanesulfonyl chloride (131 µl, 1.68 mmol) was added dropwise over 15 minutes. The mixture was allowed to warm to room temperature and stirred as such for 16 hours. The reaction was quenched with aqueous sodium bicarbonate and washed three times with ethyl acetate. The organic layers were combined, dried over anhydrous magnesium sulfate, and concentrated to afford the title compound.

Calc'd for $C_8H_{12}ClN_2O_4S_2$ [M+H]$^+$: 299. Found: 299.

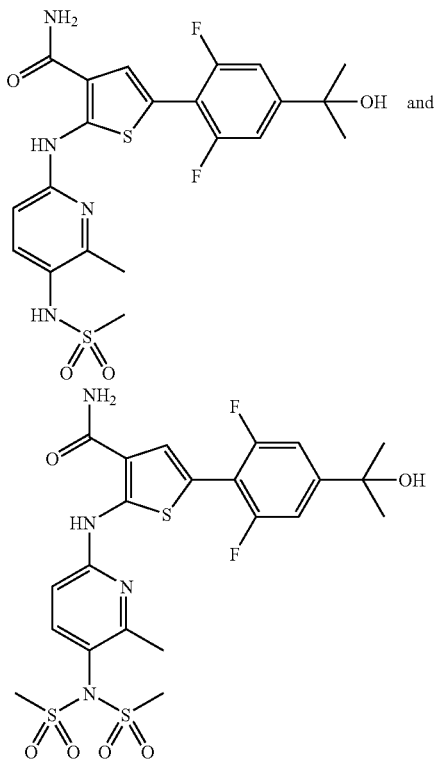

Step 2: 5-[2,6-Difluoro-4-(1-hydroxy-1-methylethyl)phenyl]-2-({6-methyl-5-[(methylsulfonyl)amino]pyridin-2-yl}amino)thiophene-3-carboxamide and 2-({5-[bis(Methylsulfonyl)amino]-6-methylpyridin-2-yl}amino)-5-[2,6-difluoro-4-(1-hydroxy-1-methylethyl)phenyl]thiophene-3-carboxamide The title compounds were prepared in one pot as described in Example 1 using 2-amino-5-[2,6-difluoro-4-(1-hydroxy-1-methylethyl)phenyl]thiophene-3-carboxamide (150 mg, 0.48 mmol) and N-(6-chloro-2-methylpyridin-3-yl)-N-(methylsulfonyl)methanesulfonamide (143 mg, 0.48 mmol) as starting materials. Mono and bis methylsulfonyl compounds were separated by column chromatography.

5-[2,6-Difluoro-4-(1-hydroxy-1-methylethyl)phenyl]-2-({6-methyl-5-[(methylsulfonyl)amino]pyridin-2-yl}amino)thiophene-3-carboxamide: Calc'd for $C_{21}H_{23}F_2N_4O_4S_2$ [M+H]$^+$: 497. Found: 497.

2-({5-[bis(Methylsulfonyl)amino]-6-methylpyridin-2-yl}amino)-5-[2,6-difluoro-4-(1-hydroxy-1-methylethyl)phenyl]thiophene-3-carboxamide: Calc'd for $C_{22}H_{25}F_2N_4O_6S_3$ [M+H]$^+$: 575. Found: 575.

Example 463

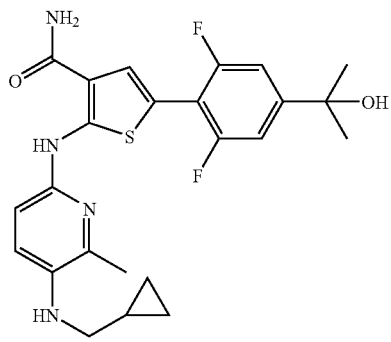 [SMILES: Cc1nc(Nc2sc(-c3c(F)cc(C(C)(C)O)cc3F)cc2C(N)=O)ccc1NCC1CC1]

2-({5-[(Cyclopropylmethyl)amino]-6-methylpyridin-2-yl}amino)-5-[2,6-difluoro-4-(1-hydroxy-1-methylethyl)phenyl]thiophene-3-carboxamide

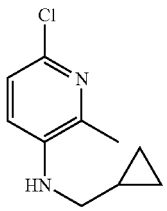

Step 1: 6-Chloro-N-(cyclopropylmethyl)-2-methylpyridin-3-amine

In a dry flask, 6-chloro-2-methylpyridin-3-amine (200 mg, 1.40 mmol) and cyclopropanecarbaldehyde (116 µl, 1.54 mmol) were taken up in 1,2-dichloroethane (5.6 ml) under argon. The resulting clear solution was stirred at room temperature for 1 hour. Sodium triacetoxyborohydride (0.47 g, 2.10 mmol) and acetic acid (160 µl, 2.81 mmol) were sequentially added to the reaction mixture, which was stirred as such for 24 hours. The reaction mixture was quenched with aqueous sodium bicarbonate and extracted three times with dichloromethane. All organic fractions were combined, dried over anhydrous magnesium sulfate, filtered, and concentrated. The resulting crude product was purified by silica gel chromatography (0-50% ethyl acetate/hexanes) to afford the title compound.

Calc'd for $C_{10}H_{14}ClN_2$ [M+H]$^+$: 197. Found: 197.

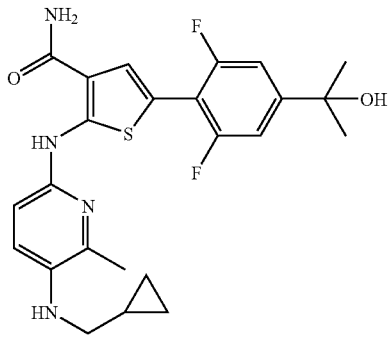 [SMILES: Cc1nc(Nc2sc(-c3c(F)cc(C(C)(C)O)cc3F)cc2C(N)=O)ccc1NCC1CC1]

Step 2: 2-({5-[(Cyclopropylmethyl)amino]-6-methylpyridin-2-yl}amino)-5-[2,6-difluoro-4-(1-hydroxy-1-methylethyl)phenyl]thiophene-3-carboxamide The title compound was prepared in the same manner described in Example 1 using 2-amino-5-[2,6-difluoro-4-(1-hydroxy-1-methylethyl)phenyl]thiophene-3-carboxamide (150 mg, 0.48 mmol) and N-(cyclopropylmethyl)-2-methylpyridin-3-amine (94 mg, 0.48 mmol) as starting materials.

Calc'd for $C_{24}H_{27}F_2N_4O_2S$ [M+H]$^+$: 473. Found: 473.

Example 464

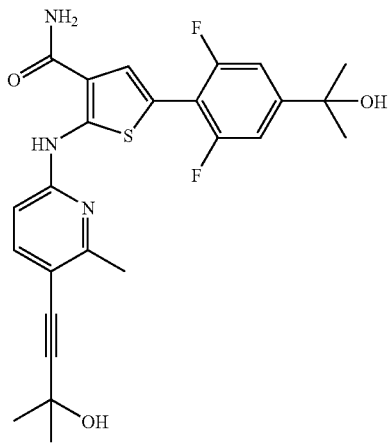 [SMILES: Cc1nc(Nc2sc(-c3c(F)cc(C(C)(C)O)cc3F)cc2C(N)=O)ccc1C#CC(C)(C)O]

5-[2,6-Difluoro-4-(1-hydroxy-1-methylethyl)phenyl]-2-{[5-(3-hydroxy-3-methylbut-1-yn-1-yl)-6-methylpyridin-2-yl]amino}thiophene-3-carboxamide

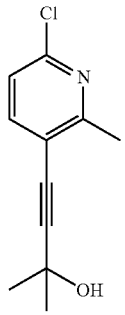

Step 1: 4-(6-Chloro-2-methylpyridin-3-yl)-2-methylbut-3-yn-2-ol

6-Chloro-3-ethynyl-2-methylpyridine (Example 432, Step 1) (200 mg, 1.32 mmol) was taken up in 4 ml tert-butyl methyl ether and added to a dry flask under argon. The flask was cooled to −78° C. and allowed to stir for 20 min. Butyllithium (0.99 ml of 1.6 M in hexanes, 1.58 mmol) was added to the reaction mixture dropwise over 30 minutes, and the mixture was allowed to stir as such for 30 min. Acetone (0.13 ml, 1.72 mmol) was taken up in 1 ml tert-butyl methyl ether and added dropwise over 30 min. The reaction mixture was allowed to warm to 0° C. and was stirred as such for 90 minutes. The reaction mixture was then allowed to warm to room temperature and stirred for 1 hour. The reaction mixture was quenched with aqueous sodium bicarbonate and extracted twice with diethyl ether. All organic fractions were combined, dried over anhydrous magnesium sulfate, filtered, and concentrated. The resulting crude product was purified by silica gel chromatography (0-50% ethyl acetate/hexanes) to afford the title compound.

Calc'd for $C_{11}H_{13}ClNO$ [M+H]$^+$: 210. Found: 210.

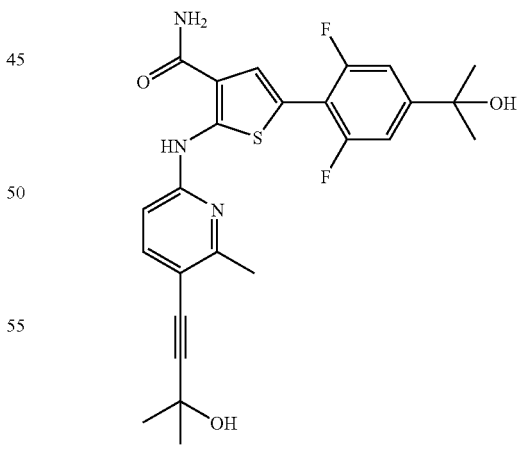

Step 2: 5-[2,6-Difluoro-4-(1-hydroxy-1-methylethyl)phenyl]-2-{[5-(3-hydroxy-3-methylbut-1-yn-1-yl)-6-methylpyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (100 mg, 0.32 mmol) and 4-(6-chloro-2-methylpyridin-3-yl)-2-methylbut-3-yn-2-ol (67 mg, 0.32 mmol) as starting materials.

Calc'd for $C_{25}H_{26}F_2N_3O_3S$ [M+H]$^+$: 486. Found: 486.

Example 465

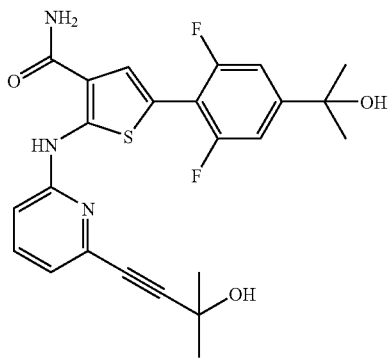 [SMILES: CC(C)(O)C#Cc1cccc(Nc2sc(-c3c(F)cc(C(C)(C)O)cc3F)cc2C(N)=O)n1]

5-[2,6-Difluoro-4-(1-hydroxy-1-methylethyl)phenyl]-2-{[6-(3-hydroxy-3-methylbut-1-yn-1-yl)pyridin-2-yl]amino}thiophene-3-carboxamide

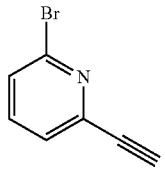

Step 1: 2-Bromo-6-ethynylpyridine 2,6-Dibromopyridine (5.33 g, 22.5 mmol), copper(I) iodide (0.071 g, 0.38 mmol), and tetrakis(triphenylphosphine)palladium (0.43 g, 0.38 mmol) were combined in a 100 ml flask, and the flask was evacuated/filled with nitrogen (2×). Toluene (30 ml) was added, followed by diisopropylamine (3.00 ml, 21.05 mmol) and trimethylsilylacetylene (1.05 ml, 7.50 mmol). The reaction vessel was wrapped in tin foil and stirred at room temperature, overnight. It was then diluted with saturated aqueous ammonium chloride and extracted with ethyl acetate (2×). The combined organic layers were washed with brine, dried over magnesium sulfate, filtered, and concentrated in vacuo. Flash chromatography (silica, 0-7% ethyl acetate/hexanes) afforded a mixture of starting material, mono-alkyne, and bis-alkyne product. This mixture was taken up in tetrahydrofuran (15 ml) and methanol (15 ml), and potassium carbonate (5.00 g, 36.2 mmol) was added. After stirring overnight at room temperature, the mixture was diluted with water and extracted with ethyl acetate (2×). The combined organic layers were washed with brine, dried over magnesium sulfate, filtered, and concentrated in vacuo. Flash chromatography (silica, 0-10% ethyl acetate/hexanes) afforded the title compound as a white solid.

$^1$H NMR (500 MHz, CDCl$_3$): δ 7.53 (m, 1H), 7.48 (d, 1H), 7.44 (d, 1H), 3.21 (s, 1H).

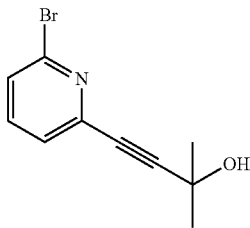

Step 2: 4-(6-Bromopyridin-2-yl)-2-methylbut-3-yn-2-ol n-Butyllithium (0.6 mL of 1.6M in hexanes, 0.96 mmol) was added to a cooled (−78° C.) solution of 2-bromo-6-ethynylpyridine (150 mg, 0.82 mmol) in tetrahydrofuran (4.1 mL). A tan slurry formed. The mixture was stirred for 30 minutes while warming to −30° C. at which time acetone (0.3 mL, 4.1 mmol) was added. The slurry dissolved to form a light orange solution. The reaction was stirred for an additional 2 hours while warming to 0° C. The reaction was quenched via the addition of saturated aqueous ammonium chloride and extracted with ethyl acetate (2×). The combined organics were dried over magnesium sulfate, filtered, concentrated in vacuo and purified via flash chromatography (0-50% ethyl acetate/hexanes) to afford the title compound as a white solid.

Calc'd for $C_{10}H_{11}BrNO$ [M+H]$^+$: 240. found 240.

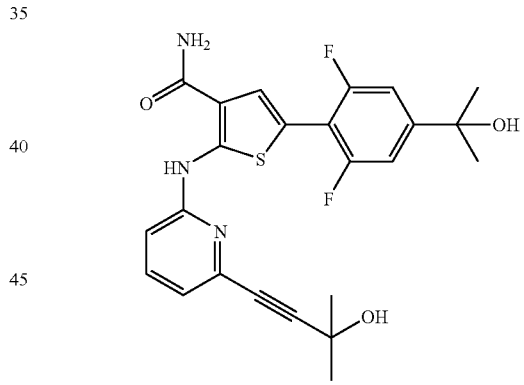

Step 3: 5-[2,6-Difluoro-4-(1-hydroxy-1-methylethyl)phenyl]-2-{[6-(3-hydroxy-3-methylbut-1-yn-1-yl)pyridin-2-yl]amino}thiophene-3-carboxamide The title compound was prepared as described in Example 1 using 2-amino-5-[2,6-difluoro-4-(1-hydroxy-1-methylethyl)phenyl]thiophene-3-carboxamide (150 mg, 0.48 mmol) and 4-(6-bromopyridin-2-yl)-2-methylbut-3-yn-2-ol (115 mg, 0.48 mmol) as starting materials.

$^1$H NMR (600 MHz, d6-DMSO): δ 12.16 (s, 1H), 7.93 (s, 1H), 7.81 (s, 1H), 7.68 (m, 1H), 7.40 (s, 1H), 7.26 (d, 2H), 7.08 (d, 1H), 7.00 (d, 1H), 5.59 (s, 1H), 5.29 (s, 1H), 1.49 (s, 6H), 1.43 (s, 6H). Calc'd for $C_{24}H_{24}F_2N_3O_3S$ [M+H]$^+$: 472. found 472.

Example 466

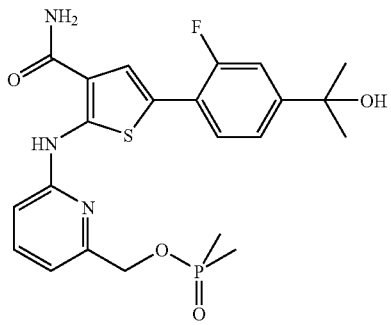 [SMILES: CC(C)(O)c1ccc(-c2cc(C(N)=O)c(Nc3cccc(COP(C)(C)=O)n3)s2)c(F)c1]

[6-({3-(Aminocarbonyl)-5-[2-fluoro-4-(1-hydroxy-1-methylethyl)phenyl]-2-thienyl}amino)pyridin-2-yl]methyl dimethylphosphinate 5-[2-Fluoro-4-(1-hydroxy-1-methylethyl)phenyl]-2-{[6-(hydroxymethyl)pyridin-2-yl]amino}thiophene-3-carboxamide (Example 43) (125 mg, 0.31 mmol), dimethylphosphinic acid (32.2 mg, 0.34 mmol), BOP (207 mg, 0.47 mmol) and DIPEA (48.3 mg, 0.37 mmol) were stirred in DMF (1 mL) at room temperature for 6 hours. Additional dimethylphosphinic acid (11.71 mg, 0.13 mmol), BOP (68.9 mg, 0.16 mmol) and DIPEA (0.033 mL, 0.19 mmol) were added and the reaction mixture was maintained at room temperature overnight. Saturated sodium bicarbonate was added and the mixture was extracted with EtOAc (×5). The combined organic extracts were washed with brine, dried over MgSO$_4$ and concentrated in vacuo. Purification of the residue by silica gel column chromatography (0-10% MeOH-EtOAc) gave the title compound as a pale yellow solid.

Calc'd for $C_{22}H_{26}FN_3O_4PS$ [M+H]$^+$: 478. Found: 478.

Example 467

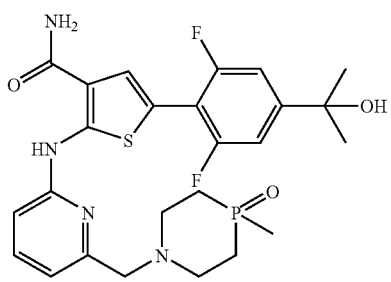 [SMILES: CC(C)(O)c1cc(F)c(-c2cc(C(N)=O)c(Nc3cccc(CN4CCP(C)(=O)CC4)n3)s2)c(F)c1]

5-[2,6-Difluoro-4-(1-hydroxy-1-methylethyl)phenyl]-2-({6-[(4-methyl-4-oxido-1,4-azaphosphinan-1-yl)methyl]pyridin-2-yl}amino)thiophene-3-carboxamide

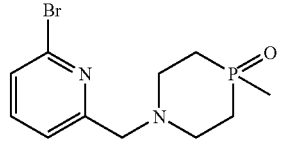 [SMILES: CP1(=O)CCN(Cc2cccc(Br)n2)CC1]

Step 1: 1-[(6-Bromopyridin-2-yl)methyl]-4-methyl-1,4-azaphosphinane 4-oxide

2-Bromo-6-(bromomethyl)pyridine (Example 190, Step 1) (500 mg, 1.99 mmol), 4-methyl-1,4-azaphosphinane 4-oxide hydrochloride (406 mg, 2.39 mmol, prepared according to the method described in WO 2008/010985), and DIEA (522 µL, 2.99 mmol) were combined in DMF (5.0 mL) and stirred at room temperature overnight. The solvent was then evaporated in vacuo and the crude residue was purified by reverse phase HPLC (MeCN/water w/0.025% TFA) to afford the title compound as a colorless foam.

Calc'd for $C_{11}H_{17}BrN_2OP$ [M+H]$^+$ 303. found 303.

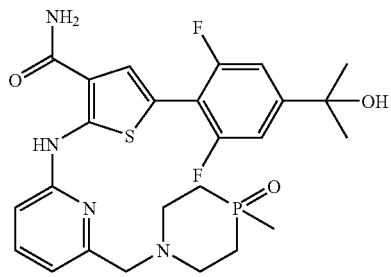 [SMILES: CC(C)(O)c1cc(F)c(-c2cc(C(N)=O)c(Nc3cccc(CN4CCP(C)(=O)CC4)n3)s2)c(F)c1]

Step 2: 5-[2,6-Difluoro-4-(1-hydroxy-1-methylethyl)phenyl]-2-({6-[(4-methyl-4-oxido-1,4-azaphosphinan-1-yl)methyl]pyridin-2-yl}amino)thiophene-3-carboxamide The title compound was synthesized from 1-[(6-bromopyridin-2-yl)methyl]-4-methyl-1,4-azaphosphinane 4-oxide (121 mg, 0.40 mmol) and 2-amino-5-[2,6-difluoro-4-(1-hydroxy-1-methylethyl)phenyl]thiophene-3-carboxamide (125 mg, 0.40 mmol) according to the general procedure in Example 1.

Calc'd for $C_{25}H_{30}F_2N_4O_3S$ [M+H]$^+$ 535. found 535.

An additional example was prepared by procedures similar to those described above and is illustrated in the following table.

TABLE 45

| Example # | Structure | Compound Name | Characterization |
|---|---|---|---|
| 468 | 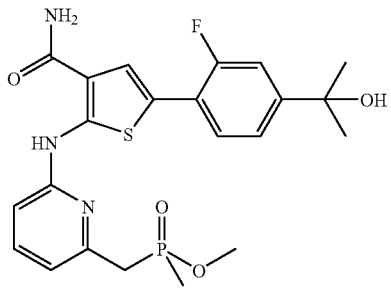 | 5-[2-fluoro-4-(1-hydroxy-1-methylethyl)phenyl]-2-({6-[(4-methyl-4-oxido-1,4-azaphosphinan-1-yl)methyl]pyridin-2-yl}amino)thiophene-3-carboxamide | Calc'd [M + H]$^+$: 517, found 517 |

Example 469

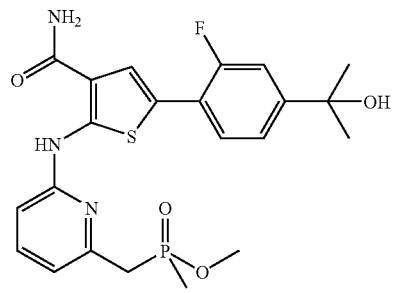 [SMILES: COP(C)(=O)Cc1cccc(Nc2sc(-c3ccc(C(C)(C)O)cc3F)cc2C(N)=O)n1]

Methyl{[6-({3-(aminocarbonyl)-5-[2-fluoro-4-(1-hydroxy-1-methylethyl)phenyl]-2-thienyl}amino)pyridin-2-yl]methyl}methylphosphinate

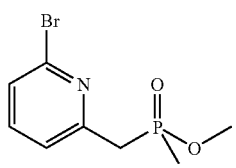

Step 1: Methyl[(6-bromopyridin-2-yl)methyl]methylphosphinate

DIEA (5.64 mL, 32.3 mmol) and MeOH (1.29 mL, 31.9 mmol) were combined in toluene (20 mL) and cooled to 0° C. Methyldichlorophosphine (1.43 ml, 15.94 mmol) in toluene (5 mL) was added dropwise over 20 minutes. Additional toluene (5 mL) was added to aid in stirring. The solution was then allowed to warm to room temperature and stirred for 1 h. The slurry then filtered to remove the salt, affording a colorless solution. 2-Bromo-6-(bromomethyl)pyridine (Example 190, Step 1) (1.00 g, 3.99 mmol) was added to the solution, and the mixture was stirred at 100° C. for 4 h. The solvent was removed in vacuo, and the crude residue was purified by flash chromatography (0-10% MeOH/CH2Cl2) to afford the title compound.

Calc'd for $C_8H_{12}BrNO_2P$ [M+H]$^+$ 264. found 264.

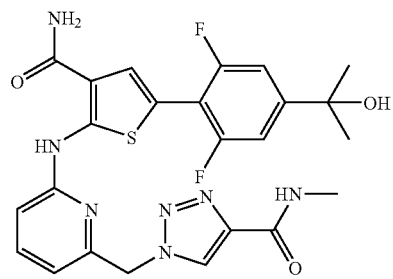 [SMILES: CNC(=O)c1cn(Cc2cccc(Nc3sc(-c4c(F)cc(C(C)(C)O)cc4F)cc3C(N)=O)n2)nn1]

Step 2: Methyl{[6-({3-(aminocarbonyl)-5-[2-fluoro-4-(1-hydroxy-1-methylethyl)phenyl]-2-thienyl}amino)pyridin-2-yl]methyl}methylphosphinate The title compound was synthesized from methyl[(6-bromopyridin-2-yl)methyl]methylphosphinate (90 mg, 0.34 mmol) and 2-amino-5-[2-fluoro-4-(1-hydroxy-1-methylethyl)phenyl]thiophene-3-carboxamide (100 mg, 0.34 mmol) according to the general procedure in Example 1.

MS calcd for $C_{22}H_{26}FN_3O_4PS$ [M+H]$^+$ 478. found 478.

Example 470

1-{[6-({3-(Aminocarbonyl)-5-[2,6-difluoro-4-(1-hydroxy-1-methylethyl)phenyl]-2-thienyl}amino)pyridin-2-yl]methyl}-N-methyl-1H-1,2,3-triazole-4-carboxamide

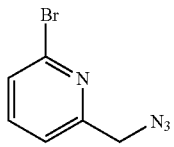 [SMILES: [N-]=[N+]=NCc1cccc(Br)n1]

Step 1: 2-(Azidomethyl)-6-bromopyridine

Sodium azide (3.11 g, 47.8 mmol) and 2-bromo-6-(bromomethyl)pyridine (Example 190, Step 1) (4.00 g, 15.94 mmol) were combined in DMSO (30 mL) and stirred at room temperature for 4 h. The mixture was subsequently diluted with water and extracted with $Et_2O$ (2×). The combined organic extracts were washed with brine, dried ($MgSO_4$), filtered, and evaporated under reduced pressure. The residue was purified by flash chromatography (0-10% EtOAc/hexanes) to yield the title compound as a colorless oil.

Calc'd for $C_6H_6BrN_4$ $[M+H]^+$ 213. found 213.

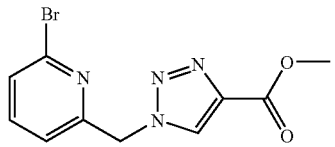 [SMILES: COC(=O)c1cn(Cc2cccc(Br)n2)nn1]

Step 2: Methyl 1-[(6-bromopyridin-2-yl)methyl]-1H-1,2,3-triazole-4-carboxylate Methyl propiolate (641 µL, 7.63 mmol) and 2-(azidomethyl)-6-bromopyridine (1.25 g, 5.87 mmol) were combined in t-BuOH (9.0 mL) and water (5.0 mL). A solution of $CuSO_4·5H_2O$ (73 mg, 0.29 mmol) in water (2.0 mL) was added, followed by sodium ascorbate (232 mg, 1.17 mmol) in water (2.0 mL). The reaction was stirred at room temperature for 18 h, during which time it became a yellow suspension. The suspension was diluted with saturated $NaHCO_3$ and extracted with EtOAc (3×). The combined organic layers were washed with brine, dried ($MgSO_4$), filtered, and concentrated under reduced pressure. The crude solid was purified by flash chromatography (40-100% EtOAc/hexanes) to afford the title compound as a colorless solid.

Calc'd for $C_{10}H_{10}BrN_4O_2$ $[M+H]^+$ 297. found 297.

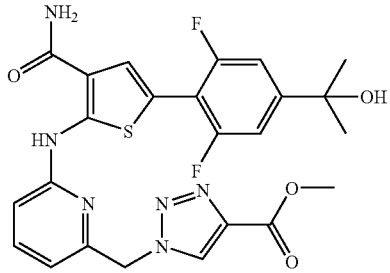 [SMILES: COC(=O)c1cn(Cc2cccc(Nc3sc(-c4c(F)cc(C(C)(C)O)cc4F)cc3C(N)=O)n2)nn1]

Step 4: Methyl 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-4-carboxylate The title compound was prepared as described in Example 1 using methyl 1-[(6-bromopyridin-2-yl)methyl]-1H-1,2,3-triazole-4-carboxylate (357 mg, 1.20 mmol) and 2-amino-5-[2,6-difluoro-4-(1-hydroxy-1-methylethyl)phenyl]thiophene-3-carboxamide (375 mg, 1.20 mmol) as starting materials.

Calc'd for $C_{24}H_{22}F_2N_6O_4SNa$ $[M+Na]^+$ 551. found 551.

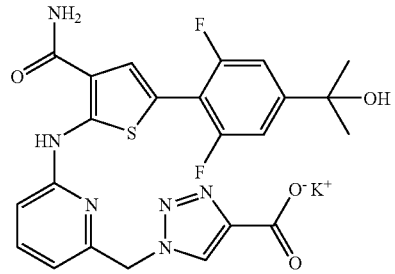 [SMILES: CC(C)(O)c1cc(F)c(-c2cc(C(N)=O)c(Nc3cccc(Cn4cc(C(=O)[O-])nn4)n3)s2)c(F)c1 ; [K+]]

Step 5: Potassium 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-4-carboxylate Methyl 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-4-carboxylate (425 mg, 0.80 mmol) was taken up in THF (5.0 mL) and MeOH (5.0 mL), and KOH (1.0 M, 1.05 mL, 1.05 mmol) was added. The reaction was stirred at room temperature overnight. Additional KOH (1.0 M, 160 µL, 0.16 mmol) was added, and the reaction was stirred for another 8 h at room temperature. The mixture was then concentrated, resuspended in MeOH, and concentrated again to give the title compound as a yellow solid that was carried on without purification.

Calc'd for $C_{23}H_{19}F_2N_6O_3S$ $[M-OH]^+$ 497. found 497.

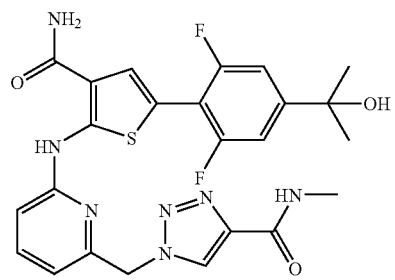

Step 6: 1-{[6-({3-(aminocarbonyl)-5-[2,6-difluoro-4-(1-hydroxy-1-methylethyl)phenyl]-2-thienyl}amino)pyridin-2-yl]methyl}-N-methyl-1H-1,2,3-triazole-4-carboxamide Potassium 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-4-carboxylate (111 mg, 0.20 mmol), HOBT (62 mg, 0.40 mmol), EDC (77 mg, 0.40 mmol), and methylamine hydrochloride (41 mg, 0.60 mmol) were combined in DMF (5.0 mL), and DIEA (105 µL, 0.60 mmol) was added. The reaction was stirred at room temperature overnight. The solution was diluted with water to precipitate an off-white solid that was collected by filtration, washed (water, MeOH, CH$_2$Cl$_2$), and dried to yield the title compound. $^1$H NMR (600 MHz, DMSO-d$_6$) δ 12.15 (s, 1H), 8.55 (s, 1H), 8.30 (q, 1H), 7.86 (s, 1H), 7.73-7.66 (m, 2H), 7.36 (s, 1H), 7.21 (d, 2H), 7.03 (d, 1H), 6.80 (d, 1H), 5.71 (s, 2H), 5.27 (s, 1H), 2.66 (d, 3H), 1.42 (s, 6H). Calc'd for C$_{24}$H$_{24}$F$_2$N$_7$O$_3$S [M+H]$^+$ 528. found 528.

Additional examples were prepared by procedures similar to those described above.

TABLE 46

| Example # | Structure | Compound Name | Characterization |
|---|---|---|---|
| 471 | 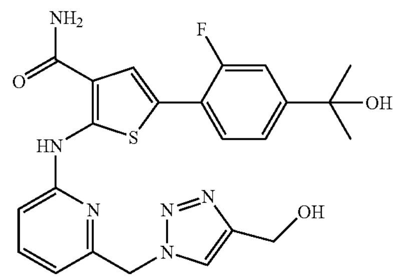 [SMILES: CC(C)(O)c1ccc(-c2cc(C(N)=O)c(Nc3cccc(Cn4cc(CO)nn4)n3)s2)c(F)c1] | 5-[2-fluoro-4-(1-hydroxy-1-methylethyl)phenyl]-2-[(6-{[4-(hydroxymethyl)-1H-1,2,3-triazol-1-yl]methyl}pyridin-2-yl)amino]thiophene-3-carboxamide | Calc'd [M + H]$^+$ 483, found 483 |
| 472 | 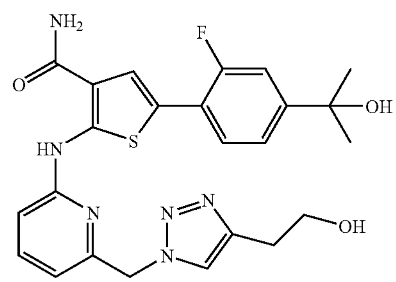 [SMILES: CC(C)(O)c1ccc(-c2cc(C(N)=O)c(Nc3cccc(Cn4cc(CCO)nn4)n3)s2)c(F)c1] | 5-[2-fluoro-4-(1-hydroxy-1-methylethyl)phenyl]-2-[(6-{[4-(2-hydroxyethyl)-1H-1,2,3-triazol-1-yl]methyl}pyridin-2-yl)amino]thiophene-3-carboxamide | Calc'd [M + H]$^+$ 497, found 497 |
| 473 | 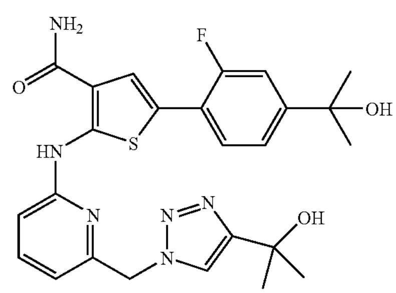 [SMILES: CC(C)(O)c1ccc(-c2cc(C(N)=O)c(Nc3cccc(Cn4cc(C(C)(C)O)nn4)n3)s2)c(F)c1] | 5-[2-fluoro-4-(1-hydroxy-1-methylethyl)phenyl]-2-[(6-{[4-(1-hydroxy-1-methylethyl)-1H-1,2,3-triazol-1-yl]methyl}pyridin-2-yl)amino]thiophene-3-carboxamide | Calc'd [M + H]$^+$ 511, found 511 |
| 474 | 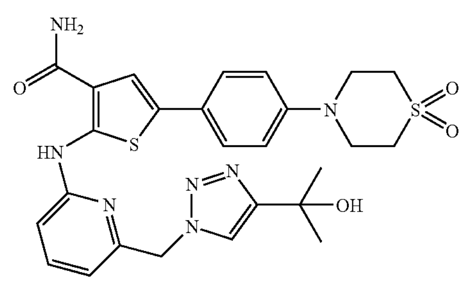 [SMILES: CC(C)(O)c1cn(Cc2cccc(Nc3sc(-c4ccc(N5CCS(=O)(=O)CC5)cc4)cc3C(N)=O)n2)nn1] | 5-[4-(1,1-dioxidothiomorpholin-4-yl)phenyl]-2-[(6-{[4-(1-hydroxy-1-methylethyl)-1H-1,2,3-triazol-1-yl]methyl}pyridine-2-yl)amino]thiophene-3-carboxamide | Calc'd [M + H]$^+$ 568, found 568 |
| 475 | 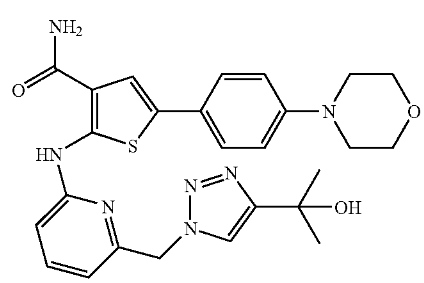 | 2-[(6-{[4-(1-hydroxy-1-methylethyl)-1H-1,2,3-triazol-1-yl]methyl}pyridin-2-yl)amino]-5-(4-morpholin-4-ylphenyl)thiophene-3-carboxamide | Calc'd [M + H]$^+$ 520, found 520 |

TABLE 46-continued

| Example # | Compound Name | Characterization |
|---|---|---|
| 476 | 2-[(6-{[4-(1-hydroxy-1-methylethyl)-1H-1,2,3-triazol-1-yl]methyl}pyridin-2-yl)amino]-5-(4-pyridin-4-ylphenyl)thiophene-3-carboxamide | Calc'd [M + H]⁺ 512, found 512 |
| 477 | 2-[(6-{[4-(1-hydroxy-1-methylethyl)-1H-1,2,3-triazol-1-yl]methyl}pyridin-2-yl)amino]-5-[4-(1H-pyrazol-1-yl)phenyl]thiophene-3-carboxamide | Calc'd [M + H]⁺ 501, found 501 |
| 478 | 2-[(6-{[4-(1-hydroxy-1-methylethyl)-1H-1,2,3-triazol-1-yl]methyl}pyridin-2-yl)amino]-5-(4-hydroxyphenyl)thiophene-3-carboxamide | Calc'd [M + H]⁺ 451, found 451 |
| 479 | 2-[(6-{[4-(1-hydroxy-1-methylethyl)-1H-1,2,3-triazol-1-yl]methyl}pyridin-2-yl)amino]-5-(2-hydroxyphenyl)thiophene-3-carboxamide | Calc'd [M + H]⁺ 451, found 451 |
| 480 | 5-(2-aminophenyl)-2-[(6-{[4-(1-hydroxy-1-methylethyl)-1H-1,2,3-triazol-1-yl]methyl}pyridin-2-yl)amino]thiophene-3-carboxamide | Calc'd [M + H]⁺ 450, found 450 |

TABLE 46-continued

| Example # | Structure | Compound Name | Characterization |
|---|---|---|---|
| 481 | 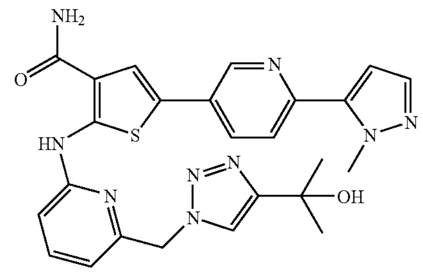 [SMILES: Cn1nccc1-c1ccc(-c2cc(C(N)=O)c(Nc3cccc(Cn4cc(C(C)(C)O)nn4)n3)s2)cn1] | 2-[(6-{[4-(1-hydroxy-1-methylethyl)-1H-1,2,3-triazol-1-yl]methyl}pyridin-2-yl)amino]-5-[6-(1-methyl-1H-pyrazol-5-yl)pyridin-3-yl]thiophene-3-carboxamide | Calc'd [M + H]$^+$ 516, found 516 |
| 482 | 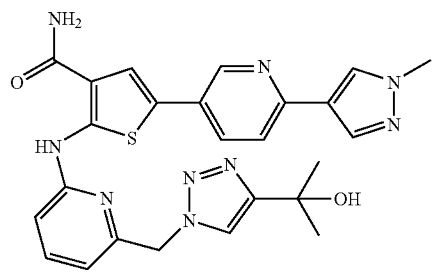 [SMILES: Cn1cc(-c2ccc(-c3cc(C(N)=O)c(Nc4cccc(Cn5cc(C(C)(C)O)nn5)n4)s3)cn2)cn1] | 2-[(6-{[4-(1-hydroxy-1-methylethyl)-1H-1,2,3-triazol-1-yl]methyl}pyridin-2-yl)amino]-5-[6-(1-methyl-1H-pyrazol-4-yl)pyridin-3-yl]thiophene-3-carboxamide | Calc'd [M + H]$^+$ 516, found 516 |
| 483 | 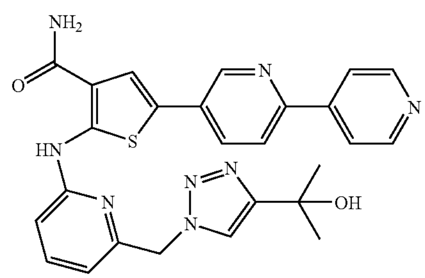 | 5-(2,4'-bipyridin-5-yl)-2-[(6-{[4-(1-hydroxy-1-methylethyl)-1H-1,2,3-triazol-1-yl]methyl}pyridin-2-yl)amino]thiophene-3-carboxamide | Calc'd [M + H]$^+$ 513, found 513 |
| 484 | 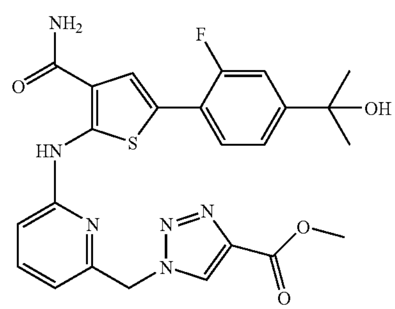 [SMILES: COC(=O)c1cn(Cc2cccc(Nc3sc(-c4ccc(C(C)(C)O)cc4F)cc3C(N)=O)n2)nn1] | methyl 1-{[6-({3-(aminocarbonyl)-5-[2-fluoro-4-(1-hydroxy-1-methylethyl)phenyl]-2-thienyl}amino)pyridin-2-yl]methyl}-1H-1,2,3-triazole-4-carboxylate | Calc'd [M − OH]$^+$ 493, found 493 |
| 485 | 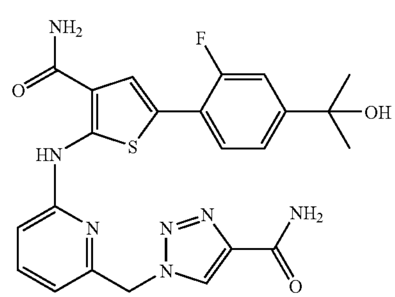 [SMILES: CC(C)(O)c1ccc(-c2cc(C(N)=O)c(Nc3cccc(Cn4cc(C(N)=O)nn4)n3)s2)c(F)c1] | 1-{[6-({3-(aminocarbonyl)-5-[2-fluoro-4-(1-hydroxy-1-methylethyl)phenyl]-2-thienyl}amino)pyridin-2-yl]methyl}-1H-1,2,3-triazole-4-carboxamide | Calc'd [M − OH]$^+$ 478, found 478 |

TABLE 46-continued

| Example # | Compound Name | Characterization |
|---|---|---|
| 486 | 1-{[6-({3-(aminocarbonyl)-5-[2-fluoro-4-(1-hydroxy-1-methylethyl)phenyl]-2-thienyl}amino)pyridin-2-yl]methyl}-N-methyl-1H-1,2,3-triazole-4-carboxamide | Calc'd [M − OH]+ 492, found 492 |
| 487 | 5-[2,6-difluoro-4-(1-hydroxy-1-methylethyl)phenyl]-2-[(6-{[4-(hydroxymethyl)-1H-1,2,3-triazol-1-yl]methyl}pyridin-2-yl)amino]thiophene-3-carboxamide | Calc'd [M + H]+ 501, found 501 |
| 488 | 5-[2,6-difluoro-4-(1-hydroxy-1-methylethyl)phenyl]-2-{[6-({4-[(dimethylamino)methyl]-1H-1,2,3-triazol-1-yl}methyl)pyridin-2-yl]amino}thiophene-3-carboxamide | Calc'd [M + H]+ 528, found 528 |
| 489 | 5-[2,6-difluoro-4-(1-hydroxy-1-methylethyl)phenyl]-2-[(6-[4-(2-hydroxyethyl)-1H-1,2,3-triazol-1-yl]methyl}pyridin-2-yl)amino]thiophene-3-carboxamide | Calc'd [M + H]+ 515, found 515 |
| 490 | 5-[2,6-difluoro-4-(1-hydroxy-1-methylethyl)phenyl]-2-[(6-{[4-(1-hydroxy-1-methylethyl)-1H-1,2,3-triazol-1-yl]methyl}pyridin-2-yl)amino]thiophene-3-carboxamide | Calc'd [M + H]+ 529, found 529 |

TABLE 46-continued

| Example # | Structure | Compound Name | Characterization |
|---|---|---|---|
| 491 | 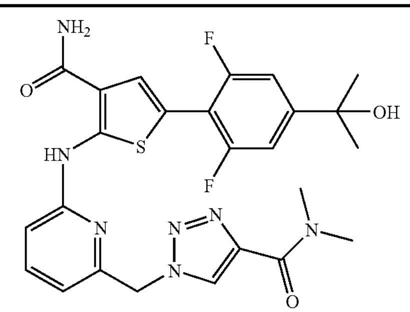 | 1-{[6-({3-(aminocarbonyl)-5-[2,6-difluoro-4-(1-hydroxy-1-methylethyl)phenyl]-2-thienyl}amino)pyridin-2-yl]methyl}-N,N-dimethyl-1H-1,2,3-triazole-4-carboxamide | Calc'd [M + H]$^+$ 542, found 542 |
| 492 | 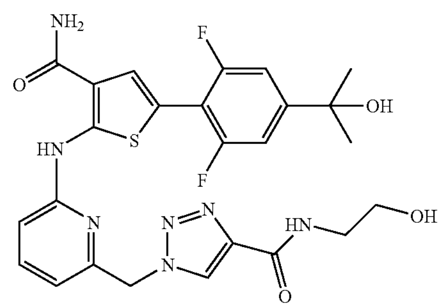 [SMILES: CC(C)(O)c1cc(F)c(-c2cc(C(N)=O)c(Nc3cccc(Cn4cc(C(=O)NCCO)nn4)n3)s2)c(F)c1] | 1-{[6-({3-(aminocarbonyl)-5-[2,6-difluoro-4-(1-hydroxy-1-methylethyl)phenyl]-2-thienyl}amino)pyridin-2-yl]methyl}-N-(2-hydroxyethyl)-1H-1,2,3-triazole-4-carboxamide | Calc'd [M + H]$^+$ 558, found 558 |
| 493 | 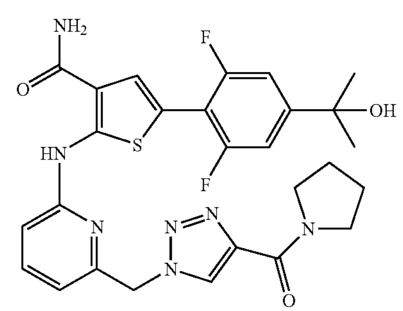 [SMILES: CC(C)(O)c1cc(F)c(-c2cc(C(N)=O)c(Nc3cccc(Cn4cc(C(=O)N5CCCC5)nn4)n3)s2)c(F)c1] | 5-[2,6-difluoro-4-(1-hydroxy-1-methylethyl)phenyl]-2-[(6-{[4-(pyrrolidin-1-ylcarbonyl)-1H-1,2,3-triazol-1-yl]methyl}pyridin-2-yl)amino]thiophene-3-carboxamide | Calc'd [M + H]$^+$ 568, found 568 |

Example 494

2-[(6-{[4-(Aminomethyl)-1H-1,2,3-triazol-1-yl]methyl}pyridin-2-yl)amino]-5-[2,6-difluoro-4-(1-hydroxy-1-methylethyl)phenyl]thiophene-3-carboxamide Step 1: tert-Butyl({1-[(6-bromopyridin-2-yl)methyl]-1H-1,2,3-triazol-4-yl}methyl)carbamate 2-(Azidomethyl)-6-bromopyridine (Example 470 Step 1) (700 mg, 3.29 mmol) and tert-butyl prop-2-yn-1-ylcarbamate (510 mg, 3.29 mmol) were combined in t-BuOH (6.0 mL) and water (3.0 mL). CuSO₄.5H₂O (41 mg, 0.16 mmol) in water (1.0 mL) was added, followed by sodium ascorbate (130 mg, 0.66 mmol) in water (2.0 mL). The reaction was stirred at room temperature for 2 h. The solution was subsequently diluted with saturated NaHCO₃ and extracted with EtOAc (3×). The combined organic layers were washed with brine, dried (MgSO₄), filtered, and evaporated. Purification by flash chromatography (40-100% EtOAc/hexanes) afforded the title compound as a colorless solid.

Calc'd for $C_{14}H_{19}BrN_5O_2$ [M+H]⁺ 368. found 368.

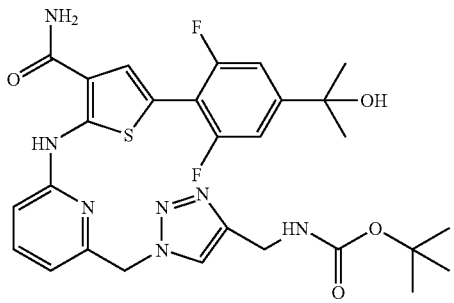 [SMILES: CC(C)(C)OC(=O)NCc1cn(Cc2cccc(Nc3sc(-c4c(F)cc(C(C)(C)O)cc4F)cc3C(N)=O)n2)nn1]

Step 2: tert-Butyl[(1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazol-4-yl)methyl]carbamate The title compound was prepared according to the procedure in Example 1 using tert-Butyl({1-[(6-bromopyridin-2-yl)methyl]-1H-1,2,3-triazol-4-yl}methyl)carbamate (147 mg, 0.40 mmol) and 2-amino-5-[2,6-difluoro-4-(1-hydroxy-1-methylethyl)phenyl]thiophene-3-carboxamide (125 mg, 0.40 mmol) as the starting materials.

Calc'd for $C_{28}H_{32}F_2N_7O_4S$ [M+H]⁺ 600. found 600.

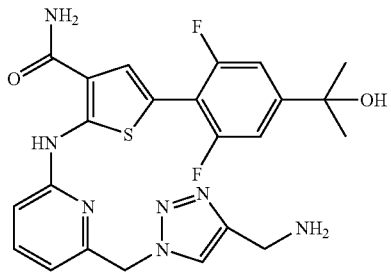 [SMILES: CC(C)(O)c1cc(F)c(-c2cc(C(N)=O)c(Nc3cccc(Cn4cc(CN)nn4)n3)s2)c(F)c1]

Step 3: 2-[(6-{[4-(Aminomethyl)-1H-1,2,3-triazol-1-yl]methyl}pyridin-2-yl)amino]-5-[2,6-difluoro-4-(1-hydroxy-1-methylethyl)phenyl]thiophene-3-carboxamide To a suspension of tert-butyl[(1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazol-4-yl)methyl]carbamate (90 mg, 0.15 mmol) in EtOAc (7.0 mL) at ° C. was added 4 M HCl in dioxane (1.88 mL, 7.50 mmol). The reaction was stirred at 0° C. for 4 h. The yellow suspension was quenched with saturated NaHCO₃ and extracted with 5:1 CH₂Cl₂:MeOH (2×). The combined organic layers were dried (MgSO₄), filtered, and evaporated. The residue was purified by reverse phase HPLC (15-75% MeCN/water w/0.025% TFA). Product fractions were neutralized with saturated NaHCO₃, extracted with 5:1 CH₂Cl₂:MeOH (2×), dried (MgSO₄), filtered, and evaporated to give the title compound as a yellow solid.

Calc'd for $C_{23}H_{24}F_2N_7O_2S$ [M+H]⁺ 500. found 500.

Example 495

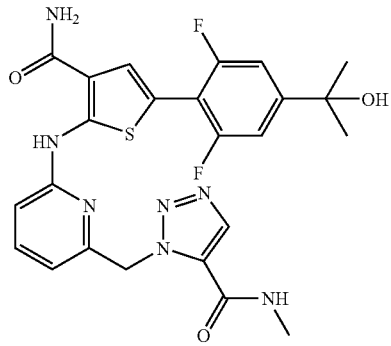 [SMILES: CNC(=O)c1cnnn1Cc1cccc(Nc2sc(-c3c(F)cc(C(C)(C)O)cc3F)cc2C(N)=O)n1]

1-{[6-({3-(Aminocarbonyl)-5-[2,6-difluoro-4-(1-hydroxy-1-methylethyl)phenyl]-2-thienyl}amino)pyridin-2-yl]methyl}-N-methyl-1H-1,2,3-triazole-5-carboxamide

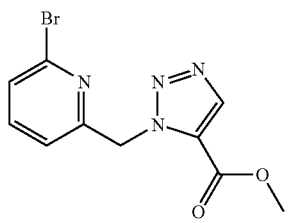 [SMILES: COC(=O)c1cnnn1Cc1cccc(Br)n1]

Step 1: Methyl 1-[(6-bromopyridin-2-yl)methyl]-1H-1,2,3-triazole-5-carboxylate 2-(Azidomethyl)-6-bromopyridine (Example 470 Step 1) (600 mg, 2.82 mmol) and methyl propiolate (355 µL, 4.22 mmol) were combined in toluene (10 mL) and stirred at reflux overnight. The solvent was evaporated, and the residue was purified by flash chromatography (20-100% EtOAc/hexanes), whereby good separation of the two regioisomeric products was achieved. TLC, LC/MS, and ¹H NMR analysis confirmed that the first spot (less polar, higher $R_f$) corresponded to the desired regioisomer. The title compound was isolated as a colorless oil.

Calc'd for $C_{10}H_{10}BrN_4O_2$ [M+H]⁺ 297. found 297.

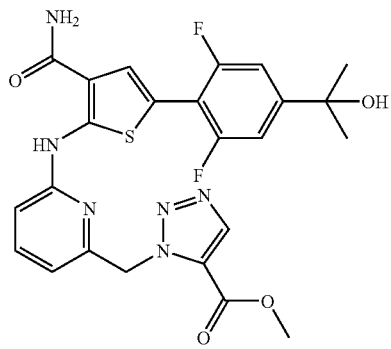 [SMILES: COC(=O)c1cnnn1Cc1cccc(Nc2sc(-c3c(F)cc(C(C)(C)O)cc3F)cc2C(N)=O)n1]

Step 2: Methyl 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-5-carboxylate The title compound was synthesized from methyl 1-[(6-bromopyridin-2-yl)methyl]-1H-1,2,3-triazole-5-carboxylate (166 mg, 0.56 mmol) and 2-amino-5-[2,6-difluoro-4-(1-hydroxy-1-methylethyl)phenyl]thiophene-3-carboxamide (175 mg, 0.56 mmol) according to the general procedure in Example 1.

Calc'd for $C_{24}H_{23}F_2N_6O_4S$ [M+H]$^+$ 529. found 529.

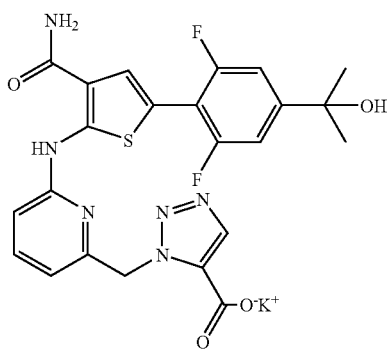

Step 3: Potassium 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-5-carboxylate Methyl 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-5-carboxylate (125 mg, 0.24 mmol) was taken up in THF (3.0 mL)/MeOH (3.0 mL), and KOH (1.0 M, 355 µL, 0.355 mmol) was added. The reaction was stirred at room temperature overnight. The mixture was then concentrated, resuspended in MeOH, and concentrated again to give the title compound as the potassium salt as a yellow solid.

Calc'd for $C_{23}H_{21}F_2N_6O_4S$ [M+H]$^+$ 515. found 515.

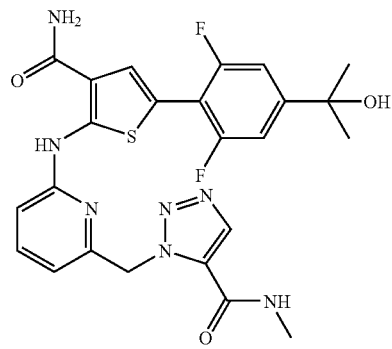 [SMILES: CNC(=O)c1cnnn1Cc1cccc(Nc2sc(-c3c(F)cc(C(C)(C)O)cc3F)cc2C(N)=O)n1]

Step 4: 1-{[6-({3-(Aminocarbonyl)-5-[2,6-difluoro-4-(1-hydroxy-1-methylethyl)phenyl]-2-thienyl}amino)pyridin-2-yl]methyl}-N-methyl-1H-1,2,3-triazole-5-carboxamide Potassium 1-{[6-({3-(aminocarbonyl)-5-[2,6-difluoro-4-(1-hydroxy-1-methylethyl)phenyl]-2-thienyl}amino)pyridin-2-yl]methyl}-1H-1,2,3-triazole-5-carboxylate (131 mg, 0.24 mmol), HOBT (72.6 mg, 0.47 mmol), EDC (91 mg, 0.47 mmol), and methylamine hydrochloride (48 mg, 0.71 mmol) were combined in DMF (5.0 mL), and DIEA (124 µL, 0.71 mmol) was added. The reaction was stirred at room temperature overnight. The solution was diluted with water. The precipitate was collected by filtration, washed with water and CH$_2$Cl$_2$, and dried to provide the title compound as an off-white solid.

Calc'd for $C_{24}H_{24}F_2N_7O_3S$ [M+H]$^+$ 528. found 528.

Additional examples were prepared by procedures similar to those described above.

TABLE 47

| Example # | Structure | Compound Name | Characterization [M + H]$^+$ |
|---|---|---|---|
| 496 | 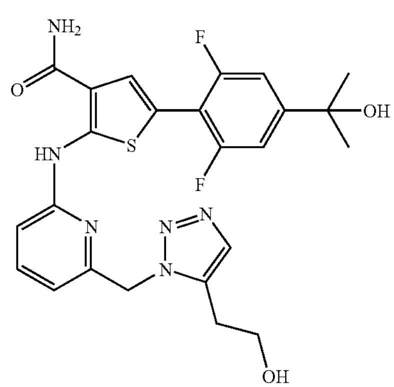 [SMILES: CC(C)(O)c1cc(F)c(-c2cc(C(N)=O)c(Nc3cccc(Cn4nncc4CCO)n3)s2)c(F)c1] | 5-[2,6-difluoro-4-(1-hydroxy-1-methylethyl)phenyl]-2-[(6-{[5-(2-hydroxyethyl)-1H-1,2,3-triazol-1-yl]methyl}pyridin-2-yl)amino]thiophene-3-carboxamide | Calc'd 515, found 515 |

Example 497

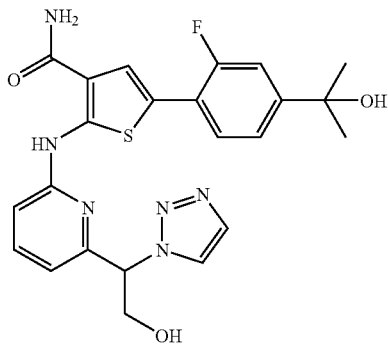 [SMILES: CC(C)(O)c1ccc(-c2cc(C(N)=O)c(Nc3cccc(C(CO)n4ccnn4)n3)s2)c(F)c1]

5-[2-Fluoro-4-(1-hydroxy-1-methylethyl)phenyl]-2-({6-[2-hydroxy-1-(1H-1,2,3-triazol-1-yl)ethyl]pyridin-2-yl}amino)thiophene-3-carboxamide

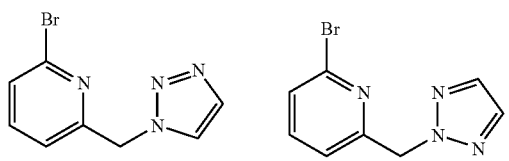 [SMILES: Brc1cccc(Cn2ccnn2)n1 ; Brc1cccc(Cn2nccn2)n1]

Step 1: 2-Bromo-6-(1H-1,2,3-triazol-1-ylmethyl)pyridine and 2-bromo-6-(2H-1,2,3-triazol-2-ylmethyl)pyridine 2-Bromo-6-(bromomethyl)pyridine (Example 190, Step 1) (1.50 g, 5.98 mmol), 1H-1,2,3-triazole (520 mL, 8.97 mmol), and $K_2CO_3$ (1.652 g, 11.96 mmol) were combined in DMF (5.0 mL) and stirred at 50° C. overnight. The mixture was diluted with water and extracted with EtOAc (2×). The combined organic layers were washed with brine, dried ($MgSO_4$), filtered, and evaporated. Flash chromatography (0-100% EtOAc/hexanes) separated the two regioisomeric products to provide 2-bromo-6-(1H-1,2,3-triazol-1-ylmethyl)pyridine (lower $R_f$) and 2-bromo-6-(2H-1,2,3-triazol-2-ylmethyl)pyridine (higher $R_f$) as colorless solids.

Calc'd for $C_8H_8BrN_4$ [M+H]$^+$ 239. found 239.

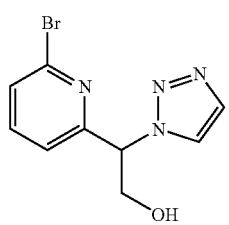 [SMILES: OCC(c1cccc(Br)n1)n1ccnn1]

Step 2: 2-(6-Bromopyridin-2-yl)-2-(1H-1,2,3-triazol-1-yl)ethanol

A solution of i-Pr$_2$NH (370 µL, 2.59 mmol) in THF (3.0 mL) was cooled to −20° C., and n-butyllithium (970 µL, 2.43 mmol) was added dropwise. After stirring for 15 minutes at −20° C., the colorless solution was cooled to −78° C. before adding 2-bromo-6-(1H-1,2,3-triazol-1-ylmethyl)pyridine (200 mg, 0.84 mmol) in THF (2.0 mL) dropwise over 30 minutes. After stirring for an additional 30 minutes at −78° C., 1H-benzotriazole-1-methanol (250 mg, 1.67 mmol) in THF (5.0 mL) was added dropwise over 25 minutes. The solution was stirred at −78° C. for 2 h. The reaction was quenched (while cold) with water and extracted with EtOAc (2×). The combined organic layers were washed with brine, dried ($MgSO_4$), filtered, and evaporated. Flash chromatography (50-100% EtOAc/hexanes) afforded the title compound as a colorless oil.

Calc'd for $C_9H_{10}BrN_4O$ [M+H]$^+$ 269. found 269.

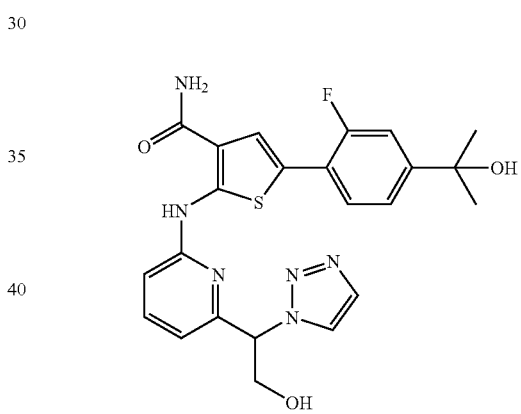

Step 3: 5-[2-Fluoro-4-(1-hydroxy-1-methylethyl)phenyl]-2-({6-[2-hydroxy-1-(1H-1,2,3-triazol-1-yl)ethyl]pyridin-2-yl}amino)thiophene-3-carboxamide The title compound was synthesized from 2-(6-bromopyridin-2-yl)-2-(1H-1,2,3-triazol-1-yl)ethanol (110 mg, 0.41 mmol) and 2-amino-5-[2-fluoro-4-(1-hydroxy-1-methylethyl)phenyl]thiophene-3-carboxamide (120 mg, 0.41 mmol) according to the general procedure in Example 1.

Calc'd for $C_{23}H_{24}FN_6O_3S$ [M+H]$^+$ 483. found 483.

Additional examples were prepared by procedures similar to those described above and are illustrated in the following table.

TABLE 48

| Example # | Structure | Compound Name | Characterization [M + H]+ |
|---|---|---|---|
| 498 | 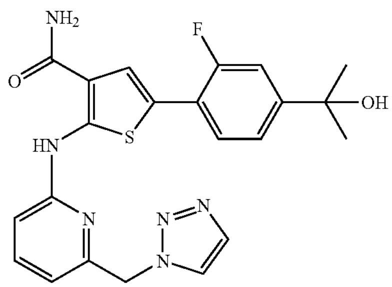 [SMILES: CC(C)(O)c1ccc(-c2cc(C(N)=O)c(Nc3cccc(Cn4ccnn4)n3)s2)c(F)c1] | 5-[2-fluoro-4-(1-hydroxy-1-methylethyl)phenyl]-2-{[6-(1H-1,2,3-triazol-1-ylmethyl)pyridin-2-yl]amino}thiophene-3-carboxamide | Calc'd 453, found 453 |
| 499 | 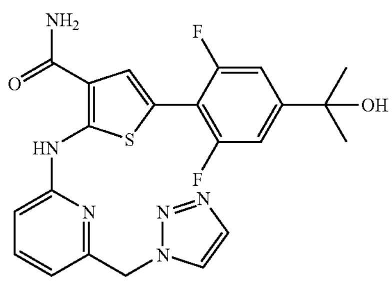 | 5-[2,6-difluoro-4-(1-hydroxy-1-methylethyl)phenyl]-2-{[6-(1H-1,2,3-triazol-1-ylmethyl)pyridin-2-yl]amino}thiophene-3-carboxamide | Calc'd 471, found 471 |
| 500 | 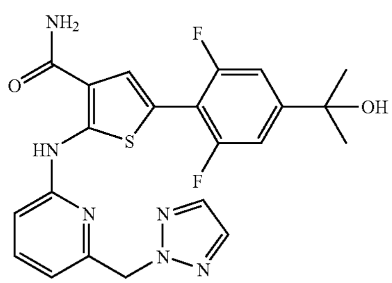 [SMILES: CC(C)(O)c1cc(F)c(-c2cc(C(N)=O)c(Nc3cccc(Cn4nccn4)n3)s2)c(F)c1] | 5-[2,6-difluoro-4-(1-hydroxy-1-methylethyl)phenyl]-2-{[6-(2H-1,2,3-triazol-2-ylmethyl)pyridin-2-yl]amino}thiophene-3-carboxamide | Calc'd 471, found 471 |
| 501 | 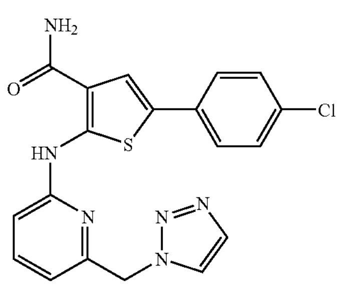 [SMILES: NC(=O)c1cc(-c2ccc(Cl)cc2)sc1Nc1cccc(Cn2ccnn2)n1] | 5-(4-chlorophenyl)-2-{[6-(1H-1,2,3-triazol-1-ylmethyl)pyridin-2-yl]amino}thiophene-3-carboxamide | Calc'd 411, found 411 |
| 502 | 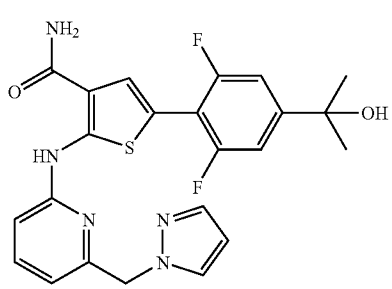 [SMILES: CC(C)(O)c1cc(F)c(-c2cc(C(N)=O)c(Nc3cccc(Cn4cccn4)n3)s2)c(F)c1] | 5-[2,6-difluoro-4-(1-hydroxy-1-methylethyl)phenyl]-2-{[6-(1H-pyrazol-1-ylmethyl)pyridin-2-yl]amino}thiophene-3-carboxamide | Calc'd 470, found 470 |

TABLE 48-continued

| Example # | Structure | Compound Name | Characterization [M + H]+ |
|---|---|---|---|
| 503 | 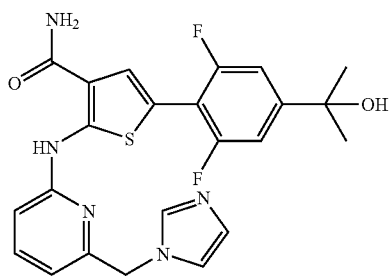 | 5-[2,6-difluoro-4-(1-hydroxy-1-methylethyl)phenyl]-2-{[6-(1H-imidazol-1-ylmethyl)pyridin-2-yl]amino}thiophene-3-carboxamide | Calc'd 470, found 470 |
| 504 | 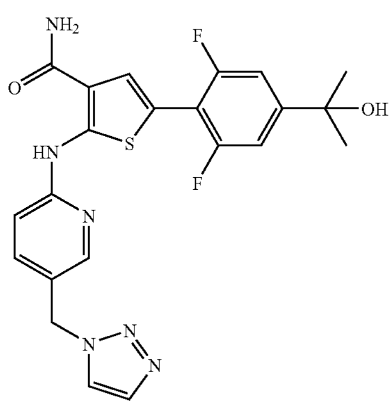 [SMILES: CC(C)(O)c1cc(F)c(-c2cc(C(N)=O)c(Nc3ccc(Cn4ccnn4)cn3)s2)c(F)c1] | 5-[2,6-difluoro-4-(1-hydroxy-1-methylethyl)phenyl]-2-{[5-(1H-1,2,3-triazol-1-ylmethyl)pyridin-2-yl]amino}thiophene-3-carboxamide | Calc'd 471, found 471 |
| 505 | 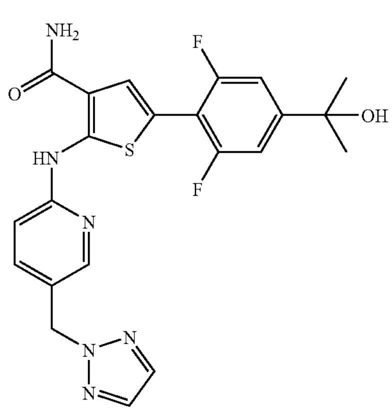 [SMILES: CC(C)(O)c1cc(F)c(-c2cc(C(N)=O)c(Nc3ccc(Cn4nccn4)cn3)s2)c(F)c1] | 5-[2,6-difluoro-4-(1-hydroxy-1-methylethyl)phenyl]-2-{[5-(2H-1,2,3-triazol-2-ylmethyl)pyridin-2-yl]amino}thiophene-3-carboxamide | Calc'd 471, found 471 |

Example 506

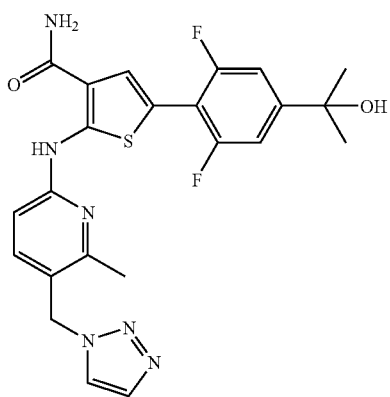 [SMILES: Cc1nc(Nc2sc(-c3c(F)cc(C(C)(C)O)cc3F)cc2C(N)=O)ccc1Cn1ccnn1]

5-[2,6-Difluoro-4-(1-hydroxy-1-methylethyl)phenyl]-2-{[6-methyl-5-(1H-1,2,3-triazol-1-ylmethyl)pyridin-2-yl]amino}thiophene-3-carboxamide

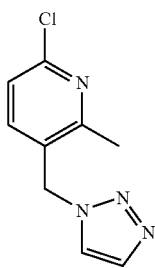 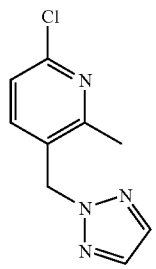

Step 1: 6-Chloro-2-methyl-3-(1H-1,2,3-triazol-1-ylmethyl)pyridine and 6-chloro-2-methyl-3-(2H-1,2,3-triazol-2-ylmethyl)pyridine 3-(Bromomethyl)-6-chloro-2-methylpyridine (Example 421, Step 2) (1.00 g, 4.54 mmol), 1H-1,2,3-triazole (315 μL, 5.44 mmol), and $K_2CO_3$ (1.25 g, 9.07 mmol) were combined in DMF (8.0 mL) and stirred at 50° C. overnight. The mixture was diluted with water and extracted with EtOAc (2×). The combined organic layers were washed with brine, dried ($MgSO_4$), filtered, and evaporated. Flash chromatography (25-100% EtOAc/hexanes) achieved separation of the two regioisomeric products. The more polar band (lower $R_f$) corresponded to 6-chloro-2-methyl-3-(1H-1,2,3-triazol-1-ylmethyl)pyridine (colorless solid), and the less polar band (higher $R_f$) corresponded to 6-chloro-2-methyl-3-(2H-1,2,3-triazol-2-ylmethyl)pyridine (colorless oil).

Calc'd for $C_9H_{10}BrClN_4[M+H]^+$ 209. found 209.

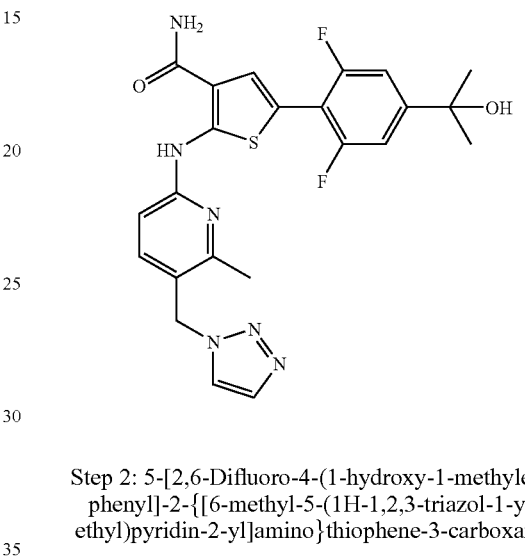

Step 2: 5-[2,6-Difluoro-4-(1-hydroxy-1-methylethyl)phenyl]-2-{[6-methyl-5-(1H-1,2,3-triazol-1-ylmethyl)pyridin-2-yl]amino}thiophene-3-carboxamide The title compound was synthesized from 6-chloro-2-methyl-3-(1H-1,2,3-triazol-1-ylmethyl)pyridine (83 mg, 0.40 mmol) and 2-amino-5-[2,6-difluoro-4-(1-hydroxy-1-methylethyl)phenyl]thiophene-3-carboxamide (130 mg, 0.42 mmol) according to the general procedure in Example 1.

Calc'd for $C_{23}H_{23}F_2N_6O_2S\ [M+H]^+$ 485. found 485.

Additional examples were prepared by procedures similar to those described above and are illustrated in the following table.

TABLE 49

| Example # | Structure | Compound Name | Characterization |
|---|---|---|---|
| 507 | 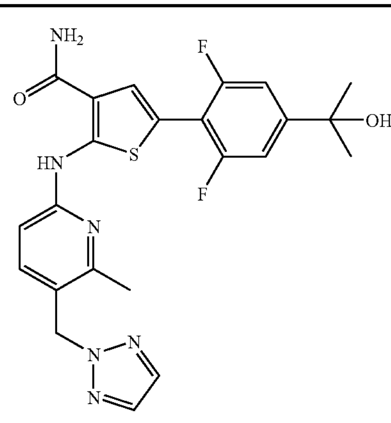 | 5-[2,6-difluoro-4-(1-hydroxy-1-methylethyl)phenyl]-2-{[6-methyl-5-(2H-1,2,3-triazol-2-ylmethyl)pyridin-2-yl]amino}thiophene-3-carboxamide | Calc'd $[M + H]^+$ 485, found 485 |

Example 508

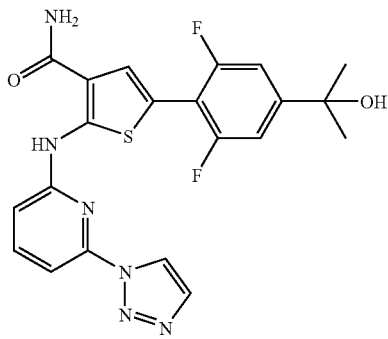 [SMILES: CC(C)(O)c1cc(F)c(-c2cc(C(N)=O)c(Nc3cccc(-n4ccnn4)n3)s2)c(F)c1]

5-[2,6-Difluoro-4-(1-hydroxy-1-methylethyl)phenyl]-2-{[6-(1H-1,2,3-triazol-1-yl)pyridin-2-yl]amino}thiophene-3-carboxamide

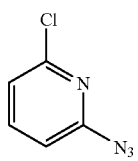

Step 1: 2-Azido-6-chloropyridine

2-Chloro-6-hydrazinopyridine (3.00 g, 20.90 mmol) was suspended in water (20 mL) and cooled to 0° C. Concentrated HCl (3.00 mL, 36.5 mmol) was added to dissolve the starting material and attain a pH of ~1. Sodium nitrite (1.73 g, 25.07 mmol) in water (10 mL) was added dropwise. The thick suspension was allowed to warm to room temperature and extracted with CH$_2$Cl$_2$ (2×). The combined organic layers were dried (MgSO$_4$), filtered, and evaporated. The crude residue was purified by flash chromatography (0-10% EtOAc/hexanes) to afford the title compound as a colorless solid.

$^1$H NMR (600 MHz, CDCl$_3$) δ 7.55 (t, 1H), 7.05 (dd, 1H), 6.70 (dd, 1H). Calc'd for C$_5$H$_4$ClN$_4$ [M+H]$^+$ 155. found 155.

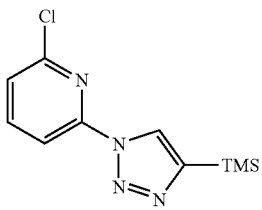 [SMILES: C[Si](C)(C)c1cn(-c2cccc(Cl)n2)nn1]

Step 2: 2-Chloro-6-[4-(trimethylsilyl)-1H-1,2,3-triazol-1-yl]pyridine

2-Azido-6-chloropyridine (500 mg, 3.24 mmol) and trimethylsilylacetylene (545 μL, 3.88 mmol) were combined in t-BuOH (5.0 mL) and water (3.0 mL) CuSO$_4$.5H$_2$O (40 mg, 0.16 mmol) in water (1.0 mL) was added, followed by sodium ascorbate (128 mg, 0.65 mmol) in water (1.0 mL). The reaction was stirred at room temperature overnight, diluted with saturated NaHCO$_3$, and extracted with EtOAc (2×). The combined organic layers were washed with brine, dried (MgSO$_4$), and evaporated to a crude residue that was purified by flash chromatography (0-40% EtOAc/hexanes) to afford the title compound as a colorless solid.

Calcd for C$_{10}$H$_{14}$ClN$_4$Si [M+H]$^+$ 253. found 253.

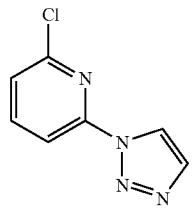 [SMILES: Clc1cccc(-n2ccnn2)n1]

Step 3: 2-Chloro-6-(1H-1,2,3-triazol-1-yl)pyridine

To a solution of 2-chloro-6-[4-(trimethylsilyl)-1H-1,2,3-triazol-1-yl]pyridine (675 mg, 2.67 mmol) in THF (10 mL) was added TBAF (1.0 M in THF, 8.01 mL, 8.01 mmol). The reaction was stirred at room temperature for 2 h. It was subsequently diluted with water and extracted with EtOAc (2×). The combined organic layers were washed with brine, dried (MgSO$_4$), filtered, and evaporated. The crude residue was purified by flash chromatography (10-60% EtOAc/hexanes) to afford the title compound as a colorless solid.

Calc'd for C$_7$H$_6$ClN$_4$ [M+H]$^+$ 181. found 181.

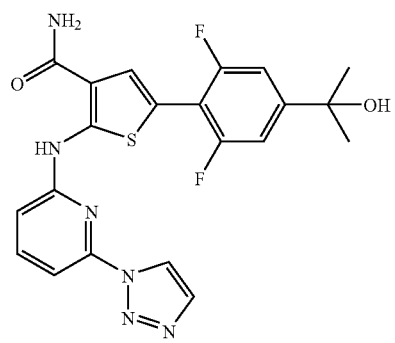 [SMILES: CC(C)(O)c1cc(F)c(-c2cc(C(N)=O)c(Nc3cccc(-n4ccnn4)n3)s2)c(F)c1]

Step 4: 5-[2,6-Difluoro-4-(1-hydroxy-1-methylethyl)phenyl]-2-{[6-(1H-1,2,3-triazol-1-yl)pyridin-2-yl]amino}thiophene-3-carboxamide The title compound was synthesized from 2-chloro-6-(1H-1,2,3-triazol-1-yl)pyridine (72 mg, 0.40 mmol) and 2-amino-5-[2,6-difluoro-4-(1-hydroxy-1-methylethyl)phenyl]thiophene-3-carboxamide (125 mg, 0.40 mmol) according to the general procedure in Example 1.

Calc'd for C$_{21}$H$_{19}$F$_2$N$_6$O$_2$S [M+H]$^+$ 457. found 457.

Example 509

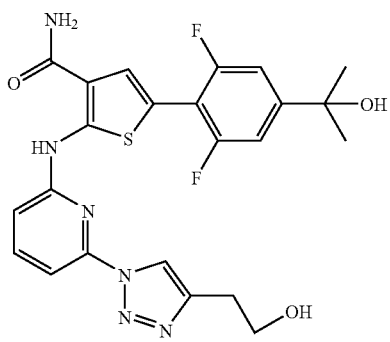 [SMILES: CC(C)(O)c1cc(F)c(-c2cc(C(N)=O)c(Nc3cccc(-n4cc(CCO)nn4)n3)s2)c(F)c1]

5-[2,6-Difluoro-4-(1-hydroxy-1-methylethyl)phenyl]-2-({6-[4-(2-hydroxyethyl)-1H-1,2,3-triazol-1-yl]pyridin-2-yl}amino)thiophene-3-carboxamide

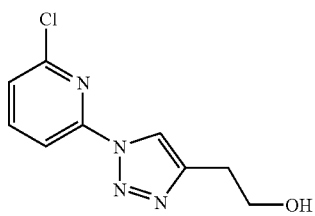 [SMILES: OCCc1cn(-c2cccc(Cl)n2)nn1]

Step 1: 2-[1-(6-Chloropyridin-2-yl)-1H-1,2,3-triazol-4-yl]ethanol

2-Azido-6-chloropyridine (Example 508 Step 1) (500 mg, 3.24 mmol) and 3-butyn-1-ol (320 µL, 4.21 mmol) were combined in t-BuOH (5.0 mL) and water (3.0 mL).

$CuSO_4 \cdot 5H_2O$ (40 mg, 0.16 mmol) in water (1.0 mL) was added, followed by sodium ascorbate (128 mg, 0.65 mmol) in water (1.0 mL) The reaction was stirred at room temperature for 3 h, diluted with saturated $NaHCO_3$, and extracted with EtOAc (2×). The combined organic layers were washed with brine, dried ($MgSO_4$), filtered, and evaporated to a yellow residue. The crude residue was purified by flash chromatography (50-100% EtOAc/hexanes) to afford the title compound as a colorless solid.

Calc'd for $C_9H_{10}ClN_4O$ [M+H]$^+$ 225. found 225.

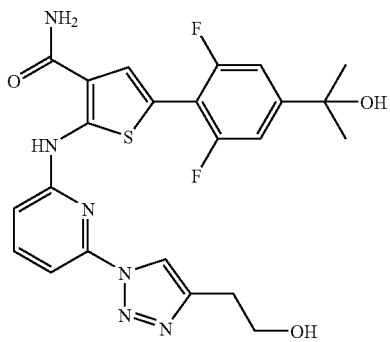 [SMILES: CC(C)(O)c1cc(F)c(-c2cc(C(N)=O)c(Nc3cccc(-n4cc(CCO)nn4)n3)s2)c(F)c1]

Step 2: 5-[2,6-Difluoro-4-(1-hydroxy-1-methylethyl)phenyl]-2-({6-[4-(2-hydroxyethyl)-1H-1,2,3-triazol-1-yl]pyridin-2-yl}amino)thiophene-3-carboxamide The title compound was synthesized from 2-[1-(6-chloropyridin-2-yl)-1H-1,2,3-triazol-4-yl]ethanol (90 mg, 0.40 mmol) and 2-amino-5-[2,6-difluoro-4-(1-hydroxy-1-methylethyl)phenyl]thiophene-3-carboxamide (125 mg, 0.40 mmol) according to the general procedure in Example 1.

Calc'd for $C_{23}H_{23}F_2N_6O_3S$ [M+H]$^+$ 501. found 501.

Example 510

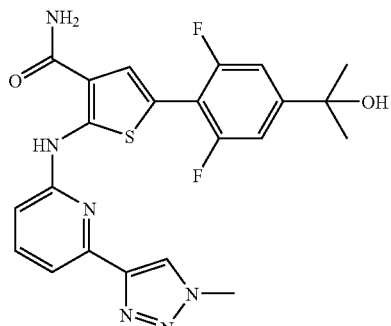

5-[2,6-Difluoro-4-(1-hydroxy-1-methylethyl)phenyl]-2-{[6-(1-methyl-1H-1,2,3-triazol-4-yl)pyridin-2-yl]amino}thiophene-3-carboxamide

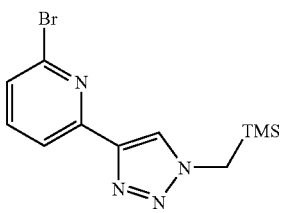 [SMILES: C[Si](C)(C)Cn1cc(-c2cccc(Br)n2)nn1]

Step 1: 2-Bromo-6-{1-[(trimethylsilyl)methyl]-1H-1,2,3-triazol-4-yl}pyridine

2-Bromo-6-ethynylpyridine (Example 465, Step 1) (350 mg, 1.92 mmol) and trimethylsilylmethyl azide (323 mg, 2.50 mmol) were combined in t-BuOH (4.0 mL) and water (3.0 mL). $CuSO_4 \cdot 5H_2O$ (24 mg, 0.096 mmol) in water (0.50 mL) was added, followed by sodium ascorbate (76 mg, 0.39 mmol) in water (0.50 mL). The reaction was stirred at room temperature overnight, diluted with saturated $NaHCO_3$, and extracted with EtOAc (2×). The combined organic layers were washed with brine, dried ($MgSO_4$), filtered, and evaporated to a yellow residue that was purified by flash chromatography (0-50% EtOAc/hexanes) to afford the title compound as a colorless solid.

Calc'd for $C_{11}H_{16}BrN_4Si$ [M+H]$^+$ 311. found 311.

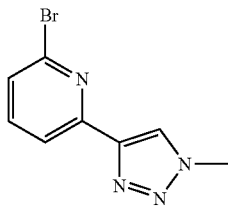

Step 2: 2-Bromo-6-(1-methyl-1H-1,2,3-triazol-4-yl)pyridine

To a solution of 2-bromo-6-{1-[(trimethylsilyl)methyl]-1H-1,2,3-triazol-4-yl}pyridine (550 mg, 1.77 mmol) in THF (10 mL) was added TBAF (1.0 M in THF, 5.30 mL, 5.30 mmol). The reaction was stirred at room temperature for 2 h. It was subsequently diluted with water and extracted with EtOAc (2×). The combined organic layers were washed with brine, dried (MgSO₄), filtered, and evaporated. Flash chromatography (20-100% EtOAc/hexanes) afforded the title compound as a colorless solid.

Calc'd for $C_8H_8BrN_4$ [M+H]⁺ 239. found 239.

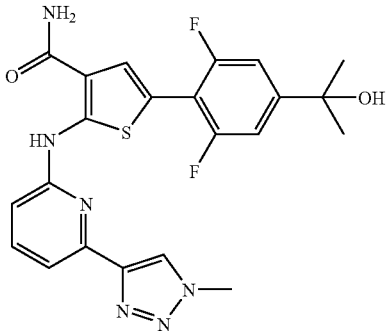 [SMILES: Cn1cc(-c2cccc(Nc3sc(-c4c(F)cc(C(C)(C)O)cc4F)cc3C(N)=O)n2)nn1]

Step 3: 5-[2,6-Difluoro-4-(1-hydroxy-1-methylethyl) phenyl]-2-{[6-(1-methyl-1H-1,2,3-triazol-4-yl)pyridin-2-yl]amino}thiophene-3-carboxamide The title compound was synthesized from 2-bromo-6-(1-methyl-1H-1,2,3-triazol-4-yl)pyridine (96 mg, 0.40 mmol) and 2-amino-5-[2,6-difluoro-4-(1-hydroxy-1-methylethyl) phenyl]thiophene-3-carboxamide (125 mg, 0.40 mmol) according to the general procedure in Example 1.

Calc'd for $C_{22}H_{21}F_2N_6O_2S$ [M+H]⁺ 471. found 471.

Example 511

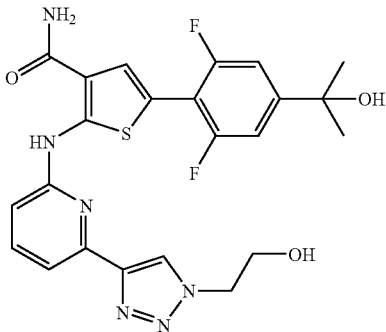 [SMILES: CC(C)(O)c1cc(F)c(-c2cc(C(N)=O)c(Nc3cccc(-c4cn(CCO)nn4)n3)s2)c(F)c1]

5-[2,6-Difluoro-4-(1-hydroxy-1-methylethyl)phenyl]-2-({6-[1-(2-hydroxyethyl)-1H-1,2,3-triazol-4-yl]pyridin-2-yl}amino)thiophene-3-carboxamide

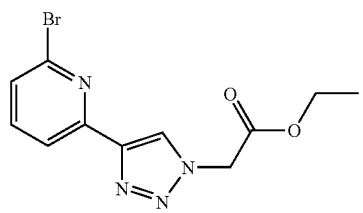 [SMILES: CCOC(=O)Cn1cc(-c2cccc(Br)n2)nn1]

Step 1: Ethyl[4-(6-bromopyridin-2-yl)-1H-1,2,3-triazol-1-yl]acetate

2-Bromo-6-ethynylpyridine (Example 465, Step 1) (350 mg, 1.92 mmol) and ethyl azidoacetate (1.08 ml, 1.92 mmol) were combined in t-BuOH (4.0 mL) and water (2.0 mL). CuSO₄.5H₂O (24 mg, 0.096 mmol) in water (1.0 mL) was added, followed by sodium ascorbate (76 mg, 0.39 mmol) in water (1.0 mL). The reaction was stirred at room temperature for 5 h, diluted with saturated NaHCO₃, and extracted with EtOAc (2×). The combined organic layers were washed with brine, dried (MgSO₄), filtered, and evaporated to a yellow residue that was purified by flash chromatography (0-30% EtOAc/hexanes) to afford the title compound as a colorless solid.

Calc'd for $C_{11}H_{12}BrN_4O_2$ [M+H]⁺ 311. found 311.

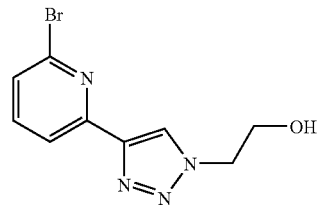 [SMILES: OCCn1cc(-c2cccc(Br)n2)nn1]

Step 2: 2-[4-(6-Bromopyridin-2-yl)-1H-1,2,3-triazol-1-yl]ethanol

To a solution of NaBH₄ (60 mg, 1.58 mmol) in MeOH (3.0 mL) at room temperature was added ethyl[4-(6-bromopyridin-2-yl)-1H-1,2,3-triazol-1-yl]acetate (245 mg, 0.79 mmol) in MeOH (7.0 mL) The reaction was stirred at room temperature for 2 h. It was then diluted with water and extracted with EtOAc (2×). The combined organic layers were washed with brine, dried (MgSO₄), filtered, and evaporated. Flash chromatography (20-100% EtOAc/hexanes) afforded the title compound as a colorless gum.

Calc'd for $C_9H_{10}BrN_4O$ [M+H]⁺ 269. found 269.

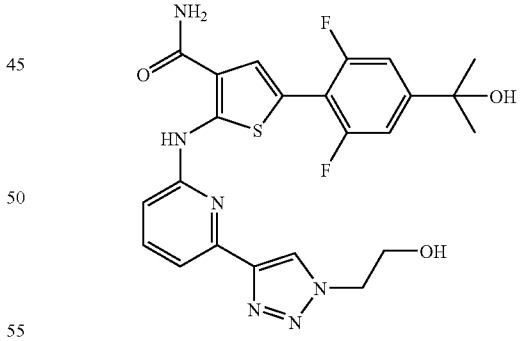

Step 3: 5-[2,6-Difluoro-4-(1-hydroxy-1-methylethyl) phenyl]-2-({6-[1-(2-hydroxyethyl)-1H-1,2,3-triazol-4-yl]pyridin-2-yl}amino)thiophene-3-carboxamide The title compound was synthesized from 2-[4-(6-bromopyridin-2-yl)-1H-1,2,3-triazol-1-yl]ethanol (108 mg, 0.40 mmol) and 2-amino-5-[2,6-difluoro-4-(1-hydroxy-1-methylethyl)phenyl]thiophene-3-carboxamide (125 mg, 0.40 mmol) according to the general procedure in Example 1.

Calc'd for $C_{23}H_{23}F_2N_6O_3S$ [M+H]⁺ 501. found 501.

Example 512

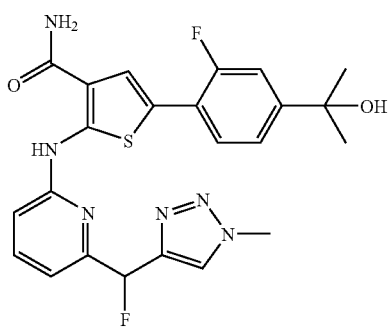 [SMILES: Cn1cc(C(F)c2cccc(Nc3sc(-c4ccc(C(C)(C)O)cc4F)cc3C(N)=O)n2)nn1]

5-[2-Fluoro-4-(1-hydroxy-1-methylethyl)phenyl]-2-({6-[fluoro(1-methyl-1H-1,2,3-triazol-4-yl)methyl]pyridin-2-yl}amino)thiophene-3-carboxamide

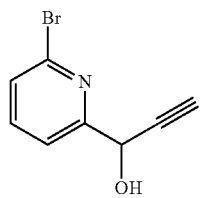

Step 1: 1-(6-Bromopyridin-2-yl)prop-2-yn-1-ol

6-Bromo-2-pyridine carboxaldehyde (3.00 g, 16.13 mmol) was dissolved in THF (50 mL) and cooled to −78° C. Ethynylmagnesium bromide (0.5 M in THF, 45.2 mL, 22.58 mmol) was added, and the reaction was allowed to warm to room temperature over 2 h. It was then quenched with saturated NH$_4$Cl and extracted with EtOAc (2×). The combined organic layers were washed with brine, dried (MgSO$_4$), filtered, and evaporated. Flash chromatography (50% EtOAc/hexanes) afforded the title compound as a yellow solid.

Calc'd for C$_8$H$_7$BrNO [M+H]$^+$ 212. found 212.

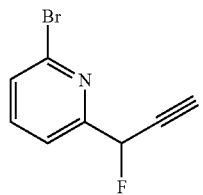

Step 2: 2-Bromo-6-(1-fluoroprop-2-yn-1-yl)pyridine 1-(6-Bromopyridin-2-yl)prop-2-yn-1-ol (1.06 g, 5.00 mmol) was dissolved in CH$_2$Cl$_2$ (20 mL) and cooled to 0° C. Diethylaminosulfur trifluoride (925 µL, 7.00 mmol) was added dropwise, and the brown solution was stirred at 0° C. for 1 h. The reaction was quenched with saturated NaHCO$_3$ and extracted with CH$_2$Cl$_2$ (3×). The combined organic layers were washed with brine, dried (MgSO$_4$), filtered, and evaporated. Flash chromatography (0-15% EtOAc/hexanes) afforded the title compound as an orange oil.

Calc'd for C$_8$H$_6$BrFN [M+H]$^+$ 214. found 214.

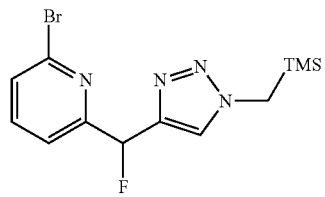 [SMILES: C[Si](C)(C)Cn1cc(C(F)c2cccc(Br)n2)nn1]

Step 3: 2-Bromo-6-(fluoro{1-[(trimethylsilyl)methyl]-1H-1,2,3-triazol-4-yl}methyl)pyridine 2-Bromo-6-(1-fluoroprop-2-yn-1-yl)pyridine (520 mg, 2.43 mmol) and trimethylsilylmethyl azide (377 mg, 2.92 mmol) were combined in t-BuOH (5.0 mL) and water (3.0 mL). CuSO$_4$·5H$_2$O (30 mg, 0.12 mmol) in water (1.0 mL) was added, followed by sodium ascorbate (96 mg, 0.49 mmol) in water (1.0 mL). The reaction was stirred at room temperature overnight, diluted with saturated NaHCO$_3$, and extracted with EtOAc (2×). The combined organic layers were washed with brine, dried (MgSO$_4$), filtered, and evaporated to a brown residue that was purified by flash chromatography (0-30% EtOAc/hexanes) to afford the title compound as a colorless solid.

Calc'd for C$_{12}$H$_{17}$BrFN$_4$Si [M+H]$^+$ 343. found 343.

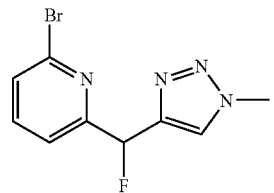

Step 4: 2-Bromo-6-[fluoro(1-methyl-1H-1,2,3-triazol-4-yl)methyl]pyridine

To a solution of 2-bromo-6-(fluoro{1-[(trimethylsilyl)methyl]-1H-1,2,3-triazol-4-yl}methyl)pyridine (500 mg, 1.46 mmol) in THF (10 mL) was added TBAF (1.0 M in THF, 4.37 mL, 4.37 mmol). The reaction was stirred at room temperature for 2 h. It was then diluted with water and extracted with EtOAc (2×). The combined organic layers were washed with brine, dried (MgSO$_4$), filtered, and evaporated. Flash chromatography (30-100% EtOAc/hexanes) provided the title compound as a colorless solid.

Calc'd for C$_9$H$_9$BrFN$_4$ [M+H]$^+$ 271. found 271.

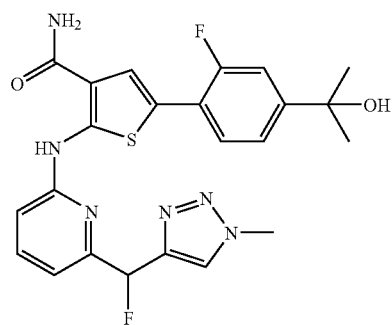 [SMILES: Cn1cc(C(F)c2cccc(Nc3sc(-c4ccc(C(C)(C)O)cc4F)cc3C(N)=O)n2)nn1]

Step 5: 5-[2-Fluoro-4-(1-hydroxy-1-methylethyl)phenyl]-2-({6-[fluoro(1-methyl-1H-1,2,3-triazol-4-yl)methyl]pyridin-2-yl}amino)thiophene-3-carboxamide The title compound was synthesized from 2-bromo-6-[fluoro(1-methyl-1H-1,2,3-triazol-4-yl)methyl]pyridine (111 mg, 0.41 mmol) and 2-amino-5-[2-fluoro-4-(1-hydroxy-1-methylethyl)phenyl]thiophene-3-carboxamide (120 mg, 0.41 mmol) according to the general procedure in Example 1.

Calc'd for $C_{23}H_{23}F_2N_6O_2S$ [M+H]$^+$ 485. found 485.

Example 513

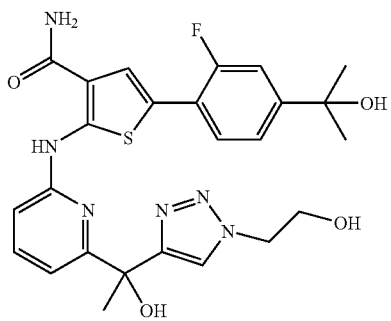 [SMILES: CC(C)(O)c1ccc(-c2cc(C(N)=O)c(Nc3cccc(C(C)(O)c4cn(CCO)nn4)n3)s2)c(F)c1]

5-[2-Fluoro-4-(1-hydroxy-1-methylethyl)phenyl]-2-[(6-{1-hydroxy-1-[1-(2-hydroxyethyl)-1H-1,2,3-triazol-4-yl]ethyl}pyridin-2-yl)amino]thiophene-3-carboxamide

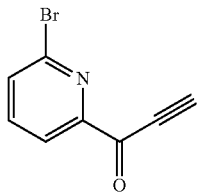

Step 1: 1-(6-Bromopyridin-2-yl)prop-2-yn-1-one

To a solution of 1-(6-bromopyridin-2-yl)prop-2-yn-1-ol (Example 512 Step 1) (1.00 g, 4.72 mmol) in CH$_2$Cl$_2$ (30 mL) was added Dess-Martin periodinane (4.00 g, 9.43 mmol). The reaction was stirred at room temperature for 2 h. It was subsequently diluted with CH$_2$Cl$_2$ and washed with 20% Na$_2$S$_2$O$_3$. The combined organic layers were dried (MgSO$_4$), filtered, and evaporated. Flash chromatography (0-25% EtOAc/hexanes) afforded the title compound as a colorless solid.

Calc'd for $C_8H_5BrNO$ [M+H]$^+$ 210. found 210.

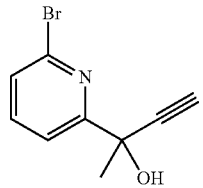

Step 2: 2-(6-Bromopyridin-2-yl)but-3-yn-2-ol 1-(6-Bromopyridin-2-yl)prop-2-yn-1-one (840 mg, 4.00 mmol) was dissolved in THF (20 mL) and cooled to −78° C. Methylmagnesium chloride (3.0 M in THF, 1.60 mL, 4.80 mmol) was added dropwise. The mixture was allowed to warm to room temperature, quenched with saturated NH$_4$Cl, and extracted with EtOAc (2×). The combined organic layers were washed with brine, dried (MgSO$_4$), and evaporated. Flash chromatography (0-50% EtOAc/hexanes) afforded the title compound as a yellow oil.

Calc'd for $C_9H_9BrNO$ [M+H]$^+$ 226. found 226.

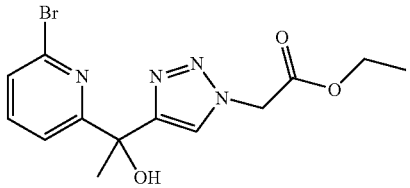 [SMILES: CCOC(=O)Cn1cc(C(C)(O)c2cccc(Br)n2)nn1]

Step 3: Ethyl{-4-[1-(6-bromopyridin-2-yl)-1-hydroxyethyl]-1H-1,2,3-triazol-1-yl}acetate 2-(6-Bromopyridin-2-yl)but-3-yn-2-ol (300 mg, 1.33 mmol) and ethyl azidoacetate (0.82 mL, 1.46 mmol) were combined in t-BuOH (3.0 mL) and water (1.0 mL). CuSO$_4$·5H$_2$O (17 mg, 0.066 mmol) in water (1.0 mL) was added, followed by sodium ascorbate (53 mg, 0.27 mmol) in water (1.0 mL). The reaction was stirred at room temperature overnight, diluted with saturated NaHCO$_3$, and extracted with EtOAc (2×). The combined organic layers were washed with brine, dried (MgSO$_4$), filtered, and evaporated. Purification by flash chromatography (10-100% EtOAc/hexanes) afforded the title compound as a colorless oil.

Calc'd for $C_{13}H_{16}BrN_4O_3$ [M+H]$^+$ 355. found 355.

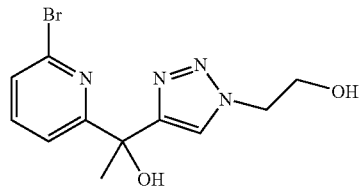 [SMILES: CC(O)(c1cn(CCO)nn1)c1cccc(Br)n1]

Step 4: 1-(6-Bromopyridin-2-yl)-1-[1-(2-hydroxyethyl)-1H-1,2,3-triazol-4-yl]ethanol To a solution of NaBH$_4$ (92 mg, 2.42 mmol) in MeOH (3.0 mL) at room temperature was added ethyl{4-[1-(6-bromopyridin-2-yl)-1-hydroxyethyl]-1H-1,2,3-triazol-1-yl}acetate (430 mg, 1.21 mmol) in MeOH (7.0 mL). The reaction was stirred at room temperature for 2 h. It was then diluted with water and extracted with EtOAc (2×) and 5:1 CH$_2$Cl$_2$:MeOH (5×). The combined organic layers were washed with brine, dried (MgSO₄), filtered, and evaporated. Flash chromatography (0-5% MeOH/EtOAc) afforded the title compound as a colorless solid.

Calc'd for $C_{11}H_{14}BrN_4O_2[M+H]^+$ 313. found 313.

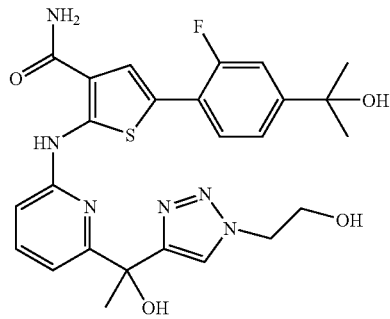 [SMILES: CC(C)(O)c1ccc(-c2cc(C(N)=O)c(Nc3cccc(C(C)(O)c4cn(CCO)nn4)n3)s2)c(F)c1]

Step 5: 5-[2-Fluoro-4-(1-hydroxy-1-methylethyl) phenyl]-2-[(6-{1-hydroxy-1-[1-(2-hydroxyethyl)- 1H-1,2,3-triazol-4-yl]ethyl}pyridin-2-yl)amino] thiophene-3-carboxamide The title compound was synthesized from 1-(6-bromopyridin-2-yl)-1-[1-(2-hydroxyethyl)-1H-1,2,3-triazol-4-yl] ethanol (128 mg, 0.41 mmol) and 2-amino-5-[2-fluoro-4-(1-hydroxy-1-methylethyl)phenyl]thiophene-3-carboxamide (120 mg, 0.41 mmol) according to the general procedure in Example 1.

Calc'd for $C_{25}H_{28}FN_6O_4S$ $[M+H]^+$ 527. found 527.

Additional examples were prepared by procedures similar to those described above and are illustrated in the following table.

TABLE 50

| Example # | Structure | Compound Name | Characterization [M + H]⁺ |
|---|---|---|---|
| 514 | 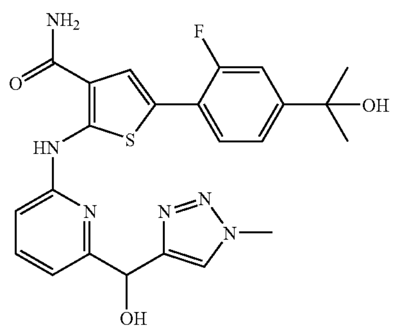 [SMILES: Cn1cc(C(O)c2cccc(Nc3sc(-c4ccc(C(C)(C)O)cc4F)cc3C(N)=O)n2)nn1] | 5-[2-fluoro-4-(1-hydroxy-1-methylethyl)phenyl]-2-({6-[hydroxy(1-methyl-1H-1,2,3-triazol-4-yl)methyl]pyridin-2-yl}amino)thiophene-3-carboxamide | Calc'd 483, found 483 |
| 515 | 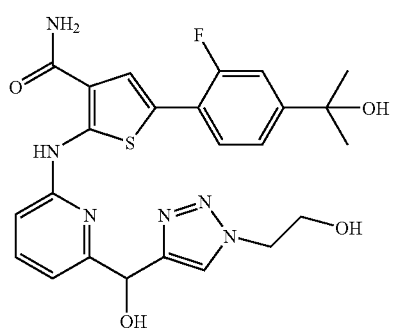 [SMILES: CC(C)(O)c1ccc(-c2cc(C(N)=O)c(Nc3cccc(C(O)c4cn(CCO)nn4)n3)s2)c(F)c1] | 5-[2-fluoro-4-(1-hydroxy-1-methylethyl)phenyl]-2-[(6-{hydroxy[1-(2-hydroxyethyl)-1H-1,2,3-triazol-4-yl]methyl}pyridin-2-yl)amino]thiophene-3-carboxamide | Calc'd 513, found 513 |
| 516 | 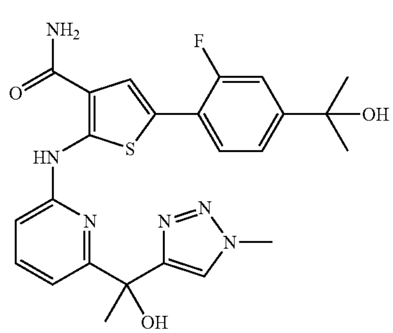 [SMILES: Cn1cc(C(C)(O)c2cccc(Nc3sc(-c4ccc(C(C)(C)O)cc4F)cc3C(N)=O)n2)nn1] | 5-[2-fluoro-4-(1-hydroxy-1-methylethyl)phenyl]-2-({6-[1-hydroxy-1-(1-methyl-1H-1,2,3-triazol-4-yl)ethyl]pyridin-2-yl}amino)thiophene-3-carboxamide | Calc'd 497, found 497 |

Example 517

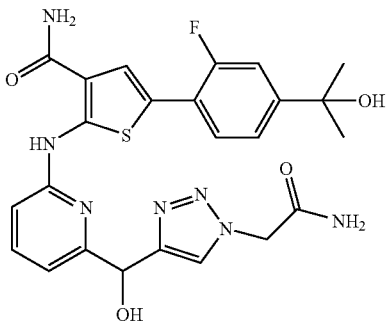 [SMILES: CC(C)(O)c1ccc(-c2cc(C(N)=O)c(Nc3cccc(C(O)c4cn(CC(N)=O)nn4)n3)s2)c(F)c1]

2-({6-[[1-(2-Amino-2-oxoethyl)-1H-1,2,3-triazol-4-yl](hydroxy)methyl]pyridin-2-yl}amino)-5-[2-fluoro-4-(1-hydroxy-1-methylethyl)phenyl]thiophene-3-carboxamide

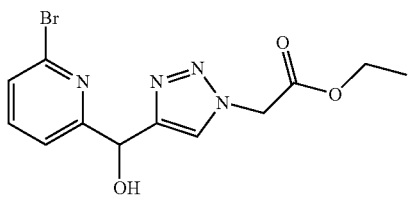 [SMILES: CCOC(=O)Cn1cc(C(O)c2cccc(Br)n2)nn1]

Step 1: Ethyl{4-[(6-bromopyridin-2-yl)(hydroxy)methyl]-1H-1,2,3-triazol-1-yl}acetate 1-(6-Bromopyridin-2-yl)prop-2-yn-1-ol (Example 512, Step 1) (500 mg, 2.36 mmol) and ethyl azidoacetate (1.46 mL, 2.59 mmol) were combined in t-BuOH (5.0 mL) and water (3.0 mL). CuSO$_4$.5H$_2$O (29 mg, 0.12 mmol) in water (1.0 mL) was added, followed by sodium ascorbate (93 mg, 0.47 mmol) in water (1.0 mL). The reaction was stirred at room temperature overnight, diluted with saturated NaHCO$_3$, and extracted with EtOAc (2×). The combined organic layers were washed with brine, dried (MgSO$_4$), filtered, and evaporated. Purification by flash chromatography (50-100% EtOAc/hexanes) afforded the title compound as a colorless solid.

Calc'd for C$_{12}$H$_{14}$BrN$_4$O$_3$ [M+H]$^+$ 341. found 341.

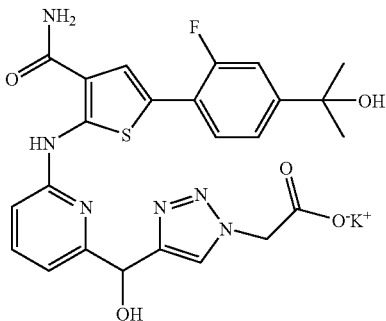

Step 2: Potassium{4-[[6-({3-(aminocarbonyl)-5-[2-fluoro-4-(1-hydroxy-1-methylethyl)phenyl]-2-thienyl}amino)pyridin-2-yl](hydroxy)methyl]-1H-1,2,3-triazol-1-yl}acetate Ethyl{4-[(6-bromopyridin-2-yl)(hydroxy)methyl]-1H-1,2,3-triazol-1-yl}acetate (203 mg, 0.60 mmol), 2-amino-5-[2-fluoro-4-(1-hydroxy-1-methylethyl)phenyl]thiophene-3-carboxamide (175 mg, 0.60 mmol), Pd$_2$ dba$_3$ (54 mg, 0.059 mmol), X-Phos (142 mg, 0.30 mmol), and K$_2$CO$_3$ (90 mg, 0.65 mmol) were combined in a vial, sealed, and evacuated/backfilled with nitrogen. Degassed t-amyl alcohol (1.50 ml) was added, and the mixture was vigorously stirred at 100° C. overnight. The reaction mixture was then diluted with MeOH, filtered through Celite, combined with silica, and evaporated. Flash chromatography (40-100% EtOAc/hexanes then 0-10% MeOH/EtOAc) provided a mixture of the methyl ester (80% by LC/MS) and ethyl ester (20% by LC/MS) products as a yellow solid (transesterified due to the MeOH used in the workup). This material (185 mg) was taken up in THF (3.0 mL)/MeOH (3.0 mL), and KOH (1.0 M, 513 µL, 0.513 mmol) was added. The reaction was stirred at room temperature for 4 h. The mixture was concentrated, resuspended in MeOH, and concentrated again to give the title salt as a yellow solid that was carried on without purification.

Calc'd for C$_{24}$H$_{24}$FN$_6$O$_5$ [M+H]$^+$ 527. found 527.

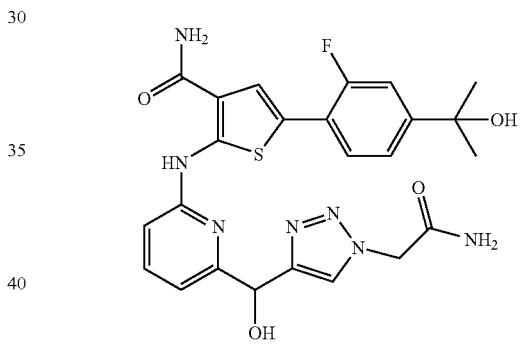

Step 3: 2-({6-[[1-(2-Amino-2-oxoethyl)-1H-1,2,3-triazol-4-yl](hydroxy)methyl]pyridin-2-yl}amino)-5-[2-fluoro-4-(1-hydroxy-1-methylethyl)phenyl]thiophene-3-carboxamide Potassium{4-[[6-({3-(aminocarbonyl)-5-[2-fluoro-4-(1-hydroxy-1-methylethyl)phenyl]-2-thienyl}amino)pyridin-2-yl](hydroxy)methyl]-1H-1,2,3-triazol-1-yl}acetate (96 mg, 0.17 mmol), HOBT (52 mg, 0.34 mmol), EDC (65 mg, 0.34 mmol), and NH$_4$Cl (46 mg, 0.85 mmol) were combined in DMF (3.0 mL), and DIEA (89 µL, 0.51 mmol) was added. The reaction was stirred at room temperature overnight. The solvent was evaporated, and the residue was purified by reverse phase HPLC (10-70% MeCN/water w/0.025% TFA). The isolated product was of insufficient purity, so flash chromatography (dry load, 0-10% MeOH/EtOAc) was performed to afford the title compound as a colorless solid.

Calc'd for C$_{24}$H$_{25}$FN$_7$O$_4$ [M+H]$^+$ 526. found 526.

An additional example was prepared by procedures similar to those described above and is illustrated in the following table.

TABLE 51

| Example # | Structure | Compound Name | Characterization |
|---|---|---|---|
| 518 | 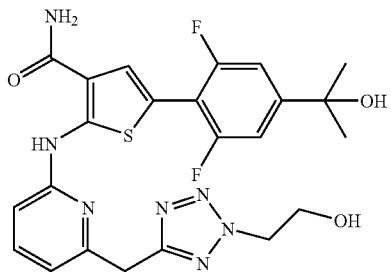 | 2-({6-[{1-[2-(dimethylamino)-2-oxoethyl]-1H-1,2,3-triazol-4-yl}(hydroxy)methyl]pyridin-2-yl}amino)-5-[2-fluoro-4-(1-hydroxy-1-methylethyl)phenyl]thiophene-3-carboxamide | Calc'd [M + H]⁺ 554, found 554 |

Example 519

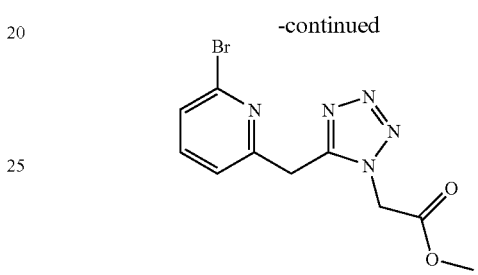

5-[2,6-Difluoro-4-(1-hydroxy-1-methylethyl)phenyl]-2-[(6-{[2-(2-hydroxyethyl)-2H-tetrazol-5-yl]methyl}pyridin-2-yl)amino]thiophene-3-carboxamide

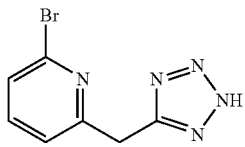 [SMILES: Brc1cccc(Cc2nn[nH]n2)n1]

Step 1: 2-Bromo-6-(2H-tetrazol-5-ylmethyl)pyridine (6-Bromopyridin-2-yl)acetonitrile (Example 235, Step 1) (1.00 g, 5.08 mmol), NaN₃ (396 mg, 6.09 mmol), and ZnBr₂ (1.14 g, 5.08 mmol) were combined in water (10 mL) in a screw-cap vial, sealed, and vigorously stirred at 110° C. for 18 h. The suspension was filtered, and the isolated solid was washed with water to provide the title compound as a colorless solid.

Calc'd for C₇H₇BrN₅ [M+H]⁺ 240. found 240.

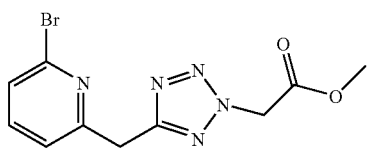

-continued

Step 2: Methyl{5-[(6-bromopyridin-2-yl)methyl]-2H-tetrazol-2-yl}acetate and methyl{5-[(6-bromopyridin-2-yl)methyl]-1H-tetrazol-1-yl}acetate 2-Bromo-6-(2H-tetrazol-5-ylmethyl)pyridine (605 mg, 2.52 mmol), K₂CO₃ (697 mg, 5.04 mmol), and methyl bromoacetate (477 μL, 5.04 mmol) were combined in DMF (10 mL) and stirred at 50° C. overnight. The mixture was diluted with saturated NaHCO₃ and extracted with EtOAc (2×). The combined organic layers were washed with brine, dried (MgSO₄), filtered, and evaporated. Flash chromatography (10-100% EtOAc/hexanes) allowed separation of the regioisomeric products. Methyl{5-[(6-bromopyridin-2-yl)methyl]-2H-tetrazol-2-yl}acetate (colorless oil) corresponded to the less polar band (higher R_f) and methyl{5-[(6-bromopyridin-2-yl)methyl]-1H-tetrazol-1-yl}acetate (colorless gum) corresponded to the more polar band (lower R_f).

Calc'd for C₁₀H₁₁BrN₅O₂ [M+H]⁺ 312. found 312.

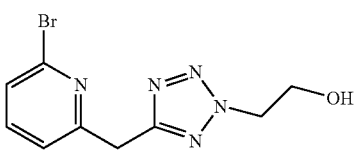 [SMILES: OCCn1nnc(Cc2cccc(Br)n2)n1]

Step 3: 2-{5-[(6-Bromopyridin-2-yl)methyl]-2H-tetrazol-2-yl}ethanol

To a solution of NaBH₄ (92 mg, 2.44 mmol) in MeOH (4.0 mL) at room temperature was added methyl{5-[(6-bromopyridin-2-yl)methyl]-2H-tetrazol-2-yl}acetate (380 mg, 1.22 mmol) in MeOH (6.0 mL). The reaction was stirred at room temperature for 2 h. It was then diluted with water and extracted with EtOAc (3×). The combined organic layers were washed with brine, dried (MgSO₄), filtered, and evaporated. Flash chromatography (40-100% EtOAc/hexanes) afforded the title compound as a colorless gum.

Calc'd for $C_9H_{11}BrN_5O$ [M+H]$^+$ 284. found 284.

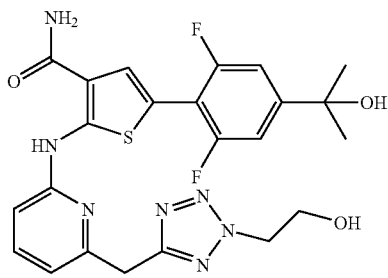 [SMILES: CC(C)(O)c1cc(F)c(-c2cc(C(N)=O)c(Nc3cccc(Cc4nnn(CCO)n4)n3)s2)c(F)c1]

Step 4: 5-[2,6-Difluoro-4-(1-hydroxy-1-methylethyl)phenyl]-2-[(6-{[2-(2-hydroxyethyl)-2H-tetrazol-5-yl]methyl}pyridin-2-yl)amino]thiophene-3-carboxamide The title compound was synthesized from 2-{5-[(6-bromopyridin-2-yl)methyl]-2H-tetrazol-2-yl}ethanol (114 mg, 0.40 mmol) and 2-amino-5-[2,6-difluoro-4-(1-hydroxy-1-methylethyl)phenyl]thiophene-3-carboxamide (125 mg, 0.40 mmol) according to the general procedure in Example 1.

Calc'd for $C_{23}H_{24}F_2N_7O_3S$ [M+H]$^+$ 516. found 516.

Additional examples were prepared by procedures similar to those described above.

TABLE 52

| Example # | Structure | Compound Name | Characterization [M + H]$^+$ |
|---|---|---|---|
| 520 | 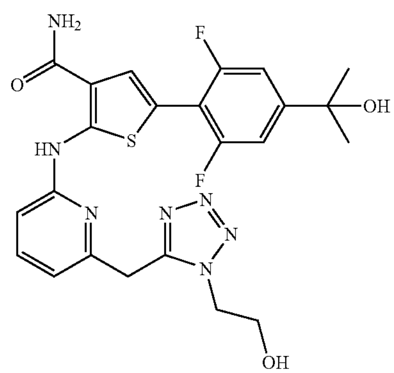 [SMILES: CC(C)(O)c1cc(F)c(-c2cc(C(N)=O)c(Nc3cccc(Cc4nnnn4CCO)n3)s2)c(F)c1] | 5-[2,6-difluoro-4-(1-hydroxy-1-methylethyl)phenyl]-2-[(6-{[1-(2-hydroxyethyl)-1H-tetrazol-5-yl]methyl}pyridin-2-yl)amino]thiophene-3-carboxamide | Calc'd 516, found 516 |
| 521 | 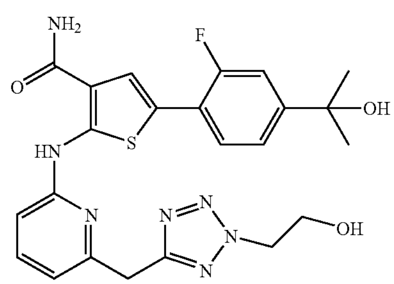 [SMILES: CC(C)(O)c1ccc(-c2cc(C(N)=O)c(Nc3cccc(Cc4nnn(CCO)n4)n3)s2)c(F)c1] | 5-[2-fluoro-4-(1-hydroxy-1-methylethyl)phenyl]-2-[(6-{[2-(2-hydroxyethyl)-2H-tetrazol-5-yl]methyl}pyridin-2-yl)amino]thiophene-3-carboxamide | Calc'd 498, found 498 |
| 522 | 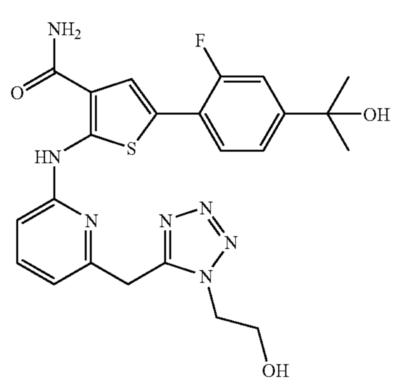 [SMILES: CC(C)(O)c1ccc(-c2cc(C(N)=O)c(Nc3cccc(Cc4nnnn4CCO)n3)s2)c(F)c1] | 5-[2-fluoro-4-(1-hydroxy-1-methylethyl)phenyl]-2-[(6-{[1-(2-hydroxyethyl)-1H-tetrazol-5-yl]methyl}pyridin-2-yl)amino]thiophene-3-carboxamide | Calc'd 498, found 498 |

TABLE 52-continued

| Example # | Structure | Compound Name | Characterization [M + H]+ |
|---|---|---|---|
| 523 | 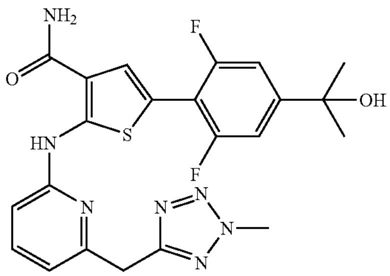 [SMILES: Cn1nnc(Cc2cccc(Nc3sc(-c4c(F)cc(C(C)(C)O)cc4F)cc3C(N)=O)n2)n1] | 5-[2,6-difluoro-4-(1-hydroxy-1-methylethyl)phenyl]-2-({6-[(2-methyl-2H-tetrazol-5-yl)methyl]pyridin-2-yl}amino)thiophene-3-carboxamide | Calc'd 486, found 486 |
| 524 | 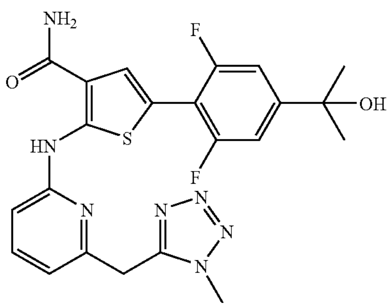 [SMILES: Cn1nnnc1Cc1cccc(Nc2sc(-c3c(F)cc(C(C)(C)O)cc3F)cc2C(N)=O)n1] | 5-[2,6-difluoro-4-(1-hydroxy-1-methylethyl)phenyl]-2-({6-[(1-methyl-1H-tetrazol-5-yl)methyl]pyridin-2-yl}amino)thiophene-3-carboxamide | Calc'd 486, found 486 |
| 525 | 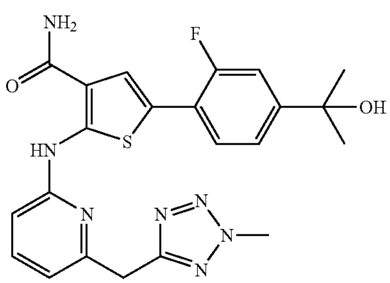 [SMILES: Cn1nnc(Cc2cccc(Nc3sc(-c4ccc(C(C)(C)O)cc4F)cc3C(N)=O)n2)n1] | 5-[2-fluoro-4-(1-hydroxy-1-methylethyl)phenyl]-2-({6-[(2-methyl-2H-tetrazol-5-yl)methyl]pyridin-2-yl}amino)thiophene-3-carboxamide | Calc'd 468, found 468 |
| 526 | 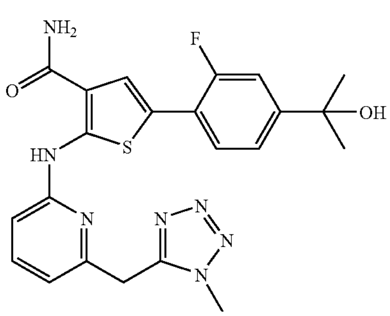 | 5-[2-fluoro-4-(1-hydroxy-1-methylethyl)phenyl]-2-({6-[(1-methyl-1H-tetrazol-5-yl)methyl]pyridin-2-yl}amino)thiophene-3-carboxamide | Calc'd 468, found 468 |

Example 527

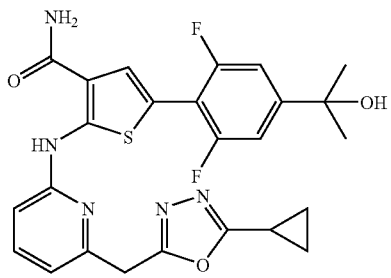 [SMILES: CC(C)(O)c1cc(F)c(-c2cc(C(N)=O)c(Nc3cccc(Cc4nnc(C5CC5)o4)n3)s2)c(F)c1]

2-({6-[(5-Cyclopropyl-1,3,4-oxadiazol-2-yl)methyl]pyridin-2-yl}amino)-5-[2,6-difluoro-4-(1-hydroxy-1-methylethyl)phenyl]thiophene-3-carboxamide

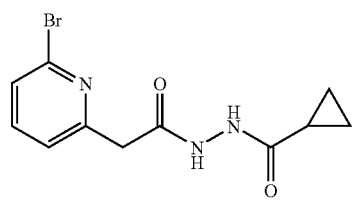 [SMILES: O=C(Cc1cccc(Br)n1)NNC(=O)C1CC1]

Step 1: N'-[2-(6-Bromopyridin-2-yl)acetyl]cyclopropanecarbohydrazide (6-Bromopyridin-2-yl)acetic acid (Example 235, Step 2) (41% wt, 1.50 g, 2.85 mmol), EDC (1.64 g, 8.54 mmol), HOBT (872 mg, 5.69 mmol), and cyclopropanecarboxylic acid hydrazide (570 mg, 5.69 mmol) were combined in DMF (15 mL), and DIEA (994 µL, 5.69 mmol) was added. The reaction was stirred overnight at room temperature. After evaporation of the DMF, the residue was diluted with water and extracted with 5:1 $CH_2Cl_2$:MeOH (3×). The combined organic layers were dried ($MgSO_4$), filtered, and evaporated. The solid residue was triturated with $CH_2Cl_2$ and filtered to isolate the title compound as a colorless solid.

Calc'd for $C_{11}H_{13}BrN_3O_2$ [M+H]$^+$ 298. found 298.

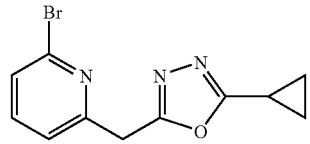 [SMILES: Brc1cccc(Cc2nnc(C3CC3)o2)n1]

Step 2: 2-Bromo-6-[(5-cyclopropyl-1,3,4-oxadiazol-2-yl)methyl]pyridine

N'-[2-(6-Bromopyridin-2-yl)acetyl]cyclopropanecarbohydrazide (200 mg, 0.67 mmol) and Burgess reagent (320 mg, 1.34 mmol) were combined in THF (4.0 mL) and heated at 100° C. for 25 min in a microwave. The reaction mixture was concentrated and directly purified by flash chromatography (10-100% EtOAc/hexanes) to afford the title compound as a colorless solid.

Calc'd for $C_{11}BrN_3O$ [M+H]$^+$ 280. found 280.

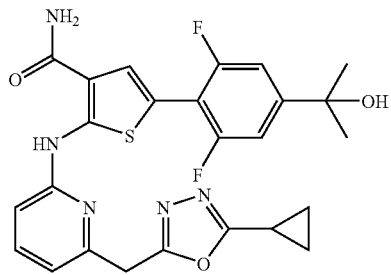 [SMILES: CC(C)(O)c1cc(F)c(-c2cc(C(N)=O)c(Nc3cccc(Cc4nnc(C5CC5)o4)n3)s2)c(F)c1]

Step 3: 2-({6-[(5-Cyclopropyl-1,3,4-oxadiazol-2-yl)methyl]pyridin-2-yl}amino)-5-[2,6-difluoro-4-(1-hydroxy-1-methylethyl)phenyl]thiophene-3-carboxamide The title compound was synthesized from 2-bromo-6-[(5-cyclopropyl-1,3,4-oxadiazol-2-yl)methyl]pyridine (94 mg, 0.34 mmol) and 2-amino-5-[2,6-difluoro-4-(1-hydroxy-1-methylethyl)phenyl]thiophene-3-carboxamide (110 mg, 0.35 mmol) according to the general procedure in Example 1.

Calc'd for $C_{25}H_{24}F_2N_5O_3S$ [M+H]$^+$ 512. found 512.

An additional example was prepared by procedures similar to those described above and is illustrated in the following table.

TABLE 53

| Example # | Structure | Compound Name | Characterization |
|---|---|---|---|
| 528 | 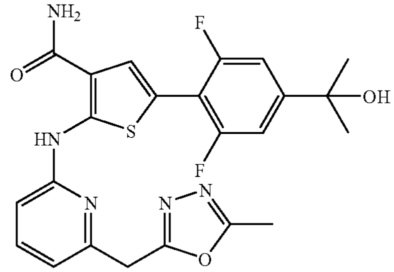 [SMILES: Cc1nnc(Cc2cccc(Nc3sc(-c4c(F)cc(C(C)(C)O)cc4F)cc3C(N)=O)n2)o1] | 5-[2,6-difluoro-4-(1-hydroxy-1-methylethyl)phenyl]-2-({6-[(5-methyl-1,3,4-oxadiazol-2-yl)methyl]pyridin-2-yl}amino)thiophene-3-carboxamide | Calc'd [M + H]$^+$ 486, found 486 |

Example 529

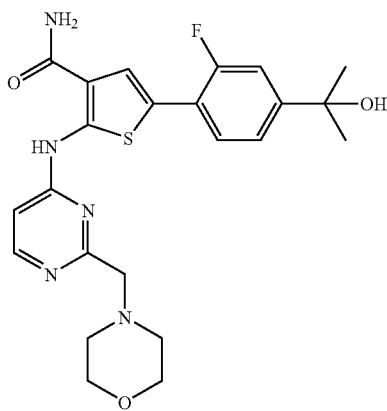

5-[2-Fluoro-4-(1-hydroxy-1-methylethyl)phenyl]-
2-{[2-(morpholin-4-ylmethyl)pyrimidin-4-yl]
amino}thiophene-3-carboxamide

Step 1.
4-[(4-Chloropyrimidin-2-yl)methyl]morpholine

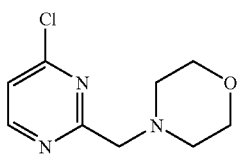 [SMILES: Clc1ccnc(CN2CCOCC2)n1]

The title compound was prepared according to the general procedure in Example 45 Step 1 using 4-chloropyrimidine-2-carbaldehyde (2 g, 14.03 mmol) and morpholine (1.467 mL, 16.84 mmol) as the starting materials.

Calc'd for $C_9H_{13}ClN_3O$ [M+H]$^+$: 214, 216. Found: 214, 216.

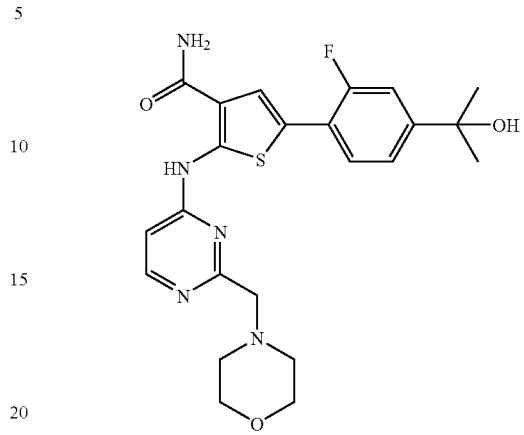

Step 2. 5-[2-Fluoro-4-(1-hydroxy-1-methylethyl) phenyl]-2-{[2-(morpholin-4-ylmethyl)pyrimidin-4-yl]amino}thiophene-3-carboxamide 2-Amino-5-[2-fluoro-4-(1-hydroxy-1-methylethyl)phenyl]thiophene-3-carboxamide (100 mg, 0.34 mmol), 4-[(4-chloropyrimidin-2-yl)methyl]morpholine (72.6 mg, 0.34 mmol), Pd$_2$dba$_3$ (31.1 mg, 0.03 mmol), K$_2$CO$_3$ (51.6 mg, 0.37 mmol) and X-Phos (81 mg, 0.17 mmol) were combined in a 2 mL microwave vial. Degassed tert-amyl alcohol (0.7 mL) was added and the vial evacuated and back-filled with N$_2$ (3×). The resulting mixture was stirred at 100° C. for 24 hours. The reaction mixture was cooled to room temperature, MeOH was added and the reaction mixture was filtered through Celite. The filtrate was combined with silica gel and concentrated in vacuo. Purification of the residue by silica gel chromatography (0-20% MeOH-EtOAc) gave the title compound as a pale yellow solid.

Calc'd for $C_{23}H_{27}FN_5O_3S$ [M+H]$^+$: 472. Found: 472.

Additional examples were prepared using procedures similar to those described above and are illustrated in the following table.

TABLE 54

| Example # | Structure | Compound Name | Characterization [M + H]$^+$ |
|---|---|---|---|
| 530 | <img> | 5-(4-tert-butylphenyl)-2-{[2-(morpholin-4-ylmethyl)pyrimidin-4-yl]amino}thiophene-3-carboxamide | Calc'd 452, found 452 |

TABLE 54-continued

| Example # | Structure | Compound Name | Characterization [M + H]+ |
|---|---|---|---|
| 531 | 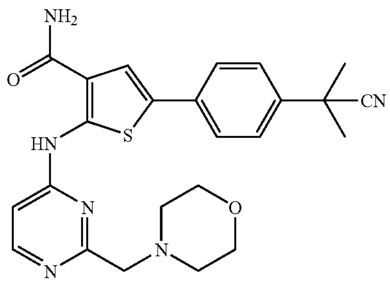 [SMILES: CC(C)(C#N)c1ccc(-c2cc(C(N)=O)c(Nc3ccnc(CN4CCOCC4)n3)s2)cc1] | 5-[4-(1-cyano-1-methylethyl)phenyl]-2-{[2-(morpholin-4-ylmethyl)pyrimidin-4-yl]amino}thiophene-3-carboxamide | Calc'd 463, found 463 |
| 532 | 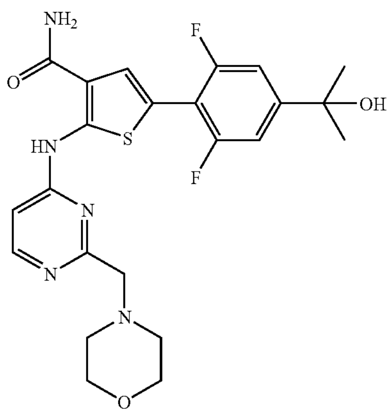 [SMILES: CC(C)(O)c1cc(F)c(-c2cc(C(N)=O)c(Nc3ccnc(CN4CCOCC4)n3)s2)c(F)c1] | 5-[2,6-difluoro-4-(1-hydroxy-1-methylethyl)phenyl]-2-{[2-(morpholin-4-ylmethyl)pyrimidin-4-yl]amino}thiophene-3-carboxamide | Calc'd 490, found 490 |
| 533 | 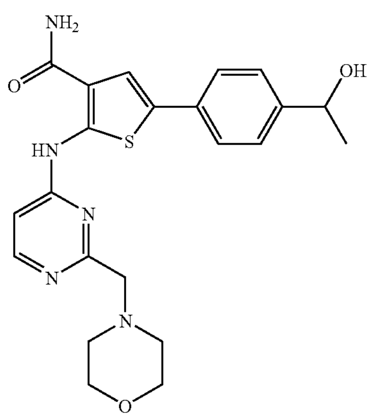 [SMILES: CC(O)c1ccc(-c2cc(C(N)=O)c(Nc3ccnc(CN4CCOCC4)n3)s2)cc1] | 5-[4-(1-hydroxyethyl)phenyl]-2-{[2-(morpholin-4-ylmethyl)pyrimidin-4-yl]amino}thiophene-3-carboxamide | Calc'd 440, found 440 |
| 534 | 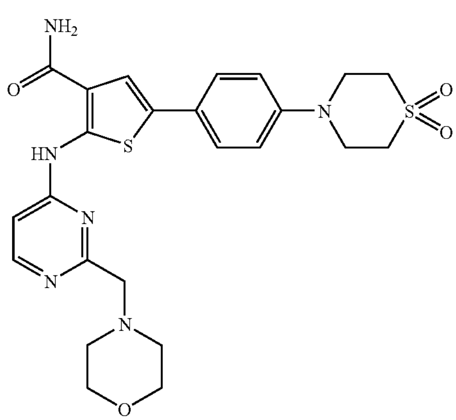 [SMILES: NC(=O)c1cc(-c2ccc(N3CCS(=O)(=O)CC3)cc2)sc1Nc1ccnc(CN2CCOCC2)n1] | 5-[4-(1,1-dioxidothiomorpholin-4-yl)phenyl]-2-{[2-(morpholin-4-ylmethyl)pyrimidin-4-yl]amino}thiophene-3-carboxamide | Calc'd 529, found 529 |

TABLE 54-continued

| Example # | Structure | Compound Name | Characterization [M + H]+ |
|---|---|---|---|
| 535 | 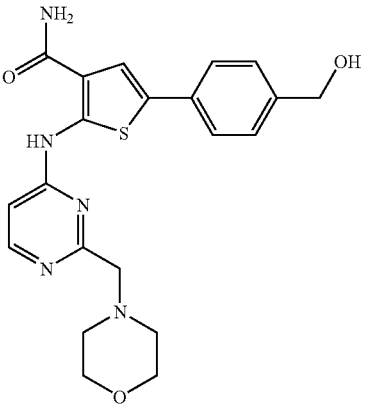 [SMILES: NC(=O)c1cc(-c2ccc(CO)cc2)sc1Nc1ccnc(CN2CCOCC2)n1] | 5[4-(hydroxymethyl)phenyl]-2-{[2-(morpholin-4-ylmethyl)pyrimidin-4-yl]amino}thiophene-3-carboxamide | Calc'd 426, found 426 |
| 536 | 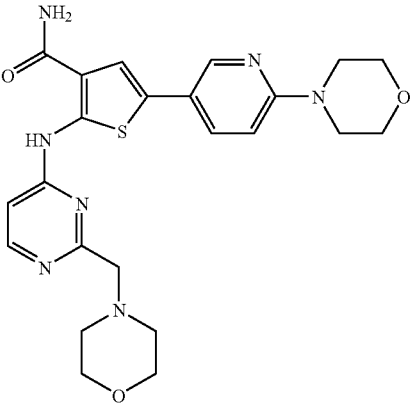 [SMILES: NC(=O)c1cc(-c2ccc(N3CCOCC3)nc2)sc1Nc1ccnc(CN2CCOCC2)n1] | 2-{[2-(morpholin-4-ylmethyl)pyrimidin-4-yl]amino}-5-(6-morpholin-4-ylpyridin-3-yl)thiophene-3-carboxamide | Calc'd 482, found 482 |
| 537 | 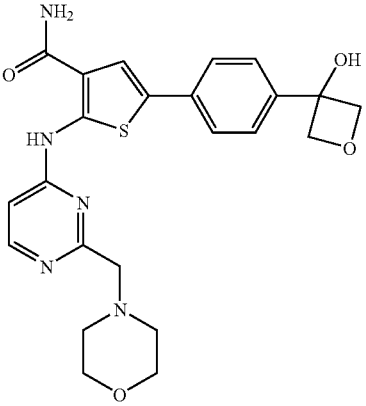 [SMILES: NC(=O)c1cc(-c2ccc(C3(O)COC3)cc2)sc1Nc1ccnc(CN2CCOCC2)n1] | 5-[4-(3-hydroxyoxetan-3-yl)phenyl]-2-{[2-(morpholin-4-ylmethyl)pyrimidin-4-yl]amino}thiophene-3-carboxamide | Calc'd 468, found 468 |

TABLE 54-continued

| Example # | Structure | Compound Name | Characterization [M + H]+ |
|---|---|---|---|
| 538 | 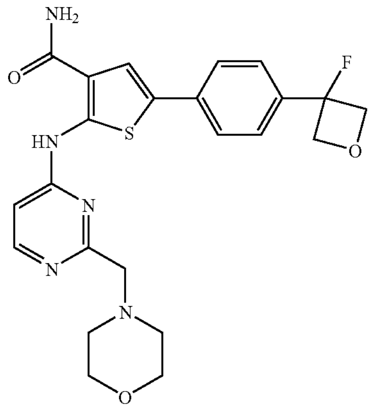 [SMILES: NC(=O)c1cc(-c2ccc(C3(F)COC3)cc2)sc1Nc1ccnc(CN2CCOCC2)n1] | 5-[4-(3-fluorooxetan-3-yl)phenyl]-2-{[2-(morpholin-4-ylmethyl)pyrimidin-4-yl]amino}thiophene-3-carboxamide | Calc'd 470, found 470 |
| 539 | 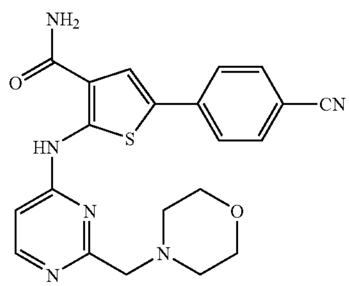 [SMILES: N#Cc1ccc(-c2cc(C(N)=O)c(Nc3ccnc(CN4CCOCC4)n3)s2)cc1] | 5-(4-cyanophenyl)-2-{[2-(morpholin-4-ylmethyl)pyrimidin-4-yl]amino}thiophene-3-carboxamide | Calc'd 421, found 421 |
| 540 | 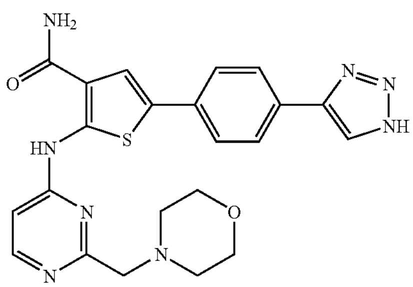 [SMILES: NC(=O)c1cc(-c2ccc(-c3c[nH]nn3)cc2)sc1Nc1ccnc(CN2CCOCC2)n1] | 2-{[2-(morpholin-4-ylmethyl)pyrimidin-4-yl]amino}-5-[4-(1H-1,2,3-triazol-4-yl)phenyl]thiophene-3-carboxamide | Calc'd 463, found 463 |
| 541 | 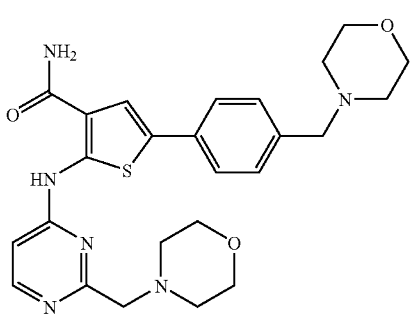 [SMILES: NC(=O)c1cc(-c2ccc(CN3CCOCC3)cc2)sc1Nc1ccnc(CN2CCOCC2)n1] | 5-[4-(morpholin-4-ylmethyl)phenyl]-2-{[2-(morpholin-4-ylmethyl)pyrimidin-4-yl]amino}thiophene-3-carboxamide | Calc'd 495, found 495 |

TABLE 54-continued

| Example # | Structure | Compound Name | Characterization [M + H]+ |
|---|---|---|---|
| 542 | 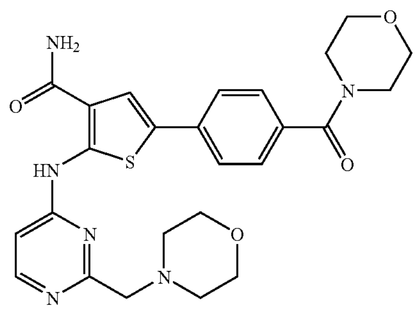 [SMILES: NC(=O)c1cc(-c2ccc(C(=O)N3CCOCC3)cc2)sc1Nc1ccnc(CN2CCOCC2)n1] | 5-[4-(morpholin-4-ylcarbonyl)phenyl]-2-{[2-(morpholin-4-ylmethyl)pyrimidin-4-yl]amino}thiophene-3-carboxamide | Calc'd 509, found 509 |
| 543 | 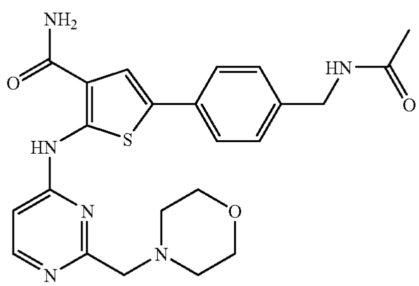 [SMILES: CC(=O)NCc1ccc(-c2cc(C(N)=O)c(Nc3ccnc(CN4CCOCC4)n3)s2)cc1] | 5-{4-[(acetylamino)methyl]phenyl}-2-{[2-(morpholin-4-ylmethyl)pyrimidin-4-yl]amino}thiophene-3-carboxamide | Calc'd 467, found 467 |
| 544 | 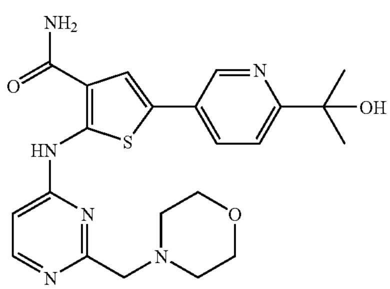 | 5-[6-(1-hydroxy-1-methylethyl)pyridin-3-yl]-2-{[2-(morpholin-4-ylmethyl)pyrimidin-4-yl]amino}thiophene-3-carboxamide | Calc'd 455, found 455 |
| 545 | 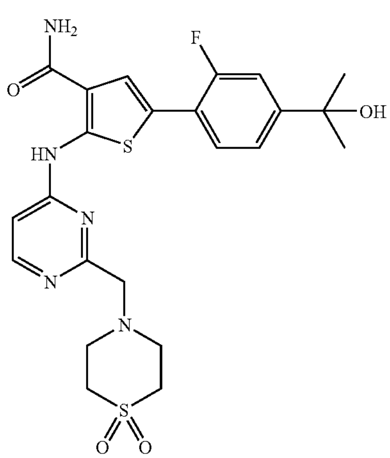 [SMILES: CC(C)(O)c1ccc(-c2cc(C(N)=O)c(Nc3ccnc(CN4CCS(=O)(=O)CC4)n3)s2)c(F)c1] | 2-({2-[(1,1-dioxidothiomorpholin-4-yl)methyl]pyrimidin-4-yl}amino)-5-[2-fluoro-4-(1-hydroxy-1-methylethyl)phenyl]thiophene-3-carboxamide | Calc'd 520, found 520 |

Example 546

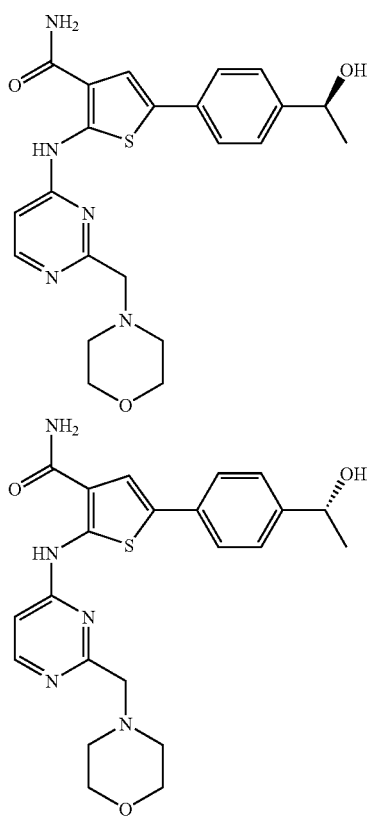

5-{4-[(1S)-1-Hydroxyethyl]phenyl}-2-{[2-(morpholin-4-ylmethyl)pyrimidin-4-yl]amino}thiophene-3-carboxamide and 5-{4-[(1R)-1-hydroxyethyl]phenyl}-2-{[2-(morpholin-4-ylmethyl)pyrimidin-4-yl]amino}thiophene-3-carboxamide The enantiomers of 5-[4-(1-hydroxyethyl)phenyl]-2-{[2-(morpholin-4-ylmethyl)pyrimidin-4-yl]amino}thiophene-3-carboxamide (Example 533) (51 mg, 0.116 mmol) were separated by chiral SFC, OD-H column, 30% IPA+0.25% isobutylamine/CO2, 10 mL/min and subsequently purified by MPLC (0-15% MeOH-DCM) to give peak 1 as a yellow solid and peak 2 as a yellow solid.
Peak 1—Calc'd for $C_{22}H_{26}N_5O_3S$ [M+H]$^+$: 440. Found: 440.
Peak 2—Calc'd for $C_{22}H_{26}N_5O_3S$ [M+H]$^+$: 440. Found: 440.

Example 547

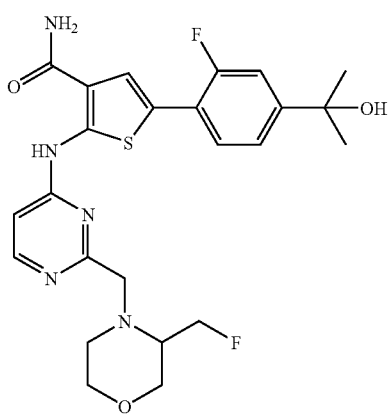 [SMILES: CC(C)(O)c1ccc(-c2cc(C(N)=O)c(Nc3ccnc(CN4CCOCC4CF)n3)s2)c(F)c1]

5-[2-Fluoro-4-(1-hydroxy-1-methylethyl)phenyl]-2-[(2-{[3-(fluoromethyl)morpholin-4-yl]methyl}pyrimidin-4-yl)amino]thiophene-3-carboxamide

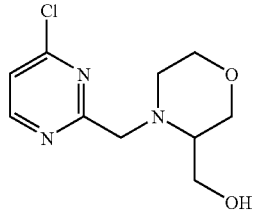 [SMILES: OCC1COCCN1Cc1nccc(Cl)n1]

Step 1. {4-[(4-Chloropyrimidin-2-yl)methyl]morpholin-3-yl}methanol

The title compound was prepared according to the general procedure in Example 45, Step 1 using 4-chloropyrimidine-2-carbaldehyde (0.573 g, 4.02 mmol) and morpholin-3-yl-methanol (0.565 g, 4.82 mmol) as the starting materials.
Calc'd for $C_{10}H_{15}ClN_3O_2$ [M+H]$^+$: 244, 246. Found: 244, 246.

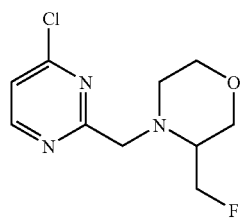 [SMILES: FCC1COCCN1Cc1nccc(Cl)n1]

Step 2. 4-[(4-Chloropyrimidin-2-yl)methyl]-3-(fluoromethyl)morpholine

{4-[(4-Chloropyrimidin-2-yl)methyl]morpholin-3-yl}methanol (200 mg, 0.821 mmol) was taken up in DCM (4 mL) and cooled to 0° C. DAST (0.119 mL, 0.903 mmol) was added and the resulting mixture stirred at 0° C. for 90 minutes. Saturated NaHCO$_3$ was added and the products extracted into EtOAc (2×). The combined organic extracts were washed with brine, dried over MgSO$_4$, filtered, and concentrated in vacuo. Purification of the residue by silica gel chromatography (12-100% EtOAc-hexanes) followed by HPLC (10-40% MeCN—H$_2$O) gave the title compound as a pale yellow gum.
Calc'd for $C_{10}H_{14}ClFN_3O$ [M+H]$^+$: 246, 248. Found: 246, 248.

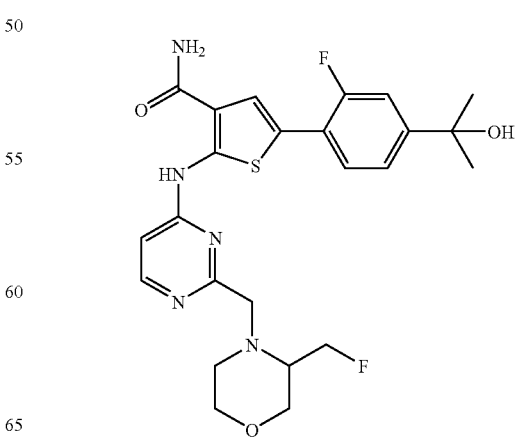

Step 3. 5-[2-Fluoro-4-(1-hydroxy-1-methylethyl)phenyl]-2-[(2-{[3-(fluoromethyl)morpholin-4-yl]methyl}pyrimidin-4-yl)amino]thiophene-3-carboxamide The title compound was prepared as described in Example 1 using 2-amino-5-[2-fluoro-4-(1-hydroxy-1-methylethyl)phenyl]thiophene-3-carboxamide (26 mg, 0.09 mmol) and 4-[(4-chloropyrimidin-2-yl)methyl]-3-(fluoromethyl)morpholine (21.70 mg, 0.09 mmol) as starting materials.
Calc'd for $C_{24}H_{28}F_2N_5O_3S$ [M+H]$^+$: 504. Found: 504.

Example 548

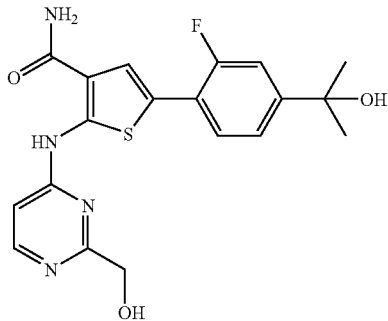 [SMILES: CC(C)(O)c1ccc(-c2cc(C(N)=O)c(Nc3ccnc(CO)n3)s2)c(F)c1]

5-[2-Fluoro-4-(1-hydroxy-1-methylethyl)phenyl]-2-{[2-(hydroxymethyl)pyrimidin-4-yl]amino}thiophene-3-carboxamide

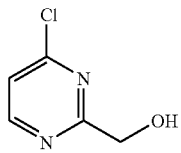

Step 1. (4-Chloropyrimidin-2-yl)methanol

4-Chloropyrimidine-2-carbaldehyde (4.53 g, 31.8 mmol) was taken up in MeOH (65 mL) and cooled to 0° C. NaBH$_4$ (1.262 g, 33.4 mmol) was added and the mixture stirred at 0° C. for 90 minutes. Water was added and the reaction mixture was extracted with CHCl$_3$ (3×).
The combined organic extracts were washed with brine, dried over MgSO$_4$, filtered, and concentrated in vacuo to give the title compound as a pale yellow solid.
$^1$H NMR (600 MHz, DMSO): 8.72 (d, 1H), 7.57 (d, 1H), 5.47 (t, 1H), 4.55 (d, 2H).

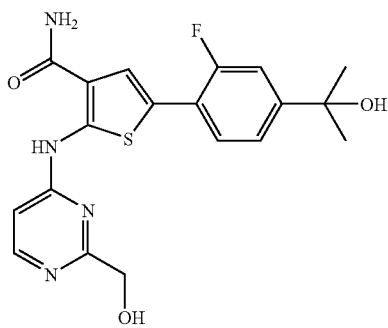 [SMILES: CC(C)(O)c1ccc(-c2cc(C(N)=O)c(Nc3ccnc(CO)n3)s2)c(F)c1]

Step 2. 5-[2-Fluoro-4-(1-hydroxy-1-methylethyl)phenyl]-2-{[2-(hydroxymethyl)pyrimidin-4-yl]amino}thiophene-3-carboxamide The title compound was prepared according to the general procedure in Example 1 using (4-chloropyrimidin-2-yl)methanol (54.0 mg, 0.37 mmol) and 2-amino-5-[2-fluoro-4-(1-hydroxy-1-methylethyl)phenyl]thiophene-3-carboxamide (100 mg, 0.34 mmol) as the starting materials.
Calc'd for $C_{19}H_{20}FN_4O_3S$ [M+H]$^+$: 403. Found: 403.

Example 549

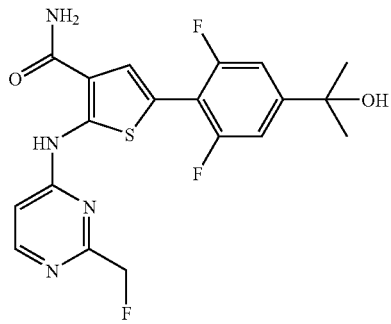 [SMILES: CC(C)(O)c1cc(F)c(-c2cc(C(N)=O)c(Nc3ccnc(CF)n3)s2)c(F)c1]

5-[2,6-Difluoro-4-(1-hydroxy-1-methylethyl)phenyl]-2-{[2-(fluoromethyl)pyrimidin-4-yl]amino}thiophene-3-carboxamide

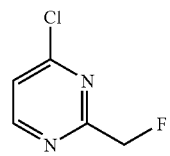

Step 1. 4-Chloro-2-(fluoromethyl)pyrimidine (4-Chloropyrimidin-2-yl)methanol (Example 548, Step 1) (121 mg, 0.84 mmol) was taken up in DCM (2.5 mL) and cooled to 0° C. DAST (0.122 mL, 0.92 mmol) was added and the resulting mixture stirred at 0° C. for 15 minutes and room temperature for 90 minutes. Saturated NaHCO$_3$ was added and the products extracted into EtOAc (2×). The combined organic extracts were washed with brine, dried over MgSO$_4$, filtered, and concentrated in vacuo. Purification of the residue by silica gel chromatography (2-40% EtOAc-hexanes) gave the title compound as a pale yellow oil.
$^1$H NMR (600 MHz, CDCl$_3$): 8.65 (d, 1H), 7.32 (d, 1H), 5.49 (d, 2H).

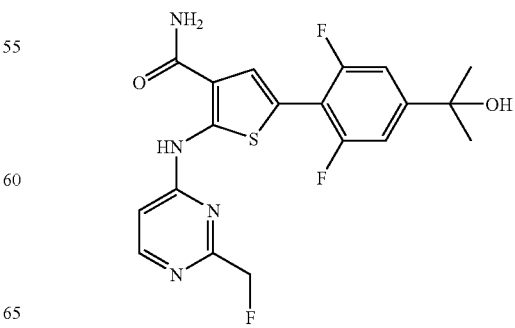

Step 2. 5-[2,6-Difluoro-4-(1-hydroxy-1-methylethyl)phenyl]-2-{[2-(fluoromethyl)pyrimidin-4-yl]amino}thiophene-3-carboxamide The title compound was prepared according to the general procedure in Example 1 using 4-chloro-2-(fluoromethyl)pyrimidine (19.71 mg, 0.13 mmol) and 2-amino-5-[2,6-difluoro-4-(1-hydroxy-1-methylethyl)phenyl]thiophene-3-carboxamide (42 mg, 0.13 mmol) as the starting materials.

Calc'd for $C_{19}H_{18}F_3N_4O_2S$ [M+H]$^+$: 423. Found: 423.

Example 550

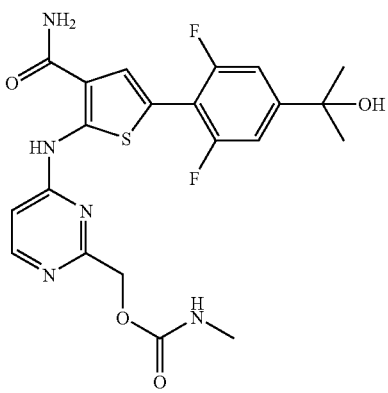

[4-({3-(Aminocarbonyl)-5-[2,6-difluoro-4-(1-hydroxy-1-methylethyl)phenyl]-2-thienyl}amino)pyrimidin-2-yl]methyl methylcarbamate

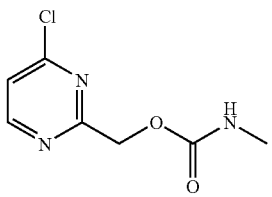

Step 1. (4-Chloropyrimidin-2-yl)methyl methylcarbamate (4-Chloropyrimidin-2-yl)methanol (Example 548, Step 1) (0.304 g, 2.10 mmol) and copper(I) chloride (0.208 g, 2.10 mmol) were taken up in DMF (10 mL) and stirred at room temperature for 5 minutes. Methyl isocyanate (0.120 g, 2.10 mmol) was added and stirring at room temperature continued for 3 hours. Water was added and the reaction mixture was extracted with EtOAc (2×). The combined organic extracts were washed with brine, dried over MgSO$_4$, filtered, and concentrated in vacuo. Purification of the residue by silica gel chromatography (12-100% EtOAc-hexanes) gave the title compound as a white solid.

Calc'd for $C_7H_9ClN_3O_2$ [M+H]$^+$: 202, 204. Found: 202, 204.

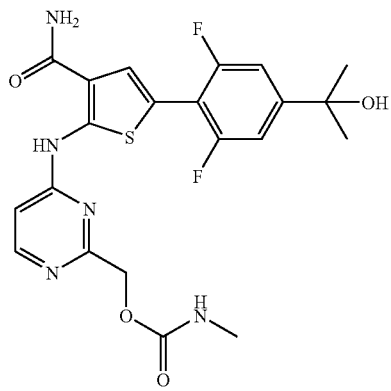

Step 2. [4-({3-(Aminocarbonyl)-5-[2,6-difluoro-4-(1-hydroxy-1-methylethyl)phenyl]-2-thienyl}amino)pyrimidin-2-yl]methyl methylcarbamate 2-Amino-5-[2,6-difluoro-4-(1-hydroxy-1-methylethyl)phenyl]thiophene-3-carboxamide (85 mg, 0.272 mmol), (4-chloropyrimidin-2-yl)methyl methylcarbamate (54.9 mg, 0.272 mmol), Pd$_2$dba$_3$ (24.92 mg, 0.027 mmol), K$_2$CO$_3$ (41.4 mg, 0.299 mmol) and X-Phos (64.9 mg, 0.136 mmol) were added to a 5 mL microwave vial. Degassed tert-amyl alcohol (0.6 mL) was added and the vial evacuated and back-filled with N$_2$ (3×). The resulting mixture was stirred at 100° C. overnight. The reaction mixture was cooled to room temperature, MeOH and silica gel were added, and the solvent was removed in vacuo. Purification of the residue twice by silica gel chromatography (0-10% MeOH-DCM) gave [4-({3-(aminocarbonyl)-5-[2,6-difluoro-4-(1-hydroxy-1-methylethyl)phenyl]-2-thienyl}amino)pyrimidin-2-yl]methyl methylcarbamate as a beige solid after triturating in DCM.

Calc'd for $C_{21}H_{22}F_2N_5O_4S$ [M+H]$^+$: 478. Found: 478.

Example 551

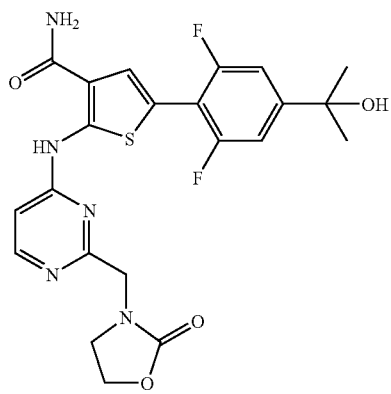 [SMILES: CC(C)(O)c1cc(F)c(-c2cc(C(N)=O)c(Nc3ccnc(CN4CCOC4=O)n3)s2)c(F)c1]

5-[2,6-Difluoro-4-(1-hydroxy-1-methylethyl)phenyl]-2-({2-[(2-oxo-1,3-oxazolidin-3-yl)methyl]pyrimidin-4-yl}amino)thiophene-3-carboxamide

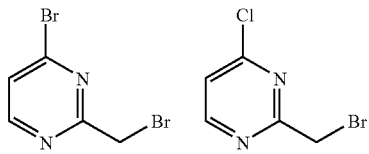

Step 1. 2-(Bromomethyl)-4-bromopyrimidine and 2-(bromomethyl)-4-chloropyrimidine (4-Chloropyrimidin-2-yl)methanol (Example 548, Step 1) (0.742 g, 5.13 mmol) was taken up in DCM (15 mL) and cooled to 0° C. before adding phosphorus tribromide (0.968 mL, 10.27 mmol). The reaction mixture was allowed to warm to room temperature overnight. The reaction mixture was cooled to 0° C., saturated NaHCO$_3$ was added dropwise and the reaction mixture was extracted with EtOAc (2×). The combined organic extracts were washed with brine, dried over MgSO$_4$, filtered, and concentrated in vacuo. Purification of the residue by silica gel chromatography (2-40% EtOAc-hexanes) gave a 1.5:1 mixture of 2-(bromomethyl)-4-bromopyrimidine (A) and 2-(bromomethyl)-4-chloropyrimidine (B) as a pale yellow oil.
A—Calc'd for C$_5$H$_5$Br$_2$N$_2$ [M+H]$^+$: 251, 253, 255. Found: 251, 253, 255.
B—Calc'd for C$_5$H$_5$BrClN$_2$ [M+H]$^+$: 207, 209, 211. Found: 207, 209, 211.

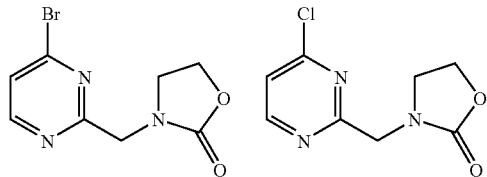

Step 2. 3-[(4-Bromopyrimidin-2-yl)methyl]-1,3-oxazolidin-2-one and 3-[(4-chloropyrimidin-2-yl)methyl]-1,3-oxazolidin-2-one 2-Oxazolidinone (55.1 mg, 0.63 mmol) was taken up in THF (2 mL) and sodium hydride (25.3 mg, 0.63 mmol) was added. The resulting mixture was stirred at room temperature for 5 minutes. A mixture of 2-(bromomethyl)-4-chloropyrimidine (35 mg, 0.17 mmol) and 4-bromo-2-(bromomethyl)pyrimidine (63.7 mg, 0.25 mmol) in THF (1 mL) was then added and the reaction allowed to stir at room temperature for 4 hours. Saturated NH$_4$Cl was added and the reaction mixture was extracted with EtOAc (2×). The combined organic extracts were dried over MgSO$_4$, filtered, and concentrated in vacuo. Purification of the residue by silica gel chromatography (40-100% EtOAc-hexanes) gave a 1.7:1 mixture of 3-[(4-bromopyrimidin-2-yl)methyl]-1,3-oxazolidin-2-one and 3-[(4-chloropyrimidin-2-yl)methyl]-1,3-oxazolidin-2-one as a white solid.
$^1$H NMR (600 MHz, DMSO) (*denotes chloro product): 8.76 (d, J=5.4 Hz, 1H)*, 8.62 (d, J=5.4 Hz, 1H), 7.76 (d, J=5.4 Hz, 1H), 7.62 (d, J=5.4 Hz, 1H)*, 4.55 (s, 2H)*, 4.54 (s, 2H), 4.31 (t, J=7.8 Hz, 2H), 4.31 (t, J=7.8 Hz, 2H)*, 3.63 (t, J=7.8 Hz, 2H), 3.63 (t, J=7.8 Hz, 2H)*.

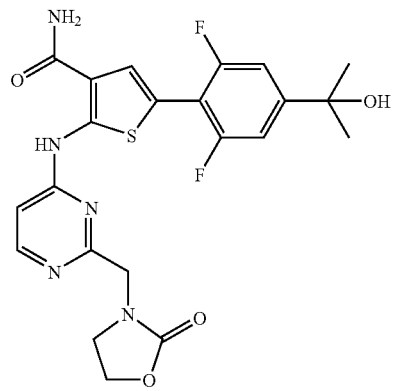 [SMILES: CC(C)(O)c1cc(F)c(-c2cc(C(N)=O)c(Nc3ccnc(CN4CCOC4=O)n3)s2)c(F)c1]

Step 3. 5-[2,6-Difluoro-4-(1-hydroxy-1-methylethyl)phenyl]-2-({2-[(2-oxo-1,3-oxazolidin-3-yl)methyl]pyrimidin-4-yl}amino)thiophene-3-carboxamide The title compound was prepared according to Example 1 using 2-amino-5-[2,6-difluoro-4-(1-hydroxy-1-methylethyl)phenyl]thiophene-3-carboxamide (85 mg, 0.27 mmol) and the mixture of 3-[(4-chloropyrimidin-2-yl)methyl]-1,3-oxazolidin-2-one (21.5 mg, 0.10 mmol) and 3-[(4-bromopyrimidin-2-yl)methyl]-1,3-oxazolidin-2-one (44.2 mg, 0.17 mmol) as the starting materials.
Calc'd for C$_{22}$H$_{22}$F$_2$N$_5$O$_4$S [M+H]$^+$: 490. Found: 490.

Additional examples were prepared using procedures similar to those described in the above examples and are illustrated in the following table.

TABLE 55

| Example # | Structure | Name | Characterization [M + H]$^+$ |
|---|---|---|---|
| 552 | (structure shown) | 5-[2,6-difluoro-4-(1-hydroxy-1-methylethyl)phenyl]-2-{[2-({[(1-methyl-1H-pyrazol-4-yl)methyl]amino)methyl)pyrimidin-4-yl]amino}thiophene-3-carboxamide | Calc'd: 514, Found: 514 |

TABLE 55-continued

| Example # | Structure | Name | Characterization [M + H]+ |
|---|---|---|---|
| 553 | 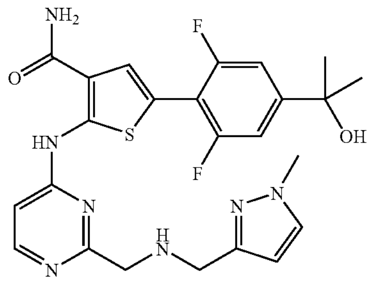 [SMILES: Cn1ccc(CNCc2nccc(Nc3sc(-c4c(F)cc(C(C)(C)O)cc4F)cc3C(N)=O)n2)n1] | 5-[2,6-difluoro-4-(1-hydroxy-1-methylethyl)phenyl]-2-{[2-({[(1-methyl-1H-pyrazol-4-yl)methyl]amino}methyl)pyrimidin-3-yl]amino}thiophene-3-carboxamide | Calc'd: 514, Found: 514 |
| 554 | 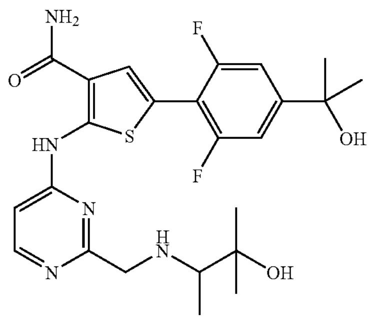 [SMILES: CC(NCc1nccc(Nc2sc(-c3c(F)cc(C(C)(C)O)cc3F)cc2C(N)=O)n1)C(C)(C)O] | 5-[2,6-difluoro-4-(1-hydroxy-1-methylethyl)phenyl]-2-{[2-{[(2-hydroxy-1,2dimethylpropyl)amino]methyl}pyrimidin-4-yl)amino]thiophene-3-carboxamide | Calc'd: 506, Found: 506 |

Example 555

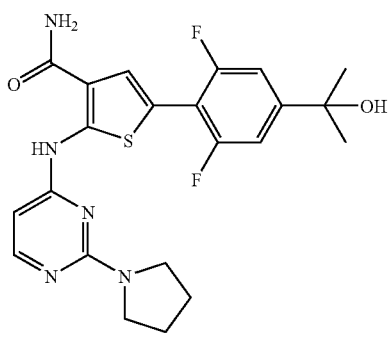 [SMILES: CC(C)(O)c1cc(F)c(-c2cc(C(N)=O)c(Nc3ccnc(N4CCCC4)n3)s2)c(F)c1]

5-[2,6-Difluoro-4-(1-hydroxy-1-methylethyl)phenyl]-2-[(2-pyrrolidin-1-ylpyrimidin-4-yl)amino]thiophene-3-carboxamide

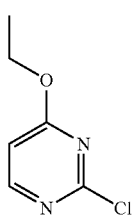

Step 1. 2-Chloro-4-ethoxypyrimidine

To a solution of 2,4-dichloropyrimidine (20 g, 0.13 mmol) in 240 mL of anhydrous EtOH was added slowly 1M NaOEt in EtOH over 2 hrs at −3° C. under nitrogen atmosphere. The resulting mixture was stirred at room temperature for 1 hour. The organic solvent was evaporated in vacuo and the residue was partioned between water and Et$_2$O. The aqueous phase was extracted with Et$_2$O and the combined organic phases were washed with brine, dried over Na$_2$SO$_4$, filtered, and concentrated to give the title compound.

$^1$H NMR (400 MHz, CDCl$_3$): 8.22 (d, 1H), 6.06 (d, 1H), 4.40 (q, 1H), 1.35 (t, 1H).

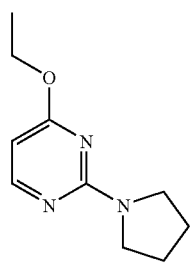

Step 2. 4-Ethoxy-2-pyrrolidin-1-ylpyrimidine

To a solution of 2-chloro-4-ethoxypyrimidine (3 g, 19 mol) in THF (410 mL) was added pyrrolidine (2.7 g, 38 mmol) and Et$_3$N (5.8 g, 57 mmol) and the reaction mixture was heated to reflux overnight. The solvent was evaporated and the residue was partioned between water and EtOAc. The aqueous phase was extracted with EtOAc. The combined organic phases were dried over sodium sulfate, filtered, and concentrated to give the title compound.

Calc'd for C$_{10}$H$_{16}$N$_3$O [M+H]$^+$: 194. Found: 194.

Step 3. 4-Chloro-2-pyrrolidin-1-ylpyrimidine

4-Ethoxy-2-pyrrolidin-1-ylpyrimidine (2.0 g, 10 mol) was added to 15 mL of POCl$_3$, followed by the addition of 0.5 ml of DMF. The reaction mixture was irradiated under microwave at 160° C. for 1.5 h. Most of the solvent was evaporated in vacuo. The residue was added in portions to ice-water containing ammonia. The precipitate was filtered off. The aqueous filtrate was extracted with EtOAc. The organic phase was dried over sodium sulfate, filtered, and concentrated. The solid precipitate was combined with the crude residue and purified by silica gel column chromatography to afford the title compound.

$^1$H NMR (400 MHz, CDCl$_3$): 8.10 (d, 1H), 6.04 (d, 1H), 3.40~3.60 (m, 4H), 1.90~2.00 (m, 4H).

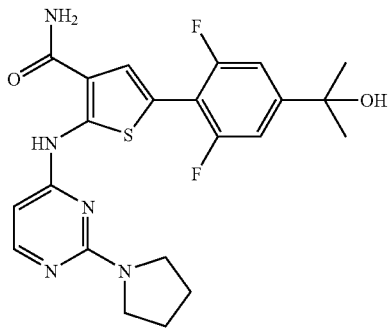 [SMILES: CC(C)(O)c1cc(F)c(-c2cc(C(N)=O)c(Nc3ccnc(N4CCCC4)n3)s2)c(F)c1]

Step 4. 5-[2,6-Difluoro-4-(1-hydroxy-1-methylethyl)phenyl]-2-[(2-pyrrolidin-1-ylpyrimidin-4-yl)amino]thiophene-3-carboxamide The title compound was prepared according to the general procedure in Example 1 using 2-amino-5-[2,6-difluoro-4-(1-hydroxy-1-methylethyl)phenyl]thiophene-3-carboxamide and 4-chloro-2-pyrrolidin-1-ylpyrimidine as the starting materials.

$^1$H NMR (400 MHz, d4-MeOH): 7.95 (d, 1H), 7.75 (s, 1H), 7.20 (s, 1H), 7.17 (s, 1H), 6.11 (d, 1H), 3.53-3.70 (m, 4H), 2.00-2.05 (m, 4H), 1.54 (s, 6H).

Example 556

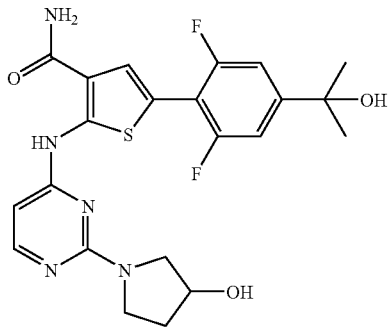 [SMILES: CC(C)(O)c1cc(F)c(-c2cc(C(N)=O)c(Nc3ccnc(N4CCC(O)C4)n3)s2)c(F)c1]

5-[2,6-Difluoro-4-(1-hydroxy-1-methylethyl)phenyl]-2-{[2-(3-hydroxypyrrolidin-1-yl)pyrimidin-4-yl]amino}thiophene-3-carboxamide

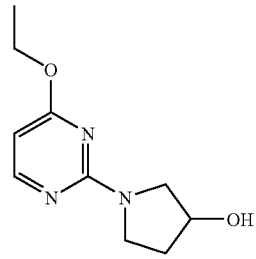

Step 1. 1-(4-Ethoxypyrimidin-2-yl)pyrrolidin-3-ol

The title compound was prepared as described in Example 555, Step 2 using 2-chloro-4-ethoxypyrimidine (2.4 g, 15 mol) and pyrrolidin-3-ol (1.6 g, 18 mmol) as the starting materials.

Calc'd for C$_{10}$H$_{16}$N$_3$O$_2$ [M+H]$^+$: 210. Found: 210.

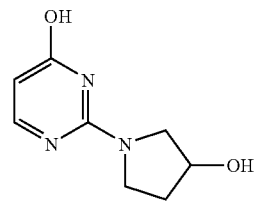 [SMILES: Oc1ccnc(N2CCC(O)C2)n1]

Step 2. 2-(3-Hydroxypyrrolidin-1-yl)pyrimidin-4-ol 1-(4-Ethoxypyrimidin-2-yl)pyrrolidin-3-ol (1.0 g, 4.8 mol) was combined with 6M HCl (24 mL, 144 mmol) and heated to reflux overnight. The mixture was concentrated in vacuo to give the title compound.

Calc'd for C$_8$H$_{12}$N$_3$O$_2$ [M+H]$^+$: 182. Found: 182.

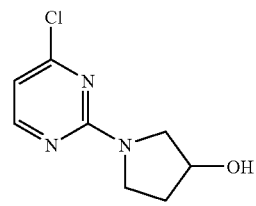 [SMILES: OC1CCN(c2nccc(Cl)n2)C1]

Step 3. 1-(4-Chloropyrimidin-2-yl)pyrrolidin-3-ol

To a solution of 2-(3-hydroxypyrrolidin-1-yl)pyrimidin-4-ol (4.0 g, 23 mol) in DMF (50 mL) was added POCl$_3$ (4.2 g, 27 mmol). The reaction mixture was stirred at 50° C. for 2 hours. The reaction mixture was poured into 200 mL ice-water. The resulting solution was concentrated at 60° C. under vacuum. The residue was purified by acidic reverse phase HPLC (10-100% acetonitrile/water+0.05% TFA modifier) to afford the title compound.

$^1$H NMR (400 MHz, d4-MeOH): 8.22 (d, 1H), 6.75 (d, 1H), 4.55 (s, 1H), 3.60~3.80 (m, 4H), 2.00~2.20 (m, 2H).

549

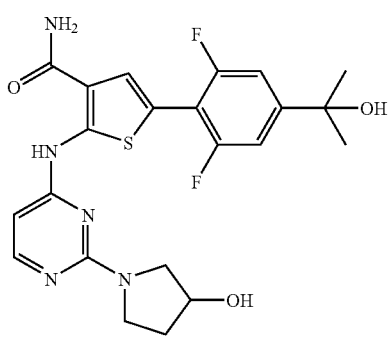 [SMILES: CC(C)(O)c1cc(F)c(-c2cc(C(N)=O)c(Nc3ccnc(N4CCC(O)C4)n3)s2)c(F)c1]

Step 4. 5-[2,6-Difluoro-4-(1-hydroxy-1-methylethyl)
phenyl]-2-{[2-(3-hydroxypyrrolidin-1-yl)pyrimidin-
4-yl]amino}thiophene-3-carboxamide The title compound was prepared according to the general procedure in Example 1 using 2-amino-5-[2,6-difluoro-4-(1-hydroxy-1-methylethyl)phenyl]thiophene-3-carboxamide and 1-(4-chloropyrimidin-2-yl)pyrrolidin-3-ol as the starting materials.

Calc'd for $C_{22}H_{24}F_2N_5O_3S$ [M+H]$^+$: 476. Found: 476.
An additional example was prepared using procedures similar to those described in the above examples and is illustrated in the following table.

550

5-[2,6-Difluoro-4-(1-hydroxy-1-methylethyl)phenyl]-2-[(2-{[4-(trimethylsilyl)-1H-1,2,3-triazol-1-yl]methyl}pyrimidin-4-yl)amino]thiophene-3-carboxamide Step 1. 2-(Azidomethyl)-4-bromopyrimidine and 2-(azidomethyl)-4-chloropyrimidine A mixture of 4-bromo-2-(bromomethyl)pyrimidine (131 mg, 0.52 mmol) and 2-(bromomethyl)-4-chloropyrimidine (72 mg, 0.35 mmol) (Example 551, Step 1) was taken up in DMSO (1.8 mL). Sodium azide (85 mg, 1.30 mmol) was added and the mixture stirred at room temperature overnight. Water was added and the reaction mixture was extracted with EtOAc (3×). The combined organic extracts were dried over MgSO$_4$ and concentrated in vacuo. Purification of the residue by silica gel column chromatography (2-40% EtOAc-hexanes) gave a 1.7:1 mixture of 2-(azidomethyl)-4-bromopyrimidine (A) and 2-(azidomethyl)-4-chloropyrimidine (B) as a pale yellow solid.

TABLE 56

| Example # | Structure | Compound Name | Characterization |
|---|---|---|---|
| 557 | 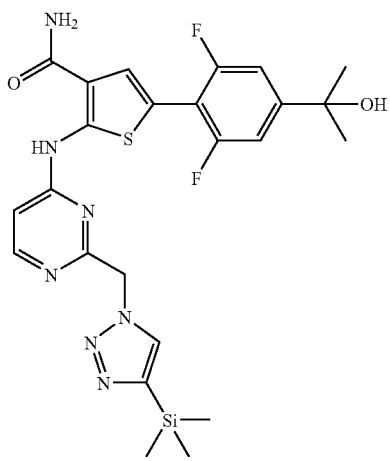 | 5-[2,6-difluoro-4-(1-hydroxy-1-methylethyl)phenyl]-2-{[2-(4-methylpiperazin-1-yl)pyrimidin-4-yl]amino}thiophene-3-carboxamide | Calc'd [M + H]$^+$: 489, Found: 489 |

Example 558

A—Calc'd for $C_5H_5BrN_5$ [M+H]$^+$: 214, 216. Found: 214, 216.

B—Calc'd for $C_5H_5ClN_5$ [M+H]$^+$: 170, 172. Found: 170, 172.

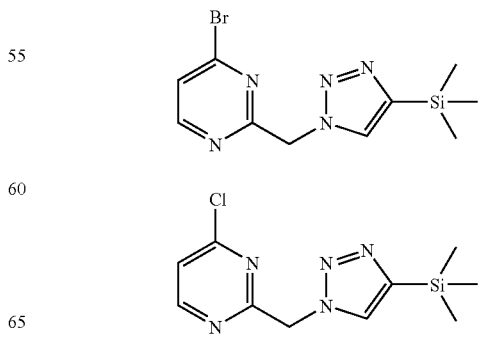

Step 2. 4-Bromo-2-{[4-(trimethylsilyl)-1H-1,2,3-triazol-1-yl]methyl}pyrimidine and 4-chloro-2-{[4-(trimethylsilyl)-1H-1,2,3-triazol-1-yl]methyl}pyrimidine 2-(Azidomethyl)-4-chloropyrimidine (39 mg, 0.23 mmol), 2-(azidomethyl)-4-bromopyrimidine (79 mg, 0.37 mmol) and trimethylsilylacetylene (0.109 mL, 0.78 mmol) were taken up in ʹBuOH (1.5 mL)/water (1.1 mL). A solution of copper(II) sulfate pentahydrate (7.47 mg, 0.03 mmol) in water (0.2 mL) was added, followed by a solution of L-ascorbic acid sodium salt (23.69 mg, 0.12 mmol) in water (0.2 mL). The resulting mixture was stirred at room temperature overnight. Saturated NaHCO₃ was added and the reaction mixture was extracted with EtOAc (×2). The combined organic extracts were washed with brine, dried over MgSO₄, filtered, and concentrated in vacuo to give a 1.6:1 mixture of 4-bromo-2-{[4-(trimethylsilyl)-1H-1,2,3-triazol-1-yl]methyl}pyrimidine (A) and 4-chloro-2-{[4-(trimethylsilyl)-1H-1,2,3-triazol-1-yl]methyl}pyrimidine (B) as an orange solid.

A—Calc'd for $C_{10}H_{15}BrN_5Si$ [M+H]⁺: 312, 314. Found: 312, 314.
B—Calc'd for $C_{10}H_{15}ClN_5Si$ [M+H]⁺: 268, 270. Found: 268, 270.

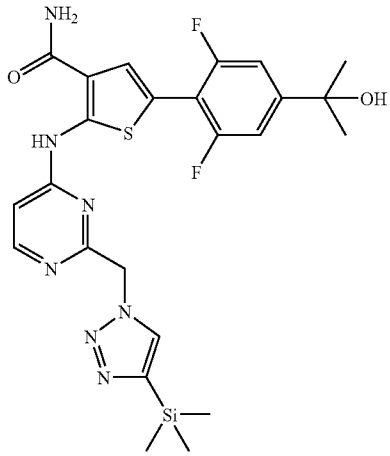 [SMILES: CC(C)(O)c1cc(F)c(-c2cc(C(N)=O)c(Nc3ccnc(Cn4cc([Si](C)(C)C)nn4)n3)s2)c(F)c1]

Step 3. 5-[2,6-Difluoro-4-(1-hydroxy-1-methylethyl)phenyl]-2-[(2-{[4-(trimethylsilyl)-1H-1,2,3-triazol-1-yl]methyl}pyrimidin-4-yl)amino]thiophene-3-carboxamide The title compound was prepared by the procedure in Example 1 using 2-amino-5-[2,6-difluoro-4-(1-hydroxy-1-methylethyl)phenyl]thiophene-3-carboxamide (62.3 mg, 0.200 mmol) and a mixture of 4-bromo-2-{[4-(trimethylsilyl)-1H-1,2,3-triazol-1-yl]methyl}pyrimidine (38 mg, 0.122 mmol) and 4-chloro-2-{[4-(trimethylsilyl)-1H-1,2,3-triazol-1-yl]methyl}pyrimidine (21 mg, 0.078 mmol) as the starting materials.

Calc'd for $C_{24}H_{28}F_2N_7O_2SSi$ [M+H]⁺: 544. Found: 544.

Example 559

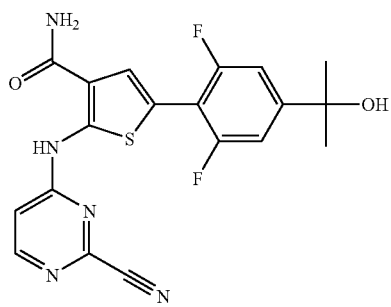 [SMILES: CC(C)(O)c1cc(F)c(-c2cc(C(N)=O)c(Nc3ccnc(C#N)n3)s2)c(F)c1]

2-[(2-Cyanopyrimidin-4-yl)amino]-5-[2,6-difluoro-4-(1-hydroxy-1-methylethyl)phenyl]thiophene-3-carboxamide

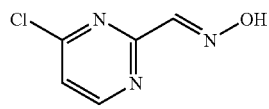

Step 1: 4-Chloropyrimidine-2-carbaldehyde oxime

Hydroxylamine hydrochloride (244 mg, 3.51 mmol), 4-chloropyrimidine-2-carboxaldehyde (500 mg, 3.51 mmol), and sodium acetate (288 mg, 3.51 mmol) were dissolved in dry ethanol (17.5 mL) and transferred to a flame-dried round bottom flask. The reaction was allowed to stir at room temperature for 20 minutes. It was then concentrated under reduced pressure, redissolved in ethyl acetate, and washed with water. The aqueous layer was extracted with ethyl acetate two times. The combined organic layers were dried over magnesium sulfate, filtered, and concentrated under reduced pressure to yield the title compound.

¹H NMR (600 MHz, d6-DMSO): δ 12.27 (s, 1H), 8.81 (d, 1H), 8.08 (s, 1H), 7.67 (d, 1H).

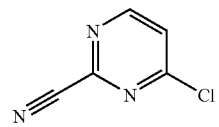

Step 2: 4-Chloropyrimidine-2-carbonitrile

4-Chloropyrimidine-2-carbaldehyde oxime (100 mg, 0.64 mmol) was placed in a flask with a stir bar and the flask was evacuated and backfilled with argon three times. Dry dichloromethane (3.7 mL) was then added and the solution was stirred at room temperature. 3,3,3-Triethyl-1-(methoxycarbonyl)diazathian-3-ium-1-ide 2,2-dioxide (529 mg, 2.22 mmol) was added in portions over 2 hours. The reaction was allowed to stir for 48 hours. It was directly purified via silica gel chromatography (0-100% ethyl acetate in hexane) to yield the title compound.

¹H NMR (600 MHz, d6-DMSO): δ 8.99 (d, 1H), 8.10 (d, 1H).

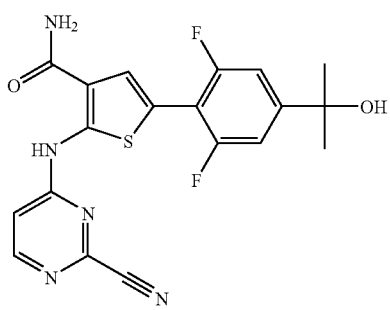 [SMILES: CC(C)(O)c1cc(F)c(-c2cc(C(N)=O)c(Nc3ccnc(C#N)n3)s2)c(F)c1]

Step 3: 2-[(2-Cyanopyrimidin-4-yl)amino]-5-[2,6-difluoro-4-(1-hydroxy-1-methylethyl)phenyl]thiophene-3-carboxamide The title compound was prepared as described in Example 1 using 2-amino-5-[2,6-difluoro-4-(1-hydroxy-1-methylethyl)phenyl]thiophene-3-carboxamide (113 mg, 0.36 mmol) and 4-chloropyrimidine-2-carbonitrile (51 mg, 0.36 mmol) as starting materials.

$^1$H NMR (600 MHz, d6-DMSO): δ 12.67 (s, 1H), 8.54 (d, 1H), 8.15 (s, 1H), 7.89 (s, 1H), 7.69 (s, 1H), 7.53 (d, 1H), 7.31 (d, 2H), 5.33, (s, 1H), 1.43 (s, 6H). Calc'd for $C_{19}H_{16}F_2N_5O_2S$ [M+H]$^+$: 416. Found: 416.

Example 560

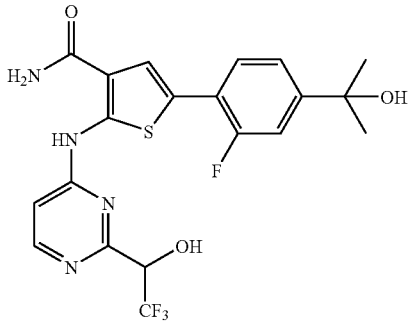 [SMILES: CC(C)(O)c1ccc(-c2cc(C(N)=O)c(Nc3ccnc(C(O)C(F)(F)F)n3)s2)c(F)c1]

5-[2-Fluoro-4-(1-hydroxy-1-methylethyl)phenyl]-2-{[2-(2,2,2-trifluoro-1-hydroxyethyl)pyrimidin-4-yl]amino}thiophene-3-carboxamide

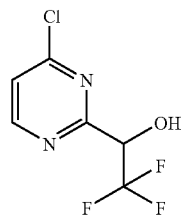 [SMILES: OC(c1nccc(Cl)n1)C(F)(F)F]

Step 1: 1-(4-Chloropyrimidin-2-yl)-2,2,2-trifluoroethanol

4-Chloropyrimidine-2-carbaldehyde (283 mg, 1.99 mmol) was dissolved in tetrahydrofuran (11.4 mL) and cooled to 0° C. Trimethyl(trifluoromethyl)silane (0.37 mL, 2.38 mmol) was added followed by 1 M tetra-n-butylammonium fluoride in tetrahydrofuran (2.38 mL, 2.38 mmol). The ice bath was removed and the reaction was stirred for 1 hour. The reaction was then diluted with water and brine and extracted with ethyl acetate three times. The organic layers were combined and dried over magnesium sulfate, filtered, and concentrated in vacuo. The resulting mixture was purified via silica gel chromatography (0-5% methanol in ethyl acetate) to afford the title compound.

$^1$H NMR (600 MHz, d6-DMSO): δ 8.88 (d, 1H), 7.79 (d, 1H), 7.14 (d, 1H), 1.53 (p, 1H).

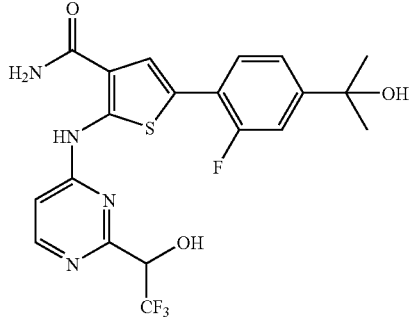 [SMILES: CC(C)(O)c1ccc(-c2cc(C(N)=O)c(Nc3ccnc(C(O)C(F)(F)F)n3)s2)c(F)c1]

Step 2: 5-[2-Fluoro-4-(1-hydroxy-1-methylethyl)phenyl]-2-{[2-(2,2,2-trifluoro-1-hydroxyethyl)pyrimidin-4-yl]amino}thiophene-3-carboxamide The title compound was prepared as described in Example 1 using 2-amino-5-[2-fluoro-4-(1-hydroxy-1-methylethyl)phenyl]thiophene-3-carboxamide (68 mg, 0.23 mmol) and 1-(4-chloropyrimidin-2-yl)-2,2,2-trifluoroethanol (49 mg, 0.23 mmol) as starting materials.

$^1$H NMR (600 MHz, d6-DMSO): δ 12.35 (s, 1H), 8.49 (d, 1H), 8.01 (s, 1H), 7.89 (s, 1H), 7.61 (t, 2H), 7.36 (m, 2H), 7.21 (d, 1H), 6.76 (d, 1H), 5.19 (s, 1H), 5.11 (p, 1H), 1.43 (s, 6H). Calc'd for $C_{20}H_{19}F_4N_4O_3S$ [M+H]$^+$: 471. Found: 471.

Example 561

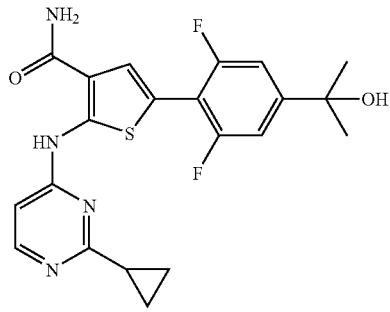 [SMILES: CC(C)(O)c1cc(F)c(-c2cc(C(N)=O)c(Nc3ccnc(C4CC4)n3)s2)c(F)c1]

2-[(2-Cyclopropylpyrimidin-4-yl)amino]-5-[2,6-difluoro-4-(1-hydroxy-1-methylethyl)phenyl]thiophene-3-carboxamide

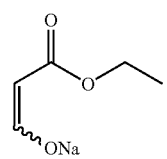

Step 1: Sodium (1Z)-3-ethoxy-3-oxoprop-1-en-1-olate

Sodium hydride (21.79 g, 545 mmol) was suspended in isopropyl ether (378 mL) in a 3-neck flask equipped with a thermometer adapter, addition funnel and a capped neck. Ethyl acetate (44.4 mL, 454 mmol) was added slowly via syringe through the capped neck. An internal temperature of 45° C. was maintained. Ethyl formate (78 mL, 962 mmol) was added via the addition funnel slowly, maintaining the temperature at 42° C. The reaction was allowed to stir overnight, at which point solid had crashed out. This solid was filtered and washed with ethyl ether (2×100 mL) and hexanes (200 mL) and the solid was dried to give the title compound.

$^1$H NMR (600 MHz, DMSO): δ 8.04 (d, J=4.8 Hz, 1H), 4.03 (d, J=4.8 Hz, 1H), 3.82 (q, J=8.4 Hz, 2H), 1.07 (t, J=8.4, 3H).

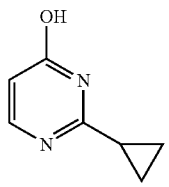

Step 2: 2-Cyclopropylpyrimidin-4-ol

Sodium (1Z)-3-ethoxy-3-oxoprop-1-en-1-olate (6.60 g, 47.8 mmol) was dissolved in water (1.5 mL) and in a second flask cyclopropanecarboximidamide hydrochloride (3 g, 24.88 mmol) was dissolved in water (2 mL) and the contents of the second flask were added to the first flask. The reaction was allowed to stir for 72 hours. The reaction was then transferred to a separatory funnel and extracted with chloroform and a small amount of methanol. The water layer was extracted again and the combined organic layers were dried over magnesium sulfate, filtered and concentrated to a pale yellow solid. Diethyl ether was then added to precipitate product. The mixture was filtered and the solid was collected and dried to give the title compound.

$^1$H NMR (600 MHz, DMSO): δ 7.73 (d, J=7.8 Hz, 1H), 6.04 (d, J=7.8 Hz, 1H), 1.87 (m, 1H), 0.97 (m, 4H)

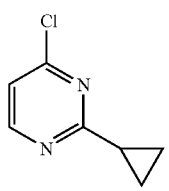

Step 3: 4-Chloro-2-cyclopropylpyrimidine

2-Cyclopropylpyrimidin-4-ol (1.0 g, 7.34 mmol) was suspended in phosphorous oxychloride (5.0 mL, 53.6 mmol) and over the course of about one hour, the solid went into solution. After three hours, the solution was concentrated, diluted with ethyl acetate, washed with saturated sodium bicarbonate, water, saturated sodium chloride, dried over magnesium sulfate, filtered and concentrated. The crude mixture was purified by silica gel chromatography to yield the title compound.

$^1$H NMR (600 MHz, DMSO): δ 8.59 (d, J=6.6 Hz, 1H), 7.43 (d, J=6.6 Hz, 1H), 2.17 (m, 1H), 1.08 (m, 2H), 0.99 (m, 2H).

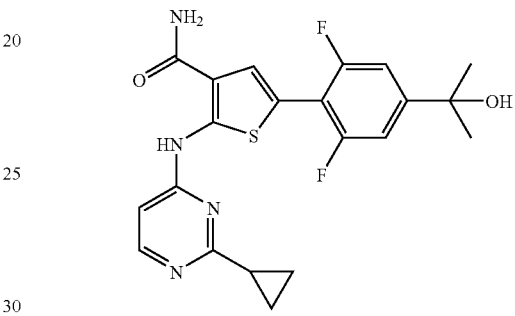

Step 4: 2-[(2-Cyclopropylpyrimidin-4-yl)amino]-5-[2,6-difluoro-4-(1-hydroxy-1-methylethyl)phenyl]thiophene-3-carboxamide The title compound was prepared by using the procedure listed in Example 1 with 2-amino-5-[2,6-difluoro-4-(1-hydroxy-1-methylethyl)phenyl]thiophene-3-carboxamide (0.10 g, 0.32 mmol) and 4-chloro-2-cyclopropylpyrimidine (0.05 g, 0.32 mmol) as the starting materials.

Calc'd for $C_{21}H_{21}F_2N_4O_2S$ [M+H]$^+$: 431. Found: 431.

An additional example was prepared using procedures similar to those described in the above examples and is illustrated in the following table.

TABLE 57

| Example # | Structure | Compound Name | Characterization |
|---|---|---|---|
| 562 | 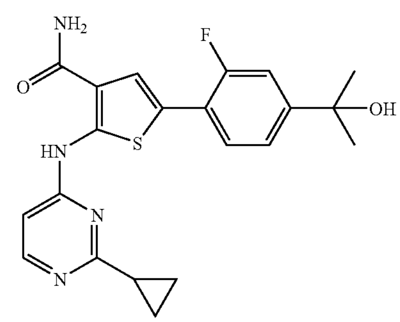 [SMILES: CC(C)(O)c1ccc(-c2cc(C(N)=O)c(Nc3ccnc(C4CC4)n3)s2)c(F)c1] | 2-[(2-cyclopropylpyrimidin-4-yl)amino]-5-[2-fluoro-4-(1-hydroxy-1-methylethyl)phenyl]thiophene-3-carboxamide | Calc'd [M + H]$^+$: 413, Found: 413 |

Example 563

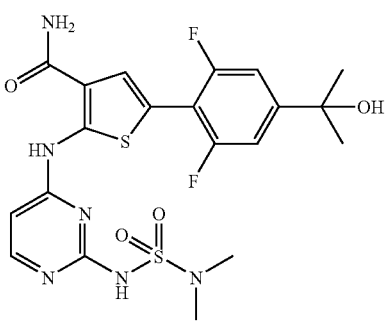 [SMILES: CN(C)S(=O)(=O)Nc1nccc(Nc2sc(-c3c(F)cc(C(C)(C)O)cc3F)cc2C(N)=O)n1]

5-[2,6-Difluoro-4-(1-hydroxy-1-methylethyl)phenyl]-2-[(2-{[(dimethylamino)sulfonyl]amino}pyrimidin-4-yl)amino]thiophene-3-carboxamide

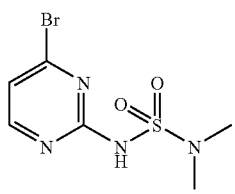

Step 1: N'-(4-bromopyrimidin-2-yl)-N,N-dimethylsulfamide 2,4-Dibromopyrimidine (0.50 g, 2.11 mmol), N,N-dimethylsulfamide (0.26 mg, 2.11 mmol), cesium carbonate (2.75 g, 8.44 mmol), Pd$_2$(dba)$_3$ (0.10 mg, 0.11 mmol), and Xantphos (0.18 mg, 0.32 mmol) were placed in a flask. Dioxane (24 mL) was added and argon was bubbled through the solution for several minutes. The reaction was then heated at 100° C. overnight. The reaction was cooled to ambient temperature, diluted with ethyl acetate, washed with saturated sodium bicarbonate, dried over magnesium sulfate, filtered and concentrated. Reverse phase HPLC was used for purification to yield the title compound.

Calc'd for C$_7$H$_{10}$BrN$_3$O$_2$S [M+H]$^+$: 280. Found: 280.

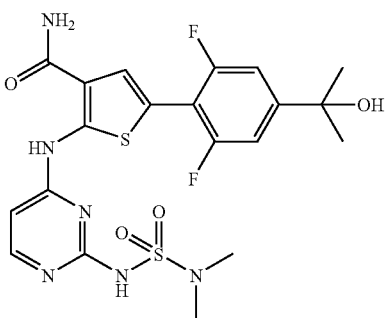 [SMILES: CN(C)S(=O)(=O)Nc1nccc(Nc2sc(-c3c(F)cc(C(C)(C)O)cc3F)cc2C(N)=O)n1]

Step 2: 5-[2,6-Difluoro-4-(1-hydroxy-1-methylethyl)phenyl]-2-[(6{[(dimethylamino)sulfonyl]amino}pyridin-2-yl)amino]thiophene-3-carboxamide The title compound was prepared by using the procedure listed in Example 1 with 2-amino-5-[2,6-difluoro-4-(1-hydroxy-1-methylethyl)phenyl]thiophene-3-carboxamide (0.10 g, 0.32 mmol) and N'-(6-bromopyridin-2-yl)-N,N-dimethylsulfamide (0.90 g, 0.32 mmol) as the starting materials.

Calc'd for C$_{21}$H$_{23}$F$_2$N$_5$O$_4$S$_2$ [M+H]$^+$: 512. Found: 512.

Example 564

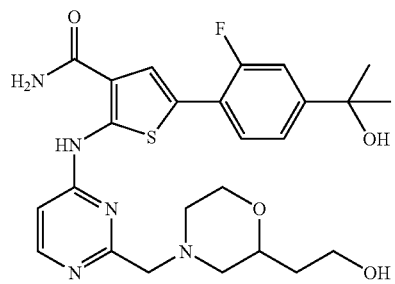 [SMILES: CC(C)(O)c1ccc(-c2cc(C(N)=O)c(Nc3ccnc(CN4CCOC(CCO)C4)n3)s2)c(F)c1]

5-[2-Fluoro-4-(1-hydroxy-1-methylethyl)phenyl]-2-[(2-{[2-(2-hydroxyethyl)morpholin-4-yl]methyl}pyrimidin-4-yl)amino]thiophene-3-carboxamide

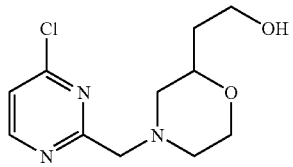 [SMILES: OCCC1CN(Cc2nccc(Cl)n2)CCO1]

Step 1: 2-{4-[(4-Chloropyrimidin-2-yl)methyl]morpholin-2-yl}ethanol

The title compound was prepared as described in Example 106, Step 1 with 4-chloropyrimidine-2-carbaldehyde (110 mg, 0.84 mmol) and 2-morpholin-2-ylethanol (100 mg, 0.70 mmol) as starting materials.

Calc'd for C$_{11}$H$_{17}$ClN$_3$O$_2$ [M+H]$^+$: 280. Found: 280.

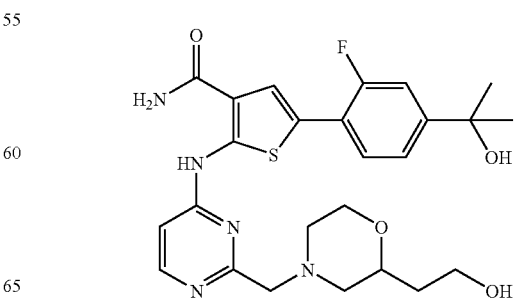

Step 2: 5-[2-Fluoro-4-(1-hydroxy-1-methylethyl)phenyl]-2-[(2-{[2-(2-hydroxyethyl)morpholin-4-yl]methyl}pyrimidin-4-yl)amino]thiophene-3-carboxamide The title compound was prepared as described in Example 106, Step 2 with 2-{4-[(4-chloropyrimidin-2-yl)methyl]morpholin-2-yl}ethanol (50 mg, 0.19 mmol) and 2-amino-5-[2-fluoro-4-(1-hydroxy-1-methylethyl)phenyl]thiophene-3-carboxamide (57 mg, 0.19 mmol) as starting materials.
Calc'd for $C_{25}H_{31}FN_5O_4S$ [M+H]$^+$: 516. Found: 516.

INTERMEDIATE 43

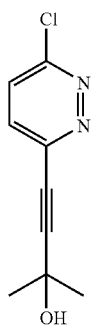

4-(6-Chloropyridazin-3-yl)-2-methylbut-3-yn-2-ol

To a solution of 3,6-dichloropyridazine (250 mg, 1.68 mmol) and 2-methylbut-3-yn-2-ol (282 mg, 3.36 mmol) in DMF (4 mL) were added CuI (64 mg, 0.33 mmol), triethylamine (0.47 mL, 3.36 mmol), and palladium tetrakis triphenylphosphine (194, 0.168 mmol). The solution was degassed and heated to 80° C. overnight. The residue was worked up with EtOAc and water, dried with MgSO$_4$, filtered, and concentrated. Column chromatography on silica gel 100% Hex to 100% EtOAc provided the title compound.
$^1$H NMR (600 MHz, CDCl$_3$) δ 7.50 (q, 2H), 1.6 (s, 6H). Calc'd for $C_9H_{10}ClN_2O$ [M+1]$^+$ (ESI): 197. Found: 197.

INTERMEDIATE 44

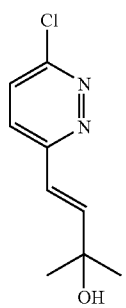

(3E)-4-(6-Chloropyridazin-3-yl)-2-methylbut-3-en-2-ol

To a solution of 3,6-dichloropyridazine (250 mg, 1.68 mmol) and [(1E)-3-hydroxy-3-methylbut-1-en-1-yl]boronic acid (218 mg, 1.68 mmol) in THF (5 mL) and 2.0 M NaHCO$_3$ (1.70 mL) was added palladium tetrakis triphenylphosphine (97 mg, 0.084 mmol). The solution was degassed with nitrogen and heated to 85° C. overnight. The residue was worked up with EtOAc and water, dried with MgSO$_4$, filtered, and concentrated. Column chromatography on silica gel 100% Hex to 100% EtOAc provided the title compound.
$^1$H NMR (600 MHz, CDCl$_3$) δ 7.50 (d, 1H), 7.44 (d, 1H), 6.90 (q, 2H), 1.44 (s, 6H). Calc'd for $C_9H_{12}ClN_2O$ [M+1]$^+$ (ESI): 199. Found: 199.

INTERMEDIATE 45

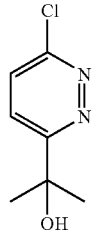

2-(6-Chloropyridazin-3-yl)propan-2-ol

To a solution of MeTHF (2.5 mL) and toluene (10 mL) was added MeMgCl (3.0 M, 9.7 mL) and stirred at −20° C. under N$_2$ atmosphere followed by the addition of t-BuOH (0.5 mL, 5.79 mmol) in MeTHF (7 mL) dropwise. The solution was allowed to stir for 30 min and warmed to 3° C. and cooled backed down to −20° C. followed by the addition of the methyl 6-chloropyridazine-3-carboxylate (1.0 g, 5.79 mmol) in portions. The solution quickly turned dark violet and stirred at 0° C. for 30 min. The solution was then poured into a flask containing 1 N HCl at −5° C. and diluted with EtOAc followed by stirring for 10 min. The layers were separated and the organic layers were washed with sat. NaHCO$_3$ and brine. The acidic aqueous layer was neutralized with sat. NaHCO$_3$ and extracted with EtOAc. The organic layers were combined and concentrated under rotary evaporation. Column chromatography Hex to 100% EtOAc provided the title compound.
$^1$H NMR (600 MHz, CDCl$_3$). δ 7.70-7.66 (d, 1H), 7.54-7.50 (d, 1H), 1.65 (s, 6H). Calc'd for $C_7H_{10}ClN_2O$ [M+1]$^+$ (ESI): 173. Found: 173.

INTERMEDIATE 46

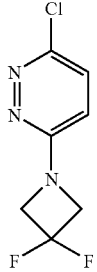

3-Chloro,6-(3,3-difluoroazetidin-1-yl)pyridazin-3-yl

A solution of 2,5-dichloropyridazine (119.1 mg, 0.80 mmol), triethylamine (0.134 ml, 0.96 mmol), and 3,3-difluoroazetidine hydrochloride (311 mg, 2.40 mmol) in dioxane (4 ml) was heated in a microwave reactor for 60 minutes at 120° C. Reaction mixture was filtered and concentrated under reduced pressure. Column chromatography on silica gel from 100% dichloromethane to 15% methanol yielded the title compound.

$^1$H NMR (600 MHz, CDCl$_3$) δ 7.52 (d, 1H), 7.04 (d, 1H), 4.50 (t, 4H). Calc'd for C$_7$H$_6$ClF$_2$N$_3$ [M+1]$^+$ (ESI): 206. Found: 206.

INTERMEDIATE 47

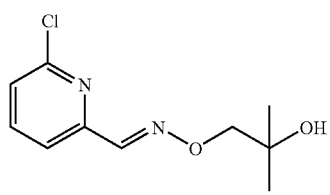

6-Bromopyridine-2-carbaldehyde
O-(2-hydroxy-2-methylpropyl)oxime

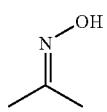

Step 1: Acetone oxime

To 1 L of water was added acetone (260 g, 4.48 mol) and hydroxylamine hydrochloride (300 g, 4.25 mol) and the mixture was cooled to −10° C. Aqueous sodium hydroxide (40%, 440 g, 4.4 mol) was added dropwise below 0° C. The mixture was stirred for 4 hours, then extracted with ether (3×500 ml). The combined organic extract was dried over MgSO$_4$, filtered, and concentrated to afford the acetone oxime.

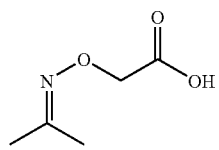

Step 2: {[(1-Methylethylidene)amino]oxy}acetic acid

To bromoacetic acid (500 g, 3.60 mol) and ice (400 g) was added dropwise 40% sodium hydroxide (375 g, 3.75 mol) at below 20° C. Acetone oxime (239 g, 3.27 mol) was added. At below 20° C., 40% sodium hydroxide (375 g, 3.27 mol) was added dropwise. The reaction mixture was allowed to warm to room temperature overnight and extracted with 500 ml of ether. The aqueous phase was acidified to pH 2 and extracted with ether (3×500 ml). The combined organic layers were dried over MgSO4, filtered, and concentrated to dryness. Hexane (250 ml) was added to the residue and the precipitate was collected to give the title compound.

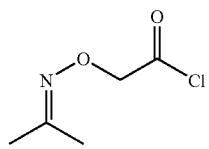

Step 3: {[(1-Methylethylidene)amino]oxy}acetyl chloride

To {[(1-methylethylidene)amino]oxy}acetic acid (286 g, 2.18 mol) was added 600 ml of toluene. Thionyl chloride (364 g, 3.06 mol) was added dropwise at room temperature. After the addition was complete, the reaction mixture was heated to reflux for 10 hours. Toluene and thionyl chloride were evaporated under vacuum and the residue was distilled to afford the title compound.

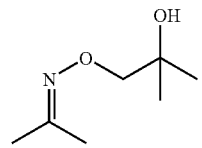

Step 4: Acetone
O-(2-hydroxy-2-methylpropyl)oxime

Methylmagnesium bromide (3 M in ether, 500 ml) was added dropwise to {[(1-methylethylidene)amino]oxy}acetyl chloride (167 g, 0.56 mol) in ether (400 ml) at 0° C. The reaction mixture was stirred for 2 hours, then added saturated ammonium chloride dropwise, diluted with water (500 ml) and extracted with ether (3×500 ml). The combined organic layers were dried over MgSO$_4$, filtered, concentrated and distilled to give the title compound.

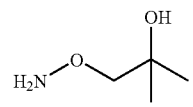

Step 5: 1-(Aminooxy)-2-methylpropan-2-ol

A solution of acetone O-(2-hydroxy-2-methylpropyl) oxime (127 g, 0.80 mol) in water (500 ml) and 37% hydrochloride (250 g) was stirred overnight at room temperature. The reaction mixture was evaporated under vacuum to dryness. Anhydrous ether (100 ml) and tetrahydrofuran (20 ml) were added. The precipitate was collected to give the title compound as the hydrochloride salt.

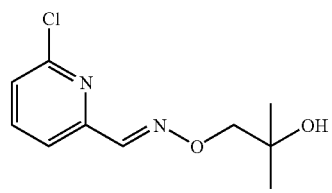

Step 6: 6-bromopyridine-2-carbaldehyde
O-(2-hydroxy-2-methylpropyl)oxime

A solution of 6-bromopyridine-2-carbaldehyde (334 mg, 1.80 mmol) and 1-(aminooxy)-2-methylpropan-2-ol hydrochloride salt (254.6 mg, 1.80 mmol) were stirred in ethanol (5 ml) for one hour at 10° C. The reaction mixture was cooled to room temperature and diluted with ethyl acetate. The organic layer was washed with water, dried over magnesium sulfate, filtered, and concentrated under reduced pressure. Column chromatography from 100% hexanes to 30% ethyl acetate afforded the title compound as E/Z mixture.

Calc'd for C$_{10}$H$_{14}$BrN$_2$O$_2$ [M+H]$^+$: 273. Found: 273.

Example 565

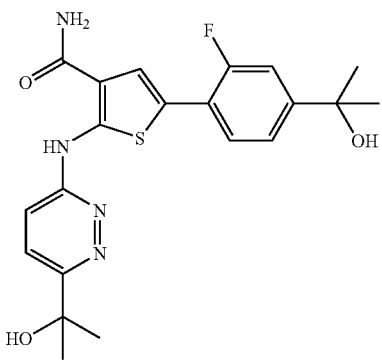 [SMILES: CC(C)(O)c1ccc(-c2cc(C(N)=O)c(Nc3ccc(C(C)(C)O)nn3)s2)c(F)c1]

5-[2-Fluoro-4-(1-hydroxy-1-methylethyl)phenyl]-2-{[6-(1-hydroxy-1-methylethyl)pyridazin-3-yl]amino}thiophene-3-carboxamide The title compound was prepared by using the procedure listed in Example 1 with starting materials 2-(6-chloropyridazin-3-yl)propan-2-ol (Intermediate 45) (117 mg, 0.68 mmol) and 2-amino-5-[2-fluoro-4-(1-hydroxy-1-methylethyl)phenyl]thiophene-3-carboxamide (200 mg, 0.68 mmol).

$^1$H NMR (600 MHz, CD$_3$OD) δ 7.90 (d, 1H), 7.74 (s, 1H), 7.64 (t, 1H), 7.39 (d, 1H), 7.12 (d, 1H), 7.10 (s, 1H), 1.62 (s, 6H), 1.54 (s, 6H). Calc'd for C$_{21}$H$_{24}$FN$_4$O$_3$S [M+H]$^+$: 431. Found: 431.

Additional examples were prepared using procedures similar to those described in the above examples and are illustrated in the following table.

TABLE 58

| Example # | Structure | Compound Name | Characterization [M + H]$^+$ |
|---|---|---|---|
| 566 | 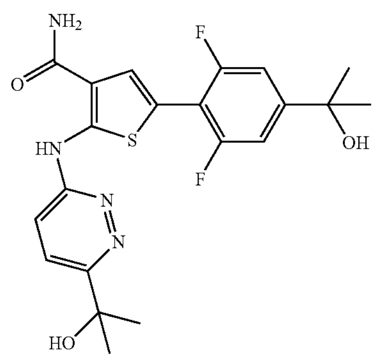 [SMILES: CC(C)(O)c1cc(F)c(-c2cc(C(N)=O)c(Nc3ccc(C(C)(C)O)nn3)s2)c(F)c1] | 5-[2,6-difluoro-4-(1-hydroxy-1-methylethyl)phenyl]-2-{[6-(1-hydroxy-1-methylethyl)pyridazin-3-yl]amino}thiophene-3-carboxamide | Calc'd: 449, Found: 449 |
| 567 | 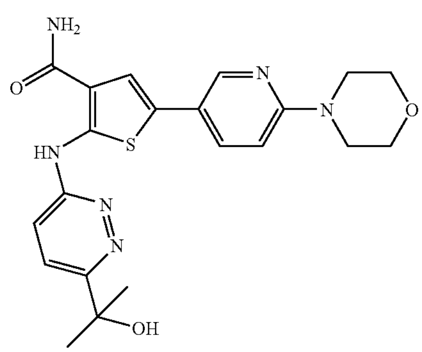 [SMILES: CC(C)(O)c1ccc(Nc2sc(-c3ccc(N4CCOCC4)nc3)cc2C(N)=O)nn1] | 2-{[6-(1-hydroxy-1-methylethyl)pyridazin-3-yl]amino}-5-(6-morpholin-4-ylpyridin-3-yl)thiophene-3-carboxamide | Calc'd: 441, Found: 441 |
| 568 | 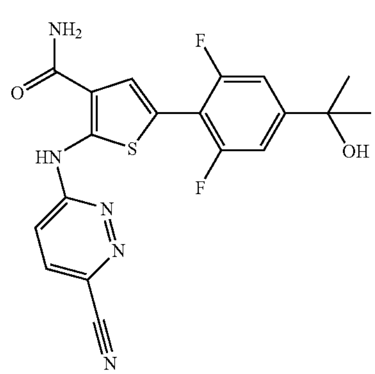 [SMILES: CC(C)(O)c1cc(F)c(-c2cc(C(N)=O)c(Nc3ccc(C#N)nn3)s2)c(F)c1] | 2-[(6-cyanopyridazin-3-yl)amino]-5-[2,6-difluoro-4-(1-hydroxy-1-methylethyl)phenyl]thiophene-3-carboxamide | Calc'd: 416, Found: 416 |

TABLE 58-continued

| Example # | Structure | Compound Name | Characterization [M + H]+ |
|---|---|---|---|
| 569 | 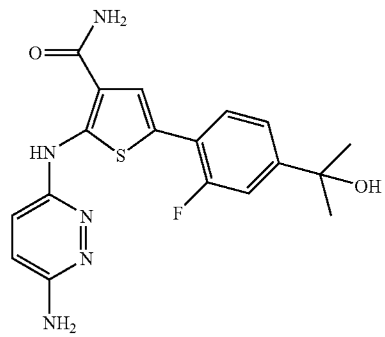 [SMILES: CC(C)(O)c1ccc(-c2cc(C(N)=O)c(Nc3ccc(N)nn3)s2)c(F)c1] | 2-[(6-aminopyridazin-3-yl)amino]-5-[2-fluoro-4-(1-hydroxy-1-methylethyl)phenyl]thiophene-3-carboxamide | Calc'd: 388, Found: 388 |
| 570 | 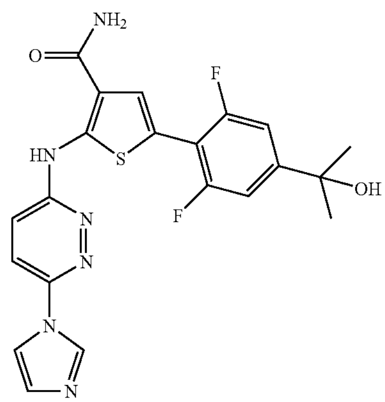 [SMILES: CC(C)(O)c1cc(F)c(-c2cc(C(N)=O)c(Nc3ccc(-n4ccnc4)nn3)s2)c(F)c1] | 5-[2,6-difluoro-4-(1-hydroxy-1-methylethyl)phenyl]-2-{[6-(1H-imidazol-1-yl)pyridazin-3-yl]amino}thiophene-3-carboxamide | Calc'd: 457, Found: 457 |
| 571 | 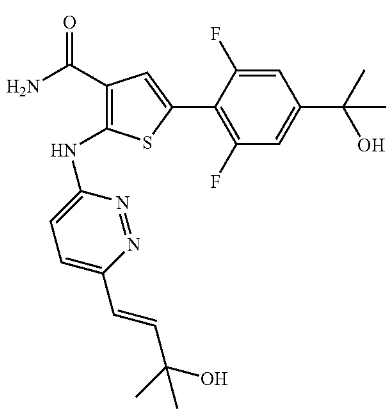 [SMILES: CC(C)(O)/C=C/c1ccc(Nc2sc(-c3c(F)cc(C(C)(C)O)cc3F)cc2C(N)=O)nn1] | 5-[2,6-difluoro-4-(1-hydroxy-1-methylethyl)phenyl]-2-({6-[(1E)-3-hydroxy-3-methylbut-1-en-1-yl]pyridazin-3-yl}amino)thiophene-3-carboxamide | Calc'd: 475, Found: 475 |
| 572 | 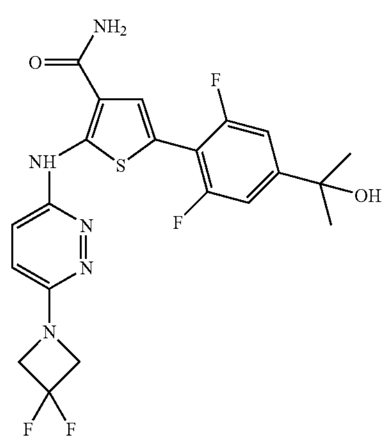 [SMILES: CC(C)(O)c1cc(F)c(-c2cc(C(N)=O)c(Nc3ccc(N4CC(F)(F)C4)nn3)s2)c(F)c1] | 2-{[6-(3,3-difluoroazetidin-1-yl)pyridazin-3-yl]amino}-5-[2,6-difluoro-4-(1-hydroxy-1-methylethyl)phenyl]thiophene-3-carboxamide | Calc'd: 482, Found: 482 |

TABLE 58-continued

| Example # | Structure | Compound Name | Characterization [M + H]+ |
|---|---|---|---|
| 573 | 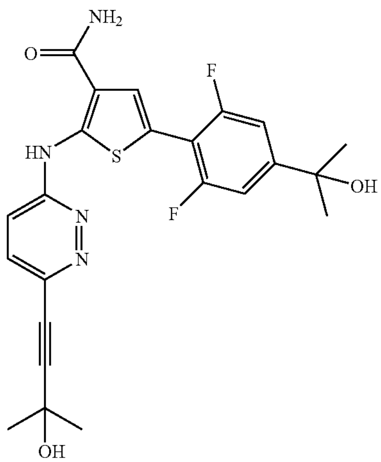 [SMILES: CC(C)(O)C#Cc1ccc(Nc2sc(-c3c(F)cc(C(C)(C)O)cc3F)cc2C(N)=O)nn1] | 5-[2,6-difluoro-4-(1-hydroxy-1-methylethyl)phenyl]-2-{[6-(3-hydroxy-3-methylbut-1-yn-1-yl)pyridazin-3-yl]amino}thiophene-3-carboxamide | Calc'd: 473, Found: 473 |
| 574 | 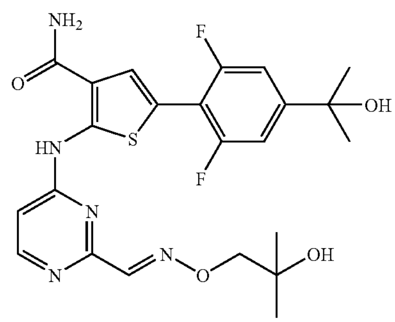 [SMILES: CC(C)(O)CO/N=C/c1nccc(Nc2sc(-c3c(F)cc(C(C)(C)O)cc3F)cc2C(N)=O)n1] | 5-[2,6-difluoro-4-(1-hydroxy-1-methylethyl)phenyl]-2-{[6-(1H-pyrazol-5-yl)pyridazin-3-yl]amino}thiophene-3-carboxamide | Calc'd: 505, Found: 505 |

Example 575

5-[2,6-Difluoro-4-(1-hydroxy-1-methylethyl)phenyl]-2-{[6-(1H-pyrazol-5-yl)pyridazin-3-yl]amino}thiophene-3-carboxamide Step 1: 2-[(6-Chloropyridazin-3-yl)amino]-5-[2,6-difluoro-4-(1-hydroxy-1-methylethyl)phenyl]thiophene-3-carboxamide To a solution of 5-[2,6-difluoro-4-(1-hydroxy-1-methylethyl)phenyl]-2-amino-thiophene-3-carboxamide (97 mg, 0.31 mmol) in THF (3 ml) was added sodium carbonate (0.776 ml, 1.55 mmol, 2 M), 2,5-dichloropyridazine (139 mg, 0.93 mmol), and 2-(dicyclohexylphosphino)-2',4',6'-tri-i-propyl-1,1'-biphenyl (37 mg, 0.08 mmol). Tris(dibenzylideneacetone)dipalladium(0) (28.4 mg, 0.031 mmol) was added last and the vial was purged with nitrogen for 5 minutes. The reaction was heated to 100° C. overnight. The crude product was washed with 3:1 chloroform:isopropanol and water. The resulting organic layer was dried over magnesium sulfate and concentrated under reduced pressure. Purification by silica gel chromatography yielded the title compound.

Calc'd for $C_{18}H_{15}ClF_2N_4O_2S$ [M+H]$^+$: 425. Found: 425.

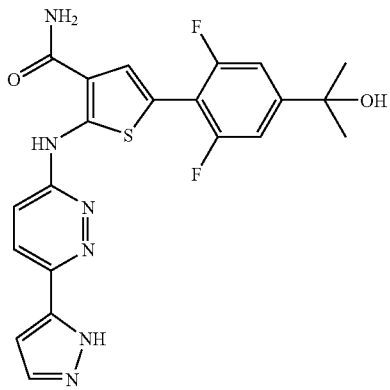 [SMILES: CC(C)(O)c1cc(F)c(-c2cc(C(N)=O)c(Nc3ccc(-c4ccn[nH]4)nn3)s2)c(F)c1]

Step 2: 5-[2,6-Difluoro-4-(1-hydroxy-1-methylethyl) phenyl]-2-{[6-(1H-pyrazol-5-yl)pyridazin-3-yl] amino}thiophene-3-carboxamide To a solution of 2-[(6-chloropyridazin-3-yl)amino]-5-[2,6-difluoro-4-(1-hydroxy-1-methylethyl)phenyl]thiophene-3-carboxamide (64 mg, 0.15 mmol) in THF (3 ml), was added 1H-pyrazol-3-yl boronic acid (34 mg, 0.30 mmol), and sodium bicarbonate (0.38 ml, 0.75 mmol, 2 M). Palladium tetrakis triphenylphosphine (35 mg, 0.03 mmol) was added last and the vial was purged with nitrogen for 5 minutes. The crude product was washed with 3:1 chloroform:isopropanol and water. The resulting organic layer was dried over magnesium sulfate and concentrated under reduced pressure. Purification by column chromatography yielded the title compound.

$^1$H NMR (600 MHz, CDCl$_3$) δ 8.14 (s, 1H), 7.78 (s, 2H), 7.44 (d, 1H), 7.19 (d, 2H), 7.01 (s, 1H), 1.54 (s, 6H). Calc'd for $C_{21}H_{18}F_2N_6O_2S$ [M+H]$^+$: 457. Found: 457.

Example 576

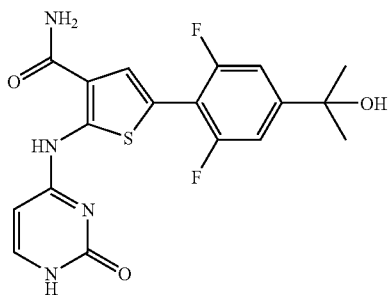 [SMILES: CC(C)(O)c1cc(F)c(-c2cc(C(N)=O)c(Nc3cc[nH]c(=O)n3)s2)c(F)c1]

5-[2,6-Difluoro-4-(1-hydroxy-1-methylethyl)phenyl]-2-[(2-oxo-1,2-dihydropyrimidin-4-yl)amino] thiophene-3-carboxamide

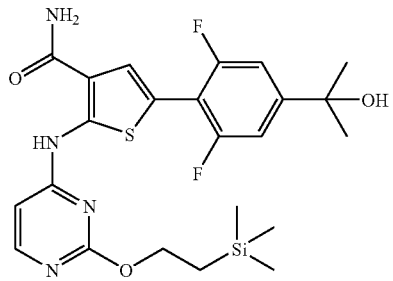 [SMILES: CC(C)(O)c1cc(F)c(-c2cc(C(N)=O)c(Nc3ccnc(OCC[Si](C)(C)C)n3)s2)c(F)c1]

Step 1. 5-[2,6-Difluoro-4-(1-hydroxy-1-methylethyl) phenyl]-2-({2-[2-(trimethylsilyl)ethoxy]pyrimidin-4-yl}amino)thiophene-3-carboxamide The title compound was prepared according to the general procedure in Example 1 using 2-amino-5-[2,6-difluoro-4-(1-hydroxy-1-methylethyl)phenyl]thiophene-3-carboxamide (1 g, 3.20 mmol) and 4-chloro-2-[2-(trimethylsilyl)ethoxy]pyrimidine (0.739 g, 3.20 mmol) (see J. Het. Chem., 1994, 989-995) as the starting materials.

Calc'd for $C_{23}H_{29}F_2N_4O_3SSi$ [M+H]$^+$: 507. Found: 507.

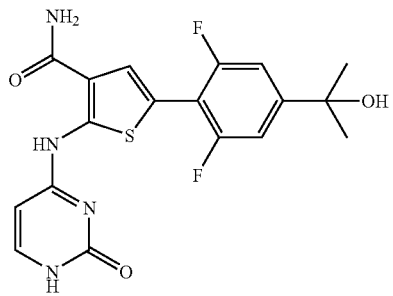 [SMILES: CC(C)(O)c1cc(F)c(-c2cc(C(N)=O)c(Nc3cc[nH]c(=O)n3)s2)c(F)c1]

Step 2. 5-[2,6-Difluoro-4-(1-hydroxy-1-methylethyl) phenyl]-2-[(2-oxo-1,2-dihydropyrimidin-4-yl)amino] thiophene-3-carboxamide 5-[2,6-Difluoro-4-(1-hydroxy-1-methylethyl)phenyl]-2-({2-[2-(trimethylsilyl)ethoxy]pyrimidin-4-yl}amino) thiophene-3-carboxamide (109 mg, 0.215 mmol) was stirred in a mixture of MeOH (10 mL) and 2N HCl (6 mL) at room temperature overnight. The solvent was removed in vacuo, saturated NaHCO$_3$ was added and the reaction mixture was extracted with EtOAc (2×). The combined organic extracts were washed with brine, dried over MgSO$_4$, filtered, and concentrated in vacuo. Purification of the residue by reverse phase HPLC (40-100% MeCN—H$_2$O) gave the title compound as a pale yellow solid after triturating in DCM.

Calc'd for $C_{18}H_{17}F_2N_4O_3S$ [M+H]$^+$: 407. Found: 407.

Example 577

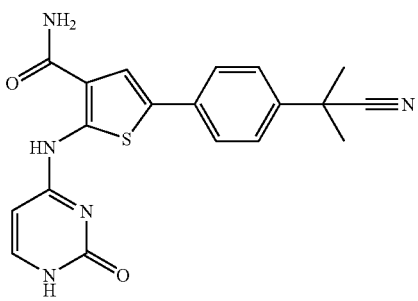 [SMILES: CC(C)(C#N)c1ccc(-c2cc(C(N)=O)c(Nc3cc[nH]c(=O)n3)s2)cc1]

5-[4-(1-Cyano-1-methylethyl)phenyl]-2-[(2-oxo-1,2-dihydropyrimidin-4-yl)amino]thiophene-3-carboxamide

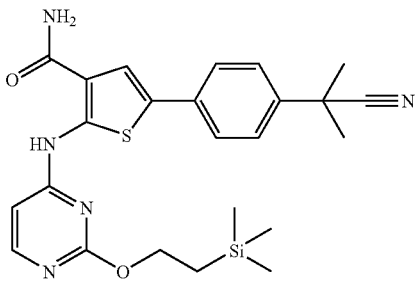 [SMILES: CC(C)(C#N)c1ccc(-c2cc(C(N)=O)c(Nc3ccnc(OCC[Si](C)(C)C)n3)s2)cc1]

Step 1. 5-[4-(1-Cyano-1-methylethyl)phenyl]-2-({2-[2-(trimethylsilyl)ethoxy]pyrimidin-4-yl}amino)thiophene-3-carboxamide The title compound was prepared according to the general procedure in Example 1 using 2-amino-5-[4-(1-cyano-1-methylethyl)phenyl]thiophene-3-carboxamide (100 mg, 0.350 mmol) and 4-chloro-2-[2-(trimethylsilyl)ethoxy]pyrimidine (81 mg, 0.350 mmol) (see J. Het. Chem., 1994, 989-995) as the starting materials.

Calc'd for $C_{24}H_{30}N_5O_2SSi$ $[M+H]^+$: 480. Found: 480.

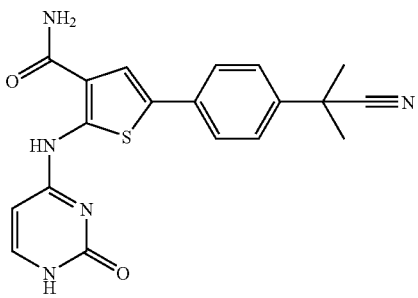 [SMILES: CC(C)(C#N)c1ccc(-c2cc(C(N)=O)c(Nc3cc[nH]c(=O)n3)s2)cc1]

Step 2. 5-[4-(1-Cyano-1-methylethyl)phenyl]-2-[(2-oxo-1,2-dihydropyrimidin-4-yl)amino]thiophene-3-carboxamide 5-[4-(1-Cyano-1-methylethyl)phenyl]-2-({2-[2-(trimethylsilyl)ethoxy]pyrimidin-4-yl}amino)thiophene-3-carboxamide (107 mg, 0.223 mmol) was stirred in a mixture of DCM (5 mL) and TFA (2 mL) at room temperature for 30 minutes. Saturated NaHCO₃ was added and the resulting precipitate collected by filtration and washed with water and DCM to give the title compound as a yellow solid.

Calc'd for $C_{19}H_{18}N_5O_2S$ $[M+H]^+$: 380. Found: 380.

Example 578

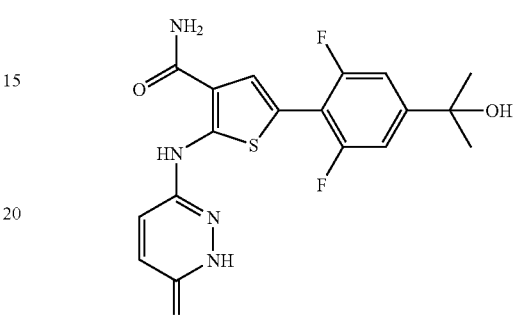

5-[2,6-Difluoro-4-(1-hydroxy-1-methylethyl)phenyl]-2-[(6-oxo-1,6-dihydropyridazin-3-yl)amino]thiophene-3-carboxamide

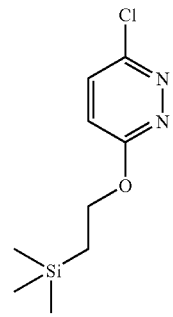

Step 1.
3-Chloro-6-[2-(trimethylsilyl)ethoxy]pyridazine 2-(Trimethylsilyl)ethanol (5.05 mL, 35.2 mmol) was taken up in THF (50 mL) and cooled to 0° C. Sodium hydride (1.48 g, 36.9 mmol) was added in 3 portions and the resulting mixture stirred at 0° C. for 15 minutes. This suspension was then added to a solution of 3,6-Dichloropyridazine (5 g, 33.6 mmol) in THF (50 mL) at 0° C. After stirring at 0° C. for 30 minutes, room temperature was attained and stirring continued overnight. Water was added followed by saturated NH₄Cl and the reaction mixture was extracted into EtOAc (2×). The combined organic extracts were washed with brine, dried over MgSO₄, filtered, and concentrated in vacuo. Purification of the residue by silica gel column chromatography (2-20% EtOAc-hexanes) gave the title compound as a white solid.

¹H NMR (600 MHz, CDCl₃): 7.32 (d, 1H), 6.88 (d, 1H), 4.56 (m, 2H), 1.15 (m, 2H), 0.05 (s, 9H).

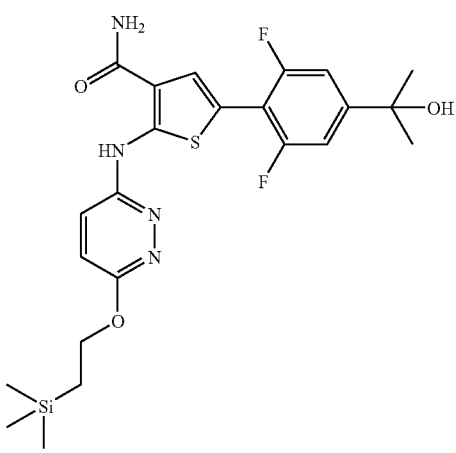 [SMILES: CC(C)(O)c1cc(F)c(-c2cc(C(N)=O)c(Nc3ccc(OCC[Si](C)(C)C)nn3)s2)c(F)c1]

Step 2. 5-[2,6-Difluoro-4-(1-hydroxy-1-methylethyl)phenyl]-2-({6-[2-(trimethylsilyl)ethoxy]pyridazin-3-yl}amino)thiophene-3-carboxamide The title compound was prepared according to the general procedure in Example 1 using 2-amino-5-[2,6-difluoro-4-(1-hydroxy-1-methylethyl)phenyl]thiophene-3-carboxamide (1 g, 3.20 mmol) and 3-chloro-6-[2-(trimethylsilyl)ethoxy]pyridazine (0.739 g, 3.20 mmol) as the starting materials.

Calc'd for $C_{23}H_{29}F_2N_4O_3SSi$ [M+H]$^+$: 507. Found: 507.

Step 3. 5-[2,6-Difluoro-4-(1-hydroxy-1-methylethyl)phenyl]-2-[(6-oxo-1,6-dihydropyridazin-3-yl)amino]thiophene-3-carboxamide 5-[2,6-Difluoro-4-(1-hydroxy-1-methylethyl)phenyl]-2-({6-[2-(trimethylsilyl)ethoxy]pyridazin-3-yl}amino)thiophene-3-carboxamide (0.61 g, 1.20 mmol) was taken up in DCM (12 mL) and TFA (0.4 mL) was added. After 30 minutes at room temperature, saturated NaHCO$_3$ was added. The resulting precipitate was collected by filtration and triturated in DCM to give the title compound as a yellow solid.

Calc'd for $C_{18}H_{17}F_2N_4O_3S$ [M+H]$^+$: 407. Found: 407.

Example 579

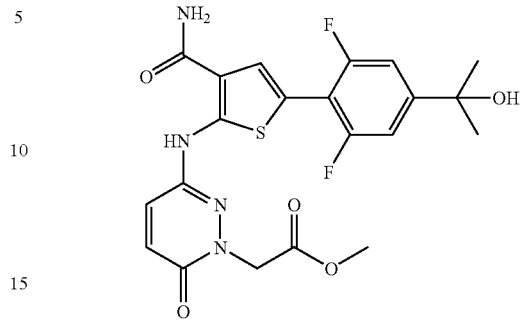

Methyl[3-({3-(aminocarbonyl)-5-[2,6-difluoro-4-(1-hydroxy-1-methylethyl)phenyl]-2-thienyl}amino)-6-oxopyridazin-1(6H)-yl]acetate 5-[2,6-Difluoro-4-(1-hydroxy-1-methylethyl)phenyl]-2-[(6-oxo-1,6-dihydropyridazin-3-yl)amino]thiophene-3-carboxamide (Example 578 Step 3) (50 mg, 0.12 mmol), K$_2$CO$_3$ (18.70 mg, 0.14 mmol) and methyl bromoacetate (0.012 mL, 0.13 mmol) were stirred in DMF (1 mL) at 80° C. overnight. The reaction mixture was cooled to room temperature, water was added and the reaction mixture was extracted into EtOAc (×2). The combined organic extracts were washed with brine, dried over MgSO$_4$, filtered, and concentrated in vacuo. Purification of the residue by silica gel column chromatography (0-15% MeOH—CHCl$_3$) gave the title compound as a yellow solid after triturating in DCM.

Calc'd for $C_{21}H_{21}F_2N_4O_5S$ [M+H]$^+$: 479. Found: 479.

Example 580

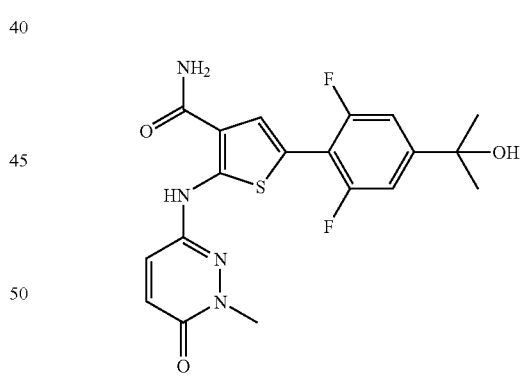

5-[2,6-Difluoro-4-(1-hydroxy-1-methylethyl)phenyl]-2-[(1-methyl-6-oxo-1,6-dihydropyridazin-3-yl)amino]thiophene-3-carboxamide 5-[2,6-Difluoro-4-(1-hydroxy-1-methylethyl)phenyl]-2-[(6-oxo-1,6-dihydropyridazin-3-yl)amino]thiophene-3-carboxamide (Example 578 Step 3) (50 mg, 0.123 mmol), K$_2$CO$_3$ (18.70 mg, 0.135 mmol) and iodomethane (8.08 µL, 0.129 mmol) were stirred in DMF (1 mL) at 80° C. overnight. The reaction mixture was cooled to room temperature, water was added and the products extracted into EtOAc (2×). The combined organic extracts were washed with brine, dried over MgSO₄ and concentrated in vacuo. Purification of the residue twice by silica gel column chromatography (0-10% MeOH—CHCl₃) followed by mass-triggered reverse phase HPLC gave the title compound as a yellow solid.

Calc'd for $C_{19}H_{19}F_2N_4O_3S$ [M+H]⁺: 421. Found: 421.

Example 581

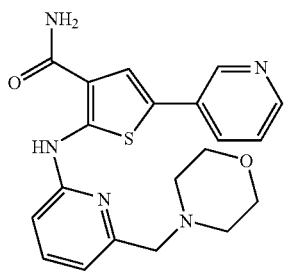 [SMILES: NC(=O)c1cc(-c2cccnc2)sc1Nc1cccc(CN2CCOCC2)n1]

2-{[6-Morpholin-4-ylmethyl)pyridine-2-yl]amino}-5-pyridin-3-ylthiophene-3-carboxamide

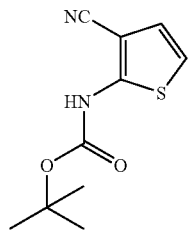

Step 1. tert-Butyl (3-cyano-2-thienyl)carbamate

Di-tert-butyl dicarbonate (56.1 ml, 242 mmol, 1.5 eq) was added to a stirred mixture of 2-amino-3-cyanothiophene (20 g, 161 mmol, 1.0 eq) and triethylamine (28.1 ml, 201 mmol, 1.25 eq) in dichloromethane (403 ml, 0.4 M) and the mixture was stirred at room temperature overnight. Di-tert-butyl dicarbonate (56.1 ml, 242 mmol) was added and the reaction was stirred for 2 h. The reaction was poured into dichloromethane (100 mL) and water (200 mL). The organic layer was washed with water and brine, dried over magnesium sulfate, filtered, and the solvent was evaporated under reduced pressure. The residue was purified by column chromatography on silica gel, eluting with ethyl acetate/hexanes to afford the title compound.

Calc'd for $C_{10}H_{13}N_2O_2S$ [M+H]⁺: 225. Found: 225.

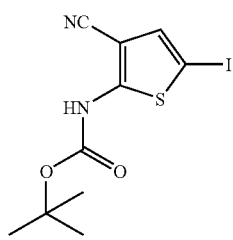

Step 2. tert-Butyl(3-cyano-5-iodo-2-thienyl)carbamate

N-Iodosuccinimide (9.28 g, 41.2 mmol, 1.0 eq) was added to a stirred mixture of tert-butyl (3-cyano-2-thienyl)carbamate (9.25 g, 4.1.2 mmol, 1.0 eq) in dichloromethane (82 ml, 0.5 M) and the mixture was stirred at room temperature for 2 h. The mixture was diluted with dichloromethane and washed with 1N sodium hydroxide (300 mL), sodium thiosulfate (2×300 mL), water (2×300 mL), and brine. The organic layers was dried over anhydrous magnesium sulfate, filtered, and concentrated under reduced pressure to afford the title compound as a solid.

Calc'd for $C_{10}H_{12}IN_2O_2S$ [M+H]⁺: 351. Found: 351.

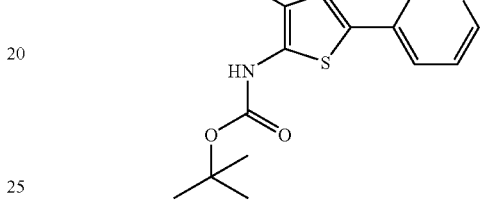

Step 3. tert-Butyl(3-cyano-5-pyridin-3-yl-2-thienyl)carbamate tert-Butyl(3-cyano-5-iodo-2-thienyl)carbamate (3.0 g, 8.57 mmol, 1.0 eq), 3-pyridyl boronic ester (3.98 g, 13.71 mmol, 1.6 eq), dibenyzlideneacetone bis(triphenylphosphine) (0.785 g, 0.857 mmol, 0.10 eq), tricyclohexylphosphine (0.601 g, 2.142 mmol, 0.25 eq), and potassium phosphate (22.26 ml, 28.3 mmol, 1.27 M in water, 3.30 eq) were combined in Dioxane (86 ml, 0.1 M) and the mixture was purged with nitrogen for 5 minutes. The reaction was heated to 100° C. for 1 h. The mixture was cooled, diluted with ethyl acetate (250 mL), washed with water, dried over magnesium sulfate, filtered and the solvent was evaporated under reduced pressure. The residue was purified by column chromatography on silica gel, eluting with ethyl acetate/hexanes to afford the title compound as a solid.

Calc'd for $C_{15}H_{16}N_3O_2S$ [M+H]⁺: 302. Found: 302.

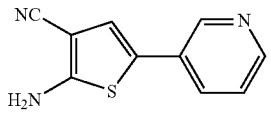

Step 4. 2-Amino-5-pyridin-3-ylthiophene-3-carbonitrile tert-Butyl(3-cyano-5-pyridin-3-yl-2-thienyl)carbamate (800 mg, 2.07 mmol) was dissolved in 4M hydrochloric acid in dioxane (10.4 ml, 41.6 mmol) and the mixture was stirred at room temperature for 6 h. The mixture was quenched with 1N sodium hydroxide (50 mL) and extracted with ethyl acetate (3×100 mL). The combined organics were dried over anhydrous magnesium sulfate, filtered, and concentrated under reduced pressure to afford the title compound as a solid.

Calc'd for $C_{10}H_8N_3S$ [M+H]⁺: 202. Found: 202.

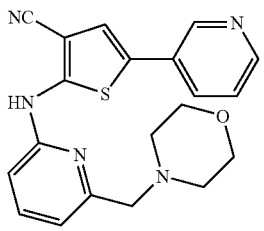

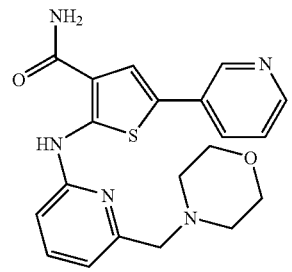 [SMILES: NC(=O)c1cc(-c2cccnc2)sc1Nc1cccc(CN2CCOCC2)n1]

Step 5. 2-{[6-(Morpholin-4-ylmethyl)pyridin-2-yl]amino}-5-pyridin-3-ylthiophene-3-carbonitrile 2-Amino-5-pyridin-3-ylthiophene-3-carbonitrile (76 mg, 0.38 mmol), 4-[(6-bromopyridin-2-yl)methyl]morpholine (Example 45, Step 1) (97 mg, 0.38 mmol), dibenyzlideneacetone bis(triphenylphosphine) (17.29 mg, 0.02 mmol), 2-dicylohexylphosphino-2',4',6'-triisopropyl-1,1-biphenyl (45.0 mg, 0.09 mmol), and potassium carbonate (57.4 mg, 0.42 mmol) were dissolved in tert-amyl alcohol (3.8 ml) and the mixture was bubbled with nitrogen for 5 min. The reaction was then heated to 100° C. overnight. The mixture was diluted with ethyl acetate and water and extracted with ethyl acetate (3×50 mL). The combined organics were washed with water and brine, dried over anhydrous magnesium sulfate, filtered, and concentrated under reduced pressure. The residue was purified by column chromatography on silica gel, eluting with dichloromethane/methanol to afford the title compound as a solid.

Calc'd for $C_{20}H_{20}N_5OS$ [M+H]$^+$: 378. Found: 378.

Step 6. 2-{[6-Morpholin-4-ylmethyl)pyridine-2-yl]amino}-5-pyridin-3-ylthiophene-3-carboxamide 2-{[6-(Morpholin-4-ylmethyl)pyridin-2-yl]amino}-5-pyridin-3-ylthiophene-3-carbonitrile (78 mg, 0.207 mmol) was added to a microwave reaction vial. Into the vial was added 1-propanol (2.8 ml) and 25% sodium hydroxide (0.8 ml) and the reaction mixture was heated in the microwave to 130° C. for 30 min. After cooling to ambient temperature, the reaction mixture was diluted with ethyl acetate and sodium bicarbonate to neutralize, extracted with ethyl acetate (3×100 mL), dried over magnesium sulfate, filtered, and the solvent was evaporated under reduced pressure. The residue was purified by column chromatography on silica gel, eluting with ethyl acetate/methanol to afford the title compound as a solid.

$^1$H NMR (600 MHz, d6-DMSO): δ 11.97 (s, 1H), 8.77 (dd, 1H), 8.40 (dd, 1H), 7.91 (s, 1H), 7.86 (dd, 1H), 7.73 (br s, 1H), 7.67 (t, 1H), 7.42 (dd, 1H), 7.39 (br s, 1H), 6.98 (d, 1H), 6.94 (d, 1H), 3.65 (s, 2H), 3.58 (ddd, 4H), 2.48 (ddd, 4H). Calc'd for $C_{20}H_{22}N_5O_2S$ [M+H]$^+$: 396. Found: 396.

Additional examples were prepared using procedures similar to those described in the above examples.

TABLE 59

| Example # | Structure | Compound Name | Characterization [M + H]$^+$ |
|---|---|---|---|
| 582 | 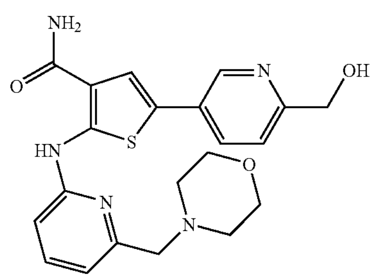 [SMILES: NC(=O)c1cc(-c2ccc(CO)nc2)sc1Nc1cccc(CN2CCOCC2)n1] | 5-[6-(hydroxymethyl)pyridin-3-yl]-2-{[6-(morpholin-4-ylmethyl)pyridin-2-yl]amino}thiophene-3-carboxamide | Calc'd 426, found 426 |
| 583 | 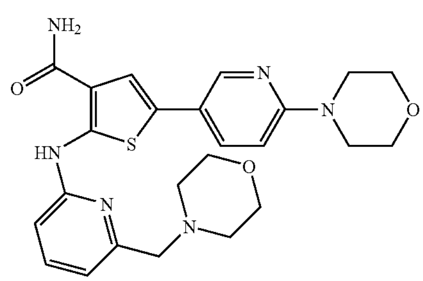 [SMILES: NC(=O)c1cc(-c2ccc(N3CCOCC3)nc2)sc1Nc1cccc(CN2CCOCC2)n1] | 2-{[6-(morpholin-4-ylmethyl)pyridin-2-yl]amino}-5-(6-morpholin-4-ylpyridin-3-yl)thiophene-3-carboxamide | Calc'd 481, found 481 |

TABLE 59-continued

| Example # | Structure | Compound Name | Characterization [M + H]+ |
|---|---|---|---|
| 584 | 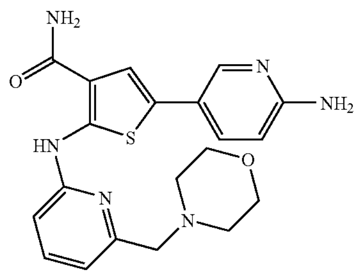 [SMILES: NC(=O)c1cc(-c2ccc(N)nc2)sc1Nc1cccc(CN2CCOCC2)n1] | 5-(6-aminopyridin-3-yl)-2-{[6-(morpholin-4-ylmethyl)pyridin-2-yl]amino}thiophene-3-carboxamide | Calc'd 411, found 411 |
| 585 | 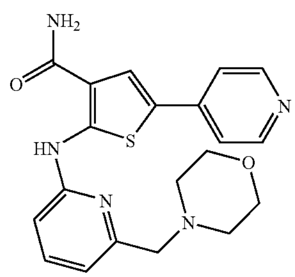 [SMILES: NC(=O)c1cc(-c2ccncc2)sc1Nc1cccc(CN2CCOCC2)n1] | 2-{[6-(morpholin-4-ylmethyl)pyridin-2-yl]amino}-5-pyridin-4-ylthiophene-3-carboxamide | Calc'd 396, found 396 |
| 586 | 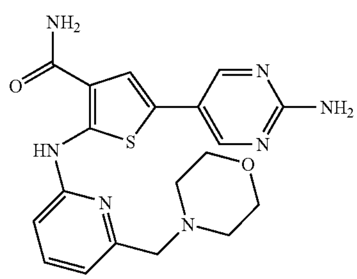 | 5-(2-aminopyrimidin-5-yl)-2-{[6-(morpholin-4-ylmethyl)pyridin-2-yl]amino}thiophene-3-carboxamide | Calc'd 412, found 412 |
| 587 | 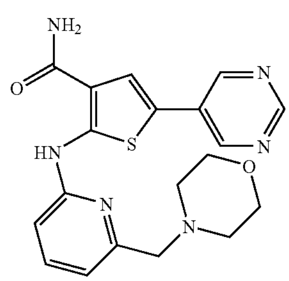 [SMILES: NC(=O)c1cc(-c2cncnc2)sc1Nc1cccc(CN2CCOCC2)n1] | 2-{[6-(morpholin-4-ylmethyl)pyridin-2-yl]amino}-5-pyrimidin-5-ylthiophene-3-carboxamide | Calc'd 397, found 397 |
| 588 | 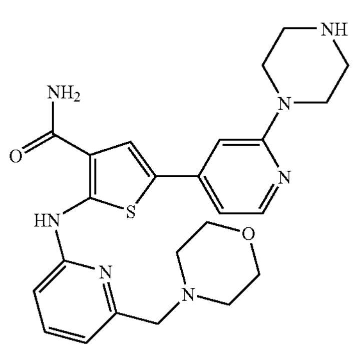 [SMILES: NC(=O)c1cc(-c2ccnc(N3CCNCC3)c2)sc1Nc1cccc(CN2CCOCC2)n1] | 2-{[6-(morpholin-4-ylmethyl)pyridin-2-yl]amino}-5-(2-piperazin-1-ylpyridin-4-yl)thiophene-3-carboxamide | Calc'd 480, found 480 |

Example 589

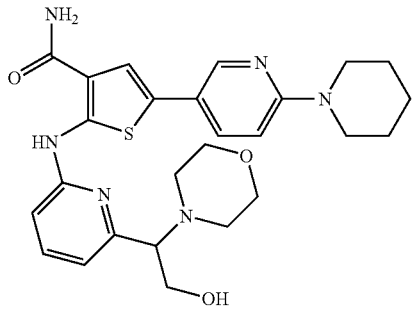 [SMILES: NC(=O)c1cc(-c2ccc(N3CCCCC3)nc2)sc1Nc1cccc(C(CO)N2CCOCC2)n1]

2-{[6-(2-Hydroxy-1-morpholin-4-ylethyl)pyridine-2-yl]amino}-5-(6-piperidin-1-ylpyridin-3-yl)thiophene-3-carboxamide

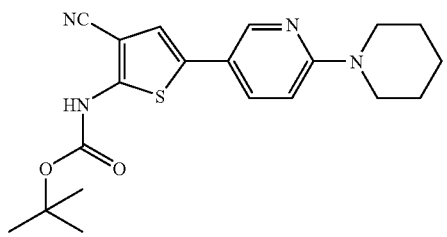

Step 1: tert-Butyl[3-cyano-5-(6-piperidin-1-ylpyridin-3-yl)-2-thienyl]carbamate The title compound was prepared from tert-butyl(3-cyano-5-iodo-2-thienyl)carbamate (Example 581 Step 2) (500 g, 1.43 mmol) and 2-piperidin-1-yl-5-(4,4,5,5-tetramethyl-1,3,2-dioxaborolan-2-yl)pyridine (658 mg, 2.29 mmol) as described in Example 581, Step 3.

Calc'd for $C_{20}H_{25}N_4O_2S$ [M+H]$^+$: 385. Found: 385.

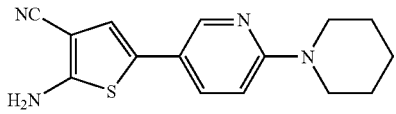

Step 2: 2-Amino-5-(6-piperidin-1-ylpyridin-3-yl)thiophene-3-carbonitrile

The title compound was prepared from tert-butyl[3-cyano-5-(6-piperidin-1-ylpyridin-3-yl)-2-thienyl]carbamate (440 mg, 1.14 mmol) as described in Example 581, Step 4.

Calc'd for $C_{15}H_{17}N_4S$ [M+H]: 285. Found: 285.

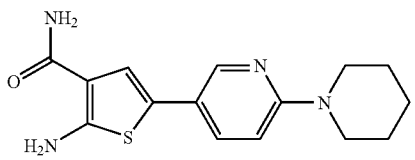 [SMILES: NC(=O)c1cc(-c2ccc(N3CCCCC3)nc2)sc1N]

Step 3: 2-Amino-5-(6-piperidin-1-ylpyridin-3-yl)thiophene-3-carboxamide

Into a microwave vial was added 2-amino-5-(6-piperidin-1-ylpyridin-3-yl)thiophene-3-carbonitrile (225 mg, 0.79 mmol), 1-propanol (6.2 ml), and 25% sodium hydroxide (1.8 ml) and the mixture was heated in the microwave to 130° C. for 30 min. The reaction mixture was diluted with ethyl acetate and sodium bicarbonate to neutralize, extracted with ethyl acetate (3×100 mL), dried over magnesium sulfate, filtered and the solvent was evaporated under reduced pressure. The residue was purified by column chromatography on silica gel, eluting with ethyl acetate/methanol to afford the title compound as a solid.

Calc'd for $C_{15}H_{19}N_4OS$ [M+H]$^+$: 303. Found: 303.

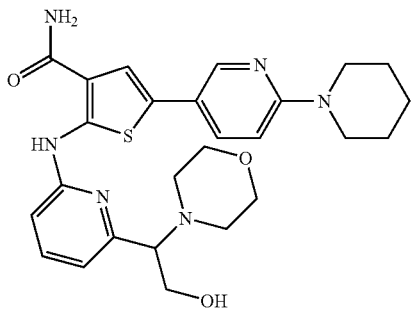 [SMILES: NC(=O)c1cc(-c2ccc(N3CCCCC3)nc2)sc1Nc1cccc(C(CO)N2CCOCC2)n1]

Step 4: 2-{[6-(2-Hydroxy-1-morpholin-4-ylethyl)pyridine-2-yl]amino}-5-(6-piperidin-1-ylpyridin-3-yl)thiophene-3-carboxamide The title compound was prepared by using the procedure listed in Example 1 with 2-amino-5-(6-piperidin-1-ylpyridin-3-yl)thiophene-3-carboxamide (70 mg, 0.23 mmol) and 2-(6-bromopyridin-2-yl)-2-morpholin-4-ylethanol (Example 141, Step 1) (66 mg, 0.23 mmol) as the starting materials.

Calc'd for $C_{26}H_{33}N_6O_3S$ [M+H]$^+$: 509. Found: 509.

Additional examples were prepared using procedures similar to those described in the above examples and are illustrated in the following table.

TABLE 60

| Example # | Structure | Compound Name | Characterization [M + H]+ |
|---|---|---|---|
| 590 | 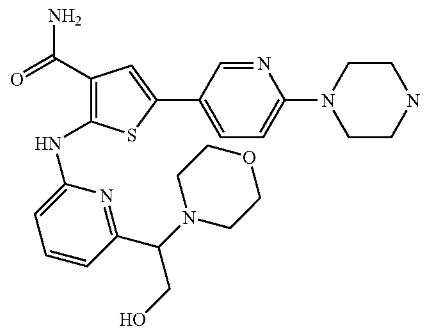 [SMILES: NC(=O)c1cc(-c2ccc(N3CCNCC3)nc2)sc1Nc1cccc(C(CO)N2CCOCC2)n1] | 2-{[6-(2-hydroxy-1-morpholin-4-ylethyl)pyridin-2-yl]amino}-5-[6-(4-methylpiperazin-1-yl)pyridin-3-yl]thiophene-3-carboxamide | Calc'd 524, found 524 |
| 591 | 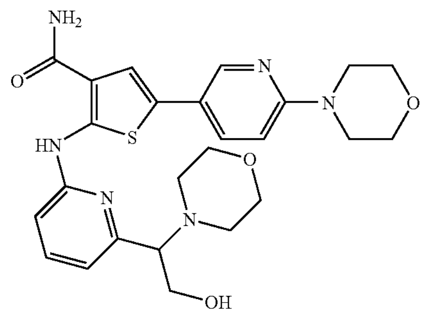 [SMILES: NC(=O)c1cc(-c2ccc(N3CCOCC3)nc2)sc1Nc1cccc(C(CO)N2CCOCC2)n1] | 2-{[6-(2-Hydroxy-1-morpholin-4-ylethyl)pyridine-2-yl]amino}-5-(6-morpholin-4-ylpyridin-3-yl)thiophene-3-carboxamide | Calc'd 511, found 511 |
| 592 | 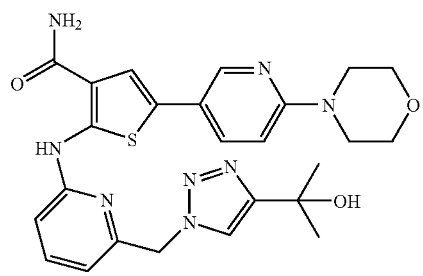 [SMILES: CC(C)(O)c1cn(Cc2cccc(Nc3sc(-c4ccc(N5CCOCC5)nc4)cc3C(N)=O)n2)nn1] | 2-[(6-{{4-(1-Hydroxy-1-methylethyl)-1H-1,2,3-triazol-1-yl]methyl}pyridine-2-yl}amino}-5-(6-morpholin-4-ylpyridin-3-yl)thiophene-3-carboxamide | Calc'd: 521, Found: 521 |
| 593 | 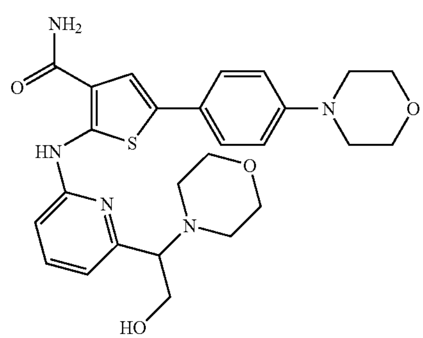 [SMILES: NC(=O)c1cc(-c2ccc(N3CCOCC3)cc2)sc1Nc1cccc(C(CO)N2CCOCC2)n1] | 2-{[6-(2-hydroxy-1-morpholin-4-ylethyl)pyridin-2-yl]amino}-5-(4-morpholin-4-ylphenyl)thiophene-3-carboxamide | Calc'd 510, found 510 |
| 594 | 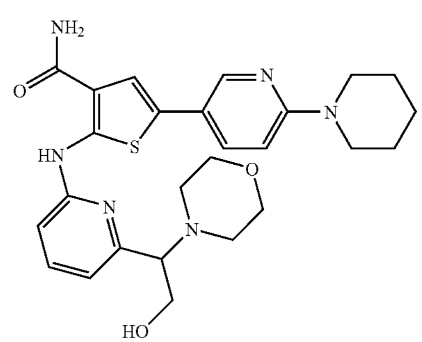 [SMILES: NC(=O)c1cc(-c2ccc(N3CCCCC3)nc2)sc1Nc1cccc(C(CO)N2CCOCC2)n1] | 2-{[6-(2-hydroxy-1-morpholin-4-ylethyl)pyridin-2-yl]amino}-5-(6-piperidin-1-ylpyridin-3-yl)thiophene-3-carboxamide | Calc'd 509, found 509 |

TABLE 60-continued

| Example # | Structure | Compound Name | Characterization [M + H]+ |
|---|---|---|---|
| 595 | 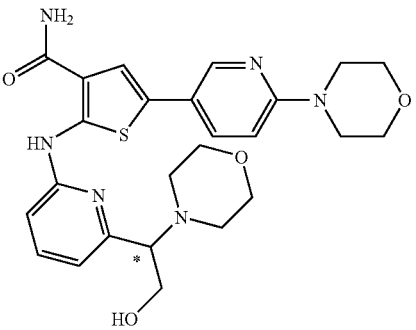<br>(Enantiomer A) | 2-({6-[(1R or S)-2-hydroxy-1-morpholin-4-ylethyl]pyridin-2-yl}amino)-5-(6-morpholin-4-ylpyridin-3-yl)thiophene-3-carboxamide | Calc'd 511, found 511 |
| 596 | 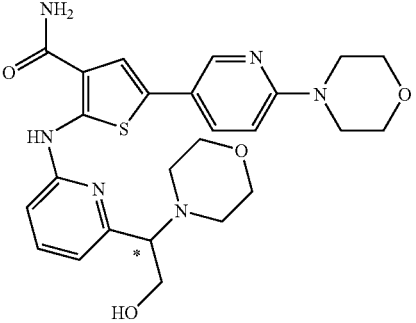<br>(Enantiomer B) | 2-({6-[(1R or S)-2-hydroxy-1-morpholin-4-ylethyl]pyridin-2-yl}amino)-5-(6-morpholin-4-ylpyridin-3-yl)thiophene-3-carboxamide | Calc'd 511, found 511 |
| 597 | 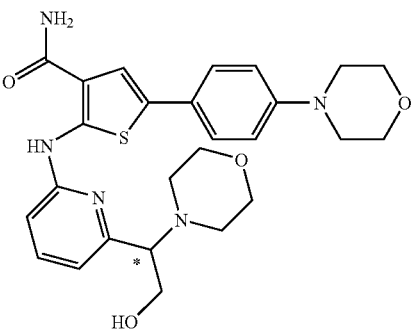<br>(Enantiomer A) | 2-({6-[(1R or S)-2-hydroxy-1-morpholin-4-ylethyl]pyridin-2-yl}amino)-5-(4-morpholin-4-ylphenyl)thiophene-3-carboxamide | Calc'd 510, found 510 |
| 598 | 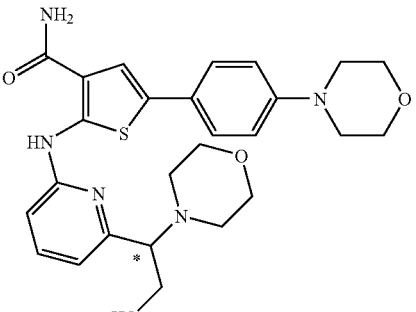<br>(Enantiomer B) | 2-({6-[(1R or S)-2-hydroxy-1-morpholin-4-ylethyl]pyridin-2-yl}amino)-5-(4-morpholin-4-ylphenyl)thiophene-3-carboxamide | Calc'd 510, found 510 |

Example 599

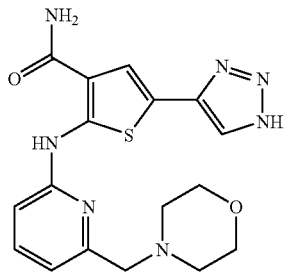 [SMILES: NC(=O)c1cc(-c2c[nH]nn2)sc1Nc1cccc(CN2CCOCC2)n1]

2-{[6-(Morpholin-4-ylmethyl)pyridin-2-yl]amino}-5-(1H-1,2,3-triazol-4-yl)thiophene-3-carboxamide

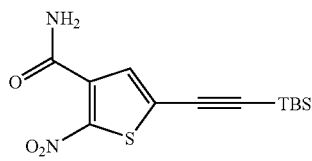

Step 1: 5-{[tert-Butyl(dimethyl)silyl]ethynyl}-2-nitrothiophene-3-carboxamide 5-Bromo-2-nitrothiophene-3-carboxamide (Intermediate 10, Step 4) (750 mg, 2.99 mmol), 2-((tert-butyldimethylsilanyl)ethynyl)boronic acid pinacol ester (954 mg, 3.58 mmol), (t-Bu$_3$P)$_2$Pd (76 mg, 0.15 mmol), and K$_3$PO$_4$ (0.742 mL, 8.96 mmol) were combined in a microwave vial and evacuated/backfilled with nitrogen. Degassed toluene (8.0 mL) was added, and the reaction was stirred at 70° C. overnight. The reaction was cooled to room temperature, diluted with EtOAc, filtered through Celite, combined with silica gel, and evaporated. Flash chromatography (dry load, 0-50% EtOAc/hexanes) afforded the title compound as an orange solid.

Calc'd for C$_{13}$H$_{19}$N$_2$O$_3$SSi [M+H]$^+$ 311. found 311.

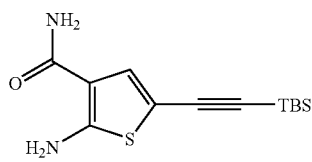

Step 2: 2-Amino-5-{[tert-butyl(dimethyl)silyl]ethynyl}thiophene-3-carboxamide To 5-{[tert-butyl(dimethyl)silyl]ethynyl}-2-nitrothiophene-3-carboxamide (100 mg, 0.32 mmol) in MeOH (8.0 mL) was added 3% Pt/C doped with 0.6% V (21 mg, 3.2 µmol). The reaction was stirred under an H$_2$ balloon at room temperature for 2 h. The solution was diluted with MeOH, filtered through Celite, combined with silica gel, and evaporated. Flash chromatography (dry load, 25-100% EtOAc/hexanes) afforded the title compound as a tan solid.

Calc'd for C$_{13}$H$_{21}$N$_2$OSSi [M+H]$^+$ 281. found 281.

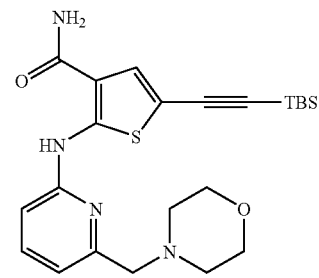

Step 3: 5-{[tert-Butyl(dimethyl)silyl]ethynyl}-2-{[6-(morpholin-4-ylmethyl)pyridin-2-yl]amino}thiophene-3-carboxamide 4-[(6-Bromopyridin-2-yl)methyl]morpholine (Example 45, Step 1) (340 mg, 1.32 mmol), 2-amino-5-{[tert-butyl(dimethyl)silyl]ethynyl}thiophene-3-carboxamide (445 mg, 1.59 mmol), Pd$_2$dba$_3$ (121 mg, 0.13 mmol), X-Phos (315 mg, 0.66 mmol), and K$_2$CO$_3$ (201 mg, 1.46 mmol) were combined in a vial, sealed, and evacuated/backfilled with nitrogen. Degassed t-amyl alcohol (3.3 ml), and the reaction was vigorously stirred at 100° C. overnight. The reaction mixture was then diluted with MeOH, combined with silica, and evaporated. Flash chromatography (dry load, 0-10% MeOH/EtOAc) afforded the title compound as a yellow solid.

Calc'd for C$_{23}$H$_{33}$N$_4$O$_2$SSi [M+H]$^+$ 457. found 457.

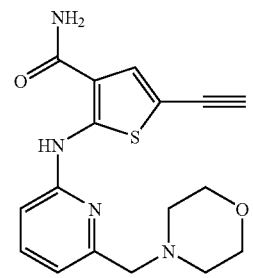 [SMILES: C#Cc1cc(C(N)=O)c(Nc2cccc(CN3CCOCC3)n2)s1]

Step 4: 5-Ethynyl-2-{[6-(morpholin-4-ylmethyl)pyridin-2-yl]amino}thiophene-3-carboxamide To a solution of 5-{[tert-butyl(dimethyl)silyl]ethynyl}-2-{[6-(morpholin-4-ylmethyl)pyridin-2-yl]amino}thiophene-3-carboxamide (435 mg, 0.95 mmol) in THF (15 mL) was added TBAF (1.0 M in THF, 2.38 mL, 2.38 mmol), and the reaction was stirred at room temperature for 6 h. The solution was diluted with water and extracted with EtOAc (2×). The organic extracts were dried over magnesium sulfate, filtered, combined with silica gel and evaporated. Flash chromatography (dry load, 0-10% MeOH/EtOAc) provided the title compound as a gray solid.

Calc'd for C$_{17}$H$_{19}$N$_4$O$_2$S [M+H]$^+$ 343. found 343.

589

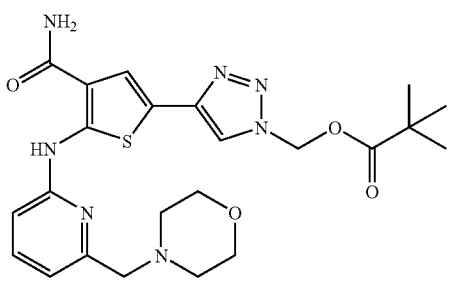 [SMILES: CC(C)(C)C(=O)OCn1cc(-c2cc(C(N)=O)c(Nc3cccc(CN4CCOCC4)n3)s2)nn1]

Step 5: [4-(4-(Aminocarbonyl)-5-{[6-(morpholin-4-ylmethyl)pyridin-2-yl]amino}-2-thienyl)-1H-1,2,3-triazol-1-yl]methyl pivalate 5-Ethynyl-2-{[6-(morpholin-4-ylmethyl)pyridin-2-yl]amino}thiophene-3-carboxamide (86 mg, 0.25 mmol) and azidomethyl pivalate (59 mg, 0.38 mmol) were combined in DMF (1.0 mL). CuSO$_4$.5H$_2$O (6.3 mg, 0.025 mmol) in water (0.2 mL) and sodium ascorbate (20 mg, 0.10 mmol) in water (0.2 mL) were added, and the reaction mixture was stirred at room temperature overnight. The reaction was concentrated to dryness, combined with MeOH and silica gel, and evaporated. Flash chromatography (dry load, 0-10% MeOH/EtOAc) afforded the title compound as a yellow solid.

Calc'd for C$_{23}$H$_{30}$N$_7$O$_4$S [M+H]$^+$ 500. found 500.

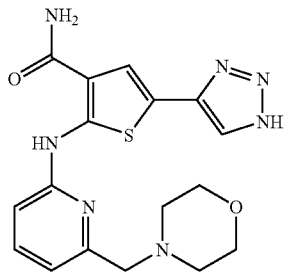 [SMILES: NC(=O)c1cc(-c2c[nH]nn2)sc1Nc1cccc(CN2CCOCC2)n1]

Step 6: 2-{[6-(Morpholin-4-ylmethyl)pyridin-2-yl]amino}-5-(1H-1,2,3-triazol-4-yl)thiophene-3-carboxamide To a suspension of [4-(4-(aminocarbonyl)-5-{[6-(morpholin-4-ylmethyl)pyridin-2-yl]amino}-2-thienyl)-1H-1,2,3-triazol-1-yl]methyl pivalate (70 mg, 0.14 mmol) in MeOH (1.5 mL) and water (1.0 mL) was added NaOH (1.0 M, 0.310 ml, 0.31 mmol). The mixture was stirred at room temperature for 45 min (the suspension became a clear orange solution). The reaction was neutralized with 2 N HCl (0.150 ml), diluted with water, and extracted with 5:1 CH$_2$Cl$_2$:MeOH (3×). The combined organic extracts were dried (MgSO$_4$), filtered, combined with silica gel, and evaporated to dryness. Flash chromatography (dry load, 0-10% MeOH/CH$_2$Cl$_2$) yielded the title compound as a colorless solid.

Calc'd for C$_{17}$H$_{20}$N$_7$O$_2$S [M+H]$^+$ 386. found 386.

Example 600

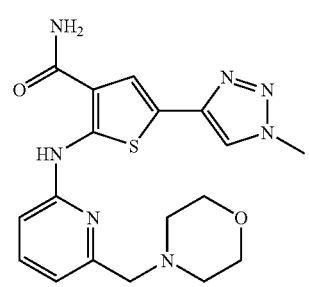 [SMILES: Cn1cc(-c2cc(C(N)=O)c(Nc3cccc(CN4CCOCC4)n3)s2)nn1]

5-(1-Methyl-1H-1,2,3-triazol-4-yl)-2-{[6-(morpholin-4-ylmethyl)pyridin-2-yl]amino}thiophene-3-carboxamide

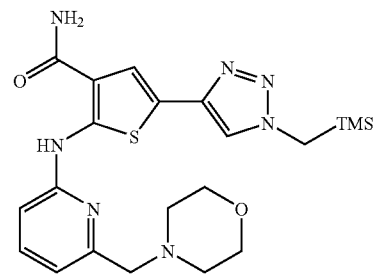 [SMILES: C[Si](C)(C)Cn1cc(-c2cc(C(N)=O)c(Nc3cccc(CN4CCOCC4)n3)s2)nn1]

Step 1: 2-{[6-(Morpholin-4-ylmethyl)pyridin-2-yl]amino}-5-{1-[(trimethylsilyl)methyl]-1H-1,2,3-triazol-4-yl}thiophene-3-carboxamide 5-Ethynyl-2-{[6-(morpholin-4-ylmethyl)pyridin-2-yl]amino}thiophene-3-carboxamide (Example 599, Step 4) (75 mg, 0.22 mmol) and trimethylsilylmethyl azide (0.65 ml, 0.44 mmol) were combined in DMF (1.0 mL). CuSO$_4$.5H$_2$O (5.5 mg, 0.022 mmol) in water (0.2 mL) and sodium ascorbate (17 mg, 0.088 mmol) in water (0.2 ml) were added, and the reaction mixture was stirred at room temperature overnight. The reaction was evaporated to dryness, combined with MeOH and silica gel, and evaporated. Flash chromatography (dry load, 0-10% MeOH/EtOAc) afforded the title compound a yellow solid.

Calc'd for C$_{21}$H$_{30}$N$_7$O$_2$SSi [M+H]$^+$ 472. found 472.

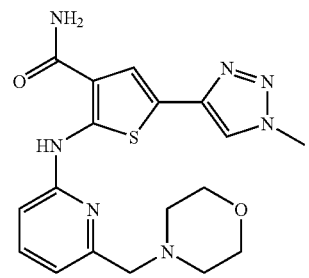 [SMILES: Cn1cc(-c2cc(C(N)=O)c(Nc3cccc(CN4CCOCC4)n3)s2)nn1]

Step 2: 5-(1-Methyl-1H-1,2,3-triazol-4-yl)-2-{[6-(morpholin-4-ylmethyl)pyridin-2-yl]amino}thiophene-3-carboxamide To a solution of 2-{[6-(morpholin-4-ylmethyl)pyridin-2-yl]amino}-5-{1-[(trimethylsilyl)methyl]-1H-1,2,3-triazol-4-yl}thiophene-3-carboxamide (65 mg, 0.14 mmol) in THF (2.0 mL) was added TBAF (1.0 M in THF, 0.276 ml, 0.276 mmol). The reaction was stirred at room temperature for 4 h. The solution was diluted with water and extracted with 5:1 $CH_2Cl_2$:MeOH (3×). The combined organic layers were dried ($MgSO_4$), filtered, and evaporated. The crude solid was triturated with $CH_2Cl_2$ and filtered to isolate the title compound as a colorless solid.

Calc'd for $C_{18}H_{22}N_7O_2S$ [M+H]$^+$ 400. found 400.

Additional examples were prepared by procedures similar to those described above and are illustrated in the following table.

TABLE 61

| Example # | Structure | Name | Characterization [M + H]$^+$ |
|---|---|---|---|
| 601 | 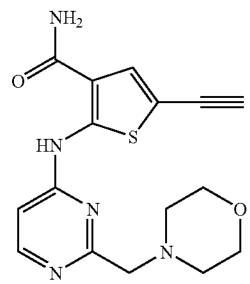 [SMILES: C#Cc1cc(C(N)=O)c(Nc2ccnc(CN3CCOCC3)n2)s1] | 5-ethynyl-2-{[2-(morpholin-4-ylmethyl)pyrimidin-4-yl]amino}thiophene-3-carboxamide | Calc'd 344, found 344 |
| 602 | 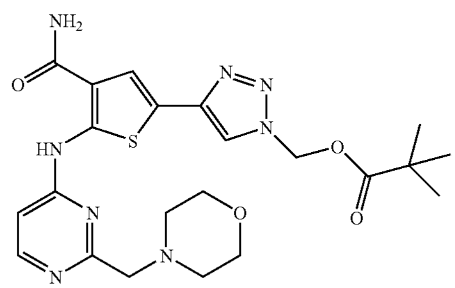 [SMILES: CC(C)(C)C(=O)OCn1cc(-c2cc(C(N)=O)c(Nc3ccnc(CN4CCOCC4)n3)s2)nn1] | [4-(4-(aminocarbonyl)-5-{[2-(morpholin-4-ylmethyl)pyrimidin-4-yl]amino}-2-thienyl)-1H-1,2,3-triazol-1-yl]methyl pivalate | Calc'd 501, found 501 |
| 603 | 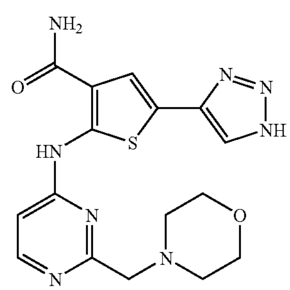 [SMILES: NC(=O)c1cc(-c2c[nH]nn2)sc1Nc1ccnc(CN2CCOCC2)n1] | 2-{[2-(morpholin-4-ylmethyl)pyrimidin-4-yl]amino}-5-(1H-1,2,3-triazol-4-yl)thiophene-3-carboxamide | Calc'd 387, found 387 |
| 604 | 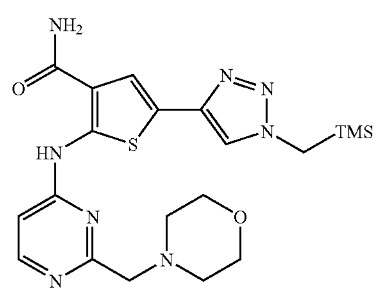 [SMILES: C[Si](C)(C)Cn1cc(-c2cc(C(N)=O)c(Nc3ccnc(CN4CCOCC4)n3)s2)nn1] | 2-{[2-(morpholin-4-ylmethyl)pyrimidin-4-yl]amino}-5-{1-[(trimethylsilyl)methyl]-1H-1,2,3-triazol-4-yl}thiophene-3-carboxamide | Calc'd 473, found 473 |

TABLE 61-continued

| Example # | Structure | Name | Characterization [M + H]+ |
|---|---|---|---|
| 605 | 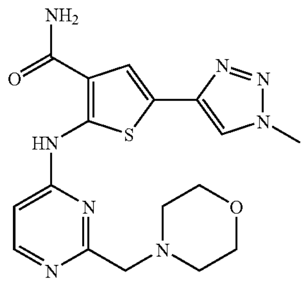 [SMILES: Cn1cc(-c2cc(C(N)=O)c(Nc3ccnc(CN4CCOCC4)n3)s2)nn1] | 5-(1-methyl-1H-1,2,3-triazol-4-yl)-2-{[2-(morpholin-4-ylmethyl)pyrimidin-4-yl]amino}thiophene-3-carboxamide | Calc'd 401, found 401 |

Example 606

2-{[2-(Morpholin-4-ylmethyl)pyrimidin-4-yl]amino}-5-(1H-1,2,4-triazol-3-yl)thiophene-3-carboxamide

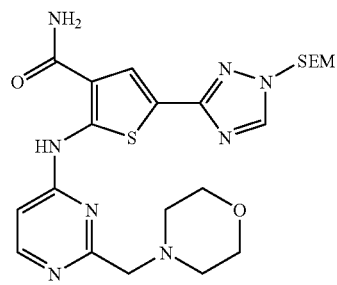 [SMILES: C[Si](C)(C)CCOCn1cnc(-c2cc(C(N)=O)c(Nc3ccnc(CN4CCOCC4)n3)s2)n1]

Step 1: 2-{[2-(Morpholin-4-ylmethyl)pyrimidin-4-yl]amino}-5-(1-{[2-(trimethylsilyl)ethoxy]methyl}-1H-1,2,4-triazol-3-yl)thiophene-3-carboxamide 4-[(4-Chloropyrimidin-2-yl)methyl]morpholine (Example 529 Step 1) (85 mg, 0.40 mmol), 2-amino-5-(1-{[2-(trimethylsilyl)ethoxy]methyl}-1H-1,2,4-triazol-3-yl)thiophene-3-carboxamide (Intermediate 40) (142 mg, 0.42 mmol), Pd$_2$dba$_3$ (36 mg, 0.040 mmol), X-Phos (95 mg, 0.20 mmol), and K$_2$CO$_3$ (61 mg, 0.44 mmol) were combined in a vial, sealed, and evacuated/backfilled with nitrogen. Degassed t-amyl alcohol (1.0 mL) was added, and the reaction was vigorously stirred at 100° C. overnight. The reaction mixture was then diluted with MeOH, combined with silica, and evaporated. Flash chromatography (dry load, 0-15% MeOH/EtOAc) afforded the title compound as an orange solid.

Calc'd for C$_{22}$H$_{33}$N$_8$O$_3$SSi [M+H]$^+$ 517. found 517.

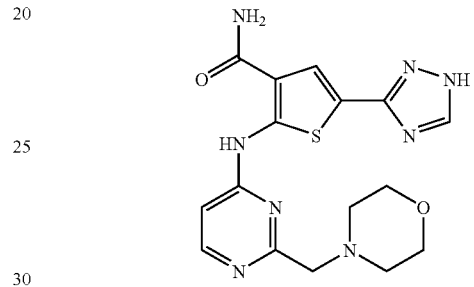

Step 2: 2-{[2-(Morpholin-4-ylmethyl)pyrimidin-4-yl]amino}-5-(1H-1,2,4-triazol-3-yl)thiophene-3-carboxamide 2-{[2-(Morpholin-4-ylmethyl)pyrimidin-4-yl]amino}-5-(1-{[2-(trimethylsilyl)ethoxy]methyl}-1H-1,2,4-triazol-3-yl)thiophene-3-carboxamide (100 mg, 0.19 mmol) was taken up in a mixture of EtOH (3.0 mL) and HCl (2.0 M, 3.00 mL, 6.00 mmol) and heated to 60° C. overnight. The reaction was not complete, so the temperature was raised to 75° C. for 6 h. The resulting suspension was filtered to isolate the title compound as a pale yellow solid (HCl salt).

Calc'd for C$_{16}$H$_{19}$N$_8$O$_2$S [M+H]$^+$ 387. found 387.

Example 607

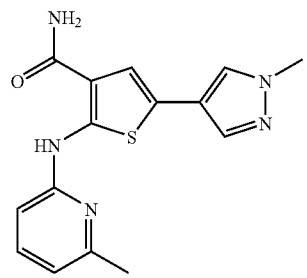 [SMILES: Cc1cccc(Nc2sc(-c3cnn(C)c3)cc2C(N)=O)n1]

5-(1-Methyl-1H-pyrazol-4-yl)-2-[(6-methylpyridin-2-yl)amino]thiophene-3-carboxamide

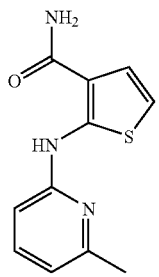 [SMILES: Cc1cccc(Nc2sccc2C(N)=O)n1]

Step 1: 2-[(6-Methylpyridin-2-yl)amino]thiophene-3-carboxamide

A suspension of 2-aminothiophene-3-carboxamide (6.26 g, 44.0 mmol), potassium carbonate (6.08 g, 44.0 mmol), 2-dicyclohexylphosphino-2',4',6'-triisopropyl-1,1-biphenyl (0.667 g, 1.40 mmol), dibenyzlideneacetone bis(triphenylphosphine) (0.293 g, 0.32 mmol), and 2-bromo-6-methylpyridine (4.55 mL, 40 mmol) in tert-amyl alcohol (80 mL) in a 250 mL round bottom flask with attached reflux condenser was placed under an argon atmosphere by performing six vacuum/argon flush cycles. The reaction was heated to reflux for 18 hours. The flask was charged with more 2-dicylohexylphosphino-2',4',6'-triisopropyl-1,1-biphenyl (0.330 g, 0.7 mmol) and dibenyzlideneacetone bis(triphenylphosphine) (0.146 g, 0.160 mmol) and refluxed for an additional 24 hours. The reaction mixture was diluted with ethyl acetate (200 mL) and saturated aqueous sodium bicarbonate, and this suspension was filtered. The layers of the filtrate were separated and the organic layer was washed with brine (100 mL), dried over sodium sulfate, filtered, and concentrated. The resulting solid was triturated with a 1:1 mixture of ethyl acetate and hexanes to afford the title compound as a grey solid.

Calc'd for $C_{11}H_{12}N_3OS$ [M+H]$^+$: 234. Found: 234.

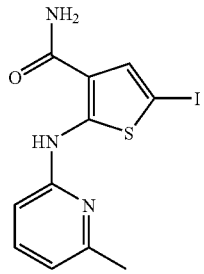 [SMILES: Cc1cccc(Nc2sc(I)cc2C(N)=O)n1]

Step 2. 5-Iodo-2-[(6-methylpyridin-2-yl)amino]thiophene-3-carboxamide

To a solution of 2-[(6-methylpyridin-2-yl)amino]thiophene-3-carboxamide (2.8 g, 12.0 mmol) in dimethylformamide (40 mL) and dichloromethane (80 mL) was added slowly N-iodosuccinimide (1.060 g, 4.71 mmol). After twenty minutes, the reaction mixture was diluted with ethyl acetate (400 mL), hexanes (40 mL), and saturated aqueous sodium bicarbonate (100 mL) and filtered through a Buchner funnel. The layers of the filtrate were separated, and the organic layer was washed with water (3×100 mL, filtering before separated layers as above) and a 5:1 mixture of brine:saturated aqueous sodium thiosulfate (120 mL). The resulting organic layer was dried over sodium sulfate, filtered through a pad of Celite, and concentrated. The resulting solid was triturated with a mixture of dichloromethane, ethyl acetate, methanol, and dichloromethane to afford the title compound as a purple powder.

Calc'd for $C_{11}H_{11}IN_3OS$ [M+H]$^+$: 360. Found: 360.

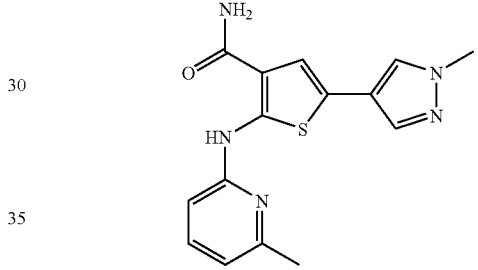

Step 3. 5-(1-Methyl-1H-pyrazol-4-yl)-2-[(6-methylpyridin-2-yl)amino]thiophene-3-carboxamide A suspension of 5-iodo-2-[(6-methylpyridin-2-yl)amino]thiophene-3-carboxamide (300 mg, 0.84 mmol), 1-methyl-4-(4,4,5,5-tetramethyl-1,3,2-dioxaborolan-2-yl)-1H-pyrazole (619 mg, 2.97 mmol), dichlorobis(triphenylphosphine)palladium (29.3 mg, 0.04 mmol), and sodium carbonate (7.5 mL, 15.0 mmol) in 1,2-dimethoxyethane (7.5 mL) sealed in a 20 mL microwave reaction vessel was purged of oxygen by doing 5 vacuum/argon flush cycles. The reaction solution was heated in a microwave for five minutes at 100° C., and then partitioned between ethyl acetate (50 mL) and water (30 mL). The layers were separated, and the aqueous layer was extracted with ethyl acetate (50 mL). The combined organic layers were dried over sodium sulfate, filtered, and concentrated. Purification by silica gel chromatography (12-100% ethyl acetate/hexanes) yielded the title compound.

Calc'd for $C_{15}H_{16}N_5OS$ [M+H]$^+$: 314. Found: 314.

Additional examples were prepared using procedures similar to those described in the above examples and are illustrated in the following table.

TABLE 62

| Example # | Structure | Compound Name | Characterization [M + H]+: |
|---|---|---|---|
| 608 | 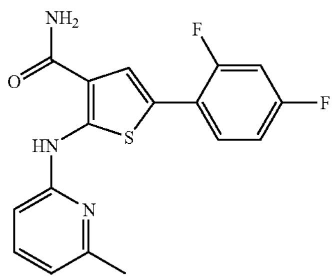 [SMILES: Cc1cccc(Nc2sc(-c3ccc(F)cc3F)cc2C(N)=O)n1] | 5-(2,4-difluorophenyl)-2-[(6-methylpyridin-2-yl)amino]thiophene-3-carboxamide | Calc'd: 346, Found: 346 |
| 609 | 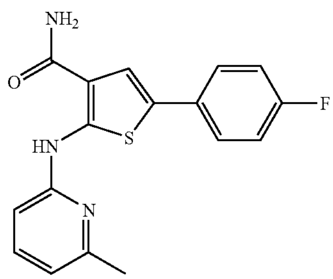 [SMILES: Cc1cccc(Nc2sc(-c3ccc(F)cc3)cc2C(N)=O)n1] | 5-(4-fluorophenyl)-2-[(6-methylpyridin-2-yl)amino]thiophene-3-carboxamide | Calc'd: 328, Found: 328 |
| 610 | 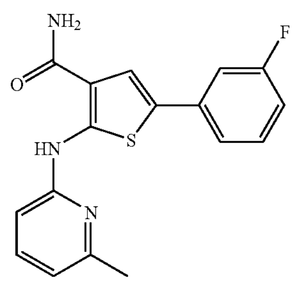 [SMILES: Cc1cccc(Nc2sc(-c3cccc(F)c3)cc2C(N)=O)n1] | 5-(3-fluorophenyl)-2-[(6-methylpyridin-2-yl)amino]thiophene-3-carboxamide | Calc'd: 328, Found: 328 |
| 611 | 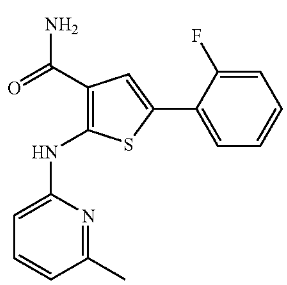 [SMILES: Cc1cccc(Nc2sc(-c3ccccc3F)cc2C(N)=O)n1] | 5-(2-fluorophenyl)-2-[(6-methylpyridin-2-yl)amino]thiophene-3-carboxamide | Calc'd: 328, Found: 328 |
| 612 | 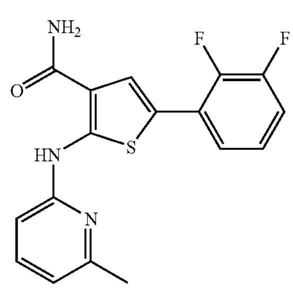 [SMILES: Cc1cccc(Nc2sc(-c3cccc(F)c3F)cc2C(N)=O)n1] | 5-(2,3-difluorophenyl)-2-[(6-methylpyridin-2-yl)amino]thiophene-3-carboxamide | Calc'd: 346, Found: 346 |

TABLE 62-continued

| Example # | Compound Name | Characterization [M + H]+: |
|---|---|---|
| 613 | 5-(2-chlorophenyl)-2-[(6-methylpyridin-2-yl)amino]thiophene-3-carboxamide | Calc'd: 344, Found: 344 |
| 614 | 5-(2,5-dichlorophenyl)-2-[(6-methylpyridin-2-yl)amino]thiophene-3-carboxamide | Calc'd: 378, Found: 378 |
| 615 | 5-[2-chloro-5-(trifluoromethyl)phenyl]-2-[(6-methylpyridin-2-yl)amino]thiophene-3-carboxamide | Calc'd: 412, Found: 412 |
| 616 | 5-(3-chlorophenyl)-2-[(6-methylpyridin-2-yl)amino}thiophene-3-carboxamide | Calc'd: 344, Found: 344 |
| 617 | 2-[(6-methylpyridin-2-yl)amino]-5-[3-(trifluoromethyl)phenyl]thiophene-3-carboxamide | Calc'd: 378, Found: 378 |

TABLE 62-continued

| Example # | Structure | Compound Name | Characterization [M + H]+: |
|---|---|---|---|
| 618 | 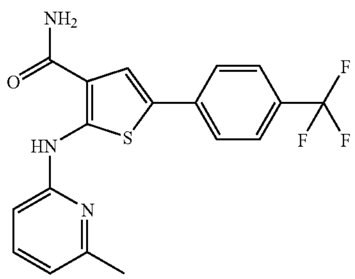 [SMILES: Cc1cccc(Nc2sc(-c3ccc(C(F)(F)F)cc3)cc2C(N)=O)n1] | 2-[(6-methylpyridin-2-yl)amino]-5-[4-(trifluoromethyl)phenyl]thiophene-3-carboxamide | Calc'd: 378, Found: 378 |
| 619 | 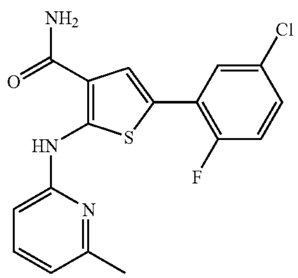 [SMILES: Cc1cccc(Nc2sc(-c3cc(Cl)ccc3F)cc2C(N)=O)n1] | 5-(5-chloro-2-fluorophenyl)-2-[(6-methylpyridin-2-yl)amino]thiophene-3-carboxamide | Calc'd: 362, Found: 362 |
| 620 | 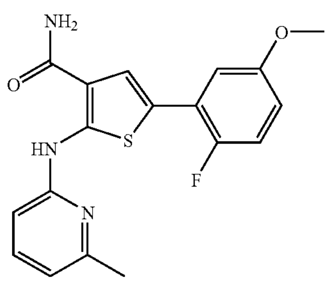 [SMILES: COc1ccc(F)c(-c2cc(C(N)=O)c(Nc3cccc(C)n3)s2)c1] | 5-(2-fluoro-5-methoxyphenyl)-2-[(6-methylpyridin-2-yl)amino]thiophene-3-carboxamide | Calc'd: 358, Found: 358 |
| 621 | 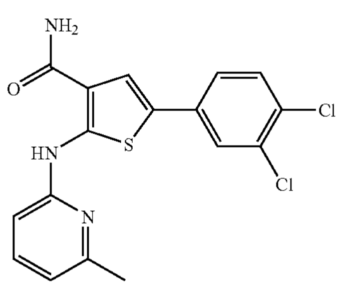 [SMILES: Cc1cccc(Nc2sc(-c3ccc(Cl)c(Cl)c3)cc2C(N)=O)n1] | 5-(3,4-dichlorophenyl)-2-[(6-methylpyridin-2-yl)amino]thiophene-3-carboxamide | Calc'd: 378, Found: 378 |
| 622 | 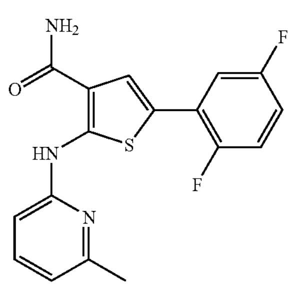 [SMILES: Cc1cccc(Nc2sc(-c3cc(F)ccc3F)cc2C(N)=O)n1] | 5-(2,5-difluorophenyl)-2-[(6-methylpyridin-2-yl)amino]thiophene-3-carboxamide | Calc'd: 346, Found: 346 |

TABLE 62-continued

| Example # | Structure | Compound Name | Characterization [M + H]+: |
|---|---|---|---|
| 623 | 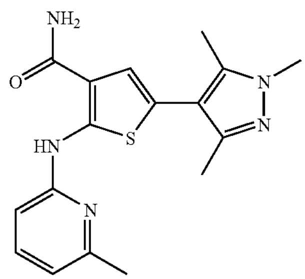 [SMILES: Cc1cccc(Nc2sc(-c3c(C)nn(C)c3C)cc2C(N)=O)n1] | 2-[(6-methylpyridin-2-yl)amino]-5-(1,3,5-trimethyl-1H-pyrazol-4-yl)thiophene-3-carboxamide | Calc'd: 342, Found: 342 |
| 624 | 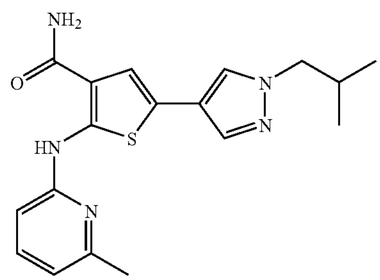 [SMILES: Cc1cccc(Nc2sc(-c3cnn(CC(C)C)c3)cc2C(N)=O)n1] | 5-(1-isobutyl-1H-pyrazol-4-yl)-2-[(6-methylpyridin-2-yl)amino]thiophene-3-carboxamide | Calc'd: 356, Found: 356 |

Pharmaceutical Composition

As a specific embodiment of this invention, 100 mg of 5-[2,6-Difluoro-4-(1-hydroxy-1-methylethyl)phenyl]-2-({6-[(2-hydroxy-2-methylpropoxy)methyl]pyridin-2-yl}amino)thiophene-3-carboxamide is formulated with sufficient finely divided lactose to provide a total amount of 580 to 590 mg to fill a size 0, hard-gelatin capsule.

Biological Assays

JAK1 Enzyme Assay

For the JAK1 enzyme assay, reactions (50 uL) contained 5×IVGN buffer (50 mM Hepes, pH 7.5, 10 mM MgCl$_2$, 0.01% Brij-35, 1 mM EGTA, 0.1 mg/ml BSA), 2 mM DTT, 2.0 µM peptide substrate, 25 µM MgATP, 400 pM JAK1 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDYFEWLE-NH2 (SEQ. ID NO.: 1); in DMSO.

JAK2 Kinase Activity Inhibition Assay and Determination of IC$_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:

1. prepare 3-fold serial diluted compound/inhibitor solutions in 100% (DMSO) at 20× of the final desired concentrations in a 96 well plate;
2. prepare a master reaction mix containing 6.67 mM MgCl$_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-CONH$_2$) (SEQ. ID NO.: 1);
3. in a black assay plate, add 2.5 µl compound/inhibitor (or DMSO) and 37.5 µl master reaction mix per well; initiate the kinase reaction by adding 10 µl of 75 µM MgATP per well, allow the reactions to proceed for 80 minutes at room temperate; (the final conditions for the reactions are: 50 nM JAK2 JH1 domain (Upstate), 2.0 µM substrate, 15 µM MgATP, 5 mM MgCl$_2$, 100 mM NaCl, 2 mM DTT, 0.1 mg/ml BSA, 50 mM Tris (pH 7.4) and 5% DMSO);
4. stop the kinase reaction with 50 µl of Stop/Detection buffer containing 10 mM EDTA, 25 mM HEPES, 0.1% TRITON X-100, 0.126 µg/ml Eu-chelate labeled anti-phosphotyrosine antibody PY20 (cat. # AD0067, PerkinElmer) and 45 µg/ml Streptavidin-allophycocyanin conjugate (cat. # PJ25S, Prozyme); and
5. read HTRF signals on a Victor reader (PerkinElmer) in HTRF mode after 60 minutes.

IC$_{50}$ was obtained by fitting the observed relationship between compound/inhibitor concentration and HTRF signal with a 4-parameter logistic equation.

Compounds of the instant invention described in Examples 1-624 are potent inhibitors of recombinant purified JAK2 kinase activity with an IC$_{50}$ of approximately 0.1 nM-30 µM. Compounds of the instant invention described in Examples 217-234 are potent inhibitors of recombinant purified JAK2 kinase activity with an IC$_{50}$ of approximately 6 nM-0.43 µM. Compounds of the instant invention described in Examples 372-391 are potent inhibitors of recombinant purified JAK2 kinase activity with an IC$_{50}$ of approximately 3 nM-37 nM.

JAK3 Enzyme Assay

For the JAK3 enzyme assay, reactions (50 uL) contained 5×IVGN buffer (50 mM Hepes, pH 7.5, 10 mM MgCl$_2$, 0.01% Brij-35, 1 mM EGTA, 0.1 mg/ml BSA), 2 mM DTT, 2.0 µM peptide substrate, 25 µM MgATP, 400 pM JAK3 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDY-FEWLE-NH2 (SEQ. ID NO.: 1); in DMSO.

TYK2 Enzyme Assay

For the TYK2 enzyme assay, reactions (50 uL) contained 5×IVGN buffer (50 mM Hepes, pH 7.5, 10 mM $MgCl_2$, 0.01% Brij-35, 1 mM EGTA, 0.1 mg/ml BSA), 2 mM DTT, 2.0 µM peptide substrate, 15 µM MgATP, 125 pM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103) Peptide substrate is amino hexanoyl biotin-EQEDEPEGDY-FEWLE-NH2 (SEQ. ID NO.: 1); in DMSO.

Assay For JAK Family Protein Kinase Activity

Materials: Streptavidin•allophycocyanin conjugate (SA•APC) and Europium•cryptate (Eu•K) were from Packard Instrument Company. Eu•K conjugated pY20 was produced as described in Cummings, R. T.; McGovern, H. M.; Zheng, S.; Park, Y. W. and Hermes, J. D. Use Of A Phosphotyrosine-Antibody Pair As A General Detection Method In Homogeneous Time Resolved Fluorescence-Application To Human Immunodeficiency Viral Protease. *Analytical Biochemistry* 1999, 33, 79-93. Homogenous time resolved fluorescence (HTRF) measurements were made using the Discovery instrument from Packard. T-stim Culture Supplement was from Collaborative Biomedical Research. Recombinant mouse IL2 was from Pharmingen or R & D.

JAK family kinase expression: JAK3, TYK2 and JAK2 kinase domains with N-terminal "Flag" affinity tags were expressed in Sf9 cells using standard baculovirus methods. The human JAK3 gene and the human TYK2 gene can be purchased from Update (now part of Millpore Corporation). Human JAK2 kinase domain was cloned from a MOLT4 cDNA library (Clonetech).

Assay for JAK family protein kinase activity: Tyrosine kinase activity was measured by detection of the tyrosine phosphorylated peptide amino hexanoyl biotin-EQEDEPEGDY-FEWLE-$NH_2$ (SEQ. ID NO.: 1); (S, hereafter) detected by time-resolved fluorescence using a europium labeled antibody to phosphotyrosine (pY20). The JAK3(JH1) catalyzed phosphorylation reactions were carried out in a 30 uL total reaction volume. The compound was run at 5% DMSO and preincubated with enzyme buffer (EB). The EB comprised Invitrogen 5× kinase buffer (50 mM Hepes, pH 7.5, 10 mM $MgCl_2$, 0.01% Brij-35, 1 mM EGTA, 0.1 mg/ml BSA), 2 mM (final) DTT, 2 µM (final) S, and 250 pM (final) JAK3 enzyme. The assay was run at ATP $K_m$ (5 µM final) for 40 to 80 minutes. Reactions were run at ambient temperature and quenched with an equal volume of quench buffer (QB) (10 mM EDTA, 25 mM HEPES, 0.1% TRITON X-100) containing 50 µg/mL SA•APC conjugate and 0.75 nM Eu•K conjugated pY20. This mixture was incubated at ambient temperature for at least 60 minutes and read on an optimized fluorescent reader at Ex=320 nm and $Em_1$=665 nm (SA-APC) and $Em_2$=615 nM (Eu). The data was analyzed by using a standard 4P fit on the ratio of the Em results: ($Em_1$÷$Em_2$)*10,000.

JAK2 384-Well HEL irf1-bla AlphaScreen™ SureFire™ p-STAT5 Assay:

Principle: When JAK2 is activated and dimerized, it phosphorylates STAT5 which translocates to the nucleus and actives the transcription of target genes. AlphaScreen™ SureFire™ p-STAT5 assay (Perkin Elmer and TGR Biosciences) uses both biotinylated anti-phospho-STAT5 antibody, which is captured by Streptavidin-coated Donor beads, and anti-total STAT5 antibody, which is captured by Protein A conjugated Acceptor beads. The irf1-bla HEL CellSensor™ cell line was created by transducing parental HEL 92.1.7 cells (ATCC) with the pLenti-bsd/irf1-bla CellSensor™ vector. When both antibodies bind to phospho-STAT5 proteins released from HEL irf1-bla cells, the Donor and Acceptor beads are brought into the close proximity (<=200 nm) and a cascade of chemical reactions is initiated to produce a greatly amplified signal. Upon laser excitation, a photosensitizer in the donor bead converts ambient oxygen to a more excited singlet state. The singlet state oxygen molecules diffuse across to react with a chemiluminescer in the acceptor bead that further activates fluorophores contained within the same bead. The fluorophores subsequently emit light at 520-620 nm. The emitted light intensity is directly proportional to the amount of phospho-STAT5 proteins released from HEL irf1-bla cells.

Growth Medium: RPMI Medium 1640 (Invitrogen) with 10% dialyzed FBS (Invitrogen), 1 µg/ml blasticidin, 0.1 mM NEAA, 1 mM sodium pyruvate and 1% Pen-Strep.

Method: On day 1, split HEL irf1-bla cells at density of 500,000 cells/ml. Incubate cells in a tissue culture flask at 37° C., 5% $CO_2$ overnight. On day 2, harvest cells and wash the once with HBSS (Invitrogen) containing 0.5% dialyzed FBS. Next, seed cells at a density of 100,000 cells/well in 8 ul of HBSS w/0.5% dialyzed FBS in 384-well microtiter plates. Temporarily put these cell plates in a 37° C., 5% $CO_2$ incubator. To prepare a compound plate, prepare serially diluted compounds in DMSO at a 500× stock concentration. Transfer 2 uL of the serially diluted compounds from the compound plate to an intermediate dilution plate containing 198 uL of HBSS w/0.5% dialyzed FBS. Next, transfer 2 uL of intermediately diluted compounds to each well of the cell plate to get 1:500 final dilution of each test compound and controls. Incubate the cell plates at 37° C., 5% $CO_2$ for 1 hr. Add 2.5 ul/well of 5× lysis buffer from the kit to cell plates. Gently agitate the plates for 5-10 min.

Make detection reagent mixture A by adding together 800 uL reaction buffer, 20 uL acceptor beads, and 200 uL activation buffer. Add 15 uL/well of detection mixture A to the cell plates and gently agitate the plates for 1-2 mM. Seal the plates with an adhesive cover and incubate at room temperature for 2 hr, avoiding exposure to light. Make detection mixture B by adding together 400 uL dilution buffer and 20 uL donor beads. Add 6 uL/well of mixture B to the cell plates and gently agitate the plates for 1-2 min. Seal the plates with an adhesive cover and incubate at room temperature for 2 hr, avoiding exposure to light. Read the plates on an AlphaScreen-capable plate reader.

Compounds of the instant invention described in Examples 1-624 are potent inhibitors of pSTAT5 in the HEL irf1-bla AlphaScreen™ SureFire™ p-STAT5 Assay activity with an inflexion point (IP) of <20 µM.

Cellular proliferation assays: CTLL-2 cells (ATCC) were maintained in 6% T-stim Culture Supplement (source of IL2) in RPMI-1640 supplemented with 10% fetal bovine serum, 1 mM sodium pyruvate, 50 µM β-mercaptoethanol, 1.4 mM L-glutamine, 10 mM HEPES, 1 mg/ml dextrose, 0.04 mM essential amino acids, 0.02 mM nonessential amino acids, penicillin and streptomycin (H10). The day before use in the proliferation assay, cells were washed and resuspended in 0.2% Tstim at a cell concentration of 5×10$^5$/ml. The next day, cells were washed and plated at 0.2-1×10$^5$ cells/well in a 96 well tissue culture plate (CoStar). 0.05 ng/ml mouse recombinant IL2 (Pharmingen), with or without a test compound, or 20 ng/ml PMA (Sigma) and 1 µCi/well [$^3$H]-thymidine were added. After overnight culture, cells were harvested with a glass fiber Filtermat (Wallac) and a Tomtek cell harvester. Tritium incorporation was measured by liquid scintillation counting on a Topcount scintillation counter (Packard).

Compounds of the instant invention described in Examples 1-624 are potent inhibitors of recombinant purified JAK3 kinase activity with an IC$_{50}$ of approximately 0.8 nM->3 µM.

In Vitro PDK1 Kinase Assay

Activated recombinant full-length mT(Glu-Glu-Phe) tagged human PDK1 is used to determine whether the compounds of the instant invention modulate the enzymatic activity of this kinase.

The cDNA, encoding full-length PDK1, is subcloned into a baculovirus expression vector pBlueBac4.5 (Invitrogen), containing an in frame middle T tag (MEYMPME) at its N-terminus. Soluble activated recombinant full-length mT(Glu-Glu-Phe) tagged human PDK1 is expressed in a baculovirus-infected Sf9 insect cells (Kemp Biotechnologies), according to the protocol recommended by the manufacturer. Immunoaffinity purification of the PDK1 kinase from the insect cell lysate is performed using a middle Tag antibody bound to Protein G-EE column. Upon elution using 50 mM Tris pH 7.4, 1 mM EDTA, 1 mM EGTA, 0.5 mM Na$_3$VO$_4$, 1 mM DTT, 50 mM NaF, Na Pyrophosphate, Na-β-glycerophosphate, 10% glycerol, Complete, 1 µM microcystein, and 50 µg/ml EYMPME peptide, fractions containing PDK1 protein are pooled together, based on SDS-PAGE and western blot analyses, and then analyzed for protein concentration using BCA Protein Assay (Pierce) with BSA as standard. The final product was aliquoted and flash frozen in liquid nitrogen before being stored at −80° C. Resulting PDK1 protein has MW of 64 kDa, is phosphorylated 'by default' and purifies as an activated kinase from insect cells.

The procedure for determining the potency of a compound to inhibit PDK1 kinase comprises the following steps:

1. Prepare 3-fold serial diluted compound solutions in 100% dimethyl sulfoxide (DMSO) at 20× of the desired final concentrations in a 384-well plate.
2. Prepare a master reaction mix containing 62.5 mM HEPES (pH 7.5), 12.5 mM MgCl2, 0.013% Brij-35, 1.25 mM EGTA, 2.5 mM dithiothreitol, 1.25 nM recombinant PDK1 and 375 nM biotinylated synthetic peptide substrate (Biotin-GGDGATMKTFCGGTPSDGDP-DGGEFTEF-COOH) (SEQ. ID NO.: 2).
3. In a black assay plate, add 2.5 µl of compound solution (or DMSO) and 22.5 µl of master reaction mix per well. Pre-incubate for 10 min. Initiate the kinase reaction by adding 6 µl of 0.25 mM MgATP per well. Allow the reactions to proceed for 25 mM at room temperature. The final conditions for the reaction are 1 nM PDK1, 300 nM peptide substrate, 5 µM MgATP, 10 mM MgCl2, 2 mM DTT, 50 mM HEPES (pH 7.5), 0.01% Brij-35, 1 mM EGTA and 5% DMSO.
4. Stop the kinase reaction with 30 µl of Stop/Detection buffer containing 10 mM EDTA, 1× Lance Detection Buffer (cat. # CR97-100, PerkinElmer), 1% Super-Blocking in TBS (cat. #37535, Pierce), 5 nM phospho-Akt(T308) monoclonal antibody (cat. #4056, Cell Signaling Technologies), 5 nM Lance labeled Eu-Anti-rabbit IgG (cat. # AD0083, PerkinElmer), and 100 nM Streptavidin-allophycocyanin conjugate (cat. # PJ25S, Prozyme).
5. Read HTRF signals on an Envision reader (PerkinElmer) in HTRF mode after 60 mM.
6. IC$_{50}$ is determined by fitting the observed relationship between compound concentration and HTRF signal with a 4-parameter logistic equation.

Compounds of the instant invention were tested in the above assay and found to have an IC$_{50}$ of approximately 150 nM->30 µM.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

What is claimed is:

1. A compound of formula I

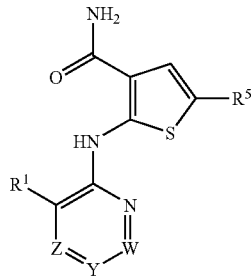

I wherein W is $CR^4$;
Y is $CR^3$;
Z is $CR^2$;
$R^1$ is hydrogen, halo, cyano or $C_{1-3}$ alkyl, wherein said alkyl group is optionally substituted with one to three halo;
$R^2$ is hydrogen, halo, cyano or $C_{1-3}$ alkyl, wherein said alkyl group is optionally substituted with one to three halo;
$R^3$ is hydrogen, halo, cyano, oxo, $SO_mR^8$, $C_{1-6}$ alkyl, $C_{2-6}$ alkenyl, $C_{2-6}$ alkynyl, $R^{11}$, $(C_{1-6}$ alkyl)$NR^7R^8$, $(C_{1-6}$ alkyl)$OR^{12}$, (C=O)$NH_2$, $NH(C=O)R^{12}$, $NH(SO_mR^8)$, $N(SO_mR^8)_2$, $NHCH_2(C_{3-6}$ cycloalkyl), $(C_{1-6}$ alkyl)$R^{11}$, $O(C_{1-6}$ alkyl)$R^{11}$, $CH_2OR^{11}$, $CH_2NH(C=O)R^{12}$, wherein said alkyl, alkenyl and alkynyl groups are optionally substituted with one to four substituents independently selected from the group consisting of halo and hydroxyl;
$R^4$ is hydrogen, halo, cyano, oxo, $NR^6R^7$, $C_{1-6}$ alkyl, $(C_{1-6}$ alkyl)$OR^{12}$, $OR^{12}$, (C=O)$OR^{12}$, $(C_{1-6}$ alkyl)$O(C_{1-6}$ alkyl)$OR^{12}$, $(C_{1-6}$ alkyl)$O(C_{1-6}$ alkyl)$R^{11}$, $CH_2NR^{10}CH_2(C=O)NHR^{11}$, $CH_2NR^{10}CH_2(C=O)NHOR^{12}$, $CH_2NR^{10}CH_2CH_2NH(C=O)OR^{12}$, $CH_2NR^{10}(C=O)R^{12}$, $CH_2NR^{10}CH_2(C=O)R^{11}$, $CH_2NR^{10}CH_2(C=O)OR^{12}$, $CH_2NR^{10}CH_2(C=O)NHR^{12}$, $CH_2NR^{10}CH_2(C=O)NHR^{11}$, $CH_2NR^{10}CH_2(C=O)NHR^{11}$, $CH_2NR^{10}CH_2(C=O)NR^6R^7$, $CH_2NR^{10}CH_2R^{11}$, $CH_2NR^{10}R^{11}$, $CH_2NR^{10}R^{12}$, CH=$NOR^{12}$, $CH_2OCH_2(C=O)NHCH_2R^{11}$, $CH_2OCH_2(C=O)R^{11}$, $CH_2OCH_2(C=O)NHR^{12}$, $CH_2OCH_2(C=O)NR^{10}R^{12}$, $CH_2OR^{11}$, $CH_2O(C_{2-7}$ alkynyl), $CH_2OR^{12}$, $CH_2O(C_{1-6}$ alkyl)$NHR^{12}$, (C=O)$NR^{10}R^{11}$, (C=O)$NR^{10}CH_2R^{11}$, (C=O)$R^{11}$, (C=O)$NR^{10}CH_2CH_2R^{11}$, (C=O)$NR^{10}R^{12}$, (C=O)$NH(C_{1-6}$ alkenyl), $CH(NH_2)(C=O)NH_2$, $CH(NH(C=O)CH_3)$ $((C=O)NH_2$, $CH(NH(C=O)OCH_3)((C=O)NH_2)$,
$CH_2NH(C=O)OCH_3$, $CH_2NH(C=O)SO_2CH_3$, $CH_2NH(C=O)R^{10}$, $CH_2NH(C=O)R^{12}$, $CH_2(C=O)NR^{10}R^{12}$), $CH_2(C=O)N(R^{10}(C_{2-6}$ alkynyl), $C_{1-6}$ alkyl (C=O)$NR^{10}R^{11}$, $CHR^{11}(C=O)NR^{10}R^{12}$, (C=O)$NR^{10}R^{12}$, $CHR^{11}(C=O)OR^{12}$, $CH_2SO_2R^{12}$, $CH_2SO_2$—$(C_{1-6}$ alkyl)-(C=O)$NR^{10}R^{12}$, $CH_2SO_2R^{11}$, $NHSO_2NR^{10}R^{12}$, $SO_2R^{12}$ or $R^{11}$, wherein said alkyl groups are optionally substituted with one to four substituents independently selected from the group consisting of halo, hydroxyl, cyano, $NR^6R^7$, $CH_2OR^{12}$, OP=O $(CH_3)_2$, P=$O(CH_3)(OCH_3)$ and $R^{11}$, and said alkenyl group is optionally substituted with one to three halo;
$R^5$ is aryl, wherein said aryl is optionally substituted with one to three substituents independently selected from the group consisting of halo, hydroxyl, cyano, $R^{12}$, $OR^{12}$, $R^{11}$, $NH_2$, $(C_{1-6}$ alkyl)$R^{11}$, (C=O)$R^{11}$, $CH_2NH$ (C=O)$R^{12}$, $CH_2O(C=O)R^{12}$, $SO_mR^8$, $CH_2$(trimethylsilyl), trimethylsilylethoxy and $NH(C=O)OR^{12}$;
$R^6$ is hydrogen or $C_{1-6}$ alkyl, wherein said alkyl group is optionally substituted with $SO_m$, —$NR^8R^9$, hydroxyl or —$OR^8$;
$R^7$ is hydrogen or $C_{1-6}$ alkyl, wherein said alkyl group is optionally substituted with $SO_m$, —$NR^8R^9$ or —$OR^8$;
$R^8$ is hydrogen or $C_{1-6}$ alkyl;
$R^9$ is hydrogen or $C_{1-6}$ alkyl;
$R^{10}$ is hydrogen, carbobenzoxy, $SO_mR^8$, $C_{1-6}$ alkyl, $(C_{1-6}$ alkyl)OH or (C=O)H;
$R^{11}$ is hydrogen, $C_{3-6}$ cycloalkyl (which is optionally substituted with one to three substituents independently selected from the group consisting of fluoro, hydroxyl and $(C_{1-6}$ alkyl)$OR^{12}$), or aryl (which is optionally substituted with one to three substituents independently selected from the group consisting of halo and $SO_mR^8$);
$R^{12}$ is hydrogen or $C_{1-6}$ alkyl, wherein said alkyl group is optionally substituted with one to four substituents independently selected from the group consisting of halo, hydroxyl, cyano, $SO_mR^8$, P=$O(CH_3)_2$, $NR^8R^9$ and $OR^8$;
m is an integer from zero to two;
or a pharmaceutically acceptable salt or stereoisomer thereof.

2. The compound of claim 1 wherein $R^5$ is aryl, wherein said aryl group is substituted with one to three substituents independently selected from the group consisting of halo, $R^{12}$, $R^{11}$ and $SO_mR^8$, or a pharmaceutically acceptable salt or stereoisomer thereof.

3. The compound of claim 2 wherein $R^5$ is aryl, wherein said aryl group is substituted with one to three substituents independently selected from the group consisting of halo and $R^{12}$ or a pharmaceutically acceptable salt or stereoisomer thereof.

4. The compound of claim 3 wherein $R^5$ is phenyl, wherein said phenyl group is substituted with one to three substituents independently selected from the group consisting of halo and $R^{12}$; $R^{12}$ is hydrogen or $C_{1-6}$ alkyl, wherein said alkyl group is optionally substituted with one to two hydroxyl; or a pharmaceutically acceptable salt or stereoisomer thereof.

5. The compound of claim 1 wherein $R^4$ is $C_{1-6}$ alkyl, $CH_2OR^{12}$, $CH_2O(C=O)NHR^{12}$ or $CH_2SO_2R^{12}$, wherein said alkyl group is optionally substituted with one to four substituents independently selected from the group consisting of hydroxyl and $R^{11}$; $R^{12}$ is $C_{1-6}$ alkyl, wherein said alkyl group is optionally substituted with one to two hydroxyl; or a pharmaceutically acceptable salt or stereoisomer thereof.

6. The compound of claim 5 wherein $R^4$ is $CH_2OR^{12}$; $R^{12}$ is $C_{1-6}$ alkyl, wherein said alkyl group is optionally substituted with hydroxyl or a pharmaceutically acceptable salt or stereoisomer thereof.

7. The compound of claim 1 which is
5-(2,4-Difluorophenyl)-2-{[6-(hydroxymethyl)pyridin-2-yl]amino}thiophene-3-carboxamide;
5-(2-Fluorophenyl)-2-{[6-(1-hydroxy-1-methylethyl)pyridin-2-yl]amino}thiophene-3-carboxamide;
5-(2-Fluorophenyl)-2-{[6-(1-hydroxyethyl)pyridin-2-yl]amino}thiophene-3-carboxamide;
2-{[5-(1-Hydroxy-1-methylethyl)pyridin-2-yl]amino}-5-phenylthiophene-3-carboxamide;
5-phenyl-2-(pyridin-2-ylamino)thiophene-3-carboxamide;
2-[(6-methylpyridin-2-yl)amino]-5-phenylthiophene-3-carboxamide;
2-[(4-methylpyridin-2-yl)amino]-5-phenylthiophene-3-carboxamide;
2-[(5-methylpyridin-2-yl)amino]-5-phenylthiophene-3-carboxamide;
2-[(3-methylpyridin-2-yl)amino]-5-phenylthiophene-3-carboxamide;
2-[(5-fluoropyridin-2-yl)amino]-5-phenylthiophene-3-carboxamide;
2-[(3-fluoropyridin-2-yl)amino]-5-phenylthiophene-3-carboxamide;
2-[(4-fluoropyridin-2-yl)amino]-5-phenylthiophene-3-carboxamide;
2-[(4-cyanopyridin-2-yl)amino]-5-phenylthiophene-3-carboxamide;
2-[(3-cyanopyridin-2-yl)amino]-5-phenylthiophene-3-carboxamide;
2-[(5-cyanopyridin-2-yl)amino]-5-phenylthiophene-3-carboxamide;
5-phenyl-2-{[5-(trifluoromethyl)pyridin-2-yl]amino}thiophene-3-carboxamide;
5-phenyl-2-{[4-(trifluoromethyl)pyridin-2-yl]amino}thiophene-3-carboxamide;
2-[(5-chloropyridin-2-yl)amino]-5-phenylthiophene-3-carboxamide;
2-{[6-(hydroxymethyl)pyridin-2-yl]amino}-5-phenylthiophene-3-carboxamide;
5-phenyl-2-{[3-(trifluoromethyl)pyridin-2-yl]amino}thiophene-3-carboxamide;
5-phenyl-2-{[6-(trifluoromethyl)pyridin-2-yl]amino}thiophene-3-carboxamide;
2-{[5-(methylsulfonyl)pyridin-2-yl]amino}-5-phenylthiophene-3-carboxamide;
5-(2,5-dichlorophenyl)-2-{[6-(1-hydroxy-1-methylethyl)pyridin-2-yl]amino}thiophene-3-carboxamide;
5-[2,6-difluoro-4-(1-hydroxy-1-methylethyl)phenyl]-2-[(6-methoxypyridin-2-yl)amino]thiophene-3-carboxamide;
5-[2,6-difluoro-4-(1-hydroxy-1-methylethyl)phenyl]-2-(pyridin-2-ylamino)thiophene-3-carboxamide;
5-[2,6-difluoro-4-(1-hydroxy-1-methylethyl)phenyl]-2-[(6-fluoropyridin-2-yl)amino]thiophene-3-carboxamide;
5-[2,6-difluoro-4-(1-hydroxy-1-methylethyl)phenyl]-2-[(4-fluoropyridin-2-yl)amino]thiophene-3-carboxamide;
2-[(6-cyanopyridin-2-yl)amino]-5-[2,6-difluoro-4-(1-hydroxy-1-methylethyl)phenyl]thiophene-3-carboxamide;
5-[2-fluoro-4-(1-hydroxy-1-methylethyl)phenyl]-2-[(5-fluoropyridin-2-yl)amino]thiophene-3-carboxamide;
2-[(5-cyanopyridin-2-yl)amino]-5-[2-fluoro-4-(1-hydroxy-1-methylethyl)phenyl]thiophene-3-carboxamide;
5-[2,6-Difluoro-4-(1-hydroxy-1-methylethyl)phenyl]-2-{[5-(methylsulfonyl)pyridin-2-yl]amino}thiophene-3-carboxamide;
5-[2-Fluoro-4-(1-hydroxy-1-methylethyl)phenyl]-2-{[5-(methylsulfonyl)pyridin-2-yl]amino}thiophene-3-carboxamide;
5-[2,6-Difluoro-4-(1-hydroxy-1-methylethyl)phenyl]-2-[(6-methylpyridin-2-yl)amino]thiophene-3-carboxamide;
5-[2,6-difluoro-4-(1-hydroxy-1-methylethyl)phenyl]-2-[(6-phenylpyridin-2-yl)amino]thiophene-3-carboxamide;
methyl 6-({3-(aminocarbonyl)-5-[2-fluoro-4-(1-hydroxy-1-methylethyl)phenyl]-2-thienyl}amino)pyridine-2-carboxylate;
6-({3-(aminocarbonyl)-5-[2-fluoro-4-(1-hydroxy-1-methylethyl)phenyl]-2-thienyl}amino)pyridine-2-carboxylic acid;
5-[2-fluoro-4-(1-hydroxy-1-methylethyl)phenyl]-2-{[5-(1-hydroxy-1-methylethyl)pyridin-2-yl]amino}thiophene-3-carboxamide;
5-[2,6-difluoro-4-(1-hydroxy-1-methylethyl)phenyl]-2-{[5-(1-hydroxy-1-methylethyl)pyridin-2-yl]amino}thiophene-3-carboxamide;
5-[2-fluoro-4-(1-hydroxy-1-methylethyl)phenyl]-2-{[6-(hydroxymethyl)pyridin-2-yl]amino}thiophene-3-carboxamide;
5-[2,6-Difluoro-4-(1-hydroxy-1-methylethyl)phenyl]-2-[(6-{[(2-hydroxy-1,2-dimethylpropyl)amino]methyl}pyridin-2-yl)amino]thiophene-3-carboxamide;
2-({6-[(dimethylamino)methyl]pyridin-2-yl}amino)-5-(2-fluorophenyl)thiophene-3-carboxamide;
5-(2,5-dichlorophenyl)-2-({6-[(dimethylamino)methyl]pyridin-2-yl}amino)thiophene-3-carboxamide;
2-{[6-({[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide;
ethyl N-{[6-({3-(aminocarbonyl)-2,6-difluoro-4-(1-hydroxy-1-methylethyl)phenyl]-2-thienyl}amino)pyridin-2-yl]methyl}glycinate;
5-[2,6-difluoro-4-(1-hydroxy-1-methylethyl)phenyl]-2-{[6-({[2-(dimethylamino)-2-oxoethyl]amino}methyl)pyridin-2-yl]amino}thiophene-3-carboxamide;
2-[(6-{[[2-(dimethylamino)-2-oxoethyl](methyl)amino]methyl}pyridin-2-yl)amino]-5-[2-fluoro-4-(1-hydroxy-1-methylethyl)phenyl]thiophene-3-carboxamide;
5-(4-Fluorophenyl)-2-({6-[(methylamino)methyl]pyridin-2-yl}amino)thiophene-3-carboxamide;
5-(2-Fluoro-4-(1-hydroxy-1-methylethyl)phenyl)-2-((6-((2-hydroxyethyl)amino)methyl)-2-pyridinyl)amino)-3-thiophenecarboxamide;

5-[2-fluoro-4-(1-hydroxy-1-methylethyl)phenyl]-2-[(6-{[(2-hydroxyethyl)(methyl)amino]methyl}pyridin-2-yl)amino]thiophene-3-carboxamide;

5-[2-fluoro-4-(1-hydroxy-1-methylethyl)phenyl]-2-{[6-({[2-(methylsulfonyl)ethyl]amino}methyl)pyridin-2-yl]amino}thiophene-3-carboxamide;

5-[2-fluoro-4-(1-hydroxy-1-methylethyl)phenyl]-2-{[6-({[(2S)-2-hydroxypropyl]amino}methyl)pyridin-2-yl]amino}thiophene-3-carboxamide;

5-[2-fluoro-4-(1-hydroxy-1-methylethyl)phenyl]-2-{[6-({[(1R)-2-hydroxy-1-methylethyl]amino}methyl)pyridin-2-yl]amino}thiophene-3-carboxamide;

5-[2-fluoro-4-(1-hydroxy-1-methylethyl)phenyl]-2-[(6-{[(2-hydroxy-2-methylpropyl)amino]methyl}pyridin-2-yl)amino]thiophene-3-carboxamide;

5-[2-fluoro-4-(1-hydroxy-1-methylethyl)phenyl]-2-[(6-{[(2-hydroxyethyl)amino]methyl}pyridin-2-yl)amino]thiophene-3-carboxamide;

5-[2-fluoro-4-(1-hydroxy-1-methylethyl)phenyl]-2-{[6-({[1-(hydroxymethyl)cyclopropyl]amino}methyl)pyridin-2-yl]amino}thiophene-3-carboxamide;

5-[2-fluoro-4-(1-hydroxy-1-methylethyl)phenyl]-2-[(6-{[(2,2,2-trifluoroethyl)amino]methyl}pyridin-2-yl)amino]thiophene-3-carboxamide;

5-[2-fluoro-4-(1-hydroxy-1-methylethyl)phenyl]-2-[(6-{[(3,3,3-trifluoro-2-hydroxypropyl)amino]methyl}pyridin-2-yl)amino]thiophene-3-carboxamide;

Tert-butyl [2-({[6-({3-(aminocarbonyl)-5-[2-fluoro-4-(1-hydroxy-1-methylethyl)phenyl]-2-thienyl}amino)pyridin-2-yl]methyl}amino)ethyl]carbamate;

5-[2,6-Difluoro-4-(1-hydroxy-1-methylethyl)phenyl]-2-[(6-{[(3-oxocyclopent-1-en-1-yl)amino]methyl}pyridine-2-yl)amino]thiophene-3-carboxamide;

5-[2,6-difluoro-4-(1-hydroxy-1-methylethyl)phenyl]-2-[(6-{[(3-oxocyclohex-1-en-1-yl)amino]methyl}pyridin-2-yl)amino]thiophene-3-carboxamide;

5-[2,6-difluoro-4-(1-hydroxy-1-methylethyl)phenyl]-2-{[6-(2-hydroxypropyl)pyridin-2-yl]amino}thiophene-3-carboxamide;

5-[2,6-difluoro-4-(1-hydroxy-1-methylethyl)phenyl]-2-{[6-(2-hydroxy-2-methylpropyl)pyridin-2-yl]amino}thiophene-3-carboxamide;

2-{[6-(1,2-Dihydroxyethyl)pyridin-2-yl]amino}-5-(2-fluorophenyl)thiophene-3-carboxamide;

5-(4-Chlorophenyl)-2-{[6-(1,2-dihydroxy-1-methylethyl)pyridin-2-yl]amino}thiophene-3-carboxamide;

5-(4-Chlorophenyl)-2-({6-[(cis)-1,2-dihydroxy-1-methylpropyl]pyridin-2-yl}amino)thiophene-3-carboxamide;

5-(2,5-dichlorophenyl)-2-{[6-(1,2-dihydroxyethyl)pyridin-2-yl]amino}thiophene-3-carboxamide;

2-{[6-(1,2-dihydroxyethyl)pyridin-2-yl]amino}-5-(4-fluorophenyl)thiophene-3-carboxamide;

2-({6-[(1S)-1,2-dihydroxy-1-methylethyl]pyridin-2-yl}amino)-5-[4-(1-hydroxy-1-methylethyl)phenyl]thiophene-3-carboxamide;

2-({6-[(1R)-1,2-dihydroxy-1-methylethyl]pyridin-2-yl}amino)-5-[4-(1-hydroxy-1-methylethyl)phenyl]thiophene-3-carboxamide;

5-(4-chlorophenyl)-2-({6-[(trans)-1,2-dihydroxy-1-methylpropyl]pyridin-2-yl}amino)thiophene-3-carboxamide;

5-[2,6-Difluoro-4-(1-hydroxy-1-methylethyl)phenyl]-2-{[6-({[2-(isopropylamino)-2-oxoethyl]amino}methyl)pyridin-2-yl]amino}thiophene-3-carboxamide;

5-[2-Fluoro-4-(1-hydroxy-1-methylethyl)phenyl]-2-({6-[({2-[(2-hydroxyethyl)amino]-2-oxoethyl}amino)methyl]pyridin-2-yl}amino)thiophene-3-carboxamide;

Benzyl{[6-({3-(aminocarbonyl)-5-[2-fluoro-4-(1-hydroxy-1-methylethyl)phenyl]-2-thienyl}amino)pyridin-2-yl]methyl}{2-[(2-hydroxyethyl)(methyl)amino]-2-oxoethyl}carbamate;

benzyl{[6-({3-(aminocarbonyl)-5-[2-fluoro-4-(1-hydroxy-1-methylethyl)phenyl]-2-thienyl}amino)pyridin-2-yl]methyl}(2-{[2-(methylsulfonyl)ethyl]amino}-2-oxoethyl)carbamate;

benzyl{[6-({3-(aminocarbonyl)-5-[2-fluoro-4-(1-hydroxy-1-methylethyl)phenyl]-2-thienyl}amino)pyridin-2-yl]methyl}{2-[(2-hydroxy-2-methylpropyl)amino]-2-oxoethyl}carbamate;

2-[(6-{[(2-{[2-(dimethylphosphoryl)ethyl]amino}-2-oxoethyl)amino]methyl}pyridin-2-yl)amino]-5-[2-fluoro-4-(1-hydroxy-1-methylethyl)phenyl]thiophene-3-carboxamide;

2-[(6-{[[2-(Cyclopentylamino)-2-oxoethyl](methylsulfonyl)amino]methyl}pyridin-2-yl)amino]-5-[2,6-difluoro-4-(1-hydroxy-1-methylethyl)phenyl]thiophene-3-carboxamide;

2-[(6-{[[2-(Cyclopentylamino)-2-oxoethyl](methyl)amino]methyl}pyridin-2-yl)amino]-5-[2,6-difluoro-4-(1-hydroxy-1-methylethyl)phenyl]thiophene-3-carboxamide;

2-{[6-({Acetyl[2-(cyclopentylamino)-2-oxoethyl]amino}methyl)pyridin-2-yl]amino}-5-[2,6-difluoro-4-(1-hydroxy-1-methylethyl)phenyl]thiophene-3-carboxamide;

5-(2,5-Dichlorophenyl)-2-{[6-(methoxymethyl)pyridin-2-yl]amino}thiophene-3-carboxamide;

5-[2,6-difluoro-4-(1-hydroxy-1-methylethyl)phenyl]-2-{[6-({2-[(2-hydroxyethyl)(methyl)amino]-2-oxoethoxy}methyl)pyridin-2-yl]amino}thiophene-3-carboxamide;

5-[2,6-difluoro-4-(1-hydroxy-1-methylethyl)phenyl]-2-{[6-({2-[(2-hydroxyethyl)amino]-2-oxoethoxy}methyl)pyridin-2-yl]amino}thiophene-3-carboxamide;

5-(2-fluoro-4-(1-hydroxy-1-methylethyl)phenyl)-2-((6-((2-((2-methoxyethyl)amino)-2-oxoethoxy)methyl)-2-pyridinyl)amino)-3-thiophenecarboxamide;

5-(2-fluoro-4-(1-hydroxy-1 methylethyl)phenyl)-2-((6-((2-oxo-2-(tetrahydro 2 furanylmethyl)amino)ethoxy)methyl)-2-pyridinyl)amino)-3-thiophenecarboxamide;

2-((6-((2-cyclohexylmethyl)amino)-2-oxoethoxy)methyl)-2-pyridinyl)amino)-5-(2-fluoro-4-(1-hydroxy-1-methylethyl)phenyl)-3-thiophenecarboxamide;

2-((6-((2-((2-dimethylamino)ethyl)amino)-2-oxoethoxy)methyl)-2-pyridinyl)amino)-5-(2-fluoro-4-(1-hydroxy-1-methylethyl)phenyl)-3-thiophenecarboxamide;

2-((6-((2-((2-dimethylamino)ethyl)amino)-2-oxoethoxy)methyl)-2-pyridinyl)amino)-5-(2-fluoro-4-(1-hydroxy-1-methylethyl)phenyl)-3-thiophenecarboxamide;

[6-({3-(Aminocarbonyl)-5-[2,6-difluoro-4-(1-hydroxy-1-methylethyl)phenyl]-2-thienyl}amino)pyridin-2-yl]methyl methylcarbamate;

5-[2,6-Difluoro-4-(1-hydroxy-1-methylethyl)phenyl]-2-({6-[(2-hydroxy-2-methylpropoxy)methyl]pyridin-2-yl}amino)thiophene-3-carboxamide;

2-({6-[(2-Hydroxy-2-methylpropoxy)methyl]pyridin-2-yl}amino)-5-[4-(methylsulfonyl)phenyl]thiophene-3-carboxamide;

5-[4-(1-Hydroxy-1-methylethyl)phenyl]-2-({6-[(2-hydroxy-2-methylpropoxy)methyl]pyridin-2-yl}amino)thiophene-3-carboxamide 5-[4-(1-cyano-1-methylethyl)phenyl]-2-({6-[(2-hydroxy-2-methylpropoxy)methyl]pyridin-2-yl}amino)thiophene-3-carboxamide;

5-{4-[(acetylamino)methyl]phenyl}-2-({6-[(2-hydroxy-2-methylpropoxy)methyl]pyridin-2-yl}amino)thiophene-3-carboxamide;

5-[2-fluoro-4-(1-hydroxy-1-methylethyl)phenyl]-2-({6-[(2-hydroxy-2-methylpropoxy)methyl]pyridin-2-yl}amino)thiophene-3-carboxamide;

5-[2,6-Difluoro-4-(1-hydroxy-1-methylethyl)phenyl]-2-{[6-(2-hydroxyethyl)pyridin-2-yl]amino}thiophene-3-carboxamide;

5-[2,6-Difluoro-4-(1-hydroxy-1-methylethyl)phenyl]-2-{[6-(2-methoxyethyl)pyridin-2-yl]amino}thiophene-3-carboxamide;

5-[2,6-difluoro-4-(1-hydroxy-1-methylethyl)phenyl]-2-{[6-(2-ethoxyethyl)pyridin-2-yl]amino}thiophene-3-carboxamide;

5-[2,6-Difluoro-4-(1-hydroxy-1-methylethyl)phenyl]-2-({6-[2-(2-hydroxy-2-methylpropoxy)ethyl]pyridin-2-yl}amino)thiophene-3-carboxamide;

5-[2,6-Difluoro-4-(1-hydroxy-1-methylethyl)phenyl]-2-{[6-({[(1R,2R)-2-hydroxycyclopentyl]oxy}methyl)pyridin-2-yl]amino}thiophene-3-carboxamide;

5-[2,6-difluoro-4-(1-hydroxy-1-methylethyl)phenyl]-2-{[6-({[(1R,2S)-2-hydroxycyclopentyl]oxy}methyl)pyridin-2-yl]amino}thiophene-3-carboxamide;

5-[2,6-difluoro-4-(1-hydroxy-1-methylethyl)phenyl]-2-{[6-({[(1R,2R)-2-hydroxycyclohexyl]oxy}methyl)pyridin-2-yl]amino}thiophene-3-carboxamide;

5-[2,6-difluoro-4-(1-hydroxy-1-methylethyl)phenyl]-2-{[6-({[(1R,2S)-2-hydroxycyclohexyl]oxy}methyl)pyridin-2-yl]amino}thiophene-3-carboxamide;

5-[2,6-difluoro-4-(1-hydroxy-1-methylethyl)phenyl]-2-{[6-({[(2S)-2-hydroxypropyl]oxy}methyl)pyridin-2-yl]amino}thiophene-3-carboxamide;

5-[2-fluoro-4-(1-hydroxy-1-methylethyl)phenyl]-2-({6-[(2-isopropoxyethoxy)methyl]pyridin-2-yl}amino)thiophene-3-carboxamide;

2-({6-[(2,2-difluoroethoxy)methyl]pyridin-2-yl}amino)-5-[2-fluoro-4-(1-hydroxy-1-methylethyl)phenyl]thiophene-3-carboxamide;

2-({6-[(cyclobutylmethoxy)methyl]pyridin-2-yl}amino)-5-[2-fluoro-4-(1-hydroxy-1-methylethyl)phenyl]thiophene-3-carboxamide;

5-[2-fluoro-4-(1-hydroxy-1-methylethyl)phenyl]-2-({6-[(3,3,3-trifluoropropoxy)methyl]pyridin-2-yl}amino)thiophene-3-carboxamide;

5-[2-fluoro-4-(1-hydroxy-1-methylethyl)phenyl]-2-({6-[(3-methoxy-3-methylbutoxy)methyl]pyridin-2-yl}amino)thiophene-3-carboxamide;

2-[(6-{[2-(dimethylamino)ethoxy]methyl}pyridin-2-yl)amino]-5-[2-fluoro-4-(1-hydroxy-1-methylethyl)phenyl]thiophene-3-carboxamide;

2-({6-[(cyclopropylmethoxy)methyl]pyridin-2-yl}amino)-5-[2-fluoro-4-(1-hydroxy-1-methylethyl)phenyl]thiophene-3-carboxamide;

2-[(6-{[(4-fluorobenzyl)oxy]methyl}pyridin-2-yl)amino]-5-[2-fluoro-4-(1-hydroxy-1-methylethyl)phenyl]thiophene-3-carboxamide;

5-[2-fluoro-4-(1-hydroxy-1-methylethyl)phenyl]-2-({6-[(hept-3-yn-1-yloxy)methyl]pyridin-2-yl}amino)thiophene-3-carboxamide;

5-[2-Fluoro-4-(1-hydroxy-1-methylethyl)phenyl]-2-{[6-(methoxymethyl)pyridin-2-yl]amino}thiophene-3-carboxamide;

2-{[6-(Ethoxymethyl)pyridin-2-yl]amino}-5-[2-fluoro-4-(1-hydroxy-1-methylethyl)phenyl]thiophene-3-carboxamide;

5-[2-Fluoro-4-(1-hydroxy-1-methylethyl)phenyl]-2-({6-[(2-methoxyethoxy)methyl]pyridin-2-yl}amino)thiophene-3-carboxamide;

5-[2,6-difluoro-4-(1-hydroxy-1-methylethyl)phenyl]-2-[(6-{[2-(methylsulfonyl)ethoxy]methyl}pyridin-2-yl)amino]thiophene-3-carboxamide;

5-[2-Fluoro-4-(1-hydroxy-1-methylethyl)phenyl]-2-{[6-(2-hydroxyethoxy)pyridin-2-yl]amino}thiophene-3-carboxamide;

2-{[6-(2-hydroxyethoxy)pyridin-2-yl]amino}-5-[4-(1-hydroxy-1-methylethyl)phenyl]thiophene-3-carboxamide;

5-[2,6-difluoro-4-(1-hydroxy-1-methylethyl)phenyl]-2-{[6-(2-hydroxyethoxy)pyridin-2-yl]amino}thiophene-3-carboxamide;

6-({3-(Aminocarbonyl)-5-[2-fluoro-4-(1-hydroxy-1-methylethyl)phenyl]-2-thienyl}amino)-N-(trans-4-hydroxycyclohexyl)pyridine-2-carboxamide;

6-({3-(Aminocarbonyl)-5-[2-fluoro-4-(1-hydroxy-1-methylethyl)phenyl]-2-thienyl}amino)-N-(cyclopropylmethyl)pyridine-2-carboxamide;

6-({3-(aminocarbonyl)-5-[2,6-difluoro-4-(1-hydroxy-1-methylethyl)phenyl]-2-thienyl}amino)-N-(trans-4-hydroxycyclohexyl)pyridine-2-carboxamide;

6-({3-(aminocarbonyl)-5-[2,6-difluoro-4-(1-hydroxy-1-methylethyl)phenyl]-2-thienyl}amino)-N-(2-hydroxyethyl)-N-methylpyridine-2-carboxamide;

6-({3-(aminocarbonyl)-5-[2,6-difluoro-4-(1-hydroxy-1-methylethyl)phenyl]-2-thienyl}amino)-N-(2-hydroxyethyl)pyridine-2-carboxamide;

6-({3-(aminocarbonyl)-5-[2-fluoro-4-(1-hydroxy-1-methylethyl)phenyl]-2-thienyl}amino)-N-(2-hydroxyethyl)pyridine-2-carboxamide;

6-({3-(aminocarbonyl)-5-[2-fluoro-4-(1-hydroxy-1-methylethyl)phenyl]-2-thienyl}amino)-N-(2-fluoroprop-2-en-1-yl)pyridine-2-carboxamide;

6-({3-(aminocarbonyl)-5-[2-fluoro-4-(1-hydroxy-1-methylethyl)phenyl]-2-thienyl}amino)-N-methylpyridine-2-carboxamide;

6-({3-(aminocarbonyl)-5-[2-fluoro-4-(1-hydroxy-1-methylethyl)phenyl]-2-thienyl}amino)-N-ethyl-N-methylpyridine-2-carboxamide;

6-({3-(aminocarbonyl)-5-[2-fluoro-4-(1-hydroxy-1-methylethyl)phenyl]-2-thienyl}amino)-N-(2-methoxyethyl)pyridine-2-carboxamide;

6-({3-(aminocarbonyl)-5-[2-fluoro-4-(1-hydroxy-1-methylethyl)phenyl]-2-thienyl}amino)-N-(2-hydroxypropyl)pyridine-2-carboxamide;

6-({3-(aminocarbonyl)-5-[2-fluoro-4-(1-hydroxy-1-methylethyl)phenyl]-2-thienyl}amino)-N-(2-hydroxy-2-methylpropyl)pyridine-2-carboxamide;

6-({3-(aminocarbonyl)-5-[2-fluoro-4-(1-hydroxy-1-methylethyl)phenyl]-2-thienyl}amino)-N,N-bis(2-hydroxyethyl)pyridine-2-carboxamide;

6-({3-(aminocarbonyl)-5-[2-fluoro-4-(1-hydroxy-1-methylethyl)phenyl]-2-thienyl}amino)-N-[(1R)-2-hydroxy-1-methylethyl]pyridine-2-carboxamide;

6-({3-(aminocarbonyl)-5-[2-fluoro-4-(1-hydroxy-1-methylethyl)phenyl]-2-thienyl}amino)-N-[(2S)-2-hydroxypropyl]pyridine-2-carboxamide;

2-[(6-{[(Cyanoacetyl)amino]methyl}pyridin-2-yl)amino]-5-[2,6-difluoro-4-(1-hydroxy-1-methylethyl)phenyl]thiophene-3-carboxamide;

2-{[6-(1-Cyano-3-hydroxypropyl)pyridin-2-yl]amino}-5-[2-fluoro-4-(1-hydroxy-1-methylethyl)phenyl]thiophene-3-carboxamide;
2-{[6-(cyanomethyl)pyridin-2-yl]amino}-5-[2-fluoro-4-(1-hydroxy-1-methylethyl)phenyl]thiophene-3-carboxamide;
2-{[6-(cyanomethyl)pyridin-2-yl]amino}-5-[2,6-difluoro-4-(1-hydroxy-1-methylethyl)phenyl]thiophene-3-carboxamide;
5-[2,6-Difluoro-4-(1-hydroxy-1-methylethyl)phenyl]-2-({6-[1-hydroxy-2-(methylamino)-2-oxoethyl]pyridin-2-yl}amino)thiophene-3-carboxamide;
2-{[6-(2-amino-1-hydroxy-2-oxoethyl)pyridin-2-yl]amino}-5-[2,6-difluoro-4-(1-hydroxy-1-methylethyl)phenyl]thiophene-3-carboxamide;
5-[2,6-difluoro-4-(1-hydroxy-1-methylethyl)phenyl]-2-({6-[2-(dimethylamino)-1-hydroxy-2-oxoethyl]pyridin-2-yl}amino)thiophene-3-carboxamide;
2-{[6-(1-Cyano-1-methylethyl)pyridin-2-yl]amino}-5-[2,6-difluoro-4-(1-hydroxy-1-methylethyl)phenyl]thiophene-3-carboxamide;
2-{[6-(1-cyanoethyl)pyridin-2-yl]amino}-5-[2,6-difluoro-4-(1-hydroxy-1-methy lethyl)phenyl]thiophene-3-carboxamide;
2-{[6-(1-Cyanocyclopropyl)pyridin-2-yl]amino}-5-[2,6-difluoro-4-(1-hydroxy-1-methylethyl)phenyl]thiophene-3-carboxamide;
2-{[6-(2-Amino-1,1-dimethyl-2-oxoethyl)pyridin-2-yl]amino}-5-[2,6-difluoro-4-(1-hydroxy-1-methylethyl)phenyl]thiophene-3-carboxamide;
5-[2-Fluoro-4-(1-hydroxy-1-methylethyl)phenyl]-2-[(6-{[(2-hydroxy-2-methylpropyl)sulfonyl]methyl}pyridin-2-yl)amino]thiophene-3-carboxamide;
5-[2,6-difluoro-4-(1-hydroxy-1-methylethyl)phenyl]-2-[(6-{[(2-hydroxy-2-methylpropyl)sulfonyl]methyl}pyridin-2-yl)amino]thiophene-3-carboxamide;
5-[2,6-difluoro-4-(1-hydroxy-1-methylethyl)phenyl]-2-({6-[(ethylsulfonyl)methyl]pyridin-2-yl}amino)thiophene-3-carboxamide;
2-({6-[(tert-butylsulfonyl)methyl]pyridin-2-yl}amino)-5-[2,6-difluoro-4-(1-hydroxy-1-methylethyl)phenyl]thiophene-3-carboxamide;
5-[2,6-difluoro-4-(1-hydroxy-1-methylethyl)phenyl]-2-({6-[(propylsulfonyl)methyl]pyridin-2-yl}amino)thiophene-3-carboxamide;
5-[2,6-difluoro-4-(1-hydroxy-1-methylethyl)phenyl]-2-({6-[(isobutylsulfonyl)methyl]pyridin-2-yl}amino)thiophene-3-carboxamide;
5-[2,6-difluoro-4-(1-hydroxy-1-methylethyl)phenyl]-2-[(6-{[(2-hydroxypropyl)sulfonyl]methyl}pyridin-2-yl)amino]thiophene-3-carboxamide;
5-[2,6-difluoro-4-(1-hydroxy-1-methylethyl)phenyl]-2-[(6-{[(4-hydroxybutyl)sulfonyl]methyl}pyridin-2-yl)amino]thiophene-3-carboxamide;
5-[2,6-difluoro-4-(1-hydroxy-1-methylethyl)phenyl]-2-{[6-({[2-(methylamino)-2-oxoethyl]sulfonyl}methyl)pyridin-2-yl]amino}thiophene-3-carboxamide;
5-[2,6-difluoro-4-(1-hydroxy-1-methylethyl)phenyl]-2-({6-[(isopropylsulfonyl)methyl]pyridin-2-yl}amino)thiophene-3-carboxamide;
5-[2,6-difluoro-4-(1-hydroxy-1-methylethyl)phenyl]-2-({2-[(ethylsulfonyl)methyl]pyrimidin-4-yl}amino)thiophene-3-carboxamide;
5-[2,6-Difluoro-4-(1-hydroxy-1-methylethyl)phenyl]-2-({6-[(methylsulfonyl)methyl]pyridin-2-yl}amino)thiophene-3-carboxamide;
5-[2-fluoro-4-(1-hydroxy-1-methylethyl)phenyl]-2-({6-[(methylsulfonyl)methyl]pyridin-2-yl}amino)thiophene-3-carboxamide;
5-[2-Fluoro-4-(1-hydroxy-1-methylethyl)phenyl]-2-{[6-(methylsulfonyl)pyridin-2-yl]amino}thiophene-3-carboxamide;
5-[2,6-difluoro-4-(1-hydroxy-1-methylethyl)phenyl]-2-{[6-(methylsulfonyl)pyridin-2-yl]amino}thiophene-3-carboxamide;
5-[2,6-difluoro-4-(1-hydroxy-1-methylethyl)phenyl]-2-({6-[(2-hydroxyethyl)(methyl)amino]pyridin-2-yl}amino)thiophene-3-carboxamide;
5-[2-fluoro-4-(1-hydroxy-1-methylethyl)phenyl]-2-({6-[3-(methylsulfonyl)phenyl]pyridin-2-yl}amino)thiophene-3-carboxamide;
6-({3-(Aminocarbonyl)-5-[2-fluoro-4-(1-hydroxy-1-methylethyl)phenyl]-2-thienyl}amino)-N,N-dimethylnicotinamide;
6-({3-(aminocarbonyl)-5-[2-fluoro-4-(1-hydroxy-1-methylethyl)phenyl]-2-thienyl}amino)-N-methylnicotinamide;
5-[2,6-difluoro-4-(1-hydroxy-1-methylethyl)phenyl]-2-({5-[(dimethylamino)methyl]pyridin-2-yl}amino)thiophene-3-carboxamide;
5-[2,6-Difluoro-4-(1-hydroxy-1-methylethyl)phenyl]-2-[(5-{[(2-hydroxy-1,2-dimethylpropyl)amino]methyl}-6-methylpyridin-2-yl)amino]thiophene-3-carboxamide;
5-[2,6-Difluoro-4-(1-hydroxy-1-methylethyl)phenyl]-2-({5-[(2-hydroxy-2-methylpropoxy)methyl]-6-methylpyridin-2-yl}amino)thiophene-3-carboxamide;
5-[2,6-Difluoro-4-(1-hydroxy-1-methylethyl)phenyl]-2-{[6-(2,2,2-trifluoro-1-hydroxyethyl)pyridin-2-yl]amino}thiophene-3-carboxamide;
5-[2-fluoro-4-(1-hydroxy-1-methylethyl)phenyl]-2-{[6-(2,2,2-trifluoro-1-hydroxyethyl)pyridin-2-yl]amino}thiophene-3-carboxamide;
5-[2,6-Difluoro-4-(1-hydroxy-1-methylethyl)phenyl]-2-{[6-(2-fluoro-1-hydroxyethyl)pyridin-2-yl]amino}thiophene-3-carboxamide;
5-[2,6-Difluoro-4-(1-hydroxy-1-methylethyl)phenyl]-2-{[5-(1-hydroxy-1-methylethyl)-6-methylpyridin-2-yl]amino}thiophene-3-carboxamide;
5-[2,6-Difluoro-4-(1-hydroxy-1-methylethyl)phenyl]-2-{[5-(1-hydroxyethyl)-6-methylpyridin-2-yl]amino}thiophene-3-carboxamide;
5-[2-fluoro-4-(1-hydroxy-1-methylethyl)phenyl]-2-{[5-(1-hydroxyethyl)-6-methylpyridin-2-yl]amino}thiophene-3-carboxamide;
5-[2-Fluoro-4-(1-methoxy-1-methylethyl)phenyl]-2-{[5-(1-methoxyethyl)-6-methylpyridin-2-yl]amino}thiophene-3-carboxamide;
2-{[6-Chloro-5-(1-hydroxy-1-methylethyl)pyridin-2-yl]amino}-5-[2-fluoro-4-(1-hydroxy-1-methylethyl)phenyl]thiophene-3-carboxamide;
5-[2,6-Difluoro-4-(1-hydroxy-1-methylethyl)phenyl]-2-{[6-fluoro-5-(1-hydroxy-1-methylethyl)pyridin-2-yl]amino}thiophene-3-carboxamide;
5-[2,6-Difluoro-4-(1-hydroxy-1-methylethyl)phenyl]-2-{[6-fluoro-5-(methylsulfonyl)pyridin-2-yl]amino}thiophene-3-carboxamide;
Methyl {[6-({3-(aminocarbonyl)-[2,6-difluoro-4-(1-hydroxy-1-methylethyl)phenyl]-2-thienyl}amino)-2-methylpyridin-3-yl]methyl}carbamate;
5-[2,6-Difluoro-4-(1-hydroxy-1-methylethyl)phenyl]-2-{[5-(1-hydroxy-1-methylethyl)-6-methoxypyridin-2-yl]amino}thiophene-3-carboxamide;

5-[2,6-Difluoro-4-(1-hydroxy-1-methylethyl)phenyl]-2-{[6-(hydroxymethyl)-5-(1-hydroxy-1-methylethyl)pyridin-2-yl]amino}thiophene-3-carboxamide;

2-[(5-Cyano-6-methylpyridin-2-yl)amino]-5-[2,6-difluoro-4-(1-hydroxy-1-methylethyl)phenyl]thiophene-3-carboxamide;

2-{[5-(Acetylamino)-6-methylpyridin-2-yl]amino}-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-({6-methyl-5-[(methylsulfonyl)amino]pyridin-2-yl}amino)thiophene-3-carboxamide;

2-({5-[bis(Methylsulfonyl)amino]-6-methylpyridin-2-yl}amino)-5-[2,6-difluoro-4-(1-hydroxy-1-methylethyl)phenyl]thiophene-3-carboxamide;

2-({5-[(Cyclopropylmethyl)amino]-6-methylpyridin-2-yl}amino)-5-[2,6-difluoro-4-(1-hydroxy-1-methylethyl)phenyl]thiophene-3-carboxamide;

5-[2,6-Difluoro-4-(1-hydroxy-1-methylethyl)phenyl]-2-{[5-(3-hydroxy-3-methylbut-1-yn-1-yl)-6-methylpyridin-2-yl]amino}thiophene-3-carboxamide;

5-[2,6-Difluoro-4-(1-hydroxy-1-methylethyl)phenyl]-2-{[6-(3-hydroxy-3-methylbut-1-yn-1-yl)pyridin-2-yl]amino}thiophene-3-carboxamide;

[6-({3-(Aminocarbonyl)-5-[2-fluoro-4-(1-hydroxy-1-methylethyl)phenyl]-2-thienyl}amino)pyridin-2-yl]methyl dimethylphosphinate;

Methyl {[6-({3-(aminocarbonyl)-5-[2-fluoro-4-(1-hydroxy-1-methylethyl)phenyl]-2-thienyl}amino)pyridin-2-yl]methyl}methylphosphinate;

5-(2,4-difluorophenyl)-2-[(6-methylpyridin-2-yl)amino]thiophene-3-carboxamide;

5-(4-fluorophenyl)-2-[(6-methylpyridin-2-yl)amino]thiophene-3-carboxamide;

5-(3-fluorophenyl)-2-[(6-methylpyridin-2-yl)amino]thiophene-3-carboxamide;

5-(2-fluorophenyl)-2-[(6-methylpyridin-2-yl)amino]thiophene-3-carboxamide;

5-(2,3-difluorophenyl)-2-[(6-methylpyridin-2-yl)amino]thiophene-3-carboxamide;

5-(2-chlorophenyl)-2-[(6-methylpyridin-2-yl)amino]thiophene-3-carboxamide;

5-(2,5-dichlorophenyl)-2-[(6-methylpyridin-2-yl)amino]thiophene-3-carboxamide;

5-[2-chloro-5-(trifluoromethyl)phenyl]-2-[(6-methylpyridin-2-yl)amino]thiophene-3-carboxamide;

5-(3-chlorophenyl)-2-[(6-methylpyridin-2-yl)amino]thiophene-3-carboxamide;

2-[(6-methylpyridin-2-yl)amino]-5-[3-(trifluoromethyl)phenyl]thiophene-3-carboxamide;

2-[(6-methylpyridin-2-yl)amino]-5-[4-(trifluoromethyl)phenyl]thiophene-3-carboxamide;

5-(5-chloro-2-fluorophenyl)-2-[(6-methylpyridin-2-yl)amino]thiophene-3-carboxamide;

5-(2-fluoro-5-methoxyphenyl)-2-[(6-methylpyridin-2-yl)amino]thiophene-3-carboxamide;

5-(3,4-dichlorophenyl)-2-[(6-methylpyridin-2-yl)amino]thiophene-3-carboxamide;

5-(2,5-difluorophenyl)-2-[(6-methylpyridin-2-yl)amino]thiophene-3-carboxamide;

or a pharmaceutically acceptable salt or stereoisomer thereof.

8. A pharmaceutical composition comprising a pharmaceutically effective amount of the compound according to claim 1, and a pharmaceutically acceptable carrier.

* * * * *

SEQUENCE LISTING

```
<160> NUMBER OF SEQ ID NOS: 2

<210> SEQ ID NO 1
<211> LENGTH: 15
<212> TYPE: PRT
<213> ORGANISM: Artificial Sequence
<220> FEATURE:
<223> OTHER INFORMATION: Completely Synthetic Amino Acid Sequence
<220> FEATURE:
<221> NAME/KEY: AMIDATION
<222> LOCATION: (15)...(15)
<223> OTHER INFORMATION: Glutamic acid amide

<400> SEQUENCE: 1

Glu Gln Glu Asp Glu Pro Glu Gly Asp Tyr Phe Glu Trp Leu Glu
1               5                   10                  15

<210> SEQ ID NO 2
<211> LENGTH: 28
```

```
<212> TYPE: PRT
<213> ORGANISM: Artificial Sequence
<220> FEATURE:
<223> OTHER INFORMATION: Completely Synthetic Amino Acid Sequence

<400> SEQUENCE: 2

Gly Gly Asp Gly Ala Thr Met Lys Thr Phe Cys Gly Gly Thr Pro Ser
 1               5                  10                  15

Asp Gly Asp Pro Asp Gly Gly Glu Phe Thr Glu Phe
            20                  25
```